US008212004B2

(12) United States Patent
Yu et al.

(10) Patent No.: US 8,212,004 B2
**(45) Date of Patent: *Jul. 3, 2012**

(54) NEUTROKINE-ALPHA FUSION PROTEINS

(75) Inventors: Guo-Liang Yu, Berkeley, CA (US); Reinhard Ebner, Gaithersburg, MD (US); Jian Ni, Germantown, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 1311 days.

This patent is subject to a terminal disclaimer.

(21) Appl. No.: 11/054,539

(22) Filed: Feb. 10, 2005

(65) Prior Publication Data

US 2005/0186637 A1 Aug. 25, 2005

Related U.S. Application Data

(63) Continuation-in-part of application No. 10/270,487, filed on Oct. 16, 2002, now abandoned, which is a continuation-in-part of application No. 09/929,493, filed on Aug. 15, 2001, now abandoned, which is a continuation-in-part of application No. 09/588,947, filed on Jun. 8, 2000, now Pat. No. 6,562,579, and a continuation-in-part of application No. 09/589,285, filed on Jun. 8, 2000, now Pat. No. 6,881,401, and a continuation-in-part of application No. 09/589,286, filed on Jun. 8, 2000, now Pat. No. 6,635,482, and a continuation-in-part of application No. 09/589,287, filed on Jun. 8, 2000, now Pat. No. 6,403,770, and a continuation-in-part of application No. 09/589,288, filed on Jun. 8, 2000, now Pat. No. 8,071,092, and a continuation-in-part of application No. 09/507,968, filed on Feb. 22, 2000, now Pat. No. 6,812,327, application No. 11/054,539, which is a continuation-in-part of application No. 09/589,285, filed on Jun. 8, 2000, now Pat. No. 6,881,401, which is a continuation of application No. 09/507,968, filed on Feb. 22, 2000, now Pat. No. 6,812,327, application No. 11/054,539, which is a continuation-in-part of application No. 09/589,288, filed on Jun. 8, 2000, (Continued)

(51) Int. Cl.
*C07K 14/475* (2006.01)
*A61K 38/16* (2006.01)

(52) U.S. Cl. .................. 530/350; 424/185.1; 424/192.1; 530/399

(58) Field of Classification Search ........................ None
See application file for complete search history.

(56) References Cited

U.S. PATENT DOCUMENTS 4,179,337 A 12/1979 Davis et al.

(Continued)

FOREIGN PATENT DOCUMENTS

CA 2 665 133 A1 5/1998

(Continued)

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Nimmanapalli et al. The growth factor fusion construct containing B-lymphocyte stimulator (BLyS) and the toxin rGel induces apoptosis specifically in BAff-R-positive CCL cells. Blood 109(6): 2557-2564, 2007.*
Kreitman et al. Recombinant immunotoxins for the treatment of haematological malignancies. Expert Opin Biol Ther 4(7): 1115-1128,2004.*
Vaughan, Nat. Biotechnol., "Human Antibodies with Sub-nanomolar Affinities Isolated from a Large Non-immunized Phage Display Library," 14: 309-314 (1996).*
U.S. Appl. No. 08/984,396, Hurle et al.
U.S. Appl. No. 09/912,293, Rosen et al.
U.S. Appl. No. 11/345,661, filed Aug. 3, 2006, Rosenblum et al.
U.S. Appl. No. 60/033,601, Gorman, D.M.
U.S. Appl. No. 60/041,797, Hurle et al.
U.S. Appl. No. 60/048,776, Masiakowsky et al.
U.S. Appl. No. 60/058,786, Tschopp, J.
U.S. Appl. No. 60/066,386, Masiakowsky et al.
U.S. Appl. No. 60/066,577, Song, H.Y.
U.S. Appl. No. 60/068,959, Tribouley et al.
U.S. Appl. No. 60/096,173, Song, H.Y.
U.S. Appl. No. 60/106,976, Lenardo et al.
U.S. Appl. No. 60/117,169, Mackay et al.
U.S. Appl. No. 60/143,228, Mackay et al.

(Continued)

*Primary Examiner* — Bridget E Bunner
(74) *Attorney, Agent, or Firm* — Leydig, Voit & Mayer, Ltd.

(57) ABSTRACT

The present invention relates to nucleic acid molecules encoding Neutrokine-alpha and/or Neutrokine-alphaSV polypeptides, including soluble forms of the extracellular domain. Neutrokine-alpha and/or Neutrokine-alphaSV polypeptides are also provided as are vectors, host cells and recombinant methods for producing the same. The invention further relates to antibodies or portions thereof that specifically bind Neutrokine-alpha and/or Neutrokine-alphaSV and diagnostic and therapeutic methods using these antibodies. Also provided are diagnostic methods for detecting immune system-related disorders and therapeutic methods for treating immune system-related disorders using the compositions of the invention.

8 Claims, 27 Drawing Sheets

Related U.S. Application Data now Pat. No. 8,071,092, which is a continuation of application No. 09/507,968, filed on Feb. 22, 2000, now Pat. No. 6,812,327.

(60) Provisional application No. 60/543,261, filed on Feb. 11, 2004, provisional application No. 60/580,387, filed on Jun. 18, 2004, provisional application No. 60/617,191, filed on Oct. 12, 2004, provisional application No. 60/368,548, filed on Apr. 1, 2002, provisional application No. 60/336,726, filed on Dec. 7, 2001, provisional application No. 60/331,478, filed on Nov. 16, 2001, provisional application No. 60/330,835, filed on Oct. 31, 2001, provisional application No. 60/329,747, filed on Oct. 18, 2001, provisional application No. 60/329,508, filed on Oct. 17, 2001, provisional application No. 60/225,628, filed on Aug. 15, 2000, provisional application No. 60/227,008, filed on Aug. 23, 2000, provisional application No. 60/234,338, filed on Sep. 22, 2000, provisional application No. 60/240,806, filed on Oct. 17, 2000, provisional application No. 60/250,020, filed on Nov. 30, 2000, provisional application No. 60/276,248, filed on Mar. 16, 2001, provisional application No. 60/293,499, filed on May 25, 2001, provisional application No. 60/296,122, filed on Jun. 7, 2001, provisional application No. 60/304,809, filed on Jul. 13, 2001, provisional application No. 60/122,388, filed on Mar. 2, 1999, provisional application No. 60/124,097, filed on Mar. 12, 1999, provisional application No. 60/126,599, filed on Mar. 26, 1999, provisional application No. 60/127,598, filed on Apr. 2, 1999, provisional application No. 60/130,412, filed on Apr. 16, 1999, provisional application No. 60/130,696, filed on Apr. 23, 1999, provisional application No. 60/131,278, filed on Apr. 27, 1999, provisional application No. 60/131,673, filed on Apr. 29, 1999, provisional application No. 60/136,784, filed on May 28, 1999, provisional application No. 60/142,659, filed on Jul. 6, 1999, provisional application No. 60/126,599, filed on Mar. 26, 1999.

(56) References Cited

U.S. PATENT DOCUMENTS

| | | | | |
|---|---|---|---|---|
| 5,223,409 | A | 6/1993 | Ladner et al. | |
| 5,281,704 | A | 1/1994 | Love | |
| 5,403,484 | A | 4/1995 | Ladner et al. | |
| 5,416,202 | A | 5/1995 | Bernhard et al. | |
| 5,474,981 | A | 12/1995 | Leder et al. | |
| 5,571,698 | A | 11/1996 | Ladner et al. | |
| 5,576,195 | A | 11/1996 | Robinson et al. | |
| 5,589,499 | A | 12/1996 | Weth | |
| 5,595,721 | A | 1/1997 | Kaminski et al. | |
| 5,605,671 | A | 2/1997 | Lyle | |
| 5,635,384 | A | 6/1997 | Walsh et al. | |
| 5,643,575 | A | 7/1997 | Martinez et al. | |
| 5,795,724 | A | 8/1998 | Hillman et al. | |
| 5,846,818 | A | 12/1998 | Robinson et al. | |
| 5,869,045 | A | 2/1999 | Hellstrom et al. | |
| 5,869,331 | A | 2/1999 | Dornburg | |
| 5,948,619 | A | 9/1999 | Bandman et al. | |
| 5,962,301 | A | 10/1999 | Horvitz et al. | |
| 5,969,102 | A | 10/1999 | Bram et al. | |
| 6,207,160 | B1 | 3/2001 | Victoria et al. | |
| 6,297,367 | B1 | 10/2001 | Tribouley | |
| 6,403,770 | B1 * | 6/2002 | Yu et al. | 530/387.3 |
| 6,475,987 | B1 | 11/2002 | Shu | |
| 6,541,224 | B2 | 4/2003 | Yu | |
| 6,562,579 | B1 * | 5/2003 | Yu et al. | 435/7.1 |
| 6,635,482 | B1 * | 10/2003 | Yu et al. | 435/326 |
| 6,689,579 | B1 | 2/2004 | Yu et al. | |
| 6,716,576 | B1 | 4/2004 | Yu et al. | |
| 6,774,106 | B2 | 8/2004 | Theill | |
| 6,812,327 | B1 * | 11/2004 | Yu et al. | 530/351 |
| 6,846,476 | B2 | 1/2005 | White | |
| 6,869,605 | B2 | 3/2005 | Browning et al. | |
| 6,875,846 | B2 | 4/2005 | Rennert et al. | |
| 6,881,401 | B1 * | 4/2005 | Yu et al. | 424/85.1 |
| 7,083,785 | B2 | 8/2006 | Browning et al. | |
| 7,118,872 | B2 | 10/2006 | Beltzer et al. | |
| 7,138,501 | B2 | 11/2006 | Ruben et al. | |
| 7,220,840 | B2 | 5/2007 | Ruben et al. | |
| 7,241,576 | B2 | 7/2007 | Aggarwal | |
| 7,259,137 | B2 | 8/2007 | Min et al. | |
| 7,317,089 | B2 | 1/2008 | Kikly | |
| 7,399,593 | B1 | 7/2008 | Farrow et al. | |
| 7,691,804 | B2 | 4/2010 | Jeffrey et al. | |
| 2001/0010925 | A1 | 8/2001 | Wiley | |
| 2002/0037852 | A1 | 3/2002 | Browning et al. | |
| 2002/0055624 | A1 | 5/2002 | Wiley | |
| 2002/0115112 | A1 | 8/2002 | Yu et al. | |
| 2002/0150579 | A1 | 10/2002 | Kimberly et al. | |
| 2002/0165156 | A1 | 11/2002 | Browning et al. | |
| 2002/0172674 | A1 | 11/2002 | Browning et al. | |
| 2003/0012783 | A1 | 1/2003 | Kindsvogel | |
| 2003/0022233 | A1 | 1/2003 | Goodwin | |
| 2003/0023038 | A1 | 1/2003 | Rennert et al. | |
| 2003/0059937 | A1 | 3/2003 | Ruben et al. | |
| 2003/0091565 | A1 | 5/2003 | Beltzer et al. | |
| 2003/0095967 | A1 | 5/2003 | MacKay et al. | |
| 2003/0148445 | A1 | 8/2003 | Shu | |
| 2003/0166546 | A1 | 9/2003 | Aggarwal | |
| 2003/0175208 | A1 | 9/2003 | Yu et al. | |
| 2003/0194743 | A1 | 10/2003 | Beltzer et al. | |
| 2003/0223996 | A1 | 12/2003 | Ruben et al. | |
| 2004/0175801 | A1 | 9/2004 | Yu et al. | |
| 2004/0175802 | A1 | 9/2004 | Yu et al. | |
| 2005/0070694 | A1 | 3/2005 | Gelfanova et al. | |
| 2005/0100548 | A1 | 5/2005 | Browning et al. | |
| 2005/0163775 | A1 | 7/2005 | Chan et al. | |
| 2005/0169924 | A1 | 8/2005 | Browning et al. | |
| 2005/0175611 | A1 | 8/2005 | Mahler et al. | |
| 2005/0186637 | A1 | 8/2005 | Yu et al. | |
| 2005/0214543 | A1 | 9/2005 | Koumura et al. | |
| 2005/0244411 | A1 | 11/2005 | MacKay et al. | |
| 2005/0255532 | A1 | 11/2005 | Ruben et al. | |
| 2006/0062789 | A1 | 3/2006 | Ruben et al. | |
| 2006/0079457 | A1 | 4/2006 | Browning et al. | |
| 2006/0084608 | A1 | 4/2006 | Beltzer et al. | |
| 2006/0171919 | A1 * | 8/2006 | Rosenblum et al. | 424/85.1 |
| 2006/0193859 | A1 | 8/2006 | Yu et al. | |
| 2006/0198784 | A1 | 9/2006 | Yu et al. | |
| 2007/0086979 | A1 | 4/2007 | Chevrier et al. | |
| 2007/0212733 | A1 | 9/2007 | Martin | |
| 2007/0293434 | A9 | 12/2007 | Beltzer et al. | |
| 2008/0254030 | A1 | 10/2008 | Mackay et al. | |
| 2008/0260737 | A1 | 10/2008 | Ponce et al. | |
| 2008/0267965 | A1 | 10/2008 | Kalled et al. | |
| 2009/0068201 | A1 | 3/2009 | Yu et al. | |
| 2009/0081213 | A1 | 3/2009 | Chevrier et al. | |
| 2009/0081231 | A1 | 3/2009 | Chevrier et al. | |
| 2009/0098129 | A1 | 4/2009 | Farrow et al. | |
| 2009/0104189 | A1 | 4/2009 | Yu et al. | |
| 2009/0110676 | A1 | 4/2009 | Mackay et al. | |
| 2009/0148462 | A1 | 6/2009 | Chevrier et al. | |
| 2009/0169565 | A1 | 7/2009 | Yu et al. | |
| 2009/0215071 | A1 | 8/2009 | Cachero et al. | |
| 2009/0221008 | A1 | 9/2009 | Yu et al. | |
| 2010/0003259 | A1 | 1/2010 | Ruben et al. | |
| 2010/0040627 | A1 | 2/2010 | Browning et al. | |
| 2010/0111953 | A1 | 5/2010 | Ruben et al. | |
| 2010/0144058 | A1 | 6/2010 | Beltzer et al. | |
| 2010/0196360 | A9 | 8/2010 | Yu et al. | |
| 2010/0261194 | A1 | 10/2010 | Yu et al. | |
| 2010/0261207 | A9 | 10/2010 | Yu et al. | |
| 2010/0330073 | A1 | 12/2010 | Yu et al. | |
| 2011/0014190 | A1 | 1/2011 | Migone et al. | |

FOREIGN PATENT DOCUMENTS

| | | | |
|---|---|---|---|
| EP | 0 439 095 | A2 | 7/1991 |
| EP | 98302526 | | 4/1998 |
| EP | 869180 | A1 | 7/1998 |
| EP | 98309632 | | 11/1998 |
| EP | 921194 | A2 | 6/1999 |
| EP | 0 577 752 | B1 | 7/2000 |
| EP | 1 157 110 | A1 | 11/2001 |
| EP | 1 294 769 | A2 | 3/2003 |
| EP | 1 294 949 | A2 | 3/2003 |
| EP | 1 309 718 | A2 | 5/2003 |
| EP | 1 146 892 | B1 | 8/2003 |
| EP | 1 141 274 | B1 | 9/2003 |
| EP | 1 354 598 | A3 | 10/2003 |
| EP | 1 415 659 | A1 | 5/2004 |
| EP | 1 456 347 | A2 | 9/2004 |
| EP | 1 507 793 | A1 | 2/2005 |
| EP | 1 577 391 | A1 | 9/2005 |
| EP | 0 910 635 | B1 | 8/2007 |
| EP | 1 860 190 | A2 | 11/2007 |
| GB | 9828628.9 | A1 | 2/1999 |
| WO | WO 93/21232 | A1 | 10/1993 |
| WO | WO-94/20540 | | 9/1994 |
| WO | WO-95/07297 | | 3/1995 |
| WO | WO 95/20398 | A1 | 8/1995 |
| WO | WO 95/24414 | A1 | 9/1995 |
| WO | WO 95/24466 | A1 | 9/1995 |
| WO | WO 95/31468 | A1 | 11/1995 |
| WO | WO 96/14328 | A1 | 5/1996 |
| WO | WO 96/34095 | A1 | 10/1996 |
| WO | WO-97/33902 | A1 | 9/1997 |
| WO | WO 97/34911 | A1 | 9/1997 |
| WO | WO 97/46251 | A1 | 12/1997 |
| WO | WO-97/49726 | | 12/1997 |
| WO | WO 98/07880 | A1 | 2/1998 |
| WO | WO-98/18921 | A1 | 5/1998 |
| WO | WO-98/27114 | A2 | 6/1998 |
| WO | WO 98/39361 | A1 | 9/1998 |
| WO | WO 98/50547 | A2 | 11/1998 |
| WO | WO-98/55620 | A1 | 12/1998 |
| WO | WO-98/55621 | A1 | 12/1998 |
| WO | WO-98/55623 | A1 | 12/1998 |
| WO | WO 99/01049 | A2 | 3/1999 |
| WO | WO-99/11791 | A1 | 3/1999 |
| WO | WO-99/12964 | A2 | 3/1999 |
| WO | WO-99/33980 | A2 | 7/1999 |
| WO | WO 99/35170 | A2 | 7/1999 |
| WO | WO 99/46295 | A1 | 9/1999 |
| WO | WO 99/47538 | A1 | 9/1999 |
| WO | WO 99/60127 | A2 | 11/1999 |
| WO | WO-00/26244 | A2 | 5/2000 |
| WO | WO-00/39295 | A1 | 7/2000 |
| WO | WO 00/40716 | A2 | 7/2000 |
| WO | WO-00/40716 | A2 | 7/2000 |
| WO | WO-00/43032 | A2 | 7/2000 |
| WO | WO-00/45836 | A1 | 8/2000 |
| WO | WO-00/47740 | A2 | 8/2000 |
| WO | WO-00/50597 | A2 | 8/2000 |
| WO | WO 00/58362 | A1 | 10/2000 |
| WO | WO-00/60079 | A2 | 10/2000 |
| WO | WO-00/67034 | A1 | 11/2000 |
| WO | WO-00/68378 | A1 | 11/2000 |
| WO | WO-00/77256 | A1 | 12/2000 |
| WO | WO 01/12812 | A2 | 2/2001 |
| WO | WO 01/24811 | A1 | 4/2001 |
| WO | WO 01/40466 | A2 | 6/2001 |
| WO | WO-01/40466 | A2 | 6/2001 |
| WO | WO 01/60397 | A1 | 8/2001 |
| WO | WO 01/81417 | A2 | 11/2001 |
| WO | WO-01/87977 | A2 | 11/2001 |
| WO | WO 02/02641 | A1 | 1/2002 |
| WO | WO 02/16411 | A2 | 2/2002 |
| WO | WO-02/18620 | | 3/2002 |
| WO | WO 02/24909 | A2 | 3/2002 |
| WO | WO 02/38766 | A2 | 5/2002 |
| WO | WO 02/066516 | A3 | 8/2002 |
| WO | WO 02/092620 | A2 | 11/2002 |
| WO | WO 02/094852 | A2 | 11/2002 |
| WO | WO 03/016468 | A2 | 2/2003 |
| WO | WO 03/030833 | A2 | 4/2003 |
| WO | WO 03/033658 | A2 | 4/2003 |
| WO | WO 03/055979 | A2 | 7/2003 |
| WO | WO 03/089569 | A2 | 10/2003 |
| WO | WO 2004/058309 | A1 | 7/2004 |
| WO | WO 2004/074511 | A1 | 9/2004 |
| WO | WO 2005/005462 | A3 | 1/2005 |
| WO | WO 2005/042009 | A1 | 5/2005 |
| WO | WO 2007/123765 | A2 | 11/2007 |
| WO | WO 2007/142667 | A2 | 12/2007 |
| WO | WO 2009/132058 | A2 | 10/2009 |
| WO | WO 2010/093993 | A2 | 8/2010 |

OTHER PUBLICATIONS

Farrah et al., GenBank Accession No. AF186114, Jan. 13, 2000.
Ferguson et al., Human Molecular Genetics 6:1589-1594 (1997).
Fujiwara et al.., GenBank Accession No. D79690, Feb. 9, 1996.
Hillier et al., GenBank Accession No. AA166695, Nov. 9, 1997.
Hillier et al., GenBank Accession No. AA682496, Dec. 19, 1997.
Hillier et al., GenBank Accession No. R16882, Apr. 14, 1995.
Hillier et al., GenBank Accession No. R16934, Apr. 14, 1995.
Hillier et al., GenBank Accession No. T87299, Mar. 17, 1995.
Marra et al., GenBank Accession No. AA422749, Oct. 16, 1997.
Marra et al., GenBank Accession No. AI182472, Oct. 8, 1998.
Myers., GenBank Accession No. G30081, Oct. 5, 1996.
NCI-CGAP., GenBank Accession No. AA906714, Jun. 9, 1998.
Zhang et al., GenBank Accession No. AF134715, Mar. 28, 2000.
Genbank Accession No. Q9Y275, Oct. 16, 2001.
Genbank report for Accession No. CAA25649 Jul. 12, 1993.
Genbank report for P01374, Jan. 23, 2007.
Baumgarth,Nicole, "Secreted IgM versus BIyS in germinal center formation," *Nature Immunol.*, (2000) 1:179.
Cyster, Jason G., "B cells on the Front Line," *Nature Immunol.*, (2000) 1:9-10.
Do et al., "Attenuation of Apoptosis Underlies B Lymphocyte Stimulator Enhancement of Humoral Immune Response," *J. Exp. Med.*, (2000) 192:953-964.
Gross et al., "TACI and BCMA are receptors for a TNF homologue implicated in B-cell autoimmune disease," *Nature*, (2000) 404:995-999.
Hatzoglou et al., "TNF Receptor Family Member BCMA (B Cell Maturation) Associates with TNF Receptor-Associated Factor (TRAF) 1, TRAF2, TRAF3 and Activates NF-κB, Elk-1, c-Jun N-Terminal Kinase, and p38 Mitogen-Activated Protein Kinase," *J. Immunol.*, (2000) 165:1322-1330.
Hu et al., "Characterization of TNFRSF19, a novel member of the tumor necrosis factor receptor superfamily," *Genomics*, 62:103-107 (1999).
Kanakaraj et al., "BlyS Binds to B Cells With High Affinity and Induces Activation of the Transcription Factors NF-κB and Elf-1," *Cytokine*, (2001) 13:25-31.
Khare et al., "Severe B Cell Hyperplasia and autoimmune disease in TALL-1 transgenic mice," *PNAS*, (2000) 97:3370-3375.
Laabi et al., "Lymphocyte Survival—Ignorance is BlyS," *Science Magazine*, (2001) 289:883.
Mackay et al., "Mice Transgenic for BAFF Develop Lymphocytic Disorders Along with Autoimmune Manifestations," *J. Exp. Med.*, (1999) 190:1697-1710.
Marsters, et al., "Interaction of the TNF homologues BlyS and APRIL with the TNF receptor homologues BCMA and TACI," *Current Biology*, (2000) 10:785-788.
Moore et al., "BlyS: Member of the Tumor Necrosis Factor Family and B Lymphocyte Stimulator," *Science*, (1999) 285:260-263.
Nardelli et al., "Synthesis and release of B-lymphocyte stimulator from myeloid cells, *Immunobiology*," (2001) 97:198-204.
Parry et al., "Pharmacokinetics and Immunological Effects of Exogenously administered Recombinant Human B Lymphocyte Stimulator (BlyS) in Mice," *J. Pharmacol. Exp. Therap.*, (2001) 296:396-404.
Schneider et al., "BAFF, a Novel Ligand of the Tumor Necrosis Factor Family, Stimulates B Cell Growth," *J. Exp. Med.*, (1999) 189:1747-1756.
Shu et al., "TALL-1 is a novel member of the TNF Family that is Down-regulated by Mitogens," *J. Leukoc. Biol.*, 65:680-683 (1999).

Thompson et al., "BAFF Binds to the Tumor Necrosis Factor Receptor-like Molecule B Cell Maturation Antigen and is Important for Maintaining the Peripheral B Cell Population," *J. Exp. Med.*, (2000) 192:129-135.

Wu et al., "Tumor Necrosis Factor (TNF) Receptor Superfamily Member TACI is a High Affinity Receiptor for TNF Family Members APRIL and BlyS," *J. Biol. Chem.*, (2000) 275:34578-34585.

Xia et al., "TACI is a TRAF-interacting Receptor for TALL-1, a Tumor Necrosis Factor Family Member Involved in B Cell Regulation," *J. Exp. Med.*, (2000) 192:137-143.

Yan et al., "Identification of a receptor for BlyS demonstrates a crucial role in humoral immunity," *Nature Immunol.*, (2000) 1:37-41.

Yu et al., "APRIL and TALL-1 and receptors BCMA and TACI: system for regulating humoral immunity," Nature Immunol., (2000) 1:252-256.

Zhang et al., "Cutting Edge: A Role for B Lymphocyte Stimulator in Systemic Lupus Erythematosus," J. Immunol., (2001) 166:6-10.

Nardelli et al., "B Lymphocyte Stimulator (BLyS): A Therapeutic Trichotomy for the treatment of B lymphocyte diseases," Leukemia and Lymphoma, (2002) 43:1367-73.

Heppeler et al., "Receptor Targeting for Tumor Localisation and Therapy with Radiopeptides," Curr. Med. Chem., 9(7):971-994 (Dec. 2000).

Karpusas et al., "Crystal Structure of Extracellular Human BAFF, a TNF Family Member that Stimulates B Lymphocytes," J. Molec. Biol., 315(5)1145-1154 (Feb. 1, 2002).

Liu et al., "Crystal Structure of sTALL-1 Reveals a Virus-like Assembly of TNF Family Ligands," Cell, 108(3):383-394 (Feb. 8, 2002).

Oren et al., "Structural basis of BLyS receptor recognition," Nature Struct. Biol., 9(4):288-292 (Apr. 2002).

Denardo et al., "Comparison of 1,4,7,10-Tetraazacyclododecane-N,N',N",N'''-tetraacetic acid (DOTA)-Peptide-ChL6, a Novel Immunoconjugate with Catabolizable Linker, to 2 Iminothiolane-2-'p-(Bromoacetamido)benzyl]-DOTA-ChL6 in Breast Cancer Xenografts," Clinical Cancer Res., 4(10):2483-2490 (Oct. 1998).

Ashkenazi, A et al., Response, Nature Immunology, (2000) 1:179.

Baker et al. Blys—an essential survival factor for B cells: basic biology, links to pathology and therapeutic target. Autoimmun Rev. 3(5):368-375, 2004.

Baker et al., "Generation and Characterization of LymphoStat-B, a Human Monoclonal Antibody that Antagonizes the Bioactivities of B Lymphocyte Stimulator," *Arthritis & Rheumatism*, 48(11):3253-3265 (2003).

Ballow et al., Immunopharmacology: immunomodulation and immunotherapy. JAMA. 1997; 278(22):2008-17.

Batten et al., BAFF Mediates Survival of Periperal Immature B Lymphocytes. *The Journal of Experimental Medicine*, (2000) 192:1453-65.

Cheema et al., Elevated Serum B Lymphocyte Stimulator Levels in Patients with Systemic Immune-Based Rheumatic Diseases, *Arthritis and Rheumatism* (2001) 44:1313-1319.

Chen et al., "Expression vectors for affinity purification and radiolabeling of proteins using *Eschericha coli* as host," *Gene*, 139:73-75 (1994).

Dorner and Putterman B cells, BAFF/zTNF4, TACI, and SLE Arthritis Research (2001) 3:197-9.

Furie et al., "Safety, Pharmacokinetic and Pharmacodynamic Results of a Phase 1 Single and Double Dose-Escalation Study of LymphoStat-B (Human Monoclonal Antibody to BLyS) in SLE Patients." 67th Annual American College of Rheumatology Scientific Meeting, Oct. 23-28, 2003, Orlando, FL.

Groom et al., Association of BAFF/BLyS overexpression and altered B cells differentiation with Sjogren's Syndrome. J Clin. Invest. (2002) 109:59-68.

Huard et al; T cell costimulation by the TNF Ligand BAFF The Journal of Iimunology (2001) 167:6225-6231.

Human Genome Sciences, Inc.'s Reply filed in the European Patent Office on Nov. 4, 2005 in conjunction with its Opposition of EP Patent No. 1141274 and supporting documents D41-D43.

Jiang,Y., et al., Polymorphism and chromosomal mapping of the mouse gene for B-cell activating factor belonging to the tumor necrosis factor family (Baff) and association with the autoimmune phenotype Immunogenetics 53 (9), 810-813 (2001).

Kayagaki, N. et al., BAFF/BLyS receptor 3 binds the B cell survival factor BAFF ligand through a discrete surface loop and promotes processing of NF-kappaB2. Immunity (2002) 10:515-24.

Kehrl et al., Effect of tumor necrosis factor alpha on mitogen-activated human B cells. J Exp. Med 1987: 166:786-791.

Liu et al., Ligand Receptor Binding revealed by the TNF family member Tall-1 Nature 421:49-56. (May 2003).

Lotz et al., The nerve growth factor/tumor necrosis factor receptor family., J Leukoc Biol 1996 60:1-7.

Marriette et al., A Role for B Lymphocyte Stimulator (TALL-1, BAFF, THANK, zTNF4) in Sjögren's Syndrome. 65th Annual American College of Rheumatology Scientific Meeting. Nov. 2001.

Mukhopadhay et al., Identification and Characterization of a Novel Cytokine, THANK, A TNF Homolgue That Activates Apoptosis, Nuclear Factor-KB, and c-Jun NH2 Terminal Kinase (1999) The Journal of Biological Chemistry 274:15978-81.

Schiemann,B., et al., An essential role for BAFF in the normal development of B cells through a BCMA-independent pathway. Science 293 (5537), 2111-2114 (2001).

Serono International SA's Reply filed in the European Patent Office on Aug. 24, 2005 in conjunction with its Opposition of EP Patent No. 1146892.

Siegel and Lenardo "To B or not to B: TNF family signally in lymphocytes" Nature Immunology (2001)2:577-8.

Stohl et. al. Blysfulness does not equal blissfulness in systemic lupus erythematosus: a therapeutic role for BLyS antagonists. Curr Dir Autoimmun. 8:289-304, 2005.

Supplementary European Search Report, European Application No. 02 78 6413, mailed Dec. 20, 2005.

Thompson et.al., BAFF-R, a newly identified TNF receptor that specifically interacts with BAFF. Science 293 (5537), 2108-2111 (2001).

Tribouley et.al., Characterization of a New member of the TNF Family Expressed on Antigen Presenting Cells, (1999) Biological Chemistry 380:1443-7.

Vaux et al., The Buzz about BAFF. J Clin. Invest. (2002) 109:17-18.

Ware. April and BAFF connect autoimmunity and cancer The journal of Exp. Med. (2000) 192:f35-f37.

Declaration of Dr. Fritz Metchers dated Dec. 1, 2006 in support of Browning et al. in Patent Interference No. 105,485.

Declaration of Dr. Mark S. Schlissel dated Dec. 1, 2006 in support of Browning et al. in Patent Interference No. 105,485.

Second Declaration of Dr. Mark S. Schlissel dated Feb. 8, 2007 in support of Browning et al. in Patent Interference No. 105,485.

Declaration of Dr. Randolph J. Noelle dated Feb. 12, 2007 in support of Yu et al. in Patent Interference No. 105,485.

Biogens' Observations in preparation for oral proceedings in defense of the Opposition of EP Patent No. 1146892 lodged by Merck Serono, S.A., and Human Genome Sciences, Inc. The Observations in preparation for oral proceedings was filed in the European Patent Office on Jan. 19, 2007.

Declaration of Dr. Georg Friedrich Melchers dated Jan. 19, 2007 filed in support of EP Patent No. 1146892 in the Opposition to EP Patent No. 1146892 lodged by Merck Serono, S.A., and Human Genome Sciences, Inc.

HGS Backgrounder, "B Lymphocyte Stimulator" dated Oct. 30, 2000.

HGS Press Release, "Human Genome Sciences Reports Results of Phase 1 Clinical Trial of Lymphostat-B™ in Patients with Systemic Lupus Erythematosus" dated Oct. 28, 2003.

HGS Press Release "Human Genome Sciences Data Support Potential of Lymphostat-B as Treatment for Autoimmune Diseases", dated Nov. 14, 2001.

HGS Press Release "Human Genome Sciences and Cambridge Antibody Technology Commit to Exclusive Development of Anti-BLyS Antibodies", dated Oct. 30, 2000.

HGS Press Release "Human Genome Sciences Receives Orphan Drug Designation for BLyS Therapeutic Protein for Treatment of Common Variable Immunodeficiency", dated Feb. 27, 2001.

HGS Press Release "Human Genome Sciences Initiates Trial of a New Drug for Systemic Lupus Erythematosus and Other Autoimmune Diseases", dated Nov. 1, 2001.

HGS Press Release "High Levels of BLyS Implicated in Lupus and Rheumatoid Arthritis Patients", dated Oct. 30, 2000.
HGS Press Release "Human Genome Sciences Announces the Discovery of a Novel immune Stimulant", dated Jul. 8, 1999.
HGS Press Release "Human Genome Sciences Initiates Phase 2 Clinical Trial of Lymphostat-B™ for the Treatment of Rheumatoid Arthritis", dated Jan. 8, 2004.
HGS Press Release "Results of Phase 1 Clinical Trial Demonstrate that Lymphostat-B™ is Safe and Biologically Active in Patients with Systemic Lupus Erythematosus", dated Apr. 21, 2003.
HGS Press Release "Human Genome Sciences and Dow Agree to Develop HGS' Radiolabeled B-Lymphocyte Stimulator", dated Oct. 30, 2000.
HGS Press Release "Human Genome Sciences Initiates Phase 2 Clinical Trial of Lymphostat-B™ for the Treatment of Systemic Lupus Erythematosus", dated Sep. 25, 2003.
HGS Press Release "Human Genome Sciences Completes Patient Enrollment in a Phase 2 Clinical Trial of Lymphostat-B™ for the Treatment of Rheumatoid Arthritis", dated Jul. 29, 2004.
HGS Press Release "Human Genome Sciences Presents Data at American Society of Hematology Meeting", dated Dec. 9, 2001.
HGS Press Release "Human Genome Sciences Reports Results of a Phase 2 Clinical Trial of Lymphostat-B™ in Patients with Rheumatoid Arthritis", dated Apr. 6, 2005.
HGS Press Release "Human Genome Sciences Completes Patient Enrollment in a Phase 2 Clinical Trial of Lymphostat-B™ for the Treatment of Systemic Lupus Erythematosus", dated Jul. 29, 2004.
HGS Press Release "Human Genome Sciences Announces Selection of Lymphostat-B™ for Participation in FDA's Continuous Marketing Application Pilot 2 Program", dated Mar. 4, 2004.
HGS Press Release "Human Genome Sciences Reports Progress in Clinical Trials of Five Drugs at JP Morgan H&Q Conference", dated Jan. 6, 2003.
HGS Press Release "Human Genome Sciences Reports Results of a Phase 2 Clinical Trial of Lymphostat-B™ in Patients with Systemic Lupus Erythematosus", dated Oct. 5, 2005.
HGS Press Release "Human Genome Sciences Provides Update of Company Progress", dated Apr. 30, 2002.
HGS Press Release "Human Genome Sciences Provides Update of Company Progress", dated May 12, 2003.
HGS Press Release "Human Genome Sciences Reports Third Quarter 2003 Financial Results", dated Oct. 28, 2003.
HGS Backgrounder "Immunoglobulin-A Deficiency", dated Sep. 2001.
HGS Press Release "Human Genome Sciences Updates Progress of Clinical Programs at Bio 2003", dated Jun. 25, 2003.
HGS Press Release "Human Genome Sciences Describes Activity of New cancer Drug at American Society of Clinical Oncology Meeting", dated May 20, 2002.
HGS Press Release "Human Genome Sciences Reports Financial Results for Full Year and Fourth Quarter 2001", dated Feb. 14, 2002.
HGS Press Release "Human Genome Sciences Reports on Progress Toward Commercialization and Announces 2006 Goals at JPMorgan Healthcare Conference", dated Jan. 10, 2006.
HGS Press Release "Human Genome Sciences Reports Financial Results for Full Year and Fourth Quarter 2002", dated Feb. 14, 2003.
HGS Backgrounder "Systemic Lupus Erythematosus", dated Nov. 1, 2000.
HGS Press Release "Human Genome Sciences Announces Full Presentaiton of Results of Phase 2 Clinical Trial of Lymphostat-B™ in Systemic Lupus Erythematosus", dated Jun. 22, 2006.
HGS Press Release "Human Genome Sciences Reports Interim Results of Phase 1 Clinical Trials of Lymphorad™[131] at 45th Annual Meeting of the American Society of Hematology", dated Dec. 9, 2003.
HGS Press Release "Human Genome Sciences Announces Clearance of Investigational New Drug Application for Lymphorad[131], A New Anticancer Drug for the Treatment of B-Cell Tumors ", dated May 14, 2002.
HGS Press Release "Human Genome Sciences Reports 1999 Financial Results", dated Feb. 10, 2000.
HGS Press Release "Human Genome Sciences Reports Financial Results for Fourth Quarter and Full Year 2000", dated Feb. 15, 2001.
HGS Press Release "Human Genome Sciences Reports Financial Results for First Quarter of 2003", dated Apr. 24, 2003.
HGS Press Release "Human Genome Sciences Files Investigational New Drug Application for Lymphorad[131]", dated Jan. 23, 2002.
HGS Press Release "Human Genome Sciences Updates Progress of Six Drugs in Clinical Trials at JPMorgan Conference", dated Jan. 12, 2004.
HGS Press Release "Human Genome Sciences and Cambridge Antibody Technology Commit to Exclusive Development of Antibody to Trail Receptor-2", dated May 20, 2002.
HGS Press Release "Human Genome Sciences Announces Advance in Hodgkin's Lymphoma", dated Jul. 14, 1999.
HGS Press Release "Human Genome Sciences Reports on Progress of Clinical Trials and Announces Goals for 2005 at JPMorgan Healthcare Conference", dated Jan. 10, 2005.
HGS Press Release "Human Genome Sciences Reports Financial Results for Fourth Quarter and Full Year 2003", dated Feb. 10, 2004.
HGS Press Release "GlaxoSmithKline Exercises Option to Lymphostat-B™", dated Jul. 7, 2005.
HGS Press Release "Human Genome Sciences Completes Construction of Antibody Manufacturing Facility", dated Feb. 21, 2001.
HGS Press Release "Human Genome Sciences Reports First Quarter Financial Results", dated Apr. 27, 2000.
HGS Press Release "Human Genome Sciences Announces Second Quarter 2002 Financial Results", dated Jul. 25, 2002.
HGS Press Release "Human Genome Sciences Breaks Ground for a Large Scale Manufacturing Plant", dated Oct. 17, 2001.
HGS Press Release "New Anti-Angiogenic Proteins Discovered", dated Aug. 5, 1999.
The European Patent Office, "Minutes of the oral Proceedings before the Opposition Division," for Biogen Inc. EP Patent 1146892, Apr. 2, 2007.
Declaration of Dr. Carl F. Ware dated and filed on Apr. 16, 2007.
Third Declaration of Dr. Mark S. Schlissel dated Apr. 15, 2007, filed Apr. 16.
Declaration of Dr. Raif S. Geha dated and filed on Apr. 16, 2007.
Nimmanapalli et al., "The growth factor fusion construct containing B-lymphocyte stimulator (BLyS) and the toxin rGel induces apoptosis specifically in BAFF-R-positive CLL cells", Blood 2007 109(6):2557-2564.
Lyu et al., "The rGel/BLyS fusion toxin specifically targets malignant B cells expressing the BLyS receptors BAFF-R, TACI, and BCMA", Mol. Cancer Ther. 2007 6(2):460-470.
Better et al., "*T Cell-targeted Immunofusion Proteins from Escherichia coli*", The Journal of Biological Chemistry, vol. 270, No. 25, Jun. 23, pp. 14951-14957, 1995.
U.S. Appl. No. 60/132,892, filed May 1, 2000, Shu.
U.S. Appl. No. 60/201,012, filed May 1, 2000, Shu.
U.S. Appl. No. 60/204,039, filed May 12, 2000, Theill.
U.S. Appl. No. 60/214,591, filed Jun. 27, 2000, Theill.
U.S. Appl. No. 60/312,808, filed Aug. 16, 2001, Gelfanova.
Biogen IDEC's opposition of EP Patent No. 1 141 274 B1. Filed in the European Patent Office on Jun. 10, 2004.
Biogen Inc. and Apoxis SA's Response (including Annexes A and B and the Main Request containing a substitute set of claims) to Human Genome Sciences and Serono's Oppositions of EP Patent No. 1146892. The Response was filed in the European Patent Office on Mar. 14, 2005.
Biogen's Observations in preparation for oral proceedings in defense of the Opposition of EP Patent No. 1146892 lodged by Merck Serono, S.A., and Human Genome Sciences, Inc. The Observations in preparation for oral proceedings was filed in the European Patent Office on Jan. 19, 2007.
Clustal V Alignment of human and mouse TACI (provided by Opponent I).
Corixa Corporation's opposition of EP Patent No. 1 141 274 B1. Filed in the European Patent Office on Jun. 6, 2004.
Declaration of Dr. Rodger G. Smith dated and filed on Dec. 14, 2004.
Second Declaration of Dr. Rodger G. Smith dated and filed on Aug. 4, 2005.
Declaration of Patent Interference No. 105,485 between U.S. Appl. No. 09/589,288 and U.S. Patent No. 6,869,605.

Eli Lilly and Company's opposition of EP Patent No. 0 939 804 including supporting documents D1-D16. Filed in the European Patent Office on May 17, 2006.
Eli Lilly and Company's Request for Revocation (Claim # HC06C02687) against European Patent (UK) No. 0 039 804 including supporting documents. Filed in the High Court of Justice, Chancery Division, Patents Court on Jul. 5, 2006.
European Search Report, European Application No. EP 05 01 2261, mailed Aug. 8, 2005.
Further experimental evidence concerning anti-TACI antibodies of EP 1 141 274 B1 Patent Example 18 (Zymogenetics' unpublished data).
Supplementary European Search Report, European Application No. EP 02 78 6413, mailed Dec. 20, 2005.
Supplementary Partial European Search Report, European Application No. EP 00 90 8739, mailed Jun. 30, 2005.
Genbank Accession No. P01374 Jul. 1, 1989.
Genbank Accession No. CAA25649 (Jul. 12, 1993).
Genbank Accession No. Q9Y275 (Feb. 21, 2001).
Genentech's opposition of EP Patent No. 1 141 274 B1. Filed in the European Patent Office on Jun. 10, 2004.
HGS Press Release "Human Genome Sciences Reports Results of a Phase 2 Clinical Trial of Lymphostat-B™ in Patients with Systemic Lupus Erythematosus" dated Oct. 5, 2005.
Human Genome Science's opposition of EP Patent No. 1 141 274 B1. Filed in the European Patent Office on Jun. 7, 2004.
Human Genome Sciences' opposition of EP Patent No. 1 146 892 B1 including Annex A. Filed in the European Patent Office on Sep. 19, 2005.
Human Genome Science Inc.'s Reply filed in the European Patent Office on Sep. 19, 2005 in conjunction with its Opposition of EP Patent No. 1 146 892.
Human Genome Sciences, Inc.'s Reply filed in the European Patent Office on Nov. 4, 2005 in conjunction with its Opposition of EP Patent No. 1 141 274 and supporting documents D41-D43.
Lexikon der Medizin "Hypertension."
Preliminary Non-Binding Decision of the Opposition Division and Summons to attend Oral Proceedings issued by the European Patent Office on Oct. 2, 2006 in the matter of Human Genome Sciences' and Serono's Opposition of EP 1 146 892.
Serono International SA's opposition of EP Patent No. 1 146 892 B1 with Annexes I and II. Filed in the European Patent Office on Aug. 24, 2005.
Serono International SA's opposition of EP Patent No. 0 939 804 including supporting documents D1-D17. Filed in the European Patent Office on May 17, 2006.
Serono International SA's Reply filed in the European Patent Office on Aug. 24, 2005 in conjunction with its Opposition of EP Patent No. 1 146 892.
Sequence alignment of "Prosite" sequence (D1) and SEQ ID No: 10 of EP 1 141 274.
Table setting out SEQ ID Nos. (provided by Opponent I).
Minutes of the Oral Proceedings before the Opposition Division, issued by the European Patent Office on Apr. 2, 2007 in the matter of Human Genome Sciences' and Serono's Opposition of EP 1 146 892.
Zymogenetics' Observation in Reply (158 pages) to Opposition of EP Patent No. 1441274 lodged by Clorixa Corporation, Human Genome Sciences, Inc., Genentech, Inc., and Biogen Idec., Inc. The Observations in Reply was filed in the European Patent Office on Jun. 7, 2005.
ZymoGenetics' opposition of EP Patent No. 0 939 804 including copies of supporting documents D1-D27. Filed in the European Patent Office on May 17, 2006.
Abbas et al., *Cellular and Molecular Immunology*, W.B. Saunders Company: Philadelphia, pp. 362 and 365 (1991).
Alberts, ed., *Molecular Biology of the Cell*, Second Edition, Garland Publishing, Inc., New York, pp. 117-118. (1989).
Arnett, Arthritis *Rheum*., "The American Rheumatism Association 1987 revised criteria for the classification of rheumatoid arthritis," 31(3):315-24 (1988).
Batten et al., "The role of BAFF in Autoimmunity: Is it just a B cell story?" The Midwinter Conference of Immunologists at Asilomar, Pacific Grove, CA (Jan. 22-25, 2005).
Bodmer et al., *Trends in Biochemical Sciences*, "The molecular architecture of the TNF superfamily," 27:19-26. (2002).
Brazelton, *Current Opinion in Immunology*, "Molecular mechanism of action of new xenobiotic immunosuppressive drugs: tacrolimus (FK506), sirolimus (rapamycin), mycophenolate mofetil and lefunomide," 8:710-720 (1996).
Caliceti et al., Bioconjug. Chem., "Biopharmaceutical Properties of Uricase Conjugated to Neutral and Amphiphilic Polymers," 10:638-646 (1999).
Chang, Blood, "A role for BLyS in this activation of innate immune cells," 108(8):2687-94 (2006).
Ciruelo et al., *Arthritis and Rheumatism*, "Cumulative rate of relapse of lupus nephritis after successful treatment with cyclophosphamide," 39:2028-2034 (1996).
Cull et al., *Proc. Natl. Acad. Sci. USA*, "Screening for receptor ligands using large libraries of peptides limited to the C terminus of the las represser," 89:1865-1869 (1992).
Cull, *Protocols in Molecular Biology*, Appendix 2.A.2.5, Supp. 35, John Wiley & Sons (1989).
Cwirla et al., *Proc. Natl. Acad. Sci. USA*, "Peptides on phage: A vast library of peptides for identifying ligands," 87:6378-6382 (1990).
Davidson and Diamond, *New England Journal of Medicine*, "Autoimmune Diseases," 345:340-350 (2001).
Delves and Roitt, *Encyclopedia of Immunology 2nd ed*. Academic Press Inc., pp. 1554-1559. (1998).
Devlin, *Science*, "Random Peptide Libraries: A Source of Specific Protein Binding Molecules," 249:404-406 (1990).
Egner, *J. Clin. Pathol*. "The use of laboratory tests in the diagnosis of SLE," 53(6):424-32 (2000).
Elgert, *Immunology: Understanding the Immune System*, Wiley-Liss: New York, pp. 24, 305 and 324-326 (1996).
Goldblum, *Clinical and Experimental Rheumatology*, "Therapy of rheumatoid arthritis with mycophenolate mofetil," Supp. 8:S117-119 (1993).
Gras et al., *International Immunology*, "BCMAp: an integral membrane protein in the Golgi apparatus of human mature B lymphocytes," 7:1093-1106. (1995).
Gross et al., *Nature*, "TACI and BCMA are receptors for a TNF homologue implicated in B-cell autoimmune disease," 404:995-999 (2000).
Felici, *J. Mol. Biol*., "Selection of Antibody Ligands from a Large Library of Oligopeptides Expressed on a Multivalent Exposition Vector," 222: 301-310 (1991).
Fell et al., *J. Immunol*., "Genetic Construction and Characterization of a Fusion Protein Consisting of a Chimeric F(ab') With Specificity for Carcinomas and Human IL-2," 146:2446-2452 (1991).
Fodor, *Nature*, "Multiplexed biochemical assays with biological chips," 364:555-556 (1993).
Gillies et al., *Proc. Natl. Acad. Sci. USA*, "Antibody-targeted interleukin 2 stimulates T-cell killing of autologous tumor cells," 89:1428-1432 (1992).
Golub and Green, eds., *Immunology A Synthesis*, Sinaver Assoc., Inc., p. 134 (1991).
Gruss, *Blood*, "Tumor necrosis factor ligand superfamily; Involvement in the pathology of malignant lymphomas," 85(12):3378-404 (1995).
Gruss, *Int. Jour. Clin. Lab. Res*., "Regulation of murine B cell growth and differentiation by CD30 ligand," 26:143-159 (1996).
Hahne et al., *J. Exp. Med*., "APRIL, a New Ligand of the Tumor Necrosis Factor Family, Stimulates Tumor Cell Growth," 188(6): 1185-90 (1998).
Hammarstrom et al., *Clin. Exp. Immunol*. "Selective IgA deficiency (StgAD) and common variable immunodeficiency (CVID)," 120(2):225-31 (2000).
Harlow and Lane eds., *Antibodies: A Laboratory Manual*, Cold Spring Harbor Press, pp. 15 and 567-569 (1988).
He, *J. Immunol*., "Lymphoma B cells evade apoptosis through the TNF family members BAFF/BLyS and APRIL," 172(5):3268-79 (2004).
Houghten, *Bio/Techniques*, "The Use of Synthetic Peptide Combinatorial Libraries for the Identification of Bioactive Peptides," 13: 412-421 (1992).

Huard et al., *International Immunology*, "BAFF production by antigen-presenting cells provides T cell co-stimulation," 16:467-475 (2004).
Hymowitz et al., *J. Biol. Chem.*, "Structures of APRIL-receptor complexes: like BCMA, TACI employs only a single cysteine-rich domain for high affinity ligand binding," 280:7218-27 (2005), with Tables S1-S4 and Fig. S1 as published in the online version of this article available at http://www.jbc.org.
Iglesias et al., *Allergol Immunopathol Review*, "Common Variable Immunodeficiency," 29:113-118 (2001).
Janeway and Travers, *Immunobiology: The Immune System in Health and Disease*, Current Biology Ltd./Garland Publishing, London. pp. 12:1-12:19. (1997).
Janeway and Travers. *Immunobiology, The Immune System in Health and Disease*, (Current Biology Ltd./Garland Publishing, London), 1:15, 1:16, 5:28 and 11:19 (1994).
Kabat et al., *Sequences of Proteins of Immunological Interest*, Fourth Edition, pp. 44, 53-54, 63, 69-70 and 76 (1987).
Kennell, *Prog. Nucleic Acid Res. Mol. Biol.*, "Principles and practices of nucleic acid hybridization," 11:259-301 (1971).
Kern, *Blood*, "Involvement of BAFF and APRIL in the resistance to apoptosis of B.CLL through an autocrine pathway," 103(2):679-88 (2004).
Koller and Smithies, *Proc. Natl. Acad. Sci. USA*, "Inactivating the $(3_2$-microglobulin locus in mouse embryonic stem cells by homologous recombination," 86: 8932-8935 (1989).
Koo et al., *FEMS Microbiology Letters*, "Cloning of a novel crystal protein gene crylK from *Bacillus* thuringiensis subsp. Morrisoni," 134:159-164 (1995).
Kreitman, *Expert Opn. Biol. Ther.*, "Recombinant Immunotoxins for the Treatment of Hematological Malignancies," 4(7):1115-1128 (2004).
Krumbholz et al., *J. Exp. Med.*, "BAFF is produced by astrocytes and up-regulated in multiple sclerosis lesions and primary central nervous system lymphoma," 201(2):195-200 (2005 ).
Kwon et al., *J. Biol. Chem.*, "Identification of a Novel Activation-inducible Protein of the Tumor Necrosis Factor Receptor Superfamily and Its Ligand," 274(10): 6056-61 (1999).
Laabi et al., *The EMBO Journal*, A new gene, BCM, on chromosome 16 is fused to the interleukin 2 gene by a t(4;16)(q26;p13) translocation in a malignant T cell.
Laabi et al., *Science Magazine*, "Lymphocyte Survival—Ignorane is BlyS," 289:883 (2001).
Lam, *Nature*, "A new type of synthetic peptide library for identifying ligand-binding activity," 354: 82-84 (1991).
Lyu, *Mol. Cancer Ther.* "The rGel/BLyS fusion toxin specifically targets malignant B cells expressing the BlyS receptors BAFF-R, TACI, and BCMA," 6(2):460-70 (2007).
Mackay, *Curr. Dir. Autoimmun.*, "The BAFF/APRIL system: an important player in systemic theumatic diseases," 8:243-65 (2005).
Mackay, *Semin. Immunol.* "The role of the BAFF/APRIL system on T cell function," Oct;18(5):284-9 (2006).
Madry et al., *International Immunology*, "The characterization of murine BCMA gene defines it as a new member of the tumor necrosis factor receptor superfamily," 10:1693-1702 (1998).
Malvar et al., *Genetics*, "The CCR4 Protein from *Saccharomyces cervisiae* Contains a Leucine-Rich Repeat Region Which is Required for its Control of *ADH2* Gene Expression," 132:951-962 (1992).
Mariette et al., *Annual Rheumatology Discussion*, "The Level of BLyS (BAFF) Correlates With the Titre of Autoantibodies in Human Sjogren's Syndrome,".
Mauri et al., *Immunity*, "LIGHT, a New member of the TNF Superfamily, and Lymphotoxin a Are Ligands for Herpesvirus Entry Mediator," 8(1): 21-30 (1998).
McGhee, *BMC Pediatr.*, "Clinical utility of antinuclear antibody tests in children," 4:13 (2004).
Melchers, *Ann. Rheum. Dis.*, "Actions of BAFF in B cell maturation and its effects on the development of autoimmune disease," 62 Supp 2:ii25-7 (2003).
Moore, *Clin. Chem.*, "Genetically engineered antibodies," 35(9):1849-53 (1989).
Moreaux, *Blood*, "BAFF and APRIL protect myeloma cells from apoptosis induced by interleukin 6 deprivation and dexamethasone," 103(8):3148-57 (2004).
Morpurgo et al., *Appl. Biochem. Biotechnol.*, "Covalent Modification of Mushroom Tyrosinase with Different Amphiphic Polymers for Pharmaceutical and Biocatalysis Applications," 56:59-72 (1996).
Nakamura et al., *Immunol. Lett.*, "Mechanisms of cellular cytotoxicity mediated by a recombinant antibody-IL2 fusion protein against human melanoma cells," 39: 91-99 (1994).
Nedwin et al., *J. Immunol.*, "Effect of Interleukin 2. Interferon-y, and Mitogens on the Production of Tumor Necrosis Factors α and β," 135(4): 2492-7 (1985).
Ng et al., *Journal of Immunology*, "B Cell-Activating Factor Belonging to the TNF Family (BAFF)-R is the Principal BAFF Receptor Facilitating BAFF Costimulation of Circulating T and B Cells," 173:807-817 (2004).
Novak, *Blood*, "Aberrant expression of B-lymphocyte stimulator by B chronic lymphocytic leukemia cells: a mechanism for survival," 100:2973-9 (2002).
Novak et al., *Blood*, "Expression of BLyS and its receptors in B-cell non-Hodgkin lymphoma: correlation with disease activity and patient outcome," 104(8):2247-53 (2004).
Otten, *Proc. Natl. Acad. Sci. U.S.A.*, "Nerve growth factor induces growth and differentiation of human B lymphocytes," 86:10059-63 (1989).
Panayi, G.S., *British Journal of Rheumatology*, "The Pathogenesis of Rheumatoid Arthritis: From Molecules to the Whole Patient," 32:533-536 (1993).
Patel et al., *The Journal of Biological Chemistry*, "Engineering an APRIL-specific B cell maturation antigen," 279:16727-16735 (2003).
Reed et al., *Seminars in Oncology*, "Modulating Apoptosis Pathways in Low Grade B-Cell Malignancies Using Biological Response Modifiers," 29:10-24. (2002).
Roth, *Cell Death Differ.*, "APRIL, a new member of the tumor necrosis family, modulates death ligand-induced apoptosis," 8:403-410 (2001).
Saxon et al., *Immunology*, "Long-term administration of 13-cis retinoic acid in common variable immunodeficiency; circulating interleukin-6 levels, B-cell surface molecule display, and in vitro and in vivo B-cell antibody production," 80(3):477-87 (1993).
Schaller et al., *Microbiology*, "Characterization of apxIVA, a new RTX determinant of Actinobacillus pleuropneumoniae," 145 (pt 8):2105-16 (1999).
Schiemann et al., *Science*, "An essential role for BAFF in the normal development of B cells through a BCMA-independent pathway," 293 (5537), 2111-2114 (2001).
Scott and Smith, *Science*, "Searching for Peptide Ligands with an Epitope Library," 249: 386-390(1990).
Shanebeck, *Eur. J. Immunol.*, "Regulation of murine B-cell growth and differentiation by CD30 ligand," 25(8):2147-53 (1995).
Smith et al., *Principles of Biochemestry: General Aspects*, McGraw-Hill Book Company: New York, pp. 194-195 (1983).
Stites and Ten, eds., *Basic and Clinical Immunology* (1991) Chap. 24, pp. 322-334.
Suda et al., *Cell*, "Molecular Cloning and Expression of the Fas Ligand, a Novel Member of the Tumor Necrosis Factor Family," 75(6): 1 169-78 (1993).
Tesoriero, *Wall Street Journal*, "Drugs in testing show promise for treating lupus," (Jan. 23, 2007).
Thompson et al., *Science*, "BAFF-R, a newly identified TNF receptor that specifically interacts with BAFF," 293 (5537), 2108-2111 (2001).
Tsokos, G.C., *Current Opinion in Rheumatology*, "Lymphocytes, cytokines, inflammation, and immune trafficking," 7:376-383 (1995).
Yan et al., *Nature Immunology*, "Identification of a receptor for BLyS demonstrates a crucial role in humoral immunity," 1(1):37-41, (2000).
Vandenberghe et al., *Biochemistry*, "The Primary Structures of the Low-Redox Potential Diheme Cytochromes c from the Phtotrophich Bacteria *Rhodobacter sphaeroides* and *Rhodobacter adriaticus* Reveal a New Structural Family of c-Type Cytochromes," vol. 37:pp. 13075-13081.
Von Bulow and Bram, *Science*, "NF-AT Activation Induced by a CAML-Interacting Member of the Tumor Necrosis Factor Receptor Superfamily," 278: 138-141 (1997).
Vorbjev et al., *Nucleosides & Nucleotides*, "Oligonucleotide Conjugated to Linear and Branched High Molecular Weight Polyethylene Glycol as Substrates," 18:2745-2750(1999).
Waldmann, T.A., *Nature Medicine*, "Immunotherapy: Past, Present and Future," 9:269-277 (2003).
Weinblatt et al., *Arthritis and Rheumatism*, "Methotrexate in rheumatoid arthritis: A five-year prospective multicenter study," 37:1492-1498 (1994).
Wiley et al., *Immunity*, "Identification and Characterization of a New Member of the TNF Family that Induces Apoptosis," 3(6): 673-82 (1995).
Winter et al., *Nature*, "Man-made antibodies,".349:293-299 (1991).
Wise et al., *The Journal of Rheumatology*, "Methotrexate in nonrenal lupus and undifferentiated connective tissue disease—a review of 36 patients," 23:1005-1010 (1996).
Ye, *Eur. J. Immunol.*, "BAFF binding to T cell-expressed BAFF-R costimulates T cell proliferation and alloresponses," 34(10):2750-9 (2004).
Zhou et al., *Blood*, "Therapeutic Potential of Antagonizing BLyS for Chronic Lymphocytic Leukemia," 98(11):808A (2001).
Cerrutti et al, *Immunology and Cell Biology*, "Plasmacytoid dendritic cells and the regulation of immunoglobulin heavy chain class switching," 83: 554-562 (2005).
Cragg et al.,*B Cell Trophic Factors and B Cell Antagonism in Autoimmune Disease* "The Biology of CD20 and its Potential as a Target for mAb Therapy," pp. 140-174 (2005).
Davies, *Nature Genetics*, "The EST express gathers speed," 364:554 (1993).
He et al., *J. Immunol.*, "HIV-1 Envelope Triggers Polyclonal Ig Class Switch Recombination through a CD40-Independent Mechanism Involving BAFF and C-Type Lectin Receptors," 176:3931-3941 (2006).
Hwang et al., *J. Mol. Cell Cardiol.*, "Single Pass Sequencing of a Unidirectional Human Fetal Heart cDNA Library to Discover Novel Genes of the Cardiovascular System," 26:1329-1333 (1994).
Kapas and Krueger, *Amer. J. Physiology*, "Tumor necrosis factor-β induces sleep, fever, and anorexia," 263(3):703-707 (1992).
Kessel et al., *Clinical and Experimental Immunology*, "Increased susceptibility of cord blood B lymphocytes to undergo spontaneous apoptosis," 145:563-570 (2006).
Scapini et al., *J. Exp Med.* "G-CSF-stimulated Neutrophils Are a Prominent Source of Functional BLyS," 197(3): 297-302 (2003).
Shoop et al., *Proceedings of the Twenty-Seventh Annual Hawaii International Conference on System Sciences*, "Automating and Streamlining Inference of Function of Plant ESTs within a Data Analysis System" Extended Abstract (1994).
Sutherland et al., *Pharmacology and Therapeutics*, "Targeting BAFF: Immunomodulation for autoimmune diseases and lymphomas," 112:774-786 (2006).
Swindell et al. Internet for the Molecular Biologist, Horizon Scientific Press: Portland, pp. 55-149 (1996).
Tai et al., *Cancer Res*, "Role of B-Cell-Activating Factor in the Adhesion and Growth of Human Multiple Myeloma Cells in the Bone Marrow Microenvironment," 66(13): 6675-6682 (2006).
Williams-Blangero et al., *PNAS*, "Genes on chromosomes 1 and 13 have significant effects on Ascaris infection," 99(8): 5533-5538 (2002).
Zganiacz et al., *J. Clin. Invest.* "TNF-α is a critical negative regulator of type 1 immune activation during intracellular bacterial infection," 113(3):401-413 (2004).
Ware, *Cytokine & Growth Factor Reviews*, "The TNF Superfamily," 14:181-184 (2003).
Waldschmidt et al., *Science*, "Long live the Mature B Cell—a BAFFling Mystery Resolved," 293:2012-2013 (2001).
Couzin, *Science*, "Magnificent Obsession," 307:1712-1715 (2005).
Fishman et al., *Nature*, "A new grammar for drug discovery," 437:491-493 (2005).
Haberman, *Genetic Engineering News*, "Strategies to Move Beyond Target Validation," 25(21): pp. 36 (2005).
Tuma, *J. Natl. Cancer Inst.*, "Phase I Antibody Risks, Trial Safety Examined," 98(14):956-958 (2006).
"Guideline on Production and Quality Control of Monoclonal Antibodies and Related Substances", issued by European Medicines Agency on Apr. 5, 2007.
CAT News Release "Cambridge Antibody Technology and Human Genome Sciences Form Alliance in Therapeutic Antibodies" dated Aug. 10, 1999.
CAT News Release "CAT and Human Genome Sciences ("HGSI") Create Major Alliance Dedicated to Developing Human Antibody Therapeutics Against Genomics Targets" dated Mar. 1, 2000.
CAT News Release "Cambridge Antibody Technology Group plc ("CAT") Open Offer & International Offering to Raise £100 Million in a New Share Issue" dated Mar. 7, 2000.
CAT News Release "Cambridge Antibody Technology: Clinical Trials Update" dated Jan. 12, 2004.
CAT News Release "Cambridge Antibody Technology Reports Recent Progress in Licensed Product Candidates" dated Oct. 5, 2005.
HGS Press Release "Cambridge Antibody Technology and Human Genome Sciences Form Alliance in Therapeutic Antibodies" dated Aug. 10, 1999.
HGS Press Release "Human Genome Sciences and Abgenix Enter a Broad Collaboration to Create Fully Human Antibody Therapeutics" dated Dec. 1, 1999.
HGS Press Release "Human Genome Sciences to Initiate Human Clinical Trials of BLyS" dated Jun. 23, 2000.
HGS Press Release "Human Genome Sciences and Medarex Announce Collaboration" dated Jul. 25, 2001.
HGS Press Release "Human Genome Sciences Announces Trial for Treatment of Immunoglobin-A Deficiency" dated Sep. 19, 2001.
Human Genome Sciences Press Release Nov. 1, 2001.
Declaration of Interference 105,485, Paper 1 filed in the United States Patent Office on Aug. 15, 2006.
Order Bd.R 104(c) in Patent Interference 105,485 dated Apr. 19, 2007.
Order Bd.R 104(c) in Patent Interference 105,485 dated Apr. 23, 2007.
Order—Priority times Bd.R. 104(c) in Patent Interference 105,485 dated Apr. 19, 2007.
Decision on Preliminary Motions in Patent Interference 105,485. Filed in the United States Patent Office on Aug. 31, 2007.
Yu Priority Statement in Patent Interference 105,485. Filed in the United States Patent Office on Dec. 1, 2006.
Browning Priority Statement in Patent Interference 105,485. Filed in the United States Patent Office on Dec. 1, 2006.
Browning Amended Priority Statement in Patent Interference 105,485. Filed in the United States Patent Office on Dec. 12, 2006.
Claims involved in Patent Interference 105,485 submitted by Human Genome Sciences . Filed in the United States Patent Office on Aug. 15, 2006.
Browning Notice of Non-filing 135(b) submitted by Biogen, Inc in Patent Interference 105,485. Filed in the United States Patent Office on Nov. 16, 2006.
Browning Observation 1 filed by Biogen, Inc. in Patent Interference 105,485. Filed in the United States Patent Office on Feb. 12, 2007.
Yu reply and Browning Observation on reply in Patent Interference 105,485. Filed in the United States Patent Office on Apr. 16, 2007 and Apr. 30, 2007.
Re-declaration of Interference in Patent Interference 105,485. Filed in the United States Patent Office on Aug. 31, 2007.
Yu Exhibit List submitted by Human Genome Sciences, Inc in Patent Interference 105,485 as of Nov. 28, 2007.
Browning Demonstrative Exhibits submitted by Biogens, Inc. in Patent Interference 105,485.
Browning combined motions submitted by Biogen, Inc. 2 to 10 Patent Interference 105,485.
Browning combined replies submitted by Biogen, Inc Patent Interference 105,485.
Yu Demonstrative Exhibits submitted by Human Genome Sciences, Inc. in Patent Interference 105,485.

Yu combined motions 1 to 6 submitted by Human Genome Sciences, Inc.. in Patent Interference 105,485.
Yu combined oppositions 1 to 7 submitted by Human Genome Sciences, Inc in Patent Interference 105,485.
Declaration of Amy Orr dated Nov. 27, 2007 in support of Yu et al. in Patent Interference 105,485.
Declaration of Biegie Lee dated Nov. 27, 2007 in support of Yu et al. in Patent Interference 105,485.
Declaration of David LaFleur dated Nov. 27, 2007 in support of Yu et al. in Patent Interference 105,485.
Declaration of Ding Liu dated Nov. 27, 2007 in support of Yu et al. in Patent Interference 105,485.
Declaration of Ellie Bouffard dated Nov. 27, 2007 in support of Yu et al. in Patent Interference 105,485.
Marked-up Declaration of Dr. Fritz Melchers dated Jan. 16, 2007 in support of Browning et al. in Patent Interference 105,485.
Declaration of Dr. Guo-Liang Yu dated Nov. 27, 2007 in support of Yu et al. in Patent Interference 105,485.
Declaration of Jeffrey Carrell dated Nov. 27, 2007 in support of Yu et al. in Patent Interference 105,485.
Declaration of Krystyna Pieri dated Nov. 27, 2007 in support of Yu et al. in Patent Interference 105,485.
Declaration of Laurie Brewer dated Nov. 28, 2007 in support of Yu et al. in Patent Interference 105,485.
Marked-up Declaration of Dr. Mark S. Schlissel dated Dec. 1, 2006 in Support of Browning et al. in Patent Interference 105,485.
Declaration of Meghan Birkholz dated Nov. 27, 2007 in support of Yu et al., in Patent Interference 105,485.
Declaration of Michael Fannon dated Nov. 27, 2007 in support of Yu et al. in Patent Interference 105,485.
Declaration of Dr. Ornella Belvedere dated Nov. 27, 2007 in support of Yu et al. in Patent Interference 105,485.
Declaration of Dr. Reinhard Ebner dated Nov. 21, 2007 in support of Yu et al. in Patent Interference 105,485.
Declaration Scott Conklin dated Nov. 26, 2007 in suppport of Yu et al. in Patent Interference 105,485.
Declaration of William Derrick dated Nov. 28, 2007 in support of Yu et al. in Patent Interference 105,485.
Second Declaration of Dr. Randolph J. Noelle dated Nov. 28, 2007 in support of Yu et al. in Patent Interference 105,485.
Declaration of Dr. David Hilbert dated Nov. 27, 2007 in support of Yu et al. in Patent Interference 105,485.
Declaration of Dr. Paul Moore dated Nov. 26, 2007 in support of Yu et al. in Patent Interference 105,485.
Transcript of Deposition of Dr. Paul Moore in Patent Interference 105,485 dated Jan. 4, 2008.
Transcript of Deposition of Dr. David Hilbert in Patent Interference 105,485 dated Jan. 5, 2008.
Transcript of Deposition of Jeffrey Carrell in Patent Interference 105,485 dated Feb. 12, 2008.
Transcript of Deposition of Krystyna Pieri in Patent Interference 105,485 dated Feb. 12, 2008.
Transcript of Deposition of Dr. Reinhard Ebner in Patent Interference 105,485 dated Feb. 15, 2008.
Transcript of Deposition of Guo-Liang Yu in Patent Interference 105,485 dated Jan. 4, 2008.
Transcript of Deposition of Amy Orr in Patent Interference 105,485 dated Feb. 22, 2008.
Transcript of Deposition of Dr. Randolph Noelle in Patent Interference 105,485 dated Feb. 26, 2008.
Transcript of Deposition of Eleanor Bouffard in Patent Interference 105,485 dated Feb. 28, 2008.
Defendant's Notice of Experiments in Reply submitted by Human Genome Sciences in support of Human Genome Sciences in UK Revocation suit HC06CO2687.
Work up experiments in relation to Defendant' Notice of Experiments in Reply submitted by Human Genome Sciences in Support of Human Genome Sciences in UK Reovcation suit HC06CO2687.
Claimant's notice of experiments submitted by Eli Lilly against Human Genome Sciences in UK Revocation suit HC06CO2687.
Defendant's reponse to claimant's notice of experiments submitted by Human Genome Sciences in suppport of Human Genome Sciences in UK Revocation suit HC06CO2687.
Alignment of BLyS and Eli Lilly's sequences submitted in UK Revocation suit HC06CO2687 dated Nov. 29, 2007.
Technician's précis of notice of the notice of experiments submitted in UK Revocation suit HC06CO2687.
Application Notice submitted by Human Genome Sciences in support of Human Genome Sciences in UK Revocation suit HC06CO2687 dated Nov. 2, 2006.
International Preliminary Exam Report submitted by Human Genome Sciences in support of Human Genome Sciences in UK Revocation suit HC06CO2687 dated Dec. 20, 1998.
Office communication from European Patent Office submitted by Human Genome Sciences in support of Human Genome Sciences in UK Revocation suit HC06CO2687 dated May 3, 2002.
Human Genome Science's response to Office communication from European Patent Office submitted by Human Genome Sciences in support of Human Genome Sciences in UK Revocation suit HC06CO2687 dated May 30, 2002.
Office communication from European Patent Office submitted by Human Genome Sciences in support of Human Genome Sciences in UK Revocation suit HC06CO2687 dated Jan. 17, 2003.
Human Genome Sciences, Inc response to office communication from European Patent Office submitted by Human Genome Sciences in support of Human Genome Sciences in UK Revocation suit HC06CO2687 dated Jan. 17, 2003.
Office Communication European Patent Office submitted by Human Genome Sciences in support of Human Genome Sciences in UK Revocation suit HC06CO2687 dated Jun. 30, 2004.
Transcript of Examiner Interview dated Oct. 1, 2004 submitted by Human Genome Sciences in support of Human Genome Sciences in UK Revocation suit HC06CO2687.
Human Genome Response to Examiner Interview of Oct. 1, 2004 submitted by Human Genome Sciences in support of Human Genome Sciences in UK Revocation suit HC06CO2687 and dated Oct. 4, 2004.
Office Communication European Patent Office submitted by Human Genome Sciences in support of Human Genome Sciences in UK Revocation suit HC06CO2687 dated Oct. 13, 2004.
Human Genome Sciences, Inc response to office communication from European Patent Office submitted by Human Genome Sciences in support of Human Genome Sciences in UK Revocation suit HC06CO2687 dated Nov. 30, 2004.
Human Genome Sciences amended claims and specification submitted by Human Genome Sciences in support of Human Genome Sciences in UK Revocation suit HC06CO2687 dated Nov. 30, 2004.
Notice of Intent to Grant EP patent No. 0 939 845 submitted by Human Genome Sciences in support of Human Genome Sciences in UK Revocation suit HC06CO2687 dated Jan. 28, 2005.
Human Genome Sciences response to Notice of Intent to Grant submitted by Human Genome Sciences in support of Human Genome Sciences in UK Revocation suit HC06CO2687 dated Jun. 7, 2005.
Transcript of hearing Nov. 8, 2006 in UK Revocation suit HC06CO2687.
Transcript of hearing Nov. 9, 2006 in UK Revocation suit HC06C02687.
Defendant's civil evidence act notice submitted by Human Genome Sciences in support of Human Genome Sciences in UK Revocation suit HC06CO2687 dated Jun. 1, 2007.
Defendant's civil evidence act notice submitted by Human Genome Sciences in support of Human Genome Sciences in UK Revocation suit HC06CO2687 dated Nov. 29, 2007.
Claimant's civil evidence act notice submitted by Eli Lilly in support of Human Genome Sciences in UK Revocation suit HC06CO2687 dated Jun. 1, 2007.
Defendant's civil evidence act notice submitted by Human Genome Sciences in support of Human Genome Sciences in UK Revocation suit HC06CO2687 dated Dec. 7, 2007.
Claimant's Further Information concerning the statement of opposition submitted by Eli Lilly in UK Revocation suit HC06CO2687 dated May 4, 2007.
Claimant's statement of case relating to SWISS-PROT submitted by Eli Lilly in UK Revocation suit HC06CO2687 dated Nov. 30, 2006.

Defendant's conditional application to further amend claim 15 submitted by Human Genome Sciences in UK Revocation suit HC06CO2687.
Claimant's grounds for opposition to further amend claim 15 submitted in UK Revocation suit HC06CO2687.
Correspondence between Human Genome Sciences and the United Kingdom Patent Office submitted by Eli Lilly in UK Revocation suit HC06CO2687.
Defendant's amended response to claimant's request for further information submitted by Human Genome Sciences in UK Revocation suit HC06CO2687.
Defendant's response to claimant's notice to admit submitted in UK Revocation suit HC06CO2687.
Defendant's response to claimant's second request for further information submitted in UK Revocation suit HC06CO2687.
Documents handed up during trial in UK Revocation suit HC06CO2687.
Claimant's response to defendant's notice of experiments in reply submitted by Eli Lilly in UK Revocation suit HC06CO2687 dated Nov. 30, 2006.
Claims from EP Patent 0 939 804 submitted by Human Genome Sciences in support of Human Genome Sciences in UK Revocation suit HC06CO2687.
Amended claims submitted by Human Genome Sciences in support of Human Genome Sciences in UK Revocation suit HC06CO2687.
Human Genome Science's response to request to attend oral hearings in UK Revocation suit HC06CO2687 dated Jun. 30, 2004.
Human Genome Science's Opening Arguments in UK Revocation suit HC06CO2687.
Human Genome Science's Closing Arguments in UK Revocation suit HC06CO2687.
Eli Lilly's Opening Arguments in UK Revocation suit HC06CO2687.
Eli Lilly's Closing Arguments in UK Revocation suit HC06CO2687.
Order Confirming Claimant's Undertaking Not to Infringe submitted in UK Revocation suit HC06CO2687.
Order for Directions submitted in UK Revocation suit HC06CO2687.
Order of Mr Justice Pumfrey submitted in UK Revocation suit HC06CO2687.
Order of Mr Justice Warren submitted in UK Revocation suit HC06CO2687.
Particulars of the Claim submitted in UK Revocation suit HC06CO2687.
Re-reamended grounds of invalidity submitted by Eli Lilly in UK Revocation suit HC06CO2687.
Statement of Opposition submitted by Eli Lilly in UK Revocation suit HC06CO2687.
Defendant Statement of Reasons to amend the claims of EP Patent No. 0 939 804 submitted by Human Genome Sciences in UK Revocation suit HC06CO2687.
Table of relevant scientific papers submitted in UK Revocation suit HC06CO2687.
Table of selected passages from EP Patent No. 0 939 804 submitted in UK Revocation suit HC06CO2687.
BioTherapeutic Overview submitted in UK Revocation suit HC06CO2687.
Cambridge Antibody Technology website printed Mar. 7, 2007 submitted in UK Revocation suit HC06CO2687.
EFPIA website printed Sep. 12, 2007 submitted in UK Revocation suit HC06CO2687.
Eli Lilly website submitted in UK Revocation suit HC06CO2687.
EMEA 2007 Antibody guidelines submitted in UK Revocation suit HC06CO2687.
Wikipedia page submitted by Eli Lilly in UK Revocation suit HC06CO2687.
Mobitech website submitted in UK Revocation suit HC06CO2687.
First Expert Report of Dr. Rolf Apweiler dated May 29, 2007 in support of Eli Lilly in UK Revocation suit HC06CO2687.
Second Expert Report of Dr. Rolf Apweiler dated Jun. 23, 2007 in support of Eli Lilly in UK Revocation suit HC06CO2687.
Fourth Expert Report of Dr. Rolf Apweiler dated Dec. 11, 2007 in support of Eli Lilly in UK Revocation suit HC06CO2687.
Witness Statement of Dr. David E. Cash dated Nov. 14, 2006 in support of Human Genome Sciences in UK Revocation suit HC06CO2687.
Witness Statement of Christa Pennachio dated Apr. 23, 2007 in support of Human Genome Sciences in UK Revocation suit HC06CO2687.
Witness Statement of Christa Pennachio dated May 15, 2007 in support of Eli Lilly in UK Revocation suit HC06CO2687.
Transcripts of trial days 1 to 13 of UK Revocation suit HC06CO2687.
Witness Statement of Dr. Stuart Farrow dated Jun. 1, 2007 in support of Human Genome Sciences in UK Revocation suit HC06CO2687.
Witness Statement of Dr. William F. Heath dated Jun. 27, 2007 in support of Eli Lilly in UK Revocation suit HC06CO2687.
First Witness Statement of Mark Hodgson dated Nov. 6, 2007 in support of Eli Lilly in UK Revocation suit HC06CO2687.
Second Witness Statement of Mark Hodgson dated Nov. 7, 2007 in support of Eli Lilly in UK Revocation suit HC06CO2687.
First Expert Report of Dr. Andrew C.R. Martin in support of Human Genome Sciences in UK Revocation suit HC06CO2687.
Second Expert Report of Dr. Andrew C.R. Martin in support of Human Genome Sciences in UK Revocation suit HC06CO2687.
First Expert Report of Dr. Randolph Noelle dated Jun. 1, 2007 in support of Human Genome Sciences in UK Revocation suit HC06CO2687.
Second Expert Report of Dr. Randolph Noelle dated Jun. 22, 2007 in support of Human Genome Sciences in UK Revocation suit HC06CO2687.
First Witness Statement of Dr. Penny X. Gilbert dated Nov. 2, 2006 in support of Human Genome Sciences in UK Revocation suit HC06CO2687.
Second Witness Statement of Dr. Penny X. Gilbert dated Nov. 6, 2006 in support of Human Genome Sciences in UK Revocation suit HC06CO2687.
First Expert Report of Dr. Jeremy Saklatvala dated May 25, 2007 in support of Eli Lilly in UK Revocation suit HC06CO2687.
Second Expert Report of Dr. Jeremy Saklatvala dated Jun. 27, 2007 in support of Eli Lilly in UK Revocation suit HC06CO2687.
Third Expert Report of Dr. Jeremy Saklatvala dated Nov. 23, 2007 in support of Eli Lilly in UK Revocation suit HC06CO2687.
Witness Statement of Simon Mark Wright dated Jun. 6, 2007 in support of Human Genome Sciences in UK Revocation suit HC06CO2687.
Witness Statement of Elisabeth Gasteiger dated Jun. 12, 2007 in support of Human Genome Sciences in UK Revocation suit HC06CO2687.
Declaration of Dr. Thi-Sau Migone dated Jul. 12, 2007 in support of Human Genome Sciences in Opposition of EP Patent No. 1141274.
Second Declaration of Carl F. Ware dated Jan. 28, 2008 in support of Browning et al. in Patent Interference 105,485.
Minutes of Oral Proceedings dated Apr. 2, 2007 in Opposition of Biogen, Inc. Patent EP 1146892.
Biogen Decision dated Nov. 27, 2007 in Opposition of Patent EP 1146892.
Zymogenetics Interlocutory Decision dated Nov. 30, 2007 in Opposition of Patent EP 1141274.
Zymogenetics Preliminary Opinion dated Mar. 15, 2007 in Opposition of Patent EP 1141274.
Extended European Search Report, European Application No. 07 01 2741.0 dated Feb. 8, 2008.
Grounds of Appeal filed by Merck Serono dated Mar. 27, 2008 in Opposition of Patent EP 1 146 892.
Human Genome Sciences Observations on Oppositions to EP 0939804 dated Apr. 2, 2008.
Auxiliary Requests 1-12 submitted by Human Genome Sciences, Inc. in defense of EP Patent No. 0 939 804. Dated May 8, 2008.
Eli Lilly's Submission in Opposition of EP Patent No. 0 939 804 including supporting documents D48-D57. Filed in the European Patent Office on Apr. 2, 2008.
Eli Lilly's Submission in Opposition of EP Patent No. 0 939 804 including supporting documents D98-D112. Filed in the European Patent Office on May 30, 2008.

Serono's Opposition of EP Patent No. 0 939 804 including supporting documents D1-D27. Filed in the European Patent Office on May 18, 2006.
Human Genome Science's Observations on the Oppositions against EP Patent No. 0 939 804 including annexes. Filed in the European Patent Office on Apr. 2, 2008.
Declaration of Dr. Andrew Martin and annexes filed in support of Human Genome Science's EP Patent No. 0 939 804 dated Mar. 26, 2008 and filed in the European Patent Office.
Declaration of Dr. David Cash and annexes filed in support of Human Genome Science's EP Patent No. 0 939 804 dated Mar. 6, 2008 and filed in the European Patent Office.
Declaration of Dr. Randolph Noelle and annexes filed in support of Human Genome Science's EP Patent No. 0 939 804 dated Mar. 23, 2008 and filed in the European Patent Office.
Declaration of Dr. Stuart Farrow and annexes filed in support of Human Genome Science's EP Patent No. 0 939 804 dated Mar. 25, 2008 and filed in the European Patent Office.
Witness statement of Christa Pange Pennacchio and annexes filed in support of Human Genome Science's EP Patent No. 0 939 804 dated Mar. 25, 2008 and filed in the European Patent Office.
List of documents, dated May 29,2008 relied upon in Opposition proceedings against Human Genome Science's EP Patent No. 0 939 804.
Human Genome Science's opposition to Biogen, Inc EP Patent No. 1 146 892 with annexes C15-C25. Filed in the European Patent Office on May 10, 2004.
Serono's opposition to Biogen, Inc EP Patent No. 1 146 892. Filed in the European Patent Office on May 21, 2004.
ZymoGenetics'response to the Oppositions against ZymoGenetics EP Patent No. 1 141 274 filed in the European Patent Office on Jun. 6, 2005.
Human Genome Science's reply to ZymoGenetics'response to the Oppositions against ZymoGenetics EP Patent No. 1 141 274 filed in the European Patent Office on Nov. 4, 2005.
Opposition Division's Preliminary Opinion and annex in the Opposition Proceedings against against ZymoGenetics EP Patent No. 1 141 274 filed in the European Patent Office on Mar. 15, 2007.
Second Declaration of Dr. Andrew Martin filed by Human Genome Sciences in support of HGS EP Patent No. 0 939 804. Filed in the European Patent Office and dated May 7, 2008.
Declaration of Dr. Penny X. Gilbert filed by Human Genome Sciences in support of HGS EP Patent No. 0 939 804. Filed in the European Patent Office and dated May 8, 2008.
Human Genome Sciences Press Release dated Dec. 1, 1999.
Transcript of Deposition of Dr. Randolph Noelle in Patent Interference 105,485 dated Apr. 5, 2007.
Declaration of Henrik Olsen in support of Yu et al. in Patent Interference 105,485 dated Dec. 16, 2007.
Browning opposition and table of content in Patent Interference 105,485. Filed in the United States Patent Office on Feb. 12, 2007.
Yu Exhibit 1200 submitted during the Deposition of Eleanor Bouffard in Patent Interference 105,485 dated Feb. 28, 2008.
Yu Exhibit 1201 submitted during the Deposition of Eleanor Bouffard in Patent Interference 105,485 dated Feb. 28, 2008.
Transcript of a Teleconference in Patent Interference 105,485 dated Feb. 11, 2008.
Claim Form submitted by Eli Lilly and Company requesting revocation of Human Genome Sciences, Inc EP Patent 0 939 804. Filed in the United Kingdom Patent Office on Jul. 5, 2006.
Human Genome Sciences, Inc Defense of EP Patent 0 939 804 filed in the United Kingdom Patent Office on Aug. 3, 2006.
Human Genome Sciences, Inc Patent in suit as proposed to be amended during UK Revocation suit HC06CO2687.
Application to Amend Claims filed by Human Genome Sciences, Inc during UK Revocation suit HC06CO2687 on Feb. 22, 2007.
Agreed Statement of Facts regarding the IMAGE EST submitted in UK Revocation suit HC06CO2687.
*Arthritis Rheum.*, "The American College of Rheumatology Response Criteria for Systemic Lupus Erythematosus Clinical Trials," 50(11):3418-3426 (2004).
Cohen (Fundamental Immunology, Paul ed. Lippincott-Raven Philadelphia, PA, 1999, chapter 33, pp. 1067-1088.
International Search Report issued in PCT Application No. PCT/US06/38756, dated Jul. 14,2008.
Looney, *Rheumatology*, "B cells as a therapeutic target in autoimmune diseases other than rheumatoid arthritis," 44 (Suppl. 2): ii13-ii17 (2005).
Schwartz et al in "Fundamental Immunology", Paul ed Raven Press, NY. NY. 1989, p. 837.
Sevach (Fundamental Immunology, Paul ed, Lippincott-Raven Philadelphia, PA, 1999, chapter 34, pp. 1089-1125.
U.S. Appl. No. 09/226,533, Gross et al.
U.S. Appl. No. 09/589,288, Yu et al.
U.S. Appl. No. 60/119,906, Boyle et al.
U.S. Appl. No. 60/122,388, Yu et al.
U.S. Appl. No. 60/149,378, MacKay et al.
U.S. Appl. No. 60/157,933, Schneider et al.
U.S. Appl. No. 60/166,271, Boyle et al.
U.S. Appl. No. 60/543,261, Yu et al.
U.S. Appl. No. 60/580,387, Yu et al.
U.S. Appl. No. 60/617,191, Yu et al.
U.S. Appl. No. 60/649,478, Rosenblum et al.
WPI/DERWENT Accession No. 2000-572093, Aug. 31, 2000.
Acosta-Rodriguez et al., *Eur. J. Immunol.*, 37:990-1000 (2007).
Badr et al., *Blood*, 111(5):2744-2754 (2008).
Bernstein et al., *Cancer Res.*, 50:1017s-1021s (1990).
Binard et al., *Journal of Autoimmunity*, 30:63-67 (2008).
Bosello et al., *Int. J. lmmunopathol. Pharmacol.*, 20(1):1-8 (2007).
Buhlmann et al., *J. Clinical Immunology*, 16(2) (1996).
Cancro, *Immunological Reviews*, 202:237-249 (2004).
Carswell et al., *Proc. Natl. Acad. Sci. U.S.A.*, 72(9):3666-3670 (1975).
Chatham et al., "Belimumab (Fully Human Monoclonal Antibody to BLyS) Improved or Stailized Systemic Lupus Erythematosus (SLE) Disease Activity Over 3 Years of Treatment," Poster presented at ACT/ACHP Annual Scientific Meeting, Oct. 24-29, 2008 (San Francisco, CA).
Czuczman et al., *J. Clin. Oncology*, 11(10):2021 (1993).
Daniel et al., *Virology*, "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity is Drastically Influenced by the Nature of the Protein Carrier," 202:540-549 (1994).
Denardo et al., *Cancer Res.*, 50:1014s (1990).
Eck et al., *J Biol. Chem.*, 264(29):17595-17605 (1989).
Falini et al., *Blood*, 85:1-14 (1995).
Freimuth, "Lessons learned from the Phase 2 belimumab SLE study: development of an SLE responder index," Jun. 1, 2009.
Fu et al., *Blood*, 107(11):4540-4548 (2006).
Furie et al., *Arthritis Res. & Therapy*, "Biologic activity and safety of belimumab, a neutralizing anti-B-lymphocyte stimulator (BLyS) monoclonal antibody: a phase I trial in patients with systemic lupus erythematosus", 10(5):1-15 (2008).
Gross et al., Immunity, "TACI-Ig neutralizes molecules critical for B cell development and autoimmune disease: Impaired B cell maturation in mice lacking BLyS," 15:289-302 (2001).
Han, et al., *J. Immunol.*, 155:556-567 (1995).
Hill et al., *Molec. Aspects Med.*, 17:455-509 (1996).
Jones et al., *Nature*, 388:225-228 (1989).
Juweid et al., *Cancer Res.*, 55:5899s (1995).
Kelsoe et al., *Nature*, 279:333-334 (1979).
Kelsoe et al., *J. Exp. Med.*, 151:289-300 (1980).
Knox et al., *Clin. Cancer Res.*, 2:457 (1996).
Laabi et al., *Nucleic Acids Research*, "The BCMA gene, preferentially expressed during B lymphoid maturation, is bidirectionally transcribed," 22:1147-1154 (1994).
Lederman et al., *Mol. Immunol.*, "A single amino acid substitution in a common African allele of the CD4 molecule ablates binding of the monoclonal antibody, OKT4," 28(11):1171-1181 (1991).
Li et al., *Proc. Natl. Acad. Sci. USA*, "β-Endorphin omission analogs:Dissociation of immunoreactivity from other biological activities," 77(6):3211-3214 (1980).
Morens et al., *J. Gen. Virol.*, 68:91-98 (1987).

Neri et al., *Clin. Cancer Res.*, "Neutralizing B-Cell—Activating Factor Antibody Improves Survival and Inhibits Osteoclastogenesis in a Severe Combined Immunodeficient Human Multiple Myeloma Model," 13(19):5903-5909 (2007).
Novak et al., *Blood*, 103:689-694 (2004).
Peitisch et al., *International Immunology*, 5(2):233-238 (1993).
Press, O.W. "Malignant Lymphomas, Including Hodgkin's Disease: Diagnosis, Management, and Special Problems," Chapter 9 Kluwer Academic Publishers. ed. B. Dana (1993).
Reth et al., *Nature*, 290:257-259 (1981).
Rosen et al., *J. Clin. Oncol.* 5:562 (1987).
Scott et al., *Current Opinion in Immunology*, 9:717-722 (1997).
Schneider, *Current Opinion in Immunology*, 17:282-289 (2005).
Shivakumar et al., *Clin. Lymphoma Myeloma*, "Targeting B-Lymphocyte Stimulator/B-Cell Activating Factor and a Proliferation-Inducing Ligand in Hematologic Malignancies," 7(2):106-108 (2006).
Smith et al., *Cell*, 73:1349-1360 (1993).
Stohl, W., "A therapeutic role for BLyS antagonists," *Lupus*, 13:317-322 (2004).
Waldmann at al., *Ann. Intern. Med.*, 116:148 (1992).
Wallach, "TNF Ligands and TNF/NGF Receptor Families" In Cytokine Reference vol. 1: Ligands, eds. Oppenheim and Feldman, Academic Press, pp. 377-411 (2001).
International Search Report issued in PCT Application No. PCT/US07/08021, dated Aug. 4, 2008.
Grounds of Appeal submitted by Human Genome Sciences, Inc. on Apr. 13, 2009 in Appeal Case T 18/09-3.3.08 in support of EP Patent 0939804.
Declaration of Dr Garnett Herrel Kelsoe III, filed in support of Human Genome Sciences' EP Patent No. 0 939 804 dated Apr. 12, 2009 and filed in the European Patent Office.
Approved Judgment by Mr Justice Kitchin in UK Revocation suit HC06CO2687 dated Jul. 31, 2008.
Quotations evidencing agreement on the closest prior art, the formulation of the technical problem and its solution by the invention. Filed in the European Patent Office as exhibit D116 in support of Human Genome Sciences' EP Patent No. 0 939 804 on Apr. 13, 2009.
Declaration of Dr. Chih-Hung Lo and Exhibits A to L filed in support of Human Genome Science's EP Patent No. 1 294 769 dated Aug. 19, 2008 and filed in the European Patent Office.
Minutes of the Oral Proceedings before the Opposition Division and the Decision Revoking the European Patent, issued by the European Patent Office on Dec. 3, 2008 in the matter of Eli Lilly and Company's Opposition of EP 0 939 804.
Judgment of Kitchin J. in *Eli Lilly and Company* v *Human Genome Sciences, Inc.* [2008] EWHC 1903 ("the English revocation action").
HGS Press Release "Human Genome Sciences Reports Phase 2 Results for LYMPHOSTAT-B (Belimumab) in Patients with Rheumatoid Arthritis," dated Nov. 17, 2005.
HGS Press Release "Human Genome Sciences Announces Positive 76-week Results of Phase 2 Clinical Trial of LYMPHOSTAT-B in Systemic Lupus Erythematosus," dated Nov. 14, 2006.
Human Genome Sciences' Press Release dated May 30, 2007.
Alignment of D41 Shu Figure 1B with D1 Gruss and Dower β-sheets. Filed in the European Patent Office as exhibit D146 in support of Human Genome Sciences' EP Patent No. 0 939 804 on Apr. 13, 2009.
Alignment of D10 Schneider Figure 1B with D1 Gruss and Dower β sheets. Filed in the European Patent Office as exhibit D147 in support of Human Genome Sciences' EP Patent No. 0 939 804 on Apr. 13, 2009.
Partial Transcript of Costs Hearing in the English Revocation Action (UK Revocation suit HC06CO2687) dated Oct. 17, 2008.
Requirement for Restriction/Election issued in U.S. Appl. No. 11/543,024, dated Feb. 28, 2007.
Non-Final Rejection issued in U.S. Appl. No. 11/543,024, dated Jul. 31, 2007.
Final Rejection issued in U.S. Appl. No. 11/543,024, dated Mar. 5, 2008.
Requirement for Restriction/Election issued in U.S. Appl. No. 09/932,613, dated Apr. 8, 2003.
Non-Final Rejection issued in U.S. Appl. No. 09/932,613, dated Jul. 14, 2004.
Final Rejection issued in U.S. Appl. No. 09/932,613, dated Apr. 20, 2005.
Requirement for Restriction/Election issued in U.S. Appl. No. 11/232,439, dated Apr. 24, 2007.
Non-Final Rejection issued in U.S. Appl. No. 11/232,439, dated May 28, 2008.
Final Rejection issued in U.S. Appl. No. 11/232,439, dated May 27, 2009.
Advisory Action issued in U.S. Patent Application No. 11/232,439, dated Aug. 14, 2009.
Non-Final Rejection issued in U.S. Appl. No. 11/232,439, dated Nov. 5, 2009.
Requirement for Restriction/Election issued in U.S. Appl. No. 09/880,748, dated May 7, 2003.
Examiner Interview Summary issued in U.S. Appl. No. 09/880,748, dated Jun. 2, 2003.
Non-Final Rejection issued in U.S. Appl. No. 09/880,748, dated Sep. 14, 2004.
Final Rejection issued in U.S. Appl. No. 09/880,748, dated May 4, 2005.
Advisory Action issued in U.S. Appl. No. 09/880,748, dated Sep. 28, 2005.
Requirement for Restriction/Election issued in U.S. Appl. No. 10/293,418, dated Mar. 6, 2006.
Non-Final Rejection issued in U.S. Appl. No. 10/293,418, dated Jun. 30, 2006.
Requirement for Restriction/Election issued in U.S. Appl. No. 11/054,515, dated Feb. 15, 2007.
Requirement for Restriction/Election issued in U.S. Appl. No. 11/054,515, dated Feb. 25, 2008.
Non-Final Rejection issued in U.S. Appl. No. 11/054,515, dated Jul. 3, 2008.
Final Rejection issued in U.S. Appl. No. 11/054,515, dated Feb. 24, 2009.
Requirement for Restriction/Election issued in U.S. Appl. No. 11/266,444, dated Apr. 24, 2007.
Non-Final Rejection issued in U.S. Appl. No. 11/266,444, dated Feb. 28, 2008.
Final Rejection issued in U.S. Appl. No. 11/266,444, dated Dec. 3, 2008.
Advisory Action issued in U.S. Appl. No. 11/266,444, dated Feb. 24, 2009.
Requirement for Restriction/Election issued in U.S. Appl. No. 10/735,865, dated Jul. 12, 2006.
Requirement for Restriction/Election issued in U.S. Appl. No. 10/739,042, dated Jul. 12, 2006.
Requirement for Restriction/Election issued in U.S. Appl. No. 09/589,287, dated Feb. 20, 2001.
Non-Final Rejection issued in U.S. Appl. No. 09/589,287, dated Nov. 6, 2001.
Examiner Interview Summary issued in U.S. Appl. No. 09/589,287, dated Nov. 27, 2001.
Examiner Interview Summary issued in U.S. Appl. No. 09/589,287, dated Dec. 21, 2001.
Notice of Allowance issued in U.S. Appl. No. 09/589,287, dated Dec. 31, 2001.
Requirement for Restriction/Election issued in U.S. Appl. No. 09/588,947, dated Mar. 8, 2001.
Non-Final Rejection issued in U.S. Appl. No. 09/588,947, dated Nov. 26, 2001.
Notice of Allowance issued in U.S. Appl. No. 09/588,947, dated Jul. 15, 2002.
Requirement for Restriction/Election issued in U.S. Appl. No. 09/589,286, dated Dec. 10, 2001.
Non-Final Rejection issued in U.S. Appl. No. 09/589,286, dated Jun. 10, 2002.
Non-Final Rejection issued in U.S. Appl. No. 09/589,286, dated Dec. 4, 2002.
Notice of Allowance issued in U.S. Appl. No. 09/589,286, dated Jun. 3, 2003.
Requirement for Restriction/Election issued in U.S. Appl. No. 09/589,285, dated Feb. 20, 2001.

Non-Final Rejection issued in U.S. Appl. No. 09/589,285, dated Nov. 6, 2001.
Final Rejection issued in U.S. Appl. No. 09/589,285, dated Sep. 6, 2002.
Non-Final Rejection issued in U.S. Appl. No. 09/589,285, dated Oct. 22, 2003.
Notice of Allowance issued in U.S. Appl. No. 09/588,285, dated May 18, 2004.
Requirement for Restriction/Election issued in U.S. Appl. No. 11/377,165, dated Jun. 27, 2008.
Non-Final Rejection issued in U.S. Appl. No. 11/377,165, dated Dec. 3, 2008.
Requirement for Restriction/Election issued in U.S. Appl. No. 11/382,837, dated May 29, 2008.
Non-Final Rejection issued in U.S. Appl. No. 11/382,837, dated Nov. 28, 2008.
Requirement for Restriction/Election issued in U.S. Appl. No. 09/929,493, dated Dec. 16, 2002.
Requirement for Restriction/Election issued in U.S. Appl. No. 10/270,487, dated Jun. 15, 2004.
Non-Final Rejection issued in U.S. Appl. No. 10/270,487, dated Feb. 10, 2005.
Requirement for Restriction/Election issued in U.S. Appl. No. 11/054,539, dated Jan. 9, 2007.
Non-Final Rejection issued in U.S. Appl. No. 11/054,539, dated May 2, 2007.
Final Rejection issued in U.S. Appl. No. 11/054,539, dated Jan. 22, 2008.
Office Communication from EPO in EP Application No. 07109688.7 mailed May 5, 2008 containing Extended European Search Report mailed Sep. 24, 2007.
Response to EP Office Communication in EP Application No. 07109688.7 mailed Nov. 7, 2008.
International Preliminary Report on Patentability issued in PCT/US2007/008021 dated Oct. 9, 2008.
Requirement for Restriction/Election issued in U.S. Appl. No. 09/589,288, dated Feb. 20, 2001.
Non-Final Rejection issued in U.S. Appl. No. 09/589,288, dated Nov. 6, 2001.
Final Rejection issued in U.S. Appl. No. 09/589,288, dated Aug. 13, 2002.
Non-Final Rejection issued in U.S. Appl. No. 09/589,288, dated Jun. 3, 2003.
Final Rejection issued in U.S. Appl. No. 09/589,288, dated Jun. 3, 2004.
Requirement for Restriction/Election issued in U.S. Appl. No. 09/507,968, dated Feb. 14, 2001.
Non-Final Rejection issued in U.S. Appl. No. 09/507,968, dated Nov. 6, 2001.
Examiner Interview Summary issued in U.S. Appl. No. 09/507,968, dated Nov. 27, 2001.
Final Rejection issued in U.S. Appl. No. 09/507,968, dated Jan. 31, 2003.
Advisory Action issued in U.S. Appl. No. 09/507,968, dated Jul. 7, 2003.
Notice of Allowance issued in U.S. Appl. No. 09/507,968, dated Sep. 5, 2003.
Examiner's Amendment issued in U.S. Appl. No. 09/507,968, dated Sep. 22, 2004.
Requirement for Restriction/Election issued in U.S. Appl. No. 09/005,874, dated Nov. 24, 1998.
Non-Final Rejection issued in U.S. Appl. No. 09/005,874, dated Aug. 10, 2000.
Non-Final Rejection issued in U.S. Appl. No. 09/005,874, dated Nov. 22, 2000.
Non-Final Rejection issued in U.S. Appl. No. 09/005,874, dated Jul. 27, 2001.
Non-Final Rejection issued in U.S. Appl. No. 09/005,874, dated Apr. 23, 2002.
Non-Final Rejection issued in U.S. Appl. No. 09/005,874, dated Mar. 27, 2003.
Examiner's Amendment issued in U.S. Appl. No. 09/005,874, dated Nov. 3, 2003.
Notice of Allowance issued in U.S. Appl. No. 09/005,874, dated Nov. 3, 2003.
Requirement for Restriction/Election issued in U.S. Appl. No. 09/255,794, dated Dec. 13, 2000.
Requirement for Restriction/Election issued in U.S. Appl. No. 09/255,794, dated Aug. 27, 2001.
Non-Final Rejection issued in U.S. Appl. No. 09/255,794, dated Feb. 8, 2002.
Examiner Interview Summary issued in U.S. Appl. No. 09/255,794, dated Jul. 2, 2002.
Non-Final Rejection issued in U.S. Appl. No. 09/255,794, dated Oct. 1, 2002.
Notice of Allowance issued in U.S. Appl. No. 09/255,794, dated Aug. 25, 2003.
Letter of Suspension issued in U.S. Appl. No. 09/589,288, dated May 9, 2005.
Examiner Interview Summary issued in U.S. Appl. No. 09/589,288, dated Feb. 15, 2006.
Examiner Interview Summary issued in U.S. Appl. No. 09/589,288, dated Jul. 20, 2006.
Interference Decision issued in U.S. Appl. No. 09/589,288, dated Jul. 17, 2008.
Examiner Interview Summary issued in U.S. Appl. No. 09/589,288, dated Apr. 24, 2009.
Examiner Interview Summary issued in U.S. Appl. No. 09/589,288, dated Jul. 14, 2009.
Notice of Allowance issued in U.S. Appl. No. 09/589,288, dated Jul. 27, 2009.
Corrected Notice of Allowance issued in U.S. Appl. No. 09/589,288, dated Sep. 22, 2009.
Requirement for Restriction/Election issued in U.S. Appl. No. 12/170,333, dated May 28, 2009.
Non-Final Rejection issued in U.S. Appl. No. 12/170,333, dated Sep. 17, 2009.
Requirement for Restriction/Election issued in U.S. Appl. No. 12/210,134, dated Jun. 24, 2009.
Requirement for Restriction/Election issued in U.S. Appl. No. 12/393,693, dated Jun. 25, 2009.
International Preliminary Examination Report issued in PCT Patent Application No. PCT/US06/38756, dated May 29, 2009.
Bendig, *Methods: A Comparison to Methods in Enzymology*, "Humanization of Rodent Monoclonal Antibodies by CDR Grafting," 8:83-93 (1995).
Non-Final Rejection issued in U.S. Appl. No. 12/210,134, dated Nov. 30, 2009.
Cope et al., *Curr. Opin. Immunol.*, "Emerging approaches for the therapy of autoimmune and chronic inflammatory disease," 16: 780-786 {2004).
Requirement for Restriction/Election issued in U.S. Appl. No. 12/552,915, dated Dec. 1, 2009.
Extended European Search Report, European Application No. 06851283.9 dated Nov. 3, 2009.
*American College of Rheumatology*, "The 1982 Revised Criteria for Classification of Systemic Lupus Erythematosus," retrieved Jun. 10, 2009 from URL:http://www.rheumatology.org/publications/classification/SLE/sle.asp.
Aguirre-Cruz et al., *J. Neurooncol.*, "Clinical relevance of non-neuronal auto-antibodies in patients with anti-Hu or anti-Yo paraneoplastic diseases," 71(1):39-41 (2005).
Eriksson et al., *Ann. Rheum. Dis.*, "Autoantibody formation in patients with rheumatoid arthritis treated with anti-TNFalpha," 64(3):403-407 (2005).
Keystone, *Arthritis Res. Ther.*, "B cell targeted therapies," 7(3):S13-S18 (2005).
Myckatyn et al., *J. Rheumatol.*, "Outcome of positive antinuclear antibodies in individuals without connective tissue disease," 30(4):736-739 (2003).
Notification of decision of the Technical Board of Appeals in Appeal Case T 18/09-3.3.08 in EP Patent 0 939 804, dated Dec. 1, 2009.
Notice of Allowance issued in U.S. Appl. No. 11/054,515, dated Dec. 21, 2009.

Nichols et al., *Eur. J. Cancer*, "Interleukin-2 Fusion Protein: An Investigational Therapy for Interleukin-2 Receptor Expressing Malignancies," 33(1):S34-S36 (1997).
Sweeney et al., *Bioconjug. Chem.*, "Interleukin 7 (IL-7) Receptor-Specific Cell Killing by $DAB_{389}$ IL-7: A Novel Agent for the Elimination of IL-7 Receptor Positive Cells," 9:201-207 (1998).
Alcami et al., *J. Immunol.*, "Blockade of Chemokine Activity by a Soluble Chemokine Binding Protein from Vaccinia Virus," 160:624-633 (1998).
Fleming et al., *J. Mol. Recognit.*, "Discovery of High-Affinity Peptide Binders to BLyS by Phage Display," 18:94-102 (2005).
Sun et al., *Biochem. Biophys. Res. Commun.*, "A Novel BLyS Antagonist Peptide Designed Based on the 3-D Complex Struc ture of BCMA and BLyS," 346:1158-1162 (2006).
Requirement for Restriction/Election issued in U.S. Appl. No. 12/135,025, dated Mar. 9, 2010.
Non-Final Rejection issued in U.S. Appl. No. 12/552,915, dated Apr. 8, 2010.
Requirement for Restriction/Election issued in U.S. Appl. No. 12/605,202, dated Apr. 8, 2010.
Requirement for Restriction/Election issued in U.S. Appl. No. 12/701,301, dated May 3, 2010.
Final Rejection issued in U.S. Appl. No. 12/170,333, dated May 28, 2010.
Final Rejection issued in U.S. Appl. No. 12/393,693, dated May 28, 2010.
HGS Press Release, "Human Genome Sciences and GlaxoSmithKline Announce Topline 76-Week Results of Phase 3 Trial of Benlysta™ in Systemic Lupus Erythematosus" (Apr. 20, 2010).
Non-Final Rejection issued in U.S. Appl. No. 12/186,404, dated Jun. 21, 2010.
"Classification Criteria for the Diagnosis of Systemic Lupus Erythematosus," retrieved Jul. 22, 2010 from http://medicalcriteria.com/criteria/sle.htm.
Final Rejection issued in U.S. Appl. No. 12/210,134, dated Jul. 21, 2010.
El-Hallak et al., *J. Pediatr.*, "Clinical Effects and Safety of Rituximab for Treatment of Refractory Pediatric Autoimmune Diseases," 150:376-382 (2007).
Tan et al., *Arthritis Rheum.*, "Range of antinuclear antibodies in "healthy" individuals," 40(9):1601-1611 (1997).
Petri et al., *N. Engl. J. Med.*, "Combined Oral Contraceptives in Women with Systemic Lupus Erythematosus," 353(24):2550-2558 (2005).
Sauge-Merle et al., *Eur. J. Biochem.*, "An active ribonucleotide reductase from *Arabidopsis thaliana*: cloning, expression and characterization of the large subunit," 266:62-69 (1999).
Esposito et al., *J. Immunol.*, "Human transaldolase and cross-reactive viral epitopes identified by autoantibodies of multiple sclerosis patients," 163:4027-4032 (1999).
International Search Report issued in PCT Application No. PCT/US01/25850, dated Apr. 1, 2003.
International Search Report issued in PCT Application No. PCT/US01/25891, dated Apr. 2, 2003.
Requirement for Restriction/Election issued in U.S. Appl. No. 09/932,322, dated Jun. 30, 2004.
Non-Final Rejection issued in U.S. Appl. No. 09/932,322, dated Feb. 9, 2005.
Final Rejection issued in U.S. Appl. No. 09/932,322, dated Aug. 24, 2005.
Notice of Allowance issued in U.S. Appl. No. 09/932,322, dated Feb. 8, 2006.
Han et al., "Characterization of Transformation Function of Cottontail Rabbit Papillomavirus E5 and E8 Genes," *Virology*, 251:253-263 (1998).
Non-Final Rejection issued in U.S. Appl. No. 12/135,025, dated Aug. 4, 2010.
Notice of Allowance issued in U.S. Appl. No. 11/054,515, dated Sep. 9, 2010.
Non-Final Rejection issued in U.S. Appl. No. 12/605,202, dated Sep. 20, 2010.
Berenbaum, "Synergy, additivism and antagonism in immunosuppression," *Clin. Exp. Immunol.*, 28:1-18 (1977).
Dooley et al., "Mycophenolate mofetil therapy in lupus nephritis: clinical observations," *J. Am. Soc. Nephrol*, 10:833-839 (1999).
Jonsson et al., "Mycophenolic acid inhibits inosine 5'-monophosphate dehydrogenase and suppresses immunoglobulin and cytokine production of B cells," *Int. Immunopharmacol.*, 3:31-37 (2003).
Koyama et al., "Raised serum APRIL levels in patients with systemic lupus erythematosus," *Ann. Rheum. Dis.* 64:1065-1067 (2005).
Ramanujam et al., "Mechanism of action of transmembrane activator and calcium modulator ligand interactor-Ig in murine systemic lupus erythematosus," *J.Immunol.* 173:3524-3534 (2004).
Stohl et al., "B lymphocyte stimulator protein-associated increase in circulating autoantibody levels may require $CD4^{+}T$ cells: lessons from HIV-infected patients," *Clin. Immunol.* 104(2)115-122 (2002).
Final Rejection issued in U.S. Appl. No. 12/552,915, dated Sep. 22, 2010.
Notice of Allowance issued in U.S. Appl. No. 12/170,333, dated Oct. 8, 2010.
Extended European Search Report, European Application No. 10156941.6 dated Aug. 16, 2010.
Non-Final Rejection issued in U.S. Appl. No. 12/701,301, dated Oct. 15, 2010.
Requirement for Restriction/Election issued in U.S. Appl. No. 12/610,128, dated Nov. 29, 2010.
Requirement for Restriction/Election issued in U.S. Appl. No. 12/275,804, dated Dec. 2, 2010.
Non-Final Rejection issued in U.S. Appl. No. 11/054,539, dated Dec. 14, 2010.
Notice of Allowance issued in U.S. Appl. No. 12/552,915, dated Dec. 21, 2010.
Requirement for Restriction/Election issued in U.S. Appl. No. 12/870,394, dated Dec. 30, 2010.
Extended European Search Report, European Application No. 10185178.0 dated Dec. 21, 2010.
Extended European Search Report, European Application No. 10185182.2 dated Dec. 23, 2010.
Extended European Search Report, European Application No. 10185185.5 dated Dec. 23, 2010.
Edwards, *J. Mol. Biol.*, "The Remarkable Flexibility of the Human Antibody Repertoire; Isolation of Over One Thousand Different Antibodies to a Single Protein, BLyS," 334(1): 103-118 (2003).
Requirement for Restriction/Election issued in U.S. Appl. No. 12/870,548, dated Feb. 3, 2011.
Requirement for Restriction/Election issued in U.S. Appl. No. 12/295,572, dated Feb. 18, 2011.
Yu Priority Statement filed in Patent Interference 105,652. Filed in the United States Patent Office on Jan. 23, 2009.
Yu Substantive Motion 1 filed in Patent Interference 105,652. Filed in the United States Patent Office on Jan. 23, 2009.
Rosenblum Preliminary Motion 1 filed in Patent Interference 105,652. Filed in the United States Patent Office on Jan. 23, 2009.
Rosenblum Re-filed Preliminary Motion 1 filed in Patent Interference 105,652. Filed in the United States Patent Office on Jan. 23, 2009.
Rosenblum Substantive Motion 2 filed in Patent Interference 105,652. Filed in the United States Patent Office on Jan. 23, 2009.
Yu Responsive Motion 2 filed in Patent Interference 105,652. Filed in the United States Patent Office on Feb. 19, 2009.
Yu Opposition 1 filed in Patent Interference 105,652. Filed in the United States Patent Office on Apr. 1, 2009.
Yu Opposition 2 filed in Patent Interference 105,652. Filed in the United States Patent Office on Apr. 1, 2009.
Rosenblum Opposition 1 filed in Patent Interference 105,652. Filed in the United States Patent Office on Apr. 1, 2009.
Rosenblum Opposition 2 filed in Patent Interference 105,652. Filed in the United States Patent Office on Apr. 1, 2009.
Yu Reply 1 filed in Patent Interference 105,652. Filed in the United States Patent Office on Apr. 24, 2009.
Yu Reply 2 filed in Patent Interference 105,652. Filed in the United States Patent Office on Apr. 24, 2009.

Rosenblum Reply 1 filed in Patent Interference 105,652. Filed in the United States Patent Office on Apr. 24, 2009.
Rosenblum Reply 2 filed in Patent Interference 105,652. Filed in the United States Patent Office on Apr. 24, 2009.
List of Exhibits filed in Patent Interference 105,652, including the corresponding PTO Form-1449 Doc. No. For each exhibit.
Application File for U.S. Appl. No. 60/225,628 filed Aug. 15, 2000 in Patent Interference 105,652 (HGS Exhibit 2001).
Application File for U.S. Appl. No. 09/929,493 filed Aug. 15, 2001 in Patent Interference 105,652 (HGS Exhibit 2002).
Application File for U.S. Appl. No. 60/336,726 filed Dec. 7, 2001 in Patent Interference 105,652 (HGS Exhibit 2003).
Application File for U.S. Appl. No. 10/270,487 filed Oct. 16, 2002 in Patent Interference 105,652 (HGS Exhibit 2004).
Application File for U.S. Appl. No. 60/543,261 filed Feb. 11, 2004 in Patent Interference 105,652 (HGS Exhibit 2005).
Application File for U.S. Appl. No. 60/580,387 filed Jun. 18, 2004 in Patent Interference 105,652 (HGS Exhibit 2006).
Helmkamp et al., "High Specific Activity Iodination of γ-Globulin with Iodine-131 Monochloride," *Cancer Res.*, 20:1495-1500 (1960). Filed May 28, 2009 in Patent Interference 105,652 (HGS Exhibit 2010).
Langone, "Radioiodination by Use of the Bolton-Hunter and Related Reagents" *Methods in Enzymology*, 70:221-247 (1980). Filed in Patent Interference 105,652 (HGS Exhibit 2011).
Office Communication mailed Jun. 23, 2008 in the HGS Involved Application. Filed in Patent Interference 105,652 (HGS Exhibit 2014).
Printouts from RDF Technologies, Inc. webpage. Filed May 28, 2009 in Patent Interference 105,652 (HGS Exhibit 2015).
Executed Declaration and Information Disclosure Statement date-stamped Apr. 12, 2006 from Application File of the RDF Involved Application. Filed in Patent Interference 105,652 (HGS Exhibit 2016).
Riccobene et al., "Rapid and Specific Targeting of 1251-Labeled B Lymphocyte Stimulator to Lymphoid Tissues and B Cell Tumors in Mice," *J. Nuc. Med.*, 44(3):422-433 (Mar. 2003). Filed in Patent Interference 105,652 (HGS Exhibit 2019).
Murray et al., "Variables Influencing Tumor Uptake of Anti-Melanoma Monoclonal Antibodies Radioiodinated Using Para-Iodobenzoyl (PIB) Conjugate," *J. Nucl. Med.*, 32(2) 279-287 (Feb. 1991). Filed in Patent Interference 105,652 (HGS Exhibit 2020).
Lyu et al., "The Growth Factor Toxin Construct rGel/BLyS Specifically Targets Tumor Cells Expressing BAFF-R, TACI, and BCMA," Abstract 1517, Am. Assoc. for Cancer Res. 96th Annual Meeting, Anaheim, CA (Apr. 16-20, 2005). Filed in Patent Interference 105,652 (HGS Exhibit 2022).
Information Disclosure Statement dated Feb. 20, 2007 from file history of the RDF Involved Application. Filed in Patent Interference 105,652 (HGS Exhibit 2023).
Shen et al., "Construction and Expression of a New Fusion Protein, Thymosin α1—cBLyS, in *E. coli*," *Biotech. Lett.*, 27:143-148 (2005). Filed in Patent Interference 105,652 (HGS Exhibit 2024).
Cao et al., "Construction and Characterization of Bi-functional EGFP/sBAFF Fusion Protein," *Biochimie*, 88:629-635 (2006). Filed in Patent Interference 105,652 (HGS Exhibit 2025).
Transcript of Deposition of Michael Rosenblum, dated Feb. 26, 2009. Filed in Patent Interference 105,652 (HGS Exhibit 2026).
Lyu et al., "The immunocytokine scFv23/TNF targeting HER-2/neu induces synergistic cytotoxic effects with 5-fluorouracil in TNF-resistant pancreatic cancer cell lines," *Biochem. Pharmacol.*, 75:836-846 (2008). Filed in Patent Interference 105,652 (HGS Exhibit 2027).
Rosenblum et al., "Design, Expression, Purification, and Characterization, in Vitro and in Vivo, of an Antimelanoma Single-chain Fv Antibody Fused to the Toxin Gelonin," *Cancer Res.*, 63:3995-4002 (2003). Filed in Patent Interference 105,652 (HGS Exhibit 2028).
Kim et al., "Overexpression of biologically active VEGF121 fusion proteins in *Escherichia coli*," *J. Biotechnol.*, 128:638-647 (2007). Filed in Patent Interference 105,652 (HGS Exhibit 2029).
Veenendaal et al., "In vitro and in vivo studies of a VEGF121/rGelonin chimeric fusion toxin targeting the neovasculature of solid tumors," *Proc. Natl. Acad. Sci.*, 99(12):7866-7871 (Jun. 2002). Filed in Patent Interference 105,652 (HGS Exhibit 2030).
Liu et al., "Targeted delivery of human pro-apoptotic enzymes to tumor cells: In vitro studies describing a novel class of recombinant highly cytotoxic agents," *Mol. Cancer Ther.*, 2(12):1341-1350 (2003). Filed in Patent Interference 105,652 (HGS Exhibit 2031).
Lyu et al., "The Growth Factor Toxin Construct rGel/BLyS Specifically Targets Tumor Cells Expressing BAFF-R, TACI, and BCMA," AACR #1517 (poster). Filed in Patent Interference 105,652 (HGS Exhibit 2032) (Apr. 1, 2009).
*Wesley Jessen Corp.* v. *Bausch & Lomb*, Inc., 209 F. Supp. 2d. 348, 398 (D. Del. 2002), *aff'd* 56 Fed. Appx. 503 (Fed. Cir. 2003). Filed in Patent Interference 105,652 (HGS Exhibit 2033).
*Bhagwat* v. *Hrastar*, Interference No. 105,516, Paper 67 at 4 (Nov. 7, 2007). Filed in Patent Interference 105,652 (HGS Exhibit 2034).
Information Disclosure Statement dated Sep. 28, 2006 from file history of the RDF Involved Application. Filed in Patent Interference 105,652 (HGS Exhibit 2035).
Supplemental Information Disclosure Statement dated Mar. 7, 2007 from file history of the RDF Involved Application. Filed in Patent Interference 105,652 (HGS Exhibit 2036).
Supplemental Information Disclosure Statement dated May 29, 2008 from file history of the RDF Involved Application. Filed in Patent Interference 105,652 (HGS Exhibit 2037).
*Ex parte Jellá*, Appeal No. 2008-1619 (BPAI Nov. 3, 2008). Filed in Patent Interference 105,652 (HGS Exhibit 2038).
Declaration of Michael Rosenblum, submitted by RDF on Dec. 12, 2003 in inter partes Reexamination No. 95/000,016 involving U.S. Patent No. 6,376,217, entitled "Fusion Proteins and Polynucleotides Encoding Gelonin Sequences." Filed in Patent Interference 105,652 (HGS Exhibit 2039).
RDF Power of Attorney from inter partes Reexamination No. 95/000,016. Filed May 28, 2009 in Patent Interference 105,652 (HGS Exhibit 2041).
HGS Objections to RDF Evidence filed in Patent Interference 105,652. Filed in the United States Patent Office on Jan. 30, 2009. (HGS Exhibit 2042).
*Chen* v. *Bouchard* Final Decision issued in Patent Interference 103,675. Filed in Patent Interference 105,652 (HGs Exhibit 2043) (May 6, 2009).
Stirpe et al., *Biotechnology*, 10(4):405-12 (1992). Filed in Patent Interference 105,652 (RDF Exhibit 1008).
Rosenblum et al., *J. Interferon Cytokine Res.*, 15(6):547-55 (1995). Filed in Patent Interference 105,652 (RDF Exhibit 1009).
Rosenblum Declaration dated Jan. 23, 2009. Filed in Patent Interference 105,652 (RDF Exhibit 1010).
Rosenblum Curriculum Vitae. Filed Jun. 30, 2009 in Patent Interference 105,652 (RDF Exhibit 1011).
Dr. Arthur Chin Louie letter dated Sep. 5, 2001. Filed in Patent Interference 105,652 (RDF Exhibit 1012).
Page 53 of Mi-ae Lyu notebook dated Oct. 7, 2003. Filed in Patent Interference 105,652 (RDF Exhibit 1013).
Page 60 of Mi-ae Lyu notebook dated Oct. 17, 2003. Filed in Patent Interference 105,652 (RDF Exhibit 1014).
Page 1-3 of Lawrence Cheung notebook dated Jan. 27, 2004. Filed in Patent Interference 105,652 (RDF Exhibit 1015).
Page 23 of Lawrence Cheung notebook dated Apr. 14, 2004. Filed in Patent Interference 105,652 (RDF Exhibit 1016).
*Noelle* v. *Lederman*, 2001 Pat. App. LEXIS 8 (2001). Filed in Patent Interference 105,652 (RDF Exhibit 1017).
HGS Amendment and Reply dated Aug. 2, 2007, U.S. Appl. No. 11/054,539. Filed in Patent Interference 105,652 (RDF Exhibit 1018).
Dr. Arthur Chin Louie letter dated Sep. 5, 2001 with facsimile cover sheet. Filed in Patent Interference 105,652 (RDF Supplemental Exhibit 1012).
Yu Miscellaneous Motion 3 filed in Patent Interference 105,652. Filed in the United States Patent Office on May 6, 2009.
HGS Miscellaneous Motion 3 (to exclude RDF Exhibitis 1010 and 1013-1016) filed in Patent Interference 105,652. Filed in the United States Patent Office on May 6, 2009.

RDF Miscellaneous Motion 1 (Motion to Exclude Evidence) filed in Patent Interference 105,652. Filed in the United States Patent Office on May 6, 2009.
HGS Opposition 1A (Opposing RDF Miscellaneous Motion 1 to exclude evidence) filed in Patent Inteference 105,652. Filed in the United States Patent Office on May 14, 2009.
RDF Opposition to HGS Miscellaneous Motion 3 (Motion to Exclude) filed in Patent Interference 105,652. Filed in the United States Patent Office on May 14, 2009.
HGS Reply 3 (to exclude RDF Exhibits 1010 and 1013-1016) filed in Patent Interference 105,652. Filed in the United States Patent Office on May 21, 2009.
HGS Exhibit List (as of May 28, 2009) filed in Patent Interference 105,652. Filed in the United States Patent Office on May 28, 2009.
HGS Demonstratives from Oral Hearing, dated Jul. 2, 2009. Filed in Patent Interference 105,652.
Transcript of Oral Hearing, dated Sep. 4, 2009. Filed in Patent Interference 105,652.
Memorandum opinion and order issued Jun. 29, 2010 in Patent Interference No. 105,652.
Judgment on preliminary motions issued Jun. 29, 2010 in Patent Interference No. 105,652.
Aggarwal et al., *Eur. Cytokine Netw.*, 7(2): 93-124 (1996).
Arai et al., *Annu. Rev. Biochem.*, 59: 783-836 (1990).
Baumann et al., *J. Biol. Chem.*, 268(12): 8414-8417 (1993).
Collins et al., *Proc. Natl. Acad. Sci. USA*, 83: 446-450 (1986).
Fujio et al., *Blood*, 95(7): 2204-2211 (2000).
Gearing et al., *Embo. J.*, 10(10): 2839-2848 (1991).
Ginaldi et al., *J. Clin. Pathol.*, 51: 364-369 (1998).
Holmes et al., *Science*, 253: 1278-1280 (1991).
Huntington et al., *Int. Immunol.*, 18(10): 1473-1485 (2006).
Janeway et al., *Immunobiology: The Immune System in Health and Disease*, Current Biology Ltd./Garland Publishing, London. pp. 2:31, 7:1-7:41 (1996).
Kawaguchi et al., *J. Allergy Clin. Immunol.*, 114(6): 1265-1273 (2004).
Lasagni et al., *Blood*, 109(10): 4127-4134 (2007).
Lavie et al., *J. Pathol.*, 202: 496-502 (2004).
Lawn et al., *Cell*, 15: 1157-1174 (1978).
Maniatis et al., *Cell*, 15: 687-701 (1978).
Miyajima et al., *Annu. Rev. Immunol.*, 10: 295-331 (1992).
Pabst et al., *Anat. Embryol.*, 192: 293-299 (1995).
Ranges et al., *J. Exp. Med.*, 167: 1472-1478 (1988).
Rochman et al. *J. Immunol.*, 178: 6720-6724 (2007).
Shan et al., *Physiol. Res.*, 55: 301-307 (2006).
Siegel et al., *Nat. Immunol.*, 1(6): 469-474 (2000).
Stein et al., *J. Clin. Invest.*, 109: 1587-1598 (2002).
Stoeckle et al., *New Biol.*, 2(4): 313-323 (1990).
Wang et al., *Nat. Immunol.*, 2(7): 632-637 (2001).
Waterston et al., *Nat. Genet.*, 1: 114-123 (1992).
Xu et al., *Acta Biochim. Biophys. Sin.*, 39(12): 964-973 (2007).
Xu et al., *Transplant. Proc.*, 41: 1552-1556 (2009).
Yokota et al., *J. Immunol.*, 140(2): 531-536 (1988).
Yoshimoto et al., *Int. Immunol.*, 18(7): 1189-1196 (2006).
Eli Lilly letter on Statement on Grounds of Appeal filed before Technical Board of Appeals in Opposition of EP Patent No. 0 939 804 (Filed in the European Patent Office on May 1, 2009).
HGS Press Release, "Human Genome Sciences and GlaxoSmithKline Announce Positive Phase 3 Study Results for Benlysta™" (Jul. 20, 2009).
Declaration of Amy Hamilton filed in Opposition of EP Patent No. 0 939 804 (Filed in the European Patent Office on Jul. 23, 2009).
Eli Lilly letter to Technical Board of Appeals regarding Response to Appeal in Opposition of EP Patent No. 0 939 804 (Filed in the European Patent Office on Jul. 23, 2009).
Eli Lilly Response to Appeal filed before Technical Board of Appeals in Opposition of EP Patent No. 0 939 804 (Filed in the European Patent Office on Jul. 23, 2009).
Declaration and Curriculum Vitae of Dr. Thomas Lane Rothstein filed in Opposition of EP Patent No. 0 939 804 (Filed in the European Patent Office on Jul. 27, 2009).
Second Declaration of Dr. John Calley filed in Opposition of EP Patent No. 0 939 804 (Filed in the European Patent Office on Jul. 27, 2009).
Signed Declaration of Dr. Thomas Lane Rothstein filed in Opposition of EP Patent No. 0 939 804 (Filed in the European Patent Office on Jul. 27, 2009).
HGS letter on Grounds of Appeal update filed before Technical Board of Appeals in Opposition of EP Patent No. 0 939 804 (Filed in the European Patent Office on Jul. 31, 2009).
Preliminary Opinion of the Board of Appeal in Appeal Case T 18/09-3.3.08 in EP Patent 0939804 (Aug. 24, 2009).
Auxiliary Request I filed before Technical Board of Appeals in Opposition of EP Patent No. 0 939 804 (Filed in the European Patent Office on Sep. 30, 2009).
Auxiliary Request II filed before Technical Board of Appeals in Opposition of EP Patent No. 0 939 804 (Filed in the European Patent Office on Sep. 30, 2009).
Auxiliary Request III filed before Technical Board of Appeals in Opposition of EP Patent No. 0 939 804 (Filed in the European Patent Office on Sep. 30, 2009).
Auxiliary Request IV filed before Technical Board of Appeals in Opposition of EP Patent No. 0 939 804 (Filed in the European Patent Office on Sep. 30, 2009).
Auxiliary Request V filed before Technical Board of Appeals in Opposition of EP Patent No. 0 939 804 (Filed in the European Patent Office on Sep. 30, 2009).
Eli Lilly Reply to Preliminary Opinion filed before Technical Board of Appeals in Opposition of EP Patent No. 0 939 804 (Filed in the European Patent Office on Sep. 30, 2009).
Further Declaration of Dr. John Calley filed in Opposition of EP Patent No. 0 939 804 (Filed in the European Patent Office on Sep. 30, 2009).
HGS Reply to Preliminary Opinion filed before Technical Board of Appeals in Opposition of EP Patent No. 0 939 804 (Filed in the European Patent Office on Sep. 30, 2009).
Main Request filed before Technical Board of Appeals in Opposition of EP Patent No. 0 939 804 (Filed in the European Patent Office on Sep. 30, 2009).
Second Declaration of Dr. Garnett Herrel Kelsoe III and list of annexes filed before Technical Board of Appeals in Opposition of EP Patent No. 0 939 804 (Filed in the European Patent Office on Sep. 30, 2009).
Second Declaration of Dr. Randolph J. Noelle filed before Technical Board of Appeals in Opposition of EP Patent No. 0 939 804 (Filed in the European Patent Office on Sep. 30, 2009).
Second Declaration of Dr. Stuart Farrow filed before Technical Board of Appeals in Opposition of EP Patent No. 0 939 804 (Filed in the European Patent Office on Sep. 30, 2009).
Summary of Respondent's Proposed Experiments filed before Technical Board of Appeals in Opposition of EP Patent No. 0 939 804 (Filed in the European Patent Office on Sep. 30, 2009).
Third Declaration of Dr. Andrew Martin and Appendix 1 filed before Technical Board of Appeals in Opposition of EP Patent No. 0 939 804 (Filed in the European Patent Office on Sep. 30, 2009).
Minutes of the Oral Proceedings before the Opposition Division, issued by the European Patent Office in the matter of Eli Lilly's Opposition of EP 0 939 804 (Oct. 26, 2009).
Eli Lilly's Skeleton Argument on appeal in UK Revocation suit HC06CO2687 (Oct. 30, 2009).
Human Genome Science's Consolidated Skeleton Argument on appeal in UK Revocation suit HC06CO2687 (Dec. 2009).
Eli Lilly's Note on the Decision of the TBA in T18/09 in UK Revocation suit HC06CO2687 (Dec. 4, 2009).
Eli Lilly's Note on why the Decision of the TBA in T18/09 is different on the Facts in UK Revocation suit HC06CO2687 (Dec. 11, 2009).
Human Genome Science's mark-up of Eli Lilly's Note on why the Decision of the TBA in T18/09 is different on the Facts in UK Revocation suit HC06CO2687 (Dec. 11, 2009).
Human Genome Science's Note on why the Invention is susceptible of Industrial Application in UK Revocation suit HC06CO2687 (Dec. 10, 2009).
Human Genome Science's Note on paragraph 26 of Judgment by Mr Justice Kitchin in UK Revocation suit HC06CO2687 (Dec. 2009).

Human Genome Science's Reply Note in UK Revocation suit HC06CO2687 (Dec. 11, 2009).
Approved Judgment by Mr Justice Jacob on appeal from the Chancery Division in UK Revocation suit HC06CO2687 (Feb. 9, 2010).
Notification of decision of the Technical Board of Appeals in Appeal Case T 18/09-3.3.08 in EP Patent 0 939 804 (Oct. 21, 2009).
HGS Press Release, "Human Genome Sciences to Sponsor Conference Call to Discuss Phase 2 Clinical Results of Lymphostat-B™ in Systemic Lupus Erythematosus" dated Oct. 5, 2005.

* cited by examiner

Neutrokine-α

```
1    AAATTCAGGATAACTCTCCTGAGGGGTGAGCCAAGCCCTGCCATGTAGTGCACGCAGGAC  60

61   ATCAACAAACACAGATAACAGGAAATGATCCATTCCCTGTGGTCACTTATTCTAAAGGCC  120

121  CCAACCTTCAAAGTTCAAGTAGTGATATGGATGACTCCACAGAAAGGGAGCAGTCACGCC  180
1                                  M  D  D  S  T  E  R  E  Q  S  R  L   12

181  TTACTTCTTGCCTTAAGAAAAGAGAAGAAATGAAACTGAAGGAGTGTGTTTCCATCCTCC  240
13     T  S  C  L  K  K  R  E  E  M  K  L  K  E  C  V  S  I  L  P   32
                                                              CD-I

241  CACGGAAGGAAAGCCCCTCTGTCCGATCCTCCAAAGACGGAAAGCTGCTGGCTGCAACCT  300
33     R  K  E  S  P  S  V  R  S  S  K  D  G  K  L  L  A  A  T  L   52
                   CD-I

301  TGCTGCTGGCACTGCTGTCTTGCTGCCTCACGGTGGTGTCTTTCTACCAGGTGGCCGCCC  360
53     L  L  A  L  L  S  C  C  L  T  V  V  S  F  Y  Q  V  A  A  L   72

361  TGCAAGGGGACCTGGCCAGCCTCCGGGCAGAGCTGCAGGGCCACCACGCGGAGAAGCTGC  420
73     Q  G  D  L  A  S  L  R  A  E  L  Q  G  H  H  A  E  K  L  P   92
                   CD-II

421  CAGCAGGAGCAGGAGCCCCCAAGGCCGGCCTGGAGGAAGCTCCAGCTGTCACCGCGGGAC  480
93     A  G  A  G  A  P  K  A  G  L  E  E  A  P  A  V  T  A  G  L   112
                   CD-III
                                             #
481  TGAAAATCTTTGAACCACCAGCTCCAGGAGAAGGCAACTCCAGTCAGAACAGCAGAAATA  540
113    K  I  F  E  P  P  A  P  G  E  G  N  S  S  Q  N  S  R  N  K   132

541  AGCGTGCCGTTCAGGGTCCAGAAGAAACAGTCACTCAAGACTGCTTGCAACTGATTGCAG  600
133    R  A  V  Q  G  P  E  E  T  V  T  Q  D  C  L  Q  L  I  A  D   152
                                                         CD-IV
```

FIG. 1A

Neutrokine-α

```
601  ACAGTGAAACACCAACTATACAAAAAGGATCTTACACATTTGTTCCATGGCTTCTCAGCT  660
153   S  E  T  P  T  I  Q  K  G  S  Y  T  F  V  P  W  L  L  S  F   172
                                             CD-V

661  TTAAAAGGGGAAGTGCCCTAGAAGAAAAAGAGAATAAAATATTGGTCAAAGAAACTGGTT  720
173   K  R  G  S  A  L  E  E  K  E  N  K  I  L  V  K  E  T  G  Y   192
           CD-V                               CD-VI

721  ACTTTTTTATATATGGTCAGGTTTTATATACTGATAAGACCTACGCCATGGGACATCTAA  780
193   F  F  I  Y  G  Q  V  L  Y  T  D  K  T  Y  A  M  G  H  L  I   212
                     CD-VI                              CD-VII

781  TTCAGAGGAAGAAGGTCCATGTCTTTGGGGATGAATTGAGTCTGGTGACTTTGTTTCGAT  840
213   Q  R  K  K  V  H  V  F  G  D  E  L  S  L  V  T  L  F  R  C   232
           CD-VII                                 CD-VIII
                                   #
841  GTATTCAAAATATGCCTGAAACACTACCCAATAATTCCTGCTATTCAGCTGGCATTGCAA  900
233   I  Q  N  M  P  E  T  L  P  N  N  S  C  Y  S  A  G  I  A  K   252
      CD-VIII                           CD-IX

901  AACTGGAAGAAGGAGATGAACTCCAACTTGCAATACCAAGAGAAAATGCACAAATATCAC  960
253   L  E  E  G  D  E  L  Q  L  A  I  P  R  E  N  A  Q  I  S  L   272
                     CD-X

961  TGGATGGAGATGTCACATTTTTTGGTGCATTGAAACTGCTGTGACCTACTTACACCATGT  1020
273   D  G  D  V  T  F  F  G  A  L  K  L  L                        285
                        CD-XI

1021 CTGTAGCTATTTTCCTCCCTTTCTCTGTACCTCTAAGAAGAAAGAATCTAACTGAAAATA  1080

1081 CCAAAAAAAAAAAAAAAAAA  1100
```

FIG.1B

|     |                                    |                |
|-----|------------------------------------|----------------|
| 1   | ........................AEEA       | TNFalpha       |
| 1   | ..........................TPPERL   | TNFbeta        |
| 1   | MSTESMIRDVEL                       | LTbeta         |
| 1   | M..........                        | FasLigand      |
| 1   | MGA....                            | Neutrokine alpha |
| 1   | MQQPFNYPYPQIYW.VDSSASSPWAPPGTV     | Neutrokine alphaSV |
| 1   | MDDSTEREQSRLTSCLKKREEMKLKECVSI     |                |
| 1   | MDDSTEREQSRLTSCLKKREEMKLKECVSI     |                |

| 17 | LPKKTGGPQ...GSRR...................... | TNFalpha |
| 8  | F........................................ | TNFbeta |
| 4  | ...LGLEGRGG.............................. | LTbeta |
| 30 | LPCPTSVPRRPGQRRPPPPPPPPPPPLPPPPP        | FasLigand |
| 31 | LPRKESPSVRSSKD...GKLLAATLLALL           | Neutrokine alpha |
| 31 | LPRKESPSVRSSKD...GKLLAATLLALL           | Neutrokine alphaSV |

| 30 | .........................CFLSLFS             | TNFalpha |
| 9  | ...LPRVRGTTLHLLLGLLVLLP                      | TNFbeta |
| 12 | ...RLQGRGSLLAVAGATSLVT                       | LTbeta |
| 60 | PPPLPLPPLKKRGNHSTGLCLVMFFM                   | FasLigand |
| 58 | SCCLTVVSFYQVAALQGDLASLRAELQGH                | Neutrokine alpha |
| 58 | SCCLTVVSFYQVAALQGDLASLRAELQGH                | Neutrokine alphaSV |

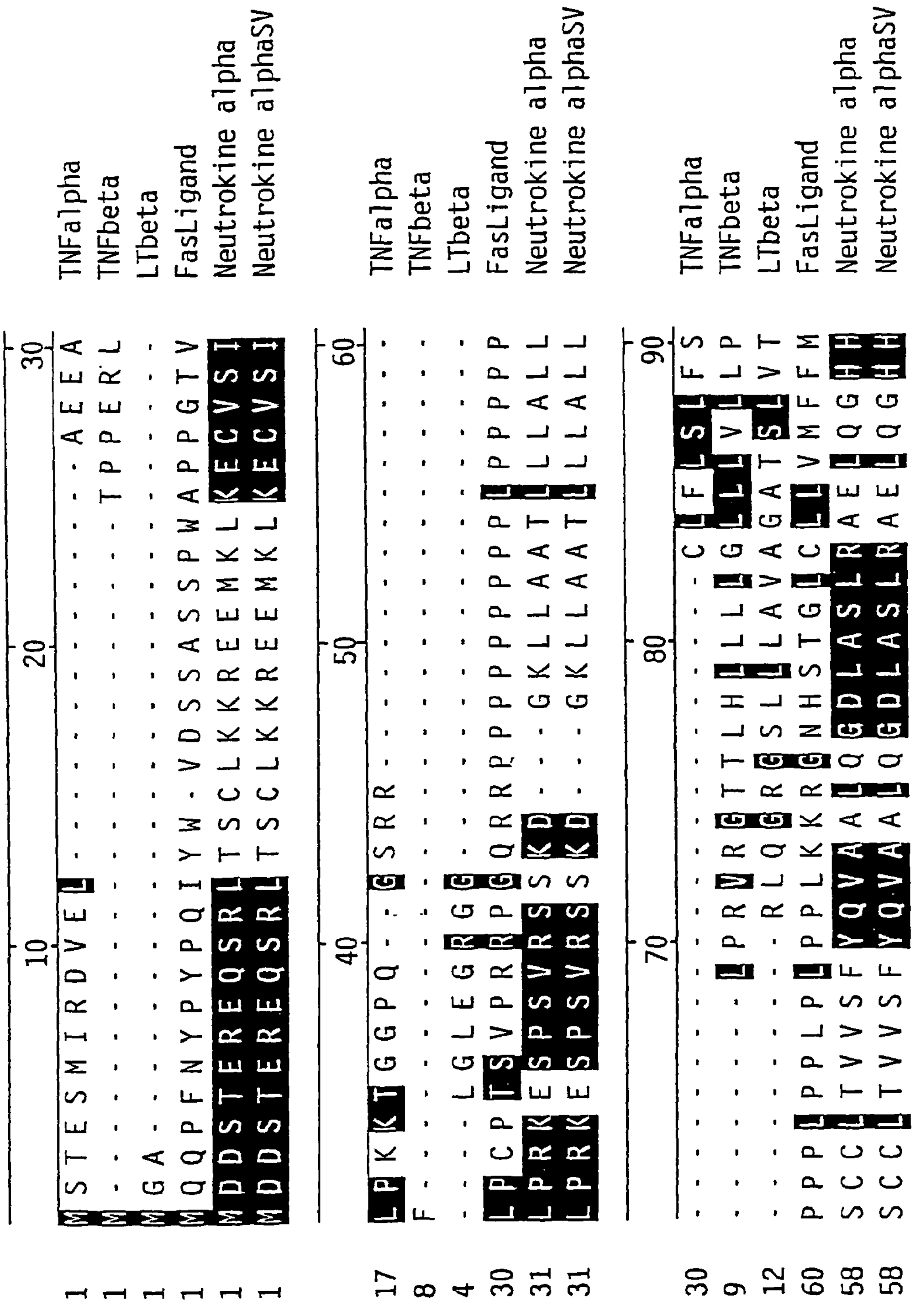

FIG.2A

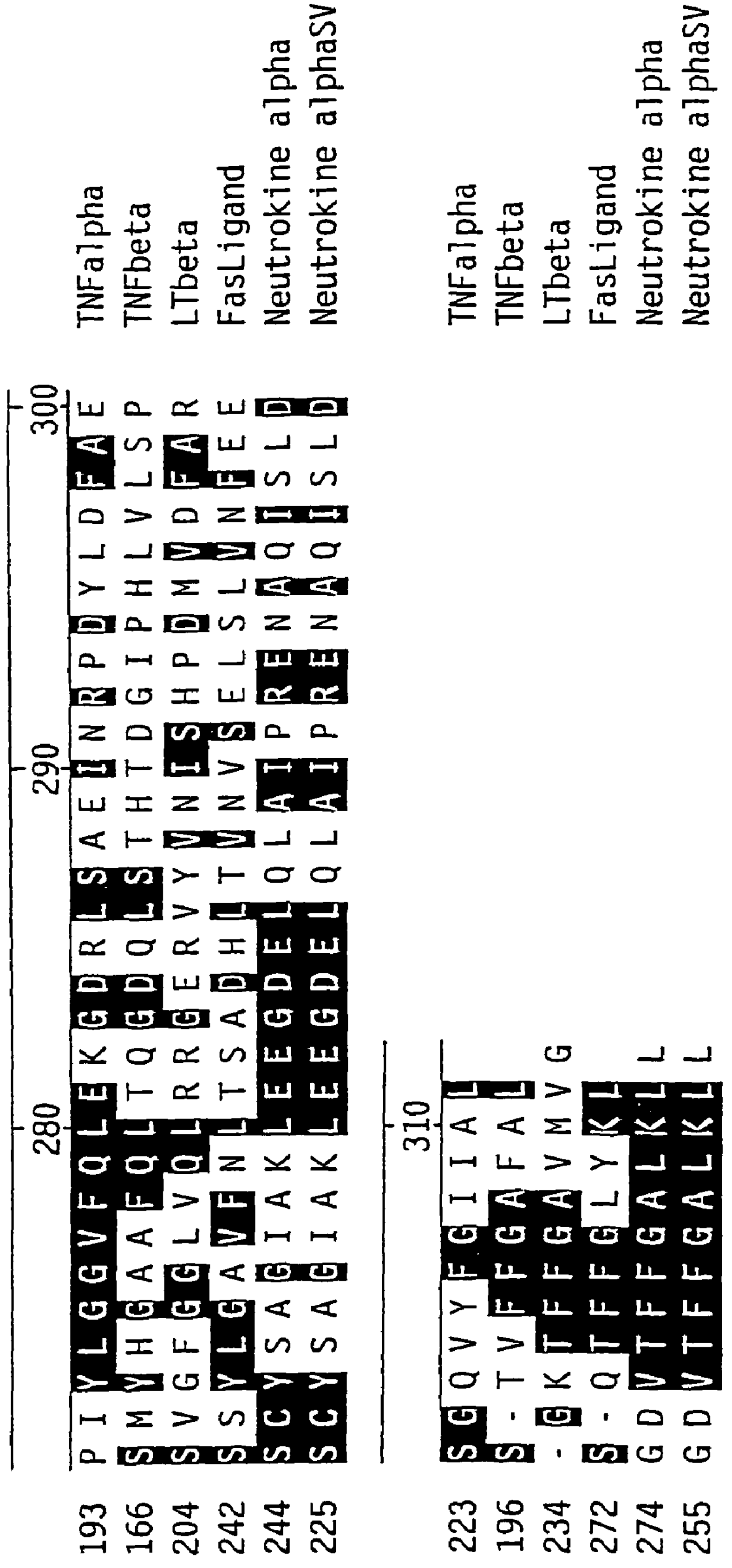

FIG.2D

| Pos | Sequence | Protein |
|---|---|---|
| 193 | P I Y L G G V F Q L E K G D R L S A E N R P D Y L D F A E | TNFalpha |
| 166 | S M H G A A F Q L T Q G D Q L S T H T D G I P H L V L S P | TNFbeta |
| 204 | S V G F G G L V Q L R R G E R V Y V N I S H P D M V D F A R | LTbeta |
| 242 | S S V L G A V F N L T S A D H L T N V S E L S L V N F E E | FasLigand |
| 244 | S C Y S A G I A K L E E G D E L Q L A I P R E N A Q I S L D | Neutrokine alpha |
| 225 | S C Y S A G I A K L E E G D E L Q L A I P R E N A Q I S L D | Neutrokine alphaSV |
| 223 | S G Q V Y F G I I A L | TNFalpha |
| 196 | S - T V F F G A F A L | TNFbeta |
| 234 | - K T F F G A V M V G | LTbeta |
| 272 | Q T F F G L Y K L | FasLigand |
| 274 | G D V T F F G A L K L L | Neutrokine alpha |
| 255 | G D V T F F G A L K L L | Neutrokine alphaSV |

```
           1                                                   50
HSOAD55R   .........A GGNTAACTCT CCTGAGGGGT GAGCCAAGCC CTGCCATGTA
HNEDU15X   ...AAATTCA GGATAACTCT CCTGAGGGGT GAGCCAAGCC CTGCCATGTA
HSLAH84R   .AATTCGGCA NAGNAAACTG GTTACTTTTT TATATATGGT CAGGTTTTAT
HLTBM08R   AATTCGGCAC GAGCAAGGCC GGCCTGGAGG AAGCTCCAGC TGTCACCGCG

           51                                                 100
HSOAD55R   GTGCACGCAG GACATCANCA A..ACACANN NNNCAGGAAA TAATCCATTC
HNEDU15X   GTGCACGCAG GACATCAACA A..ACACAGA TAACAGGAAA TGATCCATTC
HSLAH84R   ATACTGATAA GACCTACGCC ATGGGACATC TAGTTCAGAG GAAGAAGGTC
HLTBM08R   GGACTGAAAA TCTTTGAACC ACCAGCTCCA GGAGAAGGCA ACTCCAGTCA

           101                                                150
HSOAD55R   CCTGTGGTCA CTTATTCTAA AGGCCCCAAC CTTCAAAGTT CAAGTAGTGA
HNEDU15X   CCTGTGGTCA CTTATTCTAA AGGCCCCAAC CTTCAAAGTT CAAGTAGTGA
HSLAH84R   CATGTCTTTG GGGATGAATT GAGTCTGGTG ACTTTGTTTC GATGTATTCA
HLTBM08R   GAACAGCAGA AATAAGCGTG CCGTTCAGGG TCCAGAAGAA ACAGTCACTC

           151                                                200
HSOAD55R   TATGGATGAC TCCACAGAAA GGGAGCAGTC ACGCCTTACT TCTTGCCTTA
HNEDU15X   TATGGATGAC TCCACAGAAA GGGAGCAGTC ACGCCTTACT TCTTGCCTTA
HSLAH84R   AAATATGCCT GAAACACTAC CCAATAATTC CTGCTATTCA GCTGGCATTG
HLTBM08R   AAGACTGCTT GCAACTGNTT GCAGACAGTG AAACACCAAC TATACAAAAA

           201                                                250
HSOAD55R   AGAAAAGAGA AGAAATGAAA CTGNAAGGAG TGTGTTTCCA TCCTCCCACG
HNEDU15X   AGAAAAGAGA AGAAATGAAA CT.GAAGGAG TGTGTTTCCA TCCTCCCACG
HSLAH84R   CAAAACTGGN AGGAAGGA.. ...GATGAAC TCCAACTTGC AATACCAGGG
HLTBM08R   GGCTCCCTTC TGNTGCCACA TTTGGGCCAA GGAATGGAGA GATTTCTTCG

           251                                                300
HSOAD55R   GAAGGAAAGC CCCTCTNTCC GATCCTCCAA AGACGGAAAG CTGCTGGCTG
HNEDU15X   GAAGGAAAGC CCCTCTGTCC GATCCTCCAA AGACGGAAAG CTGCTGGCTG
HSLAH84R   GAAAATGCAC AATTATCACT GGGATGGAGA TGTTCACATT TTTTGGGTGC
HLTBM08R   TCTGGAAACA TTTTGCCAAA CTCTTCAGAT ACTCTTTNCT CTCTGGGAAT

           301                                                350
HSOAD55R   CAACCTTGNT GNTGGCATTG TGTTCTTGCT GNCTCAAGGT GGTGTTNTT
HNEDU15X   CAACCTTGCT GCTGGCACTG CTGTCTTGCT GCCTCACGGT GGTGTCTTTC
HSLAH84R   CATTGAAACT GCTGTGACCT NCTTACANCA NGTGCTGTTN GCTATTTTNC
HLTBM08R   CAAAGGAAAA TCTCTACTTA GATTNACACA TTTGTTCCCA TGGGTNTCTT

           351                                                400
HSOAD55R   .......... .......... .......... .......... ..........
HNEDU15X   TACCAGGTGG CCGCCCTGCA AGGGGACCTG GCCAGCCTCC GGGCAGAGCT
HSLAH84R   CTNCCTNTTC TNTGGTAACC TCTTAGGAAG GAAGGATTCT TAACTGGGAA
HLTBM08R   AAGTTTTAAA AGGGGAGTGC CCTTAGGAGG AAAAGGGGAT AAATATTGGC
```

FIG.4A

```
          401                                                   450
HSOAD55R  .......... .......... .......... .......... ..........
HNEDU15X  GCAGGGCCAC CACGCGGAGA AGCTGCCAGC AGGAGCAGGA GCCCCCAAGG
HSLAH84R  ATAACCCAAA AAAANNTTAA ANGGGTANGN GNNANANGNG GGGNNGTTNN
HLTBM08R  CAAGGNACTG GTTANTTTNT AAATATGGTC AGGTTTNTAT ANCTGGTAGG

          451                                                   500
HSOAD55R  .......... .......... .......... .......... ..........
HNEDU15X  CCGGCCTGGA GGAAGCTCCA GCTGTCACCG CGGGACTGAA AATCTTTGAA
HSLAH84R  CNNGNNGNNT TTTNGGNNTA TNTTNTNNTN GGGNNNNGTA AAAATGGGGC
HLTBM08R  CCTCGCCATG GGCATTNATT CANGGNGAGG NCNNTCTTTT GGGNTGA...

          501                                                   550
HSOAD55R  .......... .......... .......... .......... ..........
HNEDU15X  CCACCAGCTC CAGGAGAAGG CAACTCCAGT CAGAACAGCA GAAATAAGCG
HSLAH84R  CNANGGGGGN TTTTT..... .......... .......... ..........
HLTBM08R  .......... .......... .......... .......... ..........

          551                                                   600
HSOAD55R  .......... .......... .......... .......... ..........
HNEDU15X  TGCCGTTCAG GGTCCAGAAG AAACAGTCAC TCAAGACTGC TTGCAACTGA
HSLAH84R  .......... .......... .......... .......... ..........
HLTBM08R  .......... .......... .......... .......... ..........

          601                                                   650
HSOAD55R  .......... .......... .......... .......... ..........
HNEDU15X  TTGCAGACAG TGAAACACCA ACTATACAAA AAGGATCTTA CACATTTGTT
HSLAH84R  .......... .......... .......... .......... ..........
HLTBM08R  .......... .......... .......... .......... ..........

          651                                                   700
HSOAD55R  .......... .......... .......... .......... ..........
HNEDU15X  CCATGGCTTC TCAGCTTTAA AAGGGGAAGT GCCCTAGAAG AAAAAGAGAA
HSLAH84R  .......... .......... .......... .......... ..........
HLTBM08R  .......... .......... .......... .......... ..........

          701                                                   750
HSOAD55R  .......... .......... .......... .......... ..........
HNEDU15X  TAAAATATTG GTCAAAGAAA CTGGTTACTT TTTTATATAT GGTCAGGTTT
HSLAH84R  .......... .......... .......... .......... ..........
HLTBM08R  .......... .......... .......... .......... ..........

          751                                                   800
HSOAD55R  .......... .......... .......... .......... ..........
HNEDU15X  TATATACTGA TAAGACCTAC GCCATGGGAC ATCTAATTCA GAGGAAGAAG
HSLAH84R  .......... .......... .......... .......... ..........
HLTBM08R  .......... .......... .......... .......... ..........
```

FIG.4B

```
          801                                               850
HSOAD55R  .......... .......... .......... .......... ..........
HNEDU15X  GTCCATGTCT TTGGGGATGA ATTGAGTCTG GTGACTTTGT TTCGATGTAT
HSLAH84R  .......... .......... .......... .......... ..........
HLTBM08R  .......... .......... .......... .......... ..........

          851                                               900
HSOAD55R  .......... .......... .......... .......... ..........
HNEDU15X  TCAAAATATG CCTGAAACAC TACCCAATAA TTCCTGCTAT TCAGCTGGCA
HSLAH84R  .......... .......... .......... .......... ..........
HLTBM08R  .......... .......... .......... .......... ..........

          901                                               950
HSOAD55R  .......... .......... .......... .......... ..........
HNEDU15X  TTGCAAAACT GGAAGAAGGA GATGAACTCC AACTTGCAAT ACCAAGAGAA
HSLAH84R  .......... .......... .......... .......... ..........
HLTBM08R  .......... .......... .......... .......... ..........

          951                                              1000
HSOAD55R  .......... .......... .......... .......... ..........
HNEDU15X  AATGCACAAA TATCACTGGA TGGAGATGTC ACATTTTTTG GTGCATTGAA
HSLAH84R  .......... .......... .......... .......... ..........
HLTBM08R  .......... .......... .......... .......... ..........

          1001                                             1050
HSOAD55R  .......... .......... .......... .......... ..........
HNEDU15X  ACTGCTGTGA CCTACTTACA CCATGTCTGT AGCTATTTTC CTCCCTTTCT
HSLAH84R  .......... .......... .......... .......... ..........
HLTBM08R  .......... .......... .......... .......... ..........

          1051                                             1100
HSOAD55R  .......... .......... .......... .......... ..........
HNEDU15X  CTGTACCTCT AAGAAGAAAG AATCTAACTG AAAATACCAA AAAAAAAAAA
HSLAH84R  .......... .......... .......... .......... ..........
HLTBM08R  .......... .......... .......... .......... ..........

          1101
HSOAD55R  ......
HNEDU15X  AAAAAA
HSLAH84R  ......
HLTBM08R  ......
```

FIG.4C

Neutrokine-αSV

1 ATGGATGACTCCACAGAAAGGGAGCAGTCACGCCTTACTTCTTGCCTTAAGAAAAGAGAA 60
1 M D D S T E R E Q S R L T S C L K K R E 20

61 GAAATGAAACTGAAGGAGTGTGTTTCCATCCTCCCACGGAAGGAAAGCCCCTCTGTCCGA 120
21 E M K L K E C V S I L P R K E S P S V R 40
CD-I

121 TCCTCCAAAGACGGAAAGCTGCTGGCTGCAACCTTGCTGCTGGCACTGCTGTCTTGCTGC 180
41 S S K D G K L L A A T L L L A L L S C C 60
CD-I

181 CTCACGGTGGTGTCTTTCTACCAGGTGGCCGCCCTGCAAGGGGACCTGGCCAGCCTCCGG 240
61 L T V V S F Y Q V A A L Q G D L A S L R 80
CD-II

241 GCAGAGCTGCAGGGCCACCACGCGGAGAAGCTGCCAGCAGGAGCAGGAGCCCCCAAGGCC 300
81 A E L Q G H H A E K L P A G A G A P K A 100
CD-II CD-III

301 GGCCTGGAGGAAGCTCCAGCTGTCACCGCGGGACTGAAAATCTTTGAACCACCAGCTCCA 360
101 G L E E A P A V T A G L K I F E P P A P 120
CD-III

361 GGAGAAGGCAACTCCAGTCAGAACAGCAGAAATAAGCGTGCCGTTCAGGGTCCAGAAGAA 420
121 G E G N S S Q N S R N K R A V Q G P E E 140

421 ACAGGATCTTACACATTTGTTCCATGGCTTCTCAGCTTTAAAAGGGGAAGTGCCCTAGAA 480
141 T G S Y T F V P W L L S F K R G S A L E 160
CD-IV

481 GAAAAAGAGAATAAAATATTGGTCAAAGAAACTGGTTACTTTTTTATATATGGTCAGGTT 540
161 E K E N K I L V K E T G Y F F I Y G Q V 180
CD-IV CD-V

541 TTATATACTGATAAGACCTACGCCATGGGACATCTAATTCAGAGGAAGAAGGTCCATGTC 600
181 L Y T D K T Y A M G H L I Q R K K V H V 200
CD-VI CD-VII

FIG.5A

Neutrokine-αSV

```
601  TTTGGGGATGAATTGAGTCTGGTGACTTTGTTTCGATGTATTCAAAATATGCCTGAAACA  660
201  F G  D  E  L  S  L  V  T  L  F  R  C  I  Q  N  M  P  E  T   220
 CD-VIII                        CD-VIII

661  CTACCCAATAATTCCTGCTATTCAGCTGGCATTGCAAAACTGGAAGAAGGAGATGAACTC  720
221  L  P  N  N  S  C  Y  S  A  G  I  A  K  L  E  E  G  D  E  L   240
                   CD-IX                          CD-X

721  CAACTTGCAATACCAAGAGAAAATGCACAAATATCACTGGATGGAGATGTCACATTTTTT  780
241  Q  L  A  I  P  R  E  N  A  Q  I  S  L  D  G  D  V  T  F  F   260
        CD-X                                               CD-XI

781  GGTGCATTGAAACTGCTGTGACCTACTTACACCATGTCTGTAGCTATTTTCCTCCCTTTC  840
261  G  A  L  K  L  L                                              266
       CD-XI

841  TCTGTACCTCTAAGAAGAAAGAATCTAACTGAAAATACCAAAAAAAAAAAAAAAAAAAAA  900

901  AAA  903
```

FIG.5B

```
                              SEQUENCE LISTING


<160> NUMBER OF SEQ ID NOS: 59

<210> SEQ ID NO 1
<211> LENGTH: 1100
<212> TYPE: DNA
<213> ORGANISM: Homo sapiens
<220> FEATURE:
<221> NAME/KEY: CDS
<222> LOCATION: (147)..(1001)

<400> SEQUENCE: 1

aaattcagga taactctcct gaggggtgag ccaagccctg ccatgtagtg cacgcaggac      60

atcaacaaac acagataaca ggaaatgatc cattccctgt ggtcacttat tctaaaggcc     120

ccaaccttca aagttcaagt agtgat atg gat gac tcc aca gaa agg gag cag      173
                             Met Asp Asp Ser Thr Glu Arg Glu Gln
                               1               5

tca cgc ctt act tct tgc ctt aag aaa aga gaa gaa atg aaa ctg aag      221
Ser Arg Leu Thr Ser Cys Leu Lys Lys Arg Glu Glu Met Lys Leu Lys
 10                  15                  20                  25

gag tgt gtt tcc atc ctc cca cgg aag gaa agc ccc tct gtc cga tcc      269
Glu Cys Val Ser Ile Leu Pro Arg Lys Glu Ser Pro Ser Val Arg Ser
                 30                  35                  40

tcc aaa gac gga aag ctg ctg gct gca acc ttg ctg ctg gca ctg ctg      317
Ser Lys Asp Gly Lys Leu Leu Ala Ala Thr Leu Leu Leu Ala Leu Leu
             45                  50                  55

tct tgc tgc ctc acg gtg gtg tct ttc tac cag gtg gcc gcc ctg caa      365
Ser Cys Cys Leu Thr Val Val Ser Phe Tyr Gln Val Ala Ala Leu Gln
         60                  65                  70

ggg gac ctg gcc agc ctc cgg gca gag ctg cag ggc cac cac gcg gag      413
Gly Asp Leu Ala Ser Leu Arg Ala Glu Leu Gln Gly His His Ala Glu
     75                  80                  85

aag ctg cca gca gga gca gga gcc ccc aag gcc ggc ctg gag gaa gct      461
Lys Leu Pro Ala Gly Ala Gly Ala Pro Lys Ala Gly Leu Glu Glu Ala
 90                  95                 100                 105

cca gct gtc acc gcg gga ctg aaa atc ttt gaa cca cca gct cca gga      509
Pro Ala Val Thr Ala Gly Leu Lys Ile Phe Glu Pro Pro Ala Pro Gly
                110                 115                 120

gaa ggc aac tcc agt cag aac agc aga aat aag cgt gcc gtt cag ggt      557
Glu Gly Asn Ser Ser Gln Asn Ser Arg Asn Lys Arg Ala Val Gln Gly
            125                 130                 135

cca gaa gaa aca gtc act caa gac tgc ttg caa ctg att gca gac agt      605
Pro Glu Glu Thr Val Thr Gln Asp Cys Leu Gln Leu Ile Ala Asp Ser
        140                 145                 150

gaa aca cca act ata caa aaa gga tct tac aca ttt gtt cca tgg ctt      653
Glu Thr Pro Thr Ile Gln Lys Gly Ser Tyr Thr Phe Val Pro Trp Leu
    155                 160                 165

ctc agc ttt aaa agg gga agt gcc cta gaa gaa aaa gag aat aaa ata      701
Leu Ser Phe Lys Arg Gly Ser Ala Leu Glu Glu Lys Glu Asn Lys Ile
170                 175                 180                 185

ttg gtc aaa gaa act ggt tac ttt ttt ata tat ggt cag gtt tta tat      749
Leu Val Lys Glu Thr Gly Tyr Phe Phe Ile Tyr Gly Gln Val Leu Tyr
                190                 195                 200

act gat aag acc tac gcc atg gga cat cta att cag agg aag aag gtc      797
Thr Asp Lys Thr Tyr Ala Met Gly His Leu Ile Gln Arg Lys Lys Val
```

```
            205                 210                 215

cat gtc ttt ggg gat gaa ttg agt ctg gtg act ttg ttt cga tgt att      845
His Val Phe Gly Asp Glu Leu Ser Leu Val Thr Leu Phe Arg Cys Ile
        220                 225                 230

caa aat atg cct gaa aca cta ccc aat aat tcc tgc tat tca gct ggc      893
Gln Asn Met Pro Glu Thr Leu Pro Asn Asn Ser Cys Tyr Ser Ala Gly
    235                 240                 245

att gca aaa ctg gaa gaa gga gat gaa ctc caa ctt gca ata cca aga      941
Ile Ala Lys Leu Glu Glu Gly Asp Glu Leu Gln Leu Ala Ile Pro Arg
250                 255                 260                 265

gaa aat gca caa ata tca ctg gat gga gat gtc aca ttt ttt ggt gca      989
Glu Asn Ala Gln Ile Ser Leu Asp Gly Asp Val Thr Phe Phe Gly Ala
                270                 275                 280

ttg aaa ctg ctg tgacctactt acaccatgtc tgtagctatt ttcctccctt         1041
Leu Lys Leu Leu
            285

tctctgtacc tctaagaaga aagaatctaa ctgaaaatac caaaaaaaaa aaaaaaaaa    1100


<210> SEQ ID NO 2
<211> LENGTH: 285
<212> TYPE: PRT
<213> ORGANISM: Homo sapiens

<400> SEQUENCE: 2

Met Asp Asp Ser Thr Glu Arg Glu Gln Ser Arg Leu Thr Ser Cys Leu
  1               5                  10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
     50                  55                  60

Ser Phe Tyr Gln Val Ala Ala Leu Gln Gly Asp Leu Ala Ser Leu Arg
 65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255
```

```
Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285


<210> SEQ ID NO 3
<211> LENGTH: 233
<212> TYPE: PRT
<213> ORGANISM: Homo sapiens

<400> SEQUENCE: 3

Met Ser Thr Glu Ser Met Ile Arg Asp Val Glu Leu Ala Glu Glu Ala
  1               5                  10                  15

Leu Pro Lys Lys Thr Gly Gly Pro Gln Gly Ser Arg Arg Cys Leu Phe
             20                  25                  30

Leu Ser Leu Phe Ser Phe Leu Ile Val Ala Gly Ala Thr Thr Leu Phe
         35                  40                  45

Cys Leu Leu His Phe Gly Val Ile Gly Pro Gln Arg Glu Glu Phe Pro
     50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230


<210> SEQ ID NO 4
<211> LENGTH: 205
<212> TYPE: PRT
<213> ORGANISM: Homo sapiens

<400> SEQUENCE: 4

Met Thr Pro Pro Glu Arg Leu Phe Leu Pro Arg Val Arg Gly Thr Thr
  1               5                  10                  15

Leu His Leu Leu Leu Leu Gly Leu Leu Leu Val Leu Leu Pro Gly Ala
             20                  25                  30

Gln Gly Leu Pro Gly Val Gly Leu Thr Pro Ser Ala Ala Gln Thr Ala
         35                  40                  45

Arg Gln His Pro Lys Met His Leu Ala His Ser Thr Leu Lys Pro Ala
     50                  55                  60

Ala His Leu Ile Gly Asp Pro Ser Lys Gln Asn Ser Leu Leu Trp Arg
```

```
 65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205


<210> SEQ ID NO 5
<211> LENGTH: 244
<212> TYPE: PRT
<213> ORGANISM: Homo sapiens

<400> SEQUENCE: 5

Met Gly Ala Leu Gly Leu Glu Gly Arg Gly Gly Arg Leu Gln Gly Arg
  1               5                  10                  15

Gly Ser Leu Leu Leu Ala Val Ala Gly Ala Thr Ser Leu Val Thr Leu
             20                  25                  30

Leu Leu Ala Val Pro Ile Thr Val Leu Ala Val Leu Ala Leu Val Pro
         35                  40                  45

Gln Asp Gln Gly Gly Leu Val Thr Glu Thr Ala Asp Pro Gly Ala Gln
     50                  55                  60

Ala Gln Gln Gly Leu Gly Phe Gln Lys Leu Pro Glu Glu Glu Pro Glu
 65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
    130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
        195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly
```

<210> SEQ ID NO 6
<211> LENGTH: 281
<212> TYPE: PRT
<213> ORGANISM: Homo sapiens

<400> SEQUENCE: 6

```
Met Gln Gln Pro Phe Asn Tyr Pro Tyr Pro Gln Ile Tyr Trp Val Asp
  1               5                  10                  15

Ser Ser Ala Ser Ser Pro Trp Ala Pro Pro Gly Thr Val Leu Pro Cys
             20                  25                  30

Pro Thr Ser Val Pro Arg Arg Pro Gly Gln Arg Arg Pro Pro Pro Pro
         35                  40                  45

Pro Pro Pro Pro Pro Leu Pro Pro Pro Pro Pro Pro Pro Pro Leu Pro
     50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280
```

<210> SEQ ID NO 7
<211> LENGTH: 338
<212> TYPE: DNA
<213> ORGANISM: Homo sapiens
<220> FEATURE:
<221> NAME/KEY: misc_feature
<222> LOCATION: (4)
<223> OTHER INFORMATION: n equals a, t, g, or c
<220> FEATURE:
<221> NAME/KEY: misc_feature
<222> LOCATION: (59)
<223> OTHER INFORMATION: n equals a, t, g, or c
<220> FEATURE:
<221> NAME/KEY: misc_feature
<222> LOCATION: (68)..(72)
<223> OTHER INFORMATION: n equals a, t, g, or c
<220> FEATURE:
<221> NAME/KEY: misc_feature
<222> LOCATION: (213)
<223> OTHER INFORMATION: n equals a, t, g, or c
<220> FEATURE:
<221> NAME/KEY: misc_feature
<222> LOCATION: (256)
<223> OTHER INFORMATION: n equals a, t, g or c
<220> FEATURE:
<221> NAME/KEY: misc_feature
<222> LOCATION: (298)
<223> OTHER INFORMATION: n equals a, t, g or c
<220> FEATURE:
<221> NAME/KEY: misc_feature
<222> LOCATION: (301)
<223> OTHER INFORMATION: n equals a, t, g, or c
<220> FEATURE:
<221> NAME/KEY: misc_feature
<222> LOCATION: (321)
<223> OTHER INFORMATION: n equals a, t, g, or c
<220> FEATURE:
<221> NAME/KEY: misc_feature
<222> LOCATION: (336)
<223> OTHER INFORMATION: n equals a, t, g, or c

<400> SEQUENCE: 7

```
aggntaactc tcctgagggg tgagccaagc cctgccatgt agtgcacgca ggacatcanc     60

aaacacannn nncaggaaat aatccattcc ctgtggtcac ttattctaaa ggccccaacc    120

ttcaaagttc aagtagtgat atggatgact ccacagaaag ggagcagtca cgccttactt    180

cttgccttaa gaaaagagaa gaaatgaaac tgnaaggagt gtgtttccat cctcccacgg    240

aaggaaagcc cctctntccg atcctccaaa gacggaaagc tgctggctgc aaccttgntg    300

ntggcattgt gttcttgctg nctcaaggtg gtgttntt                            338
```

<210> SEQ ID NO 8
<211> LENGTH: 509
<212> TYPE: DNA
<213> ORGANISM: Homo sapiens
<220> FEATURE:
<221> NAME/KEY: misc_feature
<222> LOCATION: (10)
<223> OTHER INFORMATION: n equals a, t, g, or c
<220> FEATURE:
<221> NAME/KEY: misc_feature
<222> LOCATION: (13)
<223> OTHER INFORMATION: n equals a, t, g, or c
<220> FEATURE:
<221> NAME/KEY: misc_feature
<222> LOCATION: (209)
<223> OTHER INFORMATION: n equals a, t, g, or c
<220> FEATURE:
<221> NAME/KEY: misc_feature
<222> LOCATION: (315)
<223> OTHER INFORMATION: n equals a, t, g, or c
<220> FEATURE:
<221> NAME/KEY: misc_feature
<222> LOCATION: (322)
<223> OTHER INFORMATION: n equals a, t, g, or c
<220> FEATURE:
<221> NAME/KEY: misc_feature
<222> LOCATION: (325)
<223> OTHER INFORMATION: n equals a, t, g, or c
<220> FEATURE:
<221> NAME/KEY: misc_feature
<222> LOCATION: (334)
<223> OTHER INFORMATION: n equals a, t, g, or c
<220> FEATURE:
<221> NAME/KEY: misc_feature
<222> LOCATION: (343)
<223> OTHER INFORMATION: n equals a, t, g, or c
<220> FEATURE:
<221> NAME/KEY: misc_feature
<222> LOCATION: (347)
<223> OTHER INFORMATION: n equals a, t, g, or c
<220> FEATURE:
<221> NAME/KEY: misc_feature
<222> LOCATION: (351)
<223> OTHER INFORMATION: n equals a, t, g, or c
<220> FEATURE:
<221> NAME/KEY: misc_feature
<222> LOCATION: (356)
<223> OTHER INFORMATION: n equals a, t, g, or c
<220> FEATURE:
<221> NAME/KEY: misc_feature
<222> LOCATION: (409)..(410)
<223> OTHER INFORMATION: n equals a, t, g, or c
<220> FEATURE:
<221> NAME/KEY: misc_feature
<222> LOCATION: (416)
<223> OTHER INFORMATION: n equals a, t, g, or c
<220> FEATURE:
<221> NAME/KEY: misc_feature
<222> LOCATION: (422)
<223> OTHER INFORMATION: n equals a, t, g, or c
<220> FEATURE:
<221> NAME/KEY: misc_feature
<222> LOCATION: (424)
<223> OTHER INFORMATION: n equals a, t, g, or c
<220> FEATURE:
<221> NAME/KEY: misc_feature
<222> LOCATION: (426)..(427)
<223> OTHER INFORMATION: n equals a, t, g, or c
<220> FEATURE:
<221> NAME/KEY: misc_feature
<222> LOCATION: (429)
<223> OTHER INFORMATION: n equals a, t, g, or c
<220> FEATURE:
<221> NAME/KEY: misc_feature
<222> LOCATION: (431)
<223> OTHER INFORMATION: n equals a, t, g, or c
<220> FEATURE:
<221> NAME/KEY: misc_feature
<222> LOCATION: (433)
<223> OTHER INFORMATION: n equals a, t, g, or c
<220> FEATURE:
<221> NAME/KEY: misc_feature
<222> LOCATION: (438)..(439)
<223> OTHER INFORMATION: n equals a, t, g, or c
<220> FEATURE:
<221> NAME/KEY: misc_feature
<222> LOCATION: (443)..(444)
<223> OTHER INFORMATION: n equals a, t, g, or c
<220> FEATURE:
<221> NAME/KEY: misc_feature
<222> LOCATION: (446)..(447)
<223> OTHER INFORMATION: n equals a, t, g, or c
<220> FEATURE:
<221> NAME/KEY: misc_feature
<222> LOCATION: (449)..(450)
<223> OTHER INFORMATION: n equals a, t, g, or c
<220> FEATURE:
<221> NAME/KEY: misc_feature
<222> LOCATION: (452)..(453)
<223> OTHER INFORMATION: n equals a, t, g, or c
<220> FEATURE:
<221> NAME/KEY: misc_feature
<222> LOCATION: (458)
<223> OTHER INFORMATION: n equals a, t, g, or c
<220> FEATURE:
<221> NAME/KEY: misc_feature
<222> LOCATION: (461)..(462)
<223> OTHER INFORMATION: n equals a, t, g, or c
<220> FEATURE:
<221> NAME/KEY: misc_feature
<222> LOCATION: (466)
<223> OTHER INFORMATION: n equals a, t, g, or c
<220> FEATURE:
<221> NAME/KEY: misc_feature
<222> LOCATION: (469)
<223> OTHER INFORMATION: n equals a, t, g, or c
<220> FEATURE:
<221> NAME/KEY: misc_feature
<222> LOCATION: (471)..(472)
<223> OTHER INFORMATION: n equals a, t, g, or c
<220> FEATURE:
<221> NAME/KEY: misc_feature
<222> LOCATION: (474)
<223> OTHER INFORMATION: n equals a, t, g, or c
<220> FEATURE:
<221> NAME/KEY: misc_feature
<222> LOCATION: (478)..(481)
<223> OTHER INFORMATION: n equals a, t, g, or c
<220> FEATURE:
<221> NAME/KEY: misc_feature
<222> LOCATION: (496)
<223> OTHER INFORMATION: n equals a, t, g, or c
<220> FEATURE:
<221> NAME/KEY: misc_feature
<222> LOCATION: (498)
<223> OTHER INFORMATION: n equals a, t, g, or c
<220> FEATURE:
<221> NAME/KEY: misc_feature
<222> LOCATION: (504)
<223> OTHER INFORMATION: n equals a, t, g, or c

<400> SEQUENCE: 8
aattcggcan agnaaactgg ttactttttt atatatggtc aggttttata tactgataag 60
acctacgcca tgggacatct agttcagagg aagaaggtcc atgtctttgg ggatgaattg 120
agtctggtga ctttgtttcg atgtattcaa aatatgcctg aaacactacc caataattcc 180
tgctattcag ctggcattgc aaaactggna ggaaggagat gaactccaac ttgcaatacc 240
aggggaaaat gcacaattat cactgggatg gagatgttca catttttgg gtgccattga 300 aactgctgtg acctncttac ancangtgct gttngctatt ttncctncct nttctntggt 360
aacctcttag gaaggaagga ttcttaactg ggaaataacc caaaaaaann ttaaangggt 420
angngnnana ngnggggnng ttnncnngnn gnnttttngg nntatnttnt nntngggnnn 480
ngtaaaaatg gggccnangg gggnttttt 509

<210> SEQ ID NO 9
<211> LENGTH: 497
<212> TYPE: DNA
<213> ORGANISM: Homo sapiens
<220> FEATURE:
<221> NAME/KEY: misc_feature
<222> LOCATION: (168)
<223> OTHER INFORMATION: n equals a, t, g, or c
<220> FEATURE:
<221> NAME/KEY: misc_feature
<222> LOCATION: (213)
<223> OTHER INFORMATION: n equals a, t, g, or c
<220> FEATURE:
<221> NAME/KEY: misc_feature
<222> LOCATION: (288)
<223> OTHER INFORMATION: n equals a, t, g, or c
<220> FEATURE:
<221> NAME/KEY: misc_feature
<222> LOCATION: (325)
<223> OTHER INFORMATION: n equals a, t, g, or c
<220> FEATURE:
<221> NAME/KEY: misc_feature
<222> LOCATION: (346)
<223> OTHER INFORMATION: n equals a, t, g, or c
<220> FEATURE:
<221> NAME/KEY: misc_feature
<222> LOCATION: (406)
<223> OTHER INFORMATION: n equals a, t, g, or c
<220> FEATURE:
<221> NAME/KEY: misc_feature
<222> LOCATION: (415)
<223> OTHER INFORMATION: n equals a, t, g, or c
<220> FEATURE:
<221> NAME/KEY: misc_feature
<222> LOCATION: (419)
<223> OTHER INFORMATION: n equals a, t, g, or c
<220> FEATURE:
<221> NAME/KEY: misc_feature
<222> LOCATION: (437)
<223> OTHER INFORMATION: n equals a, t, g, or c
<220> FEATURE:
<221> NAME/KEY: misc_feature
<222> LOCATION: (442)
<223> OTHER INFORMATION: n equals a, t, g, or c
<220> FEATURE:
<221> NAME/KEY: misc_feature
<222> LOCATION: (467)
<223> OTHER INFORMATION: n equals a, t, g, or c
<220> FEATURE:
<221> NAME/KEY: misc_feature
<222> LOCATION: (473)
<223> OTHER INFORMATION: n equals a, t, g, or c
<220> FEATURE:
<221> NAME/KEY: misc_feature
<222> LOCATION: (476)
<223> OTHER INFORMATION: n equals a, t, g, or c
<220> FEATURE:
<221> NAME/KEY: misc_feature
<222> LOCATION: (481)
<223> OTHER INFORMATION: n equals a, t, g, or c
<220> FEATURE:
<221> NAME/KEY: misc_feature
<222> LOCATION: (483)..(484)
<223> OTHER INFORMATION: n equals a, t, g, or c
<220> FEATURE:
<221> NAME/KEY: misc_feature
<222> LOCATION: (494)
<223> OTHER INFORMATION: n equals a, t, g, or c

<400> SEQUENCE: 9
aattcggcac gagcaaggcc ggcctggagg aagctccagc tgtcaccgcg ggactgaaaa 60
tctttgaacc accagctcca ggagaaggca actccagtca gaacagcaga aataagcgtg 120
ccgttcaggg tccagaagaa acagtcactc aagactgctt gcaactgntt gcagacagtg 180
aaacaccaac tatacaaaaa ggctcccttc tgntgccaca tttgggccaa ggaatggaga 240
gatttcttcg tctggaaaca ttttgccaaa ctcttcagat actctttnct ctctgggaat 300
caaaggaaaa tctctactta gattnacaca tttgttccca tgggtntctt aagttttaaa 360
aggggagtgc ccttaggagg aaaaggggat aaatattggc caaggnactg gttantttnt 420
aaatatggtc aggtttntat anctggtagg cctcgccatg ggcattnatt canggngagg 480
ncnntctttt gggntga 497

<210> SEQ ID NO 10
<211> LENGTH: 27
<212> TYPE: DNA
<213> ORGANISM: Homo sapiens
<220> FEATURE:
<223> OTHER INFORMATION: Neutrokine-alpha BamHI forward primer

<400> SEQUENCE: 10
gtgggatcca gcctccgggc agagctg 27

<210> SEQ ID NO 11
<211> LENGTH: 33
<212> TYPE: DNA
<213> ORGANISM: Homo sapiens
<220> FEATURE:
<223> OTHER INFORMATION: Neutrokine-alpha HindIII reverse primer

<400> SEQUENCE: 11
gtgaagcttt tattacagca gtttcaatgc acc 33

<210> SEQ ID NO 12
<211> LENGTH: 26
<212> TYPE: DNA
<213> ORGANISM: Homo sapiens
<220> FEATURE:
<223> OTHER INFORMATION: Neutrokine-alpha BspHI forward primer

<400> SEQUENCE: 12
gtgtcatgag cctccgggca gagctg 26

<210> SEQ ID NO 13
<211> LENGTH: 33
<212> TYPE: DNA
<213> ORGANISM: Homo sapiens
<220> FEATURE:
<223> OTHER INFORMATION: Neutrokine-alpha HindIII reverse primer

<400> SEQUENCE: 13
gtgaagcttt tattacagca gtttcaatgc acc 33

<210> SEQ ID NO 14
<211> LENGTH: 28
<212> TYPE: DNA
<213> ORGANISM: Homo sapiens
<220> FEATURE:
<223> OTHER INFORMATION: Neutrokine-alpha BamHI forward primer

<400> SEQUENCE: 14
gtgggatccc cgggcagagc tgcagggc 28

<210> SEQ ID NO 15
<211> LENGTH: 33
<212> TYPE: DNA
<213> ORGANISM: Homo sapiens
<220> FEATURE:
<223> OTHER INFORMATION: Neutrokine-alpha BamHI reverse primer

<400> SEQUENCE: 15
gtgggatcct tattacagca gtttcaatgc acc 33

<210> SEQ ID NO 16
<211> LENGTH: 129
<212> TYPE: DNA
<213> ORGANISM: Homo sapiens
<220> FEATURE:
<223> OTHER INFORMATION: Neutrokine-alpha BamHI and IL-6 forward primer

<400> SEQUENCE: 16
gcgggatccg ccaccatgaa ctccttctcc acaagcgcct tcggtccagt tgccttctcc 60
ctggggctgc tcctggtgtt gcctgctgcc ttccctgccc cagttgtgag acaaggggac 120
ctggccagc 129

<210> SEQ ID NO 17
<211> LENGTH: 30
<212> TYPE: DNA
<213> ORGANISM: Homo sapiens
<220> FEATURE:
<223> OTHER INFORMATION: Neutrokine-alpha BamHI reverse primer

<400> SEQUENCE: 17
gtgggatcct tacagcagtt tcaatgcacc 30

<210> SEQ ID NO 18
<211> LENGTH: 903
<212> TYPE: DNA
<213> ORGANISM: Homo sapiens
<220> FEATURE:
<221> NAME/KEY: CDS
<222> LOCATION: (1)..(798)

```
<400> SEQUENCE: 18

atg gat gac tcc aca gaa agg gag cag tca cgc ctt act tct tgc ctt       48
Met Asp Asp Ser Thr Glu Arg Glu Gln Ser Arg Leu Thr Ser Cys Leu
  1               5                  10                  15

aag aaa aga gaa gaa atg aaa ctg aag gag tgt gtt tcc atc ctc cca       96
Lys Lys Arg Glu Glu Met Lys Leu Lys Glu Cys Val Ser Ile Leu Pro
             20                  25                  30

cgg aag gaa agc ccc tct gtc cga tcc tcc aaa gac gga aag ctg ctg      144
Arg Lys Glu Ser Pro Ser Val Arg Ser Ser Lys Asp Gly Lys Leu Leu
         35                  40                  45

gct gca acc ttg ctg ctg gca ctg ctg tct tgc tgc ctc acg gtg gtg      192
Ala Ala Thr Leu Leu Leu Ala Leu Leu Ser Cys Cys Leu Thr Val Val
     50                  55                  60

tct ttc tac cag gtg gcc gcc ctg caa ggg gac ctg gcc agc ctc cgg      240
Ser Phe Tyr Gln Val Ala Ala Leu Gln Gly Asp Leu Ala Ser Leu Arg
 65                  70                  75                  80

gca gag ctg cag ggc cac cac gcg gag aag ctg cca gca gga gca gga      288
Ala Glu Leu Gln Gly His His Ala Glu Lys Leu Pro Ala Gly Ala Gly
                 85                  90                  95

gcc ccc aag gcc ggc ctg gag gaa gct cca gct gtc acc gcg gga ctg      336
Ala Pro Lys Ala Gly Leu Glu Glu Ala Pro Ala Val Thr Ala Gly Leu
            100                 105                 110

aaa atc ttt gaa cca cca gct cca gga gaa ggc aac tcc agt cag aac      384
Lys Ile Phe Glu Pro Pro Ala Pro Gly Glu Gly Asn Ser Ser Gln Asn
        115                 120                 125

agc aga aat aag cgt gcc gtt cag ggt cca gaa gaa aca gga tct tac      432
Ser Arg Asn Lys Arg Ala Val Gln Gly Pro Glu Glu Thr Gly Ser Tyr
    130                 135                 140

aca ttt gtt cca tgg ctt ctc agc ttt aaa agg gga agt gcc cta gaa      480
Thr Phe Val Pro Trp Leu Leu Ser Phe Lys Arg Gly Ser Ala Leu Glu
145                 150                 155                 160

gaa aaa gag aat aaa ata ttg gtc aaa gaa act ggt tac ttt ttt ata      528
Glu Lys Glu Asn Lys Ile Leu Val Lys Glu Thr Gly Tyr Phe Phe Ile
                165                 170                 175

tat ggt cag gtt tta tat act gat aag acc tac gcc atg gga cat cta      576
Tyr Gly Gln Val Leu Tyr Thr Asp Lys Thr Tyr Ala Met Gly His Leu
            180                 185                 190

att cag agg aag aag gtc cat gtc ttt ggg gat gaa ttg agt ctg gtg      624
Ile Gln Arg Lys Lys Val His Val Phe Gly Asp Glu Leu Ser Leu Val
        195                 200                 205

act ttg ttt cga tgt att caa aat atg cct gaa aca cta ccc aat aat      672
Thr Leu Phe Arg Cys Ile Gln Asn Met Pro Glu Thr Leu Pro Asn Asn
    210                 215                 220

tcc tgc tat tca gct ggc att gca aaa ctg gaa gaa gga gat gaa ctc      720
Ser Cys Tyr Ser Ala Gly Ile Ala Lys Leu Glu Glu Gly Asp Glu Leu
225                 230                 235                 240

caa ctt gca ata cca aga gaa aat gca caa ata tca ctg gat gga gat      768
Gln Leu Ala Ile Pro Arg Glu Asn Ala Gln Ile Ser Leu Asp Gly Asp
                245                 250                 255

gtc aca ttt ttt ggt gca ttg aaa ctg ctg tgacctactt acaccatgtc        818
Val Thr Phe Phe Gly Ala Leu Lys Leu Leu
            260                 265

tgtagctatt ttcctccctt tctctgtacc tctaagaaga aagaatctaa ctgaaaatac    878

caaaaaaaaa aaaaaaaaaa aaaaa                                           903


<210> SEQ ID NO 19
<211> LENGTH: 266
<212> TYPE: PRT
<213> ORGANISM: Homo sapiens
```

<400> SEQUENCE: 19

```
Met Asp Asp Ser Thr Glu Arg Glu Gln Ser Arg Leu Thr Ser Cys Leu
  1               5                  10                  15

Lys Lys Arg Glu Glu Met Lys Leu Lys Glu Cys Val Ser Ile Leu Pro
             20                  25                  30

Arg Lys Glu Ser Pro Ser Val Arg Ser Ser Lys Asp Gly Lys Leu Leu
         35                  40                  45

Ala Ala Thr Leu Leu Leu Ala Leu Leu Ser Cys Cys Leu Thr Val Val
     50                  55                  60

Ser Phe Tyr Gln Val Ala Ala Leu Gln Gly Asp Leu Ala Ser Leu Arg
 65                  70                  75                  80

Ala Glu Leu Gln Gly His His Ala Glu Lys Leu Pro Ala Gly Ala Gly
                 85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Gly Ser Tyr
    130                 135                 140

Thr Phe Val Pro Trp Leu Leu Ser Phe Lys Arg Gly Ser Ala Leu Glu
145                 150                 155                 160

Glu Lys Glu Asn Lys Ile Leu Val Lys Glu Thr Gly Tyr Phe Phe Ile
                165                 170                 175

Tyr Gly Gln Val Leu Tyr Thr Asp Lys Thr Tyr Ala Met Gly His Leu
            180                 185                 190

Ile Gln Arg Lys Lys Val His Val Phe Gly Asp Glu Leu Ser Leu Val
        195                 200                 205

Thr Leu Phe Arg Cys Ile Gln Asn Met Pro Glu Thr Leu Pro Asn Asn
    210                 215                 220

Ser Cys Tyr Ser Ala Gly Ile Ala Lys Leu Glu Glu Gly Asp Glu Leu
225                 230                 235                 240

Gln Leu Ala Ile Pro Arg Glu Asn Ala Gln Ile Ser Leu Asp Gly Asp
                245                 250                 255

Val Thr Phe Phe Gly Ala Leu Lys Leu Leu
            260                 265
```

<210> SEQ ID NO 20
<211> LENGTH: 136
<212> TYPE: PRT
<213> ORGANISM: Homo sapiens

<400> SEQUENCE: 20

```
His Ser Val Leu His Leu Val Pro Ile Asn Ala Thr Ser Lys Asp Asp
  1               5                  10                  15

Ser Asp Val Thr Glu Val Met Trp Gln Pro Ala Leu Arg Arg Gly Arg
             20                  25                  30

Gly Leu Gln Ala Gln Gly Tyr Gly Val Arg Ile Gln Asp Ala Gly Val
         35                  40                  45

Tyr Leu Leu Tyr Ser Gln Val Leu Phe Gln Asp Val Thr Phe Thr Met
     50                  55                  60

Gly Gln Val Val Ser Arg Glu Gly Gln Gly Arg Gln Glu Thr Leu Phe
 65                  70                  75                  80

Arg Cys Ile Arg Ser Met Pro Ser His Pro Asp Arg Ala Tyr Asn Ser
                 85                  90                  95

Cys Tyr Ser Ala Gly Val Phe His Leu His Gln Gly Asp Ile Leu Ser
```

-continued

```
            100                 105                 110

Val Ile Ile Pro Arg Ala Arg Ala Lys Leu Asn Leu Ser Pro His Gly
        115                 120                 125

Thr Phe Leu Gly Phe Val Lys Leu
    130                 135


<210> SEQ ID NO 21
<211> LENGTH: 462
<212> TYPE: DNA
<213> ORGANISM: Homo sapiens

<400> SEQUENCE: 21

atggctgttc agggtccgga agaaaccgtt actcaggact gccttcagct gatcgcagac      60

tctgaaactc cgaccatcca gaaaggttct tacacctttg ttccttggct gctttctttc     120

aaacgtggtt ctgccctgga agagaaagaa aacaaaatcc tggttaaaga aactggttac     180

ttctttatct acggtcaggt tctttacact gataagacct acgccatggg tcacctgatt     240

cagcgtaaga aagttcacgt tttcggtgac gagctgtctc tggttactct gtttcgctgc     300

attcagaaca tgccggaaac tcttcctaac aactcctgct actctgctgg catcgcaaaa     360

ctggaagagg gtgatgaact gcagctggca attcctcgtg aaaacgcaca aatttctctg     420

gacggtgatg taaccttctt tggtgcactg aaacttctgt aa                        462


<210> SEQ ID NO 22
<211> LENGTH: 1040
<212> TYPE: DNA
<213> ORGANISM: Mus musculus
<220> FEATURE:
<221> NAME/KEY: CDS
<222> LOCATION: (1)..(468)

<400> SEQUENCE: 22

cgc gtg gta gac ctc tca gct cct cct gca cca tgc ctg cct gga tgc       48
Arg Val Val Asp Leu Ser Ala Pro Pro Ala Pro Cys Leu Pro Gly Cys
  1               5                  10                  15

cgc cat tct caa cat gat gat aat gga atg aac ctc aga aac aga act       96
Arg His Ser Gln His Asp Asp Asn Gly Met Asn Leu Arg Asn Arg Thr
             20                  25                  30

tac aca ttt gtt cca tgg ctt ctc agc ttt aaa aga gga aat gcc ttg      144
Tyr Thr Phe Val Pro Trp Leu Leu Ser Phe Lys Arg Gly Asn Ala Leu
         35                  40                  45

gag gag aaa gag aac aaa ata gtg gtg agg caa aca ggc tat ttc ttc      192
Glu Glu Lys Glu Asn Lys Ile Val Val Arg Gln Thr Gly Tyr Phe Phe
     50                  55                  60

atc tac agc cag gtt cta tac acg gac ccc atc ttt gct atg ggt cat      240
Ile Tyr Ser Gln Val Leu Tyr Thr Asp Pro Ile Phe Ala Met Gly His
 65                  70                  75                  80

gtc atc cag agg aag aaa gta cac gtc ttt ggg gac gag ctg agc ctg      288
Val Ile Gln Arg Lys Lys Val His Val Phe Gly Asp Glu Leu Ser Leu
                 85                  90                  95

gtg acc ctg ttc cga tgt att cag aat atg ccc aaa aca ctg ccc aac      336
Val Thr Leu Phe Arg Cys Ile Gln Asn Met Pro Lys Thr Leu Pro Asn
            100                 105                 110

aat tcc tgc tac tcg gct ggc atc gcg agg ctg gaa gaa gga gat gag      384
Asn Ser Cys Tyr Ser Ala Gly Ile Ala Arg Leu Glu Glu Gly Asp Glu
        115                 120                 125

att cag ctt gca att cct cgg gag aat gca cag att tca cgc aac gga      432
Ile Gln Leu Ala Ile Pro Arg Glu Asn Ala Gln Ile Ser Arg Asn Gly
    130                 135                 140

gac gac acc ttc ttt ggt gcc cta aaa ctg ctg taa ctcacttgct          478
```

Asp Asp Thr Phe Phe Gly Ala Leu Lys Leu Leu
145 150 155 ggagtgcgtg atccccttcc ctcgtcttct ctgtacctcc gagggagaaa cagacgactg 538 gaaaaactaa aagatgggga aagccgtcag cgaaagtttt ctcgtgaccc gttgaatctg 598 atccaaacca ggaaatataa cagacagcca caaccgaagt gtgccatgtg agttatgaga 658 aacggagccc gcgctcagaa agaccggatg aggaagaccg ttttctccag tcctttgcca 718 acacgcaccg caaccttgct ttttgccttg ggtgacacat gttcagaatg cagggagatt 778 tccttgtttt gcgatttgcc atgagaagag ggcccacaac tgcaggtcac tgaagcattc 838 acgctaagtc tcaggattta ctctcccttc tcatgctaag tacacacacg ctcttttcca 898 ggtaatacta tgggatacta tggaaaggtt gtttgttttt aaatctagaa gtcttgaact 958 ggcaatagac aaaaatcctt ataaattcaa gtgtaaaata aacttaatta aaaaggttta 1018 agtgtgaaaa aaaaaaaaaa aa 1040

<210> SEQ ID NO 23
<211> LENGTH: 155
<212> TYPE: PRT
<213> ORGANISM: Mus musculus

<400> SEQUENCE: 23

Arg Val Val Asp Leu Ser Ala Pro Pro Ala Pro Cys Leu Pro Gly Cys
1 5 10 15

Arg His Ser Gln His Asp Asp Asn Gly Met Asn Leu Arg Asn Arg Thr
20 25 30

Tyr Thr Phe Val Pro Trp Leu Leu Ser Phe Lys Arg Gly Asn Ala Leu
35 40 45

Glu Glu Lys Glu Asn Lys Ile Val Val Arg Gln Thr Gly Tyr Phe Phe
50 55 60

Ile Tyr Ser Gln Val Leu Tyr Thr Asp Pro Ile Phe Ala Met Gly His
65 70 75 80

Val Ile Gln Arg Lys Lys Val His Val Phe Gly Asp Glu Leu Ser Leu
85 90 95

Val Thr Leu Phe Arg Cys Ile Gln Asn Met Pro Lys Thr Leu Pro Asn
100 105 110

Asn Ser Cys Tyr Ser Ala Gly Ile Ala Arg Leu Glu Glu Gly Asp Glu
115 120 125

Ile Gln Leu Ala Ile Pro Arg Glu Asn Ala Gln Ile Ser Arg Asn Gly
130 135 140

Asp Asp Thr Phe Phe Gly Ala Leu Lys Leu Leu
145 150 155

<210> SEQ ID NO 24
<211> LENGTH: 26
<212> TYPE: DNA
<213> ORGANISM: Homo sapiens

<400> SEQUENCE: 24
ccaccagctc caggagaagg caactc 26

<210> SEQ ID NO 25
<211> LENGTH: 19
<212> TYPE: DNA
<213> ORGANISM: Homo sapiens

<400> SEQUENCE: 25
accgcgggac tgaaaatct 19

<210> SEQ ID NO 26
<211> LENGTH: 23
<212> TYPE: DNA
<213> ORGANISM: Homo sapiens

<400> SEQUENCE: 26
cacgcttatt tctgctgttc tga 23

<210> SEQ ID NO 27
<211> LENGTH: 657
<212> TYPE: DNA
<213> ORGANISM: Macaca irus

<400> SEQUENCE: 27
taccaggtgg cggccgtgca aggggacctg gccagcctcc gggcagagct gcagggccac 60
cacgcggaga agctgccagc aagagcaaga gcccccaagg ccggtctggg ggaagctcca 120
gctgtcaccg caggactgaa aatctttgaa ccaccagctc caggagaagg caactccagt 180
cagagcagca gaaataagcg tgctattcag ggtgcagaag aaacagtcat tcaagactgc 240
ttgcaactga ttgcagacag tgaaacacca actatacaaa aaggatctta cacatttgtt 300
ccatggcttc tcagctttaa aaggggaagt gccctagaag aaaaagagaa taaaatattg 360
gtcaaagaaa ctggttactt ttttatatat ggtcaggttt tatacactga taagacctat 420
gccatgggac atctaattca gaggaaaaaa gtccatgtct ttggggatga attgagtctg 480
gtgactttgt ttcgatgtat tcaaaatatg cctgaaacac tacccaataa ttcctgctat 540
tcagctggca ttgcaaaact ggaagaagga gatgaacttc aacttgcaat accacgagaa 600
aatgcacaaa tatcactgga tggagatgtc acattttttg gtgccctcaa actgctg 657

<210> SEQ ID NO 28
<211> LENGTH: 219
<212> TYPE: PRT
<213> ORGANISM: Macaca irus

<400> SEQUENCE: 28

Tyr Gln Val Ala Ala Val Gln Gly Asp Leu Ala Ser Leu Arg Ala Glu
1 5 10 15

Leu Gln Gly His His Ala Glu Lys Leu Pro Ala Arg Ala Arg Ala Pro
20 25 30

Lys Ala Gly Leu Gly Glu Ala Pro Ala Val Thr Ala Gly Leu Lys Ile
35 40 45

Phe Glu Pro Pro Ala Pro Gly Glu Gly Asn Ser Ser Gln Ser Ser Arg
50 55 60

Asn Lys Arg Ala Ile Gln Gly Ala Glu Glu Thr Val Ile Gln Asp Cys
65 70 75 80

Leu Gln Leu Ile Ala Asp Ser Glu Thr Pro Thr Ile Gln Lys Gly Ser
85 90 95

Tyr Thr Phe Val Pro Trp Leu Leu Ser Phe Lys Arg Gly Ser Ala Leu
100 105 110

Glu Glu Lys Glu Asn Lys Ile Leu Val Lys Glu Thr Gly Tyr Phe Phe
115 120 125

Ile Tyr Gly Gln Val Leu Tyr Thr Asp Lys Thr Tyr Ala Met Gly His
130 135 140

Leu Ile Gln Arg Lys Lys Val His Val Phe Gly Asp Glu Leu Ser Leu
145 150 155 160

Val Thr Leu Phe Arg Cys Ile Gln Asn Met Pro Glu Thr Leu Pro Asn

```
                165                 170                 175

Asn Ser Cys Tyr Ser Ala Gly Ile Ala Lys Leu Glu Glu Gly Asp Glu
            180                 185                 190

Leu Gln Leu Ala Ile Pro Arg Glu Asn Ala Gln Ile Ser Leu Asp Gly
        195                 200                 205

Asp Val Thr Phe Phe Gly Ala Leu Lys Leu Leu
    210                 215


<210> SEQ ID NO 29
<211> LENGTH: 657
<212> TYPE: DNA
<213> ORGANISM: Macaca mulatta (Rhesus Monkey)

<400> SEQUENCE: 29

taccaggtgg cggccgtgca aggggacctg gccagcctcc gggcagagct gcagagccac      60

cacgcggaga agctgccagc aagagcaaga gcccccaagg ccggtctggg ggaagctcca     120

gctgtcaccg cgggactgaa aatctttgaa ccaccagctc caggagaagg caactccagt     180

cagagcagca gaaataagcg tgctattcag ggtgcagaag aaacagtcat tcaagactgc     240

ttgcaactga ttgcagacag tgaaacacca actatacaaa aaggatctta cacatttgtt     300

ccatggcttc tcagctttaa aaggggaagt gccctagaag aaaaagagaa taaaatattg     360

gtcaaagaaa ctggttactt ttttatatat ggtcaggttt tatacactga taagacctat     420

gccatgggac atctaattca gaggaaaaaa gtccatgtct ttggggatga attgagtctg     480

gtgactttgt ttcgatgtat tcaaaatatg cctgaaacac tacccaataa ttcctgctat     540

tcagctggca ttgcaaaact ggaagaaggg gatgaacttc aacttgcaat accacgagaa     600

aatgcacaaa tatcactgga tggagatgtc acatttttg gtgccctcaa actgctg        657


<210> SEQ ID NO 30
<211> LENGTH: 219
<212> TYPE: PRT
<213> ORGANISM: Macaca mulatta (Rhesus Monkey)

<400> SEQUENCE: 30

Tyr Gln Val Ala Ala Val Gln Gly Asp Leu Ala Ser Leu Arg Ala Glu
  1               5                  10                  15

Leu Gln Ser His His Ala Glu Lys Leu Pro Ala Arg Ala Arg Ala Pro
             20                  25                  30

Lys Ala Gly Leu Gly Glu Ala Pro Ala Val Thr Ala Gly Leu Lys Ile
         35                  40                  45

Phe Glu Pro Pro Ala Pro Gly Glu Gly Asn Ser Ser Gln Ser Ser Arg
     50                  55                  60

Asn Lys Arg Ala Ile Gln Gly Ala Glu Glu Thr Val Ile Gln Asp Cys
 65                  70                  75                  80

Leu Gln Leu Ile Ala Asp Ser Glu Thr Pro Thr Ile Gln Lys Gly Ser
                 85                  90                  95

Tyr Thr Phe Val Pro Trp Leu Leu Ser Phe Lys Arg Gly Ser Ala Leu
            100                 105                 110

Glu Glu Lys Glu Asn Lys Ile Leu Val Lys Glu Thr Gly Tyr Phe Phe
        115                 120                 125

Ile Tyr Gly Gln Val Leu Tyr Thr Asp Lys Thr Tyr Ala Met Gly His
    130                 135                 140

Leu Ile Gln Arg Lys Lys Val His Val Phe Gly Asp Glu Leu Ser Leu
145                 150                 155                 160

Val Thr Leu Phe Arg Cys Ile Gln Asn Met Pro Glu Thr Leu Pro Asn
```

```
            165                 170                 175

Asn Ser Cys Tyr Ser Ala Gly Ile Ala Lys Leu Glu Glu Gly Asp Glu
            180                 185                 190

Leu Gln Leu Ala Ile Pro Arg Glu Asn Ala Gln Ile Ser Leu Asp Gly
        195                 200                 205

Asp Val Thr Phe Phe Gly Ala Leu Lys Leu Leu
    210                 215


<210> SEQ ID NO 31
<211> LENGTH: 38
<212> TYPE: DNA
<213> ORGANISM: Homo sapiens
<220> FEATURE:
<223> OTHER INFORMATION: Neutrokine-alpha PSC forward primer

<400> SEQUENCE: 31

ggtcgccgtt tctaacgcgg ccgttcaggg tccagaag                              38


<210> SEQ ID NO 32
<211> LENGTH: 49
<212> TYPE: DNA
<213> ORGANISM: Homo sapiens
<220> FEATURE:
<223> OTHER INFORMATION: Reverse primer for amplifying Neutrokine-alpha

<400> SEQUENCE: 32

ctggttcggc ccaaggtacc aagcttgtac cttagatctt ttctagatc                  49


<210> SEQ ID NO 33
<211> LENGTH: 21
<212> TYPE: DNA
<213> ORGANISM: Homo sapiens
<220> FEATURE:
<223> OTHER INFORMATION: forward primer that for PSC baculovirus

<400> SEQUENCE: 33

ctggtagttc ttcggagtgt g                                                21


<210> SEQ ID NO 34
<211> LENGTH: 19
<212> TYPE: DNA
<213> ORGANISM: Homo sapiens
<220> FEATURE:
<223> OTHER INFORMATION: reverse primer for PSC baculovirus

<400> SEQUENCE: 34

cgcgttagaa acggcgacc                                                   19


<210> SEQ ID NO 35
<211> LENGTH: 22
<212> TYPE: DNA
<213> ORGANISM: Homo sapiens
<220> FEATURE:
<221> NAME/KEY: misc_feature
<222> LOCATION: (7)
<223> OTHER INFORMATION: n equals deoxyinosine or dideoxyinosine
<220> FEATURE:
<221> NAME/KEY: misc_feature
<222> LOCATION: (12)
<223> OTHER INFORMATION: n equals deoxyinosine or dideoxyinosine
<220> FEATURE:
<221> NAME/KEY: misc_feature
<222> LOCATION: (16)
<223> OTHER INFORMATION: n equals deoxyinosine or dideoxyinosine
<220> FEATURE:
<223> OTHER INFORMATION: Neutrokine-alpha degenerate oligo fwd primer

<400> SEQUENCE: 35
```

taccagntgg cngccntgca ag 22

<210> SEQ ID NO 36
<211> LENGTH: 22
<212> TYPE: DNA
<213> ORGANISM: Homo sapiens
<220> FEATURE:
<221> NAME/KEY: misc_feature
<222> LOCATION: (3)
<223> OTHER INFORMATION: n equals deoxyinosine or dideoxyinosine
<220> FEATURE:
<221> NAME/KEY: misc_feature
<222> LOCATION: (14)
<223> OTHER INFORMATION: n equals deoxyinosine or dideoxyinosine
<220> FEATURE:
<221> NAME/KEY: misc_feature
<222> LOCATION: (16)..(17)
<223> OTHER INFORMATION: n equals deoxyinosine or dideoxyinosine
<220> FEATURE:
<223> OTHER INFORMATION: Neutrokine-alpha degenerate oligo rev primer

<400> SEQUENCE: 36
gtnacagcag tttnanngca cc 22

<210> SEQ ID NO 37
<211> LENGTH: 867
<212> TYPE: DNA
<213> ORGANISM: Mus musculus

<400> SEQUENCE: 37
atggatgagt ctgcaaagac cctgccacca ccgtgcctct gtttttgctc cgagaaagga 60
gaagatatga aagtgggata tgatcccatc actccgcaga aggaggaggg tgcctggttt 120
gggatctgca gggatggaag gctgctggct gctaccctcc tgctggccct gttgtccagc 180
agtttcacag cgatgtcctt gtaccagttg gctgccttgc aagcagacct gatgaacctg 240
cgcatggagc tgcagagcta ccgaggttca gcaacaccag ccgccgcggg tgctccagag 300
ttgaccgctg gagtcaaact cctgacaccg gcagctcctc gaccccacaa ctccagccgc 360
ggccacagga acagacgcgc cttccaggga ccagaggaaa cagaacaaga tgtagacctc 420
tcagctcctc ctgcaccatg cctgcctgga tgccgccatt ctcaacatga tgataatgga 480
atgaacctca gaaacatcat tcaagactgt ctgcagctga ttgcagacag cgacacgccg 540
gccttggagg agaaagagaa caaaatagtg gtgaggcaaa caggctattt cttcatctac 600
agccaggttc tatacacgga ccccatcttt gctatgggtc atgtcatcca gaggaagaaa 660
gtacacgtct ttggggacga gctgagcctg gtgaccctgt tccgatgtat tcagaatatg 720
cccaaaacac tgcccaacaa ttcctgctac tcggctggca tcgcgaggct ggaagaagga 780
gatgagattc agcttgcaat tcctcgggag aatgcacaga tttcacgcaa cggagacgac 840
accttctttg gtgccctaaa actgctg 867

<210> SEQ ID NO 38
<211> LENGTH: 289
<212> TYPE: PRT
<213> ORGANISM: Mus musculus

<400> SEQUENCE: 38

Met Asp Glu Ser Ala Lys Thr Leu Pro Pro Pro Cys Leu Cys Phe Cys
1 5 10 15

Ser Glu Lys Gly Glu Asp Met Lys Val Gly Tyr Asp Pro Ile Thr Pro
20 25 30

Gln Lys Glu Glu Gly Ala Trp Phe Gly Ile Cys Arg Asp Gly Arg Leu

```
        35                  40                  45

Leu Ala Ala Thr Leu Leu Leu Ala Leu Leu Ser Ser Ser Phe Thr Ala
     50                  55                  60

Met Ser Leu Tyr Gln Leu Ala Ala Leu Gln Ala Asp Leu Met Asn Leu
 65                  70                  75                  80

Arg Met Glu Leu Gln Ser Tyr Arg Gly Ser Ala Thr Pro Ala Ala Ala
                 85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Ala Leu Glu Glu Lys Glu Asn Lys Ile Val Val Arg
            180                 185                 190

Gln Thr Gly Tyr Phe Phe Ile Tyr Ser Gln Val Leu Tyr Thr Asp Pro
        195                 200                 205

Ile Phe Ala Met Gly His Val Ile Gln Arg Lys Lys Val His Val Phe
    210                 215                 220

Gly Asp Glu Leu Ser Leu Val Thr Leu Phe Arg Cys Ile Gln Asn Met
225                 230                 235                 240

Pro Lys Thr Leu Pro Asn Asn Ser Cys Tyr Ser Ala Gly Ile Ala Arg
                245                 250                 255

Leu Glu Glu Gly Asp Glu Ile Gln Leu Ala Ile Pro Arg Glu Asn Ala
            260                 265                 270

Gln Ile Ser Arg Asn Gly Asp Asp Thr Phe Phe Gly Ala Leu Lys Leu
        275                 280                 285

Leu


<210> SEQ ID NO 39
<211> LENGTH: 309
<212> TYPE: PRT
<213> ORGANISM: Mus musculus

<400> SEQUENCE: 39

Met Asp Glu Ser Ala Lys Thr Leu Pro Pro Pro Cys Leu Cys Phe Cys
  1               5                  10                  15

Ser Glu Lys Gly Glu Asp Met Lys Val Gly Tyr Asp Pro Ile Thr Pro
             20                  25                  30

Gln Lys Glu Glu Gly Ala Trp Phe Gly Ile Cys Arg Asp Gly Arg Leu
         35                  40                  45

Leu Ala Ala Thr Leu Leu Leu Ala Leu Leu Ser Ser Ser Phe Thr Ala
     50                  55                  60

Met Ser Leu Tyr Gln Leu Ala Ala Leu Gln Ala Asp Leu Met Asn Leu
 65                  70                  75                  80

Arg Met Glu Leu Gln Ser Tyr Arg Gly Ser Ala Thr Pro Ala Ala Ala
                 85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125
```

```
Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
            180                 185                 190

Leu Leu Ser Phe Lys Arg Gly Asn Ala Leu Glu Glu Lys Glu Asn Lys
        195                 200                 205

Ile Val Val Arg Gln Thr Gly Tyr Phe Phe Ile Tyr Ser Gln Val Leu
    210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
            260                 265                 270

Gly Ile Ala Arg Leu Glu Glu Gly Asp Glu Ile Gln Leu Ala Ile Pro
        275                 280                 285

Arg Glu Asn Ala Gln Ile Ser Arg Asn Gly Asp Asp Thr Phe Phe Gly
    290                 295                 300

Ala Leu Lys Leu Leu
305


<210> SEQ ID NO 40
<211> LENGTH: 290
<212> TYPE: PRT
<213> ORGANISM: Mus musculus

<400> SEQUENCE: 40

Met Asp Glu Ser Ala Lys Thr Leu Pro Pro Pro Cys Leu Cys Phe Cys
  1               5                  10                  15

Ser Glu Lys Gly Glu Asp Met Lys Val Gly Tyr Asp Pro Ile Thr Pro
             20                  25                  30

Gln Lys Glu Glu Gly Ala Trp Phe Gly Ile Cys Arg Asp Gly Arg Leu
         35                  40                  45

Leu Ala Ala Thr Leu Leu Leu Ala Leu Leu Ser Ser Ser Phe Thr Ala
     50                  55                  60

Met Ser Leu Tyr Gln Leu Ala Ala Leu Gln Ala Asp Leu Met Asn Leu
 65                  70                  75                  80

Arg Met Glu Leu Gln Ser Tyr Arg Gly Ser Ala Thr Pro Ala Ala Ala
                 85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Arg Thr Tyr Thr Phe Val Pro Trp Leu Leu Ser
                165                 170                 175

Phe Lys Arg Gly Asn Ala Leu Glu Glu Lys Glu Asn Lys Ile Val Val
            180                 185                 190
```

```
Arg Gln Thr Gly Tyr Phe Phe Ile Tyr Ser Gln Val Leu Tyr Thr Asp
        195                 200                 205

Pro Ile Phe Ala Met Gly His Val Ile Gln Arg Lys Lys Val His Val
    210                 215                 220

Phe Gly Asp Glu Leu Ser Leu Val Thr Leu Phe Arg Cys Ile Gln Asn
225                 230                 235                 240

Met Pro Lys Thr Leu Pro Asn Asn Ser Cys Tyr Ser Ala Gly Ile Ala
                245                 250                 255

Arg Leu Glu Glu Gly Asp Glu Ile Gln Leu Ala Ile Pro Arg Glu Asn
            260                 265                 270

Ala Gln Ile Ser Arg Asn Gly Asp Asp Thr Phe Phe Gly Ala Leu Lys
        275                 280                 285

Leu Leu
    290


<210> SEQ ID NO 41
<211> LENGTH: 152
<212> TYPE: PRT
<213> ORGANISM: Rattus sp

<400> SEQUENCE: 41

Ala Phe Gln Gly Pro Glu Glu Thr Val Ile Gln Asp Cys Leu Gln Leu
  1               5                  10                  15

Ile Ala Asp Ser Asn Thr Pro Thr Ile Arg Lys Gly Thr Tyr Thr Phe
            20                  25                  30

Val Pro Trp Leu Leu Ser Phe Lys Arg Gly Asn Ala Leu Glu Glu Lys
        35                  40                  45

Glu Asn Lys Ile Val Val Arg Gln Thr Gly Tyr Phe Phe Ile Tyr Ser
     50                  55                  60

Gln Val Leu Tyr Thr Asp Pro Ile Phe Ala Met Gly His Val Ile Gln
 65                  70                  75                  80

Arg Lys Lys Ile His Val Phe Gly Asp Glu Leu Ser Leu Val Thr Leu
                85                  90                  95

Phe Arg Cys Ile Gln Asn Met Pro Lys Thr Leu Pro Asn Asn Ser Cys
            100                 105                 110

Tyr Ser Ala Gly Ile Ala Lys Leu Glu Glu Gly Asp Glu Val Gln Leu
        115                 120                 125

Ala Ile Pro Arg Glu Asn Ala Gln Ile Ser Arg Asn Gly Asp Asp Thr
    130                 135                 140

Phe Phe Gly Ala Leu Lys Leu Leu
145                 150


<210> SEQ ID NO 42
<211> LENGTH: 165
<212> TYPE: PRT
<213> ORGANISM: Rattus sp

<400> SEQUENCE: 42

Ala Phe Gln Gly Pro Glu Glu Thr Glu Gln Asp Val Asp Leu Ser Ala
  1               5                  10                  15

Thr Pro Val Pro Ser Leu Pro Gly Asn Cys His Ala Ser His His Asp
            20                  25                  30

Glu Asn Gly Leu Asn Leu Arg Thr Arg Thr Tyr Thr Phe Val Pro Trp
        35                  40                  45

Leu Leu Ser Phe Lys Arg Gly Asn Ala Leu Glu Glu Lys Glu Asn Lys
     50                  55                  60
```

```
Ile Val Val Arg Gln Thr Gly Tyr Phe Phe Ile Tyr Ser Gln Val Leu
 65                  70                  75                  80

Tyr Thr Asp Pro Ile Phe Ala Met Gly His Val Ile Gln Arg Lys Lys
                 85                  90                  95

Ile His Val Phe Gly Asp Glu Leu Ser Leu Val Thr Leu Phe Arg Cys
            100                 105                 110

Ile Gln Asn Met Pro Lys Thr Leu Pro Asn Asn Ser Cys Tyr Ser Ala
        115                 120                 125

Gly Ile Ala Lys Leu Glu Glu Gly Asp Glu Ile Gln Leu Ala Ile Pro
    130                 135                 140

Arg Glu Asn Ala Gln Ile Ser Arg Asn Gly Asp Asp Thr Phe Phe Gly
145                 150                 155                 160

Ala Leu Lys Leu Leu
                165
```

<210> SEQ ID NO 43
<211> LENGTH: 184
<212> TYPE: PRT
<213> ORGANISM: Rattus sp

<400> SEQUENCE: 43

```
Ala Phe Gln Gly Pro Glu Glu Thr Glu Gln Asp Val Asp Leu Ser Ala
  1               5                  10                  15

Thr Pro Ala Pro Ser Leu Pro Gly Asn Cys His Ala Ser His His Asp
             20                  25                  30

Glu Asn Gly Leu Asn Leu Arg Thr Ile Ile Gln Asp Cys Leu Gln Leu
         35                  40                  45

Ile Ala Asp Ser Asn Thr Pro Thr Ile Arg Lys Gly Thr Tyr Thr Phe
     50                  55                  60

Val Pro Trp Leu Leu Ser Phe Lys Arg Gly Asn Ala Leu Glu Glu Lys
 65                  70                  75                  80

Glu Asn Lys Ile Val Val Arg Gln Thr Gly Tyr Phe Phe Ile Tyr Ser
                 85                  90                  95

Gln Val Leu Tyr Thr Asp Pro Ile Phe Ala Met Gly His Val Ile Gln
            100                 105                 110

Arg Lys Lys Ile His Val Phe Gly Asp Glu Leu Ser Leu Val Thr Leu
        115                 120                 125

Phe Arg Cys Ile Gln Asn Met Pro Lys Thr Leu Pro Asn Asn Ser Cys
    130                 135                 140

Tyr Ser Ala Gly Ile Ala Lys Leu Glu Glu Gly Asp Glu Ile Gln Leu
145                 150                 155                 160

Ala Ile Pro Arg Glu Asn Ala Gln Ile Ser Arg Asn Gly Asp Asp Thr
                165                 170                 175

Phe Phe Gly Ala Leu Lys Leu Leu
            180
```

<210> SEQ ID NO 44
<211> LENGTH: 133
<212> TYPE: PRT
<213> ORGANISM: Rattus sp

<400> SEQUENCE: 44

```
Ala Phe Gln Gly Pro Glu Glu Thr Gly Thr Tyr Thr Phe Val Pro Trp
  1               5                  10                  15

Leu Leu Ser Phe Lys Arg Gly Asn Ala Leu Glu Glu Lys Glu Asn Lys
             20                  25                  30

Ile Val Val Arg Gln Thr Gly Tyr Phe Phe Ile Tyr Ser Gln Val Leu
```

```
        35                  40                  45

Tyr Thr Asp Pro Ile Phe Ala Met Gly His Val Ile Gln Arg Lys Lys
     50                  55                  60

Ile His Val Phe Gly Asp Glu Leu Ser Leu Val Thr Leu Phe Arg Cys
 65                  70                  75                  80

Ile Gln Asn Met Pro Lys Thr Leu Pro Asn Asn Ser Cys Tyr Ser Ala
                 85                  90                  95

Gly Ile Ala Lys Leu Glu Glu Gly Asp Glu Ile Gln Leu Ala Ile Pro
            100                 105                 110

Arg Glu Asn Ala Gln Ile Ser Arg Asn Gly Asp Asp Thr Phe Phe Gly
        115                 120                 125

Ala Leu Lys Leu Leu
    130


<210> SEQ ID NO 45
<211> LENGTH: 17
<212> TYPE: PRT
<213> ORGANISM: Homo sapiens

<400> SEQUENCE: 45

Met Leu Gln Asn Ser Ala Val Leu Leu Leu Leu Val Ile Ser Ala Ser
  1               5                  10                  15

Ala


<210> SEQ ID NO 46
<211> LENGTH: 22
<212> TYPE: PRT
<213> ORGANISM: Artificial Sequence
<220> FEATURE:
<223> OTHER INFORMATION: consensus signal sequence

<400> SEQUENCE: 46

Met Pro Thr Trp Ala Trp Trp Leu Phe Leu Val Leu Leu Leu Ala Leu
  1               5                  10                  15

Trp Ala Pro Ala Arg Gly
            20


<210> SEQ ID NO 47
<211> LENGTH: 250
<212> TYPE: PRT
<213> ORGANISM: Homo sapiens

<400> SEQUENCE: 47

Met Pro Ala Ser Ser Pro Phe Leu Leu Ala Pro Lys Gly Pro Pro Gly
  1               5                  10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
     50                  55                  60

Leu Gln Gly Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                 85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125
```

```
Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250
```

<210> SEQ ID NO 48
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 48
cagactggat ccgccaccat ggatgactcc acagaaag 38

<210> SEQ ID NO 49
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 49
cagactggta ccgtcctgcg tgcactacat ggc 33

<210> SEQ ID NO 50
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 50
tggtgtcttt ctaccaggtg g 21

<210> SEQ ID NO 51
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 51
tttcttctgg accctgaacg g 21

<210> SEQ ID NO 52
<211> LENGTH: 4458
<212> TYPE: DNA
<213> ORGANISM: Artificial
<220> FEATURE:
<223> OTHER INFORMATION: pML124

<400> SEQUENCE: 52

```
gaattcaact tctccatact ttggataagg aaatacagac atgaaaaatc tcattgctga     60
gttgttattt aagcttgccc aaaaagaaga agagtcgaat gaactgtgtg cgcaggtaga    120
agctttggag attatcgtca ctgcaatgct tcgcaatatg gcgcaaaatg accaacagcg    180
gttgattgat caggtagagg gggcgctgta cgaggtaaag cccgatgcca gcattcctga    240
cgacgatacg gagctgctgc gcgattacgt aaagaagtta ttgaagcatc ctcgtcagta    300
aaaagttaat cttttcaaca gctgtcataa agttgtcacg gccgagactt atagtcgctt    360
tgtttttatt ttttaatgta tttgtaacta gtacgcaagt tcacgtaaag gaagtatctc    420
atatgcagat cttcgtgtaa accggtaccg gcaaaaccat cactctagaa gtggatcctc    480
tacgccggac gcatcgtggc cggcatcacc ggcgccacag gtgcggttgc tggcgcctat    540
atcgccgaca tcaccgatgg ggaagatcgg gctcgccact tcgggctcat gagcgcttgt    600
ttcggcgtgg gtatggtggc aggccccgtg gccgggggac tgttgggcgc catctccttg    660
catgcaccat tccttgcggc ggcggtgctc aacggcctca acctactact gggctgcttc    720
ctaatgcagg agtcgcataa gggagagcgt cgaccgatgc ccttgagagc cttcaaccca    780
gtcagctcct tccggtgggc gcggggcatg actatcgtcg ccgcacttat gactgtcttc    840
tttatcatgc aactcgtagg acaggtgccg gcagcgctct gggtcatttt cggcgaggac    900
cgctttcgct ggagcgcgac gatgatcggc ctgtcgcttg cggtattcgg aatcttgcac    960
gccctcgctc aagccttcgt cactggtccc gccaccaaac gtttcggcga gaagcaggcc   1020
attatcgccg gcatggcggc cgacgcgctg ggctacgtct tgctggcgtt cgcgacgcga   1080
ggctggatgg ccttccccat tatgattctt ctcgcttccg gcggcatcgg gatgcccgcg   1140
ttgcaggcca tgctgtccag gcaggtagat gacgaccatc agggacagct tcaaggatcg   1200
ctcgcggctc ttaccagcct aacttcgatc actggaccgc tgatcgtcac ggcgatttat   1260
gccgcctcgg cgagcacatg gaacgggttg gcatggattg taggcgccgc cctatacctt   1320
gtctgcctcc ccgcgttgcg tcgcggtgca tggagccggg ccacctcgac ctgaatggaa   1380
gccggcggca cctcgctaac ggattcacca ctccaagaat tggagccaat caattcttgc   1440
ggagaactgt gaatgcgcaa accaaccctt ggcagaacat atccatcgcg tccgccatct   1500
ccagcagccg cacgcggcgc atctcgggca gcgttgggtc ctggccacgg gtgcgcatga   1560
tcgtgctcct gtcgttgagg acccggctag gctggcgggg ttgccttact ggttagcaga   1620
atgaatcacc gatacgcgag cgaacgtgaa gcgactgctg ctgcaaaacg tctgcgacct   1680
gagcaacaac atgaatggtc ttcggtttcc gtgtttcgta aagtctggaa acgcggaagt   1740
cagcgccctg caccattatg ttccggatct gcatcgcagg atgctgctgg ctaccctgtg   1800
gaacacctac atctgtatta acgaagcgct ggcattgacc ctgagtgatt tttctctggt   1860
cccgccgcat ccataccgcc agttgtttac cctcacaacg ttccagtaac cgggcatgtt   1920
catcatcagt aacccgtatc gtgagcatcc tctctcgttt catcggtatc attaccccca   1980
tgaacagaaa tcccccttac acggaggcat cagtgaccaa acaggaaaaa accgccctta   2040
acatggcccg ctttatcaga agccagacat taacgcttct ggagaaactc aacgagctgg   2100
acgcggatga acaggcagac atctgtgaat cgcttcacga ccacgctgat gagctttacc   2160
gcagctgcct cgcgcgtttc ggtgatgacg gtgaaaacct ctgacacatg cagctcccgg   2220
agacggtcac agcttgtctg taagcggatg ccgggagcag acaagcccgt cagggcgcgt   2280
cagcgggtgt tggcgggtgt cggggcgcag ccatgaccca gtcacgtagc gatagcggag   2340
```

tgtatactgg cttaactatg cggcatcaga gcagattgta ctgagagtgc accatatatg 2400
cggtgtgaaa taccgcacag atgcgtaagg agaaaatacc gcatcaggcg ctcttccgct 2460
tcctcgctca ctgactcgct gcgctcggtc gttcggctgc ggcgagcggt atcagctcac 2520
tcaaaggcgg taatacggtt atccacagaa tcaggggata acgcaggaaa gaacatgtga 2580
gcaaaaggcc agcaaaaggc caggaaccgt aaaaaggccg cgttgctggc gtttttccat 2640
aggctccgcc cccctgacga gcatcacaaa aatcgacgct caagtcagag gtggcgaaac 2700
ccgacaggac tataaagata ccaggcgttt ccccctggaa gctccctcgt gcgctctcct 2760
gttccgaccc tgccgcttac cggatacctg tccgcctttc tcccttcggg aagcgtggcg 2820
ctttctcata gctcacgctg taggtatctc agttcggtgt aggtcgttcg ctccaagctg 2880
ggctgtgtgc acgaaccccc cgttcagccc gaccgctgcg ccttatccgg taactatcgt 2940
cttgagtcca acccggtaag acacgactta tcgccactgg cagcagccac tggtaacagg 3000
attagcagag cgaggtatgt aggcggtgct acagagttct tgaagtggtg gcctaactac 3060
ggctacacta gaaggacagt atttggtatc tgcgctctgc tgaagccagt taccttcgga 3120
aaaagagttg gtagctcttg atccggcaaa caaaccaccg ctggtagcgg tggttttttt 3180
gtttgcaagc agcagattac gcgcagaaaa aaaggatctc aagaagatcc tttgatcttt 3240
tctacggggt ctgacgctca gtggaacgaa aactcacgtt aagggatttt ggtcatgaga 3300
ttatcaaaaa ggatcttcac ctagatcctt ttaaattaaa aatgaagttt taaatcaatc 3360
taaagtatat atgagtaaac ttggtctgac agttaccaat gcttaatcag tgaggcacct 3420
atctcagcga tctgtctatt tcgttcatcc atagttgcct gactccccgt cgtgtagata 3480
actacgatac gggagggctt accatctggc cccagtgctg caatgatacc gcgagaccca 3540
cgctcaccgg ctccagattt atcagcaata aaccagccag ccggaagggc cgagcgcaga 3600
agtggtcctg caactttatc cgcctccatc cagtctatta attgttgccg ggaagctaga 3660
gtaagtagtt cgccagttaa tagtttgcgc aacgttgttg ccattgctgc aggcatcgtg 3720
gtgtcacgct cgtcgtttgg tatggcttca ttcagctccg gttcccaacg atcaaggcga 3780
gttacatgat cccccatgtt gtgcaaaaaa gcggttagct ccttcggtcc tccgatcgtt 3840
gtcagaagta agttggccgc agtgttatca ctcatggtta tggcagcact gcataattct 3900
cttactgtca tgccatccgt aagatgcttt tctgtgactg gtgagtactc aaccaagtca 3960
ttctgagaat agtgtatgcg gcgaccgagt tgctcttgcc cggcgtcaac acgggataat 4020
accgcgccac atagcagaac tttaaaagtg ctcatcattg gaaaacgttc ttcggggcga 4080
aaactctcaa ggatcttacc gctgttgaga tccagttcga tgtaacccac tcgtgcaccc 4140
aactgatctt cagcatcttt tactttcacc agcgtttctg ggtgagcaaa aacaggaagg 4200
caaaatgccg caaaaaaggg aataagggcg acacggaaat gttgaatact catactcttc 4260
ctttttcaat attattgaag catttatcag ggttattgtc tcatgagcgg atacatattt 4320
gaatgtattt agaaaaataa acaaataggg gttccgcgca catttccccg aaaagtgcca 4380
cctgacgtct aagaaaccat tattatcatg acattaacct ataaaaatag gcgtatcacg 4440
aggccctttc gtcttcaa 4458

<210> SEQ ID NO 53
<211> LENGTH: 4980
<212> TYPE: DNA
<213> ORGANISM: Artificial Sequence
<220> FEATURE:
<223> OTHER INFORMATION: pML124:MBPss-BLyS

<400> SEQUENCE: 53

```
gaattcaact tctccatact ttggataagg aaatacagac atgaaaaatc tcattgctga     60
gttgttattt aagcttgccc aaaaagaaga agagtcgaat gaactgtgtg cgcaggtaga    120
agctttggag attatcgtca ctgcaatgct tcgcaatatg gcgcaaaatg accaacagcg    180
gttgattgat caggtagagg gggcgctgta cgaggtaaag cccgatgcca gcattcctga    240
cgacgatacg gagctgctgc gcgattacgt aaagaagtta ttgaagcatc ctcgtcagta    300
aaaagttaat cttttcaaca gctgtcataa agttgtcacg gccgagactt atagtcgctt    360
tgtttttatt ttttaatgta tttgtaacta gtacgcaagt tcacgtaaag gaagtatctc    420
atatgaaaat aaaaacaggt gcacgcatcc tcgcattatc cgcattaacg acgatgatgt    480
tttccgcctc ggctctcgcc gctgttcagg gtccggaaga aaccgttact caggactgcc    540
ttcagctgat cgcagactct gaaactccga ccatccagaa aggttcttac acctttgttc    600
cttggctgct ttctttcaaa cgtggttctg ccctggaaga gaaagaaaac aaaatcctgg    660
ttaaagaaac tggttacttc tttatctacg gtcaggttct ttacactgat aagacctacg    720
ccatgggtca cctgattcag cgtaagaaag ttcacgtttt cggtgacgag ctgtctctgg    780
ttactctgtt tcgctgcatt cagaacatgc cggaaactct tcctaacaac tcctgctact    840
ctgctggcat cgcaaaactg gaagagggtg atgaactgca gctggcaatt cctcgtgaaa    900
acgcacaaat ttctctggac ggtgatgtaa ccttctttgg tgcactgaaa cttctgtaat    960
aataaggtac cggcaaaacc atcactctag aagtggatcc tctacgccgg acgcatcgtg   1020
gccggcatca ccggcgccac aggtgcggtt gctggcgcct atatcgccga catcaccgat   1080
ggggaagatc gggctcgcca cttcgggctc atgagcgctt gtttcggcgt gggtatggtg   1140
gcaggccccg tggccggggg actgttgggc gccatctcct tgcatgcacc attccttgcg   1200
gcggcggtgc tcaacggcct caacctacta ctgggctgct tcctaatgca ggagtcgcat   1260
aagggagagc gtcgaccgat gcccttgaga gccttcaacc cagtcagctc cttccggtgg   1320
gcgcggggca tgactatcgt cgccgcactt atgactgtct tctttatcat gcaactcgta   1380
ggacaggtgc cggcagcgct ctgggtcatt ttcggcgagg accgctttcg ctggagcgcg   1440
acgatgatcg gcctgtcgct tgcggtattc ggaatcttgc acgccctcgc tcaagccttc   1500
gtcactggtc ccgccaccaa acgtttcggc gagaagcagg ccattatcgc cggcatggcg   1560
gccgacgcgc tgggctacgt cttgctggcg ttcgcgacgc gaggctggat ggccttcccc   1620
attatgattc ttctcgcttc cggcggcatc gggatgcccg cgttgcaggc catgctgtcc   1680
aggcaggtag atgacgacca tcagggacag cttcaaggat cgctcgcggc tcttaccagc   1740
ctaacttcga tcactggacc gctgatcgtc acggcgattt atgccgcctc ggcgagcaca   1800
tggaacgggt tggcatggat tgtaggcgcc gccctatacc ttgtctgcct ccccgcgttg   1860
cgtcgcggtg catggagccg ggccacctcg acctgaatgg aagccggcgg cacctcgcta   1920
acggattcac cactccaaga attggagcca atcaattctt gcggagaact gtgaatgcgc   1980
aaaccaaccc ttggcagaac atatccatcg cgtccgccat ctccagcagc cgcacgcggc   2040
gcatctcggg cagcgttggg tcctggccac gggtgcgcat gatcgtgctc ctgtcgttga   2100
ggacccggct aggctggcgg ggttgcctta ctggttagca gaatgaatca ccgatacgcg   2160
agcgaacgtg aagcgactgc tgctgcaaaa cgtctgcgac ctgagcaaca acatgaatgg   2220
tcttcggttt ccgtgtttcg taaagtctgg aaacgcggaa gtcagcgccc tgcaccatta   2280
tgttccggat ctgcatcgca ggatgctgct ggctaccctg tggaacacct acatctgtat   2340
```

taacgaagcg ctggcattga ccctgagtga tttttctctg gtcccgccgc atccataccg 2400
ccagttgttt accctcacaa cgttccagta accgggcatg ttcatcatca gtaacccgta 2460
tcgtgagcat cctctctcgt ttcatcggta tcattacccc catgaacaga aatcccccttt 2520
acacggaggc atcagtgacc aaacaggaaa aaaccgccct taacatggcc cgctttatca 2580
gaagccagac attaacgctt ctggagaaac tcaacgagct ggacgcggat gaacaggcag 2640
acatctgtga atcgcttcac gaccacgctg atgagcttta ccgcagctgc ctcgcgcgtt 2700
tcggtgatga cggtgaaaac ctctgacaca tgcagctccc ggagacggtc acagcttgtc 2760
tgtaagcgga tgccgggagc agacaagccc gtcagggcgc gtcagcgggt gttggcgggt 2820
gtcggggcgc agccatgacc cagtcacgta gcgatagcgg agtgtatact ggcttaacta 2880
tgcggcatca gagcagattg tactgagagt gcaccatata tgcggtgtga aataccgcac 2940
agatgcgtaa ggagaaaata ccgcatcagg cgctcttccg cttcctcgct cactgactcg 3000
ctgcgctcgg tcgttcggct gcggcgagcg gtatcagctc actcaaaggc ggtaatacgg 3060
ttatccacag aatcagggga taacgcagga aagaacatgt gagcaaaagg ccagcaaaag 3120
gccaggaacc gtaaaaaggc cgcgttgctg gcgtttttcc ataggctccg cccccctgac 3180
gagcatcaca aaaatcgacg ctcaagtcag aggtggcgaa acccgacagg actataaaga 3240
taccaggcgt ttccccctgg aagctccctc gtgcgctctc ctgttccgac cctgccgctt 3300
accggatacc tgtccgcctt tctcccttcg ggaagcgtgg cgctttctca tagctcacgc 3360
tgtaggtatc tcagttcggt gtaggtcgtt cgctccaagc tgggctgtgt gcacgaaccc 3420
cccgttcagc ccgaccgctg cgccttatcc ggtaactatc gtcttgagtc caacccggta 3480
agacacgact tatcgccact ggcagcagcc actggtaaca ggattagcag agcgaggtat 3540
gtaggcggtg ctacagagtt cttgaagtgg tggcctaact acggctacac tagaaggaca 3600
gtatttggta tctgcgctct gctgaagcca gttaccttcg gaaaaagagt tggtagctct 3660
tgatccggca aacaaaccac cgctggtagc ggtggttttt ttgtttgcaa gcagcagatt 3720
acgcgcagaa aaaaaggatc tcaagaagat cctttgatct tttctacggg gtctgacgct 3780
cagtggaacg aaaactcacg ttaagggatt ttggtcatga gattatcaaa aaggatcttc 3840
acctagatcc ttttaaatta aaaatgaagt tttaaatcaa tctaaagtat atatgagtaa 3900
acttggtctg acagttacca atgcttaatc agtgaggcac ctatctcagc gatctgtcta 3960
tttcgttcat ccatagttgc ctgactcccc gtcgtgtaga taactacgat acgggagggc 4020
ttaccatctg gccccagtgc tgcaatgata ccgcgagacc cacgctcacc ggctccagat 4080
ttatcagcaa taaaccagcc agccggaagg gccgagcgca gaagtggtcc tgcaacttta 4140
tccgcctcca tccagtctat taattgttgc cgggaagcta gagtaagtag ttcgccagtt 4200
aatagtttgc gcaacgttgt tgccattgct gcaggcatcg tggtgtcacg ctcgtcgttt 4260
ggtatggctt cattcagctc cggttcccaa cgatcaaggc gagttacatg atcccccatg 4320
ttgtgcaaaa aagcggttag ctccttcggt cctccgatcg ttgtcagaag taagttggcc 4380
gcagtgttat cactcatggt tatggcagca ctgcataatt ctcttactgt catgccatcc 4440
gtaagatgct tttctgtgac tggtgagtac tcaaccaagt cattctgaga atagtgtatg 4500
cggcgaccga gttgctcttg cccggcgtca acacgggata ataccgcgcc acatagcaga 4560
actttaaaag tgctcatcat tggaaaacgt tcttcggggc gaaaactctc aaggatctta 4620
ccgctgttga gatccagttc gatgtaaccc actcgtgcac ccaactgatc ttcagcatct 4680
tttactttca ccagcgtttc tgggtgagca aaaacaggaa ggcaaaatgc cgcaaaaaag 4740
ggaataaggg cgacacggaa atgttgaata ctcatactct tcctttttca atattattga 4800
agcatttatc agggttattg tctcatgagc ggatacatat ttgaatgtat ttagaaaaat 4860
aaacaaatag gggttccgcg cacatttccc cgaaaagtgc cacctgacgt ctaagaaacc 4920
attattatca tgacattaac ctataaaaat aggcgtatca cgaggccctt tcgtcttcaa 4980

<210> SEQ ID NO 54
<211> LENGTH: 26
<212> TYPE: PRT
<213> ORGANISM: Artificial Sequence
<220> FEATURE:
<223> OTHER INFORMATION: MBP signal sequence

<400> SEQUENCE: 54

Met Lys Ile Lys Thr Gly Ala Arg Ile Leu Ala Leu Ser Ala Leu Thr
1 5 10 15

Thr Met Met Phe Ser Ala Ser Ala Leu Ala
20 25

<210> SEQ ID NO 55
<211> LENGTH: 178
<212> TYPE: PRT
<213> ORGANISM: Artificial Sequence
<220> FEATURE:
<223> OTHER INFORMATION: MBPss-Neutrokine-alpha

<400> SEQUENCE: 55

Met Lys Ile Lys Thr Gly Ala Arg Ile Leu Ala Leu Ser Ala Leu Thr
1 5 10 15

Thr Met Met Phe Ser Ala Ser Ala Leu Ala Ala Val Gln Gly Pro Glu
20 25 30

Glu Thr Val Thr Gln Asp Cys Leu Gln Leu Ile Ala Asp Ser Glu Thr
35 40 45

Pro Thr Ile Gln Lys Gly Ser Tyr Thr Phe Val Pro Trp Leu Leu Ser
50 55 60

Phe Lys Arg Gly Ser Ala Leu Glu Glu Lys Glu Asn Lys Ile Leu Val
65 70 75 80

Lys Glu Thr Gly Tyr Phe Phe Ile Tyr Gly Gln Val Leu Tyr Thr Asp
85 90 95

Lys Thr Tyr Ala Met Gly His Leu Ile Gln Arg Lys Lys Val His Val
100 105 110

Phe Gly Asp Glu Leu Ser Leu Val Thr Leu Phe Arg Cys Ile Gln Asn
115 120 125

Met Pro Glu Thr Leu Pro Asn Asn Ser Cys Tyr Ser Ala Gly Ile Ala
130 135 140

Lys Leu Glu Glu Gly Asp Glu Leu Gln Leu Ala Ile Pro Arg Glu Asn
145 150 155 160

Ala Gln Ile Ser Leu Asp Gly Asp Val Thr Phe Phe Gly Ala Leu Lys
165 170 175

Leu Leu

<210> SEQ ID NO 56
<211> LENGTH: 21
<212> TYPE: DNA
<213> ORGANISM: Artificial Sequence
<220> FEATURE:
<223> OTHER INFORMATION: wild-type Shine Dalgarno box and its adjacent sequence

<400> SEQUENCE: 56
tttgtacatg gagaaaataa a 21

<210> SEQ ID NO 57
<211> LENGTH: 21
<212> TYPE: DNA
<213> ORGANISM: Artificial Sequence
<220> FEATURE:
<223> OTHER INFORMATION: optimized Shine Dalgarno box and its adjacent sequence

<400> SEQUENCE: 57
cacgtaaagg aagtatctca t 21

<210> SEQ ID NO 58
<211> LENGTH: 120
<212> TYPE: PRT
<213> ORGANISM: Mus musculus

<400> SEQUENCE: 58

```
Gln Val Gln Leu Gln Gln Ser Gly Ala Glu Leu Ala Arg Pro Gly Ala
  1               5                  10                  15

Ser Val Lys Met Ser Cys Arg Ala Ser Gly Tyr Thr Phe Thr Thr Tyr
             20                  25                  30

Thr Met His Trp Val Lys Gln Arg Pro Gly Gln Gly Leu Glu Trp Ile
         35                  40                  45

Gly Tyr Ile Ile Pro Arg Asn Thr Tyr Thr Thr Phe Asn Gln Lys Phe
     50                  55                  60

Lys Asn Lys Ala Thr Leu Thr Ala Asp Lys Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg His Tyr Gly Gly Gly Tyr Trp Phe Phe Asp Val Trp Gly Ala
            100                 105                 110

Gly Thr Thr Val Thr Val Ser Ser
        115                 120
```

<210> SEQ ID NO 59
<211> LENGTH: 113
<212> TYPE: PRT
<213> ORGANISM: Mus musculus

<400> SEQUENCE: 59

```
Glu Leu Val Met Thr Gln Thr Pro Ala Ser Leu Ala Val Ser Leu Gly
  1               5                  10                  15

Gln Arg Ala Thr Ile Ser Cys Arg Gly Ser Glu Ser Val Asp Ser Tyr
             20                  25                  30

Gly Asn Ser Phe Met His Trp Tyr Gln Gln Lys Pro Gly Gln Pro Pro
         35                  40                  45

Lys Leu Leu Ile Tyr Arg Ala Ser Asn Leu Glu Ser Gly Ile Pro Ala
     50                  55                  60

Arg Phe Ser Gly Ser Gly Ser Arg Thr Asp Phe Thr Leu Thr Ile Tyr
 65                  70                  75                  80

Pro Val Glu Ala Asp Asp Val Ala Thr Tyr Tyr Cys Gln Gln Ser Asn
                 85                  90                  95

Asp Asp Pro Met Tyr Thr Phe Gly Gly Gly Thr Lys Leu Glu Ile Lys
            100                 105                 110

Arg
```

NEUTROKINE-ALPHA FUSION PROTEINS

RELATED APPLICATIONS

This application claims the benefit of U.S. Provisional Application Nos. 60/543,261 filed Feb. 11, 2004, 60/580,387 filed Jun. 18, 2004 and 60/617,191 filed Oct. 12, 2004. This application is also a continuation in-part of U.S. patent application Ser. No. 10/270,487 filed Oct. 16, 2002 which claims the benefit of U.S. Provisional Application Nos. 60/368,548 filed Apr. 1, 2002, 60/336,726 filed Dec. 7, 2001, 60/331,478 filed Nov. 16, 2001, 60/330,835 filed Oct. 31, 2001, 60/329,747 filed Oct. 18, 2001, and 60/329,508 filed Oct. 17, 2001. U.S. patent application Ser. No. 10/270,487 filed Oct. 16, 2002 is a continuation-in-part of U.S. patent application Ser. No. 09/929,493 filed Aug. 15, 2001, now abandoned, which claims benefit of U.S. Provisional Application Nos. 60/225,628 filed Aug. 15, 2000, 60/227,008 filed Aug. 23, 2000, 60/234,338 filed Sep. 22, 2000, 60/240,806 filed Oct. 17, 2000, 60/250,020 filed Nov. 30, 2000, 60/276,248 filed Mar. 16, 2001, 60/293,499 filed May 25, 2001, 60/296,122 filed Jun. 7, 2001, and 60/304,809 filed Jul. 13, 2001. U.S. patent application Ser. No. 09/929,493 is a continuation-in-part of U.S. patent application Ser. No. 09/588,947 filed Jun. 8, 2000, now U.S. Pat. No. 6,562,579 issued May 13, 2003, Ser. No. 09/589,285 filed Jun. 8, 2000, Ser. No. 09/589,286 filed Jun. 8, 2000 now U.S. Pat. No. 6,635,482 issued Oct. 21, 2003, Ser. No. 09/589,287 filed Jun. 8, 2000, now U.S. Pat. No. 6,403,770 issued Jun. 11, 2002, and Ser. No. 09/589,288 filed Jun. 8, 2000. U.S. patent application Ser. No. 09/929,493 is also a continuation-in-part of U.S. patent application Ser. No. 09/507,968 filed Feb. 22, 2000, now U.S. Pat. No. 6,812,327 issued Nov. 2, 2004, which claims the benefit of U.S. Provisional Application Nos. 60/122,388 filed Mar. 2, 1999, 60/124,097 filed Mar. 12, 1999, 60/126,599 filed Mar. 26, 1999, 60/127,598 filed Apr. 2, 1999, 60/130,412 filed Apr. 16, 1999, 60/130,696 filed Apr. 23, 1999, 60/131,278 filed Apr. 27, 1999, 60/131,673 filed Apr. 29, 1999, 60/136,784 filed May 28, 1999 and 60/142,659 filed Jul. 6, 1999. This application is also a continuation-in-part of U.S. patent application Ser. No. 09/589,285 filed Jun. 8, 2000 which is a continuation of U.S. patent application Ser. No. 09/507,968 filed Feb. 22, 2000, now U.S. Pat. No. 6,812,327 issued Nov. 2, 2004, which claims the benefit of U.S. Provisional Application Nos. 60/122,388 filed Mar. 2, 1999, 60/124,097 filed Mar. 12, 1999, 60/126,599 filed Mar. 26, 1999, 60/127,598 filed Apr. 2, 1999, 60/130,412 filed Apr. 16, 1999, 60/130,696 filed Apr. 23, 1999, 60/131,278 filed Apr. 27, 1999, 60/131,673 filed Apr. 29, 1999, 60/136,784 filed May 28, 1999 and 60/142,659 filed Jul. 6, 1999. This application is also a continuation-in-part of U.S. patent application Ser. No. 09/589,288 filed Jun. 8, 2000 which is a continuation of U.S. patent application Ser. No. 09/507,968 filed Feb. 22, 2000, now U.S. Pat. No. 6,812,327 issued Nov. 2, 2004, which claims the benefit of U.S. Provisional Application Nos. 60/122,388 filed Mar. 2, 1999, 60/124,097 filed Mar. 12, 1999, 60/126,599 filed Mar. 26, 1999, 60/127,598 filed Apr. 2, 1999, 60/130,412 filed Apr. 16, 1999, 60/130,696 filed Apr. 23, 1999, 60/131,278 filed Apr. 27, 1999, 60/131,673 filed Apr. 29, 1999, 60/136,784 filed May 28, 1999 and 60/142,659 filed Jul. 6, 1999. Each of the applications identified above is herein incorporated by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 78,428 Byte ASCII (Text) file named "ReplacementSequenceListing2nd.txt," created on Jun. 10, 2011.

FIELD OF THE INVENTION

The present invention relates to a novel cytokine which has been designated Neutrokine-alpha ("Neutrokine-alpha"). In addition, an apparent splicing variant of Neutrokine-alpha has been identified and designated Neutrokine-alphaSV. In specific embodiments, the present invention provides nucleic acid molecules encoding Neutrokine-alpha and Neutrokine-alphaSV polypeptides. In additional embodiments, Neutrokine-alpha and Neutrokine-alphaSV polypeptides are also provided, as are vectors, host cells and recombinant methods for producing the same. Neutrokine-alpha is also referred to in the art as TALL-1, THANK, BAFF, zTNF4, TNFSF13B. Neutrokine-alpha is also referred to as the BLyS™ protein, from Human Genome Sciences, Inc.

RELATED ART

Human tumor necrosis factors (TNF-alpha) and (TNF-beta, or lymphotoxin) are related members of a broad class of polypeptide mediators, which includes the interferons, interleukins and growth factors, collectively called cytokines (Beutler, B. and Cerami, A., Annu. Rev. Immunol. 7:625-655 (1989)). Sequence analysis of cytokine receptors has defined several subfamilies of membrane proteins (1) the Ig superfamily, (2) the hematopoietin (cytokine receptor superfamily) and (3) the tumor necrosis factor (TNF)/nerve growth factor (NGF) receptor superfamily (for review of TNF superfamily see, Gruss and Dower, Blood 85(12) :3378-3404 (1995) and Aggarwal and Natarajan, Eur. Cytokine Netw., 7(2):93-124 (1996)). The TNF/NGF receptor superfamily contains at least 10 different proteins. Gruss and Dower, supra. Ligands for these receptors have been identified and belong to at least two cytokine superfamilies. Gruss and Dower, supra.

Tumor necrosis factor (a mixture of TNF-alpha and TNF-beta) was originally discovered as a result of its anti-tumor activity, however, now it is recognized as a pleiotropic cytokine capable of numerous biological activities including apoptosis of some transformed cell lines, mediation of cell activation and proliferation and also as playing important roles in immune regulation and inflammation.

To date, known members of the TNF-ligand superfamily include TNF-alpha, TNF-beta (lymphotoxin-alpha), LT-beta, OX40L, Fas ligand, CD30L, CD27L, CD40L and 4-IBBL. The ligands of the TNF ligand superfamily are acidic, TNF-like molecules with approximately 20% sequence homology in the extracellular domains (range, 12%-36%) and exist mainly as membrane-bound forms with the biologically active form being a trimeric/multimeric complex. Soluble forms of the TNF ligand superfamily have only been identified so far for TNF, LT-beta, and Fas ligand (for a general review, see Grass, H. and Dower, S. K., Blood, 85(12) :3378-3404 (1995)), which is hereby incorporated by reference in its entirety. These proteins are involved in regulation of cell proliferation, activation, and differentiation, including control of cell survival or death by apoptosis or cytotoxicity (Armitage, R. J., Curr. Opin. Immunol. 6:407 (1994) and Smith, C. A., Cell 75:959 (1994)).

Tumor necrosis factor-alpha (TNF-alpha; also termed cachectin; hereinafter "TNF") is secreted primarily by monocytes and macrophages in response to endotoxin or other stimuli as a soluble homotrimer of 17 kD protein subunits (Smith, R. A. et al., J. Biol. Chem. 262:6951-6954 (1987)). A membrane-bound 26 kD precursor form of TNF has also been described (Kriegler, M. et al., Cell 53:45-53 (1988)).

Accumulating evidence indicates that TNF is a regulatory cytokine with pleiotropic biological activities. These activities include: inhibition of lipoprotein lipase synthesis ("cachectin" activity) (Beutler, B. et al., Nature 316:552 (1985)), activation of polymorphonuclear leukocytes (Klebanoff, S. J. et al., J. Immunol. 136:4220 (1986); Perussia, B., et al., J. Immunol. 138:765 (1987)), inhibition of cell growth or stimulation of cell growth (Vilcek, J. et al., J. Exp. Med. 163:632 (1986); Sugarman, B. J. et al., Science 230:943 (1985); Lachman, L. B. et al., J. Immunol. 138:2913 (1987)), cytotoxic action on certain transformed cell types (Lachman, L. B. et al., supra; Darzynkiewicz, Z. et al., Canc. Res. 44:83 (1984)), antiviral activity (Kohase, M. et al., Cell 45:659 (1986); Wong, G. H. W. et al., Nature 323:819 (1986)), stimulation of bone resorption (Bertolini, D. R. et al., Nature 319:516 (1986); Saklatvala, J., Nature 322:547 (1986)), stimulation of collagenase and prostaglandin E2 production (Dayer, J.-M. et al., J. Exp. Med. 162:2163 (1985)); and immunoregulatory actions, including activation of T cells (Yokota, S. et al., J. Immunol. 140:531 (1988)), B cells (Kehrl, J. H. et al., J. Exp. Med. 166:786 (1987)), monocytes (Philip, R. et al., Nature 323:86 (1986)), thymocytes (Ranges, G. E. et al., J. Exp. Med. 167:1472 (1988)), and stimulation of the cell-surface expression of major histocompatibility complex (MHC) class I and class II molecules (Collins, T. et al., Proc. Natl. Acad. Sci. USA 83:446 (1986); Pujol-Borrel, R. et al., Nature 326:304 (1987)).

TNF is noted for its pro-inflammatory actions which result in tissue injury, such as induction of procoagulant activity on vascular endothelial cells (Pober, J. S. et al., J. Immunol. 136:1680 (1986)), increased adherence of neutrophils and lymphocytes (Pober, J. S. et al., J. Immunol. 138:3319 (1987)), and stimulation of the release of platelet activating factor from macrophages, neutrophils and vascular endothelial cells (Camussi, G. et al., J. Exp. Med. 166:1390 (1987)).

Recent evidence implicates TNF in the pathogenesis of many infections (Cerami, A. et al., Immunol. Today 9:28 (1988)), immune disorders, neoplastic pathology, e.g., in cachexia accompanying some malignancies (Oliff, A. et al., Cell 50:555 (1987)), and in autoimmune pathologies and graft-versus host pathology (Piguet, P.-F. et al., J. Exp. Med. 166:1280 (1987)). The association of TNF with cancer and infectious pathologies is often related to the host's catabolic state. A major problem in cancer patients is weight loss, usually associated with anorexia. The extensive wasting which results is known as "cachexia" (Kern, K. A. et al. J. Parent. Enter. Nutr. 12:286-298 (1988)). Cachexia includes progressive weight loss, anorexia, and persistent erosion of body mass in response to a malignant growth. The cachectic state is thus associated with significant morbidity and is responsible for the majority of cancer mortality. A number of studies have suggested that TNF is an important mediator of the cachexia in cancer, infectious pathology, and in other catabolic states.

TNF is thought to play a central role in the pathophysiological consequences of Gram-negative sepsis and endotoxic shock (Michie, H. R. et al., Br. J. Surg. 76:670-671 (1989); Debets, J. M. H. et al., Second Vienna Shock Forum, p.463-466 (1989); Simpson, S. Q. et al., Crit. Care Clin. 5:27-47 (1989)), including fever, malaise, anorexia, and cachexia. Endotoxin is a potent monocyte/macrophage activator which stimulates production and secretion of TNF (Kornbluth, S. K. et al., J. Immunol. 137:2585-2591 (1986)) and other cytokines. Because TNF could mimic many biological effects of endotoxin, it was concluded to be a central mediator responsible for the clinical manifestations of endotoxin-related illness. TNF and other monocyte-derived cytokines mediate the metabolic and neurohormonal responses to endotoxin (Michie, H. R. et al., N. Eng. J. Med. 318:1481-1486 (1988)). Endotoxin administration to human volunteers produces acute illness with flu-like symptoms including fever, tachycardia, increased metabolic rate and stress hormone release (Revhaug, A. et al., Arch. Surg. 123:162-170 (1988)). Elevated levels of circulating TNF have also been found in patients suffering from Gram-negative sepsis (Waage, A. et al., Lancet 1:355-357 (1987); Hammerle, A. F. et al., Second Vienna Shock Forum p. 715-718 (1989); Debets, J. M. H. et al., Crit. Care Med. 17:489-497 (1989); Calandra, T. et al., J. Infec. Dis. 161:982-987 (1990)).

Passive immunotherapy directed at neutralizing TNF may have a beneficial effect in Gram-negative sepsis and endotoxemia, based on the increased TNF production and elevated TNF levels in these pathology states, as discussed above. Antibodies to a "modulator" material which was characterized as cachectin (later found to be identical to TNF) were disclosed by Cerami et al. (EPO Patent Publication 0,212,489, Mar. 4, 1987). Such antibodies were said to be useful in diagnostic immunoassay and in therapy of shock in bacterial infections. Rubin et al. (EPO Patent Publication 0,218,868, Apr. 22, 1987) disclosed monoclonal antibodies to human TNF, the hybridomas secreting such antibodies, methods of producing such antibodies, and the use of such antibodies in immunoassay of TNF. Yone et al. (EPO Patent Publication 0,288,088, Oct. 26, 1988) disclosed anti-TNF antibodies, including mAbs, and their utility in immunoassay diagnosis of pathologies, in particular Kawasaki's pathology and bacterial infection. The body fluids of patients with Kawasaki's pathology (infantile acute febrile mucocutaneous lymph node syndrome; Kawasaki, T., Allergy 16:178 (1967); Kawasaki, T., Shonica (Pediatrics) 26:935 (1985)) were said to contain elevated TNF levels which were related to progress of the pathology (Yone et al., supra).

Other investigators have described mAbs specific for recombinant human TNF which had neutralizing activity in vitro (Liang, C-M. et al. Biochem. Biophys. Res. Comm. 137:847-854 (1986); Meager, A. et al., Hybridoma 6:305-311 (1987); Fendly et al., Hybridoma 6:359-369 (1987); Bringman, T S et al., Hybridoma 6:489-507 (1987); Hirai, M. et al., J. Immunol. Meth. 96:57-62 (1987); Moller, A. et al. (Cytokine 2:162-169 (1990)). Some of these mAbs were used to map epitopes of human TNF and develop enzyme immunoassays (Fendly et al., supra; Hirai et al., supra; Moller et al., supra) and to assist in the purification of recombinant TNF (Bringman et al., supra). However, these studies do not provide a basis for producing TNF neutralizing antibodies that can be used for in vivo diagnostic or therapeutic uses in humans, due to immunogenicity, lack of specificity and/or pharmaceutical suitability.

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems (Mathison, J. C. et al., J. Clin. Invest. 81:1925-1937 (1988); Beutler, B. et al., Science 229:869-871 (1985); Tracey, K. J. et al., Nature 330:662-664 (1987); Shimamoto, Y. et al., Immunol. Lett. 17:311-318 (1988); Silva, A. T. et al., J. Infect. Dis. 162:421-427 (1990); Opal, S. M. et al., J. Infect. Dis. 161:1148-1152 (1990); Hinshaw, L. B. et al., Circ. Shock 30:279-292 (1990)).

To date, experience with anti-TNF mAb therapy in humans has been limited but shows beneficial therapeutic results, e.g., in arthritis and sepsis. See, e.g., Elliott, M. J. et al., Baillieres Clin. Rheumatol. 9:633-52 (1995); Feldmann M, et al., Ann. N. Y. Acad. Sci. USA 766:272-8 (1995); van der Poll, T. et al., Shock 3:1-12 (1995); Wherry et al., Crit. Care. Med. 21:S436-40 (1993); Tracey K. J., et al., Crit. Care Med. 21:S415-22 (1993).

Mammalian development is dependent on both the proliferation and differentiation of cells as well as programmed cell death which occurs through apoptosis (Walker, et al., Methods Achiev. Exp. Pathol. 13:18 (1988). Apoptosis plays a critical role in the destruction of immune thymocytes that recognize self antigens. Failure of this normal elimination process may play a role in autoimmune diseases (Gammon et al., Immunology Today 12:193 (1991)).

Itoh et al. (Cell 66:233 (1991)) described a cell surface antigen, Fas/CD95 that mediates apoptosis and is involved in clonal deletion of T-cells. Fas is expressed in activated T-cells, B-cells, neutrophils and in thymus, liver, heart and lung and ovary in adult mice (Watanabe-Fukunaga et al., J. Immunol. 148:1274 (1992)) in addition to activated T-cells, B-cells, neutrophils. In experiments where a monoclonal Ab is cross-linked to Fas, apoptosis is induced (Yonehara et al., J. Exp. Med. 169:1747 (1989); Trauth et al., Science 245:301 (1989)). In addition, there is an example where binding of a monoclonal Ab to Fas is stimulatory to T-cells under certain conditions (Alderson et al., J. Exp. Med. 178:2231 (1993)).

Fas antigen is a cell surface protein of relative MW of 45 Kd. Both human and murine genes for Fas have been cloned by Watanabe-Fukunaga et al., (J. Immunol. 148:1274 (1992)) and Itoh et al. (Cell 66:233 (1991)). The proteins encoded by these genes are both transmembrane proteins with structural homology to the Nerve Growth Factor/Tumor Necrosis Factor receptor superfamily, which includes two TNF receptors, the low affinity Nerve Growth Factor receptor and CD40, CD27, CD30, and OX40.

Recently the Fas ligand has been described (Suda et al., Cell 75:1169 (1993)). The amino acid sequence indicates that Fas ligand is a type II transmembrane protein belonging to the TNF family. Thus, the Fas ligand polypeptide comprises three main domains: a short intracellular domain at the amino terminal end and a longer extracellular domain at the carboxy terminal end, connected by a hydrophobic transmembrane domain. Fas ligand is expressed in splenocytes and thymocytes, consistent with T-cell mediated cytotoxicity. The purified Fas ligand has a MW of 40 kD.

Recently, it has been demonstrated that Fas/Fas ligand interactions are required for apoptosis following the activation of T-cells (Ju et al., Nature 373:444 (1995); Brunner et al., Nature 373:441 (1995)). Activation of T-cells induces both proteins on the cell surface. Subsequent interaction between the ligand and receptor results in apoptosis of the cells. This supports the possible regulatory role for apoptosis induced by Fas/Fas ligand interaction during normal immune responses.

Accordingly, there is a need to provide cytokines similar to TNF that are involved in pathological conditions. Such novel cytokines may be used to make novel antibodies or other antagonists that bind these TNF-like cytokines for diagnosis and therapy of disorders related to TNF-like cytokines.

SUMMARY OF THE INVENTION

In accordance with one embodiment of the present invention, there is provided a novel extracellular domain of a Neutrokine-alpha polypeptide, and a novel extracellular domain of a Neutrokine-alphaSV polypeptide, as well as biologically active and diagnostically or therapeutically useful fragments, analogs and derivatives thereof.

In accordance with another embodiment of the present invention, there are provided isolated nucleic acid molecules encoding human Neutrokine-alpha or Neutrokine-alphaSV, including mRNAs, DNAs, cDNAs, genomic DNAs as well as analogs and biologically active and diagnostically or therapeutically useful fragments and derivatives thereof.

The present invention provides isolated nucleic acid molecules comprising, or alternatively, consisting of, a polynucleotide encoding a cytokine and an apparent splice variant thereof that are structurally similar to TNF and related cytokines and have similar biological effects and activities. This cytokine is named Neutrokine-alpha and the invention includes Neutrokine-alpha polypeptides having at least a portion of the amino acid sequence in FIGS. 1A and 1B (SEQ ID NO:2) or amino acid sequence encoded by the cDNA clone (HNEDU15) deposited on Oct. 22, 1996 assigned ATCC number 97768. The nucleotide sequence determined by sequencing the deposited Neutrokine-alpha clone, which is shown in FIGS. 1A and 1B (SEQ ID NO:1), contains an open reading frame encoding a complete polypeptide of 285 amino acid residues including an N-terminal methionine, a predicted intracellular domain of about 46 amino acid residues, a predicted transmembrane domain of about 26 amino acids, a predicted extracellular domain of about 213 amino acids, and a deduced molecular weight for the complete protein of about 31 kDa. As for other type II transmembrane proteins, soluble forms of Neutrokine-alpha include all or a portion of the extracellular domain cleaved from the transmembrane domain and a polypeptide comprising the complete Neutrokine-alpha polypeptide lacking the transmembrane domain, i.e., the extracellular domain linked to the intracellular domain. The apparent splice variant of Neutrokine-alpha is named Neutrokine-alphaSV and the invention includes Neutrokine-alphaSV polypeptides comprising, or alternatively, consisting of, at least a portion of the amino acid sequence in FIGS. 5A and 5B (SEQ ID NO:19) or amino acid sequence encoded by the cDNA clone HDPMC52 deposited on Dec. 10, 1998 and assigned ATCC number 203518. The nucleotide sequence determined by sequencing the deposited Neutrokine-alphaSV clone, which is shown in FIGS. 5A and 5B (SEQ ID NO:18), contains an open reading frame encoding a complete polypeptide of 266 amino acid residues including an N-terminal methionine, a predicted intracellular domain of about 46 amino acid residues, a predicted transmembrane domain of about 26 amino acids, a predicted extracellular domain of about 194 amino acids, and a deduced molecular weight for the complete protein of about 29 kDa. As for other type II transmembrane proteins, soluble forms of Neutrokine-alphaSV include all or a portion of the extracellular domain cleaved from the transmembrane domain and a polypeptide comprising the complete Neutrokine-alphaSV polypeptide lacking the transmembrane domain, i.e., the extracellular domain linked to the intracellular domain.

Thus, one embodiment of the invention provides an isolated nucleic acid molecule comprising, or alternatively consisting of, a polynucleotide having a nucleotide sequence selected from the group consisting of: (a) a nucleotide sequence encoding a full-length Neutrokine-alpha polypeptide having the complete amino acid sequence in FIGS. 1A and 1B (SEQ ID NO:2) or as encoded by the cDNA clone contained in the deposit having ATCC accession number 97768; (b) a nucleotide sequence encoding the predicted extracellular domain of the Neutrokine-alpha polypeptide having the amino acid sequence at positions 73 to 285 in FIGS. 1A and 1B (SEQ ID NO:2) or as encoded by the clone contained in the deposit having ATCC accession number 97768; (c) a nucleotide sequence encoding a fragment of the polypeptide of (b) (e.g., amino acids 134-285) having Neutrokine-alpha functional activity (e.g., biological acitivity); (d) a nucleotide sequence encoding a polypeptide comprising the Neutrokine-alpha intracellular domain (predicted to constitute amino acid residues from about 1 to about 46 in FIGS. 1A and 1B (SEQ ID NO:2)) or as encoded by the clone contained in the deposit having ATCC accession number 97768; (e) a nucleotide sequence encoding a polypeptide comprising the Neutrokine-alpha transmembrane domain (predicted to constitute amino acid residues from about 47 to about 72 in FIGS. 1A and 1B (SEQ ID NO:2) or as encoded by the cDNA clone contained in the deposit having ATCC accession number 97768; (f) a nucleotide sequence encoding a soluble Neutrokine-alpha polypeptide having the extracellular and intracellular domains but lacking the transmembrane domain; and (g) a nucleotide sequence complementary to any of the nucleotide sequences in (a), (b), (c), (d), (e) or (f) above.

Further embodiments of the invention include isolated nucleic acid molecules that comprise, or alternatively consist of, a polynucleotide having a nucleotide sequence at least 80%, 85% or 90% identical, and more preferably at least 95%, 96%, 97%, 98% or 99% identical, to any of the nucleotide sequences in (a), (b), (c), (d), (e), (f) or (g) above, or a polynucleotide which hybridizes under stringent hybridization conditions to a polynucleotide in (a), (b), (c), (d), (e), (f) or (g) above. This polynucleotide which hybridizes does not hybridize under stringent hybridization conditions to a polynucleotide having a nucleotide sequence consisting of only A residues or of only T residues.

Another embodiment of the invention provides an isolated nucleic acid molecule comprising, or alternatively consisting of, a polynucleotide having a nucleotide sequence selected from the group consisting of: (a) a nucleotide sequence encoding a full-length Neutrokine-alphaSV polypeptide having the complete amino acid sequence in FIGS. 5A and 5B (SEQ ID NO:19) or as encoded by the cDNA clone contained in the ATCC Deposit deposited on Dec. 10, 1998 as ATCC Number 203518; (b) a nucleotide sequence encoding the predicted extracellular domain of the Neutrokine-alphaSV polypeptide having the amino acid sequence at positions 73 to 266 in FIGS. 1A and 1B (SEQ ID NO:2) or as encoded by the cDNA clone contained in ATCC 203518 deposited on Dec. 10, 1998; (c) a nucleotide sequence encoding a polypeptide comprising the Neutrokine-alphaSV intracellular domain (predicted to constitute amino acid residues from about 1 to about 46 in FIGS. 5A and 5B (SEQ ID NO:19)) or as encoded by the cDNA clone contained in ATCC No. 203518 deposited on Dec. 10, 1998; (d) a nucleotide sequence encoding a polypeptide comprising the Neutrokine-alphaSV transmembrane domain (predicted to constitute amino acid residues from about 47 to about 72 in FIGS. 5A and 5B (SEQ ID NO:19) or as encoded by the cDNA clone contained in ATCC No. 203518 deposited on Dec. 10, 1998; (e) a nucleotide sequence encoding a soluble Neutrokine-alphaSV polypeptide having the extracellular and intracellular domains but lacking the transmembrane domain; and (f) a nucleotide sequence complementary to any of the nucleotide sequences in (a), (b), (c), (d), or (e) above.

Further embodiments of the invention include isolated nucleic acid molecules that comprise, or alternatively consist of, a polynucleotide having a nucleotide sequence at least 80%, 85% or 90% identical, and more preferably at least 95%, 96%, 97%, 98%, or 99% identical, to any of the nucleotide sequences in (a), (b), (c), (d), (e) or (f) above, or a polynucleotide which hybridizes under stringent hybridization conditions to a polynucleotide in (a), (b), (c), (d), (e) or (f) above. This polynucleotide which hybridizes does not hybridize under stringent hybridization conditions to a polynucleotide having a nucleotide sequence consisting of only A residues or of only T residues.

In one embodiment, the invention includes isolated nucleic acid molecules that comprise, or alternatively consist of, a polynucleotide having a nucleotide sequence encoding the apparent splice variant of Neutrokine-alpha comprising, or alternatively consisting of, at least a portion of the amino acid sequence from Gly-142 to Leu-266 as shown in FIGS. 5A and 5B (SEQ ID NO:19) or amino acid sequence encoded by the cDNA clone HDPMC52 deposited on Dec. 10, 1998 and assigned ATCC Deposit No. 203518.

In another preferred embodiment, the invention include isolated nucleic acid molecules that comprise, or alternatively consist of, a polynucleotide having a nucleotide sequence encoding the apparent splice variant of Neutrokine-alpha comprising, or alternatively consisting of, at least a portion of the amino acid sequence from Ala-134 to Leu-266 as shown in FIGS. 5A and 5B (SEQ ID NO:19) or amino acid sequence encoded by the cDNA clone HDPMC52 deposited on Dec. 10, 1998 and assigned ATCC Deposit No. 203518.

In additional embodiments, the nucleic acid molecules of the invention comprise, or alternatively consist of, a polynucleotide which encodes the amino acid sequence of an epitope-bearing portion of a Neutrokine-alpha or Neutrokine-alphaSV polypeptide having an amino acid sequence in (a), (b), (c), (d), (e), (f) or (g) above. A further nucleic acid embodiment of the invention relates to an isolated nucleic acid molecule comprising, or alternatively consisting of, a polynucleotide which encodes the amino acid sequence of a Neutrokine-alpha or Neutrokine-alphaSV polypeptide having an amino acid sequence which contains at least one amino acid addition, substitution, and/or deletion but not more than 50 amino acid additions, substitutions and/or deletions, even more preferably, not more than 40 amino acid additions, substitutions, and/or deletions, still more preferably, not more than 30 amino acid additions, substitutions, and/or deletions, and still even more preferably, not more than 20 amino acid additions, substitutions, and/or deletions. Of course, in order of ever-increasing preference, it is highly preferable for a polynucleotide which encodes the amino acid sequence of a Neutrokine-alpha or Neutrokine-alphaSV polypeptide to have an amino acid sequence which contains not more than 10, 9, 8, 7, 6, 5, 4, 3, 2 or 1 or 1-100, 1-50, 1-25,1-20, 1-15, 1-10, or 1-5 amino acid additions, substitutions and/or deletions. Conservative substitutions are preferable.

The present invention also relates to recombinant vectors, which include the isolated nucleic acid molecules of the present invention, and to host cells containing the recombinant vectors, as well as to methods of making such vectors and host cells and for using them for production of Neutrokine-alpha polypeptides by recombinant techniques.

In accordance with a further embodiment of the present invention, there is provided a process for producing such polypeptides by recombinant techniques comprising culturing recombinant prokaryotic and/or eukaryotic host cells, containing a Neutrokine-alpha or Neutrokine-alphaSV nucleic acid sequence of the invention, under conditions promoting expression of said polypeptide and subsequent recovery of said polypeptide.

The invention further provides an isolated Neutrokine-alpha polypeptide comprising, or alternatively consisting of, an amino acid sequence selected from the group consisting of: (a) the amino acid sequence of the full-length Neutrokine-alpha polypeptide having the complete amino acid sequence shown in FIGS. 1A and 1B (i.e., positions 1-285 of SEQ ID NO:2) or as encoded by the cDNA plasmid contained in the deposit having ATCC accession number 97768; (b) the amino acid sequence of the full-length Neutrokine-alpha polypeptide having the complete amino acid sequence shown in SEQ ID NO:2 excepting the N-terminal methionine (i.e., positions 2 to 285 of SEQ ID NO:2); (c) a fragment of the polypeptide of (b) having Neutrokine-alpha functional activity (e.g., biological activity); (d) the amino acid sequence of the predicted extracellular domain of the Neutrokine-alpha polypeptide having the amino acid sequence at positions 73 to 285 in FIGS. 1A and 1B (SEQ ID NO:2) or as encoded by the cDNA plasmid contained in the deposit having ATCC accession number 97768; (e) an amino acid sequence encoding the mature soluble form of Neutrokine-alpha polypeptide having the amino acid sequence at positions 134-285 in FIGS. 1A and 1B (SEQ ID NO:2); (f) the amino acid sequence of the Neutrokine-alpha intracellular domain (predicted to constitute amino acid residues from about 1 to about 46 in FIGS. 1A and 1B (SEQ ID NO:2)) or as encoded by the cDNA plasmid contained in the deposit having ATCC accession number 97768; (g) the amino acid sequence of the Neutrokine-alpha transmembrane domain (predicted to constitute amino acid residues from about 47 to about 72 in FIGS. 1A and 1B (SEQ ID NO:2)) or as encoded by the cDNA plasmid contained in the deposit having ATCC accession number 97768; (h) the amino acid sequence of the soluble Neutrokine-alpha polypeptide having the extracellular and intracellular domains but lacking the transmembrane domain, wherein each of these domains is defined above; and (i) fragments of the polypeptide of (a), (b), (c), (d), (e), (f), (g) or (h). The polypeptides of the present invention also include polypeptides having an amino acid sequence at least 80% identical, more preferably at least 85% or 90% identical, and still more preferably 95%, 96%, 97%, 98% or 99% identical to those described in (a), (b), (c), (d), (e) (f), (g), (h) or (i) above, as well as polypeptides having an amino acid sequence with at least 80%, 85%, or 90% similarity, and more preferably at least 95% similarity, to those above. Additional embodiments of the invention relates to polypeptides which comprise, or alternatively consist of, the amino acid sequence of an epitope-bearing portion of a Neutrokine-alpha polypeptide having an amino acid sequence described in (a), (b), (c), (d), (e), (f), (g), (h) or (i) above. Polypeptides having the amino acid sequence of an epitope-bearing portion of a Neutrokine-alpha polypeptide of the invention include portions of such polypeptides with at least 4, at least 5, at least 6, at least 7, at least 8, and preferably at least 9, at least 10, at least 11, at least 12, at least 13, at least 14, at least 15, at least 20, at least 25, at least 30, at least 40, at least 50, and more preferably at least about 30 amino acids to about 50 amino acids, although epitope-bearing polypeptides of any length up to and including the entire amino acid sequence of a polypeptide of the invention described above also are included in the invention.

Highly preferred embodiments of the invention are directed to nucleic acid molecules comprising, or alternatively consisting of a polynucleotide having a nucleotide sequence at least 80%, 85%, 90% identical and more preferably at least 95%, 96%, 97%, 98%, 99% or 100% identical to a polynucleotide sequence encoding the Neutrokine-alpha polypeptide having the amino acid sequence at positions 134-285 in FIGS. 1A and 1B (SEQ ID NO:2). Preferred embodiments of the invention are directed to nucleic acid molecules comprising, or alternatively consisting of a polynucleotide having a nucleotide sequence at least 90% identical to a polynucleotide sequence encoding the Neutrokine-alpha polypeptide having the amino acid sequence at positions 134-285 in FIGS. 1A and 1B (SEQ ID NO:2). More preferred embodiments of the invention are directed to nucleic acid molecules comprising, or alternatively consisting of a polynucleotide having a nucleotide sequence at least 95% identical to a polynucleotide sequence encoding the Neutrokine-alpha polypeptide having the amino acid sequence at positions 134-285 in FIGS. 1A and 1B (SEQ ID NO:2). More preferred embodiments of the invention are directed to nucleic acid molecules comprising, or alternatively consisting of a polynucleotide having a nucleotide sequence at least 96% identical to a polynucleotide sequence encoding the Neutrokine-alpha polypeptide having the amino acid sequence at positions 134-285 in FIGS. 1A and 1B (SEQ ID NO:2). Additionally, more preferred embodiments of the invention are directed to nucleic acid molecules comprising, or alternatively consisting of a polynucleotide having a nucleotide sequence at least 97% to a polynucleotide sequence encoding the Neutrokine-alpha polypeptide having the amino acid sequence at positions 134-285 in FIGS. 1A and 1B (SEQ ID NO:2). Additionally, more preferred embodiments of the invention are directed to nucleic acid molecules comprising, or alternatively consisting of a polynucleotide having a nucleotide sequence at least 98% to a polynucleotide sequence encoding the Neutrokine-alpha polypeptide having the amino acid sequence at positions 134-285 in FIGS. 1A and 1B (SEQ ID NO:2). Additionally, more preferred embodiments of the invention are directed to nucleic acid molecules comprising, or alternatively consisting of a polynucleotide having a nucleotide sequence at least 99% identical to a polynucleotide sequence encoding the Neutrokine-alpha polypeptide having the amino acid sequence at positions 134-285 in FIGS. 1A and 1B (SEQ ID NO:2).

The present invention also encompasses the above polynucleotide sequences fused to a heterologous polynucleotide sequence. Polypeptides encoded by these polynucleotides and nucleic acid molecules are also encompassed by the invention.

The invention further provides an isolated Neutrokine-alphaSV polypeptide comprising, or alternatively consisting of, an amino acid sequence selected from the group consisting of: (a) the amino acid sequence of the full-length Neutrokine-alphaSV polypeptide having the complete amino acid sequence shown in FIGS. 5A and 5B (i.e., positions 1-266 of SEQ ID NO:19) or as encoded by the cDNA clone contained in ATCC No. 203518 deposited on Dec. 10, 1998; (b) the amino acid sequence of the full-length Neutrokine-alphaSV polypeptide having the complete amino acid sequence shown in SEQ ID NO:19 excepting the N-terminal methionine (i.e., positions 2 to 266 of SEQ ID NO:19); (c) the amino acid sequence of the predicted extracellular domain of the Neutrokine-alphaSV polypeptide having the amino acid sequence at positions 73 to 266 in FIGS. 5A and 5B (SEQ ID NO:19) or as encoded by the cDNA clone contained in ATCC No. 203518 deposited on Dec. 10, 1998; (d) the amino acid sequence of the Neutrokine-alphaSV intracellular domain (predicted to constitute amino acid residues from about 1 to about 46 in FIGS. 5A and 5B (SEQ ID NO:19)) or as encoded by the cDNA clone contained in ATCC No. 203518 deposited on Dec. 10, 1998; (e) the amino acid sequence of the Neutrokine-alphaSV transmembrane domain (predicted to constitute amino acid residues from about 47 to about 72 in FIGS. 5A and 5B (SEQ ID NO:19)) or as encoded by the cDNA clone contained in ATCC No. 203518 deposited on Dec. 10, 1998; (f) the amino acid sequence of the soluble Neutrokine-alphaSV polypeptide having the extracellular and intracellular domains but lacking the transmembrane domain, wherein each of these domains is defined above; and (g) fragments of the polypeptide of (a), (b), (c), (d), (e), or (f). The polypeptides of the present invention also include polypeptides having an amino acid sequence at least 80% identical, more preferably at least 85% or 90% identical, and still more preferably 95%, 96%, 97%, 98% or 99% identical to those described in (a), (b), (c), (d), (e) (f), or (g) above, as well as polypeptides having an amino acid sequence with at least 80%, 85%, or 90% similarity, and more preferably at least 95% similarity, to those above. Additional embodiments of the invention relates to polypeptides which comprise, or alternatively consist of, the amino acid sequence of an epitope-bearing portion of a Neutrokine-alphaSV polypeptide having an amino acid sequence described in (a), (b), (c), (d), (e), (f), or (g) above. Peptides or polypeptides having the amino acid sequence of an epitope-bearing portion of a Neutrokine-alphaSV polypeptide of the invention include portions of such polypeptides with at least 4, at least 5, at least 6, at least 7, at least 8, and preferably at least 9, at least 10, at least 11, at least 12, at least 13, at least 14, at least 15, at least 20, at least 25, at least 30, at least 40, at least 50, and more preferably at least about 30 amino acids to about 50 amino acids, although epitope-bearing polypeptides of any length up to and including the entire amino acid sequence of a polypeptide of the invention described above also are included in the invention.

Certain non-exclusive embodiments of the invention relate to a polypeptide which has the amino acid sequence of an epitope-bearing portion of a Neutrokine-alpha or Neutrokine-alphaSV polypeptide having an amino acid sequence described in (a), (b), (c), (d), (e), (f), (g), (h) or (i) above. In other embodiments, the invention provides an isolated antibody that binds specifically (i.e., uniquely) to a Neutrokine-alpha or Neutrokine-alphaSV polypeptide having an amino acid sequence described in (a), (b), (c), (d), (e), (f), (g), (h) or (i) above.

The invention further provides methods for isolating antibodies that bind specifically (i.e., uniquely) to a Neutrokine-alpha or Neutrokine-alphaSV polypeptide having an amino acid sequence as described herein. Such antibodies are useful diagnostically or therapeutically as described below.

The invention also provides for pharmaceutical compositions comprising soluble Neutrokine-alpha and/or Neutrokine-alphaSV polypeptides, particularly human Neutrokine-alpha and/or Neutrokine-alphaSV polypeptides, and/or anti-Neutrokine-alpha antibodies and/or anti-Neutrokine-alphaSV antibodies which may be employed, for instance, to treat, prevent, prognose and/or diagnose tumor and tumor metastasis, infections by bacteria, viruses and other parasites, immunodeficiencies, inflammatory diseases, lymphadenopathy, autoimmune diseases, graft versus host disease, stimulate peripheral tolerance, destroy some transformed cell lines, mediate cell activation, survival and proliferation, mediate immune regulation and inflammatory responses, and to enhance or inhibit immune responses.

In certain embodiments, soluble Neutrokine-alpha and/or Neutrokine-alphaSV polypeptides of the invention, or agonists thereof, are administered, to treat, prevent, prognose and/or diagnose an immunodeficiency (e.g., severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired aganunaglobulinemia, adult onset agammaglobulinemia, late-onset agammaglobulinemia, dysgammaglobulinemia, hypoganmuaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.) or conditions associated with an immunodeficiency.

In a specific embodiment, Neutrokine-alpha and/or Neutrokine-alphaSV polypeptides or polynucleotides of the invention, or agonists thereof, is administered to treat, prevent, prognose and/or diagnose common variable immunodeficiency.

In a specific embodiment, Neutrokine-alpha and/or Neutrokine-alphaSV polypeptides or polynucleotides of the invention, or agonists thereof, is administered to treat, prevent, prognose and/or diagnose X-linked agammaglobulinemia.

In another specific embodiment, Neutrokine-alpha and/or Neutrokine-alphaSV polypeptides or polynucleotides of the invention, or agonists thereof, is administered to treat, prevent, prognose and/or diagnose severe combined immunodeficiency (SCID).

In another specific embodiment, Neutrokine-alpha and/or Neutrokine-alphaSV polypeptides or polynucleotides of the invention, or agonists thereof, is administered to treat, prevent, prognose and/or diagnose Wiskott-Aldrich syndrome.

In another specific embodiment, Neutrokine-alpha and/or Neutrokine-alphaSV polypeptides or polynucleotides of the invention, or agonists thereof, is administered to treat, prevent, prognose and/or diagnose X-linked Ig deficiency with hyper IgM.

In another embodiment, Neutrokine-alpha antagonists and/or Neutrokine-alphaSV antagonists (e.g., an anti-Neutrokine-alpha antibody), are administered to treat, prevent, prognose and/or diagnose an autoimmune disease (e.g., rheumatoid arthritis, systemic lupus erhythematosus, idiopathic thrombocytopenia purpura, autoimmune hemolytic anemia, autoimmune neonatal thrombocytopenia, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), an immune-based rheumatologic disease (e.g., SLE, rheumatoid arthritis, CREST syndrome (a variant of scleroderma characterized by calcinosis, Raynaud's phenomenon, esophageal motility disorders, sclerodactyly, and telangiectasia.), Seronegative spondyloarthropathy (SpA), Polymyositis/dermatomyositis, Microscopic polyangiitis, Hepatitis C-asociated arthritis, Takayasu's arteritis, and undifferentiated connective tissue disorder), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, scleroderma with anti-collagen glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders) or conditions associated with an autoimmune disease. In a specific preferred embodiment, rheumatoid arthritis is treated, prevented, prognosed and/or diagnosed using anti-Neutrokine-alpha antibodies and/or anti-Neutrokine-alphaSV antibodies and/or other antagonist of the invention. In another specific preferred embodiment, systemic lupus erythemosus is treated, prevented, prognosed, and/or diagnosed using anti-Neutrokine-alpha antibodies and/or anti-Neutrokine-alphaSV and/or other antagonist of the invention. In another specific preferred embodiment, idiopathic thrombocytopenia purpura is treated, prevented, prognosed, and/or diagnosed using anti-Neutrokine-preferred embodiment, idiopathic thrombocytopenia purpura is treated, prevented, prognosed, and/or diagnosed using anti-Neutrokine-alpha antibodies and/or anti-Neutrokine-alphaSV and/or other antagonist of the invention. In another specific preferred embodiment IgA nephropathy is treated, prevented, prognosed and/or diagnosed using anti-Neutrokine-alpha antibodies and/or anti-Neutrokine-alphaSV and/or other antagonist of the invention. In a preferred embodiment, the autoimmune diseases and disorders and/or conditions antibodies and/or anti-Neutrokine-alphaSV antibodies.

The invention further provides compositions comprising a Neutrokine-alpha or Neutrokine-alphaSV polynucleotide, a Neutrokine-alpha or Neutrokine-alphaSV polypeptide, and/or an anti-Neutrokine-alpha antibody or anti-Neutrokine-alphaSV antibody, for administration to cells in vitro, to cells ex vivo, and to cells in vivo, or to a multicellular organism. In preferred embodiments, the compositions of the invention comprise a Neutrokine-alpha and/or Neutrokine-alphaSV polynucleotide for expression of a Neutrokine-alpha and/or Neutrokine-alphaSV polypeptide in a host organism for treatment of disease. In a most preferred embodiment, the compositions of the invention comprise a Neutrokine-alpha and/or Neutrokine-alphaSV polynucleotide for expression of a Neutrokine-alpha and/or Neutrokine-alphaSV polypeptide in a host organism for treatment of an immunodeficiency and/or conditions associated with an immunodeficiency. Particularly preferred in this regard is expression in a human patient for treatment of a dysfunction associated with aberrant endogenous activity of a Neutrokine-alpha, Neutrokine-alphaSV, Neutrokine alpha receptor, and/or Neutrokine-alphaSV receptor gene (e.g., expression to enhance the normal B-cell function by expanding B-cell numbers or increasing B cell lifespan).

The present invention further encompasses methods and compositions for preventing, treating and/or ameliorating diseases or disorders associated with aberrant or inappropriate Neutrokine-alpha, Neutrokine-alphaSV, Neutrokine-alpha receptor, and/or Neutrokine-alphaSV receptor expression or function in an animal, preferably a mammal, and most preferably a human, comprising, or alternatively consisting of, administering to an animal in which such treatment, prevention or amelioration is desired one or more Neutrokine-alpha and/or Neutrokine-alphaSV polypeptides (including molecules which comprise, or alternatively consist of, Neutrokine-alpha and/or Neutrokine-alphaSV polypeptide fragments or variants thereof) in an amount effective to treat prevent or ameliorate the disease or disorder.

The present invention further encompasses methods and compositions for killing cells of hematopoietic origin, comprising, or alternatively consisting of, contacting Neutrokine-alpha and/or Neutrokine-alphaSV polypeptide with cells of hematopoietic origin. In preferred embodiments, the cells of hematopoietic origin are B cells.

The present invention further encompasses methods and compositions for killing cells of hematopoietic origin, comprising, or alternatively consisting of, administering to an animal in which such killing is desired, a Neutrokine-alpha and/or Neutrokine-alphaSV polypeptide (e.g., a radiolabeled Neutrokine-alpha and/or Neutrokine-alphaSV polypeptide) in an amount effective to kill cells of hematopoietic origin. In preferred embodiments, the cells of hematopoietic origin are B cells.

The present invention further encompasses methods and compositions for stimulating immunoglobulin production, comprising, or alternatively consisting of, contacting an effective amount of Neutrokine-alpha and/or Neutrokine-alphaSV with cells of hematopoietic origin, wherein the effective amount of the Neutrokine-alpha and/or Neutrokine-alphaSV binding polypeptide stimulates Neutrokine-alpha and/or Neutrokine-alphaSV-mediated immunoglobulin production.

The present invention further encompasses methods and compositions for stimulating immunoglobulin production comprising, or alternatively consisting of, administering to an animal in which such stimulation is desired, a Neutrokine-alpha and/or Neutrokine-alphaSV polypeptide in an amount effective to stimulate immunoglobulin production.

The present invention further encompasses methods and compositions for stimulating proliferation of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide stimulates Neutrokine-alpha and/or Neutrokine-alphaSV-mediated cell proliferation. In preferred embodiments, the cells of hematopoietic origin are B cells.

The present invention further encompasses methods and compositions for stimulating proliferation of cells of hematopoietic origin, comprising, or alternatively consisting of, administering to an animal in which such stimulation is desired, a Neutrokine-alpha and/or Neutrokine-alphaSV polypeptide in an amount effective to stimulate Neutrokine-alpha and/or Neutrokine-alphaSV-mediated cell proliferation. In preferred embodiments, the cells of hematopoietic origin are B cells.

The present invention further encompasses methods and compositions for increasing activation of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide increases Neutrokine-alpha and/or Neutrokine-alphaSV-mediated activation of cells of hematopoietic origin. In preferred embodiments, the cells of hematopoietic origin are B cells.

The present invention further encompasses methods and compositions for increasing activation of cells of hematopoietic origin, comprising, or alternatively consisting of, administering to an animal in which such increase is desired, a Neutrokine-alpha and/or Neutrokine-alphaSV polypeptide in an amount effective to increase Neutrokine-alpha and/or Neutrokine-alphaSV-mediated activation of cells of hematopoietic origin. In preferred embodiments, the cells of hematopoietic origin are B cells.

The present invention further encompasses methods and compositions for increasing lifespan of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV binding polypeptide increases Neutrokine-alpha and/or Neutrokine-alphaSV-regulated lifespan of cells of hematopoietic origin. In preferred embodiments, the cells of hematopoietic origin are B cells.

The present invention further encompasses methods and compositions for increasing lifespan of cells of hematopoietic origin, comprising, or alternatively consisting of, administering to an animal in which such increase is desired, a Neutrokine-alpha and/or Neutrokine-alphaSV polypeptide in an amount effective to increase Neutrokine-alpha and/or Neutrokine-alphaSV-regulated lifespan of cells of hematopoietic origin. In preferred embodiments, the cells of hematopoietic origin are B cells.

The present invention further encompasses methods and compositions for inhibiting or reducing immunoglobulin production, comprising, or alternatively consisting of, contacting an effective amount of Neutrokine-alpha and/or Neutrokine-alphaSV with cells of hematopoietic origin, wherein the effective amount of the Neutrokine-alpha and/or Neutrokine-alphaSV binding polypeptide inhibits or reduces Neutrokine-alpha and/or Neutrokine-alphaSV-mediated immunoglobulin production. In preferred embodiments, the cells of hematopoietic origin are B cells.

The present invention further encompasses methods and compositions for inhibiting or reducing immunoglobulin production comprising, or alternatively consisting of, administering to an animal in which such inhibition or reduction is desired, a Neutrokine-alpha and/or Neutrokine-alphaSV polypeptide in an amount effective to inhibit ir reduce immunoglobulin production.

The present invention further encompasses methods and compositions for inhibiting or reducing proliferation of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide inhibits ir reduces Neutrokine-alpha and/or Neutrokine-alphaSV-mediated cell proliferation. In preferred embodiments, the cells of hematopoietic origin are B cells.

The present invention further encompasses methods and compositions for inhibiting or reducing proliferation of cells of hematopoietic origin, comprising, or alternatively consisting of, administering to an animal in which such inhibition or reduction is desired, a Neutrokine-alpha and/or Neutrokine-alphaSV polypeptide in an amount effective to inhibit or reduce Neutrokine-alpha and/or Neutrokine-alphaSV-mediated cell proliferation. In preferred embodiments, the cells of hematopoietic origin are B cells.

The present invention further encompasses methods and compositions for decreasing activation of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide decreases Neutrokine-alpha and/or Neutrokine-alphaSV-mediated activation of cells of hematopoietic origin. In preferred embodiments the cells of hematopoictic origin are B cells.

The present invention further encompasses methods and compositions for decreasing activation of cells of hematopoietic origin, comprising, or alternatively consisting of, administering to an animal in which such increase is desired, a Neutrokine-alpha and/or Neutrokine-alphaSV polypeptide in an amount effective to decrease Neutrokine-alpha and/or Neutrokine-alphaSV-mediated activation of cells of hematopoietic origin. In preferred embodiments the cells of hematopoietic origin are B cells.

The present invention further encompasses methods and compositions for decreasing lifespan of B cells, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV binding polypeptide decreases Neutrokine-alpha and/or Neutrokine-alphaSV-regulated lifespan of cells of hematopoietic origin. In preferred embodiments the cells of hematopoietic origin are B cells.

The present invention further encompasses methods and compositions for decreasing lifespan of cells of hematopoietic origin, comprising, or alternatively consisting of, administering to an animal in which such reduction is desired, a Neutrokine-alpha and/or Neutrokine-alphaSV polypeptide in an amount effective to decrease Neutrokine-alpha and/or Neutrokine-alphaSV-regulated lifespan of cells of hematopoietic origin. In preferred embodiments the cells of hematopoietic origin are B cells.

The present invention also provides a screening method for identifying compounds capable of enhancing or inhibiting a cellular response induced by Neutrokine-alpha and/or Neutrokine-alphaSV which involves contacting cells which express Neutrokine-alpha and/or Neutrokine-alphaSV with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another embodiment, a method for identifying Neutrokine-alpha and/or Neutrokine-alphaSV receptors is provided, as well as a screening assay for agonists and antagonists using such receptors. This assay involves determining the effect a candidate compound has on Neutrokine-alpha and/or Neutrokine-alphaSV binding to the Neutrokine-alpha and/or Neutrokine-alphaSV receptor. In particular, the method involves contacting a Neutrokine-alpha and/or Neutrokine-alphaSV receptor with a Neutrokine-alpha and/or Neutrokine-alphaSV polypeptide of the invention and a candidate compound and determining whether Neutrokine-alpha and/or Neutrokine-alphaSV polypeptide binding to the Neutrokine-alpha and/or Neutrokine-alphaSV receptor is increased or decreased due to the presence of the candidate compound. The antagonists may be employed to prevent septic shock, inflammation, cerebral malaria, activation of the HIV virus, graft-host rejection, bone resorption, rheumatoid arthritis, cachexia (wasting or malnutrition), immune system function, lymphoma, and autoimmune disorders (e.g., rheumatoid arthritis and systemic lupus erythematosus).

The present inventors have discovered that Neutrokine-alpha is expressed not only in cells of monocytic lineage, but also in kidney, lung, peripheral leukocyte, bone marrow, T cell lymphoma, B cell lymphoma, activated T cells, stomach cancer, smooth muscle, macrophages, and cord blood tissue. The present inventors have further discovered that Neutrokine-alphaSV appears to be expressed highly only in primary dendritic cells. For a number of disorders of these tissues and cells, such as tumor and tumor metastasis, infection of bacteria, viruses and other parasites, immunodeficiencies (e.g., chronic variable immunodeficiency), septic shock, inflammation, cerebral malaria, activation of the HIV virus, graft-host rejection, bone resorption, rheumatoid arthritis, autoimmune diseases (e.g., rheumatoid arthritis and systemic lupus erythematosus) and cachexia (wasting or malnutrition). It is believed that significantly higher or lower levels of Neutrokine-alpha and/or Neutrokine-alphaSV gene expression can be detected in certain tissues (e.g., bone marrow) or bodily fluids (e.g., serum, plasma, urine, synovial fluid or spinal fluid) taken from an individual having such a disorder, relative to a "standard" Neutrokine-alpha and/or Neutrokine-alphaSV gene expression level, i.e., the Neutrokine-alpha and/or Neutrokine-alphaSV expression level in tissue or bodily fluids from an individual not having the disorder. Thus, the invention provides a diagnostic method useful during diagnosis of a disorder, which involves: (a) assaying Neutrokine-alpha and/or Neutrokine-alphaSV gene expression level in cells or body fluid of an individual; (b) comparing the Neutrokine-alpha and/or Neutrokine-alphaSV gene expression level with a standard Neutrokine-alpha and/or Neutrokine-alphaSV gene expression level, whereby an increase or decrease in the assayed Neutrokine-alpha and/or Neutrokine-alphaSV gene expression level compared to the standard expression level is indicative of a disorder.

An additional embodiment of the invention is related to a method for treating an individual in need of an increased or constitutive level of Neutrokine-alpha and/or Neutrokine-alphaSV activity in the body comprising administering to such an individual a composition comprising a therapeutically effective amount of an isolated Neutrokine-alpha and/or Neutrokine-alphaSV polypeptide of the invention or an agonist thereof.

A still further embodiment of the invention is related to a method for treating an individual in need of a decreased level of Neutrokine-alpha and/or Neutrokine-alphaSV activity in the body comprising, administering to such an individual a composition comprising a therapeutically effective amount of an Neutrokine-alpha and/or Neutrokine-alphaSV antagonist. Preferred antagonists for use in the present invention are Neutrokine-alpha-specific and/or Neutrokine-alphaSV-specific antibodies.

BRIEF DESCRIPTION OF THE FIGURES

The following drawings are illustrative of embodiments of the invention and are not meant to limit the scope of the invention as encompassed by the claims.

Regions of high identity between Neutrokine-alpha, Neutrokine-alphaSV, TNF-alpha, TNF-beta, LT-beta, and the closely related Fas Ligand (an alignment of these sequences is presented in FIGS. 2A, 2B, 2C, and 2D) are underlined in FIGS. 1A and 1B. These regions are not limiting and are labeled as Conserved Domain (CD)-I, CD-II, CD-III, CD-IV, CD-V, CD-VI, CD-VII, CD-VIII, CD-IX, CD-X, and CD-XI in FIGS. 1A and 1B.

FIGS. 2A, 2B, 2C, and 2D show the regions of identity between the amino acid sequences of Neutrokine-alpha (SEQ ID NO:2) and Neutrokine-alphaSV (SEQ ID NO:19), and TNF-alpha ("TNFalpha" in FIGS. 2A, 2B, 2C, and 2D; GenBank No. Z15026; SEQ ID NO:3), TNF-beta ("TNFbeta" in FIGS. 2A, 2B, 2C, and 2D; GenBank No. Z15026; SEQ ID NO:4), Lymphotoxin-beta ("LTbeta" in FIGS. 2A, 2B, 2C, and 2D; GenBank No. LI1016; SEQ ID NO:5), and FAS ligand ("FASL" in FIGS. 2A, 2B, 2C, and 2D; GenBank No. U11821; SEQ ID NO:6), determined by the "MegAlign" routine which is part of the computer program called "DNA*STAR." Residues that match the consensus are shaded.

Figure 2B:
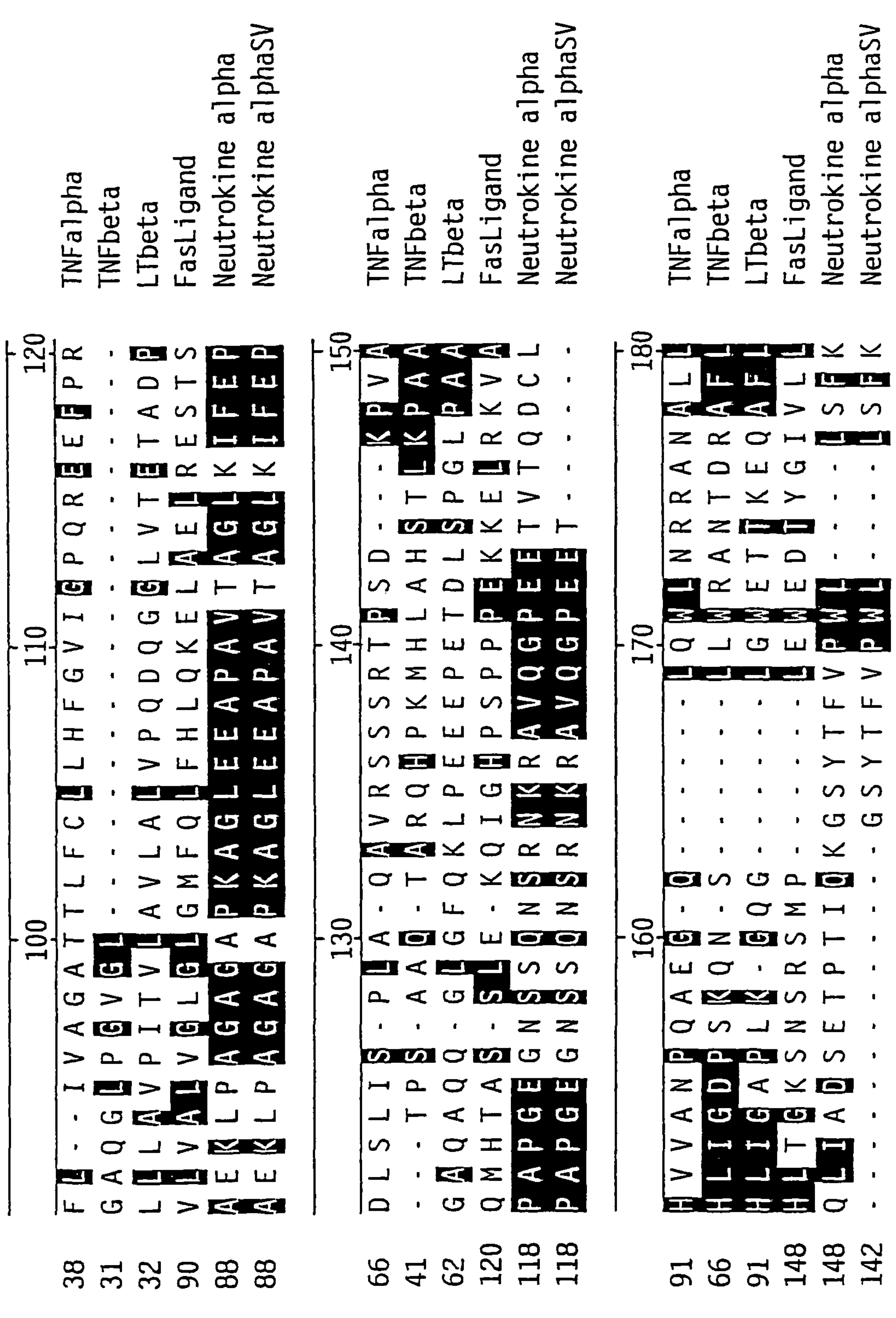
Figure 2C:
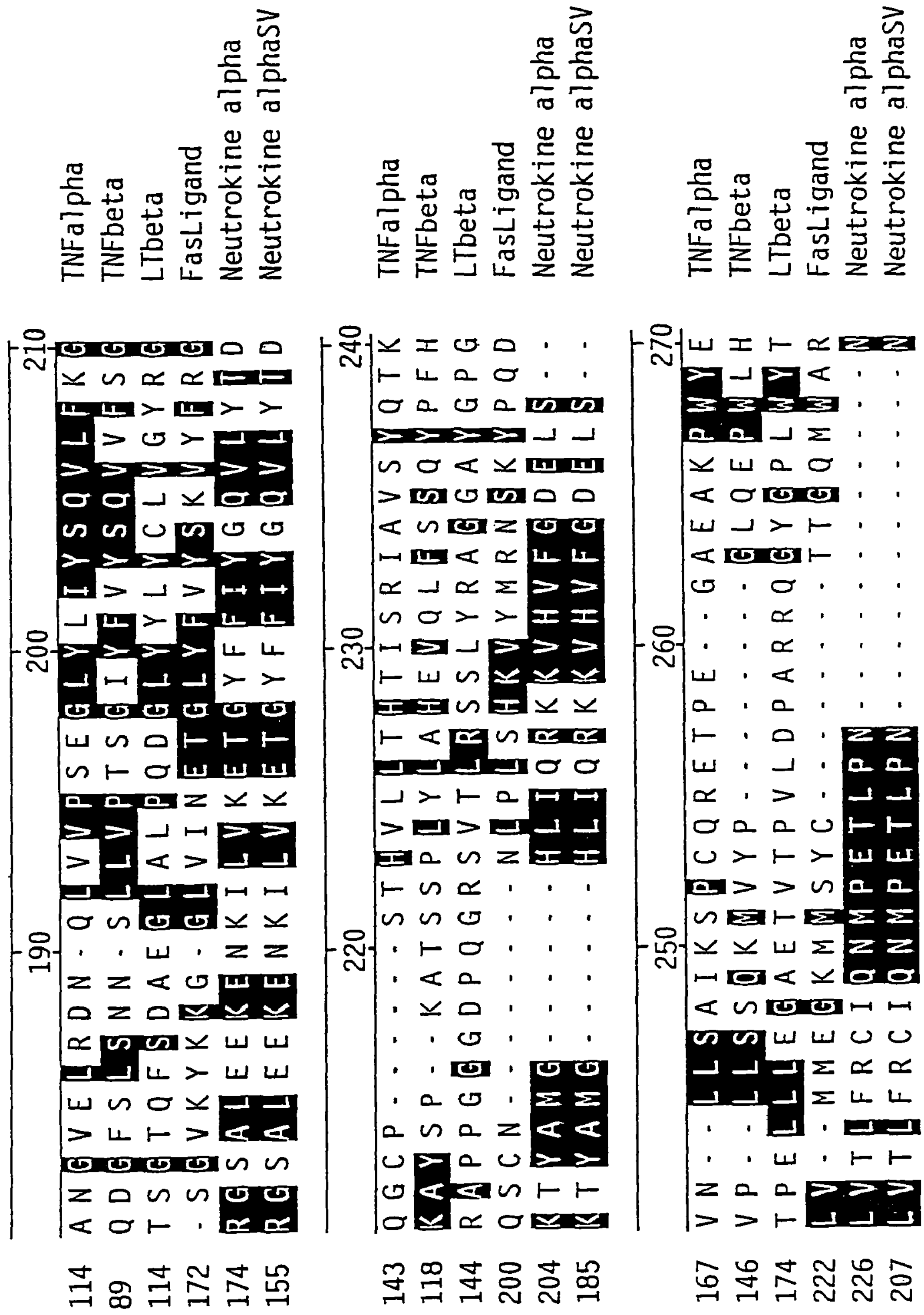
Figure 3:
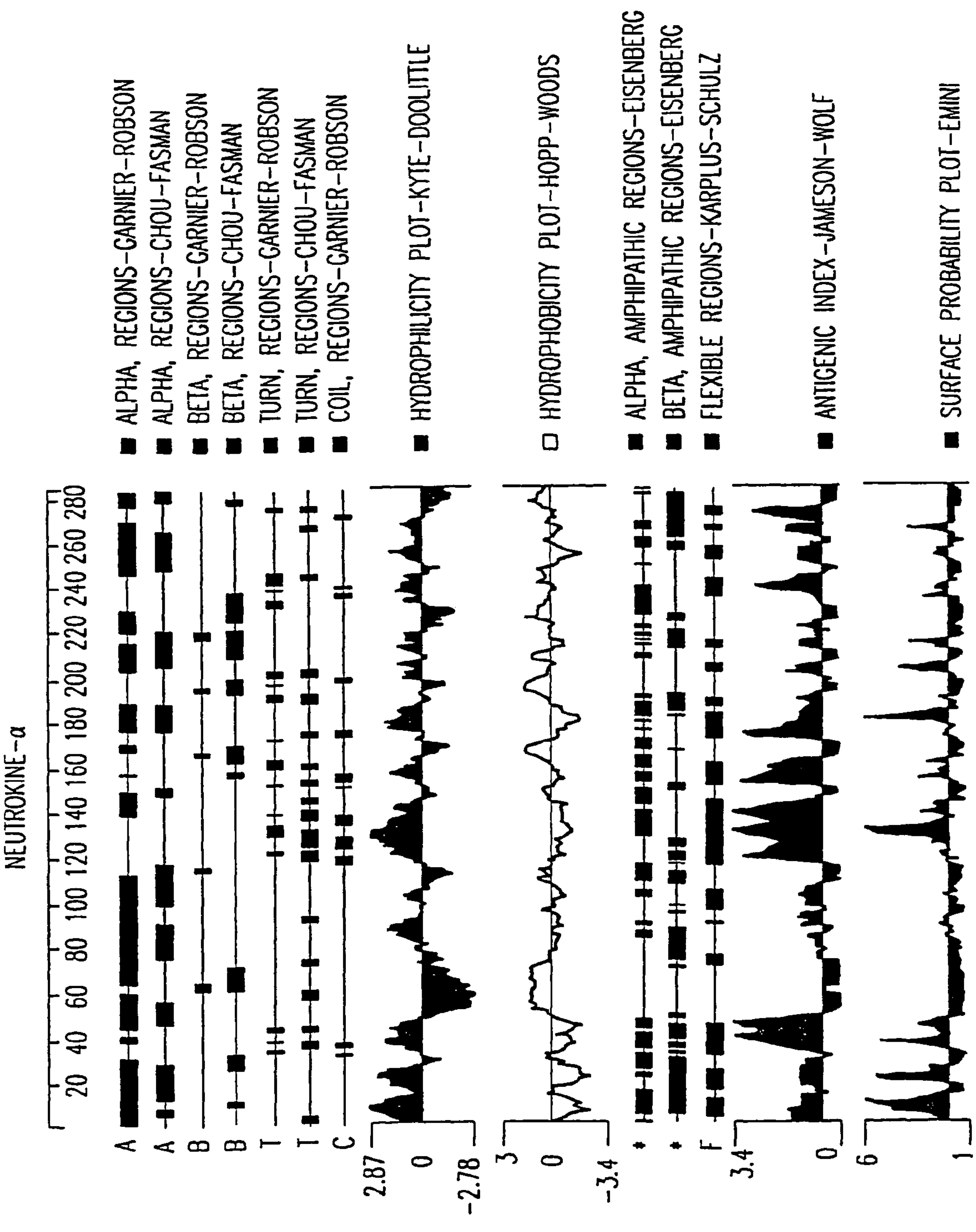

FIG. 3 shows an analysis of the Neutrokine-alpha amino acid sequence. Alpha, beta, turn and coil regions; hydrophilicity and hydrophobicity; amphipathic regions; flexible regions; antigenic index and surface probability are shown, as predicted for the amino acid sequence of SEQ ID NO:2 using the default parameters of the recited computer programs. In the "Antigenic Index—Jameson-Wolf" graph, the indicate location of the highly antigenic regions of Neutrokine-alpha i.e., regions from which epitope-bearing peptides of the invention may be obtained. Antigenic polypeptides include from about Phe-115 to about Leu-147, from about Ile-150 to about Tyr-163, from about Ser-171 to about Phe-194, from about Glu-223 to about Tyr-246, and from about Ser-271 to about Phe-278, of the amino acid sequence of SEQ ID NO:2.

The data presented in FIG. 3 are also represented in tabular form in Table 1. The columns are labeled with the headings "Res", "Position", and Roman Numerals I-XIV. The column headings refer to the following features of the amino acid sequence presented in FIG. 3, and Table 1: "Res": amino acid residue of SEQ ID NO:2 and FIGS. 1A and 1B; "Position": position of the corresponding residue within SEQ ID NO:2 and FIGS. 1A and 1B; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

FIGS. 4A, 4B, and 4C show the alignment of the Neutrokine-alpha nucleotide sequence determined from the human cDNA deposited in ATCC No. 97768 with related human cDNA clones of the invention which have been designated HSOAD55 (SEQ ID NO:7), HNEDU15 (SEQ ID NO: 1), HSLAH84 (SEQ ID NO:8) and HLTBM08 (SEQ ID NO:9).

FIGS. 5A and 5B shows the nucleotide (SEQ ID NO:18) and deduced amino acid (SEQ ID NO:19) sequences of the Neutrokine-alphaSV protein. Amino acids 1 to 46 represent the predicted intracellular domain, amino acids 47 to 72 the predicted transmembrane domain (the double-underlined sequence), and amino acids 73 to 266, the predicted extracellular domain (the remaining sequence). Potential asparagine-linked glycosylation sites are marked in FIGS. 5A and 5B with a bolded asparagine symbol (N) in the Neutrokine-alphaSV amino acid sequence and a bolded pound sign (#) above the first nucleotide encoding that asparagine residue in the Neutrokine-alphaSV nucleotide sequence. Potential N-linked glycosylation sequences are found at the following locations in the Neutrokine-alphaSV amino acid sequence: N-124 through Q-127 (N-124, S-125, S-126, Q-127) and N-223 through C-226 (N-223, N-224, S-225, C-226). Antigenic polypeptides include from about Pro-32 to about Leu-47, from about Glu-116 to about Ser-143, from about Phe-153 to about Tyr-173, from about Pro-218 to about Tyr-227, from about Ala-232 to about Gln-241; from about Ile-244 to about Ala-249; and from about Ser-252 to about Val-257 of the amino acid sequence of SEQ ID NO:19.

Regions of high identity between Neutrokine-alpha, Neutrokine-alphaSV, TNF-alpha, TNF-beta, LT-beta, and the closely related Fas Ligand (an aligment of these sequences is presented in FIG. 2) are underlined in FIGS. 1A and 1B. These conserved regions (of Neutrokine-alpha and Neutrokine-alphaSV) are labeled as Conserved Domain (CD)-I, CD-II, CD-III, CD-V, CD-VI, CD-VII, CD-VIII, CD-IX, CD-X, and CD-XI in FIGS. 5A and 5B. Neutrokine-alphaSV does not contain the sequence of CD-IV described in the legend of FIGS. 1A and 1B.

Figures 1, 7A:
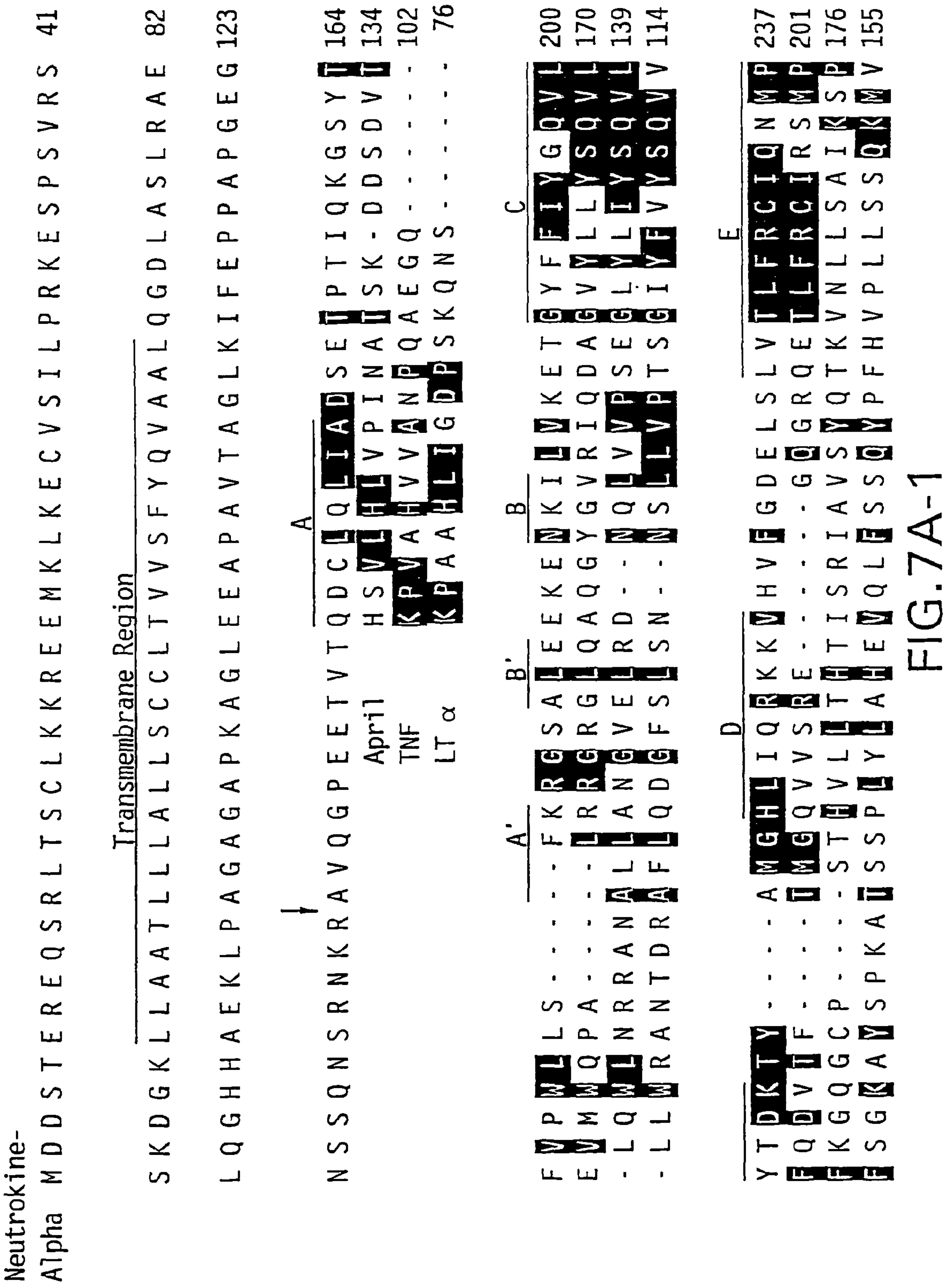
FIGS. 1A and 1B show the nucleotide (SEQ ID NO:1) and deduced amino acid (SEQ ID NO:2) sequences of Neutrokine-alpha. Amino acids 1 to 46 represent the predicted intracellular domain, amino acids 47 to 72 the predicted transmembrane domain (the double-underlined sequence), and amino acids 73 to 285, the predicted extracellular domain (the remaining sequence). Potential asparagine-linked glycosylation sites are marked in FIGS. 1A and 1B with a bolded asparagine symbol (N) in the Neutrokine-alpha amino acid sequence and a bolded pound sign (#) above the first nucleotide encoding that asparagine residue in the Neutrokine-alpha nucleotide sequence. Potential N-linked glycosylation sequences are found at the following locations in the Neutrokine-alpha amino acid sequence: N-124 through Q-127 (N-124, S-125, S-126, Q-127) and N-242 through C-245 (N-242, N-243, S-244, C-245).
Figures 2, 7A:
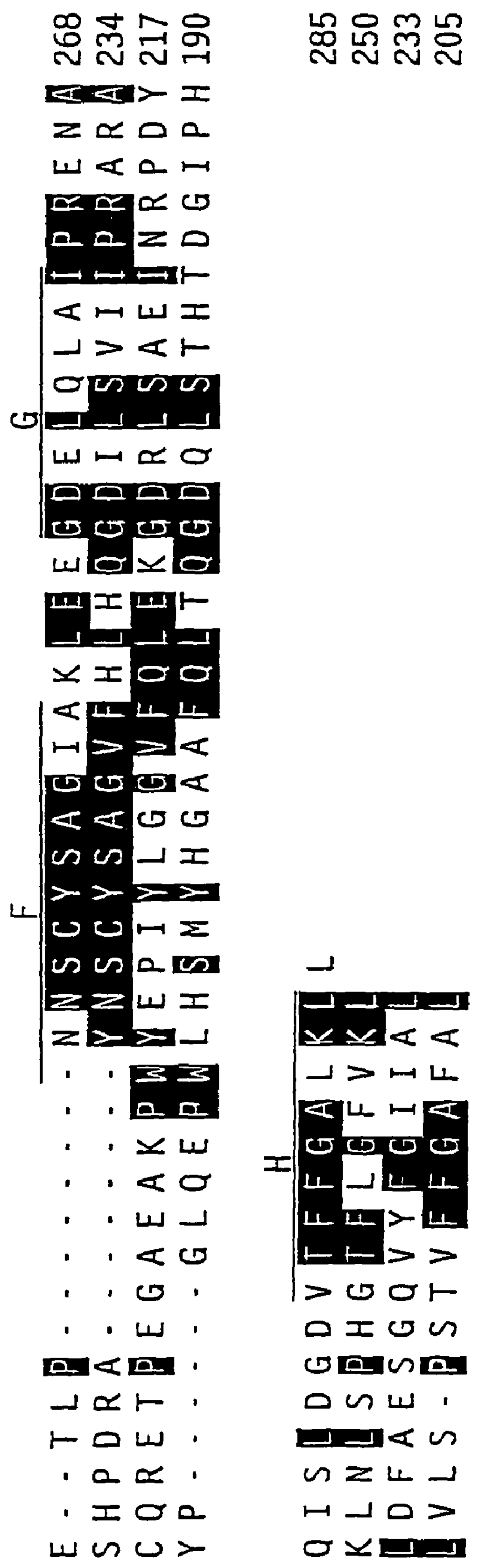

An additional alignment of the Neutrokine-alpha polypeptide sequence (SEQ ID NO:2) with APRIL, TNF alpha, and LT alpha is presented in FIGS. 7A-1 and 7A-2. In FIGS. 7A-1 and 7A-2, beta sheet regions are indicated as described below in the legend to FIGS. 7A-1 and 7A-2.

Figure 6:
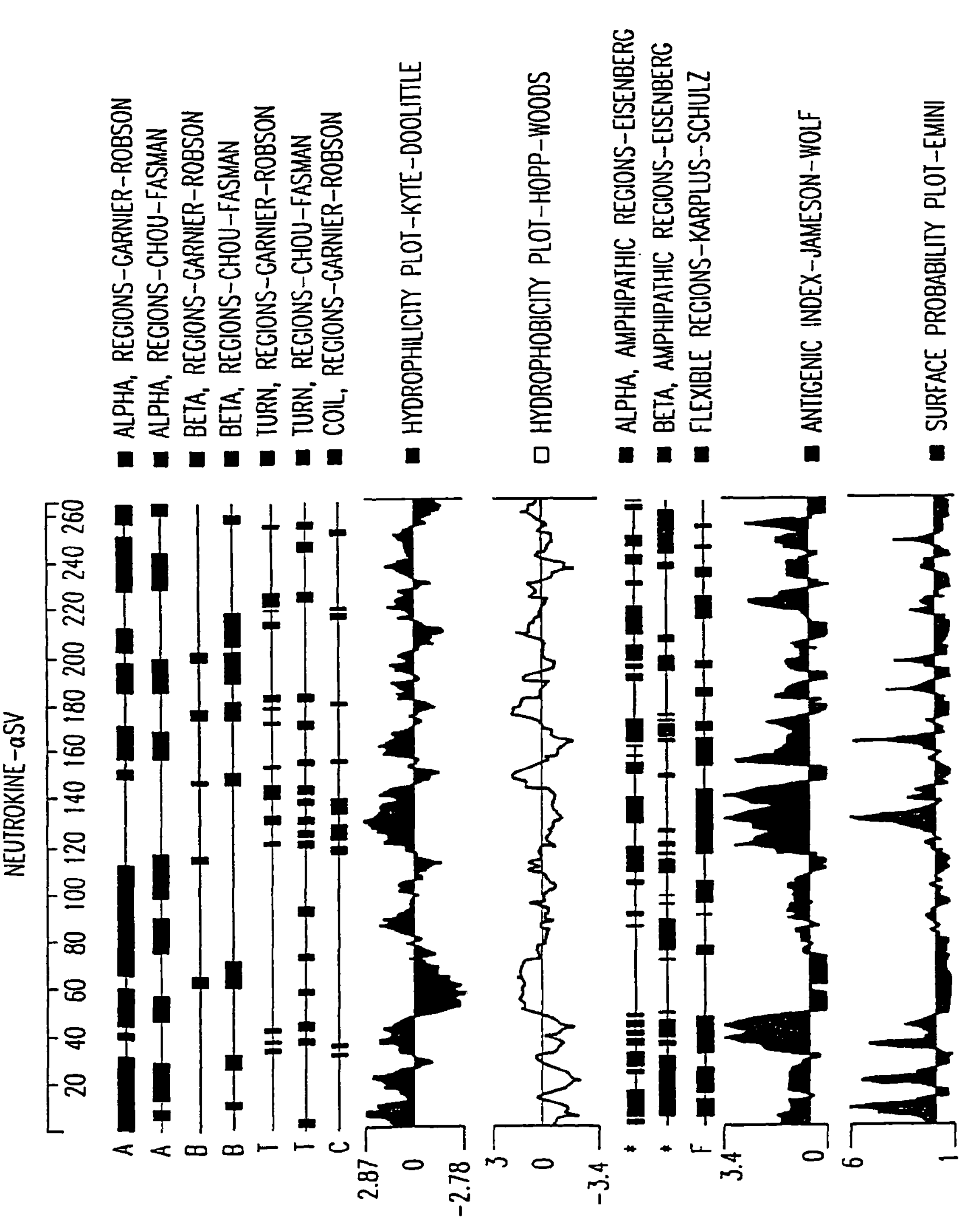

FIG. 6 shows an analysis of the Neutrokine-alphaSV amino acid sequence. Alpha, beta, turn and coil regions; hydrophilicity and hydrophobicity; amphipathic regions; flexible regions; antigenic index and surface probability are shown, as predicted for the amino acid sequence of SEQ ID NO:19 using the default parameters of the recited computer programs. The location of the highly antigenic regions of the Neutrokine-alpha protein, i.e., regions from which epitope-bearing peptides of the invention may be obtained is indicated in the "Antigenic Index—Jameson-Wolf" graph. Antigenic polypeptides include, but are not limited to, a polypeptide comprising amino acid residues from about Pro-32 to about Leu47, from about Glu-116 to about Ser-143, from about Phe-153 to about Tyr-173, from about Pro-218 to about Tyr-227, from about Ser-252 to about Thr-258, from about Ala-232 to about Gln-241; from about Ile-244 to about Ala-249; and from about Ser-252 to about Val-257, of the amino acid sequence of SEQ ID NO:19.

The data shown in FIG. 6 can be easily represented in tabular format similar to the data shown in Table 1. Such a tablular representation of the exact data disclosed in FIG. 6 can be generated using the MegAlign component of the DNA*STAR computer sequence analysis package set on default parameters. This is the identical program that was used to generate FIGS. 3 and 6 of the present application.

FIGS. 7A-1 and 7A-2. The amino-acid sequence of Neutrokine-alpha (SEQ ID NO:2) and alignment of its predicted ligand-binding domain with those of APRIL, TNF-alpha, and LT-alpha (specifically, amino acid residues 115-250 of the human APRIL polypeptide (SEQ ID NO:20; GenBank Accession No. AF046888 (nucleotide) and AAC6132 (protein)), amino acid residues 88-233 of TNF alpha (SEQ ID NO:3; GenBank Accession No. Z15026), and LT alpha ((also designated TNF-beta) amino acid residues 62-205 of SEQ ID NO:4; GenBank Accession No. Z15026)). The predicted membrane-spanning region of Neutrokine-alpha is indicated and the site of cleavage of Neutrokine-alpha is depicted with an arrow. Sequences overlaid with lines (A thru H) represent predicted beta-pleated sheet regions.

Figure 7B:
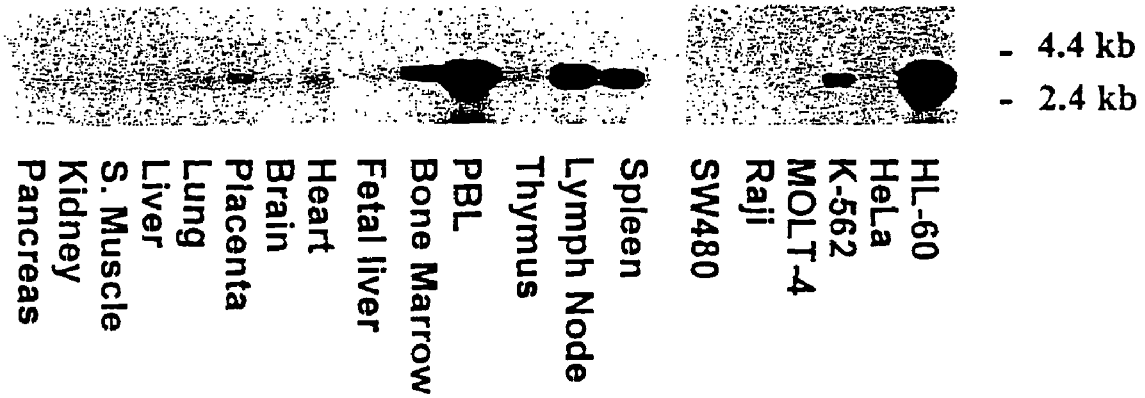

FIG. 7B. Expression of Neutrokine-alpha mRNA. Northern hybridization analysis was performed using the Neutrokine-alpha orf as a probe on blots of poly (A)+RNA (Clonetech) from a spectrum of human tissue types and a selection of cancer cell lines. A 2.6 kb Neutrokine-alpha mRNA was detected at high levels in placenta, heart, lung, fetal liver, thymus, and pancreas. The 2.6 kb Neutrokine-alpha mRNA was also detected in HL-60 and K562 cell lines.

Figure 8A:
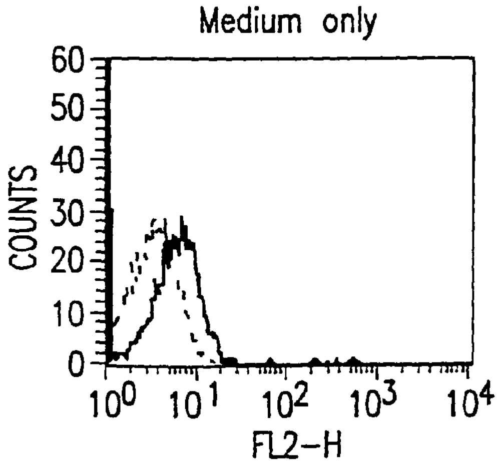
Figure 8B:
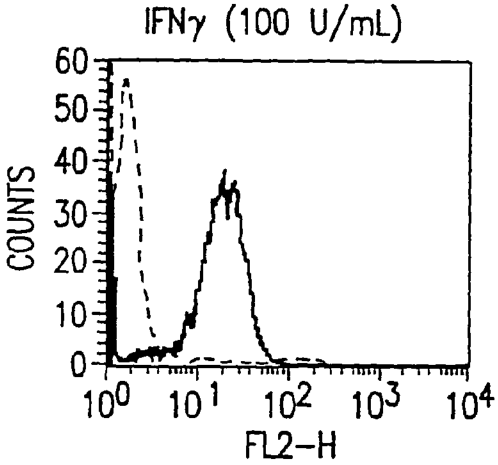
Figure 8C:
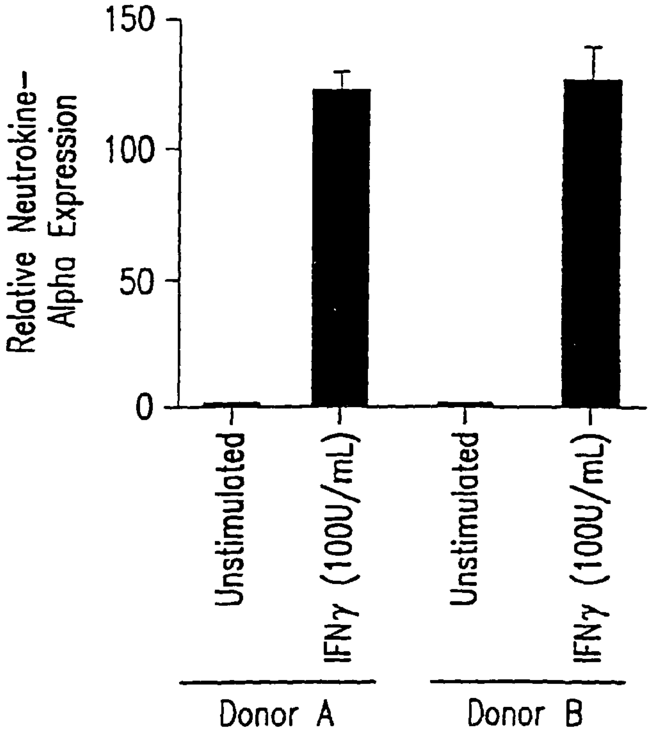

FIGS. 8A, 8B and 8C. Neutrokine-alpha expression increases following activation of human monocytes by IFN-gamma. FIGS. 8A and 8B. Flow cytometric analysis of Neutrokine-alpa protein expression on in vitro cultured monocytes. Purified monocytes were cultured for 3 days in presence or absence of IFN-gamma (100 U/ml). Cells were then stained with a Neutrokine-alpha-specific mAb (2E5) (solid lines) or an isotype-matched control (IgG1) (dashed lines). Comparable results were obtained with monocytes purified from three different donors in three independent experiments. FIG. 8C. Neutrokine-alpha-specific TaqMan primers were prepared and used to assess the relative Neutrokine-alpha mRNA expression levels in unstimulated and IFN-gamma (100 U/mL) treated monocytes. Nucleotide sequences of the TaqMan primers are as follows: (a) Probe: 5'-CCA CCA GCT CCA GGA GAA GGC AAC TC-3' (SEQ ID NO:24); (b) 5' amplification primer: 5'-ACC GCG GGA CTG AAA ATC T-3' (SEQ ID NO:25); and (c) 3' amplification primer: 5'-CAC GCT TAT TTC TGC TGT TCT GA-3' (SEQ ID NO:26).

Figure 9A:
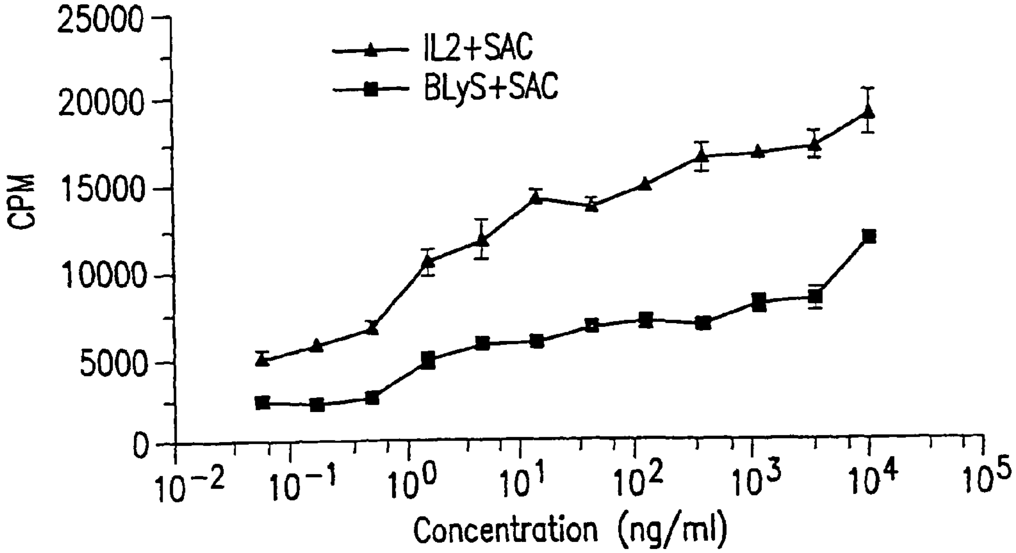
Figure 9B:
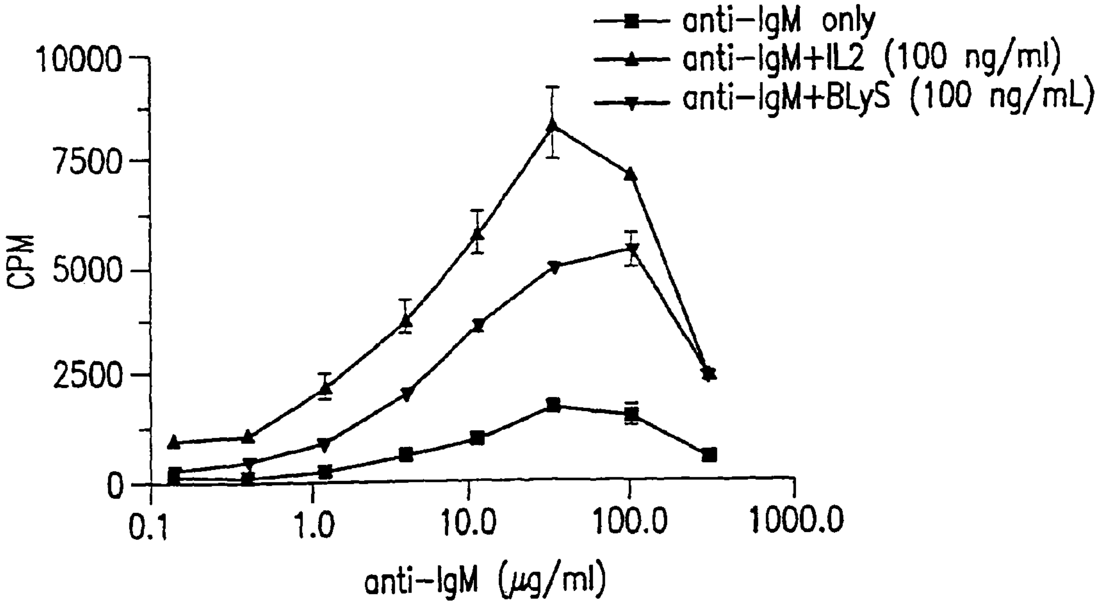

FIGS. 9A and 9B. Neutrokine-alpha is a potent B lymphocyte stimulator. FIG. 9A. The biological activity of Neutrokine-alpha was assessed in a standard B-lymphocyte co-stimulation assay utilizing Staphylococcus aureus cowan 1 SAC as the priming agent. SAC alone yielded background counts of 1427±316. Values are reported as mean±standard deviation of triplicate wells. Similar results were obtained using recombinant Neutrokine-alpha purified from stable CHO transfectants and transiently transfected HEK 293T cells. FIG. 9B. Proliferation of tonsillar B cells with Neutrokine-alpha and co-stimulation with anti-IgM. The bioassay was performed as described for SAC with the exception that individual wells were pre-coated with goat anti-human IgM antibody at 10 micrograms/mL in PBS.

Figure 10A:
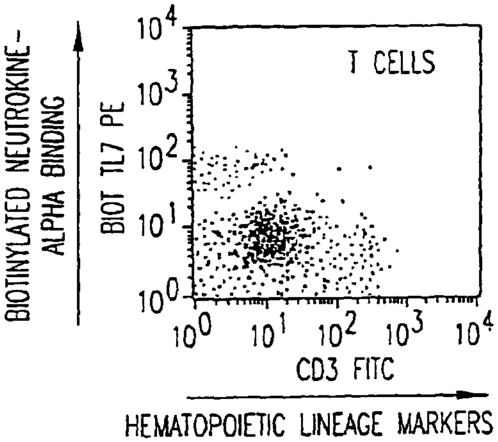
Figure 10B:
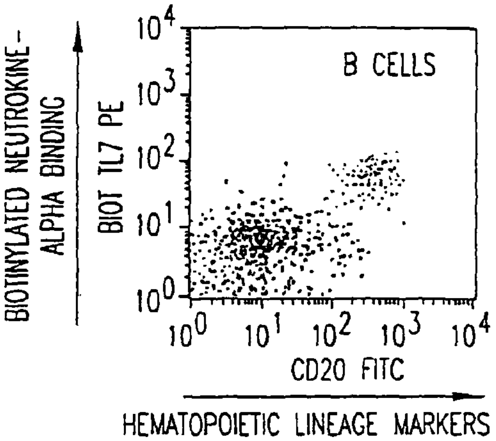
Figure 10C:
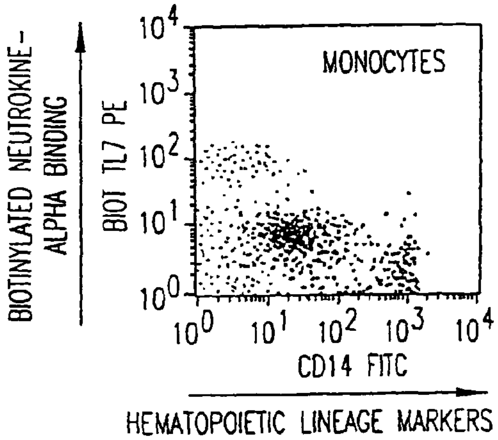
Figure 10D:
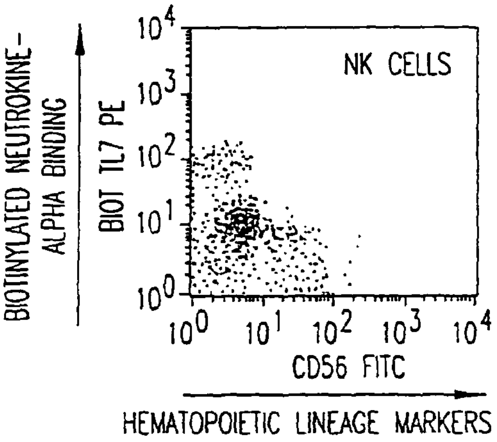
Figure 10E:
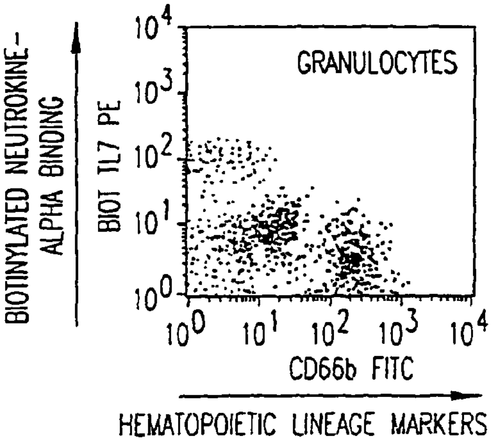
Figure 10F:
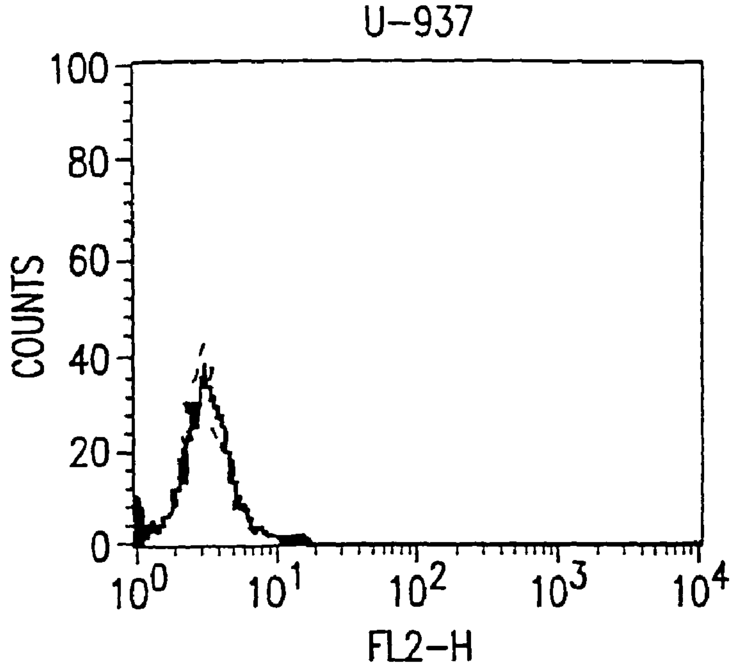
Figure 10G:
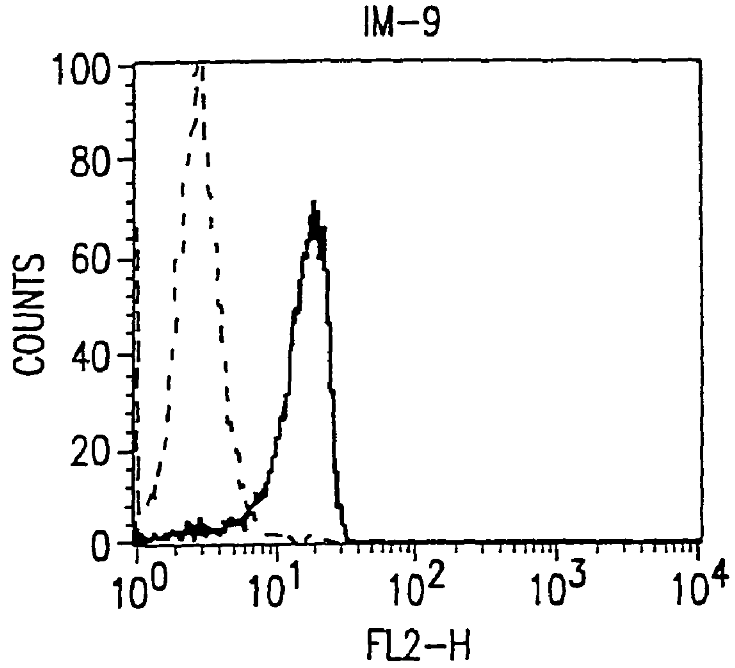

FIGS. 10A, 10B, 10C, 10D, 10E, 10F and 10G. Neutrokine-alpha receptor expression among normal human peripheral blood mononuclear cells and tumor cell lines. FIGS. 10A, 10B, 10C, 10D and 10E. Human peripheral blood nucleated cells were obtained from normal volunteers and isolated by density gradient centrifugation. Cells were stained with biotinylated Neutrokine-alpha followed by PE-conjugated streptavidin and FITC or PerCP coupled mAbs specific for CD3, CD20, CD14, CD56, and CD66b. Cells were analyzed on a Becton Dickinson FACScan using the CellQuest software. Data represent one of four independent experiments. FIGS. 10F and 10G. Neutrokine-alpha binding to histiocytic cell line U-937 and the myeloma line IM-9.

Figure 11A:
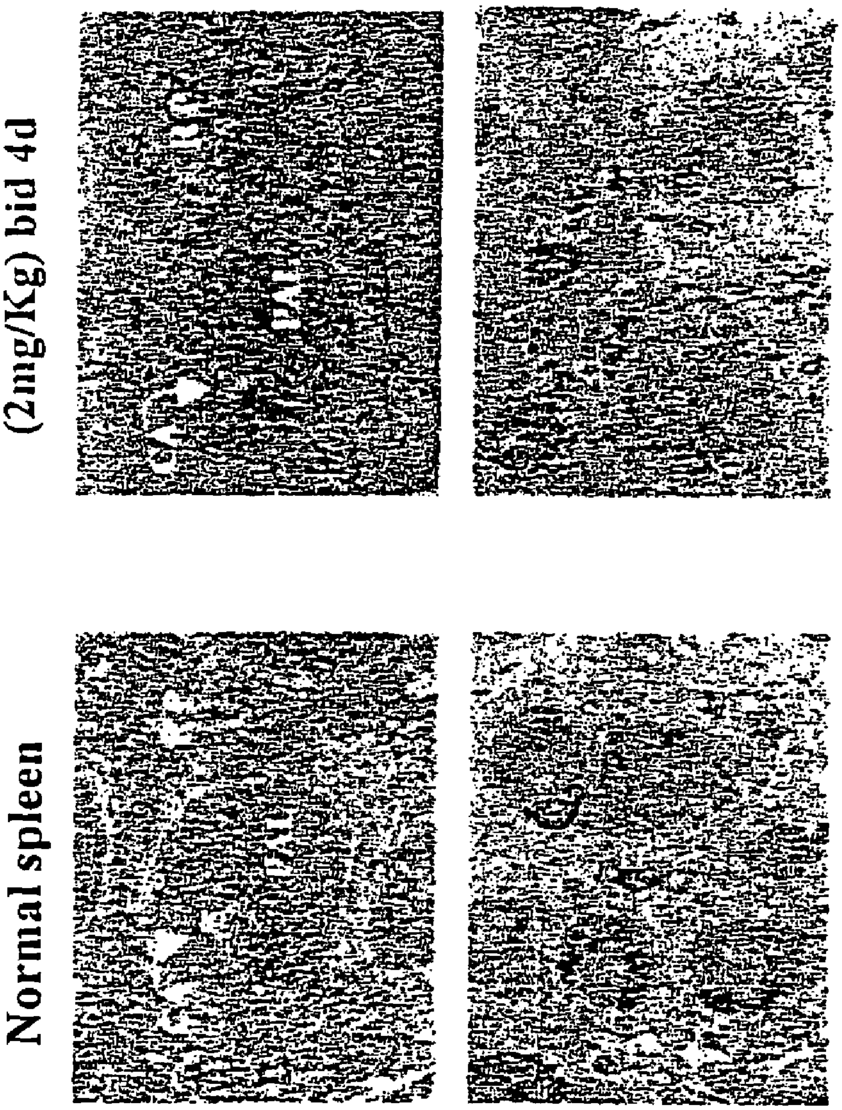
Figure 11B:
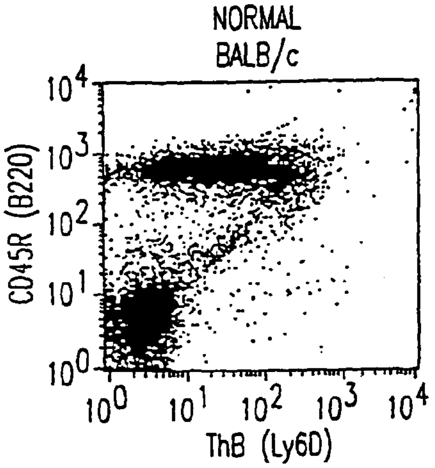
Figure 11C:
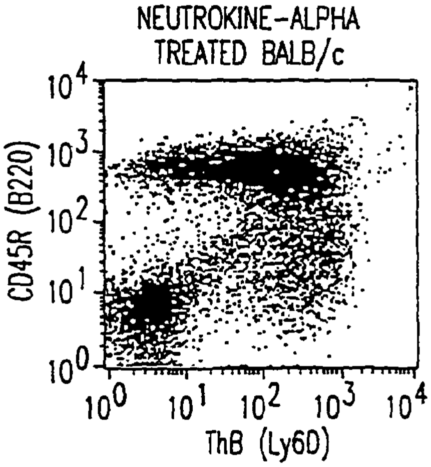
Figure 11D:
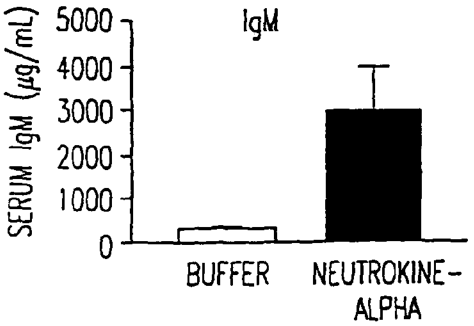
Figure 11E:
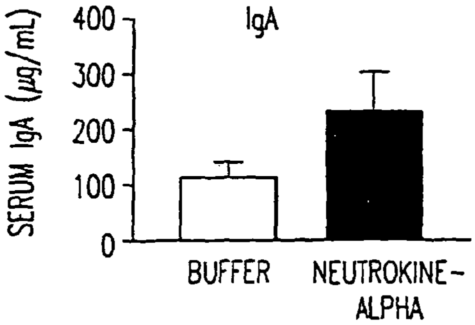
Figure 11F:
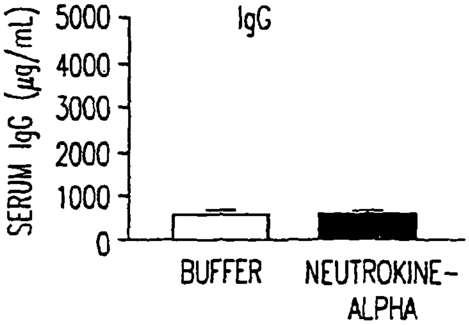

FIGS. 11A, 11B, 11C, 11D, 11E, and 11F. In vivo effects of Neutrokine-alpha administration in BALB/cAnNCR mice. FIG. 11A. Formalin-fixed spleens were paraffin embedded and 5 micrometer sections stained with hematoxylin and eosin (upper panels). The lower panels are sections taken from the same animals stained with anti-CD45R(B220) mAb and developed with horseradish-peroxidase coupled rabbit anti-rat Ig (mouse adsorbed) and the substrate diaminobenzidine tetrahydrochloride (DAB). Slides were counter-stained with Mayer's hematoxylin. CD45R(B220) expressing cells appear brown. FIGS. 11B and 11C. Flow cytometric analyses of normal (left panel) and Neutrokine-alpha-treated (right panel) stained with PE-CD45R(B220) and FITC-ThB (Ly6D). FIGS. 11D, 11E, and 11F. Serum IgM, IgG, and IgA levels in normal and Neutrokine-alpha treated mice.

Figure 12:
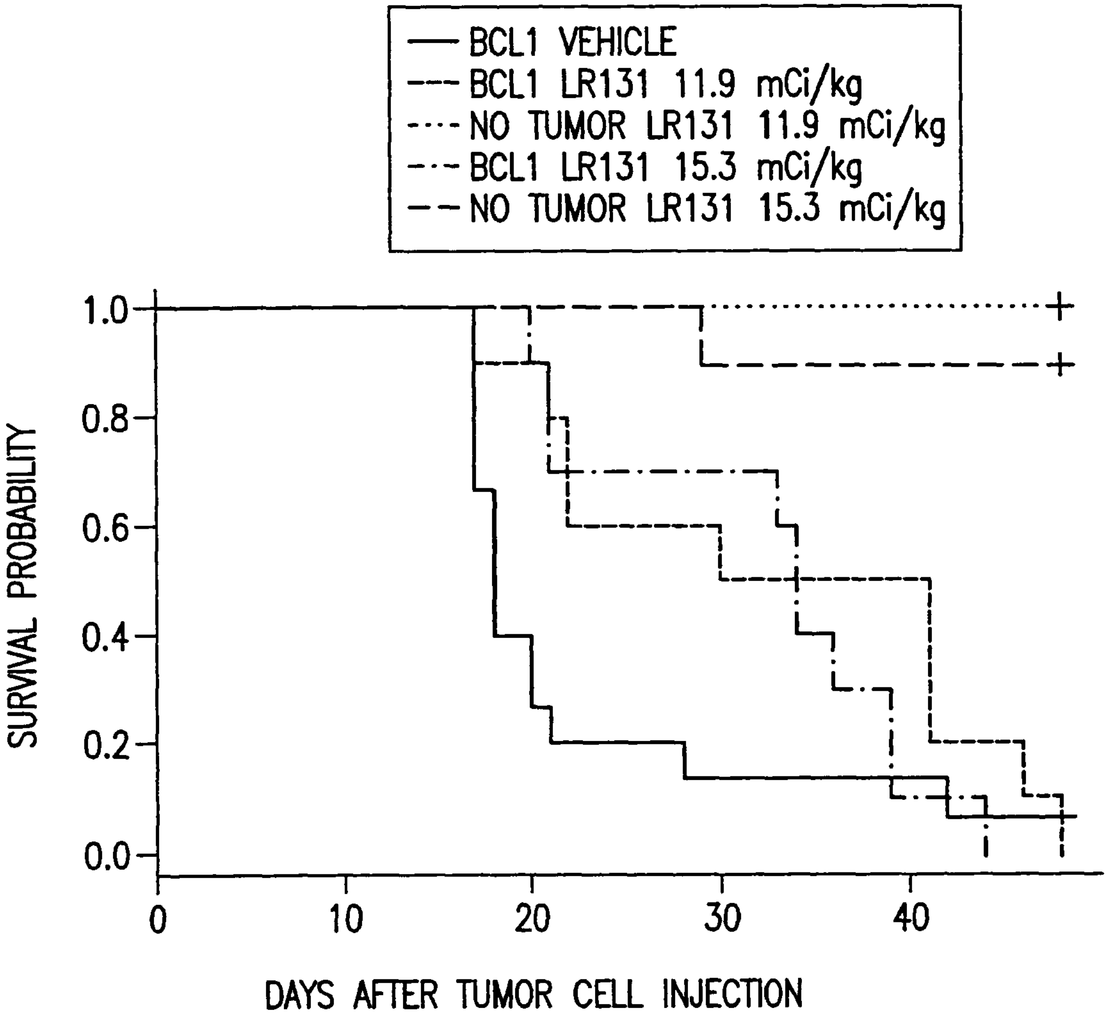

FIG. 12. Effect of $^{131}$I-labeled Neutrokine-alpha (lot TX1) on the survival of BCL1 tumor-bearing BALB/c mice. Survival curve expressed in terms of survival probability vs. time. Day 0 is the first day of tumor cell injection. Differences among the treatment groups were analyzed using the Log Rank Test for equality. Treatment with $^{131}$I-labeled Neutrokine-alpha (LR131 in figure) at doses of either 11.9 or 15.3 mCi/kg (red and blue dotted lines, respectively) significantly prolonged survival (p =0.0162 and p=0.0052, respectively) compared with vehicle-treated controls (black solid line). In the group of mice that did not have BCL1 tumors but did receive 15.3 mCi/kg of $^{131}$I-labeled Neutrokine-alpha, 10% of the mice died (yellow dashed line).

Figure 13:
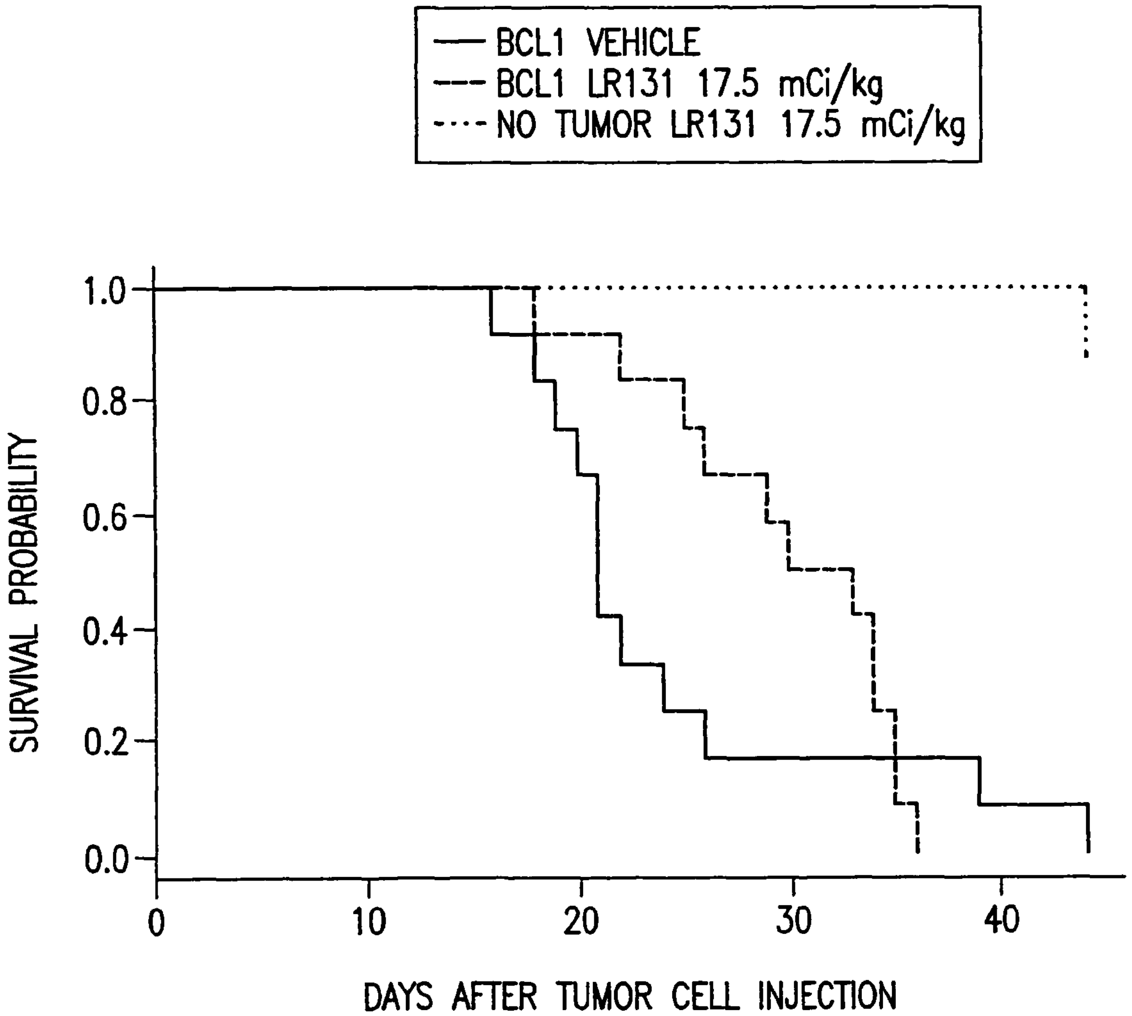

FIG. 13. Effect of $^{131}$I-labeled Neutrokine-alpha (lot TX2) on the survival of BCL1 tumor-bearing BALB/c mice. Survival curve expressed in terms of survival probability vs. time. Day 0 is the first day of tumor cell injection. Differences among the treatment groups were analyzed using the Log Rank Test for equality. Treatment with $^{131}$I-labeled Neutrokine-alpha (LR131 in figure) at a dose of 17.5 mCi/kg (dashed line) significantly prolonged survival (p=0.0348) compared with the vehicle-treated controls (black solid line). In the group of mice that did not have BCL1 tumors but did receive $^{131}$I-labeled Neutrokine-alpha, 12.5% of the mice died (dotted line).

Figure 14:
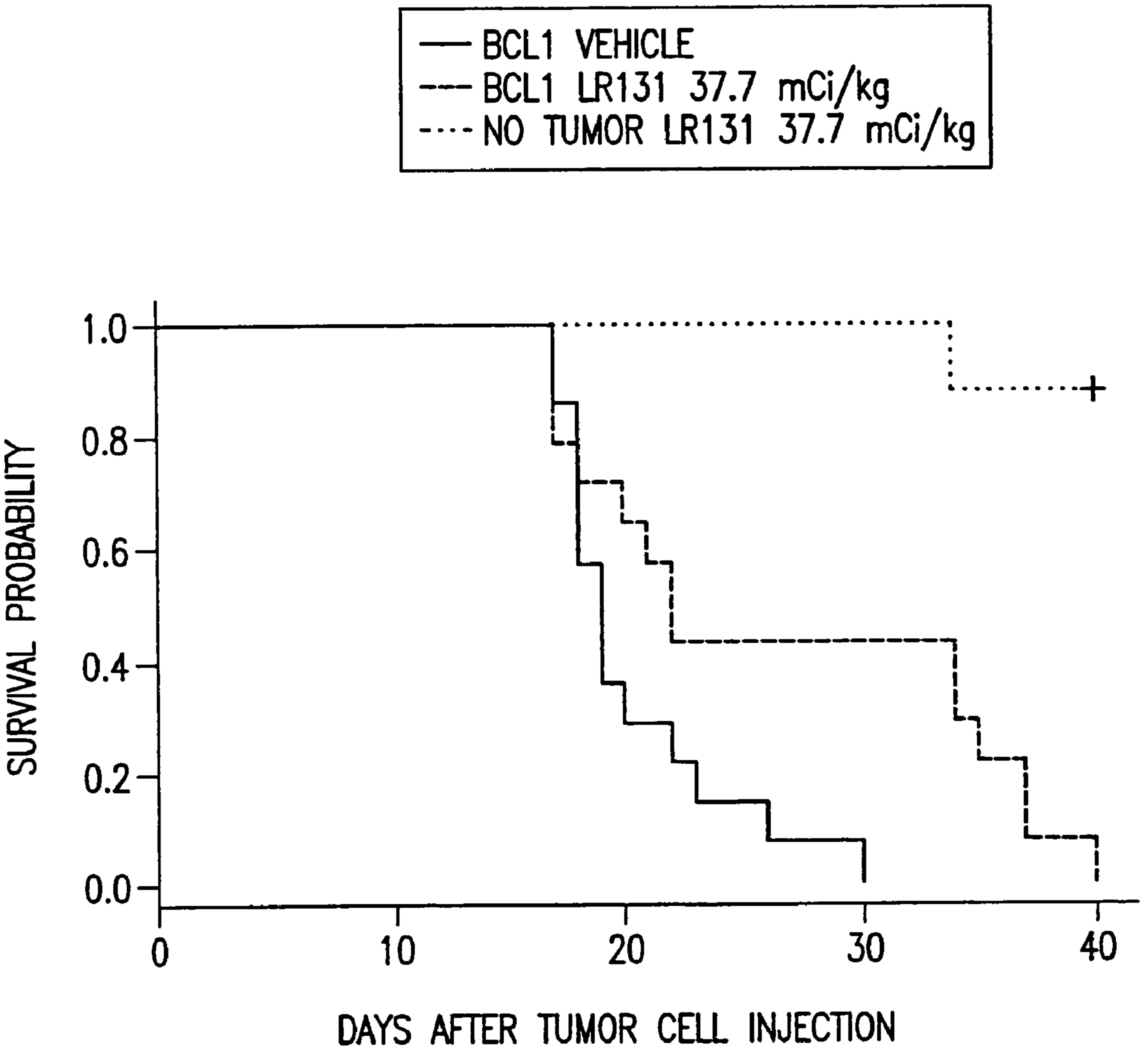

FIG. 14. Effect of $^{131}$I-labeled Neutrokine-alpha (lot TX3) on the survival of BCL1 tumor-bearing BALB/c mice. Survival curve expressed in terms of survival probability vs. time. Day 0 is the day the tumor cells were injected. Differences among the treatment groups were analyzed using the Log Rank Test for equality. Treatment with $^{131}$I-labeled Neutrokine-alpha (LR131 in figure) at a dose of 37.7 mCi/kg (dashed line) significantly prolonged survival (p=0.0212) compared to the vehicle-treated controls (solid line). In the group of mice that did not have BCL1 tumors but did receive $^{131}$I-labeled Neutrokine-alpha, 12.5% of the mice died (dotted line).

Figure 15:
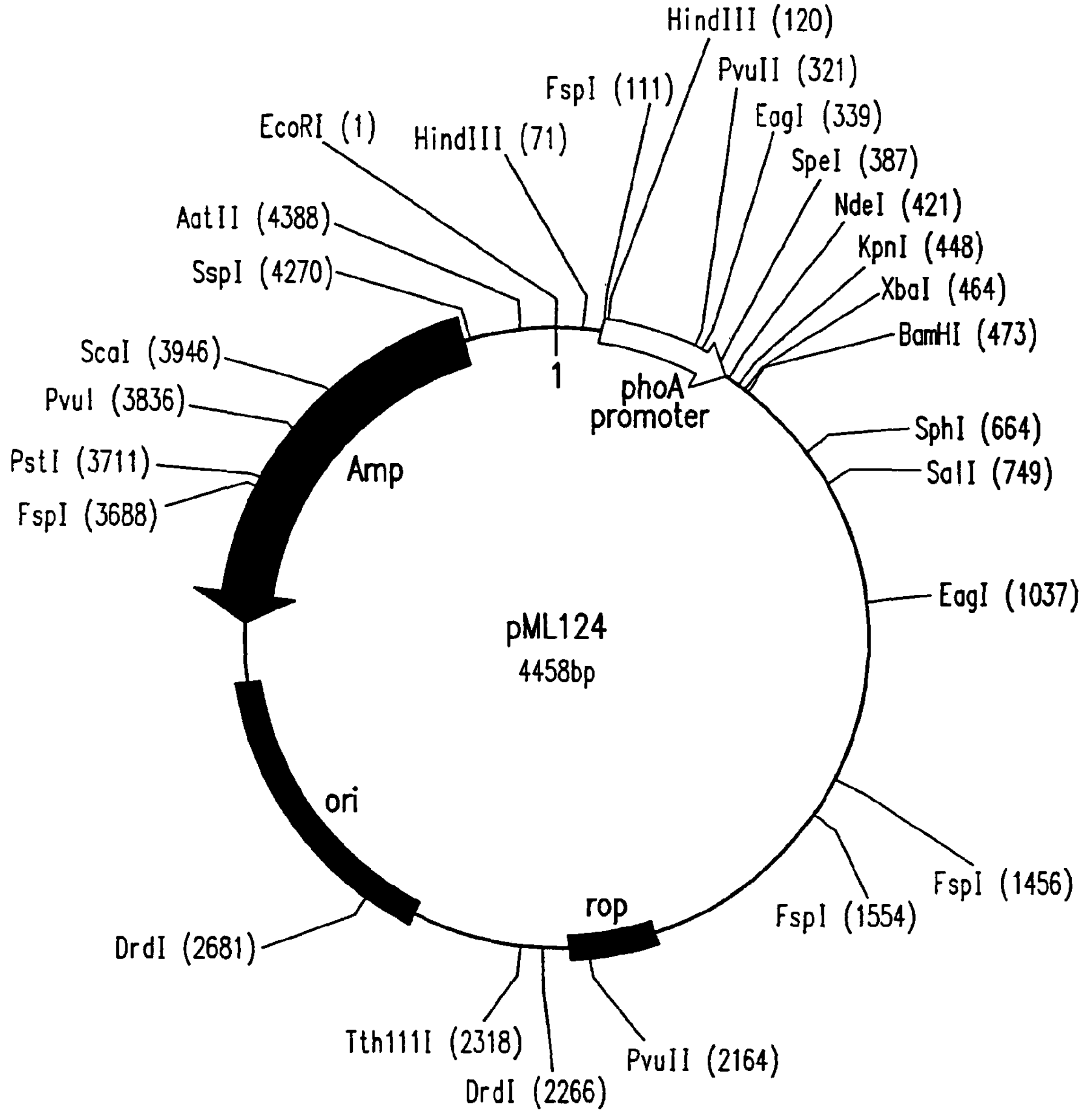

FIG. 15 shows a plasmid map of the pML124 vector. The sequence of this vector is shown in SEQ ID NO:52.

Figure 16:
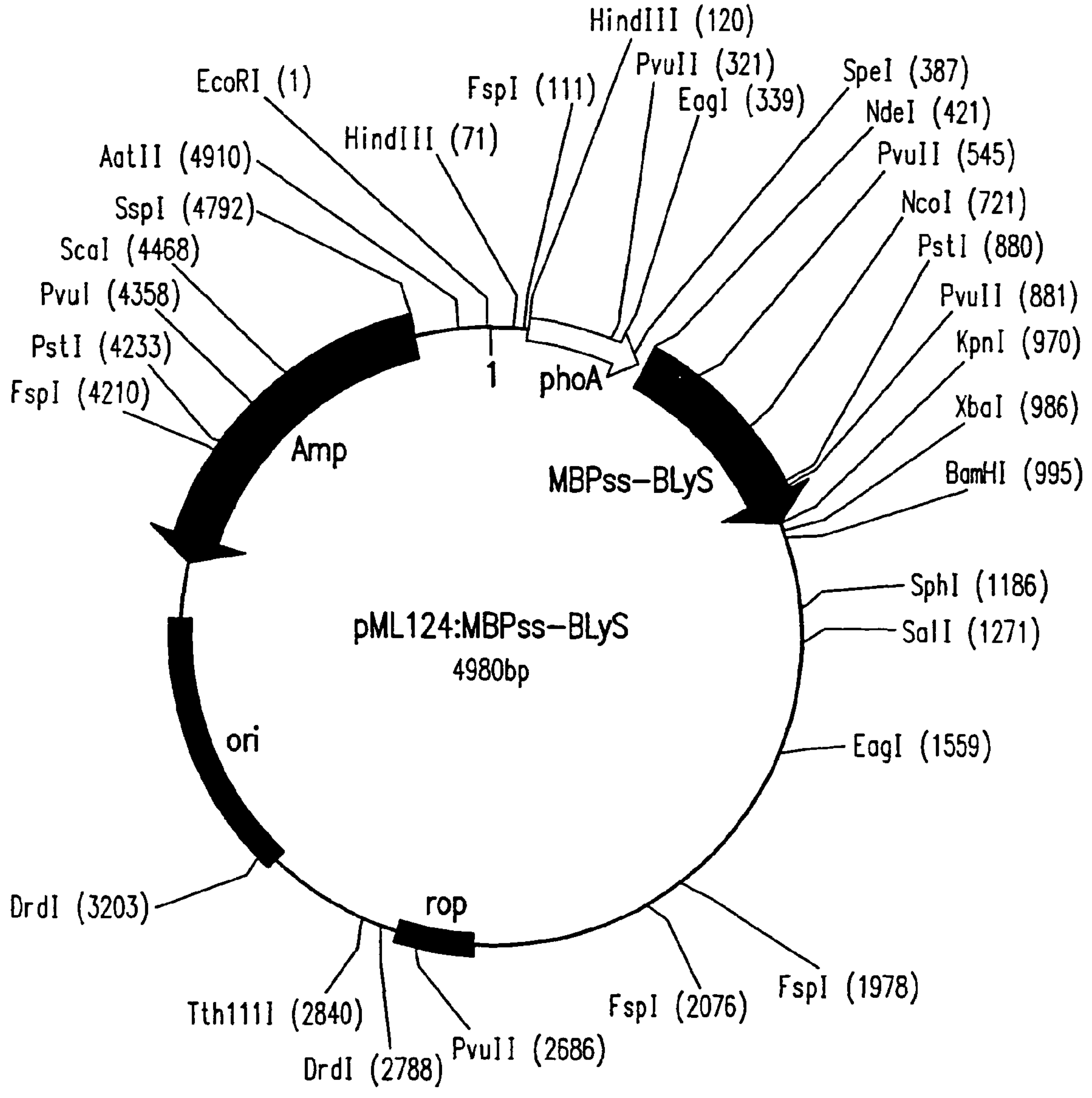

FIG. 16 shows a plasmid map of the pML124 vector containing the MBPss-Neutrokine-alpha fusion. The sequence of this vector is shown in SEQ ID NO:53.

DETAILED DESCRIPTION

The present invention provides isolated nucleic acid molecules comprising a polynucleotide encoding a Neutrokine-alpha polypeptides having the amino acid sequences shown in FIGS. 1A and 1B (SEQ ID NO:2), which was determined by sequencing a cDNA clone. The nucleotide sequence shown in FIGS. 1A and 1B (SEQ ID NO:1) was obtained by sequencing the HNEDU15 clone, which was deposited on Oct. 22, 1996 at the American Type Culture Collection, 10801 University Boulevard, Manassas, Va. 20110-2209, and assigned ATCC Accession No. 97768. The deposited clone is contained in the pBluescript SK(−) plasmid (Stratagene, La Jolla, Calif.). The ATCC deposits were made pursuant to the terms of the Budapest Treaty on the international recognition of the deposit of microorganisms for the purposes of patent procedure.

The present invention also provides isolated nucleic acid molecules comprising a polynucleotide encoding Neutrokine-alphaSV polypeptides having the amino acid sequences shown in FIGS. 5A and 5B (SEQ ID NO:19), which was determined by sequencing a cDNA clone. The nucleotide sequence shown in FIGS. 5A and 5B (SEQ ID NO:18) was obtained by sequencing the HDPMC52 clone, which was deposited on Dec. 10, 1998 at the American Type Culture Collection, and assigned ATCC Accession No. 203518. The deposited clone is contained in the pBluescript SK(−) plasmid (Stratagene, La Jolla, Calif.). The ATCC deposits were made pursuant to the terms of the Budapest Treaty on the international recognition of the deposit of microorganisms for the purposes of patent procedure.

The Neutrokine-alpha and Neutrokine-alpha polypeptides of the present invention share sequence homology with the translation products of the human mRNAs for TNF-alpha, TNF-beta, LTbeta, Fas ligand, APRIL, and LTalpha. (See, FIGS. 2A, 2B, 2C, 2D, 7A-1 and 7A-2). As noted above, TNF-alpha is thought to be an important cytokine that plays a role in cytotoxicity, necrosis, apoptosis, costimulation, proliferation, lymph node formation, immunoglobulin class switch, differentiation, antiviral activity, and regulation of adhesion molecules and other cytokines and growth factors.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A and I B, a nucleic acid molecule of the present invention encoding a Neutrokine-alpha polypeptide may be obtained using standard cloning and screening procedures, such as those for cloning cDNAs using mRNA as starting material. Illustrative of the invention, the nucleic acid molecule described in FIGS. 1A and 1B (SEQ ID NO:1) was discovered in a cDNA library derived from neutrophils. Expressed sequence tags corresponding to a portion of the Neutrokine-alpha cDNA were also found in kidney, lung, peripheral leukocyte, bone marrow, T cell lymphoma, B cell lymphoma, activated T cells, stomach cancer, smooth muscle, macrophages, and cord blood tissue. In addition, using the nucleotide information provided in FIGS. 5A and 5B, a nucleic acid molecule of the present invention encoding a Neutrokine-alphaSV polypeptide may be obtained using standard cloning and screening procedures, such as those for cloning cDNAs using mRNA as starting material. Illustrative of the invention, the nucleic acid molecule described in FIGS. 5A and 5B (SEQ ID NO:18) was discovered in a cDNA library derived from primary dendritic cells.

The Neutrokine-alpha plasmid HNEDU15 deposited as ATCC Accession No. 97768 contains an open reading frame encoding a protein of about 285 amino acid residues, a predicted intracellular domain of about 46 amino acids (amino acid residues from about 1 to about 46 in FIGS. 1A and 1B (SEQ ID NO:2)), a predicted transmembrane domain of about 26 amino acids (underlined amino acid residues from about 47 to about 72 in FIGS. 1A and 1B (SEQ ID NO:2)), a predicted extracellular domain of about 213 amino acids (amino acid residues from about 73 to about 285 in FIGS. 1A and 1B (SEQ ID NO:2)); and a deduced molecular weight of about 31 kDa. The Neutrokine-alpha polypeptide shown in FIGS. 1A and 1B (SEQ ID NO:2) is about 20% similar and about 10% identical to human TNF-alpha, which can be accessed on GenBank as Accession No. 339764.

The Neutrokine-alphaSV plasmid HDPMC52, deposited as ATCC Accession No. 203518, contains a predicted open reading frame encoding a protein of about 266 amino acid residues, a predicted intracellular domain of about 46 amino acids (amino acid residues from about 1 to about 46 in FIGS. 5A and 5B (SEQ ID NO:19)), a predicted transmembrane domain of about 26 amino acids (underlined amino acid residues from about 47 to about 72 in FIGS. 5A and 5B (SEQ ID NO:19)), a predicted extracellular domain of about 194 amino acids (amino acid residues from about 73 to about 266 in FIGS. 5A and 5B (SEQ ID NO:19)); and a deduced molecular weight of about 29 kDa. The Neutrokine-alphaSV polypeptide shown in FIGS. 5A and 5B (SEQ ID NO:19) is about 33.9% similar and about 22.0% identical to human TNF-alpha which can be accessed on GenBank as Accession No. 339764. As one of ordinary skill would appreciate, due to the possibilities of sequencing errors discussed above, the actual complete Neutrokine-alpha and/or Neutrokine-alphaSV polypeptides encoded by the deposited cDNAs, which comprise about 285 and 266 amino acids, respectively, may be somewhat shorter. In particular, the determined Neutrokine-alpha and Neutrokine-alphaSV coding sequences contain a common second methionine codon which may serve as an alternative start codon for translation of the open reading frame, at nucleotide positions 210-212 in FIGS. 1A and 1B (SEQ ID NO:1) and at nucleotide positions 64-66 in FIGS. 5A and 5B (SEQ ID NO:18). More generally, the actual open reading frame may be anywhere in the range of +20 amino acids, more likely in the range of ±10 amino acids, of that predicted from either the first or second methionine codon from the N-terminus shown in FIGS. 1A and 1B (SEQ ID NO:1) and in FIGS. 5A and 5B (SEQ ID NO:18). It will further be appreciated that, the polypeptide domains described herein have been predicted by computer analysis, and accordingly, that depending on the analytical criteria used for identifying various functional domains, the exact "address" of the extracellular, intracellular and transmembrane domains of the Neutrokine-alpha and Neutrokine-alphaSV polypeptides may differ slightly. For example, the exact location of the Neutrokine-alpha and Neutrokine-alphaSV extracellular domains in FIGS. 1A and 1B (SEQ ID NO:2) and FIGS. 5A and 5B (SEQ ID NO:19) may vary slightly (e.g., the address may "shift" by about 1 to about 20 residues, more likely about 1 to about 5 residues) depending on the criteria used to define the domain. In this case, the ends of the transmembrane domains and the beginning of the extracellular domains were predicted on the basis of the identification of the hydrophobic amino acid sequence in the above indicated positions, as shown in FIGS. 3 and 6 and in Table 1. In any event, as discussed further below, the invention further provides polypeptides having various residues deleted from the N-terminus and/or C-terminus of the complete polypeptides, including polypeptides lacking one or more amino acids from the N-termini of the extracellular domains described herein, which constitute soluble forms of the extracellular domains of the Neutrokine-alpha and Neutrokine-alphaSV polypeptides.

As indicated, nucleic acid molecules and polynucleotides of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule (DNA or RNA), which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. However, a nucleic acid contained in a clone that is a member of a library (e.g., a genomic or cDNA library) that has not been isolated from other members of the library (e.g., in the form of a homogeneous solution containing the clone and other members of the library) or a chromosome isolated or removed from a cell or a cell lysate (e.g., a "chromosome spread", as in a karyotype), is not "isolated" for the purposes of this invention. As discussed further herein, isolated nucleic acid molecules according to the present invention may be produced naturally, recombinantly, or synthetically.

Isolated nucleic acid molecules of the present invention include DNA molecules comprising, or alternatively consisting of, an open reading frame (ORF) with an initiation codon at positions 147-149 of the nucleotide sequence shown in FIGS. 1A and 1B (SEQ ID NO:1). In addition, isolated nucleic acid molecules of the invention include DNA molecules which comprise, or alternatively consist of, a sequence substantially different from those described above, but which due to the degeneracy of the genetic code, still encodes the Neutrokine-alpha protein. Of course, the genetic code is well known in the art. Thus, it would be routine for one skilled in the art to generate the degenerate variants described above. In another embodiment, the invention provides isolated nucleic acid molecules comprising, or alternatively consisting of, a sequence encoding the Neutrokine-alpha polypeptide having an amino acid sequence encoded by the cDNA contained in the plasmid having ATCC accession number 97768. Preferably, this nucleic acid molecule comprises, or alternatively consists of a sequence encoding the extracellular domain the mature or soluble polypeptide sequence of the polypeptide encoded by the cDNA contained in the plasmid having ATCC accession number 97768.

Isolated nucleic acid molecules of the present invention also include DNA molecules comprising an open reading frame (ORF) with an initiation codon at positions 1-3 of the nucleotide sequence shown in FIGS. 5A and 5B (SEQ ID NO:18). In addition, isolated nucleic acid molecules of the invention include DNA molecules which comprise, or alternatively consist of, a sequence substantially different from those described above, but which due to the degeneracy of the genetic code, still encodes the Neutrokine-alphaSV polypeptide. Of course, the genetic code is well known in the art. Thus, it would be routine for one skilled in the art to generate the degenerate variants described above. In another embodiment, the invention provides isolated nucleic acid molecules comprising, or alternatively consisting of, a sequence encoding the Neutrokine-alphaSV polypeptide having an amino acid encoded by the cDNA contained in the plasmid having ATCC accession number 203518. Preferably, this nucleic acid molecule comprises, or alternatively consists of, a sequence encoding the extracellular domain or the mature soluble polypeptide sequence of the polypeptide encoded by the cDNA contained in the plasmid having ATCC accession number 203518.

The invention further provides an isolated nucleic acid molecule comprising, or alternatively consisting of, the nucleotide sequence shown in FIGS. 1A and 1B (SEQ ID NO:1) or the nucleotide sequence of the Neutrokine-alpha cDNA contained in the plasmid having ATCC accession number 97768, or a nucleic acid molecule having a sequence complementary to one of the above sequences. In addition, the invention provides an isolated nucleic acid molecule comprising, or alternatively, consisting of, the nucleotide sequence shown in FIGS. 5A and 5B (SEQ ID NO:18) or the nucleotide sequence of the Neutrokine-alpha SV cDNA contained in the plasmid having ATCC accession number 203518, or a nucleic acid molecule having a sequence complementary to one of the above sequences. Such isolated molecules, particularly DNA molecules, have uses which include, but are not limited to, as probes for gene mapping by in situ hybridization with chromosomes, and for detecting expression of the Neutrokine-alpha and Neutrokine-alphaSV in human tissue, for instance, by Northern or Western blot analysis.

In one embodiment, the polynucleotides of the invention comprise, or alternatively consist of, the sequence shown in SEQ ID NO:22. The sequence provided as SEQ ID NO:22 was constructed from several overlapping mouse EST sequences obtained from GenBank (AI182472, AA422749, AA254047, and AI122485). The EST sequences were aligned to generate the Neutrokine-alpha-like polynucleotide sequence provided as SEQ ID NO:22. The amino acid sequence resulting from the translation of SEQ ID NO:22 is provided as SEQ ID NO:23. Fragments, variants, and derivatives of the sequences provided as SEQ ID NO:22 and SEQ ID NO:23 are also encompassed by the invention.

In another embodiment, the polynucleotides of the invention comprise, or alternatively consist of, the sequence shown in SEQ ID NO:27, and/or a sequence encoding the amino acid sequence disclosed in SEQ ID NO:28, fragments, variants, and derivatives thereof. These polynucleotides are also encompassed by the invention. For example, certain embodiments of the invention are directed to polynucleotides comprising, or alternatively consisting of, a sequence encoding a polypeptide sequence that is at least 80%, 85%, 90%, 92%, 95%, 96%, 97%, 98%, or 99% identical to amino acids 68-219 of SEQ ID NO:28. The amino acid sequence resulting from the translation of SEQ ID NO:27 is provided as SEQ ID NO:28. Polypeptides comprising, or alternatively consisting of, the amino acid sequence of SEQ ID NO:28, and fragments, variants, and derivatives of the sequence provided as SEQ ID NO:28 are also encompassed by the invention. For example, certain embodiments of the invention are directed to polypeptides comprising, or alternatively consisting of, a polypeptide sequence that is at least 80%, 85%, 90%, 92%, 95%, 96%, 97%, 98%, 99% identical to amino acids 68-219 of SEQ ID NO:28. A nucleic acid molecule having the sequence provided as SEQ ID NO:27 was obtained by RT-PCR from cyanomologous monkey (i.e., *Macaca irus*) PBMC using two degenerate primers. Briefly, total RNA was prepared from cyanomologous monkey PBMC by using Trizol (available from Life Technologies, Inc., Rockville, Md.) according to the manufacturer's protocol. Then a single stranded cDNA was synthesized from the cyanomologous monkey PBMC preparation using standard methods with an oligo-dT primer. Neutrokine-alpha-specific primers were designed based on the conserved region between the mouse and human Neutrokine-alpha molecules (SEQ ID NOs:22 and 1, respectively). A cyanomologous monkey Neutrokine-alpha nucleic acid molecule was then generated by PCR using the cDNA template in combination with the following two degenerate oligonucleotide primers. 5' primer: 5'-TAC CAG ITG GCI GCC ITG CAA G-3' (SEQ ID NO:35) and 3' primer: 5'-GTI ACA GCA GTT TIA IIG CAC C-3' (SEQ ID NO:36). In the sequence of the degenerate primers (SEQ ID NOs:35 and 36), "I" represents deoxyinosine or dideoxyinosine.

In another embodiment, the polynucleotides of the invention comprise, or alternatively consist of, the sequence shown in SEQ ID NO:29, and/or a sequence encoding the amino acid sequence disclosed in SEQ ID NO:30, fragments, variants, and derivatives thereof. These polynucleotides are also encompassed by the invention. For example, certain embodiments of the invention are directed to polynucleotides comprising, or alternatively consisting of, a sequence encoding a polypeptide sequence that is at least 80%, 85%, 90%, 92%, 95%, 96%, 97%, 98%, or 99% identical to amino acids 68-219 of SEQ ID NO:30. The amino acid sequence resulting from the translation of SEQ ID NO:29 is provided as SEQ ID NO:30. Polypeptides comprising, or alternatively consisting of, the amino acid sequence of SEQ ID NO:30, and fragments, variants, and derivatives of the sequences provided as SEQ ID NO:29 and SEQ ID NO:30 are also encompassed by the invention. For example, certain embodiments of the invention are directed to polypeptides comprising, or alternatively consisting of, a polypeptide sequence that is at least 80%, 85%, 90%, 92%, 95%, 96%, 97%, 98%, or 99% identical to amino acids 68-219 of SEQ ID NO:30. A nucleic acid molecule having the sequence provided as SEQ ID NO:29 was obtained by RT-PCR from rhesus monkey PBMC using two degenerate primers. Briefly, total RNA was prepared from rhesus monkey PBMC by using Trizol (available from Life Technologies, Inc., Rockville, Md.) according to the manufacturer's protocol. Then a single stranded cDNA was synthesized from the rhesus monkey PBMC preparation using standard methods with an oligo-dT primer. Neutrokine-alpha-specific primers were designed based on the conserved region between the mouse and human Neutrokine-alpha molecules (SEQ ID NOs:22 and 1, respectively). A rhesus monkey Neutrokine-alpha nucleic acid molecule was then generated by PCR using the cDNA template in combination with the following two degenerate oligonucleotide primers. 5' primer: 5'-TAC CAG ITG GCI GCC ITG CAA G-3' (SEQ ID NO:35) and 3' pimer: 5'-GTI ACA GCA GTT TIA IIG CAC C-3' (SEQ ID NO:36). In the sequence of the degenerate primers (SEQ ID NOs:35 and 36), "I" represents deoxyinosine or dideoxyinosine.

The invention also provides nucleic acid molecules having nucleotide sequences related to extensive portions of SEQ ID NO:1 and SEQ ID NO:18 which have been determined from the following related cDNA clones: HSOAD55 (SEQ ID NO:7), HSLAH84 (SEQ ID NO:8), and HLTBM08 (SEQ ID NO:9).

The present invention is further directed to nucleic acid molecules encoding portions of the nucleotide sequences described herein, as well as to fragments of the isolated nucleic acid molecules described herein. In one embodiment, the invention provides a polynucleotide having a nucleotide sequence representing the portion of SEQ ID NO: I which consists of the nucleotides at positions 1-1001 of SEQ ID NO:1. In another embodiment, the invention provides a polynucleotide having a nucleotide sequence representing the portion of SEQ ID NO:18 which consists of positions 1-798 of SEQ ID NO:18.

The present invention is further directed to fragments of the nucleic acid molecules (i.e. polynucleotides) described herein. By a fragment of a nucleic acid molecule having, for example, the nucleotide sequence of the cDNA contained in the plasmid having ATCC accession number 97768, a nucleotide sequence encoding the polypeptide sequence encoded by the cDNA contained in the plasmid having ATCC accession number 97768, the nucleotide sequence of SEQ ID NO:1, a nucleotide sequence encoding the polypeptide sequence of SEQ ID NO:2, the nucleotide sequence of the cDNA contained in the plasmid having ATCC accession number 203518, a nucleotide sequence encoding the polypeptide sequence encoded by the cDNA contained in the plasmid having ATCC accession number 203518, the nucleotide sequence of SEQ ID NO:18, a nucleotide sequence encoding the polypeptide sequence of SEQ ID NO:19, or the complementary strand thereto, is intended fragments at least 15 nt, and more preferably at least 20 nt or at least 25 nt, still more preferably at least 30 nt, and even more preferably, at least 40, 50, 100, 150, 200, 250, 300, 325, 350, 375, 400, 450, or 500 nt in length. These fragments have numerous uses which include, but are not limited to, diagnostic probes and primers as discussed herein. Of course, larger fragments, such as those of 501-1500 nt in length are also useful according to the present invention as are fragments corresponding to most, if not all, of the nucleotide sequences of the cDNA contained in the plasmid having ATCC accession number 97768, the nucleotide sequence of SEQ ID NO:1, the nucleotide sequences of the cDNA contained in the plasmid having ATCC accession number 203518, and the nucleotide sequence of SEQ ID NO:18. Preferred nucleic acid fragments of the present invention include nucleic acid molecules encoding polypeptides comprising, or alternatively, consisting of, epitope-bearing portions of the Neutrokine-alpha and/or Neutrokine-alphaSV polypeptide as identified in FIGS. 1A and 1B (SEQ ID NO:2) and in FIGS. 5A and 5B (SEQ ID NO:19), respectively, and described in more detail below. Polypeptides encoded by these polynucleotide fragments are also encompassed by the invention.

Also by a fragment of a nucleic acid molecule having, for example, the nucleotide sequence of SEQ ID NO:21, the nucleotide sequence of SEQ ID NO:22, the nucleotide sequence of SEQ ID NO:27, the nucleotide sequence of SEQ ID NO:29, the nucleotide sequence of SEQ ID NO:37, a nucleotide sequence encoding the polypeptide sequence of SEQ ID NO:23, a nucleotide sequence encoding the polypeptide sequence of SEQ ID NO:28, a nucleotide sequence encoding the polypeptide sequence of SEQ ID NO:30, a nucleotide sequence encoding the polypeptide sequence of SEQ ID NO:38, a nucleotide sequence encoding the polypeptide sequence of SEQ ID NO:39, a nucleotide sequence encoding the polypeptide sequence of SEQ ID NO:40, a nucleotide sequence encoding the polypeptide sequence of SEQ ID NO:41, a nucleotide sequence encoding the polypeptide sequence of SEQ ID NO:42, a nucleotide sequence encoding the polypeptide sequence of SEQ ID NO:43, a nucleotide sequence encoding the polypeptide sequence of SEQ ID NO:44, or the complementary strands thereof, is intended fragments at least 15 nt, and more preferably at least 20 nt or at least 25 nt, still more preferably at least 30 nt, and even more preferably, at least 40, 50, 100, 150, 200, 250, 300, 325, 350, 375, 400, 450, or 500 nt in length. These fragments have numerous uses which include, but are not limited to, diagnostic probes and primers as discussed herein. Of course, larger fragments, such as those of 501-1500 nt in length are also useful according to the present invention as are fragments corresponding to most, if not all, of the nucleotide sequence of SEQ ID NO:21, the nucleotide sequence of SEQ ID NO:22, the nucleotide sequence of SEQ ID NO:27, the nucleotide sequence of SEQ ID NO:29, the nucleotide sequence of SEQ ID NO:37, a nucleotide sequence encoding the polypeptide sequence of SEQ ID NO:23, a nucleotide sequence encoding the polypeptide sequence of SEQ ID NO:28, a nucleotide sequence encoding the polypeptide sequence of SEQ ID NO:30 a nucleotide sequence encoding the polypeptide sequence of SEQ ID NO:38, a nucleotide sequence encoding the polypeptide sequence of SEQ ID NO:39, a nucleotide sequence encoding the polypeptide sequence of SEQ ID NO:40, a nucleotide sequence encoding the polypeptide sequence of SEQ ID NO:41, a nucleotide sequence encoding the polypeptide sequence of SEQ ID NO:42, a nucleotide sequence encoding the polypeptide sequence of SEQ ID NO:43, a nucleotide sequence encoding the polypeptide sequence of SEQ ID NO:44, or the complementary strands thereof. Polypeptides encoded by these polynucleotide fragments are also encompassed by the invention.

Representative examples of Neutrokine-alpha polynucleotide fragments of the invention include, for example, fragments that comprise, or alternatively, consist of, a sequence from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, and/or 1051 to 1082, of SEQ ID NO:1, or the complementary strand thereto, or the cDNA contained in the plasmid having ATCC accession number 97768. In this context "about" includes the particularly recited ranges, and ranges that are larger or smaller by several (5, 4, 3, 2, or 1) nucleotides, at either terminus or at both termini.

Representative examples of Neutrokine-alphaSV polynucleotide fragments of the invention include, for example, fragments that comprise, or alternatively, consist of, a sequence from about nucleotide 1 to 50, 51 to 100, 101 to 150, 151 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, and/or 851 to 900 of SEQ ID NO:18, or the complementary strand thereto, or the cDNA contained in the plasmid having ATCC accession number 203518. In this context "about" includes the particularly recited ranges, and ranges that are larger or smaller by several (5, 4, 3, 2, or 1) nucleotides, at either terminus or at both termini.

In certain preferred embodiments, polynucleotide of the invention comprise, or alternatively, consist of, nucleotide residues 571-627, 580-627, 590-627, 600-627, 610-627, 571-

620, 580-620, 590-620, 600-620, 571-610, 580-610, 590-610, 571-600, 580-600, and/or 571-590 of SEQ ID NO:1.

In certain other preferred embodiments, polynucleotides of the invention comprise, or alternatively, consist of nucleotide residues 1-879, 25-879, 50-879,75-879, 100-879, 125-879, 150-879, 175-879, 200-879, 225-879, 250-879, 275-879, 300-879, 325-879, 350-879, 375-879, 400-879, 425-879, 450-879, 475-879, 500-879, 525-879, 550-879, 575-879, 600-879, 625-879, 650-879, 675-879, 700-879, 725-879, 750-879, 775-879, 800-879, 825-879, 850-879, 1-850, 25-850, 50-850, 75-850, 100-850, 125-850, 150-850, 175-850, 200-850, 225-850, 250-850, 275-850, 300-850, 325-850, 350-850, 375-850, 400-850, 425-850, 450-850, 475-850, 500-850, 525-850, 550-850, 575-850, 600-850, 625-850, 650-850, 675-850, 700-850, 725-850, 750-850, 775-850, 800-850, 825-850, 1-825, 25-825, 50-825, 75-825, 100-825, 125-825, 150-825, 175-825, 200-825, 225-825, 250-825, 275-825, 300-825, 325-825, 350-825, 375-825, 400-825, 425-825, 450-825, 475-825, 500-825, 525-825, 550-825, 575-825, 600-825, 625-825, 650-825, 675-825, 700-825, 725-825, 750-825, 775-825, 800-825, 1-800, 25-800, 50-800, 75-800, 100-800, 125-800, 150-800, 175-800, 200-800, 225-800, 250-800, 275-800, 300-800, 325-800, 350-800, 375-800, 400-800, 425-800, 450-800, 475-800, 500-800, 525-800, 550-800, 575-800, 600-800, 625-800, 650-800, 675-800, 700-800, 725-800, 750-800, 775-800, 1-775, 25-775, 50-775, 75-775, 100-775, 125-775, 150-775, 175-775, 200-775, 225-775, 250-775, 275-775, 300-775, 325-775, 350-775, 375-775, 400-775, 425-775, 450-775, 475-775, 500-775, 525-775, 550-775, 575-775, 600-775, 625-775, 650-775, 675-775, 700-775, 725-775, 750-775, 1-750, 25-750, 50-750, 75-750, 100-750, 125-750, 150-750, 175-750, 200-750, 225-750, 250-750, 275-750, 300-750, 325-750, 350-750, 375-750, 400-750, 425-750, 450-750, 475-750, 500-750, 525-750, 550-750, 575-750, 600-750, 625-750, 650-750, 675-750, 700-750, 725-750, 1-725, 25-725, 50-725, 75-725, 100-725, 125-725, 150-725, 175-725, 200-725, 225-725, 250-725, 275-725, 300-725, 325-725, 350-725, 375-725, 400-725, 425-725, 450-725, 475-725, 500-725, 525-725, 550-725, 575-725, 600-725, 625-725, 650-725, 675-725, 700-725, 1-700, 25-700, 50-700, 75-700, 100-700, 125-700, 150-700, 175-700, 200-700, 225-700, 250-700, 275-700, 300-700, 325-700, 350-700, 375-700, 400-700, 425-700, 450-700, 475-700, 500-700, 525-700, 550-700, 575-700, 600-700, 625-700, 650-700, 675-700, 1-675, 25-675, 50-675, 75-675, 100-675, 125-675, 150-675, 175-675, 200-675, 225-675, 250-675, 275-675, 300-675, 325-675, 350-675, 375-675, 400-675, 425-675, 450-675, 475-675, 500-675, 525-675, 550-675, 575-675, 600-675, 625-675, 650-675, 1-650, 25-650, 50-650, 75-650, 100-650, 125-650, 150-650, 175-650, 200-650, 225-650, 250-650, 275-650, 300-650, 325-650, 350-650, 375-650, 400-650, 425-650, 450-650, 475-650, 500-650, 525-650, 550-650, 575-650, 600-650, 625-650, 1-625, 25-625, 50-625, 75-625, 100-625, 125-625, 150-625, 175-625, 200-625, 225-625, 250-625, 275-625, 300-625, 325-625, 350-625, 375-625, 400-625, 425-625, 450-625, 475-625, 500-625, 525-625, 550-625, 575-625, 600-625, 1-600, 25-600, 50-600, 75-600, 100-600, 125-600, 150-600, 175-600, 200-600, 225-600, 250-600, 275-600, 300-600, 325-600, 350-600, 375-600, 400-600, 425-600, 450-600, 475-600, 500-600, 525-600, 550-600, 575-600, 1-575, 25-575, 50-575, 75-575, 100-575, 125-575, 150-575, 175-575, 200-575, 225-575, 250-575, 275-575, 300-575, 325-575, 350-575, 375-575, 400-575, 425-575, 450-575, 475-575, 500-575, 525-575, 550-575, 1-550, 25-550, 50-550, 75-550, 100-550, 125-550, 150-550, 175-550, 200-550, 225-550, 250-550, 275-550, 300-550, 325-550, 350-550, 375-550, 400-550, 425-550, 450-550, 475-550, 500-550, 525-550, 1-525, 25-525, 50-525, 75-525, 100-525, 125-525, 150-525, 175-525, 200-525, 225-525, 250-525, 275-525, 300-525, 325-525, 350-525, 375-525, 400-525, 425-525, 450-525, 475-525, 500-525, 1-500, 25-500, 50-500, 75-500, 100-500, 125-500, 150-500, 175-500, 200-500, 225-500, 250-500, 275-500, 300-500, 325-500, 350-500, 375-500, 400-500, 425-500, 450-500, 475-500, 1-475, 25-475, 50-475, 75-475, 100-475, 125-475, 150-475, 175-475, 200-475, 225-475, 250-475, 275-475, 300-475, 325-475, 350-475, 375-475, 400-475, 425-475, 450-475, 1-450, 25-450, 50-450, 75-450, 100-450, 125-450, 150-450, 175-450, 200-450, 225-450, 250-450, 275-450, 300-450, 325-450, 350-450, 375-450, 400-450, 425-450, 1-425, 25-425, 50-425, 75-425, 100-425, 125-425, 150-425, 175-425, 200-425, 225-425, 250-425, 275-425, 300-425, 325-425, 350-425, 375-425, 400-425, 1-400, 25-400, 50-400, 75-400, 100-400, 125-400, 150-400, 175-400, 200-400, 225-400, 250-400, 275-400, 300-400, 325-400, 350-400, 375-400, 1-375, 25-375, 50-375, 75-375, 100-375, 125-375, 150-375, 175-375, 200-375, 225-375, 250-375, 275-375, 300-375, 325-375, 350-375, 1-350, 25-350, 50-350, 75-350, 100-350, 125-350, 150-350, 175-350, 200-350, 225-350, 250-350, 275-350, 300-350, 325-350, 1-325, 25-325, 50-325, 75-325, 100-325, 125-325, 150-325, 175-325, 200-325, 225-325, 250-325, 275-325, 300-325, 1-300, 25-300, 50-300, 75-300, 100-300, 125-300, 150-300, 175-300, 200-300, 225-300, 250-300, 275-300, 1-275, 25-275, 50-275, 75-275, 100-275, 125-275, 150-275, 175-275, 200-275, 225-275, 250-275, 1-250, 25-250, 50-250, 75-250, 100-250, 125-250, 150-250, 175-250, 200-250, 225-250, 1-225, 25-225, 50-225, 75-225, 100-225, 125-225, 150-225, 175-225, 200-225, 1-200, 25-200, 50-200, 75-200, 100-200, 125-200, 150-200, 175-200, 1-175, 25-175, 50-175, 75-175, 100-175, 125-175, 150-175, 1-150, 25-150, 50-150, 75-150, 100-150, 125-150, 1-125, 25-125, 50-125, 75-125, 100-125, 1-100, 25-100, 50-100, 75-100, 1-75, 25-75, 50-75, 1-50, 25-50, and/or 1-25 of SEQ ID NO:18.

In certain additional preferred embodiments, polynucleotides of the invention comprise, or alternatively, consist of nucleotide residues 400-627, 425-627, 450-627, 475-627, 500-627, 525-627, 550-627, 575-627, 600-627, 400-600, 425-600, 450-600, 475-600, 500-600, 525-600, 550-600, 575-600, 400-575, 425-575, 450-575, 475-575, 500-575, 525-575, 550-575, 400-550, 425-550, 450-550, 475-550, 500-550, 525-550, 400-500, 425-500, 450-500, 475-500, 400-475, 425-475, 450-475, 400-450, 425-450, 571-800, 600-800, 625-800, 650-800, 675-800, 700-800, 725-800, 750-800, 775-800, 571-775, 600-775, 625-775, 650-775, 675-775, 700-775, 725-775, 750-775, 571-750, 600-750, 625-750, 650-750, 675-750, 700-750, 725-750, 571-725, 600-725, 625-725, 650-725, 675-725, 700-725, 571-700, 600-700, 625-700, 650-700, 675-700, 571-675, 600-675, 625-675, 650-675, 571-650, 600-650, 625-650, 571-625, 600-625, and/or 571-600 of SEQ ID NO:1.

In additional preferred embodiments, polynucleotides of the invention comprise, or alternatively, consist of nucleotide residues 147-500, 147-450, 147-400, 147-350, 200-500, 200-450, 200-400, 200-350, 250-500, 250-450, 250-400, 250-350, 300-500, 300-450, 300-400, 300-350, 350-750, 350-700, 350-650, 350-600, 350-550, 400-750, 400-700, 400-650, 400-600, 400-550, 425-750, 425-700, 425-650, 425-600, 425-550, 450-1020, 450-1001, 450-950, 450-900, 450-850, 450-800, 450-775, 500-1001, 500-950, 500-900, 500-850, 500-800, 500-775, 550-1001, 550-950, 550-900, 550-850, 550-800, 550-775, 600-1001, 600-950, 600-900, 600-850, 600-800, 600-775, 650-1001, 650-950, 650-900, 650-

850, 650-800, 650-775, 700-1001, 700-950, 700-900, 700-850, 700-800, 700-775, 825-1082, 850-1082, 875-1082, 900-1082, 925-1082, 950-1082, 975-1082, 1000-1082, 1025-1082, and/or 1050-1082 of SEQ ID NO:1.

Preferably, the polynucleotide fragments of the invention encode a polypeptide which demonstrates a Neutrokine-alpha and/or Neutrokine-alphaSV functional activity. By a polypeptide demonstrating "functional activity" is meant, a polypeptide capable of displaying one or more known functional activities associated with a full-length and/or secreted Neutrokine-alpha polypeptide and/or Neutrokine-alphaSV polypeptide. Such functional activities include, but are not limited to, biological activity (e.g., ability to stimulate B cell proliferation, survival, differentiation, and/or activation), antigenicity (ability to bind or compete with a Neutrokine-alpha and/or Neutrokine-alphaSV polypeptide for binding to an anti-Neutrokine-alpha and/or anti-Neutrokine-alphaSV antibody), immunogenicity (ability to generate antibody which binds to a Neutrokine-alpha and/or Neutrokine-alphaSV polypeptide), ability to form multimers (as described below in the "Neutrokine-alpha Polypeptides" section) with Neutrokine-alpha and/or Neutrokine-alphaSV polypeptides of the invention, ability to form heteromultimers (as described below in the "Neutrokine-alpha Polypeptides" section) with APRIL polypeptides (e.g., SEQ ID NO:20 or SEQ ID NO:47; PCT International Publication Number WO97/33902; GenBank Accession No. AF046888 (nucleotide) and AAC6132 (protein); J. Exp. Med. 188(6):1185-1190), ability to bind to a receptor or ligand (e.g., transmembrane activator and CAML interactor (TACI, GenBank accesion number AAC51790), BAFF-R (GenBank Acession Number NP_443177) and B-cell maturation antigen (BCMA, GenBank accession number NP_001183)) for a Neutrokine-alpha and/or Neutrokine-alphaSV polypeptide, and ability to stimulate a Neutrokine-alpha and/or Neutrokine-alphaSV receptor signalling cascade (e.g., to activate calcium-modulator and cyclophilin ligand ("CAML"), calcineurin, nuclear factor of activated T cells transcription factor ("NF-AT"), nuclear factor-kappa B ("NF-kappa B"), activator protein-I (AP-I), SRF, extracellular-signal regulated kinase 1 (ERK-1), polo like kinases (PLK), ELF-1, high mobility group 1 (HMG-1), and/or high mobility group Y (HMG-Y)).

In additional specific embodiments, the polynucleotide fragments of the invention encode a polypeptide comprising, or alternatively, consisting of the predicted intracellular domain (amino acids 1 to 46 of SEQ ID NO:2), the predicted transmembrane domain (amino acids 47 to 72 of SEQ ID NO:2), the predicted extracellular domain (amino acids 73 to 285 of SEQ ID NO:2), or the predicted TNF conserved domain (amino acids 191 to 284 of SEQ ID NO:2) of Neutrokine-alpha. In additional embodiments, the polynucleotide fragments of the invention encode a polypeptide comprising, or alternatively, consisting of any combination of 1, 2, 3, or all 4 of the above recited domains. Polypeptides encoded by these polynucleotides are also encompassed by the invention.

In additional specific embodiments, the polynucleotide fragments of the invention encode a polypeptide comprising, or alternatively, consisting of the predicted intracellular domain (amino acids 1 to 46 of SEQ ID NO:19), the predicted transmembrane domain (amino acids 47 to 72 of SEQ ID NO:19), the predicted extracellular domain (amino acids 73 to 266 of SEQ ID NO:19), or the predicted TNF conserved domain (amino acids 172 to 265 of SEQ ID NO:19) of Neutrokine-alphaSV. In additional embodiments, the polynucleotide fragments of the invention encode a polypeptide comprising, or alternatively, consisting of any combination of 1, 2, 3, or all 4 of the above recited domains. Polypeptides encoded by these polynucleotides are also encompassed by the invention.

In another embodiment, polynucleotide fragments of the invention comprise, or alternatively consist of, polynucleotides which encode an amino acid sequence selected from residues Met-1 to Lys-113, Leu-114 to Thr-141, Ile-142 to Lys-160, Gly-161 to Gln-198, Val-199 to Ala-248, and Gly-250 to Leu-285 of SEQ ID NO:2. Moreover, polynucleotides that encode any combination of two, three, four, five or more of these amino acid sequences are also encompassed by the invention. Polypeptides encoded by these polynucleotides are also encompassed by the invention.

In another embodiment, polynucleotide fragments of the invention comprise, or alternatively consist of, polynucleotides which encode an amino acid sequence selected from residues Met-1 to Lys-113, Leu-114 to Thr-141, Gly-142 to Gln-179, Val-180 to Ala-229, and Gly-230 to Leu-266 of SEQ ID NO:19. Moreover, polynucleotides that encode any combination of two, three, four, five or more of these amino acid sequences are also encompassed by the invention. Polypeptides encoded by these polynucleotides are also encompassed by the invention.

In another embodiment, polynucleotide fragments of the invention comprise, or alternatively consist of, polynucleotides which encode an amino acid sequence selected from residues Met-1 to Lys-106, Leu-107 to Thr-134, Glu-135 to Asn-165, Ile-167 to Lys-184, Gly-185 to Gln-224, Val-225 to Ala-272, and Gly-273 to Leu-309 of SEQ ID NO:39. Moreover, polynucleotides that encode any combination of two, three, four, five or more of these amino acid sequences are also encompassed by the invention. Polypeptides encoded by these polynucleotides are also encompassed by the invention.

In another embodiment, polynucleotide fragments of the invention comprise, or alternatively consist of, polynucleotides which encode an amino acid sequence selected from residues Tyr-1 to Lys-47, Leu48 to Thr-75, Ile-76 to Lys-94, Gly-95 to Gln-132, Val-133 to Ala-182, and Gly-183 to Ala-219 of SEQ ID NO:28. Moreover, polynucleotides that encode any combination of two, three, four, five or more of these amino acid sequences are also encompassed by the invention. Polypeptides encoded by these polynucleotides are also encompassed by the invention.

In another embodiment, polynucleotide fragments of the invention comprise, or alternatively consist of, polynucleotides which encode an amino acid sequence selected from residues Tyr-1 to Lys-47, Leu-48 to Thr-75, Ile-76 to Lys-94, Gly-95 to Gln-132, Val-133 to Ala-182, and Gly-183 to Ala-219 of SEQ ID NO:30. Moreover,polynucleotides that encode any combination of two, three, four, five or more of these amino acid sequences are also encompassed by the invention. Polypeptides encoded by these polynucleotides are also encompassed by the invention.

In another embodiment, the polynucleotides of the invention comprise, or alternatively consist of, the sequence shown in SEQ ID NO:21. The sequence shown as SEQ ID NO:21 encodes a polypeptide consisting of an initiating methionine residue linked to residues Ala-134 through Leu-285 of the Neutrokine-alpha polypeptide sequence shown as SEQ ID NO:2. Polypeptides encoded by these polynucleotides are also encompassed by the invention.

In certain additional preferred embodiments, polynucleotides of the invention comprise, or alternatively, consist of nucleotide residues 1-459, 15-459, 30-459, 45-459, 60-459, 75-459, 90-459, 105-459, 120-459, 135-459, 150-459, 165-459, 180-459, 195-459, 210-459, 225-459, 240-459, 255-459, 270-459, 285-459, 300-459, 315-459, 330-459, 345-

459, 360-459, 375-459, 390-459, 405-459, 420-459, 435-459, 450-459, 1-450, 15-450, 30-450, 45-450, 60-450, 75-450, 90-450, 105-450, 120-450, 135-450, 150-450, 165-450, 180-450, 195-450, 210-450, 225-450, 240-450, 255-450, 270-450, 285-450, 300-450, 315-450, 330-450, 345-450, 360-450, 375-450, 390-450, 405-450, 420-450, 435-450, 1-435, 15-435, 30-435, 45-435, 60-435, 75-435, 90-435, 105-435, 120-435, 135-435, 150-435, 165-435, 180-435, 195-435, 210-435, 225-435, 240-435, 255-435, 270-435, 285-435, 300-435, 315-435, 330-435, 345-435, 360-435, 375-435, 390-435, 405-435, 420-435, 1-420, 15-420, 30-420, 45-420, 60-420, 75-420, 90-420, 105-420, 120-420, 135-420, 150-420, 165-420, 180-420, 195-420, 210-420, 225-420, 240-420, 255-420, 270-420, 285-420, 300-420, 315-420, 330-420, 345-420, 360-420, 375-420, 390-420, 405-420, 1-405, 15-405, 30-405, 45-405, 60-405, 75-405, 90-405, 105-405, 120-405, 135-405, 150-405, 165-405, 180-405, 195-405, 210-405, 225-405, 240-405, 255-405, 270-405, 285-405, 300-405, 315-405, 330-405, 345-405, 360-405, 375-405, 390-405, 1-390, 15-390, 30-390, 45-390, 60-390, 75-390, 90-390, 105-390, 120-390, 135-390, 150-390, 165-390, 180-390, 195-390, 210-390, 225-390, 240-390, 255-390, 270-390, 285-390, 300-390, 315-390, 330-390, 345-390, 360-390, 375-390, 1-375, 15-375, 30-375, 45-375, 60-375, 75-375, 90-375, 105-375, 120-375, 135-375, 150-375, 165-375, 180-375, 195-375, 210-375, 225-375, 240-375, 255-375, 270-375, 285-375, 300-375, 315-375, 330-375, 345-375, 360-375, 1-360, 15-360, 30-360, 45-360, 60-360, 75-360, 90-360, 105-360, 120-360, 135-360, 150-360, 165-360, 180-360, 195-360, 210-360, 225-360, 240-360, 255-360, 270-360, 285-360, 300-360, 315-360, 330-360, 345-360, 1-345, 15-345, 30-345, 45-345, 60-345, 75-345, 90-345, 105-345, 120-345, 135-345, 150-345, 165-345, 180-345, 195-345, 210-345, 225-345, 240-345, 255-345, 270-345, 285-345, 300-345, 315-345, 330-345, 1-330, 15-330, 30-330, 45-330, 60-330, 75-330, 90-330, 105-330, 120-330, 135-330, 150-330, 165-330, 180-330, 195-330, 210-330, 225-330, 240-330, 255-330, 270-330, 285-330, 300-330, 315-330, 1-315, 15-315, 30-315, 45-315, 60-315, 75-315, 90-315, 105-315, 120-315, 135-315, 150-315, 165-315, 180-315, 195-315, 210-315, 225-315, 240-315, 255-315, 270-315, 285-315, 300-315, 1-300, 15-300, 30-300, 45-300, 60-300, 75-300, 90-300, 105-300, 120-300, 135-300, 150-300, 165-300, 180-300, 195-300, 210-300, 225-300, 240-300, 255-300, 270-300, 285-300, 1-285, 15-285, 30-285, 45-285, 60-285, 75-285, 90-285, 105-285, 120-285, 135-285, 150-285, 165-285, 180-285, 195-285, 210-285, 225-285, 240-285, 255-285, 270-285, 1-270, 15-270, 30-270, 45-270, 60-270, 75-270, 90-270, 105-270, 120-270, 135-270, 150-270, 165-270, 180-270, 195-270, 210-270, 225-270, 240-270, 255-270, 1-255, 15-255, 30-255, 45-255, 60-255, 75-255, 90-255, 105-255, 120-255, 135-255, 150-255, 165-255, 180-255, 195-255, 210-255, 225-255, 240-255, 1-240, 15-240, 30-240, 45-240, 60-240, 75-240, 90-240, 105-240, 120-240, 135-240, 150-240, 165-240, 180-240, 195-240, 210-240, 225-240, 1-225, 15-225, 30-225, 45-225, 60-225, 75-225, 90-225, 105-225, 120-225, 135-225, 150-225, 165-225, 180-225, 195-225, 210-225, 1-210, 15-210, 30-210, 45-210, 60-210, 75-210, 90-210, 105-210, 120-210, 135-210, 150-210, 165-210, 180-210, 195-210, 1-195, 15-195, 30-195, 45-195, 60-195, 75-195, 90-195, 105-195, 120-195, 135-195, 150-195, 165-195, 180-195, 1-180, 15-180, 30-180, 45-180, 60-180, 75-180, 90-180, 105-180, 120-180, 135-180, 150-180, 165-180, 1-165, 15-165, 30-165, 45-165, 60-165, 75-165, 90-165, 105-165, 120-165, 135-165, 150-165, 1-150, 15-150, 30-150, 45-150, 60-150, 75-150, 90-150, 105-150, 120-150, 135-150, 1-135, 15-135, 30-135, 45-135, 60-135, 75-135, 90-135, 105-135, 120-135, 1-120, 15-120, 30-120, 45-120, 60-120, 75-120, 90-120, 105-120, 1-105, 15-105, 30-105, 45-105, 60-105, 75-105, 90-105, 1-90, 15-90, 30-90, 45-90, 60-90, 75-90, 1-75, 15-75, 30-75, 45-75, 60-75, 1-60, 15-60, 30-60, 45-60, 1-45, 15-45, 30-45, 1-30, and/or 15-30 of SEQ ID NO:21. Polypeptides encoded by these polynucleotides are also encompassed by the invention.

Accordingly, specific embodiments of the invention are directed to polynucleotides encoding polypeptides which comprise, or alternatively consist of, the amino acid sequence of beta pleated sheet region A, A', B, B', C, D, E, F, G, or H disclosed in FIGS. 7A-1 and 7A-2 and described in Example 6. Additional embodiments of the invention are directed to polynucleotides encoding Neutrokine-alpha polypeptides which comprise, or alternatively consist of, any combination of 1, 2, 3, 4, 5, 6, 7, 8, 9 or all 10 of beta pleated sheet regions A-H disclosed in FIGS. 7A-1 and 7A-2 and described in Example 6. Additional preferred embodiments of the invention are directed to polypeptides which comprise, or alternatively consist of, the Neutrokine-alpha amino acid sequence of beta pleated sheet region A, A', B, B', C, D, E, F, G, or H disclosed in FIGS. 7A-1 and 7A-2 and described in Example 6. Additional embodiments of the invention are directed Neutrokine-alpha polypeptides which comprise, or alternatively consist of, any combination of 1, 2, 3, 4, 5, 6, 7, 8, 9 or all 10 of beta pleated sheet regions A through H disclosed in FIGS. 7A-1 and 7A-2 and described in Example 6.

In certain other preferred embodiments, polynucleotides of the invention comprise, or alternatively consist of, nucleotide residues 34-57, 118-123, 133-141, 151-159, 175-216, 232-255, 280-315, 328-357, 370-393, and/or 430-456 of SEQ ID NO:21. Polypeptides encoded by these polynucleotides are also encompassed by the invention. These polynucleotide and polypeptide fragments correspond to the predicted beta-pleated sheet regions shown in FIGS. 7A-1 and 7A-2. In certain embodiments, polynucleotides of the invention comprise, or alternatively consist of, a polynucleotide sequence at least 90%, 95%, 96%, 97%, 98% or 99% identical to the polynucleotide sequence encoding one, two, three, four, five, six, seven, eight, nine or ten of the beta-pleated sheet regions described above. The present invention also encompasses the above polynucleotide sequences fused to a heterologous polynucleotide sequence. Polypeptides encoded by these polynucleotide sequences are also encompassed by the invention. In another embodiment, the invention provides an isolated nucleic acid molecule comprising a polynucleotide which hybridizes under stringent hybridization conditions to one, two, three, four, five, six, seven, eight, nine or ten of the beta-pleated sheet polynucleotides of the invention described above. The meaning of the phrase "stringent conditions" as used herein is described infra.

In further preferred embodiments, polynucleotides of the invention comprise, or alternatively consist of, nucleotide residues 576-599, 660-665, 675-683, 693-701, 717-758, 774-803, 822-857, 870-899, 912-935, and/or 972-998 of SEQ ID NO:1. Polypeptides encoded by these polynucleotide fragments are also encompassed by the invention. These polynucleotide and polypeptide fragments correspond to the predicted beta-pleated sheet regions shown in FIGS. 7A-1 and 7A-2.

In additional preferred embodiments, polynucleotides of the invention comprise, or alternatively consist of, nucleotide residues 457-462, 472-480, 490-498, 514-555, 571-600, 619-654, 667-696, 699-732, and/or 769-795 of SEQ ID NO:18. Polypeptides encoded by these polynucleotide fragments are also encompassed by the invention. These polynucleotide and polypeptide fragments correspond to the predicted beta-pleated sheet regions shown in FIGS. 7A-1 and 7A-2.

In yet further preferred embodiments, polynucleotides of the invention comprise, or alternatively consist of, nucleotide residues 124-129, 139-147, 157-165, 181-222, 238-267, 286-321, 334-363, 376-399, and/or 436-462 of SEQ ID NO:22. Polypeptides encoded by these polynucleotide fragments are also encompassed by the invention. These polynucleotide and polypeptide fragments correspond to the predicted beta-pleated sheet regions shown in FIGS. 7A-1 and 7A-2. Polypeptides comprising, or alternatively, consisting of the amino acid sequence of any combination of one, two, three, four, five, six, seven, eight, nine, ten, or all of these regions are encompassed by the invention.

The relative positions of several intron/exon boundaries were determined for the mouse Neutrokine-alpha (SEQ ID NO:39) based on sequence analysis of mouse genomic DNA. The apparent second exon from the 5' end of the mouse Neutrokine-alpha genomic clone (preliminarily designated "Exon 2") consists of Tyr-187 to Gln-222 of the sequence shown in SEQ ID NO:39. The apparent third exon from the 5' end of the mouse Neutrokine-alpha genomic clone (preliminarily designated "Exon 3") comprises Val-223 to Gly-273 of the sequence shown in SEQ ID NO:39.

Thus, in one embodiment, the invention provides polynucleotides encoding polypeptides comprising, or alternatively consisting of, the amino acid sequence of residues Tyr-187 to Gln-222 of SEQ ID NO:39. The present invention is also directed to nucleic acid molecules comprising, or alternatively, consisting of, a polynucleotide sequence at least 80%, 85%, 90%, 95%, 96%, 97%, 98% or 99% identical to the polynucleotide sequence encoding the mouse Neutrokine-alpha polypeptides described above. The present invention also encompasses the above polynucleotide sequences fused to a heterologous polynucleotide sequence. Polypeptides encoded by these nucleic acids and/or polynucleotide sequences are also encompassed by the invention.

In another embodiment, the invention provides polynucleotides encoding polypeptides comprising, or alternatively consisting of, the amino acid sequence of residues Val-223 to Gly-273 of SEQ ID NO:39. The present invention is also directed to nucleic acid molecules comprising, or alternatively, consisting of, a polynucleotide sequence at least 80%, 85%, 90%, 95%, 96%, 97%, 98%, or 99% identical to the polynucleotide sequence encoding the mouse Neutrokine-alpha polypeptides described above. The present invention also encompasses the above polynucleotide sequences fused to a heterologous polynucleotide sequence. Polypeptides encoded by these nucleic acids and/or polynucleotide sequences are also encompassed by the invention.

Moreover, the relative positions of the corresponding intron/exon boundaries were determined for human Neutrokine-alpha (SEQ ID NO:1 and SEQ ID NO:2) based on an alignment of the sequences of mouse and human Neutrokine-alpha polypeptides. The apparent second exon from the 5' end of human Neutrokine-alpha (also preliminarily designated "Exon 2") consists of, Tyr-163 to Gln-198 of the sequence shown in SEQ ID NO:2. The apparent third exon from the 5' end of human Neutrokine-alpha (also preliminarily designated "Exon 3") consists of, Val-199 to Gly-249 of the sequence shown in SEQ ID NO:2.

Thus, in one embodiment, the invention provides polynucleotides encoding polypeptides comprising, or alternatively consisting of, the amino acid sequence of residues Tyr-163 to Gln-198 of SEQ ID NO:2. The present invention is also directed to nucleic acid molecules comprising, or alternatively, consisting of, a polynucleotide sequence at least 80%, 85%, 90%, 95%, 96%, 97%, 98% or 99% identical to the polynucleotide sequence encoding the Neutrokine-alpha polypeptides described above. The present invention also encompasses the above polynucleotide sequences fused to a heterologous polynucleotide sequence. Polypeptides encoded by these nucleic acids and/or polynucleotide sequences are also encompassed by the invention.

In another embodiment, the invention provides polynucleotides encoding polypeptides comprising, or alternatively consisting of, the amino acid sequence of residues Val-199 to Gly-249 of SEQ ID NO:2. The present invention is also directed to nucleic acid molecules comprising, or alternatively, consisting of, a polynucleotide sequence at least 80%, 85%, 90%, 95%, 96%, 97%, 98% or 99% identical to the polynucleotide sequence encoding the Neutrokine-alpha polypeptides described above. The present invention also encompasses the above polynucleotide sequences fused to a heterologous polynucleotide sequence. Polypeptides encoded by these nucleic acids and/or polynucleotide sequences are also encompassed by the invention.The functional activity of Neutrokine-alpha and/or Neutrokine-alphaSV polypeptides, and fragments, variants derivatives, and analogs thereof, can be assayed by various methods as described herein and as are well known in the art.

For example, in one embodiment where one is assaying for the ability to bind or compete with full-length Neutrokine-alpha and/or Neutrokine-alphaSV polypeptide for binding to anti-Neutrokine-alpha and/or anti-Neutrokine-alphaSV antibody or binding to Neutrokine-alpha receptor(s) and/or Neutrokine-alphaSV receptor(s) on B cells, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a Neutrokine-alpha and/or Neutrokine-alphaSV ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94-123. In another embodiment, physiological correlates of Neutrokine-alpha and/or Neutrokine-alphaSV binding to its substrates (signal transduction) can be assayed.

In addition, assays described herein (see e,g., Examples 6 and 7) and otherwise known in the art may routinely be applied to measure the ability of Neutrokine-alpha and/or Neutrokine-alphaSV polypeptides and fragments, variants derivatives and analogs thererof to elicit Neutrokine-alpha and/or Neutrokine-alphaSV related biological activity (e.g., to stimulate, or alternatively to inhibit (in the case of Neutrokine-alpha and/or Neutrokine-alphaSV antagonists) signalling mediated by Neutrokine-alpha and/or Neutrokine-alphaSV; to stimulate, or alternatively to inhibit B cell proliferation, differentiation and/or activation; and/or to increase or decrease B cell survival in vitro or in vivo).

Other methods will be known to the skilled artisan and are within the scope of the invention.

In additional embodiments, the polynucleotides of the invention encode polypeptides comprising, or alternatively consisting of, functional attributes of Neutrokine-alpha and Neutrokine-alphaSV. Preferred embodiments of the invention in this regard include fragments that comprise, or alternatively consist of, alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of Neutrokine-alpha and Neutrokine-alphaSV polypeptides.

It is believed one or more of the beta pleated sheet regions of Neutrokine-alpha disclosed in FIGS. 7A-1 and 7A-2 is important for dimerization and also for interactions between Neutrokine-alpha and its ligands.

Certain preferred regions in this regard are set out in FIG. 3 (Table I). The data presented in FIG. 3 and that presented in Table I, merely present a different format of the same results obtained when the amino acid sequence of SEQ ID NO:2 is analyzed using the default parameters of the DNA*STAR computer algorithm.

The above-mentioned preferred regions set out in FIG. 3 and in Table I include, but are not limited to, regions of the aforementioned types identified by analysis of the amino acid sequence set out in FIGS. 1A and 1B. As set out in FIG. 3 and in Table I, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index. Among highly preferred polynucleotides in this regard are those that encode polypeptides comprising, or alternatively consisting of, regions of Neutrokine-alpha and/or Neutrokine-alphaSV that combine several structural features, such as several (e.g., 1, 2, 3 or 4) of the features set out above. Polypeptides encoded by the polynucleotides are also encompassed by the invention.

Additionally, the data presented in columns VIII, IX, XIII, and XIV of Table I can routinely be used to determine regions of Neutrokine-alpha which exhibit a high degree of potential for antigenicity (column VIII of Table I represents hydrophilicity according to Kyte-Doolittle; column IX of Table I represents hydrophobicity according to Hopp-Woods; column XIII of Table I represents antigenic index according to Jameson-Wolf; and column XIV of Table I represents surface probability according to Emini). Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response. The data presented in FIG. 6 can also routinely be presented in a similar tabular format by simply examining the amino acid sequence disclosed in FIG. 6 (SEQ ID NO:19) using the modules and algorithms of the DNA*STAR set on default parameters. As above, the amino acid sequence presented in FIG. 6 can also be used to determine regions of Neutrokine-alpha which exhibit a high degree of potential for antigenicity whether presented as a Figure (as in FIG. 6) or a table (as in Table I).

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | . | . | 0.73 | −0.71 | . | . | . | 0.95 | 1.39 |
| Asp | 2 | A | . | . | . | . | T | . | 1.12 | −0.66 | * | . | . | 1.15 | 1.56 |
| Asp | 3 | A | . | . | . | . | T | . | 1.62 | −1.09 | * | . | . | 1.15 | 2.12 |
| Ser | 4 | A | . | . | . | . | T | . | 2.01 | −1.51 | . | . | . | 1.15 | 4.19 |
| Thr | 5 | A | . | . | . | . | T | . | 2.40 | −2.13 | . | . | F | 1.30 | 4.35 |
| Glu | 6 | A | A | . | . | . | . | . | 2.70 | −1.73 | * | * | F | 0.90 | 4.51 |
| Arg | 7 | A | A | . | . | . | . | . | 2.81 | −1.34 | * | * | F | 0.90 | 4.51 |
| Glu | 8 | A | A | . | . | . | . | . | 2.00 | −1.73 | * | * | F | 0.90 | 6.12 |
| Gln | 9 | A | A | . | . | . | . | . | 1.99 | −1.53 | * | * | F | 0.90 | 2.91 |
| Ser | 10 | A | . | . | B | . | . | . | 2.00 | −1.04 | * | * | F | 0.90 | 2.15 |
| Arg | 11 | A | . | . | B | . | . | . | 1.33 | −0.66 | * | * | F | 0.90 | 1.66 |
| Leu | 12 | A | . | . | B | . | . | . | 0.41 | −0.09 | * | * | F | 0.45 | 0.51 |
| Thr | 13 | A | . | . | B | . | . | . | 0.46 | 0.20 | * | * | F | −0.15 | 0.32 |
| Ser | 14 | A | A | . | . | . | . | . | 0.50 | −0.19 | * | * | . | 0.30 | 0.32 |
| Cys | 15 | A | A | . | . | . | . | . | 0.91 | −0.19 | * | * | . | 0.30 | 0.78 |
| Leu | 16 | A | A | . | . | . | . | . | 0.80 | −0.87 | * | * | F | 0.90 | 1.06 |
| Lys | 17 | A | A | . | . | . | . | . | 1.61 | −1.36 | . | * | F | 0.90 | 1.37 |
| Lys | 18 | A | A | . | . | . | . | . | 1.32 | −1.74 | . | * | F | 0.90 | 4.44 |
| Arg | 19 | A | A | . | . | . | . | . | 1.67 | −1.70 | . | * | F | 0.90 | 5.33 |
| Glu | 20 | A | A | . | . | . | . | . | 1.52 | −2.39 | . | * | F | 0.90 | 5.33 |
| Glu | 21 | A | A | . | . | . | . | . | 2.38 | −1.70 | . | * | F | 0.90 | 2.20 |
| Met | 22 | A | A | . | . | . | . | . | 2.33 | −1.70 | . | * | F | 0.90 | 2.24 |
| Lys | 23 | A | A | . | . | . | . | . | 1.62 | −1.70 | * | * | F | 0.90 | 2.24 |
| Leu | 24 | A | A | . | . | . | . | . | 0.66 | −1.13 | * | * | F | 0.75 | 0.69 |
| Lys | 25 | A | A | . | . | . | . | . | 0.36 | −0.49 | . | * | F | 0.45 | 0.52 |
| Glu | 26 | A | A | . | B | . | . | . | −0.53 | −0.71 | * | * | . | 0.60 | 0.35 |
| Cys | 27 | A | A | . | B | . | . | . | −0.74 | −0.03 | * | * | . | 0.30 | 0.30 |
| Val | 28 | A | A | . | B | . | . | . | −1.00 | −0.03 | * | * | . | 0.30 | 0.12 |
| Ser | 29 | A | A | . | B | . | . | . | −0.08 | 0.40 | * | * | . | −0.30 | 0.11 |
| Ile | 30 | A | . | . | B | . | . | . | −0.08 | 0.40 | * | * | . | −0.30 | 0.40 |
| Leu | 31 | A | . | . | B | . | . | . | −0.08 | −0.17 | * | . | . | 0.45 | 1.08 |
| Pro | 32 | . | . | . | B | . | . | C | 0.29 | −0.81 | * | . | F | 1.10 | 1.39 |
| Arg | 33 | . | . | . | . | T | . | . | 0.93 | −0.81 | . | * | F | 1.50 | 2.66 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Lys | 34 | . | . | . | . | T | . | . | 0.93 | −1.07 | . | . | F | 1.84 | 4.98 |
| Glu | 35 | . | . | . | . | . | . | C | 0.97 | −1.37 | * | * | F | 1.98 | 4.32 |
| Ser | 36 | . | . | . | . | . | T | C | 1.89 | −1.16 | * | * | F | 2.52 | 1.64 |
| Pro | 37 | . | . | . | . | . | T | C | 1.80 | −1.16 | * | * | F | 2.86 | 1.60 |
| Ser | 38 | . | . | . | . | T | T | | 1.39 | −0.77 | * | . | F | 3.40 | 1.24 |
| Val | 39 | A | . | . | . | . | T | . | 1.39 | −0.39 | . | * | F | 2.36 | 1.24 |
| Arg | 40 | A | . | . | . | . | . | . | 1.39 | −0.77 | * | * | F | 2.46 | 1.60 |
| Ser | 41 | A | . | . | . | . | . | . | 1.34 | −1.20 | * | * | F | 2.46 | 2.00 |
| Ser | 42 | . | . | . | . | T | T | . | 1.60 | −1.16 | . | * | F | 3.06 | 2.67 |
| Lys | 43 | . | . | . | . | T | T | . | 1.09 | −1.80 | . | * | F | 3.06 | 2.72 |
| Asp | 44 | . | . | . | . | T | T | . | 1.13 | −1.11 | * | * | F | 3.40 | 1.67 |
| Gly | 45 | A | . | . | . | . | T | . | 0.43 | −0.81 | * | * | F | 2.66 | 1.03 |
| Lys | 46 | A | A | . | . | . | . | . | 0.14 | −0.70 | . | . | F | 1.77 | 0.52 |
| Leu | 47 | A | A | . | . | . | . | . | 0.13 | −0.20 | * | . | . | 0.98 | 0.31 |
| Leu | 48 | A | A | . | . | . | . | . | −0.72 | 0.29 | * | . | . | 0.04 | 0.46 |
| Ala | 49 | A | A | . | . | . | . | . | −1.53 | 0.54 | . | * | . | −0.60 | 0.19 |
| Ala | 50 | A | A | . | . | . | . | . | −2.00 | 1.23 | . | . | . | −0.60 | 0.19 |
| Thr | 51 | A | A | . | . | . | . | . | −2.63 | 1.23 | . | . | . | −0.60 | 0.19 |
| Leu | 52 | A | A | . | . | . | . | . | −2.63 | 1.04 | . | . | . | −0.60 | 0.19 |
| Leu | 53 | A | A | . | . | . | . | . | −2.63 | 1.23 | . | . | . | −0.60 | 0.15 |
| Leu | 54 | A | A | . | . | . | . | . | −2.34 | 1.41 | . | . | . | −0.60 | 0.09 |
| Ala | 55 | A | A | . | . | . | . | . | −2.42 | 1.31 | . | . | . | −0.60 | 0.14 |
| Leu | 56 | A | A | . | . | . | . | . | −2.78 | 1.20 | . | . | . | −0.60 | 0.09 |
| Leu | 57 | A | . | . | . | . | T | . | −2.78 | 1.09 | . | . | . | −0.20 | 0.06 |
| Ser | 58 | A | . | . | . | . | T | . | −2.28 | 1.09 | . | . | . | −0.20 | 0.05 |
| Cys | 59 | A | . | . | . | . | T | . | −2.32 | 1.07 | . | . | . | −0.20 | 0.09 |
| Cys | 60 | A | . | . | . | . | T | . | −2.59 | 1.03 | . | . | . | −0.20 | 0.08 |
| Leu | 61 | . | . | B | B | . | . | . | −2.08 | 0.99 | . | . | . | −0.60 | 0.04 |
| Thr | 62 | . | . | B | B | . | . | . | −1.97 | 0.99 | . | . | . | −0.60 | 0.11 |
| Val | 63 | . | . | B | B | . | . | . | −1.91 | 1.20 | . | . | . | −0.60 | 0.17 |
| Val | 64 | . | . | B | B | . | . | . | −1.24 | 1.39 | . | . | . | −0.60 | 0.33 |
| Ser | 65 | . | . | B | B | . | . | . | −1.43 | 1.10 | . | . | . | −0.60 | 0.40 |
| Phe | 66 | A | . | . | B | . | . | . | −1.21 | 1.26 | . | . | . | −0.60 | 0.40 |
| Tyr | 67 | A | . | . | B | . | . | . | −1.49 | 1.11 | . | . | . | −0.60 | 0.54 |
| Gln | 68 | A | . | . | B | . | . | . | −1.44 | 0.97 | . | . | . | −0.60 | 0.41 |
| Val | 69 | A | . | . | B | . | . | . | −0.59 | 1.27 | . | . | . | −0.60 | 0.39 |
| Ala | 70 | A | . | . | B | . | . | . | −0.63 | 0.89 | . | . | . | −0.60 | 0.43 |
| Ala | 71 | A | . | . | B | . | . | . | 0.07 | 0.56 | . | * | . | −0.60 | 0.25 |
| Leu | 72 | A | . | . | . | . | T | . | −0.50 | 0.16 | . | * | . | 0.10 | 0.55 |
| Gln | 73 | A | . | . | . | . | T | . | −1.09 | 0.20 | . | . | F | 0.25 | 0.45 |
| Gly | 74 | A | . | . | . | . | T | . | −0.53 | 0.20 | . | . | F | 0.25 | 0.45 |
| Asp | 75 | A | . | . | . | . | T | . | −0.76 | 0.09 | . | * | F | 0.25 | 0.73 |
| Leu | 76 | A | A | . | . | . | . | . | −0.06 | 0.09 | . | * | F | −0.15 | 0.35 |
| Ala | 77 | A | A | . | . | . | . | . | 0.17 | −0.31 | . | * | . | 0.30 | 0.69 |
| Ser | 78 | A | A | . | . | . | . | . | 0.17 | −0.24 | . | * | . | 0.30 | 0.42 |
| Leu | 79 | A | A | . | . | . | . | . | −0.30 | −0.24 | . | * | . | 0.30 | 0.88 |
| Arg | 80 | A | A | . | . | . | . | . | −0.30 | −0.24 | . | * | . | 0.30 | 0.72 |
| Ala | 81 | A | A | . | . | . | . | . | 0.17 | −0.34 | . | * | . | 0.30 | 0.93 |
| Glu | 82 | A | A | . | . | . | . | . | 0.72 | −0.30 | . | * | . | 0.45 | 1.11 |
| Leu | 83 | A | A | . | . | . | . | . | 0.99 | −0.49 | . | * | . | 0.30 | 0.77 |
| Gln | 84 | A | A | . | . | . | . | . | 1.21 | 0.01 | . | * | . | −0.15 | 1.04 |
| Gly | 85 | A | A | . | . | . | . | . | 1.10 | 0.01 | * | * | . | −0.30 | 0.61 |
| His | 86 | A | A | . | . | . | . | . | 1.73 | 0.01 | * | * | . | −0.15 | 1.27 |
| His | 87 | A | A | . | . | . | . | . | 0.92 | −0.67 | . | * | . | 0.75 | 1.47 |
| Ala | 88 | A | A | . | . | . | . | . | 1.52 | −0.39 | . | * | . | 0.45 | 1.22 |
| Glu | 89 | A | A | . | . | . | . | . | 0.93 | −0.39 | . | . | . | 0.45 | 1.39 |
| Lys | 90 | A | A | . | . | . | . | . | 0.93 | −0.39 | * | . | F | 0.60 | 1.03 |
| Leu | 91 | A | . | . | . | . | T | . | 0.38 | −0.46 | * | . | . | 0.85 | 1.01 |
| Pro | 92 | A | . | . | . | . | T | . | 0.07 | −0.46 | . | . | . | 0.70 | 0.59 |
| Ala | 93 | A | . | . | . | . | T | . | 0.07 | −0.03 | . | . | . | 0.70 | 0.29 |
| Gly | 94 | A | . | . | . | . | T | . | −0.14 | 0.47 | . | . | . | −0.20 | 0.36 |
| Ala | 95 | A | . | . | . | . | . | . | −0.14 | 0.21 | . | * | . | −0.10 | 0.36 |
| Gly | 96 | A | . | . | . | . | . | . | 0.08 | −0.21 | . | . | F | 0.65 | 0.71 |
| Ala | 97 | A | . | . | . | . | . | . | −0.06 | −0.21 | . | . | F | 0.65 | 0.72 |
| Pro | 98 | A | . | . | . | . | . | . | −0.28 | −0.21 | . | * | F | 0.65 | 0.71 |
| Lys | 99 | A | A | . | . | . | . | . | 0.07 | −0.03 | . | . | F | 0.45 | 0.59 |
| Ala | 100 | A | A | . | . | . | . | . | 0.66 | −0.46 | . | . | F | 0.60 | 1.01 |
| Gly | 101 | A | A | . | . | . | . | . | 0.41 | −0.96 | . | . | F | 0.90 | 1.13 |
| Leu | 102 | A | A | . | . | . | . | . | 0.79 | −0.89 | . | . | F | 0.75 | 0.57 |
| Glu | 103 | A | A | . | . | . | . | . | 0.41 | −0.46 | * | . | F | 0.45 | 0.88 |
| Glu | 104 | A | A | . | . | . | . | . | −0.49 | −0.46 | * | . | F | 0.45 | 0.89 |
| Ala | 105 | A | A | . | . | . | . | . | −0.21 | −0.24 | . | . | . | 0.30 | 0.81 |
| Pro | 106 | A | A | . | . | . | . | . | −0.46 | −0.44 | . | . | . | 0.30 | 0.67 |
| Ala | 107 | A | A | . | . | . | . | . | 0.01 | 0.06 | . | . | . | −0.30 | 0.39 |
| Val | 108 | A | A | . | . | . | . | . | −0.80 | 0.49 | . | * | . | −0.60 | 0.38 |
| Thr | 109 | A | A | . | . | . | . | . | −0.76 | 0.67 | . | * | . | −0.60 | 0.20 |
| Ala | 110 | A | A | . | . | . | . | . | −1.06 | 0.24 | * | * | . | −0.30 | 0.40 |
| Gly | 111 | A | A | . | . | . | . | . | −1.54 | 0.43 | * | * | . | −0.60 | 0.38 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 112 | A | A | . | . | . | . | . | −0.96 | 0.57 | * | * | . | −0.60 | 0.23 |
| Lys | 113 | . | A | B | . | . | . | . | −0.31 | 0.09 | * | * | . | −0.30 | 0.39 |
| Ile | 114 | . | A | B | . | . | . | . | −0.21 | 0.01 | * | . | . | −0.30 | 0.61 |
| Phe | 115 | . | A | B | . | . | . | . | −0.21 | 0.01 | * | . | . | 0.15 | 1.15 |
| Glu | 116 | . | A | . | . | . | . | C | −0.08 | −0.17 | * | . | F | 1.25 | 0.58 |
| Pro | 117 | . | A | . | . | . | . | C | 0.39 | 0.26 | * | * | F | 1.10 | 1.28 |
| Pro | 118 | . | . | . | . | . | . | C | 0.34 | −0.00 | . | . | F | 2.20 | 1.47 |
| Ala | 119 | . | . | . | . | . | T | C | 0.89 | −0.79 | . | * | F | 3.00 | 1.47 |
| Pro | 120 | . | . | . | . | . | T | C | 1.59 | −0.36 | . | * | F | 2.25 | 0.94 |
| Gly | 121 | . | . | . | . | T | T | . | 1.29 | −0.39 | . | * | F | 2.15 | 0.98 |
| Glu | 122 | . | . | . | . | T | T | . | 1.20 | −0.43 | . | . | F | 2.00 | 1.30 |
| Gly | 123 | . | . | . | . | . | . | C | 1.41 | −0.54 | . | . | F | 1.60 | 1.12 |
| Asn | 124 | . | . | . | . | . | T | C | 2.00 | −0.57 | . | . | F | 1.50 | 1.97 |
| Ser | 125 | . | . | . | . | . | T | C | 1.91 | −0.60 | . | * | F | 1.50 | 1.82 |
| Ser | 126 | . | . | . | . | . | T | C | 2.37 | −0.21 | . | * | F | 1.54 | 2.47 |
| Gln | 127 | . | . | . | . | . | T | C | 2.37 | −0.64 | . | * | F | 2.18 | 3.01 |
| Asn | 128 | . | . | . | . | . |  | C | 2.76 | −0.64 | . | . | F | 2.32 | 3.61 |
| Ser | 129 | . | . | . | . | . | T | C | 2.87 | −1.03 | . | . | F | 2.86 | 5.39 |
| Arg | 130 | . | . | . | . | T | T | . | 2.58 | −1.41 | * | . | F | 3.40 | 6.09 |
| Asn | 131 | . | . | . | . | T | T | . | 2.02 | −1.31 | * | . | F | 3.06 | 3.83 |
| Lys | 132 | . | . | . | . | T | T | . | 2.02 | −1.07 | * | . | F | 2.72 | 2.12 |
| Arg | 133 | . | . | . | . | T | . | . | 1.68 | −1.06 | * | . | F | 2.18 | 1.88 |
| Ala | 134 | . | . | . | . | . | . | C | 1.77 | −0.63 | * | . | F | 1.64 | 1.15 |
| Val | 135 | . | . | . | . | . | . | C | 1.66 | −0.60 | * | . | F | 1.49 | 0.89 |
| Gln | 136 | . | . | . | . | . | . | C | 1.66 | −0.60 | * | . | F | 1.83 | 0.79 |
| Gly | 137 | . | . | . | . | . | T | C | 1.30 | −0.60 | * | . | F | 2.52 | 1.35 |
| Pro | 138 | . | . | . | . | . | T | C | 0.33 | −0.61 | * | . | F | 2.86 | 2.63 |
| Glu | 139 | . | . | . | . | T | T | . | 0.61 | −0.61 | * | . | F | 3.40 | 1.13 |
| Glu | 140 | A | . | . | . | . | T | . | 1.47 | −0.53 | * | . | F | 2.66 | 1.64 |
| Thr | 141 | A | . | . | . | . | . | . | 1.47 | −0.56 | . | . | F | 2.12 | 1.84 |
| Val | 142 | A | . | . | . | . | . | . | 1.14 | −0.99 | . | . | F | 1.78 | 1.77 |
| Thr | 143 | A | . | . | . | . | T | . | 0.54 | −0.41 | . | . | F | 1.19 | 0.55 |
| Gln | 144 | A | . | . | . | . | T | . | 0.54 | 0.27 | * | . | F | 0.25 | 0.31 |
| Asp | 145 | A | . | . | . | . | T | . | −0.27 | 0.19 | * | . | F | 0.25 | 0.73 |
| Cys | 146 | A | . | . | . | . | T | . | −0.84 | 0.23 | * | . | . | 0.10 | 0.42 |
| Leu | 147 | A | A | . | . | . | . | . | −0.58 | 0.43 | * | . | . | −0.60 | 0.17 |
| Gln | 148 | A | A | . | . | . | . | . | −0.27 | 0.53 | * | . | . | −0.60 | 0.10 |
| Leu | 149 | A | A | . | . | . | . | . | −0.57 | 0.53 | * | * | . | −0.30 | 0.32 |
| Ile | 150 | A | A | . | . | . | . | . | −0.57 | 0.34 | * | . | . | 0.30 | 0.52 |
| Ala | 151 | . | A | . | . | . | . | C | −0.21 | −0.34 | . | * | . | 1.40 | 0.52 |
| Asp | 152 | . | . | . | . | T | T | . | 0.39 | −0.26 | . | * | F | 2.45 | 0.91 |
| Ser | 153 | . | . | . | . | . | T | C | 0.08 | −0.51 | . | . | F | 3.00 | 2.00 |
| Glu | 154 | . | . | . | . | . | T | C | −0.00 | −0.71 | . | . | F | 2.70 | 2.86 |
| Thr | 155 | . | . | . | . | . | T | C | 0.89 | −0.53 | * | . | F | 2.40 | 1.20 |
| Pro | 156 | . | . | . | B | . | . | C | 1.52 | −0.13 | * | . | F | 1.56 | 1.55 |
| Thr | 157 | . | . | . | B | T | . | . | 1.18 | −0.51 | * | . | F | 1.92 | 1.79 |
| Ile | 158 | A | . | . | B | . | . | . | 1.18 | −0.09 | . | . | F | 1.08 | 1.23 |
| Gln | 159 | . | . | . | . | T | T | . | 0.93 | −0.19 | . | . | F | 2.04 | 1.07 |
| Lys | 160 | . | . | . | . | T | T | . | 0.93 | 0.14 | * | . | F | 1.60 | 1.16 |
| Gly | 161 | . | . | . | . | T | T | . | 0.44 | 0.14 | * | . | F | 1.44 | 2.38 |
| Ser | 162 | . | . | . | . | T | T | . | −0.10 | 0.24 | * | . | F | 1.28 | 1.19 |
| Tyr | 163 | . | . | . | B | T | . | . | 0.58 | 0.49 | * | . | . | 0.12 | 0.44 |
| Thr | 164 | . | . | B | B | . | . | . | 0.29 | 0.91 | * | . | . | −0.44 | 0.69 |
| Phe | 165 | . | . | B | B | . | . | . | −0.57 | 1.40 | * | . | . | −0.60 | 0.54 |
| Val | 166 | . | . | B | B | . | . | . | −1.03 | 1.70 | . | . | . | −0.60 | 0.29 |
| Pro | 167 | . | . | B | B | . | . | . | −1.03 | 1.63 | . | . | . | −0.60 | 0.16 |
| Trp | 168 | A | . | . | B | . | . | . | −1.49 | 1.53 | . | * | . | −0.60 | 0.25 |
| Leu | 169 | A | . | . | B | . | . | . | −1.13 | 1.53 | * | . | . | −0.60 | 0.29 |
| Leu | 170 | A | . | . | B | . | . | . | −0.32 | 0.89 | * | . | . | −0.30 | 0.38 |
| Ter | 171 | A | . | . | . | . | . | . | 0.19 | 0.46 | * | . | . | 0.20 | 0.71 |
| Phe | 172 | . | . | . | . | T | . | . | 0.10 | −0.03 | * | . | . | 1.80 | 0.85 |
| Lys | 173 | . | . | . | . | T | T | . | −0.20 | −0.33 | * | . | F | 2.60 | 1.38 |
| Arg | 174 | . | . | . | . | . | T | C | −0.20 | −0.51 | . | . | F | 3.00 | 1.04 |
| Gly | 175 | . | . | . | . | . | T | C | 0.61 | −0.21 | . | . | F | 2.25 | 0.99 |
| Ser | 176 | A | . | . | . | . | T |  | 0.91 | −1.00 | * | . | F | 2.05 | 0.86 |
| Ala | 177 | A | A | . | . | . | . | . | 1.66 | −1.00 | * | . | F | 1.35 | 0.76 |
| Leu | 178 | A | A | . | . | . | . | . | 1.61 | −1.00 | . | . | F | 1.20 | 1.54 |
| Glu | 179 | A | A | . | . | . | . | . | 1.50 | −1.43 | . | . | F | 0.90 | 1.98 |
| Glu | 180 | A | A | . | . | . | . | . | 1.89 | −1.41 | * | . | F | 0.90 | 3.16 |
| Lys | 181 | A | A | . | . | . | . | . | 1.30 | −1.91 | * | . | F | 0.90 | 7.66 |
| Glu | 182 | A | A | . | . | . | . | . | 1.08 | −1.91 | . | . | F | 0.90 | 3.10 |
| Asn | 183 | A | A | . | . | . | . | . | 1.03 | −1.23 | * | * | F | 0.90 | 1.48 |
| Lys | 184 | A | A | . | . | . | . | . | 1.08 | −0.59 | * | . | F | 0.75 | 0.55 |
| Ile | 185 | A | A | . | . | . | . | . | 1.08 | −0.59 | * | * | . | 0.60 | 0.63 |
| Leu | 186 | A | A | . | . | . | . | . | 0.72 | −0.59 | * | * | . | 0.60 | 0.68 |
| Val | 187 | A | A | . | . | . | . | . | 0.38 | −0.50 | . | * | . | 0.30 | 0.49 |
| Lys | 188 | A | A | . | . | . | . | . | 0.13 | −0.07 | * | * | F | 0.45 | 0.69 |
| Glu | 189 | A | . | . | . |  | T | . | −0.61 | 0.00 | * | * | F | 0.40 | 1.32 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Thr | 190 | . | . | . | . | T | T | . | −0.42 | 0.10 | . | * | F | 0.80 | 1.54 |
| Gly | 191 | . | . | . | . | T | T | . | −0.50 | 0.24 | * | . | F | 0.65 | 0.67 |
| Tyr | 192 | . | . | . | . | T | T | . | 0.11 | 0.93 | * | * | . | 0.20 | 0.27 |
| Phe | 193 | . | . | B | B | . | . | . | −0.28 | 1.69 | . | . | . | −0.60 | 0.29 |
| Phe | 194 | . | . | B | B | . | . | . | −0.28 | 1.63 | . | * | . | −0.60 | 0.29 |
| Ile | 195 | . | . | B | B | . | . | . | −0.82 | 1.60 | . | . | . | −0.60 | 0.32 |
| Tyr | 196 | . | . | B | B | . | . | . | −1.29 | 1.49 | . | . | . | −0.60 | 0.28 |
| Gly | 197 | . | . | . | B | T | . | . | −1.29 | 1.39 | . | . | . | −0.20 | 0.26 |
| Gln | 198 | . | . | . | B | T | . | . | −0.90 | 1.36 | . | . | . | −0.20 | 0.59 |
| Val | 199 | . | . | . | B | . | . | C | −0.20 | 1.16 | . | . | . | −0.40 | 0.54 |
| Leu | 200 | . | . | . | B | . | . | C | 0.73 | 0.40 | . | . | . | −0.10 | 0.92 |
| Tyr | 201 | . | . | . | . | T | T | . | 0.67 | −0.03 | . | . | . | 1.25 | 1.06 |
| Thr | 202 | . | . | . | . | T | T | . | 0.77 | 0.06 | . | . | F | 0.80 | 2.06 |
| Asp | 203 | . | . | . | . | T | T | . | 0.18 | 0.17 | . | . | F | 0.80 | 3.91 |
| Lys | 204 | A | . | . | . | . | T | . | 0.43 | −0.01 | . | . | F | 1.00 | 2.52 |
| Thr | 205 | A | A | . | . | . | . | . | 0.90 | −0.16 | . | . | F | 0.60 | 1.73 |
| Tyr | 206 | A | A | . | . | . | . | . | 1.11 | −0.21 | . | . | . | 0.45 | 1.03 |
| Ala | 207 | A | A | . | . | . | . | . | 0.61 | 0.29 | . | . | . | −0.30 | 0.70 |
| Met | 208 | A | A | . | . | . | . | . | −0.28 | 0.97 | . | . | . | −0.60 | 0.40 |
| Gly | 209 | A | A | . | B | . | . | . | −0.32 | 1.17 | * | . | . | −0.60 | 0.18 |
| His | 210 | A | A | . | B | . | . | . | 0.10 | 0.81 | * | . | . | −0.60 | 0.31 |
| Leu | 211 | A | A | . | B | . | . | . | 0.39 | 0.31 | . | . | . | −0.30 | 0.61 |
| Ile | 212 | A | A | . | B | . | . | . | 1.02 | −0.30 | . | . | . | 0.45 | 1.22 |
| Gln | 213 | A | A | . | B | . | . | . | 0.77 | −0.73 | . | * | . | 0.75 | 1.80 |
| Arg | 214 | A | A | . | B | . | . | . | 1.08 | −0.59 | . | * | F | 0.90 | 1.62 |
| Lys | 215 | A | A | . | B | . | . | . | 0.26 | −0.77 | * | * | F | 0.90 | 3.14 |
| Lys | 216 | A | A | . | B | . | . | . | 0.37 | −0.81 | . | * | F | 0.90 | 1.35 |
| Val | 217 | . | A | B | B | . | . | . | 0.91 | −0.43 | * | * | . | 0.30 | 0.60 |
| His | 218 | . | A | B | B | . | . | . | 0.91 | −0.00 | . | * | . | 0.30 | 0.29 |
| Val | 219 | . | A | B | B | . | . | . | 0.80 | −0.00 | * | * | . | 0.30 | 0.25 |
| Phe | 220 | . | . | B | B | . | . | . | −0.06 | −0.00 | * | . | . | 0.30 | 0.57 |
| Gly | 221 | A | . | . | B | . | . | . | −0.40 | 0.04 | . | * | . | −0.30 | 0.35 |
| Asp | 222 | A | . | . |  | . | . | . | −0.36 | −0.07 | * | . | . | 0.50 | 0.63 |
| Glu | 223 | A | . | . |  | . | . | . | −1.18 | −0.03 | * | . | . | 0.50 | 0.60 |
| Leu | 224 | A | . | . | B | . | . | . | −0.63 | −0.17 | . | . | . | 0.30 | 0.45 |
| Ser | 225 | A | . | . | B | . | . | . | −0.74 | −0.11 | . | . | . | 0.30 | 0.39 |
| Leu | 226 | A | . | . | B | . | . | . | −1.10 | 0.57 | . | * | . | −0.60 | 0.18 |
| Val | 227 | A | . | . | B | . | . | . | −0.99 | 1.36 | . | * | . | −0.60 | 0.19 |
| Thr | 228 | A | . | . | B | . | . | . | −1.66 | 0.67 | * | * | . | −0.60 | 0.28 |
| Leu | 229 | A | . | . | B | . | . | . | −1.73 | 0.86 | * | . | . | −0.60 | 0.18 |
| Phe | 230 | A | . | . | B | . | . | . | −1.43 | 0.86 | * | . | . | −0.60 | 0.17 |
| Arg | 231 | A | . | . | B | . | . | . | −0.62 | 0.61 | * | . | . | −0.60 | 0.21 |
| Cys | 232 | . | . | . | B | T | . | . | −0.37 | 0.53 | * | . | . | −0.20 | 0.41 |
| Ile | 233 | . | . | . | B | T | . | . | −0.27 | 0.46 | * | . | . | −0.20 | 0.46 |
| Gln | 234 | . | . | . | B | T | . | . | 0.54 | 0.10 | * | . | . | 0.10 | 0.37 |
| Asn | 235 | . | . | . | B | . | . | C | 0.93 | 0.10 | * | . | . | 0.05 | 1.19 |
| Met | 236 | . | . | . | B | . | . | C | 0.01 | 0.01 | * | . | F | 0.20 | 2.44 |
| Pro | 237 | . | . | . | B | . | . | C | 0.47 | 0.01 | * | . | F | 0.44 | 1.16 |
| Glu | 238 | . | . | . | . | T | . | . | 1.36 | 0.04 | * | . | F | 1.08 | 1.12 |
| Thr | 239 | . | . | . | . | . | . | C | 1.36 | 0.04 | * | . | F | 1.12 | 1.82 |
| Leu | 240 | . | . | . | . | . | . | C | 1.06 | −0.17 | * | . | F | 1.96 | 1.89 |
| Pro | 241 | . | . | . | . | T | . | . | 0.99 | −0.21 | . | . | F | 2.40 | 1.46 |
| Asn | 242 | . | . | . | . | T | . | . | 0.96 | 0.36 | . | . | F | 1.41 | 0.54 |
| Asn | 243 | . | . | . | . | T | T | . | 0.66 | 0.63 | . | . | F | 1.22 | 1.03 |
| Ser | 244 | . | . | . | . | T | T | . | 0.38 | 0.33 | . | . | F | 1.13 | 0.89 |
| Cys | 245 | . | . | . | . | T | T | . | 0.84 | 0.40 | . | . | . | 0.74 | 0.56 |
| Tyr | 246 | . | . | . | . | T | T | . | 0.17 | 0.43 | . | . | . | 0.20 | 0.35 |
| Ser | 247 | A | . | . | . | . | . | . | −0.42 | 0.71 | . | . | . | −0.40 | 0.18 |
| Ala | 248 | A | A | . | . | . | . | . | −0.38 | 0.83 | . | . | . | −0.60 | 0.34 |
| Gly | 249 | A | A | . | . | . | . | . | −0.89 | 0.26 | . | . | . | −0.30 | 0.43 |
| Ile | 250 | A | A | . | . | . | . | . | −0.22 | 0.19 | * | . | . | −0.30 | 0.27 |
| Ala | 251 | A | A | . | . | . | . | . | 0.02 | −0.20 | * | . | . | 0.30 | 0.46 |
| Lys | 252 | A | A | . | . | . | . | . | −0.02 | −0.70 | . | . | . | 0.60 | 0.80 |
| Leu | 253 | A | A | . | . | . | . | . | 0.57 | −0.70 | . | . | F | 0.90 | 1.13 |
| Glu | 254 | A | A | . | . | . | . | . | 0.91 | −1.39 | . | . | F | 0.90 | 1.87 |
| Glu | 255 | A | A | . | . | . | . | . | 0.99 | −1.89 | . | . | F | 0.90 | 1.62 |
| Gly | 256 | A | A | . | . | . | . | . | 1.58 | −1.20 | . | * | F | 0.90 | 1.62 |
| Asp | 257 | A | A | . | . | . | . | . | 0.72 | −1.49 | . | * | F | 0.90 | 1.62 |
| Glu | 258 | A | A | . | . | . | . | . | 0.94 | −0.80 | * | * | F | 0.75 | 0.77 |
| Leu | 259 | A | A | . | . | . | . | . | 0.06 | −0.30 | * | * | . | 0.30 | 0.79 |
| Gln | 260 | A | A | . | . | . | . | . | −0.16 | −0.04 | * | . | . | 0.30 | 0.33 |
| Leu | 261 | A | A | . | . | . | . | . | 0.30 | 0.39 | * | . | . | −0.30 | 0.30 |
| Ala | 262 | A | A | . | . | . | . | . | 0.30 | 0.39 | * | . | . | −0.30 | 0.70 |
| Ile | 263 | A | A | . | . | . | . | . | 0.30 | −0.30 | . | * | . | 0.30 | 0.70 |
| Pro | 264 | A | . | . | . | . | T | . | 0.52 | −0.30 | . | * | F | 1.00 | 1.37 |
| Arg | 265 | A | . | . | . | . | T | . | 0.52 | −0.49 | . | * | F | 1.00 | 1.37 |
| Glu | 266 | A | . | . | . | . | T | . | 0.44 | −0.59 | * | * | F | 1.30 | 3.38 |
| Asn | 267 | A | . | . | . | . | T | . | 0.73 | −0.59 | * | * | F | 1.30 | 1.53 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 268 | A | . | . | . | . | . | . | 0.81 | −0.63 | * | * | . | 0.95 | 1.05 |
| Gln | 269 | A | . | . | . | . | . | . | 1.02 | 0.06 | * | * | . | −0.10 | 0.50 |
| Ile | 270 | A | . | . | . | . | . | . | 0.57 | 0.06 | . | * | . | 0.15 | 0.52 |
| Ser | 271 | . | . | . | . | . | . | C | 0.57 | 0.09 | . | * | . | 0.60 | 0.51 |
| Leu | 272 | . | . | . | . | . | . | C | −0.29 | −0.41 | . | * | F | 1.60 | 0.49 |
| Asp | 273 | . | . | . | . | T | T | . | −0.01 | −0.17 | . | * | F | 2.25 | 0.52 |
| Gly | 274 | . | . | . | . | T | T | . | −0.71 | −0.37 | . | * | F | 2.50 | 0.56 |
| Asp | 275 | . | . | . | . | T | T | . | −0.52 | 0.03 | . | * | F | 1.65 | 0.59 |
| Val | 276 | A | . | . | . | . | T | . | −0.57 | 0.13 | . | * | F | 1.00 | 0.30 |
| Thr | 277 | A | . | . | B | . | . | . | −0.34 | 0.56 | . | * | . | −0.10 | 0.30 |
| Phe | 278 | A | . | . | B | . | . | . | −1.16 | 0.63 | . | * | . | −0.35 | 0.18 |
| Phe | 279 | A | . | . | B | . | . | . | −0.77 | 1.31 | . | * | . | −0.60 | 0.20 |
| Gly | 280 | A | A | . | . | . | . | . | −1.58 | 0.67 | . | * | . | −0.60 | 0.28 |
| Ala | 281 | A | A | . | . | . | . | . | −1.53 | 0.87 | . | * | . | −0.60 | 0.27 |
| Leu | 282 | A | A | . | . | . | . | . | −1.61 | 0.77 | * | . | . | −0.60 | 0.26 |
| Lys | 283 | A | A | . | . | . | . | . | −1.30 | 0.41 | * | . | . | −0.60 | 0.33 |
| Leu | 284 | A | A | . | . | . | . | . | −0.99 | 0.41 | . | . | . | −0.60 | 0.42 |
| Leu | 285 | A | A | . | . | . | . | . | −1.03 | 0.34 | * | . | . | −0.30 | 0.65 |

Additional preferred nucleic acid fragments of the present invention include nucleic acid molecules comprising, or alternatively, consisting of a sequence encoding one or more epitope-bearing portions of Neutrokine-alpha. In particular, such nucleic acid fragments of the present invention include nucleic acid molecules comprising, or alternatively consisting of, a sequence encoding a polypeptide selected from: from about Phe-115 to about Leu-147, from about Ile-150 to about Tyr-163, from about Ser-171 to about Phe-194, from about Glu-223 to about Tyr-246, and from about Ser-271 to about Phe-278, of the amino acid sequence of SEQ ID NO:2. In this context, "about" means the particularly recited ranges and ranges larger or smaller by several, a few, 5, 4, 3, 2 or 1 amino acid residues at either or both the amino- and carboxy-termini. Polypeptides encoded by these nucleic acid molecules are also encompassed by the invention. Polypeptide fragments which bear antigenic epitopes of the Neutrokine-alpha may be easily determined by one of skill in the art using the above-described analysis of the Jameson-Wolf antigenic index, as shown in FIG. 3. Methods for determining other such epitope-bearing portions of Neutrokine-alpha are described in detail below.

Additional preferred nucleic acid fragments of the present invention include nucleic acid molecules comprising, or alternatively consisting of a sequence encoding one or more epitope-bearing portions of Neutrokine-alphaSV. In particular, such nucleic acid fragments of the present invention include nucleic acid molecules comprising, or alternatively consisting of a sequence encoding a polypeptide selected from about Pro-32 to about Leu-47, from about Glu-116 to about Ser-143, from about Phe-153 to about Tyr-173, from about Pro-218 to about Tyr-227, from about Ser-252 to about Thr-258, from about Ala-232 to about Gln-241; from about Ile-244 to about Ala-249; and from about Ser-252 to about Val-257, of the amino acid sequence of SEQ ID NO:19. In this context, "about" means the particularly recited ranges and ranges larger or smaller by several, a few, 5, 4, 3, 2 or 1 amino acid residues at either or both the amino- and carboxy-termini. Polypeptides encoded by these nucleic acid molecules are also encompassed by the invention. Polypeptide fragments which bear antigenic epitopes of the Neutrokine-alpha may be easily determined by one of skill in the art using the above-described analysis of the Jameson-Wolf antigenic index. Methods for determining other such epitope-bearing portions of Neutrokine-alphaSV are described in detail below.

In specific embodiments, the polynucleotides of the invention are less than 100,000 kb, 50,000 kb, 10,000 kb, 1,000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise at least 15, at least 30, at least 50, at least 100, or at least 250, at least 500, or at least 1000 contiguous nucleotides of Neutrokine-alpha coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide set forth in FIGS. 1A and 1B (SEQ ID NO:1) or FIGS. 5A and 5B (SEQ ID NO:18). In further embodiments, polynucleotides of the invention comprise at least 15, at least 30, at least 50, at least 100, or at least 250, at least 500, or at least 1000 contiguous nucleotides of Neutrokine-alpha coding sequence, but do not comprise all or a portion of any Neutrokine-alpha intron. In another embodiment, the nucleic acid comprising Neutrokine-alpha coding sequence does not contain coding sequences of a genomic flanking gene (i.e., 5' or 3' to the Neutrokine-alpha gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

In another embodiment, the invention provides an isolated nucleic acid molecule comprising a polynucleotide which hybridizes under stringent hybridization conditions to a portion of the polynucleotide in a nucleic acid molecule of the invention described above, for instance, the sequence complementary to the coding and/or noncoding sequence depicted in FIGS. 1A and 1B (SEQ ID NO:1), the sequence of the cDNA clone contained in the deposit having ATCC accession no. 97768, the sequence complementary to the coding sequence and/or noncoding sequence depicted in FIGS. 5A and 5B (SEQ ID NO:18), the sequence of the cDNA clone contained in the deposit having ATCC accession no. 203518, the sequence complementary to the coding sequence and/or noncoding sequence (i.e., transcribed, untranslated) depicted in SEQ ID NO:21, the sequence complementary to the coding sequence and/or noncoding sequence depicted in SEQ ID NO:22, the sequence complementary to the coding sequence and/or noncoding sequence depicted in SEQ ID NO:27, the sequence complementary to the coding sequence and/or noncoding sequence depicted in SEQ ID NO:29, the sequence complementary to the coding sequence and/or noncoding sequence depicted in SEQ ID NO:37, or fragments (such as, for example, the open reading frame or a fragment thereof) of these sequences, as described herein. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 (e.g., 40, 50, or 60) nucleotides, and even more preferably about any integer in the range of 30-70 or 80-150 nucleotides, or the entire length of the reference polynucleotide. These have uses, which include, but are not limited to, diagnostic probes and primers as discussed above and in more detail below. By a portion of a polynucleotide of "at least about 20 nt in length," for example, is intended to include the particularly recited ranges, larger or smaller by several (i.e. 5, 4, 3, 2, 1, or 0) amino acids, at either extreme or at both extremes of the nucleotide sequence of the reference polynucleotide (e.g., the sequence of one or both of the deposited cDNAs, the complementary strand of the nucleotide sequence shown in FIGS. 1A and 1B (SEQ ID NO:1), the complementary strand of the nucleotide sequence shown in FIGS. 5A and 5B (SEQ ID NO:18), the complementary strand of the nucleotide sequence shown in SEQ ID NO:21, the complementary strand of the nucleotide sequence shown in SEQ ID NO:22, the complementary strand of the nucleotide sequence shown in SEQ ID NO:27, the complementary strand of the nucleotide sequence shown in SEQ ID NO:29, and/or the complementary strand of the nucleotide sequence shown in SEQ ID NO:37). Of course, a polynucleotide which hybridizes only to a poly A sequence (such as the 3' terminal poly (A) tract of the Neutrokine-alpha cDNA shown in FIGS. 1A and 1B (SEQ ID NO:1), the 3' terminal poly(A) tract of the Neutrokine-alphaSV cDNA shown in FIGS. 5A and 5B (SEQ ID NO:18) or the 3' terminal poly(A) tract of the Neutrokine-alphaSV cDNA shown in SEQ ID NO:22), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

As indicated, nucleic acid molecules of the present invention which encode a Neutrokine-alpha polypeptide or a Neutrokine-alphaSV polypeptide may include, but are not limited to, polynucleotides encoding the amino acid sequence of the respective extracellular domains of the polypeptides, by themselves; and the coding sequence for the extracellular domains of the respective polypeptides and additional sequences, such as those encoding the intracellular and transmembrane domain sequences, or a pre-, or pro- or prepro-protein sequence; the coding sequence of the respective extracellular domains of the polypeptides, with or without the aforementioned additional coding sequences.

Also encoded by nucleic acids of the invention are the above protein sequences together with additional, non-coding sequences, including for example, but not limited to, introns and non-coding 5' and 3' sequences, such as the transcribed, non-translated sequences that play a role in transcription, mRNA processing, including splicing and polyadenylation signals, for example, ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this embodiment of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37: 767 (1984). As discussed below, other such fusion proteins include the Neutrokine-alpha or the Neutrokine-alphaSV polypeptides fused to Fc at the N- or C-terminus.

The present invention further relates to variants of the nucleic acid molecules of the present invention, which encode portions, analogs or derivatives of the Neutrokine-alpha or Neutrokine-alphaSV polypeptides of SEQ ID NO:2. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., Nucl. Acids Res. 13:4331 (1986); and Zoller et al., Nucl. Acids Res. 10:6487 (1982)), cassette mutagenesis (see e.g., Wells et al., Gene 34:315 (1985)), restriction selection mutagenesis (see e.g., Wells er al., Philos. Trans. R. Soc. London SerA 317:415 (1986)).

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the Neutrokine-alpha and/or Neutrokine-alphaSV polypeptides or portions thereof. Also especially preferred in this regard are conservative substitutions.

Additional embodiments of the invention are directed to isolated nucleic acid molecules comprising a polynucleotide which encodes the amino acid sequence of a Neutrokine-alpha and/or Neutrokine-alphaSV polypeptide (e.g., a Neutrokine-alpha and/or Neutrokine-alphaSV polypeptide fragment described herein) having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions, 10-20 conservative amino acid substitutions, 5-10 conservative amino acid substitutions, 1-5 conservative amino acid substitutions, 3-5 conservative amino acid substitutions, or 1-3 conservative amino acid substitutions. Of course, in order of ever-increasing preference, it is highly preferable for a polynucleotide which encodes the amino acid sequence of a Neutrokine-alpha and/or Neutrokine-alphaSV polypeptide to have an amino acid sequence which contains not more than 10, 9, 8, 7, 6, 5, 4, 3, 2 or 1 conservative amino acid substitutions.

Further embodiments include an isolated nucleic acid molecule comprising, or alternatively consisting of, a polynucleotide having a nucleotide sequence at least 80%, 85%, or 90% identical, and more preferably at least 95%, 96%, 97%, 98% or 99% identical to a polynucleotide selected from the group consisting of: (a) a nucleotide sequence encoding the Neutrokine-alpha polypeptide having the complete amino acid sequence in FIGS. 1A and 1B (i.e., positions 1 to 285 of SEQ ID NO:2); (b) a nucleotide sequence encoding the Neutrokine-alpha polypeptide having the complete amino acid sequence in SEQ ID NO:2 excepting the N-terminal methionine (i.e., positions 2 to 285 of SEQ ID NO:2); (c) a fragment of the polypeptide of (b) having Neutrokine-alpha functional activity (e.g., antigenic or biological activity); (d) a nucleotide sequence encoding the predicted extracellular domain of the Neutrokine-alpha polypeptide having the amino acid sequence at positions 73-285 in FIGS. 1A and 1B (SEQ ID NO:2); (e) a nucleotide sequence encoding the Neutrokine-alpha polypeptide having the amino acid sequence at positions 134-285 in FIGS. 1A and 1B (SEQ ID NO:2); (f) a nucleotide sequence encoding the Neutrokine-alpha polypeptide having the complete amino acid sequence encoded by the cDNA clone contained in the deposit having ATCC accession number 97768; (g) a nucleotide sequence encoding the extracellular domain of the Neutrokine-alpha polypeptide having the amino acid sequence encoded by the cDNA contained in the deposit having ATCC accession number 97768; and (h) a nucleotide sequence complementary to any of the nucleotide sequences in (a), (b), (c), (d), (e), (f), (g), or (h) above.The present invention also encompasses the above polynucleotide sequences fused to a heterologous polynucleotide sequence. Polypeptides encoded by these polynucleotides and nucleic acid molecules are also encompassed by the invention.

Highly preferred embodiments of the invention are directed to nucleic acid molecules comprising, or alternatively consisting of a polynucleotide having a nucleotide sequence at least 80%, 85%, 90% identical and more preferably at least 95%, 96%, 97%, 98%, 99% or 100% identical to a polynucleotide sequence encoding the Neutrokine-alpha polypeptide having the amino acid sequence at positions 134-285 in FIGS. 1A and 1B (SEQ ID NO:2). Preferred embodiments of the invention are directed to nucleic acid molecules comprising, or alternatively consisting of a polynucleotide having a nucleotide sequence at least 90% identical to a polynucleotide sequence encoding the Neutrokine-alpha polypeptide having the amino acid sequence at positions 134-285 in FIGS. 1A and 1B (SEQ ID NO:2). More preferred embodiments of the invention are directed to nucleic acid molecules comprising, or alternatively consisting of a polynucleotide having a nucleotide sequence at least 95% identical to a polynucleotide sequence encoding the Neutrokine-alpha polypeptide having the amino acid sequence at positions 134-285 in FIGS. 1A and 1B (SEQ ID NO:2). More preferred embodiments of the invention are directed to nucleic acid molecules comprising, or alternatively consisting of a polynucleotide having a nucleotide sequence at least 96% identical to a polynucleotide sequence encoding the Neutrokine-alpha polypeptide having the amino acid sequence at positions 134-285 in FIGS. 1A and 1B (SEQ ID NO:2).

Additionally, more preferred embodiments of the invention are directed to nucleic acid molecules comprising, or alternatively consisting of a polynucleotide having a nucleotide sequence at least 97% to a polynucleotide sequence encoding the Neutrokine-alpha polypeptide having the amino acid sequence at positions 134-285 in FIGS. 1A and 1B (SEQ ID NO:2). Additionally, more preferred embodiments of the invention are directed to nucleic acid molecules comprising, or alternatively consisting of a polynucleotide having a nucleotide sequence at least 98% to a polynucleotide sequence encoding the Neutrokine-alpha polypeptide having the amino acid sequence at positions 134-285 in FIGS. 1A and 1B (SEQ ID NO:2). Additionally, more preferred embodiments of the invention are directed to nucleic acid molecules comprising, or alternatively consisting of a polynucleotide having a nucleotide sequence at least 99% identical to a polynucleotide sequence encoding the Neutrokine-alpha polypeptide having the amino acid sequence at positions 134-285 in FIGS. 1A and 1B (SEQ ID NO:2).

A further embodiment of the invention relates to an isolated nucleic acid molecule comprising a polynucleotide which encodes the amino acid sequence of a Neutrokine-alphaSV polypeptide (e.g., a Neutrokine-alphaSV polypeptide fragment described herein) having an amino acid sequence which contains at least one conservative amino acid substitution, but not more than 50 conservative amino acid substitutions, even more preferably, not more than 40 conservative amino acid substitutions, stil more preferably not more than 30 conservative amino acid substitutions, and still even more preferably not more than 20 conservative amino acid substitutions. Of course, in order of ever-increasing preference, it is highly preferable for a polynucleotide which encodes the amino acid sequence of a Neutrokine-alpha polypeptide to have an amino acid sequence which contains not more than 7-10, 5-10, 3-7, 3-5, 2-5, 1-5, 1-3, 10, 9, 8, 7, 6, 5, 4, 3, 2 or 1 conservative amino acid substitutions.

Further embodiments include an isolated nucleic acid molecule comprising, or alternatively, consisting of a polynucleotide having a nucleotide sequence at least 80%, 85% or 90% identical, and more preferably at least 95%, 96%, 97%, 98% or 99% identical to a polynucleotide selected from the group consisting of: (a) a nucleotide sequence encoding the Neutrokine-alphaSV polypeptide having the complete amino acid sequence in FIGS. 5A and 5B (i.e., positions I to 266 of SEQ ID NO:19); (b) a nucleotide sequence encoding the Neutrokine-alphaSV polypeptide having the complete amino acid sequence in SEQ ID NO:19 excepting the N-terminal methionine (i.e., positions 2 to 266 of SEQ ID NO:2); (c) a nucleotide sequence encoding the predicted extracellular domain of the Neutrokine-alphaSV polypeptide having the amino acid sequence at positions 73-266 in FIGS. 5A and 5B (SEQ ID NO:19); (d) a nucleotide sequence encoding the Neutrokine-alphaSV polypeptide having the complete amino acid sequence encoded by the cDNA clone contained in the deposit having ATCC accession number 203518; (e) a nucleotide sequence encoding the extracellular domain of the Neutrokine-alphaSV polypeptide having the amino acid sequence encoded by the cDNA clone contained in the deposit having ATCC accession number 203518; and (f) a nucleotide sequence complementary to any of the nucleotide sequences in (a), (b), (c), (d) or (e), above.

Further, the invention includes a polynucleotide comprising, or alternatively, consisting of, a sequence at least 90%, or at least 95%, identical to any portion of at least about 10 contiguous nucleotides, about 20 contiguous nucleotides, about 25 contiguous nucleotides, or about 30 contiguous nucleotides, preferably at least about 40 nucleotides, or at least about 50 nucleotides, of the sequence from nucleotide 1 to nucleotide 1082 in FIGS. 1A and 1B (SEQ ID NO:1), preferably excluding the nucleotide sequences determined from the above-listed 4 cDNA clones and the nucleotide sequences from nucleotide 797 to 1082, 810 to 1082, and 346 to 542. The invention also includes a polynucleotide comprising, or alternatively consisting of, a sequence at least 90%, or at least 95%, identical to any portion of at least about 10 contiguous nucleotides, about 20 contiguous nucleotides, about 25 contiguous nucleotides, or about 30 contiguous nucleotides, preferably at least about 40 nucleotides, or at least about 50 nucleotides, of the sequence in FIGS. 5A and 5B (SEQ ID NO:18), preferably excluding the nucleotide sequences determined from the above-listed 4 cDNA clones. The invention also includes a polynucleotide comprising, or alternatively consisting of a sequence at least 90%, or at least 95%, identical to any portion of at least about 10 contiguous nucleotides, about 20 contiguous nucleotides, about 25 contiguous nucleotides, or about 30 contiguous nucleotides, preferably at least about 40 nucleotides, or at least about 50 nucleotides, of the sequence in SEQ ID NO:21, preferably excluding the nucleotide sequences determined from the above-listed 4 cDNA clones. The invention also includes a polynucleotide comprising a sequence at least 90%, or at least 95%, identical to any portion of at least about 10 contiguous nucleotides, about 20 contiguous nucleotides, about 25 contiguous nucleotides, or about 30 contiguous nucleotides, preferably at least about 40 nucleotides, or at least about 50 nucleotides, of the sequence in SEQ ID NO:22, preferably excluding the nucleotide sequences determined from the above-listed 4 cDNA clones. The invention also includes a polynucleotide comprising a sequence at least 90%, or at least 95%, identical to any portion of at least about 10 contiguous nucleotides, about 20 contiguous nucleotides, about 25 contiguous nucleotides, or about 30 contiguous nucleotides, preferably at least about 40 nucleotides, or at least about 50 nucleotides, of the sequence in SEQ ID NO:27, preferably excluding the nucleotide sequences determined from the above-listed 4 cDNA clones. The invention also includes a polynucleotide comprising a sequence at least 90%, or at least 95%, identical to any portion of at least about 10 contiguous nucleotides, about 20 contiguous nucleotides, about 25 contiguous nucleotides, or about 30 contiguous nucleotides, preferably at least about 40 nucleotides, or at least about 50 nucleotides, of the sequence in SEQ ID NO:29, preferably excluding the nucleotide sequences determined from the above-listed 4 cDNA clones. The invention also includes a polynucleotide comprising a sequence at least 90%, or at least 95%, identical to any portion of at least about 10 contiguous nucleotides, about 20 contiguous nucleotides, about 25 contiguous nucleotides, or about 30 contiguous nucleotides, preferably at least about 40 nucleotides, or at least about 50 nucleotides, of the sequence in SEQ ID NO:37, preferably excluding the nucleotide sequences determined from the above-listed 4 cDNA clones. In this context "about" includes the particularly recited ranges, larger or smaller by several (i.e. 5, 4, 3, 2 or 1) amino acids, at either extreme or at both extremes.

By a polynucleotide having a nucleotide sequence at least, for example, 95% "identical" to a reference nucleotide sequence encoding a Neutrokine-alpha and/or Neutrokine-alphaSV polypeptide is intended that the nucleotide sequence of the polynucleotide is identical to the reference sequence except that the polynucleotide sequence may include up to five mismatches per each 100 nucleotides of the reference nucleotide sequence encoding the Neutrokine-alpha and/or Neutrokine-alphaSV polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire nucleotide sequence encoding Neutrokine-alpha or Neutrokine-alphaSV, as shown in FIGS. 1A and 1B (SEQ ID NO:1) and FIGS. 5A and 5B (SEQ ID NO:18), respectively, or any Neutrokine-alpha such as, for example, the Neutrokine-alpha polynucleotides shown as SEQ ID NOs:21, 22, 27, 29, or 37, or any Neutrokine-alpha or Neutrokine-alphaSV polynucleotide fragment as described herein.

As a practical matter, whether any particular nucleic acid molecule is at least 80%, 85%, 90%, 95%, 96%, 97%, 98%, or 99% identical to, for instance, the nucleotide sequences shown in FIGS. 1A and 1B, or the nucleotide sequences shown in FIGS. 5A and 5B, or to the nucleotides sequence of the deposited cDNA clones, or to any Neutrokine-alpha polynucleotide such as, for example, the Neutrokine-alpha polynucleotides shown as SEQ ID NOs:21, 22, 27, 29, or 37, or fragments thereof, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (Advances in Applied Mathematics 2:482-489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag and colleagues (Comp. App. Biosci. 6:237-245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 80%, 85%, 90%, 92%, 95%, 96%, 97%, 98% or 99% identical to the nucleic acid sequences (i.e., polynucleotides) disclosed herein (e.g., those disclosed in FIGS. 1A and 1B (SEQ ID NO:1) or to the nucleic acid sequence of the deposited cDNAs), irrespective of whether they encode a polypeptide having Neutrokine-alpha and/or Neutrokine-alphaSV functional activity (e.g., biological activity). In addition, the present application is also directed to nucleic acid molecules at least 80%, 85%, 90%, 92%, 95%, 96%, 97%, 98% or 99% identical to the nucleic acid sequence shown in FIGS. 5A and 5B (SEQ ID NO:18) or to the nucleic acid sequence of the deposited cDNA, irrespective of whether they encode a polypeptide having Neutrokine-alphaSV activity. Moreover, the present application is also directed to nucleic acid molecules at least 80%, 85%, 90%, 92%, 95%, 96%, 97%, 98%, 99% identical to the nucleic acid sequence shown in SEQ ID NOs:21, 22, 27, 29, or 37, irrespective of whether they encode a polypeptide having Neutrokine-alpha activity. This is because even where a particular nucleic acid molecule does not encode a polypeptide having Neutrokine-alpha and/or Neutrokine-alphaSV activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Neutrokine-alpha and/or Neutrokine-alphaSV activity include, inter alia, (1) isolating the Neutrokine-alpha and/or Neutrokine-alphaSV gene or allelic variants thereof in a cDNA library; (2) in situ hybridization (e.g., "FISH") to metaphase chromosomal spreads to provide precise chromosomal location of the Neutrokine-alpha and/or Neutrokine-alphaSV gene, as described in Verma et al., Human Chromosomes: A Manual of Basic Techniques, Pergamon Press, New York (1988); and Northern Blot analysis for detecting Neutrokine-alpha and/or Neutrokine-alphaSV mRNA expression in specific tissues.

Preferred, however, are nucleic acid molecules having sequences at least 80%, 85%, 90%, 92%, 95%, 96%, 97%, 98% or 99% identical to the nucleic acid sequences disclosed herein (e.g., the nucleotide sequence shown in FIGS. 1A and 1B (SEQ ID NO:1) and the nucleic acid sequence of the deposited cDNAs, or fragments thereof), which do, in fact, encode a polypeptide having Neutrokine-alpha and/or Neutrokine-alphaSV polypeptide functional activity (e.g., biological activity). Also preferred are nucleic acid molecules having sequences at least 80%, 85%, 90%, 92%, 95%, 96%, 97%, 98% or 99% identical to the nucleic acid sequence shown in FIGS. 5A and 5B (SEQ ID NO:18) or to the nucleic acid sequence of the deposited cDNA which do, in fact, encode a polypeptide having Neutrokine-alpha and/or Neutrokine-alphaSV polypeptide functional activity (e.g., biological activity). Also preferred are nucleic acid molecules having sequences at least 80%, 85%, 90%, 92%, 95%, 96%, 97%, 98% or 99% identical to the nucleic acid sequence shown SEQ ID NOs:21, 22, 27, 29, or 37, which do, in fact, encode a polypeptide having Neutrokine-alpha and/or Neutrokine-alphaSV polypeptide functional activity (e.g., biological activity).

By "a polypeptide having Neutrokine-alpha polypeptide functional activity" (e.g., biological activity) and "a polypeptide having Neutrokine-alphaSV polypeptide functional activity" (e.g., biological activity) are intended polypeptides exhibiting activity similar, but not necessarily identical, to an activity of the extracellular domain or the full-length Neutrokine-alpha or Neutrokine-alphaSV polypeptides of the invention, as measured in a particular functional assay (e.g., immunological or biological assay). For example, Neutrokine-alpha and/or Neutrokine-alphaSV polypeptide functional activity can be measured by the ability of a polypeptide sequence described herein to form multimers (e.g., homodimers and homotrimers) with the complete Neutrokine-alpha and/or Neutrokine-alphaSV or extracellular domain of Neutrokine-alpha and/or Neutrokine-alphaSV, and to bind a Neutrokine-alpha and/or Neutrokine-alphaSV ligand. Additionally, Neutrokine-alpha and/or Neutrokine-alphaSV polypeptide functional activity can be measured by the ability of a polypeptide sequence described herein to form heteromultimers with APRIL (e.g., SEQ ID NO:20 and SEQ ID NO:47) or APRIL fragments or variants, especially the extracellular soluble domain of APRIL (e.g., amino acids 105-250 of SEQ ID NO:47). Neutrokine-alpha and/or Neutrokine-alphaSV polypeptide functional activity can be also be measured by determining the ability of a polypeptide of the invention to induce lymphocyte (e.g., B cell) proliferation, differentiation or activation and/or to extend B cell survival. These functional assays can be routinely performed using techniques described herein (e.g., see Example 6) and otherwise known in the art. Additionally, Neutrokine-alpha or Neutrokine-alphaSV polypeptides of the present invention modulate cell proliferation, cytotoxicity, cell survival and cell death. An in vitro cell proliferation, cytotoxicity, cell survival, and cell death assay for measuring the effect of a protein on certain cells can be performed by using reagents well known and commonly available in the art for detecting cell replication and/or death. For instance, numerous such assays for TNF-related protein activities are described in the various references in this disclosure. Briefly, an example of such an assay involves collecting human or animal (e.g., mouse) cells and mixing with (1) transfected host cell-supernatant containing Neutrokine-alpha protein (or a candidate polypeptide) or (2) nontransfected host cell-supernatant control, and measuring the effect on cell numbers or viability after incubation of certain period of time. Such cell proliferation and/or survival modulation activities as can be measured in this type of assay are useful for treating tumor, tumor metastasis, infections, autoimmune diseases, inflammation and other immune-related diseases.

Neutrokine-alpha modulates cell proliferation and differentiation in a dose-dependent manner in the above-described assay. Accordingly, it is preferred that "a polypeptide having Neutrokine-alpha polypeptide functional activity" (e.g., biological activity) includes polypeptides that also exhibit any of the same cell modulatory (particularly immunomodulatory) activities in the above-described assays in a dose-dependent manner. Although the degree of dose-dependent activity need not be identical to that of the Neutrokine-alpha polypeptides, preferably, "a polypeptide having Neutrokine-alpha polypeptide functional activity" will exhibit substantially similar dose-dependence in a given activity as compared to the Neutrokine-alpha polypeptides (i.e., the candidate polypeptide will exhibit greater activity or not more than about 25-fold less and, preferably, not more than about tenfold less activity relative to the reference Neutrokine-alpha polypeptides).

In certain preferred embodiments, "a polypeptide having Neutrokine-alpha polypeptide functional activity" (e.g., biological activity) and "a polypeptide having Neutrokine-alphaSV polypeptide functional activity" (e.g., biological activity) includes polypeptides that also exhibit any of the same B cell (or other cell type) modulatory (particularly immunomodulatory) activities described in FIGS. 8A, 8B, 8C, 9A, 9B, 10A, 10B, 10C, 10D, 10E, 10F, 11A, 11B, 11C, 11D, 11E, and 11F and in Example 6.

Like other members of TNF family, Neutrokine-alpha exhibits activity on leukocytes including, for example, monocytes, lymphocytes (e.g., B cells) and neutrophils. For this reason Neutrokine-alpha is active in directing the proliferation, differentiation and migration of these cell types. Such activity is useful for immune enhancement or suppression, myeloprotection, stem cell mobilization, acute and chronic inflammatory control and treatment of leukemia. Assays for measuring such activity are known in the art. For example, see Peters et al., Immun. Today 17:273 (1996); Young et al., J. Exp. Med. 182:1111 (1995); Caux et al., Nature 390:258 (1992); and Santiago-Schwarz et al., Adv. Exp. Med. Biol. 378:7 (1995).

Of course, due to the degeneracy of the genetic code, one of ordinary skill in the art will immediately recognize that a large number of the nucleic acid molecules having a sequence at least 80%, 85%, 90%, 92%, 95%, 96%, 97%, 98%, or 99% identical to the nucleic acid sequence contained in cDNA clone deposited in ATCC accession no. 97768, or the nucleic acid sequence shown in FIGS. 1A and 1B (SEQ ID NO:1), or fragments thereof, will encode a polypeptide "having Neutrokine-alpha polypeptide functional activity" (e.g., biological activity). One of ordinary skill in the art will also immediately recognize that a large number of the nucleic acid molecules having a sequence at least 80%, 85%, 90%, 92%, 95%, 96%, 97%, 98%, or 99% identical to the nucleic acid sequence contained in cDNA clone deposited in ATCC accession no. 203518 or the nucleic acid sequence shown in FIGS. 5A and 5B (SEQ ID NO:18) will encode a polypeptide "having Neutrokine-alphaSV polypeptide functional activity" (e.g., biological activity). In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Neutrokine-alpha and/or Neutrokine-alphaSV activity. This is because the skilled artisan is fully aware of amino acid substitutions that are either less likely or not likely to significantly effect protein function (e.g., replacing one aliphatic amino acid with a second aliphatic amino acid), as further described below.

Similarly, polynucleotides encoding polypeptides which contain all or some portion of the region V-142 through K-160 of SEQ ID NO:2 are likely to be valuable diagnostic and therapeutic polynucleotides with regard to detecting and/or altering expression of either Neutrokine-alpha or Neutrokine-alphaSV polynucleotides. In addition, polynucleotides which span the junction of amino acid residues T-141 and G-142 of the Neutrokine-alphaSV polypeptide shown in SEQ ID NO:19 (in between which the V-142 through K-160 amino acid sequence of Neutrokine-alpha is apparently inserted), are also likely to be useful both diagnostically and therapeutically. Such T-141/G-142 spanning polynucleotides will exhibit a much higher likelihood of hybridization with Neutrokine-alphaSV polynucleotides than with Neutrokine-alpha polynucleotides. A partial, non-limiting, non-exclusive list of such Neutrokine-alphaSV polypeptides which are encoded by polynucleotides of the invention includes polypeptides comprising, or alternatively consisting of, an amino acid sequence selected from the following: G-121 through E-163; E-122 through E-163; G-123 through E-163; N-124 through E-163; S-125 through E-163; S-126 through E-163; Q-127 through E-163; S-129 through E-163; R-130 through E-163; N-131 through E-163; K-132 through E-163; R-133 through E-163; A-134 through E-163; V-135 through E-163; Q-136 through E-163; G-137 through E-163; P-138 through E-163; E-139 through E-163; E-140 through E-163; T-141 through E-163; G-142 through E-163; S-143 through E-163; Y-144 through E-163; T-145 through E-163; F-146 through E-163; V-147 through E-163; P-148 through E-163; W-149 through E-163; L-150 through E-163; L-151 through E-163; S-162 through E-163; F-153 through E-163; K-154 through E-163; R-155 through E-163; G-156 through E-163; S-157 through E-163; A-158 through E-163; L-159 through E-163; E-160 through E-163; E-161 through E-163; K-162 through E-163; G-121 through K-162; G-121 through K-162; G-121 through E-161; G-121 through E-160; G-121 through L-159; G-121 through A-158; G-121 through S-157; G-121 through G-156; G-121 through R-155; G-121 through K-154; G-121 through F-153; G-121 through S-152; G-121 through L-151; G-121 through L-150; G-121 through W-149; G-121 through P-148; G-121 through V-147; G-121 through F-146; G-121 through T-145; G-121 through Y-144; G-121 through S-143; G-121 through G-142; G-121 through T-141; G-121 through E-140; G-121 through E-139; G-121 through P-138; G-121 through G-137; G-121 through Q-136; G-121 through V-135; G-121 through A-134; G-121 through R-133; G-121 through K-132; G-121 through N-131; G-121 through R-130; G-121 through S-129; G-121 through N-128; G-121 through Q-127; G-121 through S-126; G-121 through S-125; G-121 through N-124; G-121 through G-123; and G-121 through E-122 of SEQ ID NO:19. Polypeptides encoded by these polynucleotides are also encompassed by the invention.

Vectors and Host Cells

The present invention also relates to vectors which include the isolated DNA molecules of the present invention, host cells which are genetically engineered with the recombinant vectors, or which are otherwise engineered to produce the polypeptides of the invention, and the production of Neutrokine-alpha and/or Neutrokine-alphaSV polypeptides, or fragments thereof, by recombinant or synthetic techniques.

In one embodiment, the polynucleotides of the invention are joined to a vector (e.g., a cloning or expression vector). The vector may be, for example, a phage, plasmid, viral or retroviral vector. Retroviral vectors may be replication competent or replication defective. In the latter case, viral propagation generally will occur only in complementing host cells. The polynucleotides may be joined to a vector containing a selectable marker for propagation in a host. Introduction of the vector construct into the host cell can be effected by techniques known in the art which include, but are not limited to, calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

Generally, recombinant expression vectors will include origins of replication and selectable markers permitting transformation of the host cell, e.g., the ampicillin resistance gene of *E. coli* and *S. cerevisiae* TRPI gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, for example, stabilization or simplified purification of expressed recombinant product.

In one embodiment, the DNA of the invention is operatively associated with an appropriate heterologous regulatory element (e.g., promoter or enhancer), such as, the phage lambda PL promoter, the *E. coli* lac, trp, phoA, and tac promoters, the SV40 early and late promoters and promoters of retroviral LTRs, to name a few. Other suitable promoters will be known to the skilled artisan.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacteria cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293 and Bowes melanoma cells; and plant cells. Appropriate culture mediums and conditions for the above-described host cells are known in the art.

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed. Selection of appropriate vectors and promoters for expression in a host cell is a well-known procedure and the requisite techniques for expression vector construction, introduction of the vector into the host and expression in the host are routine skills in the art.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium*, and various species within the genera *Pseudomonas, Streptomyces*, and *Staphylococcus*, although others may also be employed as a matter of choice. As a representative, but nonlimiting example, useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed. Among vectors preferred for use in bacteria include pHE4-5 (ATCC Accession No. 209311; and variations thereof), pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Preferred expression vectors for use in yeast systems include, but are not limited to, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, pPIC9K, and PAO815 (all available from Invitrogen, Carlsbad, Calif.). Among preferred eukaryotic vectors are pWLNEO, pSV2CAT, pOG44, pXT1 and pSG available from Stratagene; and pSVK3, pBPV, pMSG and pSVL (available from Pharmacia). Other suitable vectors will be readily apparent to the skilled artisan.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

In one embodiment, the yeast *Pichia pastoris* is used to express Neutrokine-alpha protein in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111-21 (1985); Koutz, P. J, et al., Yeast 5:167-77 (1989); Tschopp, J. F., et al., Nucl. Acids Res. 15:3859-76 (1987). Thus, a heterologous coding sequence, such as, for example, a Neutrokine-alpha or Neutrokine-alphaSV polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a Neutrokine-alpha or Neutrokine-alphaSV polypeptide of the invention, as set forth herein, in a *Pichea* yeast system essentially as described in "*Pichia* Protocols: Methods in Molecular Biology," D. R. Higgins and J. Cregg, eds. The Humana Press, Totowa, N.J., 1998. This expression vector allows expression and secretion of a Neutrokine-alpha or Neutrokine-alphaSV protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-SI, pPIC3.5K, and PAO815, as one skilled in the art would readily appreciate, as long as the proposed expression construct provides appropriately located signals for transcription, translation, secretion (if desired), and the like, including an in-frame AUG as required.

In one embodiment, high-level expression of a heterologous coding sequence, such as, for example, a Neutrokine-alpha or Neutrokine-alphaSV polynucleotide of the present invention, may be achieved by cloning the beterologous polynucleotide of the invention into an expression vector such as, for example, pGAPZ or pGAPZalpha, and growing the yeast culture in the absence of methanol.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Various mammalian cell culture systems can also be employed to express recombinant protein. Examples of mammalian expression systems include the COS-7 lines of monkey kidney fibroblasts, described by Gluzman (Cell 23:175 (1981)), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

In a specific embodiment, constructs designed to express a portion of the extracellular domain of the Neutrokine-alpha (e.g., amino acid residues Ala-134 through Leu-285) are preferred. One of skill in the art would be able to use the polynucleotide and polypeptide sequences provided as SEQ ID NO:1 and SEQ ID NO:2, respectively, or SEQ ID NO:18 and SEQ ID NO:19, respectively, to design polynucleotide primers to generate such an expression construct.

In another embodiment, constructs designed to express the entire predicted extracellular domain of the Neutrokine-alpha (i.e., amino acid residues Gln-73 through Leu-285) are preferred. One of skill in the art would be able to use the polynucleotide and polypeptide sequences provided as SEQ ID NO:1 and SEQ ID NO:2, respectively, or SEQ ID NO:18 and SEQ ID NO:19, respectively, to design polynucleotide primers to generate such an expression construct.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., Neutrokine-alpha coding sequence), and/or to include genetic material (e.g., heterologous polynucleotide sequences) that is operably associated with Neutrokine-alpha polynucleotides of the invention, and which activates, alters, and/or amplifies endogenous Neutrokine-alpha polynucleotides. For example, techniques known in the art may be used to operably associate heterologous control regions (e.g., promoter and/or enhancer) and endogenous Neutrokine-alpha polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijistra et al., Nature 342:435-438 (1989), the disclosures of each of which are incorporated by reference in their entireties).

The host cells described infra can be used in a conventional manner to produce the gene product encoded by the recombinant sequence. Alternatively, cell-free translation systems can also be employed to produce the polypeptides of the invention using RNAs derived from the DNA constructs of the present invention.

The polypeptide of the invention may be expressed or synthesized in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

In one embodiment, polynucleotides encoding Neutrokine-alpha and/or Neutrokine-alphaSV polypeptides of the invention may be fused to signal sequences which will direct the localization of a protein of the invention to particular compartments of a prokaryotic or eukaryotic cell and/or direct the secretion of a protein of the invention from a prokaryotic or eukaryotic cell. For example, in *E. coli*, one may wish to direct the expression of the protein to the periplasmic space. Examples of signal sequences or proteins (or fragments thereof) to which the polypeptides of the invention may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, polynucleotides encoding Neutrokine-alpha and/or Neutrokine-alphaSV polypeptides of the invention may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that may be fused to a polypeptide of the invention in order to direct its secretion in mammalian cells include, but are not limited to, the MPIF-1 signal sequence (amino acids 1-21 of GenBank Accession number AAB51134), the stanniocalcin signal sequence (MLQNSAVLLLLVISASA, SEQ ID NO:45), and a consensus signal sequence (MPTWAWWLFLVLLLALWAPARG, SEQ ID NO:46). A suitable signal sequence that may be used in conjunction with baculoviral expression systems is the gp67 signal sequence, (amino acids 1-19 of GenBank Accession Number AAA72759).

A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fe part after the fusion protein has been expressed, detected and purified in the advantageous manner described. This is the case when Fe portion proves to be a hindrance to use in therapy and diagnosis, for example when the fusion protein is to be used as antigen for immunizations. In drug discovery, for example, human proteins, such as hIL-5 has been fused with Fe portions for the purpose of high-throughput screening assays to identify antagonists of hIL-5. See, D. Bennett et al., J. Molecular Recognition 8:52-58 (1995) and K. Johanson et al., J. Biol. Chem. 270:9459-9471 (1995).

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Polypeptides of the invention can be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105-111). For example, a peptide corresponding to a fragment of the complete Neutrokine-alpha or Neutrokine-alphaSV polypeptides of the invention can be synthesized by use of a peptide synthesizer. Furthermore, if desired, nonclassical amino acids or chemical amino acid analogs can be introduced as a substitution or addition into the Neutrokine-alpha or Neutrokine-alphaSV polynucleotide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses Neutrokine-alpha or Neutrokine-alphaSV polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, radioisotopic or affinity label to allow for detection and isolation of the protein.

Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, $^{213}Bi$, or other radioisotopes such as, for example, iodine ($^{131}I$, $^{125}I$, $^{123}I$, $^{121}I$), carbon ($^{14}C$), sulfur ($^{35}S$), tritium ($^{3}H$), indium ($^{115m}In$, $^{113m}In$, $^{112}In$, $^{111}In$), and technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, and $^{117}Tin$.

In specific embodiments, Neutrokine-alpha and/or Neutrokine-alphaSV polypeptides of the invention may be labeled with Europium. For example, Neutrokine-alpha and/or Neutrokine-alphaSV polypeptides of the invention may be labelled with Europium using the DELFIA Eu-labeling kit (catalog# 1244-302, Perkin Elmer Life Sciences, Boston, Mass.) following manufacturer's instructions.

In specific embodiments, Neutrokine-alpha and/or Neutrokine-alphaSV polypeptides of the invention are attached to macrocyclic chelators useful for conjugating radiometal ions, including but not limited to, $^{111}$In, $^{177}$Lu, $^{90}$Y, $^{166}$Ho, and $^{153}$Sm, to polypeptides. In a preferred embodiment, the radiometal ion associated with the macrocyclic chelators attached to Neutrokine-alpha and/or Neutrokine-alphaSV polypeptides of the invention is $^{111}$In. In another preferred embodiment, the radiometal ion associated with the macrocyclic chelator attached to Neutrokine-alpha and/or Neutrokine-alphaSV polypeptides of the invention is $^{90}$Y. In specific embodiments, the macrocyclic chelator is 1,4,7,10-tetraazacyclododecane-N,N',N",N'"-tetraacetic acid (DOTA). In other specific embodiments, the DOTA is attached to the Neutrokine-alpha and/or Neutrokine-alphaSV polypeptide of the invention via a linker molecule. Examples of linker molecules useful for conjugating DOTA to a polypeptide are commonly known in the art—see, for example, DeNardo et al., Clin Cancer Res. 4(10):2483-90,1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art could readily adapt the method disclosed therein in order to conjugate chelating agents to other polypeptides.

In one embodiment, Neutrokine-alpha and/or Neutrokine-alphaSV polypeptides of the invention may be labeled with biotin. In other related embodiments, biotinylated Neutrokine-alpha and/or Neutrokine-alphaSV polypeptides of the invention may be used, for example, as an imaging agent or as a means of identifying one or more Neutrokine-alpha and/or Neutrokine-alphaSV receptor(s) or other coreceptor or coligand molecules.

Also provided by the invention are chemically modified derivatives of Neutrokine-alpha or Neutrokine-alphaSV which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, asparfic acid, glutamic acid, cysteine and combinations thereof) of the protein.

One may specifically desire proteins chemically modified at the N-terminus. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3,4, 5, 6, 7, 8, 9, 10, 12, 15, 17, 20, or more polyethylene glycol molecules. Similarly, the average degree of substitution within ranges such as 1-3, 24, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., Crit. Rev. Thera. Drug Carrier Sys. 9:249-304 (1992).

The Neutrokine-alpha and/or Neutrokine-alphaSV polypeptides can be recovered and purified by known methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Neutrokine-alpha Polypeptides

The Neutrokine-alpha and/or Neutrokine-alphaSV polypeptides of the invention may be in monomers or multimers (i.e., dimers, trimers, tetramers and higher multimers). Accordingly, the present invention relates to monomers and multimers of the Neutrokine-alpha and/or Neutrokine-alphaSV polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

In a nonexclusive embodiment, the multimers of the invention comprise at least one Neutrokine-alpha—human serum albumin fusion protein as described herein. In another nonexclusive embodiment, the multimers of the invention are trimeric and comprise one, two or three Neutrokine-alpha—human serum albumin fusion proteins as described herein.

Multimers encompassed by the invention may be homomers or heteromers. As used herein, the term homomer, refers to a multimer containing only Neutrokine-alpha and/or Neutrokine-alphaSV polypeptides of the invention (including Neutrokine-alpha and/or Neutrokine-alphaSV fragments, variants, and fusion proteins, as described herein). These homomers may contain Neutrokine-alpha and/or Neutrokine-alphaSV polypeptides having identical or different amino acid sequences. In a specific embodiment, a homomer of the invention is a multimer containing only Neutrokine-alpha and/or Neutrokine-alphaSV polypeptides having an identical amino acid sequence. In another specific embodiment, a homomer of the invention is a multimer containing Neutrokine-alpha and/or Neutrokine-alphaSV polypeptides having different amino acid sequences. In specific embodiments, the multimer of the invention is a homodimer (e.g., containing Neutrokine-alpha and/or Neutrokine-alphaSV polypeptides having identical or different amino acid sequences) or a homotrimer (e.g., containing Neutrokine-alpha and/or Neutrokine-alphaSV polypeptides having identical or different amino acid sequences). In a preferred embodiment, the multimer of the invention is a homotrimer. In additional embodiments, the homomeric multimer of the invention is at least a homodimer, at least a homotrimer, or at least a homotetramer.

As used herein, the term heteromer refers to a multimer containing heterologous polypeptides (i.e., polypeptides of a different protein) in addition to the Neutrokine-alpha and/or Neutrokine-alphaSV polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer. In highly preferred embodiments, the heteromeric multimer of the invention is a heterotrimer comprising both Neutrokine alpha-polypeptides and APRIL polypeptides (e.g., SEQ ID NO:20 or SEQ ID NO:47; PCT International Publication Number WO97/33902; GenBank Accession No. AF046888 (nucleotide) and AAC6132 (protein); J. Exp. Med. 188(6):1185-1190). In other highly preferred embodiments, the heteromeric multimer of the invention is a heterotrimer consisting of one Neutrokine alpha-polypeptide and two APRIL polypeptides. In other highly preferred embodiments, the heteromeric multimer of the invention is a heterotrimer consisting of two Neutrokine alpha-polypeptides and one APRIL polypeptide.

In a further nonexclusive embodiment, the heteromers of the invention comprise CD40 ligand polypeptide sequence(s), or biologically active fragment(s) or variant(s) thereof.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the Neutrokine-alpha and/or Neutrokine-alphaSV polypeptides of the invention. Such covalent associations may involve one or more amino acid residues contained in the polypeptide sequence (e.g., that recited in SEQ ID NO:2 or SEQ ID NO:19, or contained in the polypeptide encoded by the clones deposited in connection with this application). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a Neutrokine-alpha and/or Neutrokine-alphaSV fusion protein. In one example, covalent associations are between the heterologous sequence contained in a fusion protein of the invention (see, e.g., U.S. Pat. No. 5,478,925). In a specific example, the covalent associations are between the heterologous sequence contained in a Neutrokine-alpha-Fc and/or Neutrokine-alphaSV-Fc fusion protein of the invention (as described herein). In another specific example, covalent associations of fusion proteins of the invention are between heterologous polypeptide sequence from another TNF family ligand/receptor member that is capable of forming covalently associated multimers, such as for example, oseteoprotegerin (see, e.g., International Publication No. WO 98/49305, the contents of which are herein incorporated by reference in its entirety). In another specific example, covalent associations of fusion proteins of the invention are between heterologous polypeptide sequence from CD40L, or a soluble fragment thereof. In another embodiment, two or more Neutrokine-alpha and/or Neutrokine-alpha polypeptides of the invention are joined through synthetic linkers (e.g., peptide, carbohydrate or soluble polymer linkers). Examples include those peptide linkers described in U.S. Pat. No. 5,073,627 (hereby incorporated by reference). Proteins comprising multiple Neutrokine-alpha and/or Neutrokine-alphaSV polypeptides separated by peptide linkers may be produced using conventional recombinant DNA technology.

Another method for preparing multimer Neutrokine-alpha and/or Neutrokine-alphaSV polypeptides of the invention involves use of Neutrokine-alpha and/or Neutrokine-alphaSV polypeptides fused to a leucine zipper or isoleucine zipper polypeptide sequence. Leucine zipper or isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers or isoleucine zippers are naturally occurring peptides and derivatives thereof that dimerize or trimerize. Examples of leucine zipper domains suitable for producing soluble multimeric Neutrokine-alpha and/or Neutrokine-alphaSV proteins are those described in PCT application WO 94/10308, hereby incorporated by reference. Recombinant fusion proteins comprising a soluble Neutrokine-alpha and/or Neutrokine-alphaSV polypeptide fused to a peptide that dimerizes or trimerizes in solution are expressed in suitable host cells, and the resulting soluble multimeric Neutrokine-alpha and/or Neutrokine-alphaSV is recovered from the culture supernatant using techniques known in the art.

Certain members of the TNF family of proteins are believed to exist in trimeric form (Beutler and Huffel, Science 264:667, 1994; Banner et al., Cell 73:431, 1993). Thus, trimeric Neutrokine-alpha and/or Neutrokine-alphaSV may offer the advantage of enhanced biological activity. Preferred leucine zipper moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric Neutrokine-alpha and/or Neutrokine-alphaSV.

In another example, proteins of the invention are associated by interactions between the Flag® polypeptide sequence contained in Flag®-Neutrokine alpha or Flag®-Neutrokine-alphaSV fusion proteins of the invention. In a further embodiment, proteins of the invention are associated by interactions between the heterologous polypeptide sequence contained in Flag®-Neutrokine-alpha or Flag®-Neutrokine-alphaSV fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

In one embodiment, the invention provides an isolated Neutrokine-alpha polypeptide having the amino acid sequence encoded by the cDNA clone contained in ATCC No. 97768, or the amino acid sequence in FIGS. 1A and 1B (SEQ ID NO:2), or a polypeptide comprising a portion (i.e., a fragment) of the above polypeptides. In another embodiment, the invention provides an isolated Neutrokine-alphaSV polypeptide having the amino acid encoded by the cDNA clone contained in ATCC No. 203518, or the amino acid sequence in FIGS. 5A and 5B (SEQ ID NO:19), or a polypeptide comprising a portion (i.e, fragment) of the above polypeptides.

Polypeptide fragments of the present invention include polypeptides comprising or alternatively, consisting of, an amino acid sequence contained in SEQ ID NO:2, encoded by the cDNA contained in the plasmid having ATCC accession number 97768, or encoded by nucleic acids which hybridize (e.g., under stringent hybridization conditions) to the nucleotide sequence contained in the deposited clone, or the complementary strand of the nucleotide sequence shown in FIGS. 1A-B (SEQ ID NO:1.

Additionally, polypeptide fragments of the present invention include polypeptides comprising or alternatively, consisting of, an amino acid sequence contained in SEQ ID NO:19, encoded by the cDNA contained in the plasmid having ATCC accession number 203518, or encoded by nucleic acids which hybridize (e.g., under stringent hybridization conditions) to the nucleotide sequence contained in the deposited clone, or the complementary strand of the nucleotide sequence shown in FIGS. 5A-B (SEQ ID NO:18).

Additionally, polypeptide fragments of the present invention include polypeptides comprising or alternatively, consisting of, an amino acid sequence encoded by nucleic acids which hybridize (e.g., under hybridization conditions described herein) to the complementary strand of the nucleotide sequence shown in SEQ ID NO:21.

Polypeptide fragments of the present invention also include polypeptides comprising or alternatively, consisting of, an amino acid sequence contained in SEQ ID NO:23, or encoded by nucleic acids which hybridize (e.g., under hybridization conditions described herein) to the complementary strand of the nucleotide sequence shown in SEQ ID NO:22.

In addition, polypeptide fragments of the present invention include polypeptides comprising or alternatively, consisting of, an amino acid sequence contained in SEQ ID NO:28, or encoded by nucleic acids which hybridize (e.g., under hybridization conditions described herein) to the complementary strand of the nucleotide sequence shown in SEQ ID NO:27.

Additionally, polypeptide fragments of the present invention include polypeptides comprising or alternatively, consisting of, an amino acid sequence contained in SEQ ID NO:30, or encoded by nucleic acids which hybridize (e.g., under hybridization conditions described herein) to the complementary strand of the nucleotide sequence shown in SEQ ID NO:29.

Additionally, polypeptide fragments of the present invention include polypeptides comprising or alternatively, consisting of, an amino acid sequence contained in SEQ ID NO:38, or encoded by nucleic acids which hybridize (e.g., under hybridization conditions described herein) to the complementary strand of the nucleotide sequence shown in SEQ ID NO:37.

Additionally, polypeptide fragments of the present invention include polypeptides comprising or alternatively, consisting of, an amino acid sequence contained in SEQ ID NO:39, or encoded by nucleic acids which hybridize (e.g., under hybridization conditions described herein) to the complementary strand of a nucleotide sequence encoding the polypeptide of SEQ ID NO:39.

Additionally, polypeptide fragments of the present invention include polypeptides comprising or alternatively, consisting of, an amino acid sequence contained in SEQ ID NO:40, or encoded by nucleic acids which hybridize (e.g., under hybridization conditions described herein) to the complementary strand of a nucleotide sequence encoding the polypeptide of SEQ ID NO:40.

Additionally, polypeptide fragments of the present invention include polypeptides comprising or alternatively, consisting of, an amino acid sequence contained in SEQ ID NO:41, or encoded by nucleic acids which hybridize (e.g., under hybridization conditions described herein) to the complementary strand of a nucleotide sequence encoding the polypeptide of SEQ ID NO:41.

Additionally, polypeptide fragments of the present invention include polypeptides comprising or alternatively, consisting of, an amino acid sequence contained in SEQ ID NO:42, or encoded by nucleic acids which hybridize (e.g., under hybridization conditions described herein) to the complementary strand of a nucleotide sequence encoding the polypeptide of SEQ ID NO:42.

Additionally, polypeptide fragments of the present invention include polypeptides comprising or alternatively, consisting of, an amino acid sequence contained in SEQ ID NO:43, or encoded by nucleic acids which hybridize (e.g., under hybridization conditions described herein) to the complementary strand of a nucleotide sequence encoding the polypeptide of SEQ ID NO:43.

Additionally, polypeptide fragments of the present invention include polypeptides comprising or alternatively, consisting of, an amino acid sequence contained in SEQ ID NO:44, or encoded by nucleic acids which hybridize (e.g., under hybridization conditions described herein) to the complementary strand of a nucleotide sequence encoding the polypeptide of SEQ ID NO:44.

Polypeptide fragments of the present invention include polypeptides comprising or alternatively, consisting of, an amino acid sequence contained in SEQ ID NO:2, encoded by the cDNA contained in the deposited clone, or encoded by nucleic acids which hybridize (e.g., under stringent hybridization conditions) to the nucleotide sequence contained in the deposited clone, or shown in FIGS. 1A and 1B (SEQ ID NO:1) or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from about amino acid residues: 1 to 50, 51 to 100, 101 to 150, 151 to 200, 201 to 250, and/or 251 to 285 of SEQ ID NO:2. Moreover, polypeptide fragments can be at least 10, 20, 30, 40, 50, 60, 70, 80, 90, 100, 110, 120, 130, 140, 150, 175 or 200 amino acids in length.

In specific embodiments, polypeptide fragments of the invention comprise, or alternatively consist of, amino acid residues: 1-46, 31-44, 47-72, 73-285, 73-83, 94-102, 148-152, 166-181, 185-209, 210-221, 226-237, 244-249, 253-265, and/or 277-284, as depicted in FIGS. 1A and 1B (SEQ ID NO:2). Polynucleotides encoding these polypeptides are also encompassed by the invention.

It will be recognized by one of ordinary skill in the art that mutations targeted to regions of a Neutrokine-alpha polypeptide of the invention which encompass the nineteen amino acid residue insertion which is not found in the Neutrokine-alphaSV polypeptide sequence (i.e., amino acid residues Val- 142 through Lys-160 of the sequence presented in FIGS. 1A and 1B and in SEQ ID NO:2) may affect the observed biological activities of the Neutrokine-alpha polypeptide. More specifically, a partial, non-limiting and non-exclusive list of such residues of the Neutrokine-alpha polypeptide sequence which may be targeted for mutation includes the following amino acid residues of the Neutrokine-alpha polypeptide sequence as shown in SEQ ID NO:2: V-142; T-143; Q-144; D-145; C-146; L-147; Q-148; L-149; I-150; A-151; D-152; S-153; E-154; T-155; P-156; T-157; I-158; Q-159; and K160. Polynucleotides encoding Neutrokine-alpha polypeptides which have one or more mutations in the region from V-142 through K-160 of SEQ ID NO:2 are contemplated. Polypeptides encoded by these polynucleotides are also encompassed by the invention.

Polypeptide fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from about amino acid residues: I to 15, 16-30, 3146, 47-55, 56-72, 73-104, 105-163, 163-188, 186-210 and 210-284 of the amino acid sequence disclosed in SEQ ID NO:2. Additional representative examples of polypeptide fragments of the invention, include, for example, fragments that comprise or alternatively, consist of from about amino acid residues: 1 to 143, 1-150, 47-143, 47-150, 73-143, 73-150, 100-150, 140-145, 142-148, 140-150, 140-200, 140-225, and 140-266 of the amino acid sequence disclosed in SEQ ID NO:19. Moreover, polypeptide fragments can be at least 10, 20, 30, 40, 50, 60, 70, 80, 90, 100, 110, 120, 130, 140, 150, 175 or 200 amino acids in length. In this context, "about" means the particularly recited ranges and ranges larger or smaller by several, a few, 5, 4, 3, 2 or I amino acid residues at either or both the amino- and carboxy-termini. Polynucleotides encoding these polypeptide fragments are also encompassed by the invention.

Additional preferred embodiments encompass polypeptide fragments comprising, or alternatively consisting of, the predicted intracellular domain of Neutrokine-alpha (amino acid residues 146 of SEQ ID NO:2), the predicted transmembrane domain of Neutrokine-alpha (amino acid residues 47-72 of SEQ ID NO:2), the predicted extracellular domain of Neutrokine-alpha (amino acid residues 73-285 of SEQ ID NO:2), the predicted TNF conserved domain of Neutrokine-alpha (amino acids 191 to 284 of SEQ ID NO:2), and a polypeptide comprising, or alternatively, consisting of the predicted intracellular domain fused to the predicted extracellular domain of Neutrokine-alpha (amino acid residues 146 fused to amino acid residues 73-285 of SEQ ID NO:2). Polynucleotides encoding these polypeptides are also encompassed by the invention.

Further additional preferred embodiments encompass polypeptide fragments comprising, or alternatively consisting of, the predicted intracellular domain of Neutrokine-alphaSV (amino acid residues 1-46 of SEQ ID NO:19), the predicted transmembrane domain of Neutrokine-alphaSV (amino acid residues 47-72 of SEQ ID NO:19), the predicted extracellular domain of Neutrokine-alphaSV (amino acid residues 73-266 of SEQ ID NO:19), the predicted TNF conserved domain of Neutrokine-alphaSV (amino acids 172 to 265 of SEQ ID NO:19), and a polypeptide comprising, or alternatively, consisting of the predicted intracellular domain fused to the predicted extracellular domain of Neutrokine-alphaSV (amino acid residues 1-46 fused to amino acid residues 73-266 of SEQ ID NO:19). Polynucleotides encoding these polypeptides are also encompassed by the invention.

Certain additional embodiments of the invention encompass polypeptide fragments comprising, or alternatively consisting of, the predicted beta-pleated sheet regions identified in FIGS. 7A-1 and 7A-2. These polypeptide fragments of the invention comprise, or alternatively consist of, amino acid residues Gln-144 to Ala-151, Phe-172 to Lys-173, Ala-177 to Glu-179, Asn-183 to Ile-185, Gly-191 to Lys-204, His-210 to Val-219, Leu-226 to Pro-237, Asn-242 to Ala-251, Gly-256 to Ile-263 and/or Val-276 to Leu-284 of SEQ ID NO:2. In another, nonexclusive embodiment, these polypeptide fragments of the invention also comprise, or alternatively consist of, amino acid residues Phe-153 to Lys-154, Ala-158 to Glu-160, Asn-164 to Ile-166, Gly-172 to Lys-185, His-191 to Val-200, Leu-207 to Pro-218, Asn-223 to Ala-232, Gly-237 to Ile-244 and/or Val-257 to Leu-265 of SEQ ID NO:19; and amino acid residues Phe-42 to Lys-43, Ala-47 to Glu-49, Asn-53 to Ile-55, Gly-61 to Pro-74, His-80 to Val-89, Leu-96 to Pro-107, Asn-112 to Ala-121, Gly-126 to 11e-133 and/or Asp-146 to Leu-154 of SEQ ID NO:23. In further nonexclusive embodiments, these polypeptide fragments of the invention also comprise, or alternatively consist of, amino acid residues Gln-78 to Ala-85; Phe-106 to Lys-107, Ala-111 to Glu-113, Asn-117 to Ile-119, Gly-125 to Lys-138, His-144 to Val-153, Leu-160 to Pro-171, Asn-176 to Ala-185, Gly-190 to Ile-197 and/or Val-210 to Leu-218 of SEQ ID NO:28; and amino acid residues Gln-78 to Ala-85; Phe-106 to Lys-107, Ala-111 to Glu-113, Asn-117 to Ile-119, Gly-125 to Lys-138, His-144 to Val-153, Leu-160 to Pro-171, Asn-176 to Ala-185, Gly-190 to Ile-197 and/or Val-210 to Leu-218 of SEQ ID NO:30. Polynucleotides encoding these polypeptide fragments are also provided.

A partial, non-limiting, and exemplary list of polypeptides of the invention which comprise, or alternatively consist of, combinations of amino acid sequences of the invention includes, for example, [Met-1 to Lys-113] fused to [Leu-114 to Thr-141] fused to [Val-142 to Lys-160] fused to [Gly-161 to Gln-198] fused to [Val-199 to Ala-248] fused to [Gly-249 to Leu-285] of SEQ ID NO:2; or [Met-1 to Lys-113] fused to [Val-142 to Lys-160] fused to [Gly-161 to Gln-198] fused to [Val-199 to Ala-248] fused to [Gly-249 to Leu-285] of SEQ ID NO:2; or [Met-1 to Lys-113] fused to [Leu-114 to Thr-141] fused to [Val-142 to Lys-160] fused to [Gly-161 to Gln-198] fused to [Gly-249 to Leu-285] of SEQ ID NO:2. Other combinations may include the polypeptide fragments in an order other than that recited above (e.g., [Leu-114 to Thr-141] fused to [Val-199 to Ala-248] fused to [Gly-249 to Leu-285] fused to [Val-142 to Lys-160] of SEQ ID NO:2). Other combinations may also include heterologous polypeptide fragments as described herein and/or other polypeptides or polypeptide fragments of the present invention (e.g., [Met-1 to Lys-113] fused to [Leu-114 to Thr-141] fused to [Val-142 to Lys-160] fused to [Gly-161 to Gln-198] fused to [Gly-249 to Leu-285] of SEQ ID NO:2 fused to a FLAG tag; or [Met-1 to Lys-113] of SEQ ID NO:2 fused to [Leu-114 to Thr-141] of SEQ ID NO:2 fused to [Glu-135 to Asn-165] of SEQ ID NO:39 fused to [Val-142 to Lys-160] of SEQ ID NO:2 fused to [Gly-161 to Gln-198] of SEQ ID NO:2 fused to [Val-199 to Ala-248] of SEQ ID NO:2 fused to [Gly-249 to Leu-285] of SEQ ID NO:2). Polynucleotides encoding any of these polypeptides are encompassed by the invention.

An additional partial, non-limiting, and exemplary list of polypeptides of the invention which comprise, or alternatively consist of, combinations of amino acid sequences includes, for example, [Met-1 to Lys-113] fused to [Leu-114 to Thr-141] fused to [Gly-142 to Gln-179] fused to [Val-180 to Ala-229] fused to [Gly-230 to Leu-266] of SEQ ID NO:19; [Met-1 to Lys-113] fused to [Gly-142 to Gln-179] fused to

[Val-180 to Ala-229] fused to [Gly-230 to Leu-266] of SEQ ID NO:19; or [Met-1 to Lys-113] fused to [Leu-114 to Thr-141] fused to [Gly-142 to Gln-179] fused to [Gly-230 to Leu-266] of SEQ ID NO:19. Other combinations may include the polypeptide fragments in an order other than that recited above (e.g., [Leu-114 to Thr-141] fused to [Val-180 to Ala-229] fused to [Gly-230 to Leu-266] fused to [Gly-142 to Gln-179] of SEQ ID NO:19). Other combinations may also include heterologous polypeptide fragments as described herein and/or other polypeptides or polypeptide fragments of the present invention (e.g., [Met-1 to Lys-113] fused to [Leu-114 to Thr-141] fused to [Gly-142 to Gln-179] fused to [Gly-230 to Leu-266] of SEQ ID NO:19 fused to a FLAG tag or, [Met-1 to Lys-113] of SEQ ID NO:19 fused to [Leu-114 to Thr-141] of SEQ ID NO:19 fused to [Glu-135 to Asn-165] of SEQ ID NO:39 fused to [Gly-142 to Gln-179] of SEQ ID NO:19 fused to [Val-180 to Ala-229] of SEQ ID NO:19 fused to [Gly-230 to Leu-266] of SEQ ID NO:19). Polynucleotides encoding any of these polypeptides are encompassed by the invention.

A further partial, non-limiting, and exemplary list of polypeptides of the invention which comprise, or alternatively consist of, combinations of amino acid sequences includes, for example, [Met-1 to Lys-106] fused to [Leu-107 to Thr-134] fused to [Ile-166 to Lys-184] fused to [Gly-185 to Gln-222] fused to [Val-223 to Ala-272] fused to [Gly-273 to Leu-309] of SEQ ID NO:39; [Met-1 to Lys-106] fused to [Glu-135 to Asn-165] fused to [Ile-166 to Lys-184] fused to [Gly-185 to Gln-222] fused to [Val-223 to Ala-272] fused to [Gly-273 to Leu-309] of SEQ ID NO:39; or [Met-1 to Lys-106] fused to [Leu-107 to Thr-134] fused to [Glu-135 to Asn-165] fused to [Ile-166 to Lys-184] fused to [Gly-185 to Gln-222] fused to [Gly-273 to Leu-309] of SEQ ID NO:39. Other combinations may include the polypeptide fragments in an order other than that recited above (e.g., [Met-1 to Lys-106] fused to [Gly-185 to Gln-222] fused to [Ile-166 to Lys-184] fused to [Val-223 to Ala-272] fused to [Leu-107 to Thr-134] fused to [Gly-273 to Leu-309] of SEQ ID NO:39). Other combinations may also include heterologous polypeptide fragments as described herein and/or other polypeptides or polypeptide fragments of the present invention (e.g., [Met-1 to Lys-106] fused to [Glu-135 to Asn-165] fused to [Ile-166 to Lys-184] fused to [Gly-185 to Gln-222] fused to [Val-223 to Ala-272] fused to [Gly-273 to Leu-309] of SEQ ID NO:39 fused to a FLAG tag). Polynucleotides encoding any of these polypeptides are encompassed by the invention.

A further partial, non-limiting, and exemplary list of polypeptides of the invention which comprise, or alternatively consist of, combinations of amino acid sequences includes, for example, [Met-1 to Lys-106] fused to [Leu-107 to Thr-134] fused to [Glu-135 to Asn-165] fused to [Ile-166 to Pro-180] fused to [Ala-181 to Gln-202] fused to [Val-203 to Ala-252] fused to [Gly-253 to Leu-289] of SEQ ID NO:38; [Met-1 to Lys-106] fused to [Leu-107 to Thr-134] fused to [Ile-166 to Pr0-180] fused to [Ala-181 to Gln-202] fused to [Val-203 to Ala-252] fused to [Gly-253 to Leu-289] of SEQ ID NO:38; [Met-1 to Lys-106] fused to [Leu-107 to Thr-134] fused to [Glu-135 to Asn-165] fused [Ala-181 to Gln-202] fused to [Val-203 to Ala-252] fused to [Gly-253 to Leu-289] of SEQ ID NO:38; [Met-1 to Lys-106] fused to [Leu-107 to Thr-134] fused to [Ala-181 to Gln-202] fused to [Val-203 to Ala-252] fused to [Gly-253 to Leu-289] of SEQ ID NO:38; Other combinations may include the polypeptide fragments in an order other than that recited above (e.g., [Met-1 to Lys-106] fused to [Ala-181 to Gln-202] fused to [Ile-166 to Pro-180] fused to [Val-203 to Ala-252] fused to [Leu-107 to Thr-134] fused to [Gly-253 to Leu-289] of SEQ ID NO:38). Other combinations may also include heterologous polypeptide fragments as described herein and/or other polypeptides or polypeptide fragments of the present invention (e.g., [Met-1 to Lys-106] fused to [Glu-135 to Asn-165] fused to [Ile-166 to Pro-180] fused to [Ala-181 to Gln-202] fused to [Val-203 to Ala-252] fused to [Gly-253 to Leu-289] of SEQ ID NO:38 fused to a FLAG tag). Polynucleotides encoding any of these polypeptides are encompassed by the invention.

A further partial, non-limiting, and exemplary list of polypeptides of the invention which comprise, or alternatively consist of, combinations of amino acid sequences includes, for example, [Met-1 to Lys-106] fused to [Leu-107 to Thr-134] fused to [Glu-135 to Asn-165] fused to [Arg-166 to Gln-203] fused to [Val-204 to Ala-253] fused to [Gly-254 to Leu-290] of SEQ ID NO:40; [Met-1 to Lys-106] fused [Glu-135 to Asn-165] fused to [Arg-166 to Gln-203] fused to [Val-204 to Ala-253] fused to [Gly-254 to Leu-290] of SEQ ID NO:40; [Met-1 to Lys-106] fused to [Leu-107 to Thr-134] fused to [Arg-166 to Gln-203] fused to [Val-204 to Ala-253] fused to [Gly-254 to Leu-290] of SEQ ID NO:40; or [Met-1 to Lys-106] fused to [Leu-107 to Thr-134] fused to [Glu-135 to Asn-165] fused to [Arg-166 to Gln-203] fused to [Gly-254 to Leu-290] of SEQ ID NO:40. Other combinations may include the polypeptide fragments in an order other than that recited above (e.g., [Met-1 to Lys-106] fused to [Arg-166 to Gln-203] fused to [Val-204 to Ala-253] fused to [Leu-107 to Thr-134] fused to [Gly-254 to Leu-290] of SEQ ID NO:40). Other combinations may also include heterologous polypeptide fragments as described herein and/or other polypeptides or polypeptide fragments of the present invention (e.g., [Met-1 to Lys-106] fused to [Glu-135 to Asn-165] fused to [Arg-166 to Gln-202] fused to [Val-204 to Ala-253] fused to [Gly-254 to Leu-290] of SEQ ID NO:38 fused to a FLAG tag). Polynucleotides encoding any of these polypeptides are encompassed by the invention.

A further partial, non-limiting, and exemplary list of polypeptides of the invention which comprise, or alternatively consist of, combinations of amino acid sequences includes, for example, [Tyr-1 to Lys-47] fused to [Leu48 to Thr-75] fused to [Val-76 to Lys-94] fused to [Gly-95 to Gln-132] fused to [Val-133 to Ala-182] fused to [Gly-183 to Leu-219] of SEQ ID NO:28; [Tyr-1 to Lys-47] fused to [Leu48 to Thr-75] fused to [Val-76 to Lys-94] fused to [Val-133 to Ala-182] of SEQ ID NO:28; or [Tyr-1 to Lys-47] fused to [Val-76 to Lys-94] fused to [Val-133 to Ala-182] fused to [Gly-183 to Leu-219] of SEQ ID NO:28. Other combinations may include the polypeptide fragments in an order other than that recited above (e.g., [Tyr-1 to Lys47] fused to [Gly-183 to Leu-219] fused to [Val-133 to Ala-182] fused to [Leu48 to Thr-75] of SEQ ID NO:28). Other combinations may also include heterologous polypeptide fragments as described herein and/or other polypeptides or polypeptide fragments of the present invention (e.g., [Leu48 to Thr-75] fused to [Val-76 to Lys-94] fused to [Gly-95 to Gln-132] fused to [Val-133 to Ala-182] of SEQ ID NO:28 fused to an Fc receptor tag). Polynucleotides encoding any of these polypeptides are encompassed by the invention.

A further partial, non-limiting, and exemplary list of polypeptides of the invention which comprise, or alternatively consist of, combinations of amino acid sequences includes, for example, [Tyr-1 to Lys47] fused to [Leu48 to Thr-75] fused to [Val-76 to Lys-94] fused to [Gly-95 to Gln-132] fused to [Val-133 to Ala-182] fused to [Gly-183 to Leu-219] of SEQ ID NO:30; [Tyr-1 to Lys-47] fused to [Leu48 to Thr-75] fused to [Val-76 to Lys-94] fused to [Va-133 to Ala-182] of SEQ ID NO:30; or [Tyr-1 to Lys-47] fused to [Val-76 to Lys-94] fused to [Val-133 to Ala-182] fused to

[Gly-183 to Leu-219] of SEQ ID NO:30. Other combinations may include the polypeptide fragments in an order other than that recited above (e.g., [Tyr-l to Lys47] fused to [Gly-183 to Leu-219] fused to [Val-133 to Ala-182] fused to [Leu48 to Thr-75] of SEQ ID NO:30). Other combinations may also include heterologous polypeptide fragments as described herein and/or other polypeptides or polypeptide fragments of the present invention (e.g., [Leu48 to Thr-75] fused to [Val-76 to Lys-94] fused to [Gly-95 to Gln-132] fused to [Val-133 to Ala-182] of SEQ ID NO:30 fused to an Fc receptor tag). Polynucleotides encoding any of these polypeptides are encompassed by the invention.

A further partial, non-limiting, and exemplary list of polypeptides of the invention which comprise, or alternatively consist of, combinations of amino acid sequences includes, for example, [Ala-1 to Thr-8] fused to [Val-9 to Lys-27] fused to [Gly-28 to Gln-65] fused to [Val-66 to Ala-115] fused to [Gly-116 to Leu-152] of SEQ ID NO:41; [Ala-1 to Thr-8] fused to [Gly-28 to Gln-65] fused to [Val-66 to Ala-115] fused to [Gly-116 to Leu-152] of SEQ ID NO:41; [Ala-1 to Thr-8] fused to [Val-9 to Lys-27] fused to [Gly-28 to Gln-65] fused to [Gly-116 to Leu-152] of SEQ ID NO:41; Other combinations may include the polypeptide fragments in an order other than that recited above (e.g[Ala-1 to Thr-8] fused to [Gly-116 to Leu-152] fused to [Val-66 to Ala-115] fused to [Val-9 to Lys-27] of SEQ ID NO:41). Other combinations may also include heterologous polypeptide fragments as described herein and/or other polypeptides or polypeptide fragments of the present invention (e.g., [Ala-1 to Thr-8] fused to [Val-9 to Lys-27] fused to [Gly-28 to Gln-65] fused to [Val-66 to Ala-115] fused to [Gly-116 to Leu-152] of SEQ ID NO:41 fused to an Fc receptor tag). Polynucleotides encoding any of these polypeptides are encompassed by the invention.

A further partial, non-limiting, and exemplary list of polypeptides of the invention which comprise, or alternatively consist of, combinations of amino acid sequences includes, for example, [Ala-1 to Thr-8] fused to [Glu-9 to Thr-40] fused to [Arg-41 to Gln-78] fused to [Val-79 to Ala-128] fused to [Gly-129 to Leu-165] of SEQ ID NO:42; [Ala-1 to Thr-8] fused to [Arg-41 to Gln-78] fused to [Val-79 to Ala-128] fused to [Gly-129 to Leu-165] of SEQ ID NO:42; [Ala-1 to Thr-8] fused to [Glu-9 to Thr-40] fused to [Arg-41 to Gln-78] fused to [Gly-129 to Leu-165] of SEQ ID NO:4. Other combinations may include the polypeptide fragments in an order other than that recited above (e.g[Ala-1 to Thr-8] fused to [Gly-129 to Leu-165] fused to [Val-79 to Ala-128] fused to [Arg-41 to Gln-78] fused to [Glu-9 to Thr-40] of SEQ ID NO:42). Other combinations may also include heterologous polypeptide fragments as described herein and/or other polypeptides or polypeptide fragments of the present invention (e.g., [Ala-1 to Thr-8] fused to [Glu-9 to Thr40] fused to [Arg41 to Gln-78] fused to [Val-79 to Ala-128] fused to [Gly-129 to Leu-165] of SEQ ID NO:42 fused to an Fc receptor tag). Polynucleotides encoding any of these polypeptides are encompassed by the invention.

A further partial, non-limiting, and exemplary list of polypeptides of the invention which comprise, or alternatively consist of, combinations of amino acid sequences includes, for example, [Ala-1 to Thr-8] fused to [Glu-9 to Thr40] fused to [Ile-41 to Lys-59] fused to [Gly-60 to Gln-97] fused to [Val-98 to Ala-147] fused to [Gly-148 to Leu-184] of SEQ ID NO:43; [Ala-1 to Thr-8] fused [Gly-60 to Gln-97] fused to [Gly-148 to Leu-184] of SEQ ID NO:43; [Ala-1 to Thr-8] fused to [Glu-9 to Thr-40] fused to [Gly-60 to Gln-97] fused to [Val-98 to Ala-147] fused to [Gly-148 to Leu-184] of SEQ ID NO:43; [Ala-1 to Thr-8] fused to [Ile-41 to Lys-59] fused to [Gly-60 to Gln-97] fused to [Val-98 to Ala-147] fused to [Gly-148 to Leu-184] of SEQ ID NO:43; or [Ala-1 to Thr-8] fused to [Glu-9 to Thr40] fused to [Ile-41 to Lys-59] fused to [Gly-60 to Gln-97] fused to [Gly-148 to Leu-184] of SEQ ID NO:43; Other combinations may include the polypeptide fragments in an order other than that recited above (e.g., [Ala-1 to Thr-8] fused to [Gly-148 to Leu-184] fused to [Val-98 to Ala-147] fused to [Ile-41 to Lys-59] fused to [Glu-9 to Thr-40] fused to [Gly-60 to Gln-97] of SEQ ID NO:43). Other combinations may also include heterologous polypeptide fragments as described herein and/or other polypeptides or polypeptide fragments of the present invention (e.g., [Ala-1 to Thr-8] fused to [Glu-9 to Thr-40] fused to [Ile-41 to Lys-59] fused to [Val-98 to Ala-147] fused to [Gly-148 to Leu-184] of SEQ ID NO:43 fused to an Fe receptor tag). Polynucleotides encoding any of these polypeptides are encompassed by the invention.

Additional embodiments of the invention encompass Neutrokine-alpha and/or Neutrokine-alphaSV polypeptide fragments comprising, or alternatively consisting of, functional regions of polypeptides of the invention, such as the Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index set out in FIGS. 3 and 6 and in Table I and as described herein. In a preferred embodiment, the polypeptide fragments of the invention are antigenic. The data presented in columns VIII, IX, XIII, and XIV of Table I can be used to routinely determine regions of Neutrokine-alpha which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response. Among highly preferred fragments of the invention are those that comprise regions of Neutrokine-alpha and/or Neutrokine-alphaSV that combine several structural features, such as several (e.g., 1, 2, 3 or 4) of the features set out above. Polynucleotides encoding these polypeptides are also encompassed by the invention.

In another embodiment, the invention provides a polypeptide comprising, or alternatively consisting of, an epitope-bearing portion of a polypeptide of the invention. Polynucleotides encoding these polypeptides are also encompassed by the invention. The epitope of this polypeptide portion is an immunogenic or antigenic epitope of a polypeptide of the invention. An “immunogenic epitope” is defined as a part of a protein that elicits an antibody response when the whole protein is the immunogen. On the other hand, a region of a protein molecule to which an antibody can bind is defined as an “antigenic epitope.” The number of immunogenic epitopes of a protein generally is less than the number of antigenic epitopes. See, for instance, Geysen et al., Proc. Natl. Acad. Sci. USA 81:3998-4002 (1983).

As to the selection of polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Leamer, R. A. (1983) “Antibodies that react with predetermined sites on proteins”, Science, 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptdes and polypeptides of the invention are therefore useful to raise antibodies, including monoclonal antibodies, that bind specifically to a polypeptide of the invention. See, for instance, Wilson et al., Cell 37:767-778 (1984) at 777.

Antigenic epitope-bearing peptides and polypeptides of the invention preferably contain a sequence of at least 4, at least 5, at least 6, at least 7, more preferably at least 8, at least 9, at least 10, at least I1, at least 12, at least 15, at least 20, at least 25, at least 30, at least 40, at least 50, and, most preferably, between about 15 to about 30 amino acids contained within the amino acid sequence of a polypeptide of the invention. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof.

Non-limiting examples of antigenic polypeptides or peptides that can be used to generate Neutrokine-alpha- and/or Neutrokine-alphaSV-specific antibodies include: a polypeptide comprising, or alternatively consisting of, amino acid residues from about Phe-115 to about Leu-147 in FIGS. 1A and 1B (SEQ ID NO:2); a polypeptide comprising, or alternatively consisting of, amino acid residues from about Ile-150 to about Tyr-163 in FIGS. 1A and 1B (SEQ ID NO:2); a polypeptide comprising, or alternatively consisting of, amino acid residues from about Ser-171 to about Phe-194 in FIGS. 1A and 1B (SEQ ID NO:2); a polypeptide comprising, or alternatively consisting of, amino acid residues from about Glu-223 to about Tyr-246 in FIGS. 1A and 1B (SEQ ID NO:2); and a polypeptide comprising, or alternatively consisting of, amino acid residues from about Ser-271 to about Phe-278 in FIGS. 1A and 1B (SEQ ID NO:2). In this context, "about" means the particularly recited ranges and ranges larger or smaller by several, a few, 5, 4, 3, 2 or 1 amino acid residues at either or both the amino- and carboxy-termini. These polypeptide fragments have been determined to bear antigenic epitopes of the Neutrokine-alpha polypeptide by the analysis of the Jameson-Wolf antigenic index, as shown in FIG. 3 and Table I, above.

Non-limiting examples of antigenic polypeptides or peptides that can be used to generate Neutrokine-alpha- and/or Neutrokine-alphaSV-specific antibodies include: a polypeptide comprising, or alternatively consisting of, amino acid residues from about Pro-32 to about Leu-47 in FIGS. 5A and 5B (SEQ ID NO:19); a polypeptide comprising, or alternatively consisting of, amino acid residues from about Glu-116 to about Ser-143 in FIGS. 5A and 5B (SEQ ID NO:19); a polypeptide comprising, or alternatively consisting of, amino acid residues from about Phe-153 to about Tyr-173 in FIGS. 5A and 5B (SEQ ID NO:19); a polypeptide comprising, or alternatively consisting of, amino acid residues from about Pro-218 to about Tyr-227 in FIGS. 5A and 5B (SEQ ID NO:19); a polypeptide comprising, or alternatively consisting of, amino acid residues from about Ala-232 to about Gln-241 in FIGS. 5A and 5B (SEQ ID NO:19); a polypeptide comprising, or alternatively consisting of, amino acid residues from about Ile-244 to about Ala-249 in FIGS. 5A and 5B (SEQ ID NO:19); and a polypeptide comprising, or alternatively consisting of, amino acid residues from about Ser-252 to about Val-257 in FIGS. 5A and 5B (SEQ ID NO:19). In this context, "about" means the particularly recited ranges and ranges larger or smaller by several, a few, 5, 4, 3, 2 or 1 amino acid residues at either or both the amino- and carboxy-termini. Polynucleotides encoding these polypeptides are also encompassed by the invention. These polypeptide fragments have been determined to bear antigenic epitopes of the Neutrokine-alphaSV polypeptide by the analysis of the Jameson-Wolf antigenic index, as shown in FIG. 6 and a tabular representation of the data presented in FIG. 6 generated by the Protean component of the DNA*STAR computer program (as set forth above).

The epitope-bearing peptides and polypeptides of the invention may be produced by any conventional means. See, e.g., Houghten, R. A. (1985) General method for the rapid solid-phase synthesis of large numbers of peptides: specificity of antigen-antibody interaction at the level of individual amino acids. Proc. Natl. Acad. Sci. USA 82:5131-5135; this "Simultaneous Multiple Peptide Synthesis (SMPS)" process is further described in U. S. Pat. No. 4,631,211 to Houghten et al. (1986).

Epitope-bearing peptides and polypeptides of the invention have uses that include, but are not limited to, to induce antibodies according to methods well known in the art. See, for instance, Sutcliffe et al., supra; Wilson et al., supra; Chow, M. et al., Proc. Natl. Acad. Sci. USA 82:910-914; and Bittle, F. J. et al., J. Gen. Virol. 66:2347-2354 (1985). Immunogenic epitope-bearing peptdes of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1-C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC deposit No. 97768, or encoded by a polynucleotide that hybridizes to the complement of the sequence of SEQ ID NO:1 or the cDNA sequence contained in ATCC deposit No. 97768 (e.g., under hybridization conditions described herein). The present invention further encompasses polynucleotide sequences comprising, or alternatively consisting of, a sequence encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand (e.g., under hybridization conditions described herein).

The present invention also encompasses polypeptides comprising, or alternatively consisting of, an epitope of the polypeptide having an amino acid sequence of SEQ ID NO:19, or an epitope of the polypeptide sequence encoded by a polynucleotide sequence contained in ATCC deposit No. 203518, or encoded by a polynucleotide that hybridizes to the complement of the sequence of SEQ ID NO:18 or the cDNA sequence contained in ATCC deposit No. 203518 (e.g., under hybridization conditions described herein). The present invention further encompasses polynucleotide sequences comprising, or alternatively consisting of, a sequence encoding an epitope of a polypeptide sequence of the invention (such as, for example, the sequence disclosed in SEQ ID NO:18), polynucleotide sequences of the complementary strand of a polynucleotide sequence encoding an epitope of the invention, and polynucleotide sequences which hybridize to the complementary strand (e.g., under hybridization conditions described herein).

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998- 4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross- reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptdes containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof(see, e.g., U.S. Pat. No. 5,876,969, issued March 2, 1999, EP Patent 0413 622, and U.S. Pat. No. 5,766,883 issued Jun. 16, 1998, herein incorporated by reference in their entirety)), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

In another embodiment, the Neutrokine-alpha and/or Neutrokine-alphaSV polypeptides of the present invention and the epitope-bearing fragments thereof are fused with a heterologous antigen (e.g., polypeptide, carbohydrate, phospholipid, or nucleic acid). In specific embodiments, the heterologous antigen is an immunogen.

In a more specific embodiment, the heterologous antigen is the gp120 protein of HIV, or a fragment thereof. Polynucleotides encoding these polypeptides are also encompassed by the invention.

In another embodiment, the Neutrokine-alpha and/or Neutrokine-alphaSV polypeptides of the present invention and the epitope-bearing fragments thereof are fused with polypeptide sequences of another TNF ligand family member (or biologically active fragments or variants thereof). In a specific embodiment, the Neutrokine-alpha and/or Neutrokine-alphaSV polypeptides of the present invention are fused with a CD40L polypeptide sequence. In a preferred embodiment, the CD40L polypeptide sequence is soluble.

The techniques of gene-shuffling, motif-shuffling, exon-shuffling, and/or codon-shuffling (collectively referred to as "DNA shuffling") may be employed to modulate the activities of Neutrokine-alpha and/or Neutrokine-alphaSV thereby effectively generating agonists and antagonists of Neutrokine-alpha and/or Neutrokine-alphaSV. See generally, U.S. Pat. Nos. 5,605,793, 5,811,238, 5,830,721, 5,834,252, and 5,837,458, and Patten, P. A., et al., Curr. Opinion Biotechnol. 8:724-33 (1997); Harayama, S. Trends Biotechnol. 16(2):76-82 (1998); Hansson, L. O., et al., J. Mol. Biol. 287:265-76 (1999); and Lorenzo, M. M. and Blasco, R. Biotechniques 24(2):308-13 (1998) (each of these patents and publications are hereby incorporated by reference). In one embodiment alteration of Neutrokine-alpha and/or Neutrokine-alphaSV polynucleotides and corresponding polypeptides may be achieved by DNA shuffling. DNA shuffling involves the assembly of two or more DNA segments into a desired Neutrokine-alpha and/or Neutrokine-alphaSV molecule by homologous, or site-specific, recombination. In another embodiment, Neutrokine-alpha and/or Neutrokine-alphaSV polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of Neutrokine-alpha and/or Neutrokine-alphaSV may be recombined with one or more components, motifs, sections, parts, domains, fragments, etc. of one or more heterologous molecules. In preferred embodiments, the heterologous molecules are, for example, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-IBBL, DcR3, OX40L, TNF-gamma (International Publication No. WO 96/14328), AIM-I (International Publication No. WO 97/33899), AIM-II (International Publication No. WO 97/34911), APRIL (J. Exp. Med. 188(6):1185-1190), endokine-alpha (International Publication No. WO 98/07880), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TRIO (International Publication No. WO 98/54202),312C2 (International Publication No. WO 98/06842), TR12, CAD, and v-FLIP. In further embodiments, the heterologous molecules are any member of the TNF family.

In a preferred embodiment, Neutrokine-alpha and/or Neutrokine-alphaSV polypeptides of the invention (inlcuding biologically active fragments or variants thereof), are fused with soluble CD40L polypeptides, or biologically acitve fragments or variants thereof.

In another preferred embodiment, Neutrokine-alpha and/or Neutrokine-alphaSV polypeptides of the invention (inlcuding biologically active fragments or variants thereof), are fused with soluble APRIL polypeptides (e.g., SEQ ID NO:20 or SEQ ID NO:47), or biologically acitve fragments or variants thereof.

To improve or alter the characteristics of Neutrokine-alpha and/or Neutrokine-alphaSV polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. For instance, for many proteins, including the extracellular domain or the mature form(s) of a secreted protein, it is known in the art that one or more amino acids may be deleted from the N-terminus or C-terminus without substantial loss of biological function. For instance, Ron et al., J. Biol. Chem., 268:2984-2988 (1993) reported modified KGF proteins that had heparin binding activity even if 3, 8, or 27 amino-terminal amino acid residues were missing.

In the present case, since the protein of the invention is a member of the TNF polypeptide family, deletions of N-terminal amino acids up to the Gly (G) residue at position 191 in FIGS. 1A and 1B (SEQ ID NO:2) may retain some biological activity such as, for example, the ability to stimulate lymphocyte (e.g., B cell) proliferation, differentiation, and/or activation, and cytotoxicity to appropriate target cells. Polypeptides having further N-terminal deletions including the Gly (G) residue would not be expected to retain biological activities because it is known that this residue in TNF-related polypeptides is in the beginning of the conserved domain required for biological activities. However, even if deletion of one or more amino acids from the N-terminus of a protein results in modification or loss of one or more biological functions of the protein, other functional activities may still be retained. Thus, the ability of the shortened protein to induce and/or bind to antibodies which recognize the complete or extracellular domain of the protein generally will be retained when less than the majority of the residues of the complete or extracellular domain of the protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the Neutrokine-alpha shown in FIGS. 1A and 1B (SEQ ID NO:2), up to the glycine residue at position 191 (Gly-191 residue from the amino terminus), and polynucleotides encoding such polypeptides. In particular, the present invention provides polypeptides comprising, or alternatively consisting of, the amino acid sequence of residues $n^1$-285 of SEQ ID NO:2, where $n^1$ is an integer in the range of the amino acid position of amino acid residues 2-190 of the amino acid sequence in SEQ ID NO:2. Polynucleotides encoding these polypeptides are also encompassed by the invention. More in particular, the invention provides polynucleotides encoding polypeptides comprising, or alternatively consisting of, an amino acid sequence selected from the group consisting of residues 2-285, 3-285, 4-285, 5-285, 6-285, 7-285, 8-285, 9-285, 10-285, 11-285, 12-285, 13-285, 14-285, 15-285, 16-285, 17-285, 18-285, 19-285, 20-285, 21-285, 22-285, 23-285, 24-285, 25-285, 26-285, 27-285, 28-285, 29-285, 30-285, 31-285, 32-285, 33-285, 34-285, 35-285, 36-285, 37-285, 38-285, 39-285, 40-285, 41-285, 42-285, 43-285, 44-285, 45-285, 46-285, 47-285, 48-285, 49-285, 50-285, 51-285, 52-285, 53-285, 54-285, 55-285, 56-285, 57-285, 58-285, 59-285, 60-285, 61-285, 62-285, 63-285, 64-285, 65-285, 66-285, 67-285, 68-285, 69-285, 70-285, 71-285, 72-285, 73-285, 74-285, 75-285, 76-285, 77-285, 78-285, 79-285, 80-285, 81-285, 82-285, 83-285, 84-285, 85-285, 86-285, 87-285, 88-285, 89-285, 90-285, 91-285, 92-285, 93-285, 94-285, 95-285, 96-285, 97-285, 98-285, 99-285, 100-285, 101-285, 102-285, 103-285, 104-285, 105-285, 106-285, 107-285, 108-285, 109-285, 110-285, 111-285, 112-285, 113-285, 114-285, 115-285, 116-285, 117-285, 118-285, 119-285, 120-285, 121-285, 122-285, 123-285, 124-285, 125-285, 126-285, 127-285, 128-285, 129-285, 130-285, 131-285, 132-285, 133-285, 134-285, 135-235, 136-235, 137-235, 138-285, 139-285, 140-285, 141-285, 142-285, 143-285, 144-285, 145-285, 146-285, 147-285, 148-285, 149-285, 150-285, 151-285, 152-285, 153-285, 154-285, 155-285, 156-285, 157-285, 158-285, 159-285, 160-285, 161-285, 162-285, 163-285, 164-285, 165-285, 166-285, 167-285, 168-285, 169-285, 170-285, 171-285, 172-285, 173-285, 174-285, 175-285, 176-285, 177-285, 178-285, 179-285, 180-285, 181-285, 182-285, 183-285, 184-285, 185-285, 186-285, 187-285, 188-285, 189-285, and 190-285 of SEQ ID No:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the Neutrokine-alpha and/or Neutrokine-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98%, or 99% identical to the amino acid sequence described above, and polynucleotides that encode such polypeptides.

Furthermore, since the predicted extracellular domain of the Neutrokine-alpha polypeptides of the invention may itself elicit biological activity, deletions of N- and C-terminal amino acid residues from the predicted extracellular region of the polypeptide (spanning positions Gln-73 to Leu-285 of SEQ ID NO:2) may retain some biological activity such as, for example, ligand binding, stimulation of lymphocyte (e.g., B cell) proliferation, differentiation, and/or activation, and modulation of cell replication or modulation of target cell activities. However, even if deletion of one or more amino acids from the N-terminus of the predicted extracellular domain of a Neutrokine-alpha polypeptide results in modification or loss of one or more biological functions of the polypeptide, other functional activities may still be retained. Thus, the ability of the shortened polypeptides to induce and/or bind to antibodies which recognize the complete or mature or extracellular domains of the polypeptides generally will be retained when less than the majority of the residues of the complete or mature or extracellular domains of the polypeptides are removed from the N-terminus. Whether a particular polypeptide lacking N-terminal residues of a complete polypeptide retains such immunologic activities can readily be determined by routine methods described herein and otherwise known in the art.

Accordingly, the present invention further provides polypeptides having one or more residues deleted from the amino terminus of the amino acid sequence of Neutrokine-alpha shown in SEQ ID NO:2, up to the glycine residue at position number 280, and polynucleotides encoding such polypeptides. In particular, the present invention provides polypeptides comprising, or alternatively consisting of, the amino acid sequence of residues $n^2$-285 of SEQ ID NO:2, where $n^2$ is an integer in the range of the amino acid position of amino acid residues 73-280 in SEQ ID NO:2, and 73 is the position of the first residue from the N-terminus of the predicted extracellular domain of the Neutrokine-alpha polypeptide (disclosed in SEQ ID NO:2). Polynucleotides encoding these polypeptides are also encompassed by the invention. More in particular, in certain embodiments, the invention provides polynucleotides encoding polypeptides comprising, or alternatively consisting of, an amino acid sequence selected from the group consisting of residues of Q-73 to L-285; G-74 to L-285; D-75 to L-285; L-76 to L-285; A-77 to L-285; S-78 to L-285; L-79 to L-285; R-80 to L-285; A-81 to L-285; E-82 to L-285; L-83 to L-285; Q-84 to L-285; G-85 to L-285; H-86 to L-285; H-87 to L-285; A-88 to L-285; E-89 to L-285; K-90 to L-285; L-91 to L-285; P-92 to L-285; A-93 to L-285; G-94 to L-285; A-95 to L-285; G-96 to L-285; A-97 to L-285; P-98 to L-285; K-99 to L-285; A-100 to L-285; G-101 to L-285; L-102 to L-285; E-103 to L-285; E-104 to L-285; A-105 to L-285; P-106 to L-285; A-107 to L-285; V-108 to L-285; T-109 to L-285; A-110 to L-285; G-111 to L-285; L-112 to L-285; K-113 to L-285; O-114 to L-285; F-115 to L-285; E-116 to L-285; P-117 to L-285; P-118 to L-285; A-119 to L-285; P-120 to L-285; G-121 to L-285; E-122 to L-285; G-123 to L-285; N-124 to L-285; S-125 to L-285; S-126 to L-285; Q-127 to L-285; N-128 to L-285; S-129 to L-285; R-130 to L-285; N-131 to L-285; K-132 to L-285; R-133 to L-285; A-134 to L-285; V-135 to L-285; Q-136 to L-285; G-137 to L-285; P-138 to L-285; E-139 to L-285; E-140 to L-285; T-141 to L-285; V-142 to L-285; T-143 to L-285; Q-144 to L-285; D-145 to L-285; C-146 to L-285; L-147 to L-285; Q-148 to L-285; L-149 to L-285; I-150 to L-285; A-151 to L-285; D-152 to L-285; S-153 to L-285; E-154 to L-285; T-155 to L-285; P-156 to L-285; T-157 to L-285; I-158 to L-285; Q-159 to L-285; K-160 to L-285; G-161 to L-285; S-162 to L-285; Y-163 to L-285; T-164 to L-285; F-165 to L-285; V-166 to L-285; P-167 to L-285; W-168 to L-285; L-169 to L-285; L-170 to L-285; S-171 to L-285; F-172 to L-285; K-173 to L-285; R-174 to L-285; G-175 to L-285; S-176 to L-285; A-177 to L-285; L-178 to L-285; E-179 to L-285; E-180 to L-285; K-181 to L-285; E-182 to L-285; N-183 to L-285; K-184 to L-285; I-185 to L-285; L-186 to L-285; V-187 to L-285; K-188 to L-285; E-189 to L-285; T-190 to L-285; G-191 to L-285; Y-192 to L-285; F-193 to L-285; F-194 to L-285; I-195 to L-285; Y-196 to L-285; G-197 to L-285; Q-198 to L-285; V-199 to L-285; L-200 to L-285; Y-201 to L-285; T-202 to L-285; D-203 to L-285; K-204 to L-285; T-205 to L-285; Y-206 to L-285; A-207 to L-285; M-208 to L-285; G-209 to L-285; H-210 to L-285; L-211 to L285; I-212 to L-285; Q-213 to L-285; R-214 to L-285; K-215 to L-285; K-216 to L-285; V-217 to L-285; H-218 to L-285; V-219 to L-285; F-220 to L-285; G-221 to L-285; D-222 to L-285; E-223 to L-285; L-224 to L-285; S-225 to L-285; L-226 to L-285; V-227 to L-285; T-228 to L-285; L-229 to L-285; F-230 to L-285; R-231 to L-285; C-232 to L-285; I-233 to L-285; Q-234 to L285; N-235 to L-285; M-236 to L-285; P-237 to L-285; E-238 to L-285; T-239 to L-285; L-240 to L-285; P-241 to L-285; N-242 to L-285; N-243 to L-285; S-244 to L-285; C-245 to L-285; Y-246 to L-285; S-247 to L-285; A-248 to L-285; G-249 to L-285; I-250 to L-285; A-251 to L-285; K-252 to L-285; L-253 to L-285; E-254 to L-285; E-255 to L-285; G-256 to L-285; D-257 to L-285; E-258 to L-285; L-259 to L-285; Q-260 to L-285; L-261 to L-285; A-262 to L-285; I-263 to L-285; P-264 to L-285; R-265 to L-285; E-266 to L-285; N-267 to L-285; A-268 to L-285; Q-269 to L-285; I-270 to L-285; S-271 to L-285; L-272 to L-285; D-273 to L-285; G-274 to L-285; D-275 to L-285; V-276 to L-285; T-277 to L-285; F-278 to L-285; F-279 to L-285; and G-280 to L-285 of SEQ ID NO:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the Neutrokine-alpha and/or Neutrokine-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

Highly preferred embodiments of the invention are directed to nucleic acid molecules comprising, or alternatively consisting of a polynucleotide having a nucleotide sequence at least 80%, 85%, 90% identical and more preferably at least 95%, 96%, 97%, 98%, 99% or 100% identical to a polynucleotide sequence encoding the Neutrokine-alpha polypeptide having the amino acid sequence at positions 134-285 in FIGS. 1A and 1B (SEQ ID NO:2). Preferred embodiments of the invention are directed to nucleic acid molecules comprising, or alternatively consisting of a polynucleotide having a nucleotide sequence at least 90% identical to a polynucleotide sequence encoding the Neutrokine-alpha polypeptide having the amino acid sequence at positions 134-285 in FIGS. 1A and 1B (SEQ ID NO:2). More preferred embodiments of the invention are directed to nucleic acid molecules comprising, or alternaively consisting of a polynucleotide having a nucleotide sequence at least 95% identical to a polynucleotide sequence encoding the Neutrokine-alpha polypeptide having the amino acid sequence at positions 134-285 in FIGS. 1A and 1B (SEQ ID NO:2). More preferred embodiments of the invention are directed to nucleic acid molecules comprising, or alternatively consisting of a polynucleotide having a nucleotide sequence at least 96% identical to a polynucleotide sequence encoding the Neutrokine-alpha polypeptide having the amino acid sequence at positions 134-285 in FIGS. 1A and 1B (SEQ ID NO:2).

Additionally, more preferred embodiments of the invention are directed to nucleic acid molecules comprising, or alternatively consisting of a polynucleotide having a nucleotide sequence at least 97% to a polynucleotide sequence encoding the Neutrokine-alpha polypeptide having the amino acid sequence at positions 134-285 in FIGS. 1A and 1B (SEQ ID NO:2). Additionally, more preferred embodiments of the invention are directed to nucleic acid molecules comprising, or alternatively consisting of a polynucleotide having a nucleotide sequence at least 98% to a polynucleotide sequence encoding the Neutrokine-alpha polypeptide having the amino acid sequence at positions 134-285 in FIGS. 1A and 1B (SEQ ID NO:2). Additionally, more preferred embodiments of the invention are directed to nucleic acid molecules comprising, or alternatively consisting of a polynucleotide having a nucleotide sequence at least 99% identical to a polynucleotide sequence encoding the Neutrokine-alpha polypeptide having the amino acid sequence at positions 134-285 in FIGS. 1A and 1B (SEQ ID NO:2).

In specific embodiments, a polypeptide comprising, or alternatively consisting of, one of the following N-terminally deleted polypeptide fragments of Neutrokine-alpha and/or Neutrokine-alphaSV are preferred: amino acid residues Ala-71 through Leu-285, amino acid residues Ala-81 through Leu-285, amino acid residues Leu-112 through Leu-285, amino acid residues Ala-134 through Leu-285, amino acid residues Leu-147 through Leu-285, and amino acid residues Gly-161 through Leu-285 of SEQ ID NO:2. Polynucleotides encoding these polypeptides are also encompassed by the invention.

Similarly, many examples of biologically functional C-terminal deletion muteins are known. For instance, Interferon gamma shows up to ten times higher activities by deleting 8-10 amino acid residues from the carboxy terminus of the protein (Döbeli et al., J. Biotechnology 7:199-216 (1988). Since the present protein is a member of the TNF polypeptide family, deletions of C-terminal amino acids up to the leucine residue at position 284 are expected to retain most if not all biological activity such as, for example, ligand binding, the ability to stimulate lymphocyte (e.g., B cell) proliferation, differentiation, and/or activation, and modulation of cell replication. Polypeptides having deletions of up to about 10 additional C-terminal residues (i.e., up to the glycine residue at position 274) also may retain some activity such as receptor binding, although such polypeptides would lack a portion of the conserved TNF domain which extends to about Leu-284 of SEQ ID NO:2. However, even if deletion of one or more amino acids from the C-terminus of a protein results in modification or loss of one or more biological functions of the protein, other functional activities may still be retained. Thus, the ability of the shortened protein to induce and/or bind to antibodies which recognize the complete or mature protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues deleted from the carboxy terminus of the amino acid sequence of the Neutrokine-alpha polypeptide shown in FIGS. 1A and 1B (SEQ ID NO:2), up to the glycine residue at position 274 (Gly-274) and polynucleotides encoding such polypeptides. In particular, the present invention provides polypeptides comprising, or alternatively consisting of, the amino acid sequence of residues 1-$m^1$ of the amino acid sequence in SEQ ID NO:2, where $m^1$ is any integer in the range of the amino acid position of amino acid residues 274-284 in SEQ ID NO:2. Polynucleotides encoding these polypeptdes are also encompassed by the invention. More in particular, the invention provides polynucleotides encoding polypeptides comprising, or alternatively consisting of, an amino acid sequence selected from the group consisting of residues 1-274, 1-275, 1-276, 1-277, 1-278, 1-279, 1-280, 1-281, 1-282, 1-283 and 1-284 of SEQ ID NO:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the Neutrokine-alpha and/or Neutrokine-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98%, or 99% identical to the amino acid sequence described above, and polynucleotides that encode such polypeptides.

Also provided are polypeptides comprising, or alternatively consisting of, one or more amino acids deleted from both the amino and the carboxyl termini, which may be described generally as having residues $n^1$-$m^1$ of SEQ ID NO:2, where $n^1$ and $m^1$ are integers as defined above. Also included are a nucleotide sequence encoding a polypeptide comprising, or alternatively consisting of, a portion of the complete Neutrokine-alpha amino acid sequence encoded by the deposited cDNA clone contained in ATCC Accession No. 97768 where this portion excludes from 1 to 190 amino acids from the amino terminus or from 1 to 1 amino acids from the C-terminus of the complete amino acid sequence (or any combination of these N-terminal and C-terminal deletions) encoded by the cDNA clone in the deposited plasmid. Polynucleotides encoding all of the above deletion polypeptides are encompassed by the invention.

Similarly, deletions of C-terminal amino acid residues of the predicted extracellular domain of Neutrokine-alpha up to the leucine residue at position 79 of SEQ ID NO:2 may retain some biological activity, such as, for example, ligand binding, stimulation of lymphocyte (e.g., B cell) proliferation, differentiation, and/or activation, and modulation of cell replication or modulation of target cell activities. Polypeptides having further C-terminal deletions including Leu-79 of SEQ ID NO:2 would not be expected to retain biological activities.

However, even if deletion of one or more amino acids from the C-terminus of a polypeptide results in modification or loss of one or more biological functions of the polypeptide, other functional activities may still be retained. Thus, the ability of the shortened polypeptide to induce and/or bind to antibodies which recognize the complete, mature or extracellular forms of the polypeptide generally will be retained when less than the majority of the residues of the complete, mature or extracellular forms of the polypeptide are removed from the C-terminus. Whether a particular polypeptide lacking C-terminal residues of the predicted extracellular domain retains such immunologic activities can readily be determined by routine methods described herein and otherwise known in the art.

Accordingly, the present invention further provides polypeptides having one or more residues deleted from the carboxy terminus of the amino acid sequence of the predicted extracellular domain of Neutrokine-alpha polypeptide shown in SEQ ID NO:2, up to the leucine residue at position 79 of SEQ ID NO:2, and polynucleotides encoding such polypeptides. In particular, the present invention provides polypeptides comprising, or alternatively consisting of, the amino acid sequence of residues 73-$m^2$ of the amino acid sequence in SEQ ID NO:2, where $m^2$ is any integer in the range of the amino acid position of amino acid residues 79 to 285 in the amino acid sequence in SEQ ID NO:2, and residue 78 is the position of the first residue at the C-terminus of the predicted extracellular domain of the Neutrokine-alpha polypeptide (disclosed in SEQ ID NO:2). Polypeptides encoded by these polynucleotides are also encompassed by the invention. More in particular, in certain embodiments, the invention provides polynucleotides encoding polypeptides comprising, or alternatively consisting of, an amino acid sequence selected from the group consisting of residues Q-73 to Leu-285; Q-73 to L-284; Q-73 to K-283; Q-73 to L-282; Q-73 to A-281; Q-73 to G-280; Q-73 to F-279; Q-73 to F-278; Q-73 to T-277; Q-73 to V-276; Q-73 to D-275; Q-73 to G-274; Q-73 to D-273; Q-73 to L-272; Q-73 to S-271; Q-73 to I-270; Q-73 to Q-269; Q-73 to A-268; Q-73 to N-267; Q-73 to E-266; Q-73 to R-265; Q-73 to P-264; Q-73 to I-263; Q-73 to A-262; Q-73 to L-261; Q-73 to Q-260; Q-73 to L-259; Q-73 to E-258; Q-73 to D-257; Q-73 to G-256; Q-73 to E-255; Q-73 to E-254; Q-73 to L-253; Q-73 to K-252; Q-73 to A-251; Q-73 to I-250; Q-73 to G-249; Q-73 to A-248; Q-73 to S-247; Q-73 to Y-246; Q-73 to C-245; Q-73 to S-244; Q-73 to N-243; Q-73 to N-242; Q-73 to P-241; Q-73 to L-240; Q-73 to T-239; Q-73 to E-238; Q-73 to P-237; Q-73 to M-236; Q-73 to N-235; Q-73 to Q-234; Q-73 to I-233; Q-73 to C-232; Q-73 to R-231; Q-73 to F-230; Q-73 to L-229; Q-73 to T-228; Q-73 to V-227; Q-73 to L-226; Q-73 to S-225; Q-73 to L-224; Q-73 to E-223; Q-73 to D-222; Q-73 to G-221; Q-73 to F-220; Q-73 to V-219; Q-73 to H-218; Q-73 to V-217; Q-73 to K-216; Q-73 to K-215; Q-73 to R-214; Q-73 to Q-213; Q-73 to I-212; Q-73 to L-211; Q-73 to H-210; Q-73 to G-209; Q-73 to M-208; Q-73 to A-207; Q-73 to Y-206; Q-73 to T-205; Q-73 to K-204; Q-73 to D-203; Q-73 to T-202; Q-73 to Y-201; Q-73 to L-200; Q-73 to V-199; Q-73 to Q-198; Q-73 to G-197; Q-73 to Y-196; Q-73 to I-195; Q-73 to F-194; Q-73 to F-193; Q-73 to Y-192; Q-73 to G-191; Q-73 to T-190; Q-73 to E-189; Q-73 to K-188; Q-73 to V-187; Q-73; Q-73 to L-186; Q-73 to I-185; Q-73 to K-184; Q-73 to N-183; Q-73 to E-182; Q-73 to K-181; Q-73 to E-180; Q-73 to E-179; Q-73 to L-178; Q-73 to A-177; Q-73 to S-176; Q-73 to G-175; Q-73 to R-174; Q-73 to K-173; Q-73 to F-172; Q-73 to S-171; Q-73 to L-170; Q-73 to L-169; Q-73 to W-168; Q-73 to P-167; Q-73 to V-166; Q-73 to F-165; Q-73 to T-164; Q-73 to Y-163; Q-73 to S-162; Q-73 to G-161; Q-73 to K-160; Q-73 to Q-159; Q-73 to I-158; Q-73 to T-157; Q-73 to P-156; Q-73 to T-155; Q-73 to E-154; Q-73 to S-153; Q-73 to D152, Q-73 to A-151; Q-73 to I-150; Q-73 to L-149; Q-73 to Q-148; Q-73 to L-147; Q-73 to C-146; Q-73 to D-145; Q-73 to Q-144; Q-73 to T-143; Q-73 to V-142; Q-73 to T-141; Q-73 to E-140; Q-73 to E-139; Q-73 to P-138; Q-73 to G-137; Q-73 to Q-136; Q-73 to V-135; Q73 to R-134; Q-73 to R-133; Q-73 to K-132; Q-73 to N-131; Q-73 to R-130; Q-73 to S-129; Q-73 to N-128; Q-73 to Q-127; Q-73 to Q-126; Q-73 to S-125; Q-73 to N-124; Q-73 to G-123; Q-73 to E-122; Q-73 to G-121; Q-73 to P-120; Q-73 to A-119; Q-73 to P-118; Q-73 to P-117; Q-73 to E-116; Q-73 to F-115; Q-73 to I-114; Q-73 to K-113; Q-73 to L-112; Q-73 to G-111; Q-73 to A-110; Q-73 to T-109; Q-73 to V-108; Q-73 to A-107; Q-73 to P-106; Q-73 to A-105; Q-73 to E-104; Q-73 to E-103; Q-73 to L-102; Q-73 to G-101; Q-73 to A-100; Q-73 to K-99; Q-73 to P-98; Q-73 to A-97; Q-73 to G-96; Q-73 to A-95; Q-73 to G-94; Q-73 to A-93; Q-73 to P-92; Q-73 to L-91; Q-73 to K-90; Q-73 to E-89; Q-73 to A-88; Q-73 to H-87; Q-73 to H-86; Q-73 to G-85; Q-73 to Q-84; Q-73 to L-83; Q-73 to E-82; Q-73 to A-81; Q-73 to R-80; and Q-73 to L-79 of SEQ ID NO:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the Neutrokine-alpha and/or Neutrokine-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

The invention also provides polypeptides having one or more amino acids deleted from both the amino and the carboxyl termini of the predicted extracellular domain of Neutrokine-alpha, which may be described generally as having residues $n^2$-$m^2$ of SEQ ID NO:2 where $n^2$ and $m^2$ are integers as defined above.

In another embodiment, a nucleotide sequence encoding a polypeptide consisting of a portion of the extracellular domain of the Neutrokine-alpha amino acid sequence encoded by the cDNA plasmid contained in the deposit having ATCC accession no. 97768, where this portion excludes from 1 to about 206 amino acids from the amino terminus of the extracellular domain of the amino acid sequence encoded by the cDNA plasmid contained in the deposit having ATCC accession no. 97768, or from I to about 206 amino acids from the carboxy terminus of the extracellular domain of the amino acid sequence encoded by the cDNA plasmid contained in the deposit having ATCC accession no. 97768, or any combination of the above amino terminal and carboxy terminal deletions, of the entire extracellular domain of the amino acid sequence encoded by the cDNA plasmid contained in the deposit having ATCC accession no.97768.

As mentioned above, even if deletion of one or more amino acids from the N-terminus of a polypeptide results in modification or loss of one or more functional activities (e.g., biological activity) of the polypeptide, other functions or biological activities may still be retained. Thus, the ability of a shortened Neutrokine-alpha mutein to induce and/or bind to antibodies which recognize the full-length or mature forms or the extracellular domain of the polypeptide generally will be retained when less than the majority of the residues of the full-length or mature or extracellular domain of the polypeptide are removed from the N-terminus. Whether a particular polypeptide lacking N-terminal residues of a complete polypeptide retains such immunologic activities can readily be determined by routine methods described herein and otherwise known in the art. It is not unlikely that a Neutrokine-alpha mutein with a large number of deleted N-terminal amino acid residues may retain some functional (e.g., biological or immunogenic) activities. In fact, peptides composed of as few as six Neutrokine-alpha amino acid residues may often evoke an immune response.

Accordingly, the present invention further provides polypeptides having one or more residues deleted from the amino terminus of the predicted full-length amino acid sequence of the Neutrokine-alpha shown in SEQ ID NO:2, up to the glycine residue at position number 280 of the sequence shown SEQ ID NO:2 and polynucleotides encoding such polypeptides. In particular, the present invention provides polypeptides comprising the amino acid sequence of residues $n^3$-285 of the sequence shown in SEQ ID NO:2, where $n^3$ is an integer in the range of the amino acid position of amino acid residues 1 to 280 of the amino acid sequence in SEQ ID NO:2.

More in particular, the invention provides polynucleotides encoding polypeptdes comprising, or alternatively consisting of, an amino acid sequence selected from the group consisting of residues of D-2 to L-285; D-3 to L-285; S-4 to L-285; T-5 to L-285; E-6 to L-285; R-7 to L-285; E-8 to L-285; Q-9 to L-285; S-10 to L-285; R-11 to L-285; L-12 to L-285; T-13; to L-285; S-14 to L-285; C-15 to L-285; L-16 to L-285; K-17 to L-285; K-18 to L-285; R-19 to L-285; E-20 to L-285; E-21 to L-285; M-22 to L-285; K-23 to L-285; L-24 to L-285; K-25 to L-285; E-26 to L-285; C-27 to L-285; V-28 to L-285; S-29 to L-285; I-30 to L-285; L-31 to L-285; P-32 to L-285; R-33 to L-285; K-34 to L-285; E-35 to L-285; S-36 to L-285; P-37 to L-285; S-38 to L-285; V-39 to L-285; R-40 to L-285; S-41 to L-285; S-42 to L-285; K-43 to L-285; D-44 to L-285; G-45 to L-285; K-46 to L-285; L-47 to L-285; L-48 to L-285; A-49 to L-285; A-50 to L-285; T-51 to L-285; L-52 to L-285; L-53 to L-285; L-54 to L-285; A-55 to L-285; L-56 to L-285; L-57 to L-285; S-58 to L-285; C-59 to L-285; C-60 to L-285; L-61 to L-285; T-62 to L-285; V-63 to L-285; V-64 to L-285; S-65 to L-285; F-66 to L-285; Y-67 to L-285; Q-68 to L-285; V-69 to L-285; A-70 to L-285; A-71 to L-285; L-72 to L-285; Q-73 to L-285; G-74 to L-285; D-75 to L-285; L-76 to L-285; A-77 to L-285; S-78 to L-285; L-79 to L-285; R-80 to L-285; A-81 to L-285; E-82 to L-285; L-83 to L-285; Q-84 to L-285; G-85 to L-285; H-86 to L-285; H-87 to L-285; A-88 to L-285; E-89 to L-285; K-90 to L-285; L-91 to L-285; P-92 to L-285; A-93 to L-285; G-94 to L-285; A-95 to L-285; G-96 to L-285; A-97 to L-285; P-98 to L-285; K-99 to L-285; A-100 to L-285; G-101 to L-285; L-102 to L-285; E-103 to L-285; E-104 to L-285; A-105 to L-285; P-106 to L-285; A-107 to L-285; V-108 to L-285; T-109 to L-285; A-110 to L-285; G-111 to L-285; L-112 to L-285; K-113 to L-285; I-114 to L-285; F-115 to L-285; E-116 to L-285; P-117 to L-285; P-118 to L-285; A-119 to L-285; P-120 to L-285; G-121 to L-285; E-122 to L-285; G-123 to L-285; N-124 to L-285; S-125 to L-285; S-126 to L-285; Q-127 to L-285; N-128 to L-285; S-129 to L-285; R-130 to L-285; N-131 to L-285; K-132 to L-285; R-133 to L-285; A-134 to L-285; V-135 to L-285; Q-136 to L-285; G-137 to L-285; P-138 to L-285; E-139 to L-285; E-140 to L-285; T-141 to L-285; V-142 to L-285; T-143 to L-285; Q-144 to L-285; D-145 to L-285; C-146 to L-285; L-146 to L-285; Q-148 to L-285; L-149 to L-285; I-150 to L-285; A-151 to L-285; D-152 to L-285; S-153 to L-285; E-154 to L-285; T-155 to L-285; P-156 to L-285; T-157 to L-285; I-158 to L-285; Q-159 to L-285; K-160 to L-285; G-161 to L-285; S-162 to L-285; Y-163 to L-285; T-164 to L-285; F-165 to L-285; V-166 to L-285; P-167 to L-285; W-168 to L-285; L-169 to L-285; L-170 to L-285; S-171 to L-285; F-172 to L-285; K-173 to L-285; R-174 to L-285; G-175 to L-285; S-176 to L-285; A-177 to L-285; L-178 to L-285; E-179 to L-285; E-180 to L-285; K-181 to L-285; E-182 to L-285; N-183 to L-285; K-184 to L-285; I-185 to L-285; L-186 to L-285; V-187 to L-285; K-188 to L-285;

E-189 to L-285; T-190 to L-285; G-191 to L-285; Y-192 to L-285; F-193 to L-285; F-194 to L-285; I-194 to L-285; Y-196 to L-285; G-197 to L-285; Q-198 to L-285; V-199 to L-285; L-200 to L-285; Y-201 to L-285; T-202 to L-285; D-203 to L-285; K-204 to L-285; T-205 to L-285; Y-206 to L-285; A-207 to L-285; M-208 to L-285; G-209 to L-285; H-210 to L-285; L-211 to L-285; I-212 to L-285; Q-213 to L-285; R-214 to L-285; K-215 to L-285; K-216 to L-285; V-217 to L-285; H-218 to L-285; V-219 to L-285; F-220 to L-285; G-221 to L-285; D-222 to L-285; E-223 to L-285; L-224 to L-285; S-225 to L-285; L-226 to L-285; V-227 to L-285; T-228 to L-285; L-229 to L-285; F-230 to L-285; R-231 to L-285; C-232 to L-285; 1-233 to L-285; Q-234 to L-285; N-235 to L-285; M-236 to L-285; P-237 to L-285; E-238 to L-285; T-239 to L-285; L-240 to L-285; P-241 to L-285; N-242 to L-285; N-243 to L-285; S-244 to L-285; C-245 to L-285; Y-246 to L-285; S-247 to L-285; A-248 to L-285; G-249 to L-285; I-250 to L-285; A-251 to L-285; K-252 to L-285; L-253 to L-285; E-254 to L-285; E-255 to L-285; G-256 to L-285; D-257 to L-285; E-258 to L-285; L-259 to L-285; Q-260 to L-285; L-261 to L-285; A-262 to L-285; I-263 to L-285; P-264 to L-285; R-265 to L-285; E-266 to L-285; N-267 to L-285; A-268 to L-285; Q-269 to L-285; 1-270 to L-285; S-271 to L-285; L-272 to L-285; D-273 to L-285; G-274 to L-285; D-275 to L-285; V-276 to L-285; T-277 to L-285; F-278 to L-285; F-279 to L-285; and G-280 to L-285 of SEQ ID NO:2. The present application is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the Neutrokine-alpha and/or Neutrokine-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 80%, 85%, 90%, 92%, 95%, 96%, 97%, 98%, or 99%, identical to the amino acid sequence described above, and polynucleotides that encode such polypeptides.

Also as mentioned above, even if deletion of one or more amino acids from the C-terminus of a protein results in modification or loss of one or more functional activities (e.g., biological activity) of the protein, other functional activities may still be retained. Thus, the ability of a shortened Neutrokine-alpha mutein to induce and/or bind to antibodies which recognize the complete or mature form or the extracellular domain of the polypeptide generally will be retained when less than the majority of the residues of the complete or mature form or the extracellular domain of the polypeptide are removed from the C-terminus. Whether a particular polypeptide lacking C-terminal residues of a complete polypeptide retains such immunologic activities can readily be determined by routine methods described herein and otherwise known in the art. It is not unlikely that a Neutrokine-alpha mutein with a large number of deleted C-terminal amino acid residues may retain some functional (e.g., biological or immunogenic) activities. In fact, peptides composed of as few as six Neutrokine-alpha amino acid residues may often evoke an immune response.

Accordingly, the present invention further provides in another embodiment, polypeptides having one or more residues deleted from the carboxy terminus of the amino acid sequence of the Neutrokine-alpha shown in SEQ ID NO:2, up to the glutamic acid residue at position number 6, and polynucleotides encoding such polypeptides. In particular, the present invention provides polypeptides comprising the amino acid sequence of residues 1-$m^3$ of SEQ ID NO:2, where $m^3$ is an integer in the range of the amino acid position of amino acid residues 6-284 of the amino acid sequence in SEQ ID NO:2.

More in particular, the invention provides polynucleotides encoding polypeptides comprising, or alternatively consisting of an amino acid sequence selected from the group consisting of residues M-1 to L-284; M-1 to K-283; M-1 to L-282; M-1 to A-281; M-1 to G-280; M-1 to F-279; M-1 to F-278; M-1 to T-277; M-1 to V-276; M-1 to D-275; M-1 to G-274; M-1 to D-273; M-1 to L-272; M-1 to S-271; M-1 to I-270; M-1 to Q-269; M-1 to A-268; M-1 to N-267; M-1 to E-266; M-1 to R-265; M-1 to P-264; M-1 to I-263; M-1 to A-262; M-1 to L-261; M-1 to Q-260; M-1 to L-259; M-1 to E-258; M-1 to D-257; M-1 to G-256; M-1 to E-255; M-1 to E-254; M-1 to L-253; M-1 to K-252; M-1 to A-251; M-1 to I-250; M-1 to G-249; M-1 to A-248; M-1 to S-247; M-1 to Y-246; M-1 to C-245; M-1 to S-244; M-1 to N-243; M-1 to N-242; M-1 to P-241; M-1 to L-240; M-1 to T-239; M-1 to E-238; M-1 to P-237; M-1 to M-236; M-1 to N-235; M-1 to Q-234; M-1 to I-233; M-1 to C-232; M-1 to R-231; M-1 to F-230; M-1 to L-229; M-1 to T-228; M-1 to V-227; M-1 to L-226; M-1 to S-225; M-1 to L-224; M-1 to E-223; M-1 to D-222; M-1 to G-221; M-1 to F-220; M-1 to V-219; M-1 to H-218; M-1 to V-217; M-1 to K-216; M-1 to K-215; M-1 to R-214; M-1 to Q-213; M-1 to I-212; M-1 to L-211; M-1 to H-210; M-1 to G-209; M-1 to M-208; M-1 to A-207; M-1 to Y-206; M-1 to T-205; M-1 to K-204; M-1 to D-203; M-1 to T-202; M-1 to Y-201; M-1 to L-200; M-1 to V-199; M-1 to Q-198; M-1 to G-197; M-1 to Y-196; M-1 to I-195; M-1 to F-194; M-1 to F-193; M-1 to Y-192; M-1 to G-191; M-1 to T-190; M-1 to E-189; M-1 to K-188; M-1 to V-187; M-1 to L-186; M-1 to I-185; M-1 to K-184; M-1 to N-183; M-1 to E-182; M-1 to K-181; M-1 to E-180; M-1 to E-179; M-1 to L-178; M-1 to A-177; M-1 to S-176; M-1 to G-175; M-1 to R-174; M-1 to K-173; M-1 to F-172; M-1 to S-171; M-1 to L-170; M-1 to L-169; M-1 to W-168; M-1 to P-167; M-1 to V-166; M-1 to F-165; M-1 to T-164; M-1 to Y-163; M-1 to S-162; M-1 to G-161; M-1 to K-160; M-1 to Q-159; M-1 to I-158; M-1 to T-157; M-1 to P-156; M-1 to T-155; M-1 to E-154; M-1 to S-153; M-1 to D-152; M-1 to A-151; M-1 to I-150; M-1 to L-149; M-1 to Q-148; M-1 to L-147; M-1 to C-146; M-1 to D-145; M-1 to Q-144; M-1 to T-143; M-1 to V-142; M-1 to T-141; M-1 to E-140; M-1 to E-139; M-1 to P-138; M-1 to G-137; M-1 to Q-136; M-1 to V-135; M-1 to A-134; M-1 to R-133; M-1 to K-132; M-1 to N-131; M-1 to R-130; M-1 to S-129; M-1 to N-128; M-1 to Q-127; M-1 to S-126; M-1 to S-125; M-1 to N-124; M-1 to G-123; M-1 to E-122; M-1 to G-121; M-1 to P-120; M-1 to A-119; M-1 to P-118; M-1 to P-117; M-1 to E-116; M-1 to F-115; M-1 to I-114; M-1 to K-113; M-1 to L-112; M-1 to G-111; M-1 to A-110; M-1 to T-109; M-1 to V-108; M-1 to A-107; M-1 to P-106; M-1 to A-105; M-1 to E-104; M-1 to E-103; M-1 to L-102; M-1 to G-101; M-1 to A-100; M-1 to K-99; M-1 to P-98; M-1 to A-97; M-1 to G-96; M-1 to A-95; M-1 to G-94; M-1 to A-93; M-1 to P-92; M-1 to L-91; M-1 to K-90; M-1 to E-89; M-1 to A-88; M-1 to H-87; M-1 to H-86; M-1 to G-85; M-1 to Q-84; M-1 to L-83; M-1 to E-82; M-1 to A-81; M-1 to R-80; M-1 to L-79; M-1 to S-78; M-1 to A-77; M-1 to L-76; M-1 to D-75; M-1 to G-74; M-1 to Q-73; M-1 to L-72; M-1 to A-71; M-1 to A-70; M-1 to V-69; M-1 to Q-68; M-1 to Y-67; M-1 to F-66; M-1 to S-65; M-1 to V-64; M-1 to V-63; M-1 to T-62; M-1 to L-61; M-1 to C-60; M-1 to C-59; M-1 to S-58; M-1 to L-57; M-1 to L-56; M-1 to A-55; M-1 to L-54; M-1 to L-53; M-1 to L-52; M-1 to T-51; M-1 to A-50; M-1 to A-49; M-1 to L-48; M-1 to L-47; M-1 to K-46; M-1 to G-45; M-1 to D-44; M-1 to K-43; M-1 to S-42; M-1 to S-41; M-1 to R-40;

M-1 to V-39; M-1 to S-38; M-1 to P-37; M-1 to S-36; M-1 to E-35; M-1 to K-34; M-1 to R-33; M-1 to P-32; M-1 to L-31; M-1 to I-30; M-1 to S-29; M-1 to V-28; M-1 to C-27; M-1 to E-26; M-1 to K-25; M-1 to L-24; M-1 to K-23; M-1 to M-22; M-1 to E-21; M-1 to E-20; M-1 to R-19; M-1 to K-18; M-1 to K-17; M-1 to L-16; M-1 to C-15; M-1 to S-14; M-1 to T-13; M-1 to L-12; M-1 to R-11; M-1 to S-10; M-1 to Q-9; M-1 to E-8; M-1 to R-7; and M-1 to E-6 of SEQ ID NO:2. The present application is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the Neutrokine-alpha and/or Neutrokine-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 80%, 85%, 90%, 92%, 95%, 96%, 97%, 98% or 99% identical to the amino acid sequence described above, and polynucleotides that encode such polypeptides.

The invention also provides polypeptides having one or more amino acids deleted from both the amino and the carboxyl termini of a Neutrokine-alpha polypeptide, which may be described generally as having residues $n^3$-$m^3$ of SEQ ID NO:2, where $n^3$ and $m^3$ are integers as defined above.

Furthermore, since the predicted extracellular domain of the Neutrokine-alphaSV polypeptides of the invention may itself elicit functional activity (e.g., biological activity), deletions of N- and C-terminal amino acid residues from the predicted extracellular region of the polypeptide at positions Gln-73 to Leu-266 of SEQ ID NO:19 may retain some functional activity, such as, for example, ligand binding, to stimulation of lymphocyte (e.g., B cell) proliferation, differentiation, and/or activation, modulation of cell replication, modulation of target cell activities and/or immunogenicity. However, even if deletion of one or more amino acids from the N-terminus of the predicted extracellular domain of a Neutrokine-alphaSV polypeptide results in modification or loss of one or more functional activities of the polypeptide, other functional activities may still be retained. Thus, the ability of the shortened polypeptides to induce and/or bind to antibodies which recognize the complete or mature or extracellular domains of the polypeptides generally will be retained when less than the majority of the residues of the complete or mature or extracellular domains of the polypeptides are removed from the N-terminus. Whether a particular polypeptide lacking N-terminal residues of a complete polypeptide retains such immunologic activities can readily be determined by routine methods described herein and otherwise known in the art.

Accordingly, the present invention further provides polypeptides having one or more residues deleted from the amino terminus of the amino acid sequence of Neutrokine-alphaSV shown in SEQ ID NO:19, up to the glycine residue at position number 261, and polynucleotides encoding such polypeptides. In particular, the present invention provides polypeptides comprising the amino acid sequence of residues $n^4$-266 of SEQ ID NO:19, where $n^4$ is an integer in the range of the amino acid position of amino acid residues 73-261 of the amino acid sequence in SEQ ID NO:19, and 261 is the position of the first residue from the N-terminus of the predicted extracellular domain Neutrokine-alphaSV polypeptide (shown in SEQ ID NO:19).

More in particular, in certain embodiments, the invention provides polynucleotides encoding polypeptides comprising, or alternatively consisting of, an amino acid sequence selected from the group consisting of residues of Q-73 to L-266; G-74 to L-266; D-75 to L-266; L-76 to L-266; A-77 to L-266; S-78 to L-266; L-79 to L-266; R-80 to L-266; A-81 to L-266; E-82 to L-266; L-83 to L-266; Q-84 to L-266; G-85 to L-266; H-86 to L-266; H-87 to L-266; A-88 to L-266; E-89 to L-266; K-90 to L-266; L-91 to L-266; P-92 to L-266; A-93 to L-266; G-94 to L-266; A-95 to L-266; G-96 to L-266; A-97 to L-266; P-98 to L-266; K-99 to L-266; A-100 to L-266; G-101 to L-266; L-102 to L-266; E-103 to L-266; E-104 to L-266; A-105 to L-266; P-106 to L-266; A-107 to L-266; V-108 to L-266; T-109 to L-266; A-110 to L-266; G-111 to L-266; L-112 to L-266; K-113 to L-266; I-114 to L-266; F-115 to L-266; E-116 to L-266; P-117 to L-266; P-118 to L-266; A-119 to L-266; P-120 to L-266; G-121 to L-266; E-122 to L-266; G-123 to L-266; N-124 to L-266; S-125 to L-266; S-126 to L-266; Q-127 to L-266; N-128 to L-266; S-129 to L-266; R-130 to L-266; N-131 to L-266; K-132 to L-266; R-133 to L-266; A-134 to L-266; V-135 to L-266; Q-136 to L-266; G-137 to L-266; P-138 to L-266; E-139 to L-266; E-140 to L-266; T-141 to L-266; G-142 to L-266; S-143 to L-266; Y-144 to L-266; T-145 to L-266; F-146 to L-266; V-147 to L-266; P-148 to L-266; W-149 to L-266; L-150 to L-266; L-151 to L-266; S-152 to L-266; F-153 to L-266; K-154 to L-266; R-155 to L-266; G-156 to L-266; S-157 to L-266; A-158 to L-266; L-159 to L-266; E-160 to L-266; E-161 to L-266; K-162 to L-266; E-163 to L-266; N-164 to L-266; K-165 to L-266; I-166 to L-266; L-167 to L-266; V-168 to L-266; K-169 to L-266; E-170 to L-266; T-171 to L-266; G-172 to L-266; Y-173 to L-266; F-174 to L-266; F-175 to L-266; I-176 to L-266; Y-177 to L-266; G-178 to L-266; Q-179 to L-266; V-180 to L-266; L-181 to L-266; Y-182 to L-266; T-183 to L-266; D-184 to L-266; K-185 to L-266; T-186 to L-266; Y-187 to L-266; A-188 to L-266; M-189 to L-266; G-190 to L-266; H-191 to L-266; L-192 to L266; I-193 to L-266; Q-194 to L-266; R-194 to L-266; R-195 to L-266; K-196 to L-266; K-197 to L-266; V-198 to L-266; H-199 to L-266; V-200 to L-266; F-201 to L-266; G-202 to L-266; D-203 to L-266; E-204 to L-266; L-205 to L-266; S-206 to L-266; L-207 to L-266; V-208 to L-266; T-209 to L-266; L-210 to L-266; F-211 to L-266; R-212 to L-266; C-213 to L-266; I-214 to L-266; Q-215 to L-266; N-216 to L-266; M-217 to L-266; P-218 to L-266; E-219 to L-266; T-220 to L-266; L-221 to L-266; P-222 to L-266; N-223 to L-266; N-224 to L-266; S-225 to L-266; C-226 to L-266; Y-227 to L-266; S-228 to L-266; A-229 to L-266; G-230 to L-266; I-231 to L-266; A-232 to L-266; K-233 to L-266; L-234 to L-266; E-235 to L-266; E-236 to L-266; G-237 to L-266; D-238 to L-266; E-239 to L-266; L-240 to L-266; Q-241 to L-266; L-242 to L-266; A-243 to L-266; I-244 to L-266; P-245 to L-266; R-246 to L-266; E-247 to L-266; N-248 to L-266; A-249 to L-266; Q-250 to L-266; I-251 to L-266; S-252 to L-266; L-253 to L-266; D-254 to L-266; G-255 to L-266; D-256 to L-266; V-257 to L-266; T-258 to L-266; F-259 to L-266; F-260 to L-266; and G-261 to L-266 of SEQ ID NO:19. The present application is also directed to nucleic acid molecules comprising, or alternatively, consisting of, a polynucleotide sequence at least 80%, 85%, 90%, 92%, 95%, 96%, 97%, 98%, 99%, identical to the polynucleotide sequence encoding the Neutrokine-alpha and/or Neutrokine-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 80%, 85%, 90%, 92%, 95%, 96%, 97%, 98% or 99% identical to the amino acid sequence described above, and polynucleotides that encode such polypeptides.

Similarly, deletions of C-terminal amino acid residues of the predicted extracellular domain of Neutrokine-alphaSV up to the leucine residue at position 79 of SEQ ID NO:19 may retain some functional activity, such as, for example, ligand binding, the ability to stimulate lymphocyte (e.g., B cell) proliferation, differentiation, and/or activation, modulation of cell replication, modulation of target cell activities and/or immunogenicity. Polypeptides having further C-terminal deletions including Lcu-79 of SEQ ID NO:19 would not be expected to retain biological activities.

However, even if deletion of one or more amino acids from the C-terminus of a polypeptide results in modification or loss of one or more functional activities (e.g., biological activity) of the polypeptide, other functional activities may still be retained. Thus, the ability of the shortened polypeptide to induce and/or bind to antibodies which recognize the complete, mature or extracellular forms of the polypeptide generally will be retained when less than the majority of the residues of the complete, mature or extracellular forms of the polypeptide are removed from the C-terminus. Whether a particular polypeptide lacking C-terminal residues of the predicted extracellular domain retains such immunologic activities can readily be determined by routine methods described herein and otherwise known in the art.

Accordingly, the present invention further provides polypeptides having one or more residues from the carboxy terminus of the amino acid sequence of the predicted extracellular domain of Neutrokine-alphaSV shown in SEQ ID NO:19, up to the leucine residue at position 79 of SEQ ID NO:19, and polynucleotides encoding such polypeptides. In particular, the present invention provides polypeptides having the amino acid sequence of residues 73-$m^4$ of the amino acid sequence in SEQ ID NO:19, where $m^4$ is any integer in the range of the amino acid position of amino acid residues 79-265 of the amino acid sequence in SEQ ID NO: 19.

More in particular, in certain embodiments, the invention provides polynucleotides encoding polypeptides comprising, or alternatively consisting of, an amino acid sequence selected from the group consisting of residues Q-73 to L-265; Q-73 to K-264; Q-73 to L-263; Q-73 to A-262; Q-73 to G-261; Q-73 to F-260; Q-73 to F-259; Q-73 to T-258; Q-73 to V-257; Q-73 to D-256; Q-73 to G-255; Q-73 to D-254; Q-73 to L-253; Q-73 to S-252; Q-73 to I-251; Q-73 to Q-250; Q-73 to A-249; Q-73 to N-248; Q-73 to E-247; Q-73 to R-246; Q-73 to P-245; Q-73 to I-244; Q-73 to A-243; Q-73 to L-242; Q-73 to Q-241; Q-73 to L-240; Q-73 to E-239; Q-73 to D-238; Q-73 to G-237; Q-73 to E-236; Q-73 to E-235; Q-73 to L-234; Q-73 to K-233; Q-73 to A-232; Q-73 to I-231; Q-73 to G-230; Q-73 to A-229; Q-73 to S-228; Q-73 to Y-227; Q-73 to C-226; Q-73 to S-225; Q-73 to N-224; Q-73 to N-223; Q-73 to P-222; Q-73 to L-221; Q-73 to T-220; Q-73 to E-219; Q-73 to P-218; Q-73 to M-217; Q-73 to N-216; Q-73 to Q-215; Q-73 to I-214; Q-73 to C-213; Q-73 to R-212; Q-73 to F-211; Q-73 to L-210; Q-73 to T-209; Q-73 to V-208; Q-73 to L-207; Q-73 to S-206; Q-73 to L-205; Q-73 to E-204; Q-73 to D-203; Q-73 to G-202; Q-73 to F-201; Q-73 to V-200; Q-73 to H-199; Q-73 to V-198; Q-73 to K-197; Q-73 to K-196; Q-73 to R-195; Q-73 to Q-194; Q-73 to I-193; Q-73 to L-192; Q-73 to H-191; Q-73 to G-190; Q-73 to Q-7389; Q-73 to A-188; Q-73 to Y-187; Q-73 to T-186; Q-73 to K-185; Q-73 to D-184; Q-73 to T-183; Q-73 to Y-182; Q-73 to L-181; Q-73 to V-180; Q-73 to Q-179; Q-73 to G-178; Q-73 to Y-177; Q-73 to I-176; Q-73 to F-175; Q-73 to F-174; Q-73 to Y-173; Q-73 to G-172; Q-73 to T-171; Q-73 to E-170; Q-73 to K-169; Q-73 to V-168; Q-73 to L-167; Q-73 to I-166; Q-73 to K-165; Q-73 to N-164; Q-73 to E-163; Q-73 to K-162; Q-73 to E-161; Q-73 to E-160; Q-73 to L-159; Q-73 to A-158; Q-73 to S-157; Q-73 to G-156; Q-73 to R-155; Q-73 to K-154; Q-73 to F-153; Q-73 to S-152; Q-73 to L-151; Q-73 to L-150; Q-73 to W-149; Q-73 to P-148; Q-73 to V-147; Q-73 to F-146; Q-73 to T-145; Q-73 to Y-144; Q-73 to S-143; Q-73 to G-142; Q-73 to T-141; Q-73 to E-140; Q-73 to E-139; Q-73 to P-138; Q-73 to G-137; Q-73 to Q-136; Q-73 to V-135; Q-73 to A-134; Q-73 to R-133; Q-73 to K-132; Q-73 to N-131; Q-73 to R-130; Q-73 to S-129; Q-73 to N-128; Q-73 to Q-127; Q-73 to S-126; Q-73 to S-125; Q-73 to N-124; Q-73 to G-123; Q-73 to E-122; Q-73 to G-121; Q-73 to P-120; Q-73 to A-119; Q-73 to P-118; Q-73 to P-117; Q-73 to E-116; Q-73 to F-115; Q-73 to I-114; Q-73 to K-113; Q-73 to L-112; Q-73 to G-111; Q-73 to A-110; Q-73 to T-109; Q-73 to V-108; Q-73 to A-107; Q-73 to P-106; Q-73 to A-105; Q-73 to E-104; Q-73 to E-103; Q-73 to L-102; Q-73 to G-101; Q-73 to A-100; Q-73 to K-99; Q-73 to P-98; Q-73 to A-97; Q-73 to G-96; Q-73 to A-95; Q-73 to G-94; Q-73 to A-93; Q-73 to P-92; Q-73 to L-91; Q-73 to K-90; Q-73 to E-89; Q-73 to A-88; Q-73 to H-87; Q-73 to H-86; Q-73 to G-85; Q-73 to Q-84; Q-73 to L-83; Q-73 to E-82; Q-73 to A-81; Q-73 to R-80; Q-73 to L-79; and Q-73 to S-78 of SEQ ID NO:19. The present application is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the Neutrokine-alpha and/or Neutrokine-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 80%, 85%, 90%, 92%, 95%, 96%, 97%, 98% or 99% identical to the amino acid sequence described above, and polynucleotides that encode such polypeptides.

The invention also provides polypeptides having one or more amino acids deleted from both the amino and the carboxyl termini of the predicted extracellular domain of Neutrokine-alphaSV, which may be described generally as having residues $n^4$-$m^4$ of SEQ ID NO:19 where $n^4$ and $m^4$ are integers as defined above.

In another embodiment, a nucleotide sequence encoding a polypeptide consisting of a portion of the extracellular domain of the Neutrokine-alphaSV amino acid sequence encoded by the cDNA clone contained in the deposit having ATCC Accession No. 203518, where this portion excludes from 1 to about 260 amino acids from the amino terminus of the extracellular domain of the amino acid sequence encoded by cDNA clone contained in the deposit having ATCC Accession No. 203518, or from 1 to about 187 amino acids from the carboxy terminus of the extracellular domain of the amino acid sequence encoded by cDNA clone contained in the deposit having ATCC Accession No. 203518, or any combination of the above amino terminal and carboxy terminal deletions, of the entire extracellular domain of the amino acid sequence encoded by the cDNA clone contained in the deposit having ATCC Accession No. 203518.

As mentioned above, even if deletion of one or more amino acids from the N-terminus of a polypeptide results in modification or loss of one or more functional activities (e.g., biological activity) of the polypeptide, other functional activities may still be retained. Thus, the ability of a shortened Neutrokine-alphaSV mutein to induce and/or bind to antibodies which recognize the full-length or mature forms or the extracellular domain of the polypeptide generally will be retained when less than the majority of the residues of the full-length or mature or extracellular domain of the polypeptide are removed from the N-terminus. Whether a particular polypeptide lacking N-terminal residues of a complete polypeptide retains such immunologic activities can readily be determined by routine methods described herein and otherwise known in the art. It is not unlikely that a Neutrokine-alphaSV mutein with a large number of deleted N-terminal amino acid residues may retain functional (e.g., immunogenic) activities. In fact, peptides composed of as few as six Neutrokine-alphaSV amino acid residues may often evoke an immune response.

Accordingly, the present invention further provides polypeptides having one or more residues deleted from the amino terminus of the predicted full-length amino acid sequence of the Neutrokine-alphaSV shown in SEQ ID NO:19, up to the glycine residue at position number 261 of the sequence shown SEQ ID NO:19 and polynucleotides encoding such polypeptides. In particular, the present invention provides polypeptides comprising the amino acid sequence of residues $n^5$-266 of the sequence shown in SEQ ID NO:19, where $n^5$ is an integer in the range of the amino acid position of amino acid residues 1 to 261 of the amino acid sequence in SEQ ID NO:19.

More in particular, the invention provides polynucleotides encoding polypeptides comprising, or alternatively consisting of, an amino acid sequence selected from the group consisting of residues of D-2 to L-266; D-3 to L-266; S-4 to L-266; E-6 to L-266; R-7 to L-266; E-8 to L-266; Q-9 to L-266; S-10 to L-266; R-11 to L-266; L-12 to L-266; T-13 to L-266; S-14 to L-266; C-15 to L-266; L-16 to L-266; K-17 to L-266; K-18 to L-266; R-19 to L-266; E-20 to L-266; E-21 to L-266; M-22 to L-266; K-23 to L-266; L-24 to L-266; K-25 to L-266; E-26 to L-266; C-27 to L-266; V-28 to L-266; S-29 to L-266; I-30 to L-266; L-31 to L-266; P-32 to L-266; R-33 to L-266; K-34 to L-266; E-35 to L-266; S-36 to L-266; P-37 to L-266; S-38 to L-266; V-39 to L-266; R-40 to L-266; S-41 to L-266; S-42 to L-266; K-43 to L-266; D-44 to L-266; G-45 to L-266; K-46 to L-266; L-47 to L-266; L-48 to L-266; A-49 to L-266; A-50 to L-266; T-51 to L-266; L-52 to L-266; L-53 to L-266; L-54 to L-266; A-55 to L-266; L-56 to L-266; L-57 to L-266; S-58 to L-266; C-59 to L-266; C-60 to L-266; L-61 to L-266; T-62 to L-266; V-63 to L-266; V-64 to L-266; S-65 to L-266; F-66 to L-266; Y-67 to L-266; Q-68 to L-266; V-69 to L-266; A-70 to L-266; A-71 to L-266; T-72 to L-266; Q-73 to L-266; G-74 to L-266; D-75 to L-266; L-76 to L-266; A-77 to L-266; S-78 to L-266; L-79 to L-266; R-80 to L-266; A-81 to L-266; E-82 to L-266; L-83 to L-266; Q-84 to L-266; G-85 to L-266; H-86 to L-266; H-87 to L-266; A-88 to L-266; E-89 to L-266; K-90 to L-266; L-91 to L-266; P-92 to L-266; A-93 to L-266; G-94 to L-266; A-95 to L-266; G-96 to L-266; A-97 to L-266; P-98 to L-266; K-99 to L-266; A-100 to L-266; G-101 to L-266; L-102 to L-266; E-103 to L-266; E-104 to L-266; A-105 to L-266; P-106 to L-266; A-107 to L-266; V-108 to L-266; T-109 to L-266; A-110 to L-266; G-111 to L-266; L-112 to L-266; K-113 to L-266; I-114 to L-266; F-115 to L-266; E-116 to L-266; P-117 to L-266; P-118 to L-266; A-119 to L-266; P-120to L-266; G-121 to L-266; E-122 to L-266; G-123 to L-266; N-124 to L-266; S-125 to L-266; S-126 to L-266; Q-127 to L-266; N-128 to L-266; S-129 to L-266; R-130 to L-266; N-131 to L-266; K-132 to L-266; R-133 to L-266; A-134 to L-266; V-135 to L-266; Q-136 to L-266; G-137 to L-266; P-138 to L-266; E-139 to L-266; E-140 to L-266; T-141 to L-266; G-142 to L-266; S-143 to L-266; Y-144 to L-266; T-145 to L-266; F-146 to L-266; V-147 to L-266; P-148 to L-266; W-149 to L-266; L-150 to L-266; L-151 to L-266; S-152 to L-266; F-153 to L-266; K-154 to L-266; R-155 to L-266; G-156 to L-266; S-157 to L-266; A-158 to L-266; L-159 to L-266; E-160 to L-266; E-161 to L-266; K-162 to L-266; E-163 to L-266; N-164 to L-266; K-165 to L-266; 1-166 to L-266; L-167 to L-266; V-168 to L-266; K-169 to L-266; E-170 to L-266; T-171 to L-266; G-172 to L-266; Y-173 to L-266; F-174 to L-266; F-175 to L-266; -176 to L-266; Y-177 to L-266; G-178 to L-266; Q-179 to L-266; V-180 to L-266; L-181 to L-266; Y-182 to L-266; T-183 to L-266; D-184 to L-266; K-185 to L-266; T-186 to L-266; Y-187 to L-266; A-188 to L-266; M-189 to L-266; G-190 to L-266; H-191 to L-266; L-192 to L-266; I-193 to L-266; Q-194 to L-266; R-195 to L-266; K-196 to L-266; K-197 to L-266; V-198 to L-266; H-199 to L-266; V-200 to L-266; F-201 to L-266; G-202 to L-266; D-203 to L-266; E-204 to L-266; L-205 to L-266; S-206 to L-266; L-207 to L-266; V-208 to L-266; T-209 to L-266; L-210 to L-266; F-211 to L-266; R-212 to L-266; C-213 to L-266; I-214 to L-266; Q-215 to L-266; N-216 to L-266; M-217 to L-266; P-218 to L-266; E-219 to L-266; T-220 to L-266; L-221 to L-266; P-222 to L-266; N-223 to L-266; N-224 to L-266; S-225 to L-266; C-226 to L-266; Y-227 to L-266; S-228 to L-266; A-229 to L-266; G-230 to L-266; I-231 to L-266; A-232 to L-266; K-233 to L-266; L-234 to L-266; E-235 to L-266; E-236 to L-266; G-237 to L-266; D-238 to L-266; E-239 to L-266; L-240 to L-266; Q-241 to L-266; L-242 to L-266; A-243 to L-266; I-244 to L-266; P-245 to L-266; R-246 to L-266; E-247 to L-266; N-248 to L-266; A-249 to L-266; Q-250 to L-266; I-251 to L-266; S-252 to L-266; L-253 to L-266; D-254 to L-266; G-255 to L-266; D-256 to L-266; V-257 to L-266; T-258 to L-266; F-259 to L-266; F-260 to L-266; and G-261 to L-266 of SEQ ID NO:19. The present application is also directed to nucleic acid molecules comprising, or alternatively, consisting of, a polynucleotide sequence at least 80%, 85%, 90%, 92%, 95%, 96%, 97%, 98%, or 99% identical to the polynucleotide sequence encoding the Neutrokine-alpha and/or Neutrokine-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 80%, 85%, 90%, 92%, 95%, 96%, 97%, 98% or 99% identical to the amino acid sequence described above, and polynucleotides that encode such polypeptides.

Also as mentioned above, even if deletion of one or more amino acids from the C-terminus of a protein results in modification or loss of one or more functional activities (e.g., biological activities) of the protein, other functional activities may still be retained. Thus, the ability of a shortened Neutrokine-alphaSV mutein to induce and/or bind to antibodies which recognize the complete or mature form or the extracellular domain of the polypeptide generally will be retained when less than the majority of the residues of the complete or mature form or the extracellular domain of the polypeptide are removed from the C-terminus. Whether a particular polypeptide lacking C-terminal residues of a complete polypeptide retains such immunologic activities can readily be determined by routine methods described herein and otherwise known in the art. It is not unlikely that a Neutrokine-alphaSV mutein with a large number of deleted C-terminal amino acid residues may retain some functional (e.g., immunogenic) activities. In fact, peptides composed of as few as six Neutrokine-alphaSV amino acid residues may often evoke an immune response.

Accordingly, the present invention further provides in another embodiment, polypeptides having one or more residues deleted from the carboxy terminus of the amino acid sequence of the Neutrokine-alphaSV shown in SEQ ID NO:19, up to the glutamic acid residue at position number 6, and polynucleotides encoding such polypeptides. In particular, the present invention provides polypeptides comprising the amino acid sequence of residues 1-$m^5$ of SEQ ID NO: 19, where $m^5$ is an integer in the range of the amino acid position of amino acid residues 6 to 265 in the amino acid sequence of SEQ ID NO: 19.

More in particular, the invention provides polynucleotides encoding polypeptides comprising, or alternatively consisting of, an amino acid sequence selected from the group consisting of residues M-1 to L-265; M-1 to K-264; M-1 to L-263; M-1 to A-262; M-1 to G-261; M-1 to F-260; M-1 to F-259; M-1 to T-258; M-1 to V-257; M-1 to D-256; M-l to G-255; M-1 to D-254; M-1 to L-253; M-1 to S-252; M-1 to I-251; M-1 to Q-250; M-1 to A-249; M-1 to N-248; M-1 to E-247; M-1 to R-246; M-1 to P-245; M-1 to I-244; M-1 to A-243; M-1 to L-242; M-1 to Q-241; M-1 to L-240; M-1 to E-239; M-1 to D-238; M-1 to G-237; M-1 to E-236; M-1 to E-235; M-1 to L-234; M-1 to K-233; M-1 to A-232; M-1 to I-231; M-1 to G-230; M-1 to A-229; M-1 to S-228; M-1 to Y-227; M-1 to C-226; M-1 to S-225; M-1 to N-224; M-1 to N-223; M-1 to P-222; M-1 to L-221; M-1 to T-220; M-1 to E-219; M-1 to P-218; M-1 to M-217; M-1 to N-216; M-1 to Q-215; M-1 to I-214; M-1 to C-213; M-1 to R-212; M-1 to F-211; M-1 to L-210; M-1 to T-209; M-1 to V-208; M-1 to L-207; M-1 to S-206; M-1 to L-205; M-1 to E-204; M-1 to D-203; M-1 to G-202; M-1 to F-201; M-1 to V-200; M-1 to H-199; M-1 to V-198; M-1 to K-197; M-1 to K-196; M-1 to R-195; M-1 to Q-194; M-1 to I-193; M-1 to L-192; M-1 to H-191; M-1 to G-190; M-1 to M-189; M-1 to A-188; M-1 to Y-187; M-1 to T-186; M-1 to K-185; M-1 to D-184; M-1 to T-183; M-1 to Y-182; M-1 to L-181; M-1 to V-180; M-1 to Q-179; M-1 to G-178; M-1 to Y-177; M-1 to I-176; M-1 to F-175; M-1 to F-174; M-1 to Y-173; M-1 to G-172; M-1 to T-171; M-1 to E-170; M-1 to K-169; M-1 to V-168; M-1 to L-167; M-1 to I-166; M-1 to K-165; M-1 to N-164; M-1 to E-163; M-1 to K-162; M-1 to E-161; M-1 to E-160; M-1 to L-159; M-1 to A-158; M-1 to S-157; M-1 to G-156; M-1 to R-155; M-1 to K-154; M-1 to F-153; M-1 to S-152; M-1 to L-151; M-1 to L-150; M-1 to W-149; M-1 to P-148; M-1 to V-147; M-1 to F-146; M-1 to T-145; M-1 to Y-144; M-1 to S-143; M-1 to G-142; M-1 to T-141; M-1 to E-140; M-1 to E-139; M-1 to P-138; M-1 to G-137; M-1 to Q-136; M-1 to V-135; M-1 to A-134; M-1 to R-133; M-1 to K-132; M-1 to N-131; M-1 to R-130; M-1 to S-129; M-1 to N-128; M-1 to Q-127; M-1 to S-126; M-1 to S-125; M-1 to N-124; M-1 to G-123; M-1 to E-122; M-1 to G-121; M-1 to P-120; M-1 to A-119; M-1 to P-118; M-1 to P-117; M-1 to E-116; M-1 to F-115; M-1 to I-114; M-1 to K-113; M-1 to L-112; M-1 to G-111; M-1 to A-110; M-1 to T-109; M-1 to V-108; M-1 to A-107; M-1 to P-106; M-1 to A-105; M-1 to E-104; M-1 to E-103; M-1 to L-102; M-1 to G-101; M-1 to A-100; M-1 to K-99; M-1 to P-98; M-1 to A-97; M-1 to G-96; M-1 to A-95; M-1 to G-94; M-1 to A-93; M-1 to P-92; M-1 to L-91; M-1 to K-90; M-1 to E-89; M-1 to A-88; M-1 to H-87; M-1 to H-86; M-1 to G-85; M-1 to Q-84; M-1 to L-83; M-1 to E-82; M-1 to A-81; M-1 to R-80; M-1 to L-79; M-1 to S-78; M-1 to A-77; M-1 to L-76; M-1 to D-75; M-1 to G-74; M-1 to Q-73; M-1 to L-72; M-1 to A-71; M-1 to A-70; M-1 to V-69; M-1 to Q-68; M-1 to Y-67; M-1 to F-66; M-1 to S-65; M-1 to V-64; M-1 to V-63; M-1 to T-62; M-1 to L-61; M-1 to C-60; M-1 to C-59; M-1 to S-58; M-1 to L-57; M-1 to L-56; M-1 to A-55; M-1 to L-54; M-1 to L-53; M-1 to L-52; M-1 to T-51; M-1 to A-50; M-1 to A-49; M-1 to L-48; M-1 to L-47; M-1 to K-46; M-1 to G-45; M-1 to D-44; M-1 to K-43; M-1 to S-42; M-1 to S-41; M-1 to R-40; M-1 to V-39; M-1 to S-38; M-1 to P-37; M-1 to S-36; M-1 to E-35; M-1 to K-34; M-1 to R-33; M-1 to P-32; M-1 to L-31; M-1 to I-30; M-1 to S-29; M-1 to V-28; M-1 to C-27; M-1 to E-26; M-1 to K-25; M-1 to L-24; M-1 to K-23; M-1 to M-22; M-1 to E-21; M-1 to E-20; M-1 to R-19; M-1 to K-18; M-1 to K-17; M-1 to L-16; M-1 to C-15; M-1 to S-14; M-1 to T-13; M-1 to L-12; M-1 to R-11; M-1 to S-10; M-1 to Q-9; M-1 to E-8; M-1 to R-7; and M-1 to E-6 of SEQ ID NO:19. The present application is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the Neutrokine-alpha and/or Neutrokin-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 80%, 85%, 90%, 92%, 95%, 96%, 97%, 98%, or 99% identical to the amino acid sequence described above, and polynucleotides that encode such polypeptides.

The invention also provides polypeptides having one or more amino acids deleted from both the amino and the carboxyl tenmini of a Neutrokine-alphaSV polypeptide, which may be described generally as having residues $n^5$-$m^5$ of SEQ ID NO:19, where $n^5$ and $m^5$ are integers as defined above.

In additional embodiments, the present invention provides polypeptides comprising the amino acid sequence of residues 134-$m^6$ of SEQ ID NO:2, where $m^6$ is an integer from 140 to 285, corresponding to the position of the amino acid residue in SEQ ID NO:2. For example, the invention provides polynucleotides encoding polypeptides comprising, or alternatively consisting of, an amino acid sequence selected from the group consisting of residues A-134 to Leu-285; A-134 to L-284; A-134 to K-283; A-134 to L-282; A-134 to A-281; A-134 to G-280; A-134 to F-279; A-134 to F-278; A-134 to T-277; A-134 to V-276; A-134 to D-275; A-134 to G-274; A-134 to D-273; A-134 to L-272; A-134 to S-271; A-134 to I-270; A-134 to Q-269; A-134 to A-268; A-134 to N-267; A-134 to E-266; A-134 to R-265; A-134 to P-264; A-134 to I-263; A-134 to A-262; A-134 to L-261; A-134 to Q-260; A-134 to L-259; A-134 to E-258; A-134 to D-257; A-134 to G-256; A-134 to E-255; A-134 to E-254; A-134 to L-253; A-134 to K-252; A-134 to A-251; A-134 to I-250; A-134 to G-249; A-134 to A-248; A-134 to S-247; A-134 to Y-246; A-134 to C-245; A-134 to S-244; A-134 to N-243; A-134 to N-242; A-134 to P-241; A-134 to L-240; A-134 to T-239; A-134 to E-238; A-134 to P-237; A-134 to M-236; A-134 to N-235; A-134 to Q-234; A-134 to I-233; A-134 to C-232; A-134 to R-231; A-134 to F-230; A-134 to L-229; A-134 to T-228; A-134 to V-227; A-134 to L-226; A-134 to S-225; A-134 to L-224; A-134 to E-223; A-134 to D-222; A-134 to G-221; A-134 to F-220; A-134 to V-219; A-134 to H-218; A-134 to V-217; A-134 to K-216; A-134 to K-215; A-134 to R-214; A-134 to Q-213; A-134 to I-212; A-134 to L-211; A-134 to H-210; A-134 to G-209; A-134 to M-208; A-134 to A-207; A-134 to Y-206; A-134 to T-205; A-134 to K-204; A-134 to D-203; A-134 to T-202; A-134 to Y-201; A-134 to L-200; A-134 to V-199; A-134 to Q-198; A-134 to G-197; A-134 to Y-196; A-134 to I-195; A-134 to F-194; A-134 to F-193; A-134 to Y-192; A-134 to G-191; A-134 to T-190; A-134 to E-189; A-134 to K-188; A-134 to V-187; A-134 to L-186; A-134 to I-185; A-134 to K-184; A-134 to N-183; A-134 to E-182; A-134 to K-181; A-134 to E-180; A-134 to E-179; A-134 to L-178; A-134 to A-177; A-134 to S-176; A-134 to G-175; A-134 to R-174; A-134 to K-173; A-134 to F-172; A-134 to S-171; A-134 to L-170; A-134 to L-169;

A-134 to W-168; A-134 to P-167; A-134 to V-166; A-134 to F-165; A-134 to T-164; A-134 to Y-163; A-134 to S-162; A-134 to G-161; A-134 to K-160; A-134 to Q-159; A-134 to I-158; A-134 to T-157; A-134 to P-156; A-134 to T-155; A-134 to E-154; A-134 to S-153; A-134 to D-152; A-134 to A-151; A-134 to I-150; A-134 to L-149; A-134 to Q-148; A-134 to L-147; A-134 to C-146; A-134 to D-145; A-134 to Q-144; A-134 to T-143; A-134 to V-142; A-134 to T-141; A-134 to E-140 of SEQ ID NO:2. The present application is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the Neutrokine-alpha and/or Neutrokine-alphaSV polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 80%, 85%, 90%, 92%, 95%, 96%, 97%, 98% or 99% identical to the amino acid sequence described above, and polynucleotides that encode such polypeptides.

Additional preferred polypeptide fragments of the invention comprise, or alternatively consist of, an amino acid sequence selected from the group consisting of residues: M-1 to C-15; D-2 to L-16; D-3 to K-17; S-4 to K-18; T-5 to R-19; E-6 to E-20; R-7 to E-21; E-8 to M-22; Q-9 to K-23; S-10 to L-24; R-11 to K-25; L-12 to E-26; T-13 to C-27; S-14 to V-28; C-15 to S-29; L-16 to I-30; K-17 to L-31; K-18 to P-32; R-19 to R-33; E-20 to K-34; E-21 to E-35; M-22 to S-36; K-23 to P-37; L-24 to S-38; K-25 to V-39; E-26 to R-40; C-27 to S-41; V-28 to S-42; S-29 to K-43; I-30 to D-44; L-31 to G-45; P-32 to K-46; R-33 to L-47; K-34 to L-48; E-35 to A-49; S-36 to A-50; P-37 to T-51; S-38 to L-52; V-39 to L-53; R-40 to L-54; S-41 to A-55; S-42 to L-56; K-43 to L-57; D-44 to S-58; G-45 to C-59; K-46 to C-60; L-47 to L-61; L-48 to T-62; A-49 to V-63; A-50 to V-64; T-51 to S-65; L-52 to F-66; L-53 to Y-67; L-54 to Q-68; A-55 to V-69; L-56 to A-70; L-57 to A-71; S-58 to L-72; C-59 to Q-73; C-60 to G-74; L-61 to D-75; T-62 to L-76; V-63 to A-77; V-64 to S-78; S-65 to L-79; F-66 to R-80; Y-67 to A-81; Q-68 to E-82; V-69 to L-83; A-70 to Q-84; A-71 to G-85; L-72 to H-86; Q-73 to H-87; G-74 to A-88; D-75 to E-89; L-76 to K-90; A-77 to L-91; S-78 to P-92; L-79 to A-93; R-80 to G-94; A-81 to A-95; E-82 to G-96; L-83 to A-97; Q-84 to P-98; G-85 to K-99; H-86 to A-100; H-87 to G-101; A-88 to L-102; E-89 to E-103; K-90 to E-104; L-91 to A-105; P-92 to P-106; A-93 to A-107; G-94 to V-108; A-95 to T-109; G-96 to A-110; A-97 to G-111; P-98 to L-112; K-99 to K-113; A-100 to I-114; G-101 to F-115; L-102 to E-116; E-103 to P-117; E-104 to P-118; A-105 to A-119; P-106 to P-120; A-107 to G-121; V-108 to E-122; T-109 to G-123; A-110 to N-124; G-111 to S-125; L-112 to S-126; K-113 to Q-127; I-114 to N-128; F-115 to S-129; E-116 to R-130; P-117 to N-131; P-118 to K-132; A-119 to R-133; P-120 to A-134; G-121 to V-135; E-122 to Q-136; G-123 to G-137; N-124 to P-138; S-125 to E-139; S-126 to E-140; Q-127 to T-141; N-128 to V-142; S-129 to T-143; R-130 to Q-144; N-131 to D-145; K-132 to C-146; R-133 to L-147; A-134 to Q-148; V-135 to L-149; Q-136 to I-150; G-137 to A-151; P-138 to D-152; E-139 to S-153; E-140 to E-154; T-141 to T-155; V-142 to P-156; T-143 to T-157; Q-144 to I-158; D-145 to Q-159; C-146 to K-160; L-147 to G-161; Q-148 to S-162; L-149 to Y-163; I-150 to T-164; A-151 to F-165; D-152 to V-166; S-153 to P-167; E-154 to W-168; T-155 to L-169; P-156 to L-170; T-157 to S-171; I-158 to F-172; Q-159 to K-173; K-160 to R-174; G-161 to G-175; S-162 to S-176; Y-163 to A-177; T-164 to L-178; F-165 to E-179; V-166 to E-180; P-167 to K-181; W-168 to E-182; L-169 to N-183; L-170 to K-184; S-171 to I-185; F-172 to L-186; K-173 to V-187; R-174 to K-188; G-175 to E-189; S-176 to T-190; A-177 to G-191; L-178 to Y-192; E-179 to F-193; E-180 to F-194; K-181 to I-195; E-182 to Y-196; N-183 to G-197; K-184 to Q-198; I-185 to V-199; L-186 to L-200; V-187 to Y-201; K-188 to T-202; E-189 to D-203; T-190 to K-204; G-191 to T-205; Y-192 to Y-206; F-193 to A-207, F-194 to M-208; I-195 to G-209; Y-196 to H-210; G-197 to L-211; Q-198 to I-212; V-199 to Q-213; L-200 to R-214; Y-201 to K-215; T-202 to K-216; D-203 to V-217; K-204 to H-218; T-205 to V-219; Y-206 to F-220; A-207 to G-221; M-208 to D-222; G-209 to E-223; H-210 to L-224; L-211 to S-225; I-212 to L-226; Q-213 to V-227; R-214 to T-228; K-215 to L-229; K-216 to F-230; V-217 to R-231; H-218 to C-232; V-219 to I-233; F-220 to Q-234; G-221 to N-235; D-222 to M-236; E-223 to P-237; L-224 to E-238; S-225 to T-239; L-226 to L-240; V-227 to P-241; T-228 to N-242; L-229 to N-243; F-230 to S-244; R-231 to C-245; C-232 to Y-246; I-233 to S-247; Q-234 to A-248; N-235 to G-249; M-236 to I-250; P-237 to A-251; E-238 to K-252; T-239 to L-253; L-240 to E-254; P-241 to E-255; N-242 to G-256; N-243 to D-257; S-244 to E-258; C-245 to L-259; Y-246 to Q-260; S-247 to L-261; A-248 to A-262; G-249 to I-263; I-250 to P-264; A-251 to R-265; K-252 to E-266; L-253 to N-267; E-254 to A-268; E-255 to Q-269; G-256 to I-270; D-257 to S-271; E-258 to L-272; L-259 to D-273; Q-260 to G-274; L-261 to D-275; A-262 to V-276; I-263 to T-277; P-264 to F-278; R-265 to F-279; E-266 to G-280; N-267 to A-281; A-268 to L-282; Q-269 to K-283; I-270 to L-284; and S-271 to L-285 of SEQ ID NO:2. Preferably, these polypeptide fragments have one or more functional activities (e.g., biological activity, antigenicity, and immunogenicity) of Neutrokine-alpha and/or Neutrokine-alpha SV polypeptides of the invention and may be used, for example, to generate or screen for antibodies, as described further below. The present invention is also directed to polypeptides comprising, or alternatively, consisting of, an amino acid sequence at least 80%, 85%, 90%, 92%, 95%, 96%, 97%, 98% or 99% identical to an amino acid sequence described above. The present invention also encompasses the above amino acid sequences fused to a heterologous amino acid sequence as described herein. Polynucleotides encoding these polypeptides are also encompassed by the invention.

Additional preferred polypeptide fragments of the invention comprise, or alternatively consist of, an amino acid sequence selected from the group consisting of residues: M-1 to C-15; D-2 to L-16; D-3 to K-17; S-4 to K-18; T-5 to R-19; E-6 to E-20; R-7 to E-21; E-8 to M-22; Q-9 to K-23; S-10 to L-24; R-11 to K-25; L-12 to E-26; T-13 to C-27; S-14 to V-28; C-15 to S-29; L-16 to I-30; K-17 to L-31; K-18 to P-32; R-19 to R-33; E-20 to K-34; E-21 to E-35; M-22 to S-36; K-23 to P-37; L-24 to S-38; K-25 to V-39; E-26 to R-40; C-27 to S-41; V-28 to S-42; S-29 to K-43; I-30 to D-44; L-31 to G-45; P-32 to K-46; R-33 to L-47; K-34 to L-48; E-35 to A-49; S-36 to A-50; P-37 to T-51; S-38 to L-52; V-39 to L-53; R-40 to L-54; S-41 to A-55; S-42 to L-56; K-43 to L-57; D-44 to S-58; G-45 to C-59; K-46 to C-60; L-47 to L-61; L-48 to T-62; A-49 to V-63; A-50 to V-64; T-51 to S-65; L-52 to F-66; L-53 to Y-67; L-54 to Q-68; A-55 to V-69; L-56 to A-70; L-57 to A-71; S-58 to L-72; C-59 to Q-73; C-60 to G-74; L-61 to D-75; T-62 to L-76; V-63 to A-77; V-64 to S-78; S-65 to L-79; F-66 to R-80; Y-67 to A-81; Q-68 to E-82; V-69 to L-83; A-70 to Q-84; A-71 to G-85; L-72 to H-86; Q-73 to H-87; G-74 to A-88; D-75 to E-89; L-76 to K-90; A-77 to L-91; S-78 to P-92; L-79 to A-93; R-80 to G-94; A-81 to A-95; E-82 to G-96; L-83 to A-97; Q-84 to P-98; G-85 to K-99; H-86 to A-100; H-87 to G-101;

A-88 to L-102; E-89 to E-103; K-90 to E-104; L-91 to A-105; P-92 to P-106; A-93 to A-107; G-94 to V-108; A-95 to T-109; G-96 to A-110; A-97 to G-111; P-98 to L-112; K-99 to K-113; A-100 to I-114;G-101 to F-115; L-102 to E-116; E-103 to P-117; E-104 to P-118; A-105 to A-119; P-106 to P-120; A-107 to G-121; V-108 to E-122; T-109 to G-123; A-110 to N-124; G-111 to S-125; L-112 to S-126; K-113 to Q-127; I-114 to N-128; F-115 to S-129; E-116 to R-130; P-117 to N-131; P-118 to K-132; A-119 to R-133; P-120 to A-134; G-121 to V-135; E-122 to Q-136; G-123 to G-137; N-124 to P-138; S-125 to E-139; S-126 to E-140; Q-127 to T-141; N-128 to G-142; S-129 to S-143; R-130 to Y-144; N-131 to T-145; K-132 to F-146; R-133 to V-147; A-134 to P-148; V-135 to W-149; Q-136 to L-150; G-137 to L-151; P-138 to S-152; E-139 to F-153; E-140 to K-154; T-141 to R-155; G-142 to G-156; S-143 to S-157; Y-144 to A-158; T-145 to L-159; F-146 to E-160; V-147 to E-161; P-148 to K-162; W-149 to E-163; L-150 to N-164; L-151 to K-165; S-152 to I-166; F-153 to L-167; K-154 to V-168; R-155 to K-169; G-156 to E-170; S-157 to T-171; A-158 to G-172; L-159 to Y-173; E-160 to F-174; E-161 to F-175; K-162 to I-176; E-163 to Y-177; N-164 to G-178; K-165 to Q-179; I-166 to V-180; L-167 to L-181; V-168 to Y-182; K-169 to T-183; E-170 to D-184; T-171 to K-185; G-172 to T-186; Y-173 to Y-187; F-174 to A-188; F-175 to M-189; I-176 to G-190; Y-177 to H-191; G-178 to L-192; Q-179 to I-193; V-180 to Q-194; L-181 to R-195; Y-182 to K-196; T-183 to K-197; D-184 to V-198; K-185 to H-199; T-186 to V-200; Y-187 to F-201; A-188 to G-202; M-189 to D-203; G-190 to E-204; H-191 to L-205; L-192 to S-206; I-193 to L-207; Q-194 to V-208; R-295 to T-209; K-196 to L-210; K-197 to F-211; V-198 to R-212; H-199 to C-213; V-200 to I-214; F-201 to Q-215; G-202 to N-216; D-203 to M-217; E-204 to P-218; L-205 to E-219; S-206 to T-220; L-207 to L-221; V-208 to P-222; T-209 to N-223; L-210 to N-224; F-211 to S-225; R-212 to C-226; C-213 to Y-227; I-214 to S-228; Q-215 to A-229; N-216 to G-230; M-217 to I-231; P-218 to A-232; E-219 to K-233; T-220 to L-234; L-221 to E-235; P-222 to E-236; N-223 to G-237; N-224 to D-238; S-225 to E-239; C-226 to L-240; Y-227 to Q-241; S-228 to L-242; A-229 to A-243; G-230 to I-244; I-231 to P-245; A-232 to R-246; K-233 to E-247; L-234 to N-248; E-235 to A-249; E-236 to Q-250; G-237 to I-251; D-238 to S-252; E-239 to L-253; L-240 to D-254; Q-241 to G-255; L-242 to D-256; A-243 to V-257; I-244 to T-258; P-245 to F-259; R-246 to F-260; E-247 to G-261; N-248 to A-262; A-249 to L-263; Q-250 to K-264; I-251 to L-265; and S-252 to L-266 of SEQ ID NO:19. Preferably, these polypeptide fragments have one or more functional activities (e.g., biological activity, antigenicity, and immunogenicity) of Neutrokine-alpha and/or Neutrokine-alpha SV polypeptides of the invention and may be used, for example, to generate or screen for antibodies, as described further below. The present invention is also directed to polypeptides comprising, or alternatively, consisting of, an amino acid sequence at least 80%, 85%, 90%, 92%, 95% 96%, 97%, 98%, or 99% identical to an amino acid sequence described above. The present invention also encompasses the above amino acid sequences fused to a heterologous amino acid sequence as described herein. Polynucleotides encoding these polypeptides are also encompassed by the invention.

Additional preferred polypeptide fragments of the invention comprise, or alternatively consist of, an amino acid sequence selected from the group consisting of residues: M-1 to F-15; D-2 to C-16; E-3 to S-17; S-4 to E-18; A-5 to K-19; K-6 to G-20; T-7 to E-21; L-8 to D-22; P-9 to M-23; P-10 to K-24; P-11 to V-25; C-12 to G-26; L-13 to Y-27; C-14 to D-28; F-15 to P-29; C-16 to I-30; S-17 to T-31; E-18 to P-32; K-19 to Q-33; G-20 to K-34; E-21 to E-35; D-22 to E-36; M-23 to G-37; K-24 to A-38; V-25 to W-39; G-26 to F-40; Y-27 to G-41; D-28 to I-42; P-29 to C-43; I-30 to R-44; T-31 to D-45; P-32 to G-46; Q-33 to R-47; K-34 to L-48; E-35 to L-49; E-36 to A-50; G-37 to A-51; A-38 to T-52; W-39 to L-53; F-40 to L-54; G-41 to L-55; I-42 to A-56; C-43 to L-57; R-44 to L-58; D-45 to S-59; G-46 to S-60; R-47 to S-61; L-48 to F-62; L-49 to T-63; A-50 to A-64; A-51 to M-65; T-52 to S-66; L-53 to L-67; L-54 to Y-68; L-55 to Q-69; A-56 to L-70; L-57 to A-71; L-58 to A-72; S-59 to L-73; S-60 to Q-74; S-61 to A-75; F-62 to D-76; T-63 to L-77; A-64 to M-78; M-65 to N-79; S-66 to L-80; L-67 to R-81; Y-68 to M-82; Q-69 to E-83; L-70 to L-84; A-71 to Q-85; A-72 to S-86; L-73 to Y-87; Q-74 to R-88; A-75 to G-89; D-76 to S-90; L-77 to A-91; M-78 to T-92; N-79 to P-93; L-80 to A-94; R-81 to A-95; M-82 to A-96; E-83 to G-97; L-84 to A-98; Q-85 to P-99; S-86 to E-100; Y-87 to L-101; R-88 to T-102; G-89 to A-103; S-90 to G-104; A-91 to V-105; T-92 to K-106; P-93 to L-107; A-94 to L-108; A-95 to T-109; A-96 to P-110; G-97 to A-111; A-98 to A-112; P-99 to P-113; E-100 to R-114; L-101 to P-115; T-102 to H-116; A-103 to N-117; G-104 to S-118; V-105 to S-119; K-106 to R-120; L-107 to G-121; L-108 to H-122; T-109 to R-123; P-110 to N-124; A-111 to R-125; A-112 to R-126; P-113 to A-127; R-114 to F-128; P-115 to Q-129; H-116 to G-130; N-117 to P-131; S-118 to E-132; S-119 to E-133; R-120 to T-134; G-121 to E-135; H-122 to Q-136; R-123 to D-137; N-124 to V-138; R-125 to D-139; R-126 to L-140; A-127 to S-141; F-128 to A-142; Q-129 to P-143; G-130 to P-144; P-131 to A-145; E-132 to P-146; E-133 to C-147; T-134 to L-148; E-135 to P-149; Q-136 to G-150; D-137 to C-151; V-138 to R-152; D-139 to H-153; L-140 to S-154; S-141 to Q-155; A-142 to H-156; P-143 to D-157; P-144 to D-158; A-145 to N-159; P-146 to G-160; C-147 to M-161; L-148 to N-162; P-149 to L-163; G-150 to R-164; C-151 to N-165; R-152 to I-166; H-153 to I-167; S-154 to Q-168; Q-155 to D-169; H-156 to C-170; D-157 to L-171; D-158 to Q-172; N-159 to L-173; G-160 to I-174; M-161 to A-175; N-162 to D-176; L-163 to S-177; R-164 to D-178; N-165 to T-179; I-166 to P-180; I-167 to A-181; Q-168 to L-182; D-169 to E-183; C-170 to E-184; L-171 to K-185; Q-172 to E-186; L-173 to N-187; I-174 to K-188; A-175 to I-189; D-176 to V-190; S-177 to V-191; D-178 to R-192; T-179 to Q-193; P-180 to T-194; A-181 to G-195; L-182 to Y-196; E-183 to F-197; E-184 to F-198; K-185 to I-199; E-186 to Y-200; N-187 to S-201; K-188 to Q-202; I-189 to V-203; V-190 to L-204; V-191 to Y-205; R-192 to T-206; Q-193 to D-207; T-194 to P-208; G-195 to I-209; Y-196 to F-210; F-197 to A-211; F-198 to M-212; I-199 to G-213; Y-200 to H-214; S-201 to V-215; Q-202 to I-216; V-203 to Q-217; L-204 to R-218; Y-205 to K-219; T-206 to K-220; D-207 to V-221; P-208 to H-222; I-209 to V-223; F-210 to F-224; A-211 to G-225; M-212 to D-226; G-213 to E-227; H-214 to L-228; V-215 to S-229; I-216 to L-230; Q-217 to V-231; R-218 to T-232; K-219 to L-233; K-220 to F-234; V-221 to R-235; H-222 to C-236; V-223 to I-237; F-224 to Q-238; G-225 to N-239; D-226 to M-240; E-227 to P-241; L-228 to K-242; S-229 to T-243; L-230 to L-244; V-231 to P-245; T-232 to N-246; L-233 to N-247; F-234 to S-248; R-235 to C-249; C-236 to Y-250; I-237 to S-251; Q-238 to A-252; N-239 to G-253; M-240 to I-254; P-241 to A-255; K-242 to R-256; T-243 to L-257; L-244 to E-258; P-245 to E-259; N-246 to G-260; N-247 to D-261; S-248 to E-262; C-249 to I-263; Y-250 to Q-264; S-251 to L-265; A-252 to A-266; G-253 to I-267; I-254 to P-268; A-255 to R-269; R-256 to E-270; L-257 to N-271; E-258 to A-272; E-259 to Q-273; G-260 to I-274; D-261 to S-275; E-262 to R-276; I-263 to N-277; Q-264 to G-278; L-265 to D-279;

A-266 to D-280; I-267 to T-281; P-268 to F-282; R-269 to F-283; E-270 to G-284; N-271 to A-285; A-272 to L-286; Q-273 to K-287; I-274 to L-288; and S-275 to L-289; of SEQ ID NO:38. Preferably, these polypeptide fragments have one or more functional activities (e.g., biological activity, antigenicity, and immunogenicity) of Neutrokine-alpha and/or Neutrokine-alpha SV polypeptides of the invention and may be used, for example, to generate or screen for antibodies, as described further below. The present invention is also directed to polypeptides comprising, or alternatively, consisting of, an amino acid sequence at least 80%, 85%, 90%, 92%, 95%, 96%, 97%, 98%, or 99% identical to an amino acid sequence described above. The present invention also encompasses the above amino acid sequences fused to a heterologous amino acid sequence as described herein. Polynucleotides encoding these polypeptides are also encompassed by the invention.

It will be recognized by one of ordinary skill in the art that some amino acid sequences of the Neutrokine-alpha and Neutrokine-alphaSV polypeptides can be varied without significant effect of the structure or function of the polypeptide. If such differences in sequence are contemplated, it should be remembered that there will be critical areas on the polypeptide which determine activity.

Thus, the invention further includes variations of the Neutrokine-alpha polypeptide which show Neutrokine-alpha polypeptide functional activity (e.g., biological activity) or which include regions of Neutrokine-alpha polypeptide such as the polypeptide fragments described herein. The invention also includes variations of the Neutrokine-alphaSV polypeptide which show Neutrokine-alphaSV polypeptide functional activity (e.g., biological activity) or which include regions of Neutrokine-alphaSV polypeptide such as the polypeptide fragments described herein. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," Science 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and lie; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of FIGS. 1A and 1B (SEQ ID NO:2), or that encoded by the deposited cDNA plasmid, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the extracellular domain of the polypeptide is fused with another compound, such as a compound to increase the half-life of the polypeptide (for example, polyethylene glycol), or (iv) one in which the additional amino acids are fused to the extracellular domain of the polypeptide, such as an IgG Fc fusion region peptide or leader or secretory sequence or a sequence which is employed for purification of the extracellular domain of the polypeptide or a proprotein sequence. Such fragments, derivatives and analogs are deemed to be within the scope of those skilled in the art from the teachings herein.

Furthermore, the fragment, derivative or analog of the polypeptide of FIGS. 5A and 5B (SEQ ID NO:19), or that encoded by the deposited cDNA plasmid, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the extracellular domain of the polypeptide is fused with another compound, such as a compound to increase the half-life of the polypeptide (for example, polyethylene glycol), or (iv) one in which the additional amino acids are fused to the extracellular domain of the polypeptide, such as, a soluble biologically active fragment of another TNF ligand family member (e.g., CD40 Ligand), an IgG Fc fusion region peptide or leader or secretory sequence or a sequence which is employed for purification of the extracellular domain of the polypeptide or a proprotein sequence. Such fragments, derivatives and analogs are deemed to be within the scope of those skilled in the art from the teachings herein.

Thus, the Neutrokine-alpha and/or Neutrokine-alphaSV polypeptides of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 11).

TABLE II

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In one embodiment of the invention, polypeptide comprises, or alternatively consists of, the amino acid sequence of a Neutrokine-alpha or Neutrokine-alphaSV polypeptide having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions. Of course, in order of ever-increasing preference, it is highly preferable for a peptide or polypeptide to have an amino acid sequence which comprises the amino acid sequence of a Neutrokine-alpha polypeptide, which contains at least one, but not more than 10, 9, 8, 7, 6, 5, 4, 3, 2 or 1 conservative amino acid substitutions.

For example, site directed changes at the amino acid level of Neutrokine-alpha can be made by replacing a particular amino acid with a conservative substitution. Preferred conservative substitution mutations of the Neutrokine-alpha amino acid sequence provided in SEQ ID NO:2 include: M1 replaced with A, G, I, L, S, T, or V; D2 replaced with E; D3 replaced with E; S4 replaced with A, G, I, L, T, M, or V; T5 replaced with A, G, I, L, S, M, or V; E6 replaced with D; R7 replaced with H, or K; E8 replaced with D; Q9 replaced with N; S10 replaced with A, G, I, L, T, M, or V; R11 replaced with H, or K; L12 replaced with A, G, I, S, T, M, or V; T13 replaced with A, G, I, L, S, M, or V; S14 replaced with A, G, I, L, T, M, or V; L16 replaced with A, G, I, S, T, M, or V; K17 replaced with H, or R; K18 replaced with H, or R; R19 replaced with H, or K; E20 replaced with D; E21 replaced with D; M22 replaced with A, G, I, L, S, T, or V; K23 replaced with H, or R; L24 replaced with A, G, I, S, T, M, or V; K25 replaced with H, or R; E26 replaced with D; V28 replaced with A, G, I, L, S, T, or M; S29 replaced with A, G, I, L, T, M, or V; I30 replaced with A, G, L, S, T, M, or V; L31 replaced with A, G, I, S, T, M, or V; R33 replaced with H, or K; K34 replaced with H, or R; E35 replaced with D; S36 replaced with A, G, I, L, T, M, or V; S38 replaced with A, G, I, L, T, M, or V; V39 replaced with A, G, I, L, S, T, or M; R40 replaced with H, or K; S41 replaced with A, G, I, L, T, M, or V; S42 replaced with A, G, I, L, T, M, or V; K43 replaced with H, or R; D44 replaced with E; G45 replaced with A, I, L, S, T, M, or V; K46 replaced with H, or R; L47 replaced with A, G, I, S, T, M, or V; L48 replaced with A, G, I, S, T, M, or V; A49 replaced with G, I, L, S, T, M, or V; A50 replaced with G, I, L, S, T, M, or V; T51 replaced with A, G, I, L, S, M, or V; L52 replaced with A, G, I, S, T, M, or V; L53 replaced with A, G, I, S, T, M, or V; L54 replaced with A, G, I, S, T, M, or V; A55 replaced with G, I, L, S, T, M, or V; L56 replaced with A, G, I, S, T, M, or V; L57 replaced with A, G, I, S, T, M, or V; S58 replaced with A, G, I, L, T, M, or V; L61 replaced with A, G, I, S, T, M, or V; T62 replaced with A, G, I, L, S, M, or V; V63 replaced with A, G, I, L, S, T, or M; V64 replaced with A, G, I, L, S, T, or M; S65 replaced with A, G, I, L, T, M, or V; F66 replaced with W, or Y; Y67 replaced with F, or W; Q68 replaced with N; V69 replaced with A, G, I, L, S, T, or M; A70 replaced with G, I, L, S, T, M, or V; A71 replaced with G, I, L, S, T, M, or V; L72 replaced with A, G, I, S, T, M, or V; Q73 replaced with N; G74 replaced with A, I, L, S, T, M, or V; D75 replaced with E; L76 replaced with A, G, I, S, T, M, or V; A77 replaced with G, I, L, S, T, M, or V; S78 replaced with A, G, I, L, T, M, or V; L79 replaced with A, G, I, S, T, M, or V; R80 replaced with H, or K; A81 replaced with G, I, L, S, T, M, or V; E82 replaced with D; L83 replaced with A, G, I, S, T, M, or V; Q84 replaced with N; G85 replaced with A, I, L, S, T, M, or V; H86 replaced with K, or R; H87 replaced with K, or R; A88 replaced with G, I, L, S, T, M, or V; E89 replaced with D; K90 replaced with H, or R; L91 replaced with A, G, I, S, T, M, or V; A93 replaced with G, I, L, S, T, M, or V; G94 replaced with A, I, L, S, T, M, or V; A95 replaced with G, I, L, S, T, M, or V; G96 replaced with A, I, L, S, T, M, or V; A97 replaced with G, I, L, S, T, M, or V; K99 replaced with H, or R; A100 replaced with G, I, L, S, T, M, or V; G101 replaced with A, I, L, S, T, M, or V; L102 replaced with A, G, I, S, T, M, or V; E103 replaced with D; E104 replaced with D; A105 replaced with G, I, L, S, T, M, or V; A107 replaced with G, I, L, S, T, M, or V; V108 replaced with A, G, I, L, S, T, or M; T109 replaced with A, G, I, L, S, M, or V; A110 replaced with G, I, L, S, T, M, or V; G111 replaced with A, I, L, S, T, M, or V; L112 replaced with A, G, I, S, T, M, or V; K113 replaced with H, or R; I114 replaced with A, G, L, S, T, M, or V; F115 replaced with W, or Y; E116 replaced with D; A119 replaced with G, I, L, S, T, M, or V; G121 replaced with A, I, L, S, T, M, or V; E122 replaced with D; G123 replaced with A, I, L, S, T, M, or V; N124 replaced with Q; S125 replaced with A, G, I, L, T, M, or V; S126 replaced with A, G, I, L, T, M, or V; Q127 replaced with N; N128 replaced with Q; S129 replaced with A, G, I, L, T, M, or V; R130 replaced with H, or K; N131 replaced with Q; K132 replaced with H, or R; R133 replaced with H, or K; A134 replaced with G, I, L, S, T, M, or V; V135 replaced with A, G, L, S, T, or M; Q136 replaced with N; G137 replaced with A, I, L, S, T, M, or V; E139 replaced with D; E140 replaced with D; T141 replaced with A, G, I, L, S, M, or V; V142 replaced with A, G, I, L, S, T, or M; T143 replaced with A, G, I, L, S, M, or V; Q144 replaced with N; D145 replaced with E; L147 replaced with A, G, I, S, T, M, or V; Q148 replaced with N; L149 replaced with A, G, I, S, T, M, or V; I150 replaced with A, G, L, S, T, M, or V; A151 replaced with G, I, L, S, T, M, or V; D152 replaced with E; S153 replaced with A, G, I, L, T, M, or V; E154 replaced with D; T155 replaced with A, G, I, L, S, M, or V; T157 replaced with A, G, I, L, S, M, or V; I158 replaced with A, G, L, S, T, M, or V; Q159 replaced with N; K160 replaced with H, or R; G161 replaced with A, I, L, S, T, M, or V; S162 replaced with A, G, I, L, T, M, or V; Y163 replaced with F, or W; T164 replaced with A, G, I, L, S, M, or V; F165 replaced with W, or Y; V166 replaced with A, G, I, L, S, T, or M; W168 replaced with F, or Y; L169 replaced with A, G, I, S, T, M, or V; L170 replaced with A, G, I, S, T, M, or V; S171 replaced with A, G, I, L, T, M, or V; F172 replaced with W, or Y; K173 replaced with H, or R; R174 replaced with H, or K; G175 replaced with A, I, L, S, T, M, or V; S176 replaced with A, G, I, L, T, M, or V; A177 replaced with G, I, L, S, T, M, or V; L178 replaced with A, G, I, S, T, M, or V; E179 replaced with D; E180 replaced with D; K181 replaced with H, or R; E182 replaced with D; N183 replaced with Q; K184 replaced with H, or R; I185 replaced with A, G, L, S, T, M, or V; L186 replaced with A, G, I, S, T,M, or V; V187 replaced with A, G, I, L, S, T, or M; K188 replaced with H, or R; E189 replaced with D; T190 replaced with A, G, I, L, S, M, or V; G191 replaced with A, I, L, S, T, M, or V; Y192 replaced with F, or W; F193 replaced with W, or Y; F194 replaced with W, or Y; I195 replaced with A, G, L, S, T, M, or V; Y196 replaced with F, or W; G197 replaced with A, I, L, S, T, M, or V; Q198 replaced with N; V199 replaced with A, G, I, L, S, T, or M; L200 replaced with A, G, I, S, T, M, or V; Y201 replaced with F, or W; T202 replaced with A, G, I, L, S, M, or V; D203 replaced with E; K204 replaced with H, or R; T205 replaced with A, G, I, L, S, M, or V; Y206 replaced with F, or W; A207 replaced with G, I, L, S, T, M, or V; M208 replaced with A, G, I, L, S, T, or V; G209 replaced with A, I, L, S, T, M, or V; H210 replaced with K, or R; L211 replaced with A, G, I, S, T, M, or V; I212 replaced with A, G, L, S, T, M, or V; Q213 replaced with N; R214 replaced with H, or K; K215 replaced with H, or R; K216 replaced with H, or R; V217 replaced with A, G, I, L, S, T, or M; H218 replaced with K, or R; V219 replaced with A, G, I, L, S, T, or M; F220 replaced with W, or Y; G221 replaced with A, I, L, S, T, M, or V; D222 replaced with E; E223 replaced with D; L224 replaced with A, G, I, S, T, M, or V; S225 replaced with A, G, I, L, T, M, or V; L226 replaced with A, G, I, S, T, M, or V; V227 replaced with A, G, I, L, S, T, or M; T228 replaced with A, G, I, L, S, M, or V; L229 replaced with A, G, I, S, T, M, or V; F230 replaced with W, or Y; R231 replaced with H, or K; I233 replaced with A, G, L, S, T, M, or V; Q234 replaced with N; N235 replaced with Q; M236 replaced with A, G, I, L, S, T, or V; E238 replaced with D; T239 replaced with A, G, I, L, S, M, or V; L240 replaced with A, G, I, S, T, M, or V; N242 replaced with Q; N243 replaced with Q; S244 replaced with A, G, I, L, T, M, or V; Y246 replaced with F, or W; S247 replaced with A, G, I, L, T, M, or V; A248 replaced with G, I, L, S, T, M, or V; G249 replaced with A, I, L, S, T, M, or V; I250 replaced with A, G, L, S, T, M, or V; A251 replaced with G, I, L, S, T, M, or V; K252 replaced with H, or R; L253 replaced with A, G, I, S, T, M, or V; E254 replaced with D; E255 replaced with D; G256 replaced with A, I, L, S, T, M, or V; D257 replaced with E; E258 replaced with D; L259 replaced with A, G, I, S, T, M, or V; Q260 replaced with N; L261 replaced with A, G, I, S, T, M, or V; A262 replaced with G, I, L, S, T, M, or V; I263 replaced with A, G, L, S, T, M, or V; R265 replaced with H, or K; E266 replaced with D; N267 replaced with Q; A268 replaced with G, I, L, S, T, M, or V; Q269 replaced with N; I270 replaced with A, G, L, S, T, M, or V; S271 replaced with A, G, I, L, T, M, or V; L272 replaced with A, G, I, S, T, M, or V; D273 replaced with E; G274 replaced with A, I, L, S, T, M, or V; D275 replaced with E; V276 replaced with A, G, I, L, S, T, or M; T277 replaced with A, G, I, L, S, M, or V; F278 replaced with W, or Y; F279 replaced with W, or Y; G280 replaced with A, I, L, S, T, M, or V; A281 replaced with G, I, L, S, T, M, or V; L282 replaced with A, G, I, S, T, M, or V; K283 replaced with H, or R; L284 replaced with A, G, I, S, T, M, or V; and/or L285 replaced with A, G, I, S, T, M, or V. Polynucleotides encoding these polypeptides are also encompassed by the invention. The resulting Neutrokine-alpha proteins of the invention may be routinely screened for Neutrokine-alpha and/or Neutrokine-alphaSV functional activity and/or physical properties (such as, for example, enhanced or reduced stability and/or solubility). Preferably, the resulting proteins of the invention have an increased and/or a decreased Neutrokine-alpha and/or Neutrokine-alphaSV functional activity. More preferably, the resulting Neutrokine-alpha and/or Neutrokine-alphaSV proteins of the invention have more than one increased and/or decreased Neutrokine-alpha and/or Neutrokine-alpha SV functional activity and/or physical property.

In another embodiment, site directed changes at the amino acid level of Neutrokine-alphaSV can be made by replacing a particular amino acid with a conservative substitution. Preferred conservative substitution mutations of the Neutrokine-alphaSV amino acid sequence provided in SEQ ID NO:19 include: M1 replaced with A, G, I, L, S, T, or V; D2 replaced with E; D3 replaced with E; S4 replaced with A, G, I, L, T, M, or V; T5 replaced with A, G, I, L, S, M, or V; E6 replaced with D; R7 replaced with H, or K; E8 replaced with D; Q9 replaced with N; S10 replaced with A, G, I, L, T, M, or V; R11 replaced with H, or K; L12 replaced with A, G, I, S, T, M, or V; T13 replaced with A, G, I, L, S, M, or V; S14 replaced with A, G, I, L, T, M, or V; L16 replaced with A, G, I, S, T, M, or V; K17 replaced with H, or R; K18 replaced with H, or R; R19 replaced with H, or K; E20 replaced with D; E21 replaced with D; M22 replaced with A, G, I, L, S, T, or V; K23 replaced with H, or R; L24 replaced with A, G, I, S, T, M, or V; K25 replaced with H, or R; E26 replaced with D; V28 replaced with A, G, I, L, S, T, or M; S29 replaced with A, G, I, L, T, M, or V; I30 replaced with A, G, L, S, T, M, or V; L31 replaced with A, G, I, S, T. M, or V; R33 replaced with H, or K; K34 replaced with H, or R; E35 replaced with D; S36 replaced with A, G, I, L, T, M, or V; S38 replaced with A, G, I, L, T, M, or V; V39 replaced with A, G, I, L, S, T, or M; R40 replaced with H, or K; S41 replaced with A, G, I, L, T, M, or V; S42 replaced with A, G, I, L, T, M, or V; K43 replaced with H, or R; D44 replaced with E; G45 replaced with A, I, L, S, T, M, or V; K46 replaced with H, or R; L47 replaced with A, G, I, S, T, M, or V; L48 replaced with A, G, I, S, T, M, or V; A49 replaced with G, I, L, S, T, M, or V; A50 replaced with G, I, L, S, T, M, or V; T51 replaced with A, G, I, L, S, M, or V; L52 replaced with A, G, I, S, T, M, or V; L53 replaced with A, G, I, S, T, M, or V; L54 replaced with A, G, I, S, T, M, or V; A55 replaced with G, I, L, S, T, M, or V; L56 replaced with A, G, I, S, T, M, or V; L57 replaced with A, G, I, S, T, M, or V; S58 replaced with A, G, I, L, T, M, or V; L61 replaced with A, G, I, S, T, M, or V; T62 replaced with A, G, I, L, S, M, or V; V63 replaced with A, G, I, L, S, T, or M; V64 replaced with A, G, I, L, S, T, or M; S65 replaced with A, G, I, L, T, M, or V; F66 replaced with W, or Y; Y67 replaced with F, or W; Q68 replaced with N; V69 replaced with A, G, I, L, S, T, or M; A70 replaced with G, I, L, S, T, M, or V; A71 replaced with G, I, L, S, T, M, or V; L72 replaced with A, G, I, S, T, M, or V; Q73 replaced with N; G74 replaced with A, I, L, S, T, M, or V; D75 replaced with E; L76 replaced with A, G, I, S, T, M, or V; A77 replaced with G, I, L, S, T, M, or V; S78 replaced with A, G, I, L, T, M, or V; L79 replaced with A, G, I, S, T, M, or V; R80 replaced with H, or K; A81 replaced with G, I, L, S, T, M, or V; E82 replaced with D; L83 replaced with A, G, I, S, T, M, or V; Q84 replaced with N; G85 replaced with A, I, L, S, T, M, or V; H86 replaced with K, or R; H87 replaced with K, or R; A88 replaced with G, I, L, S, T, M, or V; E89 replaced with D; K90 replaced with H, or R; L91 replaced with A, G, I, S, T, M, or V; A93 replaced with G, I, L, S, T, M, or V; G94 replaced with A, I, L, S, T, M, or V; A95 replaced with G, I, L, S, T, M, or V; G96 replaced with A, I, L, S, T, M, or V; A97 replaced with G, I, L, S, T, M, or V; K99 replaced with H, or R; A100 replaced with G, I, L, S, T, M, or V; G101 replaced with A, I, L, S, T, M, or V; L102 replaced with A, G, I, S, T, M, or V; E103 replaced with D; E104 replaced with D; A105 replaced with G, I, L, S, T, M, or V; A107 replaced with G, I, L, S, T, M, or V; V108 replaced with A, G, I, L, S, T, or M; T109 replaced with A, G, I, L, S, M, or V; A110 replaced with G, I, L, S, T, M, or V; G111 replaced with A, I, L, S, T, M, or V; L112 replaced with A, G, I, S, T, M, or V; K113 replaced with H, or R; I114 replaced with A, G, L, S, T, M, or V; F115 replaced with W, or Y; E116 replaced with D; A119 replaced with G, I, L, S, T, M, or V; G121 replaced with A, I, L, S, T, M, or V; E122 replaced with D; G123 replaced with A, I, L, S, T, M, or V; N124 replaced with Q; S125 replaced with A, G, I, L, T, M, or V; S126 replaced with A, G, I, L, T, M, or V; Q127 replaced with N; N128 replaced with Q; S129 replaced with A, G, I, L, T, M, or V; R130 replaced with H, or K; N131 replaced with Q; K132 replaced with H, or R; R133 replaced with H, or K; A134 replaced with G,I, L, S, T, M, or V; V135 replaced with A, G, I, L, S, T, or M; Q136 replaced with N; G137 replaced with A, I, L, S, T, M, or V; E139 replaced with D; E140 replaced with D; T141 replaced with A, G, I, L, S, M, or V; G142 replaced with A, I, L, S, T, M, or V; S143 replaced with A, G, I, L, T, M, or V; Y144 replaced with F, or W; T145 replaced with A, G, I, L, S, M, or V; F146 replaced with W, or Y; V147 replaced with A, G, I, L, S, T, or M; W149 replaced with F, or Y; L150 replaced with A, G, I,S, T, M, or V; L151 replaced with A, G, I, S, T, M, or V; S152 replaced with A, G, I, L, T, M, or V; F153 replaced with W, or Y; K154 replaced with H, or R; R155 replaced with H, or K; G156 replaced with A, I, L, S, T, M, or V; S157 replaced with A, G, I, L, T, M, or V; A158 replaced with G, I, L, S, T, M, or V; L159 replaced with A, G, I, S, T, M, or V; E160 replaced with D; E161 replaced with D; K162 replaced with H, or R; E163 replaced with D; N164 replaced with Q; K165 replaced with H, or R; I166 replaced with A, G, L, S, T, M, or V; L167 replaced with A, G, I, S, T, M, or V; V168 replaced with A, G, I, L, S, T, or M; K169 replaced with H, or R; E170 replaced with D; T171 replaced with A, G, I, L, S, M, or V; G172 replaced with A, I, L, S, T, M, or V; Y173 replaced with F, or W; F174 replaced with W, or Y; F175 replaced with W, or Y; I176 replaced with A, G, L, S, T, M, or V; Y177 replaced with F, or W; G178 replaced with A, I, L, S, T, M, or V; Q179 replaced with N; V180 replaced with A, G, I, L, S, T, or M; L181 replaced with A, G, I, S, T, M, or V; Y182 replaced with F, or W; T183 replaced with A, G, I, L, S, M, or V; D184 replaced with E; K185 replaced with H, or R; T186 replaced with A, G, I, L, S, M, or V; Y187 replaced with F, or W; A188 replaced with G, I, L, S, T, M, or V; M189 replaced with A, G, I, L, S, T, or V; G190 replaced with A, I, L, S, T, M, or V; H191 replaced with K, or R; L192 replaced with A, G, I, S, T, M, or V; I193 replaced with A, G, L, S, T, M, or V; Q194 replaced with N; R195 replaced with H, or K; K196 replaced with H, or R; K197 replaced with H, or R; V198 replaced with A, G, I, L, S, T, or M; H199 replaced with K, or R; V200 replaced with A, G, I, L, S, T, or M; F201 replaced with W, or Y; G202 replaced with A, I, L, S, T, M, or V; D203 replaced with E; E204 replaced with D; L205 replaced with A, G, I, S, T, M, or V; S206 replaced with A, G, I, L, T, M, or V; L207 replaced with A, G, I, S, T, M, or V; V208 replaced with A, G, I, L, S, T, or M; T209 replaced with A, G, I, L, S, M, or V; L210 replaced with A, G, I, S, T, M, or V; F211 replaced with W, or Y; R212 replaced with H, or K; I214 replaced with A, G, L, S, T, M, or V; Q215 replaced with N; N216 replaced with Q; M217 replaced with A, G, I, L, S, T, or V; E219 replaced with D; T220 replaced with A, G, I, L, S, M, or V; L221 replaced with A, G, I, S, T, M, or V; N223 replaced with Q; N224 replaced with Q; S225 replaced with A, G, I, L, T, M, or V; Y227 replaced with F, or W; S228 replaced with A, G, I, L, T, M, or V; A229 replaced with G, I, L, S, T, M, or V; G230 replaced with A, I, L, S, T, M, or V; I231 replaced with A, G, L, S, T, M, or V; A232 replaced with G, I, L, S, T, M, or V; K233 replaced with H, or R; L234 replaced with A, G, I, S, T, M, or V; E235 replaced with D; E236 replaced with D; G237 replaced with A, I, L, S, T, M, or V; D238 replaced with E; E239 replaced with D; L240 replaced with A, G, I, S, T, M, or V; Q241 replaced with N; L242 replaced with A, G, I, S, T, M, or V; A243 replaced with G, I, L, S, T, M, or V; I244 replaced with A, G, L, S, T, M, or V; R246 replaced with H, or K; E247 replaced with D; N248 replaced with Q; A249 replaced with G, I, L, S, T, M, or V; Q250 replaced with N; I251 replaced with A, G, L, S, T, M, or V; S252 replaced with A, G, I, L, T, M, or V; L253 replaced with A, G, I, S, T, M, or V; D254 replaced with E; G255 replaced with A, I, L, S, T, M, or V; D256 replaced with E; V257 replaced with A, G, I, L, S, T, or M; T258 replaced with A, G, I, L, S, M, or V; F259 replaced with W, or Y; F260 replaced with W, or Y; G261 replaced with A, I, L, S, T, M, or V; A262 replaced with G, I, L, S, T, M, or V; L263 replaced with A, G, I, S, T, M, or V; K264 replaced with H, or R; L265 replaced with A, G, I, S, T, M, or V; and/or L266 replaced with A, G, I, S, T, M, or V. Polynucleotides encoding these polypeptides are also encompassed by the invention. The resulting Neutrokine-alpha proteins of the invention may be routinely screened for Neutrokine-alpha and/or Neutrokine-alphaSV functional activity and/or physical properties (such as, for example, enhanced or reduced stability and/or solubility). Preferably, the resulting proteins of the invention have an increased and/or a decreased Neutrokine-alpha and/or Neutrokine-alphaSV functional activity. More preferably, the resulting Neutrokine-alpha and/or Neutrokine-alphaSV proteins of the invention have more than one increased and/or decreased Neutrokine-alpha and/or Neutrokine-alpha SV functional activity and/or physical property.

In another embodiment, site directed changes at the amino acid level of Neutrokine-alpha can be made by replacing a particular amino acid with a conservative substitution. Preferred conservative substitution mutations of the Neutrokine-alpha amino acid sequence provided in SEQ ID NO:23 include: R1 replaced with H, or K; V2 replaced with A, G, I, L, S, T, or M; V3 replaced with A, G, I, L, S, T, or M; D4 replaced with E; L5 replaced with A, G, I, S, T, M, or V; S6 replaced with A, G, I, L, T, M, or V; A7 replaced with G, I, L, S, T, M, or V; A10 replaced with G, I, L, S, T, M, or V; L13 replaced with A, G, I, S, T, M, or V; G15 replaced with A, I, L, S, T, M, or V; R17 replaced with H, or K; H18 replaced with K, or R; S19 replaced with A, G, I, L, T, M, or V; Q20 replaced with N; H21 replaced with K, or R; D22 replaced with E; D23 replaced with E; N24 replaced with Q; G25 replaced with A, I, L, S, T, M, or V; M26 replaced with A, G, I, L, S, T, or V; N27 replaced with Q; L28 replaced with A, G, I, S, T, M, or V; R29 replaced with H, or K; N30 replaced with Q; R31 replaced with H, or K; T32 replaced with A, G, I, L, S, M, or V; Y33 replaced with F, or W; T34 replaced with A, G, I, L, S, M, or V; F35 replaced with W, or Y; V36 replaced with A, G, I, L, S, T, or M; W38 replaced with F, or Y; L39 replaced with A, G, I, S, T, M, or V; L40 replaced with A, G, I, S, T, M, or V; S41 replaced with A, G, I, L, T, M, or V; F42 replaced with W, or Y; K43 replaced with H, or R; R44 replaced with H, or K; G45 replaced with A, I, L, S, T, M, or V; N46 replaced with Q; A47 replaced with G, I, L, S, T, M, or V; L48 replaced with A, G, I, S, T, M, or V; E49 replaced with D; E50 replaced with D; K51 replaced with H, or R; E52 replaced with D; N53 replaced with Q; K54 replaced with H, or R; I55 replaced with A, G, L, S, T, M, or V; V56 replaced with A, G, I, L, S, T, or M; V57 replaced with A, G, I, L, S, T, or M; R58 replaced with H, or K; Q59 replaced with N; T60 replaced with A, G, I, L, S, M, or V; G61 replaced with A, I, L, S, T, M, or V; Y62 replaced with F, or W; F63 replaced with W, or Y; F64 replaced with W, or Y; I65 replaced with A, G, L, S, T, M, or V; Y66 replaced with F, or W; S67 replaced with A, G, I, L, T, M, or V; Q68 replaced with N; V69 replaced with A, G, I, L, S, T, or M; L70 replaced with A, G, I, S, T, M, or V; Y71 replaced with F, or W; T72 replaced with A, G, I, L, S, M, or V; D73 replaced with E; I75 replaced with A, G, L, S, T, M, or V; F76 replaced with W, or Y; A77 replaced with G, I, L, S, T, M, or V; M78 replaced with A, G, I, L, S, T, or V; G79 replaced with A, I, L, S, T, M, or V; H80 replaced with K, or R; V81 replaced with A, G, I, L, S, T, or M; I82 replaced with A, G, L, S, T, M, or V; Q83 replaced with N; R84 replaced with H, or K; K85 replaced with H, or R; K86 replaced with H, or R; V87 replaced with A, G, I, L, S, T, or M; H88 replaced with K, or R; V89 replaced with A, G, I, L, S, T, or M; F90 replaced with W, or Y; G91 replaced with A, I, L, S, T, M, or V; D92 replaced with E; E93 replaced with D; L94 replaced with A, G, I, S, T, M, or V; S95 replaced with A, G, I, L, T, M, or V; L96 replaced with A, G, I, S, T, M, or V; V97 replaced with A, G, I, L, S, T, or M; T98 replaced with A, G, I, L, S, M, or V; L99 replaced with A, G, I, S, T, M, or V; F100 replaced with W, or Y; R101 replaced with H, or K; I103 replaced with A, G, L, S, T, M, or V; Q104 replaced with N; N105 replaced with Q; M106 replaced with A, G, I, L, S, T, or V; K108 replaced with H, or R; T109 replaced with A, G, I, L, S, M, or V; L110 replaced with A, G, I, S, T, M, or V; N112 replaced with Q; N113 replaced with Q; S114 replaced with A, G, I, L, T, M, or V; Y116 replaced with F, or W; S117 replaced with A, G, I, L, T, M, or V; A118 replaced with G, I, L, S, T, M, or V; G119 replaced with A, I, L, S, T, M, or V; I120 replaced with A, G, L, S, T, M, or V; A121 replaced with G, I, L, S, T, M, or V;

R122 replaced with H, or K; L123 replaced with A, G, I, S, T, M, or V; E124 replaced with D; E125 replaced with D; G126 replaced with A, I, L, S, T, M, or V; D127 replaced with E; E128 replaced with D; I129 replaced with A, G, L, S, T, M, or V; Q130 replaced with N; L131 replaced with A, G, I, S, T, M, or V; A132 replaced with G, I, L, S, T, M, or V; I133 replaced with A, G, L, S, T, M, or V; R135 replaced with H, or K; E136 replaced with D; N137 replaced with Q; A138 replaced with G, I, L, S, T, M, or V; Q139 replaced with N; I140 replaced with A, G, L, S, T, M, or V; S141 replaced with A, G, I, L, T, M, or V; R142 replaced with H, or K; N143 replaced with Q; G144 replaced with A, I, L, S, T, M, or V; D145 replaced with E; D146 replaced with E; T147 replaced with A, G, I, L, S, M, or V; F148 replaced with W, or Y; F149 replaced with W, or Y; G150 replaced with A, I, L, S, T, M, or V; A151 replaced with G, I, L, S, T, M, or V; L152 replaced with A, G, I, S, T, M, or V; K153 replaced with H, or R; L154 replaced with A, G, I, S, T, M, or V; and/or L155 replaced with A, G, I, S, T, M, or V. Polynucleotides encoding these polypeptides are also encompassed by the invention. The resulting Neutrokine-alpha proteins of the invention may be routinely screened for Neutrokine-alpha and/or Neutrokine-alphaSV functional activity and/or physical properties (such as, for example, enhanced or reduced stability and/or solubility). Preferably, the resulting proteins of the invention have an increased and/or a decreased Neutrokine-alpha and/or Neutrokine-alphaSV functional activity. More preferably, the resulting Neutrokine-alpha and/or Neutrokine-alphaSV proteins of the invention have more than one increased and/or decreased Neutrokine-alpha and/or Neutrokine-alpha SV functional activity and/or physical property.

In another embodiment, site directed changes at the amino acid level of Neutrokine-alpha can be made by replacing a particular amino acid with a conservative substitution. Preferred conservative substitution mutations of the Neutrokine-alpha amino acid sequence provided in SEQ ID NO:38 include: M1 replaced with A, G, I, L, S, T, or V; D2 replaced with E; E3 replaced with D; S4 replaced with A, G, I, L, T, M, or V; A5 replaced with G, I, L, S, T, M, or V; K6 replaced with H, or R; T7 replaced with A, G, I, L, S, M, or V; L8 replaced with A, G, I, S, T, M, or V; L13 replaced with A, G, I, S, T, M, or V; F15 replaced with W, or Y; S17 replaced with A, G, I, L, T, M, or V; E18 replaced with D; K19 replaced with H, or R; G20 replaced with A, I, L, S, T, M, or V; E21 replaced with D; D22 replaced with E; M23 replaced with A, G, I, L, S, T, or V; K24 replaced with H, or R; V25 replaced with A, G, I, L, S, T, or M; G26 replaced with A, I, L, S, T, M, or V; Y27 replaced with F, or W; D28 replaced with E; I30 replaced with A, G, L, S, T, M, or V; T31 replaced with A, G, I, L, S, M, or V; Q33 replaced with N; K34 replaced with H, or R; E35 replaced with D; E36 replaced with D; G37 replaced with A, I, L, S, T, M, or V; A38 replaced with G, I, L, S, T, M, or V; W39 replaced with F, or Y; F40 replaced with W, or Y; G41 replaced with A, I, L, S, T, M, or V; I42 replaced with A, G, L, S, T, M, or V; R44 replaced with H, or K; D45 replaced with E; G46 replaced with A, I, L, S, T, M, or V; R47 replaced with H, or K; L48 replaced with A, G, I, S, T, M, or V; L49 replaced with A, G, I, S, T, M, or V; A50 replaced with G, I, L, S, T, M, or V; A51 replaced with G, I, L, S, T, M, or V; T52 replaced with A, G, I, L, S, M, or V; L53 replaced with A, G, I, S, T, M, or V; L54 replaced with A, G, I, S, T, M, or V; L55 replaced with A, G, I, S, T, M, or V; A56 replaced with G, I, L, S, T, M, or V; L57 replaced with A, G, I, S, T, M, or V; L58 replaced with A, G, I, S, T, M, or V; S59 replaced with A, G, I, L, T, M, or V; S60 replaced with A, G, I, L, T, M, or V; S61 replaced with A, G, I, L, T, M, or V; F62 replaced with W, or Y; T63 replaced with A, G, I, L, S, M, or V; A64 replaced with G, I, L, S, T, M, or V; M65 replaced with A, G, I, L, S, T, or V; S66 replaced with A, G, I, L, T, M, or V; L67 replaced with A, G, I, S, T, M, or V; Y68 replaced with F, or W; Q69 replaced with N; L70 replaced with A, G, I, S, T, M, or V; A71 replaced with G, I, L, S, T, M, or V; A72 replaced with G, I, L, S, T, M, or V; L73 replaced with A, G, I, S, T, M, or V; Q74 replaced with N; A75 replaced with G, I, L, S, T, M, or V; D76 replaced with E; L77 replaced with A, G, I, S, T, M, or V; M78 replaced with A, G, I, L, S, T, or V; N79 replaced with Q; L80 replaced with A, G, I, S, T, M, or V; R81 replaced with H, or K; M82 replaced with A, G, I, L, S, T, or V; E83 replaced with D; L84 replaced with A, G, I, S, T, M, or V; Q85 replaced with N; S86 replaced with A, G, I, L, T, M, or V; Y87 replaced with F, or W; R88 replaced with H, or K; G89 replaced with A, I, L, S, T, M, or V; S90 replaced with A, G, I, L, T, M, or V; A91 replaced with G, I, L, S, T, M, or V; T92 replaced with A, G, I, L, S, M, or V; A94 replaced with G, I, L, S, T, M, or V; A95 replaced with G, I, L, S, T, M, or V; A96 replaced with G, I, L, S, T, M, or V; G97 replaced with A, I, L, S, T, M, or V; A98 replaced with G, I, L, S, T, M, or V; E100 replaced with D; L101 replaced with A, G, I, S, T, M, or V; T102 replaced with A, G, I, L, S, M, or V; A103 replaced with G, I, L, S, T, M, or V; G104 replaced with A, I, L, S, T, M, or V; V105 replaced with A, G, I, L, S, T, or M; K106 replaced with H, or R; L107 replaced with A, G, I, S, T, M, or V; L108 replaced with A, G, I, S, T, M, or V; T109 replaced with A, G, I, L, S, M, or V; A111 replaced with G, I, L, S, T, M, or V; A112 replaced with G, I, L, S, T, M, or V; R114 replaced with H, or K; H116 replaced with K, or R; N117 replaced with Q; S118 replaced with A, G, I, L, T, M, or V; S119 replaced with A, G, I, L, T, M, or V; R120 replaced with H, or K; G121 replaced with A, I, L, S, T, M, or V; H122 replaced with K, or R; R123 replaced with H, or K; N124 replaced with Q; R125 replaced with H, or K; R126 replaced with H, or K; A127 replaced with G, I, L, S, T, M, or V; F128 replaced with W, or Y; Q129 replaced with N; G130 replaced with A, I, L, S, T, M, or V; E132 replaced with D; E133 replaced with D; T134 replaced with A, G, I, L, S, M, or V; E135 replaced with D; Q136 replaced with N; D137 replaced with E; V138 replaced with A, G, I, L, S, T, or M; D139 replaced with E; L140 replaced with A, G, I, S, T, M, or V; S141 replaced with A, G, I, L, T, M, or V; A142 replaced with G, I, L, S, T, M, or V; A145 replaced with G, I, L, S, T, or V; L148 replaced with A, G, I, S, T, M, or V; G150 replaced with A, I, L, S, T, M, or V; R152 replaced with H, or K; H153 replaced with K, or R; S154 replaced with A, G, I, L, T, M, or V; Q155 replaced with N; H156 replaced with K, or R; D157 replaced with E; D158 replaced with E; N159 replaced with Q; G160 replaced with A, I, L, S, T, M, or V; M161 replaced with A, G, I, L, S, T, or V; N162 replaced with Q; L163 replaced with A, G, I, S, T, M, or V; R164 replaced with H, or K; N165 replaced with Q; I166 replaced with A, G, L, S, T, M, or V; I167 replaced with A, G, L, S, T, M, or V; Q168 replaced with N; D169 replaced with E; L171 replaced with A, G, I, S, T, M, or V; Q172 replaced with N; L173 replaced with A, G, I, S, T, M, or V; I174 replaced with A, G, L, S, T, M, or V; A175 replaced with G, I, L, S, T, M, or V; D176 replaced with E; S177 replaced with A, G, I, L, T, M, or V; D178 replaced with E; T179 replaced with A, G, I, L, S, M, or V; A181 replaced with G, I, L, S, T, M, or V; L182 replaced with A, G, I, S, T, M, or V; E183 replaced with D; E184 replaced with D; K185 replaced with H, or R; E186 replaced with D; N187 replaced with Q; K188 replaced with H, or R; I189 replaced with A, G, L, S, T, M, or V; V190 replaced with A, G, I, L, S, T, or M; V191 replaced with A, G, I, L, S, T, or M; R192 replaced with H, or K; Q193 replaced with N; T194 replaced with A, G, I, L, S, M, or V; G195 replaced with A, I, L, S, T, M, or V; Y196 replaced with F, or W; F197 replaced with W, or Y; F198 replaced with W, or Y; I199replaced with A, G, L, S, T, M, or V; Y200 replaced with F, or W; S201 replaced with A, G, I, L, T, M, or V; Q202 replaced with N; V203 replaced with A, G, I, L, S, T, or M; L204 replaced with A, G, I, S, T, M, or V; Y205 replaced with F, or W; T206 replaced with A, G, I, L, S, M, or V; D207 replaced with E; I209 replaced with A, G, L, S, T, M, or V; F210 replaced with W, or Y; A211 replaced with G, I, L, S, T, M, or V; M212 replaced with A, G, I, L, S, T, or V; G213 replaced with A, I, L, S, T, M, or V; H214 replaced with K, or R; V215 replaced with A, G, I, L, S, T, or M; I216 replaced with A, G, L, S, T, M, or V; Q217 replaced with N; R218 replaced with H, or K; K219 replaced with H, or R; K220 replaced with H, or R; V221 replaced with A, G, I, L, S, T, or M; H222 replaced with K, or R; V223 replaced with A, G, I, L, S, T, or M; F224 replaced with W, or Y; G225 replaced with A, I, L, S, T, M, or V; D226 replaced with E; E227 replaced with D; L228 replaced with A, G, I, S, T, M, or V; S229 replaced with A, G, I, L, T, M, or V; L230 replaced with A, G, I, S, T, M, or V; V231 replaced with A, G, I, L, S, T, or M; T232 replaced with A, G, I, L, S, M, or V; L233 replaced with A, G, I, S, T, M, or V; F234 replaced with W, or Y; R235 replaced with H, or K; I237 replaced with A, G, L, S, T, M, or V; Q238 replaced with N; N239 replaced with Q; M240 replaced with A, G, I, L, S, T, or V; K242 replaced with H, or R; T243 replaced with A, G, I, L, S, M, or V; L244 replaced with A, G, I, S, T, M, or V; N246 replaced with Q; N247 replaced with Q; S248 replaced with A, G, I, L, T, M, or V; Y250 replaced with F, or W; S251 replaced with A, G, I, L, T, M, or V; A252 replaced with G, I, L, S, T, M, or V; G253 replaced with A, I, L, S, T, M, or V; I254 replaced with A, G, L, S, T, M, or V; A255 replaced with G, I, L, S, T, M, or V; R256 replaced with H, or K; L257 replaced with A, G, I, S, T, M, or V; E258 replaced with D; E259 replaced with D; G260 replaced with A, I, L, S, T, M, or V; D261 replaced with E; E262 replaced with D; I263 replaced with A, G, L, S, T, M, or V; Q264 replaced with N; L265 replaced with A, G, I, S, T, M, or V; A266 replaced with G, I, L, S, T, M, or V; I267 replaced with A, G, L, S, T, M, or V; R269 replaced with H, or K; E270 replaced with D; N271 replaced with Q; A272 replaced with G, I, L, S, T, M, or V; Q273 replaced with N; I274 replaced with A, G, L, S, T, M, or V; S275 replaced with A, G, I, L, T, M, or V; R276 replaced with H, or K; N277 replaced with Q; G278 replaced with A, I, L, S, T, M, or V; D279 replaced with E; D280 replaced with E; T281 replaced with A, G, I, L, S, M, or V; F282 replaced with W, or Y; F283 replaced with W, or Y; G284 replaced with A, I, L, S, T, M, or V; A285 replaced with G, I, L, S, T, M, or V; I286 replaced with A, G, I, S, T, M, or V; K287 replaced with H, or R; L288 replaced with A, G, I, S, T, M, or V; and/or L289 replaced with A, G, I, S, T, M, or V. Polynucleotides encoding these polypeptides are also encompassed by the invention. The resulting Neutrokine-alpha proteins of the invention may be routinely screened for Neutrokine-alpha and/or Neutrokine-alphaSV functional activity and/or physical properties (such as, for example, enhanced or reduced stability and/or solubility). Preferably, the resulting proteins of the invention have an increased and/or a decreased Neutrokine-alpha and/or Neutrokine-alphaSV functional activity. More preferably, the resulting Neutrokine-alpha and/or Neutrokine-alphaSV proteins of the invention have more than one increased and/or decreased Neutrokine-alpha and/or Neutrokine-alpha SV functional activity and/or physical property.

Amino acids in the Neutrokine-alpha and/or Neutrokine-alphaSV polypeptides of the present invention that are essential for function can be identified by methods known in the art, such as site-directed mutagenesis or alanine-scanning mutagenesis (Cunningham and Wells, Science 244:1081-1085 (1989)). The latter procedure introduces single alanine mutations at every residue in the molecule. The resulting mutant molecules are then tested for functional activity, such ligand binding and the ability to stimulate lymphocyte (e.g., B cell) as, for example, proliferation, differentiation, and/or activation.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).

In another embodiment, the invention provides for polypeptides having amino acid sequences containing non-conservative substitutions of the amino acid sequence provided in SEQ ID NO:2. For example, non-conservative substitutions of the Neutrokine-alpha protein sequence provided in SEQ ID NO:2 include: M1 replaced with D, E, H, K, R, N, Q, F, W, Y, P, or C; D2 replaced with H, K, R, A, G, I, L, S, T, M, V, N, Q, F, W, Y, P, or C; D3 replaced with H, K, R, A, G, I, L, S, T, M, V, N, Q, F, W, Y, P, or C; S4 replaced with D, E, H, K, R, N, Q, F, W, Y, P, or C; T5 replaced with D, E, H, K, R, N, Q, F, W, Y, P, or C; E6 replaced with H, K, R, A, G, I, L, S, T, M, V, N, Q, F, W, Y, P, or C; R7 replaced with D, E, A, G, I, L, S, T, M, V, N, Q, F, W, Y, P, or C; E8 replaced with H, K, R, A, G, I, L, S, T, M, V, N, Q, F, W, Y, P, or C; Q9 replaced with D, E, H, K, R, A, G, I, L, S, T, M, V, F, W, Y, P, or C; S10 replaced with D, E, H, K, R, N, Q, F, W, Y, P, or C; R11 replaced with D, E, A, G, I, L, S, T, M, V, N, Q, F, W, Y, P, or C; L12 replaced with D, E, H, K, R, N, Q, F, W, Y, P, or C; T13 replaced with D, E, H, K, R, N, Q, F, W, Y, P, or C; S14 replaced with D, E, H, K, R, N, Q, F, W, Y, P, or C; C15 replaced with D, E, H, K, R, A, G, I, L, S, T, M, V, N, Q, F, W, Y, or P; L16 replaced with D, E, H, K, R, N, Q, F, W, Y, P, or C; K17 replaced with D, E, A, G, I, L, S, T, M, V, N, Q, F, W. Y, P, or C; K18 replaced with D, E, A, G, I, L, S, T, M, V, N, Q, F, W, Y, P, or C; R19 replaced with D, E, A, G, I, L, S, T, M, V, N, Q, F, W, Y, P, or C; E20 replaced with H, K, R, A, G, I, L, S, T, M, V, N, Q, F, W, Y, P, or C; E21 replaced with H, K, R, A, G, I, L, S, T, M, V, N, Q, F, W, Y, P, or C; M22 replaced with D, E, H, K, R, N, Q, F, W, Y, P, or C; K23 replaced with D, E, A, G, I, L, S, T, M, V, N, Q, F, W, Y, P, or C; L24 replaced with D, E, H, K, R, N, Q, F, W, Y, P, or C; K25 replaced with D, E, A, G, I, L, S, T, M, V, N, Q, F, W, Y, P, or C; E26 replaced with H, K, R, A, G, I, L, S, T, M, V, N, Q, F, W, Y, P, or C; C27 replaced with D, E, H, K, R, A, G, I, L, S, T, M, V, N, Q, F, W, Y, or P; V28 replaced with D, E, H, K, R, N, Q, F, W, Y, P, or C; S29 replaced with D, E, H, K, R, N, Q, F, W, Y, P, or C; I30 replaced with D, E, H, K, R, N, Q, F, W, Y, P, or C; L31 replaced with D, E, H, K, R, N, Q, F, W, Y, P, or C; P32 replaced with D, E, H, K, R, A, G, I, L, S, T, M, V, N, Q, F, W, Y, or C; R33 replaced with D, E, A, G, I, L, S, T, M, V, N, Q, F, W, Y, P, or C; K34 replaced with D, E, A, G, I, L, S, T, M, V, N, Q, F, W, Y, P, or C; E35 replaced with H, K, R, A, G, I, L, S, T, M, V, N, Q, F, W,Y, P, or C; S36 replaced with D, E, H, K, R, N, Q, F, W, Y, P, or C; P37 replaced with D, E, H, K, R, A, G, I, L, S, T, M, V, N, Q, F, W, Y, or C; S38 replaced with D, E, H, K, R, N, Q, F, W, Y, P, or C; V39 replaced with D, E, H, K, R, N, Q, F, W, Y, P, or C; R40 replaced with D, E, A, G, I, L, S, T, M, V, N, Q, F, W, Y, P, or C; S41 replaced with D, E, H, K, R, N, Q, F, W, Y, P, or C; S42 replaced with D, E, H, K, R, N, Q, F, W, Y, P, or C; K43 replaced with D, E, A, G, I, L, S, T, M, V, N, Q, F, W, Y, P, or C; D44 replaced with H, K, R, A, G, I, L, S, T, M, V, N, Q, F, W, Y, P, or C; G45 replaced with D, E, H, K, R, N, Q, F, W, Y, P, or C; K46 replaced with D, E, A, G, I, L, S, T, M, V, N, Q, F, W, Y, P, or C; L47 replaced with D, E, H, K, R, N, Q, F, W, Y, P, or C; L48 replaced with D, E, H, K, R, N, Q, F, W, Y, P, or C; A49 replaced with D, E, H, K, R, N, Q, F, W, Y, P, or C; A50 replaced with D, E, H, K, R, N, Q, F, W, Y, P, or C; T51 replaced with D, E, H, K, R, N, Q, F, W, Y, P, or C; L52 replaced with D, E, H, K, R, N, Q, F, W, Y, P, or C; L53 replaced with D, E, H, K, R, N, Q, F, W, Y, P, or C; L54 replaced with D, E, H, K, R, N, Q, F, W, Y, P, or C; A55 replaced with D, E, H, K, R, N, Q, F, W, Y, P, or C; L56 replaced with D, E, H, K, R, N, Q, F, W, Y, P, or C; L57 replaced with D, E, H, K, R, N, Q, F, W, Y, P, or C; S58 replaced with D, E, H, K, R, N, Q, F, W, Y, P, or C; C59 replaced with D, E, H, K, R, A, G, I, L, S, T, M, V, N, Q, F, W, Y, or P; C60 replaced with D, E, H, K, R, A, G, I, L, S, T, M, V, N, Q, F, W, Y, or P; L61 replaced with D, E, H, K, R, N, Q, F, W, Y, P, or C; T62 replaced vith D, E, H, K, R, N, Q, F, W, Y, P, or C; V63 replaced with D, E, H, K, R, N, Q, F, W, Y, P, or C; V64 replaced with D, E, H, K, R, N, Q, F, W, Y, P, or C; S65 replaced with D, E, H, K, R, N, Q, F, W, Y, P, or C; F66 replaced with D, E, H, K, R, N, Q, A, G, I, L, S, T, M, V, P, or C; Y67 replaced with D, E, H, K, R, N, Q, A, G, I, L, S, T, M, V, P, or C; Q68 replaced with D, E, H, K, R, A, G, I, L, S, T, M, V, F, W, Y, P, or C; V69 replaced with D, E, H, K, R, N, Q, F, W, Y, P, or C; A70 replaced with D, E, H, K, R, N, Q, F, W, Y, P, or C; A71 replaced with D, E, H, K, R, N, Q, F, W, Y, P, or C; L72 replaced with D, E, H, K, R, N, Q, F, W, Y, P, or C; Q73 replaced with D, E, H, K, R, A, G, I, L, S, T, M, V, F, W, Y, P, or C; G74 replaced with D, E, H, K, R, N, Q, F, W, Y, P, or C; D75 replaced with H, K, R, A, G, I, L, S, T, M, V, N, Q, F, W, Y, P, or C; L76 replaced with D, E, H, K, R, N, Q, F, W, Y, P, or C; A77 replaced with D, E, H, K, R, N, Q, F, W, Y, P, or C; S78 replaced with D, E, H, K, R, N, Q, F, W, Y, P, or C; L79 replaced with D, E, H, K, R, N, Q, F, W, Y, P, or C; R80 replaced with D, E, A, G, I, L, S, T, M, V, N, Q, F, W, Y, P, or C; A81 replaced with D, E, H, K, R, N, Q, F, W, Y, P, or C; E82 replaced with H, K, R, A, G, I, L, S, T, M, V, N, Q, F, W, Y, P, or C; L83 replaced with D, E, H, K, R, N, Q, F, W, Y, P, or C; Q84 replaced with D, E, H, K, R, A, G, I, L, S, T, M, V, F, W, Y, P, or C; G85 replaced with D, E, H, K, R, N, Q, F, W, Y, P, or C; H86 replaced with D, E, A, G, I, L, S, T, M, V, N, Q, F, W, Y, P, or C; H87 replaced with D, E, A, G, I, L, S, T, M, V, N, Q, F, W, Y, P, or C; A88 replaced with D, E, H, K, R, N, Q, F, W, Y, P, or C; E89 replaced with H, K, R, A, G, I, L, S, T, M, V, N, Q, F, W, Y, P, or C; K90 replaced with D, E, A, G, I, L, S, T, M, V, N, Q, F, W, Y, P, or C; L91 replaced with D, E, H, K, R, N, Q, F, W, Y, P, or C; P92 replaced with D, E, H, K, R, A, G, I, L, S, T, M, V, N, Q, F, W, Y, or C; A93 replaced with D, E, H, K, R, N, Q, F, W, Y, P, or C; G94 replaced with D, E, H, K, R, N, Q, F, W, Y, P, or C; A95 replaced with D, E, H, K, R, N, Q, F, W, Y, P, or C; G96 replaced with D, E, H, K, R, N, Q, F, W, Y, P, or C; A97 replaced with D, E, H, K, R, N, Q, F, W, Y, P, or C; P98 replaced with D, E, H, K, R, A, G, I, L, S, T, M, V, N, Q, F, W, Y, or C; K99 replaced with D, E, A, G, I, L, S, T, M, V, N, Q, F, W, Y, P, or C; A100 replaced with D, E, H, K, R, N, Q, F, W, Y, P, or C; G101 replaced with D, E, H, K, R, N, Q, F, W, Y, P, or C; L102 replaced with D, E, H, K, R, N, Q, F, W, Y, P, or C; E103 replaced with H, K, R, A, G, I, L, S, T, M, V, N, Q, F, W, Y, P, or C; E104 replaced with H, K, R, A, G, I, L, S, T, M, V, N, Q, F, W, Y, P, or C; A105 replaced with D, E, H, K, R, N, Q, F, W, Y, P, or C; P106 replaced with D, E, H, K, R, A, G, I, L, S, T, M, V, N, Q, F, W, Y, or C; A107 replaced with D, E, H, K, R, N, Q, F, W, Y, P, or C; V108 replaced with D, E, H, K, R, N, Q, F, W, Y, P, or C; T109 replaced with D, E, H, K, R, N, Q, F, W, Y, P, or C; A110 replaced with D, E, H, K, R, N, Q, F, W, Y, P, or C; G111 replaced with D, E, H, K, R, N, Q, F, W, Y, P, or C; L112 replaced with D, E, H, K, R, N, Q, F, W, Y, P, or C; K113 replaced with D, E, A, G, I, L, S, T, M, V, N, Q, F, W, Y, P, or C; I114 replaced with D, E, H, K, R, N, Q, F, W, Y, P, or C; F115 replaced with D, E, H, K, R, N, Q, A, G, I, L, S, T, M, V, P, or C; E116 replaced with H, K, R, A, G, I, L, S, T, M, V, N, Q, F, W, Y, P, or C; P117 replaced with D, E, H, K, R, A, G, I, L, S, T, M, V, N, Q, F, W, Y, or C; P118 replaced with D, E, H, K, R, A, G, I, L, S, T, M, V, N, Q, F, W, Y, or C; A119 replaced with D, E, H, K, R, N, Q, F, W, Y, P, or C; P120 replaced with D, E, H, K, R, A, G, I, L, S, T, M, V, N, Q, F, W, Y, or C; G121 replaced with D, E, H, K, R, N, Q, F, W, Y, P, or C; E122 replaced with H, K, R, A, G, I, L, S, T, M, V, N, Q, F, W, Y, P, or C; G123 replaced with D, E, H, K, R, N, Q, F, W, Y, P, or C; N124 replaced with D, E, H, K, R, A, G, I, L, S, T, M, V, F, W, Y, P, or C; S125 replaced with D, E, H, K, R, N, Q, F, W, Y, P, or C; S126 replaced with D, E, H, K, R, N, Q, F, W, Y, P, or C; Q127 replaced with D, E, H, K, R, A, G, I, L, S, T, M, V, F, W, Y, P, or C; N128 replaced with D, E, H, K, R, A, G, I, L, S, T, M, V, F, W, Y, P, or C; S129 replaced with D, E, H, K, R, N, Q, F, W, Y, P, or C; R130 replaced with D, E, A, G, I, L, S, T, M, V, N, Q, F, W, Y, P, or C; N131 replaced with D, E, H K, R, A, G, I, L, S, T, M, V, F, W, Y, P, or C; K132 replaced with D, E, A, G, I, L, S, T, M, V, N, Q, F, W, Y, P, or C; R133 replaced with D, E, A, G, I, L, S, T, M, V, N, Q, F, W, Y, P, or C; A134 replaced with D, E, H, K, R, N, Q, F, W, Y, P, or C; V135 replaced with D, E, H, K, R, N, Q, F, W, Y, P, or C; Q136 replaced with D, E, H, K, R, A, G, I, L, S, T, M, V, F, W, Y, P, or C; G137 replaced with D, E, H, K, R, N, Q, F, W, Y, P, or C; P138 replaced with D, E, H, K, R, A, G, I, L, S, T, M, V, N, Q, F, W, Y, or C; E139 replaced with H, K, R, A, G, I, L, S, T, M, V, N, Q, F, W, Y, P, or C; E140 replaced with H, K, R, A, G, I, L, S, T, M, V, N, Q, F, W, Y, P, or C; T141 replaced with D, E, H, K, R, N, Q, F, W, Y, P, or C; V142 replaced with D, E, H, K, R, N, Q, F, W, Y, P, or C; T143 replaced with D, E, H, K, R, N, Q, F, W, Y, P, or C; Q144 replaced with D, E, H, K, R, A, G, I, L, S, T, M, V, F, W, Y, P, or C; D145 replaced with H, K, R, A, G, I, L, S, T, M, V, N, Q, F, W, Y, P, or C; C146 replaced with D, E, H, K, R, A, G, I, L, S, T, M, V, N, Q, F, W, Y, or P; L147 replaced with D, E, H, K, R, N, Q, F, W, Y, P, or C; Q148 replaced with D, E, H, K, R, A, G, I, L, S, T, M, V, F, W, Y, P, or C; L149 replaced with D, E, H, K, R, N, Q, F, W, Y, P, or C; I150 replaced with D, E, H, K, R, N, Q, F, W, Y, P, or C; A151 replaced with D, E, H, K, R, N, Q, F, W, Y, P, or C; D152 replaced with H, K, R, A, G, I, L, S, T, M, V, N, Q, F, W, Y, P, or C; S153 replaced with D, E, H, K, R, N, Q, F, W, Y, P, or C; E154 replaced with H, K, R, A, G, I, L, S, T, M, V, N, Q, F, W, Y, P, or C; T155 replaced with D, E, H, K, R, N, Q, F, W, Y, P, or C; P156 replaced with D, E, H, K, R, A, G, I, L, S, T, M, V, N, Q, F, W, Y, or C; T157 replaced with D, E, H, K, R, N, Q, F, W, Y, P, or C; I158 replaced with D, E, H, K, R, N, Q, F, W, Y, P, or C; Q159 replaced with D, E, H, K, R, A, G, I, L, S, T, M, V, F, W, Y, P, or C; K160 replaced with D, E, A, G, I, L, S, T, M, V, N, Q, F, W, Y, P, or C; G161 replaced with D, E, H, K, R, N, Q, F, W, Y, P, or C; S162 replaced with D, E, H, K, R, N, Q, F, W, Y, P, or C; Y163 replaced with D, E, H, K, R, N, Q, A, G, I, L, S, T, M, V, P, or C; T164 replaced with D, E, H, K, R, N, Q, F, W, Y, P, or C; F165 replaced with D, E, H, K, R, N, Q, A, G, I, L, S, T, M, V, P, or C; V166 replaced with D, E, H, K, R, N, Q, F, W, Y, P, or C; P167 replaced with D, E, H, K, R, A, G, I, L, S, T, M, V, N, Q, F, W, Y, or C; W168 replaced with D, E, H, K, R, N, Q, A, G, I, L, S, T, M, V, P, or C; L169 replaced with D, E, H, K, R, N, Q, F, W, Y, P, or C; L170 replaced with D, E, H, K, R, N, Q, F, W, Y, P, or C; S171 replaced with D, E, H, K, R, N, Q, F, W, Y, P, or C; F172 replaced with D, E, H, K, R, N, Q, A, G, I, L, S, T, M, V, P, or C; K173 replaced with D, E, A, G, I, L, S, T, M, V, N, Q, F, W, Y, P, or C; R174 replaced with D, E, A, G, I, L, S, T, M, V, N, Q, F, W, Y, P, or C; G175 replaced with D, E, H, K, R, N, Q, F, W, Y, P, or C; S176 replaced with D, E, H, K, R, N, Q, F, W, Y, P, or C; A177 replaced with D, E, H, K, R, N, Q, F, W, Y, P, or C; L178 replaced with D, E, H, K, R, N, Q, F, W, Y, P, or C; E179 replaced with H, K, R, A, G, I, L, S, T, M, V, N, Q, F, W, Y, P, or C; E180 replaced with H, K, R, A, G I, L, S, T, M, V, N, Q, F, W, Y, P, or C; K181 replaced with D, E, A, G, I, L, S, T, M, V, N, Q, F, W, Y, P, or C; E182 replaced with H, K, R, A, G, I, L, S, T, M, V, N, Q, F, W, Y, P, or C; N183 replaced with D, E, H, K, R, A, G, I, L, S, T, M, V, F, W, Y, P, or C; K184 replaced with D, E, A, G, I, L, S, T, M, V, N, Q, F, W, Y, P, or C; I185 replaced with D, E, H, K, R, N, Q, F, W, Y, P, or C; L186 replaced with D, E, H, K, R, N, Q, F, W, Y, P, or C; V187 replaced with D, E, H, K, R, N, Q, F, W, Y, P, or C; K188 replaced with D, E, A, G, I, L, S, T, M, V, N, Q, F, W, Y, P, or C; E189 replaced with H, K, R, A, G, I, L, S, T, M, V, N, Q, F, W, Y, P, or C; T190 replaced with D, E, H, K, R, N, Q, F, W, Y, P, or C; G191 replaced with D, E, H, K, R, N, Q, F, W, Y, P, or C; Y192 replaced with D, E, H, K, R, N, Q, A, G, I, L, S, T, M, V, P, or C; F193 replaced with D, E, H, K, R, N, Q, A, G, I, L, S, T, M, V, P, or C; F194 replaced with D, E, H, K, R, N, Q, A, G, I, L, S, T, M, V, P, or C; I195 replaced with D, E, H, K, R, N, Q, F, W, Y, P, or C; Y196 replaced with D, E, H, K, R, N, Q, A, G, I, L, S, T, M, V, P, or C; G197 replaced with D, E, H, K, R, N, Q, F, W, Y, P, or C; Q198 replaced with D, E, H, K, R, A, G, I, L, S, T, M, V, F, W, Y, P, or C; V199 replaced with D, E, H, K, R, N, Q, F, W, Y, P, or C; L200 replaced with D, E, H, K, R, N, Q, F, W, Y, P, or C; Y201 replaced with D, E, H, K, R, N, Q, A, G, I, L, S, T, M, V, P, or C; T202 replaced with D, E, H, K, R, N, Q, F, W, Y, P, or C; D203 replaced with H, K, R, A, G, I, L, S, T, M, V, N, Q, F, W, Y, P, or C; K204 replaced with D, E, A, G, I, L, S, T, M, V, N, Q, F, W, Y, P, or C; T205 replaced with D, E, H, K, R, N, Q, F, W, Y, P, or C; Y206 replaced with D, E, H, K, R, N, Q, A, G, I, L, S, T, M, V, P, or C; A207 replaced with D, E, H, K, R, N, Q, F, W, Y, P, or C; M208 replaced with D, E, H, K, R, N, Q, F, W, Y, P, or C; G209 replaced with D, E, H, K, R, N, Q, F, W, Y, P, or C; H210 replaced with D, E, A, G, I, L, S, T, M, V, N, Q, F, W, Y, P, or C; L211 replaced with D, E, H, K, R, N, Q, F, W, Y, P, or C; I212 replaced with D, E, H, K, R, N, Q, F, W, Y, P, or C; Q213 replaced with D, E, H, K, R, A, G, I, L, S, T, M, V, F, W, Y, P, or C; R214 replaced with D, E, A, G, I, L, S, T, M, V, N, Q, F, W, Y, P, or C; K215 replaced with D, E, A, G, I, L, S, T, M, V, N, Q, F, W, Y, P, or C; K216 replaced with D, E, A, G, I, L, S, T, M, V, N, Q, F, W, Y, P, or C; V217 replaced with D, E, H, K, R, N, Q, F, W, Y, P, or C; H218 replaced with D, E, A, G, I, L, S, T, M, V, N, Q, F, W, Y, P, or C; V219 replaced with D, E, H, K, R, N, Q, F, W, Y, P, or C; F220 replaced with D, E, H, K, R, N, Q, A, G, I, L, S, T, M, V, P, or C; G221 replaced with D, E, H, K, R, N, Q, F, W, Y, P, or C; D222 replaced with H, K, R, A, G, I, L, S, T, M, V, N, Q, F, W, Y, P, or C; E223 replaced with H, K, R, A, G, I, L, S, T, M, V, N, Q, F, W, Y, P, or C; L224 replaced with D, E, H, K, R, N, Q, F, W, Y, P, or C; S225 replaced with D, E, H, K, R, N, Q, F, W, Y, P, or C; L226 replaced with D, E, H, K, R, N, Q, F, W, Y, P, or C; V227 replaced with D, E, H, K, R, N, Q, F, W, Y, P, or C; T228 replaced with D, E, H, K, R, N, Q, F, W, Y, P, or C; L229 replaced with D, E, H, K, R, N, Q, F, W, Y, P, or C; F230 replaced with D, E, H, K, R, N, Q, A, G, I, L, S, T, M, V, P, or C; R231 replaced with D, E, A, G, I, L, S, T, M, V, N, Q, F, W, Y, P, or C; C232 replaced with D, E, H, K, R, A, G, I, L, S, T, M, V, N, Q, F, W, Y, or P; I233 replaced with D, E, H, K, R, N, Q, F, W, Y, P, or C; Q234 replaced with D, E, H, K, R, A, G, I, L, S, T, M, V, F, W, Y, P, or C; N235 replaced with D, E, H, K, R, A, G, I, L, S, T, M, V, F, W, Y, P, or C; M236 replaced with D, E, H, K, R, N, Q, F, W, Y, P, or C; P237 replaced with D, E, H, K, R, A, G, I, L, S, T, M, V, N, Q, F, W, Y, or C; E238 replaced with H, K, R, A, G, I, L, S, T, M, V, N, Q, F, W, Y, P, or C; T239 replaced with D, E, H, K, R, N, Q, F, W, Y, P, or C; L240 replaced with D, E, H, K, R, N, Q, F, W, Y, P, or C; P241 replaced with D, E, H, K, R, A, G, I, L, S, T, M, V, N, Q, F, W, Y, or C; N242 replaced with D, E, H, K, R, A, G, I, L, S, T, M, V, F, W, Y, P, or C; N243 replaced with D, E, H, K, R, A, G, I, L, S, T, M, V, F, W, Y, P, or C; S244 replaced with D, E, H, K, R, N, Q, F, W, Y, P, or C; C245 replaced with D, E, H, K, R, A, G, I, L, S, T, M, V, N, Q, F, W, Y, or P; Y246 replaced with D, E, H, K, R, N, Q, A, G, I, L, S, T, M, V, P, or C; S247 replaced with D, E, H, K, R, N, Q, F, W, Y, P, or C; A248 replaced with D, E, H, K, R, N, Q, F, W, Y, P, or C; G249 replaced with D, E, H, K, R, N, Q, F, W, Y, P, or C; I250 replaced with D, E, H, K, R, N, Q, F, W, Y, P, or C; A251 replaced with D, E, H, K, R, N, Q, F, W, Y, P, or C; K252 replaced with D, E, A, G, I, L, S, T, M, V, N, Q, F, W, Y, P, or C; L253 replaced with D, E, H, K, R, N, Q, F, W, Y, P, or C; E254 replaced with H, K, R, A, G, I, L, S, T, M, V, N, Q, F, W, Y, P, or C; E255 replaced with H, K, R, A, G, I, L, S, T, M, V, N, Q, F, W, Y, P, or C; G256 replaced with D, E, H, K, R, N, Q, F, W, Y, P, or C; D257 replaced with H, K, R, A, G, I, L, S, T, M, V, N, Q, F, W, Y, P, or C; E258 replaced with H, K, R, A, G, I, L, S, T, M, V, N, Q, F, W, Y, P, or C; L259 replaced with D, E, H, K, R, N, Q, F, W, Y, P, or C; Q260 replaced with D, E, H, K, R, A, G, I, L, S, T, M, V, F, W, Y, P, or C; L261 replaced with D, E, H, K, R, N, Q, F, W, Y, P, or C; A262 replaced with D, E, H, K, R, N, Q, F, W, Y, P, or C; I263 replaced with D, E, H, K, R, N, Q, F, W, Y, P, or C; P264 replaced with D, E, H, K, R, A, G, I, L, S, T, M, V, N, Q, F, W, Y, or C; R265 replaced with D, E, A, G, I, L, S, T, M, V, N, Q, F, W, Y, P, or C; E266 replaced with H, K, R, A, G, I, L, S, T, M, V, N, Q, F, W, Y, P, or C; N267 replaced with D, E, H, K, R, A, G, I, L, S, T, M, V, F, W, Y, P, or C; A268 replaced with D, E, H, K, R, N, Q, F, W, Y, P, or C; Q269 replaced with D, E, H, K, R, A, G, I, L, S, T, M, V, F, W, Y, P, or C; I270 replaced with D, E, H, K, R, N, Q, F, W, Y, P, or C; S271 replaced with D, E, H, K, R, N, Q, F, W, Y, P, or C; L272 replaced with D, E, H, K, R, N, Q, F, W, Y, P, or C; D273 replaced with H, K, R, A, G, I, L, S, T, M, V, N, Q, F, W, Y, P, or C; G274 replaced with D, E, H, K, R, N, Q, F, W, Y, P, or C; D275 replaced with H, K, R, A, G, I, L, S, T, M, V, N, Q, F, W, Y, P, or C; V276 replaced with D, E, H, K, R, N, Q, F, W, Y, P, or C; T277 replaced with D, E, H, K, R, N, Q, F, W, Y, P, or C; F278 replaced with D, E, H, K, R, N, Q, A, G, I, L, S, T M, V, P, or C; F279 replaced with D, E, H, K, R, N, Q, A, G, I, L, S, T, M, V, P, or C; G280 replaced with D, E, H, K, R, N, Q, F, W, Y, P, or C; A281 replaced with D, E, H, K, R, N, Q, F, W, Y, P, or C; L282 replaced with D, E, H, K, R, N, Q, F, W, Y, P, or C; K283 replaced with D, E, A, G, I, L, S, T, M, V, N, Q, F, W, Y, P, or C; L284 replaced with D, E, H, K, R, N, Q, F, W, Y, P, or C; and/or L285 replaced with D, E, H, K, R, N, Q, F, W, Y, P, or C. Polynucleotides encoding these polypeptides are also encompassed by the invention. The resulting Neutrokine-alpha proteins of the invention may be routinely screened for Neutrokine-alpha and/or Neutrokine-alphaSV functional activities and/or physical properties (such as, for example, enhanced or reduced stability and/or solubility) described throughout the specification and known in the art. Preferably, the resulting proteins of the invention have an increased and/or a decreased Neutrokine-alpha and/or Neutrokine-alphaSV functional activity. More preferably, the resulting Neutrokine-alpha and/or Neutrokine-alphaSV proteins of the invention have more than one increased and/or decreased Neutrokine-alpha and/or Neutrokine-alphaSV functional activity and/or physical property.

In an additional embodiment, Neutrokine-alpha polypeptides of the invention comprise, or alternatively consist of, more than one amino acid (e.g., 2, 3, 4, 5, 6, 7, 8, 9, 10, 15, 20, 30 and 50) replaced with the substituted amino acids as described above (either conservative or nonconservative).

In another embodiment of the invention, non-conservative substitutions of the Neutrokine-alphaSV protein sequence provided in SEQ ID NO:19 include: M1 replaced with D, E, H, K, R, N, Q, F, W, Y, P, or C; D2 replaced with H, K, R, A, G, I, L, S, T, M, V, N, Q, F, W, Y, P, or C; D3 replaced with H, K, R, A, G, I, L, S, T, M, V, N, Q, F, W, Y, P, or C; S4 replaced with D, E, H, K, R, N, Q, F, W, Y, P, or C; T5 replaced with D, E, H, K, R, N, Q, F, W, Y, P, or C; E6 replaced with H, K, R, A, G, I, L, S, T, M, V, N, Q, F, W, Y, P, or C; R7 replaced with D, E, A, G, I, L, S, T, M, V, N, Q, F, W, Y, P, or C; E8 replaced with H, K, R, A, G, I, L, S, T, M, V, N, Q, F, W, Y, P, or C; Q9 replaced with D, E, H, K, R, A, G, I, L, S, T, M, V, F, W, Y, P, or C; S10 replaced with D, E, H, K, R, N, Q, F, W, Y, P, or C; R11 replaced with D, E, A, G, I, L, S, T, M, V, N, Q, F, W, Y, P, or C; L12 replaced with D, E, H, K, R, N, Q, F, W, Y, P, or C; T13 replaced with D, E, H, K, R, N, Q, F, W, Y, P, or C; S14 replaced with D, E, H, K, R, N, Q, F, W, Y, P, or C; C15 replaced with D, E, H, K, R, A, G, I, L, S, T, M, V, N, Q, F, W, Y, or P; L16 replaced with D, E, H, K, R, N, Q, F, W, Y, P, or C; K17 replaced with D, E, A, G, I, L, S, T, M, V, N, Q, F, W, Y, P, or C; K18 replaced with D, E, A, G, I, L, S, T, M, V, N, Q, F, W, Y, P, or C; R19 replaced with D, E, A, G, I, L, S, T, M, V, N, Q, F, W, Y, P, or C; E20 replaced with H, K, R, A, G, I, L, S, T, M, V, N, Q, F, W, Y, P, or C; E21 replaced with H, K, R, A, G, I, L, S, T, M, V, N, Q, F, W, Y, P, or C; M22 replaced with D, E, H, K, R, N, Q, F, W, Y, P, or C; K23 replaced with D, E, A, G, I, L, S, T, M, V, N, Q, F, W, Y, P, or C; L24 replaced with D, E, H, K, R, N, Q, F, W, Y, P, or C; K25 replaced with D, E, A, G, I, L, S, T, M, V, N, Q, F, W, Y, P, or C; E26 replaced with H, K, R, A, G, I, L, S, T, M, V, N, Q, F, W, Y, P, or C; C27 replaced with D, E, H, K, R, A, G, I, L, S, T, M, V, N, Q, F, W, Y, or P; V28 replaced with D, E, H, K, R, N, Q, F, W, Y, P, or C; S29 replaced with D, E, H, K, R, N, Q, F, W, Y, P, or C; I30 replaced with D, E, H, K, R, N, Q, F, W, Y, P, or C; L31 replaced with D, E, H, K, R, N, Q, F, W, Y, P, or C; P32 replaced with D, E, H, K, R, A, G, I, L, S, T, M, V, N, Q, F, W, Y, or C; R33 replaced with D, E, A, G, I, L, S, T, M, V, N, Q, F, W, Y, P, or C; K34 replaced with D, E, A, G, I, L, S, T, M, V, N, Q, F, W, Y, P, or C; E35 replaced with H, K, R, A, G, I, L, S, T, M, V, N, Q, F, W, Y, P, or C; S36 replaced with D, E, H, K, R, N, Q, F, W, Y, P, or C; P37 replaced with D, E, H, K, R, A, G, I, L, S, T, M, V, N, Q, F, W, Y, or C; S38 replaced with D, E, H, K, R, N, Q, F, W, Y, P, or C; V39 replaced with D, E, H, K, R, N, Q, F, W, Y, P, or C; R40 replaced with D, E, A, G, I, L, S, T, M, V, N, Q, F, W, Y, P, or C; S41 replaced with D, E, H, K, R, N, Q, F, W, Y, P, or C; S42 replaced with D, E, H, K, R, N, Q, F, W, Y, P, or C; K43 replaced with D, E, A, G, I, L, S, T, M, V, N, Q, F, W, Y, P, or C; D44 replaced with H, K, R, A, G, I, L, S, T, M, V, N, Q, F, W, Y, P, or C; G45 replaced with D, E, H, K, R, N, Q, F, W, Y, P, or C; K46 replaced with D, E, A, G, I, L, S, T, M, V, N, Q, F, W, Y, P, or C; LA7 replaced with D, E, H, K, R, N, Q, F, W, Y, P, or C; LA8 replaced with D, E, H. K, R, N, Q, F, W, Y, P, or C; A49 replaced with D, E, H, K, R, N, Q, F, W, Y, P, or C; A50 replaced with D, E, H, K, R, N, Q, F, W, Y, P, or C; T51 replaced with D, E, H, K, R, N, Q, F, W, Y, P, or C; L52 replaced with D, E, H, K, R, N, Q, F, W, Y, P, or C; L53 replaced with D, E, H, K, R, N, Q, F, W, Y, P, or C; L54 replaced with D, E, H, K, R, N, Q, F, W, Y, P, or C; A55 replaced with D, E, H, K, R, N, Q, F, W, Y, P, or C; L56 replaced with D, E, H, K, R, N, Q, F, W, Y, P, or C; L57 replaced with D, E, H, K, R, N, Q, F, W, Y, P, or C; S58 replaced with D, E, H, K, R, N, Q, F, W, Y, P, or C; C59 replaced with D, E, H, K, R, A, G, I, L, S, T, M, V, N, Q, F, W, Y, or P; C60 replaced with D, E, H, K, R, A, G, I, L, S, T, M, V, N, Q, F, W, Y, or P; L61 replaced with D, E, H, K, R, N, Q, F, W, Y, P, or C; T62 replaced with D, E, H, K, R, N, Q, F, W, Y, P, or C; V63 replaced with D, E, H, K, R, N, Q, F, W, Y, P, or C; V64 replaced with D, E, H, K, R, N, Q, F, W, Y, P, or C; S65 replaced with D, E, H, K, R, N, Q, F, W, Y, P, or C; F66 replaced with D, E, H, K, R, N, Q, A, G, I, L, S, T, M, V, P, or C; Y67 replaed with D, E, H, K, R, N, Q, A, G, I, L, S, T, M, V, P, or C; Q68 replaced with D, E, H, K, R, A, G, I, L, S, T, M, V, F, W, Y, P, or C; V69 replaced with D, E, H, K, R, N, Q, F, W, Y, P, or C; A70 replaced with D, E, H, K, R, N, Q, F, W, Y, P, or C; A71 replaced with D, E, H, K, R, N, Q, F, W, Y, P, or C; L72 replaced with D, E, H, K, R, N, Q, F, W, Y, P, or C; Q73 replaced with D, E, H, K, R, A, G, I, L, S, T, M, V, F, W, Y, P, or C; G74 replaced with D, E, H, K, R, N, Q, F, W, Y, P, or C; D75 replaced with H, K, R, A, G, I, L, S, T, M, V, N, Q, F, W, Y, P, or C; L76 replaced with D, E, H, K, R, N, Q, F, W, Y, P, or C; A77 replaced with D, E, H, K, R, N, Q, F, W, Y, P, or C; S78 replaced with D, E, H, K, R, N, Q, F, W, Y, P, or C; L79 replaced with D, E, H, K, R, N, Q, F, W, Y, P, or C; R80 replaced with D, E, A, G, I, L, S, T, M, V, N, Q, F, W, Y, P, or C; A81 replaced with D, E, H, K, R, N, Q, F, W, Y, P, or C; E82 replaced with H, K, R, A, G, I, L, S, T, M, V, N, Q, F, W, Y, P, or C; L83 replaced with D, E, H, K, R, N, Q, F, W, Y, P, or C; Q84 replaced with D, E, H, K, R, A, G, I, L, S, T, M, V, F, W, Y, P, or C; G85 replaced with D, E, H, K, R, N, Q, F, W, Y, P, or C; H86 replaced with D, E, A, G, I, L, S, T, M, V, N, Q, F, W, Y, P, or C; H87 replaced with D, E, A, G, I, L, S, T, M, V, N, Q, F, W, Y, P, or C; A88 replaced with D, E, H, K, R, N, Q, F, W, Y, P, or C; E89 replaced with H, K, R, A, G, I, L, S, T, M, V, N, Q, F, W, Y, P, or C; K90 replaced with D, E, A, G, I, L, S, T, M, V, N, Q, F, W, Y, P, or C; L91 replaced with D, E, H, K, R, N, Q, F, W, Y, P, or C; P92 replaced with D, E, H, K, R, A, G, I, L, S, T, M, V, N, Q, F, W, Y, or C; A93 replaced with D, E, H, K, R, N, Q, F, W, Y, P, or C; G94 replaced with D, E, H, K, R, N, Q, F, W, Y, P, or C; A95 replaced with D, E, H, K, R, N, Q, F, W, Y, P, or C; G96 replaced with D, E, H, K, R, N, Q, F, W, Y, P, or C; A97 replaced with D, E, H, K, R, N, Q, F, W, Y, P, or C; P98 replaced with D, E, H, K, R, A, G, I, L, S, T, M, V, N, Q, F, W, Y, or C; K99 replaced with D, E, A, G, I, L, S, T, M, V, N, Q, F, W, Y, P, or C; A100 replaced with D, E, H, K, R, N, Q, F, W, Y, P, or C; G101 replaced with D, E, H, K, R, N, Q, F, W, Y, P, or C; L102 replaced with D, E, H, K, R, N, Q, F, W, Y, P, or C; E103 replaced with H, K, R, A, G, I, L, S, T, M, V, N, Q, F, W, Y, P, or C; E104 replaced with H, K, R, A, G, I, L, S, T, M, V, N, Q, F, W, Y, P, or C; A105 replaced with D, E, H, K, R, N, Q, F, W, Y, P, or C; P106 replaced with D, E, H, K, R, A, G, I, L, S, T, M, V, N, Q, F, W, Y, or C; A107 replaced with D, E, H, K, R, N, Q, F, W, Y, P, or C; V108 replaced with D, E, H, K, R, N, Q, F, W, Y, P, or C; T109 replaced with D, E, H, K, R, N, Q, F, W, Y, P, or C; A110 replaced with D, E, H, K, R, N, Q, F, W, Y, P, or C; G111 replaced with D, E, H, K, R, N, Q, F, W, Y, P, or C; L112 replaced with D, E, H, K, R, N, Q, F, W, Y, P, or C; K113 replaced with D, E, A, G, I, L, S, T, M, V, N, Q, F, W, Y, P, or C; I114 replaced with D, E, H, K, R, N, Q, F, W, Y, P, or C; F115 replaced with D, E, H, K, R, N, Q, A, G, I, L, S, T, M, V, P, or C; E116 replaced with H, K, R, A, G, I, L, S, T, M, V, N, Q, F, W, Y, P, or C; P117 replaced with D, E, H, K, R, A, G, I, L, S, T, M, V, N, Q, F, W, Y, or C; P118 replaced with D, E, H, K, R, A, G, I, L, S, T, M, V, N, Q, F, W, Y, or C; A119 replaced with D, E, H, K, R, N, Q, F, W, Y, P, or C; P120 replaced with D, E, H, K, R, A, G, I, L, S, T, M, V, N, Q, F, W, Y, or C; G121 replaced with D, E, H, K, R, N, Q, F, W, Y, P, or C; E122 replaced with H, K, R, A, G, I, L, S, T, M, V, N, Q, F, W, Y, P, or C; G123 replaced with D, E, H, K, R, N, Q, F, W, Y, P, or C; N124 replaced with D, E, H, K, R, A, G, I, L, S, T, M, V, F, W, Y, P, or C; S125 replaced with D, E, H, K, R, N, Q, F, W, Y, P, or C; S126 replaced with D, E, H, K, R, N, Q, F, W, Y, P, or C;

Q127 replaced with D, E, H, K, R, A, G, I, L, S, T, M, V, F, W, Y, P, or C; N128 replaced with D, E, H, K, R, A, G, I, L, S, T, M, V, F, W, Y, P, or C; S129 replaced with D, E, H, K, R, N, Q, F, W, Y, P, or C; R130 replaced with D, E, A, G, I, L, S, T, M, V, N, Q, F, W, Y, P, or C; N131 replaced with D, E, H, K, R, A, G, I, L, S, T, M, V, F, W, Y, P, or C; K132 replaced with D, E, A, G, I, L, S, T, M, V, N, Q, F, W, Y, P, or C; R133 replaced with D, E, A, G, I, L, S, T, M, V, N, Q, F, W, Y, P, or C; A134 replaced with D, E, H, K, R, N, Q, F, W, Y, P, or C; V135 replaced with D, E, H, K, R, N, Q, F, W, Y, P, or C; Q136 replaced with D, E, H, K, R, A, G, I, L, S, T, M, V, F, W, Y, P, or C; G137 replaced with D, E, H, K, R, N, Q, F, W, Y, P, or C; P138 replaced with D, E, H, K, R, A, G, I, L, S, T, M, V, N, Q, F, W, Y, or C; E139 replaced with H, K, R, A, G, I, L, S, T, M, V, N, Q, F, W, Y, P, or C; E140 replaced with H, K, R, A, G, I, L, S, T, M, V, N, Q, F, W, Y, P, or C; T141 replaced with D, E, H, K, R, N, Q, F, W, Y, P, or C; G142 replaced with D, E, H, K, R, N, Q, F, W, Y, P, or C; S143 replaced with D, E, H, K, R, N, Q, F, W, Y, P, or C; Y144 replaced with D, E, H, K, R, N, Q, A, G, I, L, S, T, M, V, P, or C; T145 replaced with D, E, H, K, R, N, Q, F, W, Y, P, or C; F146 replaced with D, E, H, K, R, N, Q, A, G, I, L, S, T, M, V, P, or C; V147 replaced with D, E, H, K, R, N, Q, F, W, Y, P, or C; P148 replaced with D, E, H, K, R, A, G, I, L, S, T, M, V, N, Q, F, W, Y, or C; W149 replaced with D, E, H, K, R, N, Q, A, G, I, L, S, T, M, V, P, or C; L150 replaced with D, E, H, K, R, N, Q, F, W, Y, P, or C; L151 replaced with D, E, H, K, R, N, Q, F, W, Y, P, or C; S152 replaced with D, E, H, K, R, N, Q, F, W, Y, P, or C; F153 replaced with D, E, H, K, R, N, Q, A, G, I, L, S, T, M, V, P, or C; K154 replaced with D, E, A, G, I, L, S, T, M, V, N, Q, F, W, Y, P, or C; R155 replaced with D, E, A, G, I, L, S, T, M, V, N, Q, F, W, Y, P, or C; G156 replaced with D, E, H, K, R, N, Q, F, W, Y, P, or C; S157 replaced with D, E, H, K, R, N, Q, F, W, Y, P, or C; A158 replaced with D, E, H, K, R, N, Q, F, W, Y, P, or C; L159 replaced with D, E, H, K, R, N, Q, F, W, Y, P, or C; E160 replaced with H, K, R, A, G, I, L, S, T, M, V, N, Q, F, W, Y, P, or C; E161 replaced with H, K, R, A, G, I, L, S, T, M, V, N, Q, F, W, Y, P, or C; K162 replaced with D, E, A, G, I, L, S, T, M, V, N, Q, F, W, Y, P, or C; E163 replaced with H, K, R, A, G, I, L, S, T, M, V, N, Q, F, W, Y, P, or C; N164 replaced with D, E, H, K, R, A, G, I, L, S, T, M, V, F, W, Y, P, or C; K165 replaced with D, E, A, G, I, L, S, T, M, V, N, Q, F, W, Y, P, or C; I166replaced with D, E, H, K, R, N, Q, F, W, Y, P, or C; L167 replaced with D, E, H, K, R, N, Q, F, W, Y, P, or C; V168 replaced with D, E, H, K, R, N, Q, F, W, Y, P, or C; K169 replaced with D, E, A, G, I, L, S, T, M, V, N, Q, F, W, Y, P, or C; E170 replaced with H, K, R, A, G, I, L, S, T, M, V, N, Q, F, W, Y, P, or C; T171 replaced with D, E, H, K, R, N, Q, F, W, Y, P, or C; G172 replaced with D, E, H, K, R, N, Q, F, W, Y, P, or C; Y173 replaced with D, E, H, K, R, N, Q, A, G, I, L, S, T, M, V, P, or C; F174 replaced with D, E, H, K, R, N, Q, A, G, I, L, S, T, M, V, P, or C; F175 replaced with D, E, H, K, R, N, Q, A, G, I, L, S, T, M, V, P, or C; I176 replaced with D, E, H, K, R, N, Q, F, W, Y, P, or C; Y177 replaced with D, E, H, K, R, N, Q, A, G, I, L, S, T, M, V, P, or C; G178 replaced with D, E, H, K, R, N, Q, F, W, Y, P, or C; Q179 replaced with D, E, H, K, R, A, G, I, L, S, T, M, V, F, W, Y, P, or C; V180 replaced with D, E, H, K, R, N, Q, F, W, Y, P, or C; L181 replaced with D, E, H, K, R, N, Q, F, W, Y, P, or C; Y182 replaced with D, E, H, K, R, N, Q, A, G, I, L, S, T, M, V, P, or C; T183 replaced with D, E, H, K, R, N, Q, F, W, Y, P, or C; D184 replaced with H, K, R, A, G, I, L, S, T, M, V, N, Q, F, W, Y, P, or C; K185 replaced with D, E, A, G, I, L, S, T, M, V, N, Q, F, W, Y, P, or C; T186 replaced with D, E, H, K, R, N, Q, F, W, Y, P, or C; Y187 replaced with D, E, H, K, R, N, Q, A, G, I, L, S, T, M, V, P, or C; A188 replaced with D, E, H, K, R, N, Q, F, W, Y, P, or C; M189 replaced with D, E, H, K, R, N, Q, F, W, Y, P, or C; G190 replaced with D, E, H, K, R, N, Q, F, W, Y, P, or C; H191 replaced with D, E, A, G, I, L, S, T, M, V, N, Q, F, W, Y, P, or C; L192 replaced with D, E, H, K, R, N, Q, F, W, Y, P, or C; I193 replaced with D, E, H, K, R, N, Q, F, W, Y, P, or C; Q194 replaced with D, E, H, K, R, A, G, I, L, S, T, M, V, F, W, Y, P, or C; R195 replaced with D, E, A, G, I, L, S, T, M, V, N, Q, F, W, Y, P, or C; K196 replaced with D, E, A, G, I, L, S, T, M, V, N, Q, F, W, Y, P, or C; K197 replaced with D, E, A, G, I, L, S, T, M, V, N, Q, F, W, Y, P, or C; V198 replaced with D, E, H, K, R, N, Q, F, W, Y, P, or C; H199 replaced with D, E, A, G, I, L, S, T, M, V, N, Q, F, W, Y, P, or C; V200 replaced with D, E, H, K, R, N, Q, F, W, Y, P, or C; F201 replaced with D, E, H, K, R, N, Q, A, G, I, L, S, T, M, V, P, or C; G202 replaced with D, E, H, K, R, N, Q, F, W, Y, P, or C; D203 replaced with H, K, R, A, G, I, L, S, T, M, V, N, Q, F, W, Y, P, or C; E204 replaced with H, K, R, A, G, I, L, S, T, M, V, N, Q, F, W, Y, P, or C; L205 replaced with D, E, H, K, R, N, Q, F, W, Y, P, or C; S206 replaced with D, E, H, K, R, N, Q, F, W, Y, P, or C; L207 replaced with D, E, H, K, R, N, Q, F, W, Y, P, or C; V208 replaced with D, E, H, K, R, N, Q, F, W, Y, P, or C; T209 replaced with D, E, H, K, R, N, Q, F, W, Y, P, or C; L210 replaced with D, E, H, K, R, N, Q, F, W, Y, P, or C; F211 replaced with D, E, H, K, R, N, Q, A, G, I, L, S, T, M, V, P, or C; R212 replaced with D, E, A, G, I, L, S, T, M, V, N, Q, F, W, Y, P, or C; C213 replaced with D, E, H, K, R, A, G, I, L, S, T, M, V, N, Q, F, W, Y, or P; I214 replaced with D, E, H, K, R, N, Q, F, W, Y, P, or C; Q215 replaced with D, E, H, K, R, A, G, I, L, S, T, M, V, F, W, Y, P, or C; N216 replaced with D, E, H, K, R, A, G, I, L, S, T, M, V, F, W, Y, P, or C; M217 replaced with D, E, H, K, R, N, Q, F, W, Y, P, or C; P218 replaced with D, E, H, K, R, A, G, I, L, S, T, M, V, N, Q, F, W, Y, or C; E219 replaced with H, K, R, A, G, I, L, S, T, M, V, N, Q, F, W, Y, P, or C; T220 replaced with D, E, H, K, R, N, Q, F, W, Y, P, or C; L221 replaced with D, E, H, K, R, N, Q, F, W, Y, P, or C; P222 replaced with D, E, H, K, R, A, G, I, L, S, T, M, V, N, Q, F, W, Y, or C; N223 replaced with D, E, H, K, R, A, G, I, L, S, T, M, V, F, W, Y, P, or C; N224 replaced with D, E, H, K, R, A, G, I, L, S, T, M, V, F, W, Y, P, or C; S225 replaced with D, E, H, K, R, N, Q, F, W, Y, P, or C; C226 replaced with D, E, H, K, R, A, G, I, L, S, T, M, V, N, Q, F, W, Y, or P; Y227 replaced with D, E, H, K, R, N, Q, A, G, I, L, S, T, M, V, P, or C; S228 replaced with D, E, H, K, R, N, Q, F, W, Y, P, or C; A229 replaced with D, E, H, K, R, N, Q, F, W, Y, P, or C; G230 replaced with D, E, H, K, R, N, Q, F, W, Y, P, or C; I231 replaced with D, E, H, K, R, N, Q, F, W, Y, P, or C; A232 replaced with D, E, H, K, R, N, Q, F, W, Y, P, or C; K233 replaced with D, E, A, G, I, L, S, T, M, V, N, Q, F, W, Y, P, or C; L234 replaced with D, E, H, K, R, N, Q, F, W, Y, P, or C; E235 replaced with H, K, R, A, G, I, L, S, T, M, V, N, Q, F, W, Y, P, or C; E236 replaced with H, K, R, A, G, I, L, S, T, M, V, N, Q, F, W, Y, P, or C; G237 replaced with D, E, H, K, R, N, Q, F, W, Y, P, or C; D238 replaced with H, K, R, A, G, I, L, S, T, M, V, N, Q, F, W, Y, P, or C; E239 replaced with H, K, R, A, G, I, L, S, T, M, V, N, Q, F, W, Y, P, or C; L240 replaced with D, E, H, K, R, N, Q, F, W, Y, P, or C; Q241 replaced with D, E, H, K, R, A, G, I, L, S, T, M, V, F, W, Y, P, or C; L242 replaced with D, E, H, K, R, N, Q, F, W, Y, P, or C; A243 replaced with D, E, H, K, R, N, Q, F, W, Y, P, or C; I244 replaced with D, E, H, K, R, N, Q, F, W, Y, P, or C; P245 replaced with D, E, H, K, R, A, G, I, L, S, T, M, V, N, Q, F, W, Y, or C; R246 replaced with D, E, A, G, I, L, S, T, M, V, N, Q, F, W, Y, P, or C; E247 replaced with H, K, R, A, G, I, L, S, T, M, V, N, Q, F, W, Y, P, or C; N248 replaced with D, E, H, K, R, A, G, I, L, S, T, M, V, F, W, Y, P, or C; A249 replaced with D, E, H, K, R, N, Q, F, W, Y, P, or C; Q250 replaced with D, E, H, K, R, A, G, I, L, S, T, M, V, F, W, Y, P, or C; I251 replaced with D, E, H, K, R, N, Q, F, W, Y, P, or C; S252 replaced with D, E, H, K, R, N, Q, F, W, Y, P, or C; L253 replaced with D, E, H, K, R, N, Q, F, W, Y, P, or C; D254 replaced with H, K, R, A, G, I, L, S, T, M, V, N, Q, F, W, Y, P, or C; G255 replaced with D, E, H, K, R, N, Q, F, W, Y, P, or C; D256 replaced with H, K, R, A, G, I, L, S, T, M, V, N, Q, F, W, Y, P, or C; V257 replaced with D, E, H, K, R, N, Q, F, W, Y, P, or C; T258 replaced with D, E, H, K, R, N, Q, F, W, Y, P, or C; F259 replaced with D, E, H, K, R, N, Q, A, G, I, L, S, T, M, V, P, or C; F260 replaced with D, E, H, K, R, N, Q, A, G, I, L, S, T, M, V, P, or C; G261 replaced with D, E, H, K, R, N, Q, F, W, Y, P, or C; A262 replaced with D, E, H, K, R, N, Q, F, W, Y, P, or C; L263 replaced with D, E, H, K, R, N, Q, F, W, Y, P, or C; K264 replaced with D, E, A, G, I, L, S, T, M, V, N, Q, F, W, Y, P, or C; L265 replaced with D, E, H, K, R, N, Q, F, W, Y, P, or C; and/or L266 replaced with D, E, H, K, R, N, Q, F, W, Y, P, or C. Polynucleotides encoding these polypeptides are also encompassed by the invention. The resulting Neutrokine-alpha proteins of the invention may be routinely screened for Neutrokine-alpha and/or Neutrokine-alphaSV functional activities and/or physical properties (such as, for example, enhanced or reduced stability and/or solubility) described throughout the specification and known in the art. Preferably, the resulting proteins of the invention have an increased and/or a decreased Neutrokine-alpha and/or Neutrokine-alphaSV functional activity. More preferably, the resulting Neutrokine-alpha and/or Neutrokine-alphaSV proteins of the invention have more than one increased and/or decreased Neutrokine-alpha and/or Neutrokine-alphaSV functional activity and/or physical property.

In an additional embodiment, Neutrokine-alpha polypeptides of the invention comprise, or alternatively consist of, more than one amino acid (e.g., 2, 3, 4, 5, 6, 7, 8, 9, 10, 15, 20, 30 and 50) replaced with the substituted amino acids as described above (either conservative or nonconservative).

For example, preferred non-conservative substitutions of the Neutrokine-alpha protein sequence provided in SEQ ID NO:23 include: R1 replaced with D, E, A, G, I, L, S, T, M, V, N, Q, F, W, Y, P, or C; V2 replaced with D, E, H, K, R, N, Q, F, W, Y, P, or C; V3 replaced with D, E, H, K, R, N, Q, F, W, Y, P, or C; D4 replaced with H, K, R, A, G, I, L, S, T, M, V, N, Q, F, W, Y, P, or C; L5 replaced with D, E, H, K, R, N, Q, F, W, Y, P, or C; S6 replaced with D, E, H, K, R, N, Q, F, W, Y, P, or C; A7 replaced with D, E, H, K, R, N, Q, F, W, Y, P, or C; P8 replaced with D, E, H, K, R, A, G, I, L, S, T, M, V, N, Q, F, W, Y, or C; P9 replaced with D, E, H, K, R, A, G, I, L, S, T, M, V, N, Q, F, W, Y, or C; A10 replaced with D, E, H, K, R, N, Q, F, W, Y, P, or C; P11 replaced with D, E, H, K, R, A, G, I, L, S, T, M, V, N, Q, F, W, Y, or C; C12 replaced with D, E, H, K, R, A, G, I, L, S, T, M, V, N, Q, F, W, Y, or P; L13 replaced with D, E, H, K, R, N, Q, F, W, Y, P, or C; P14 replaced with D, E, H, K, R, A, G, I, L, S, T, M, V, N, Q, F, W, Y, or C; G15 replaced with D, E, H, K, R, N, Q, F, W, Y, P, or C; C16 replaced with D, E, H, K, R, A, G, I, L, S, T, M, V, N, Q, F, W, Y, or P; R17 replaced with D, E, A, G, I, L, S, T, M, V, N, Q, F, W, Y, P, or C; H18 replaced with D, E, A, G, I, L, S, T, M, V, N, Q, F, W, Y, P, or C; S19 replaced with D, E, H, K, R, N, Q, F, W, Y, P, or C; Q20 replaced with D, E, H, K, R, A, G, I, L, S, T, M, V, F, W, Y, P, or C; H21 replaced with D, E, A, G, I, L, S, T, M, V, N, Q, F, W, Y, P, or C; D22 replaced with H, K, R, A, G, I, L, S, T, M, V, N, Q, F, W, Y, P, or C; D23 replaced with H, K, R, A, G, I, L, S, T, M, V, N, Q, F, W, Y, P, or C; N24 replaced with D, E, H, K, R, A, G, I, L, S, T, M, V, F, W, Y, P, or C; G25 replaced with D, E, H, K, R, N, Q, F, W, Y, P, or C; M26 replaced with D, E, H, K, R, N, Q, F, W, Y, P, or C; N27 replaced with D, E, H, K, R, A, G, I, L, S, T, M, V, F, W, Y, P, or C; L28 replaced with D, E, H, K, R, N, Q, F, W, Y, P, or C; R29 replaced with D, E, A, G, I, L, S, T, M, V, N, Q, F, W, Y, P, or C; N30 replaced with D, E, H, K, R, A, G, I, L, S, T, M, V, F, W, Y, P, or C; R31 replaced with D, E, A, G, I, L, S, T, M, V, N, Q, F, W, Y, P, or C; T32 replaced with D, E, H, K, R, N, Q, F, W, Y, P, or C; Y33 replaced with D, E, H, K, R, N, Q, A, G, I, L, S, T, M, V, P, or C; T34 replaced with D, E, H, K, R, N, Q, F, W, Y, P, or C; F35 replaced with D, E, H, K, R, N, Q, A, G, I, L, S, T, M, V, P, or C; V36 replaced with D, E, H, K, R, N, Q, F, W, Y, P, or C; P37 replaced with D, E, H, K, R, A, G, I, L, S, T, M, V, N, Q, F, W, Y, or C; W38 replaced with D, E, H, K, R, N, Q, A, G, I, L, S, T, M, V, P, or C; L39 replaced with D, E, H, K, R, N, Q, F, W, Y, P, or C; L40 replaced with D, E, H, K, R, N, Q, F, W, Y, P, or C; S41 replaced with D, E, H, K, R, N, Q, F, W, Y, P, or C; F42 replaced with D, E, H, K, R, N, Q, A, G, I, L, S, T, M, V, P, or C; K43 replaced with D, E, A, G, I, L, S, T, M, V, N, Q, F, W, Y, P, or C; R44 replaced with D, E, A, G, I, L, S, T, M, V, N, Q, F, W, Y, P, or C; G45 replaced with D, E, H, K, R, N, Q, F, W, Y, P, or C; N46 replaced with D, E, H, K, R, A, G, I, L, S, T, M, V, F, W, Y, P, or C; A47 replaced with D, E, H, K, R, N, Q, F, W, Y, P, or C; L48 replaced with D, E, H, K, R, N, Q, F, W, Y, P, or C; E49 replaced with H, K, R, A, G, I, L, S, T, M, V, N, Q, F, W, Y, P, or C; E50 replaced with H, K, R, A, G, I, L, S, T, M, V, N, Q, F, W, Y, P, or C; K51 replaced with D, E, A, G, I, L, S, T, M, V, N, Q, F, W, Y, P, or C; E52 replaced with H, K, R, A, G, I, L, S, T, M, V, N, Q, F, W, Y, P, or C; N53 replaced with D, E, H, K, R, A, G, I, L, S, T, M, V, F, W, Y, P, or C; K54 replaced with D, E, A, G, I, L, S, T, M, V, N, Q, F, W, Y, P, or C; I55 replaced with D, E, H, K, R, N, Q, F, W, Y, P, or C; V56 replaced with D, E, H, K, R, N, Q, F, W, Y, P, or C; V57 replaced with D, E, H, K, R, N, Q, F, W, Y, P, or C; R58 replaced with D, E, A, G, I, L, S, T, M, V, N, Q, F, W, Y, P, or C; Q59 replaced with D, E, H, K, R, A, G, I, L, S, T, M, V, F, W, Y, P, or C; T60 replaced vith D, E, H, K, R, N, Q, F, W, Y, P, or C; G61 replaced with D, E, H, K, R, N, Q, F, W, Y, P, or C; Y62 replaced with D, E, H, K, R, N, Q, A, G, I, L, S, T, M, V, P, or C; F63 replaced with D, E, H, K, R, N, Q, A, G, I, L, S, T, M, V, P, or C; F64 replaced with D, E, H, K, R, N, Q, A, G, I, L, S, T, M, V, P, or C; I65 replaced with D, E, H, K, R, N, Q, F, W, Y, P, or C; Y66 replaced with D, E, H, K, R, N, Q, A, G, I, L, S, T, M, V, P, or C; S67 replaced with D, E, H, K, R, N, Q, F, W, Y, P, or C; Q68 replaced with D, E, H, K, R, A, G, I, L, S, T, M, V, F, W, Y, P, or C; V69 replaced with D, E, H, K, R, N, Q, F, W, Y, P, or C; L70 replaced with D, E, H, K, R, N, Q, F, W, Y, P, or C; Y71 replaced with D, E, H, K, R, N, Q, A, G, I, L, S, T, M, V, P, or C; T72 replaced with D, E, H, K, R, N, Q, F, W, Y, P, or C; D73 replaced with H, K, R, A, G, I, L, S, T, M, V, N, Q, F, W, Y, P, or C; P74 replaced with D, E, H, K, R, A, G, I, L, S, T, M, V, N, Q, F, W, Y, or C; I75 replaced with D, E, H, K, R, N, Q, F, W, Y, P, or C; F76 replaced with D, E, H, K, R, N, Q, A, G, I, L, S, T, M, V, P, or C; A77 replaced with D, E, H, K, R, N, Q, F, W, Y, P, or C; M78 replaced with D, E, H, K, R, N, Q, F, W, Y, P, or C; G79 replaced with D, E, H, K, R, N, Q, F, W, Y, P, or C; H80 replaced with D, E, A, G, I, L, S, T, M, V, N, Q, F, W, Y, P, or C; V81 replaced with D, E, H, K, R, N, Q, F, W, Y, P, or C; I82 replaced with D, E, H, K, R, N, Q, F, W, Y, P, or C; Q83 replaced with D, E, H, K, R, A, G, I, L, S, T, M, V, F, W, Y, P, or C; R84 replaced with D, E, A, G, I, L, S, T, M, V, N, Q, F, W, Y, P, or C; K85 replaced with D, E, A, G, I, L, S, T, M, V, N, Q, F, W, Y, P, or C; K86 replaced with D, E, A, G, I, L, S, T, M, V, N, Q, F, W, Y, P, or C; V87 replaced with D, E, H, K, R, N, Q, F, W, Y, P, or C; H88 replaced with D, E, A, G, I, L, S, T, M, V, N, Q, F, W, Y, P, or C; V89 replaced with D, E, H, K, R, N, Q, F, W, Y, P, or C; F90 replaced with D, E, H, K, R, N, Q, A, G, I, L, S, T, M, V, P, or C; G91 replaced with D, E, H, K, R, N, Q, F, W, Y, P, or C; D92 replaced with H, K, R, A, G, I, L, S, T, M, V, N, Q, F, W, Y, P, or C; E93 replaced with H, K, R, A, G, I, L, S, T, M, V, N, Q, F, W, Y, P, or C; L94 replaced with D, E, H, K, R, N, Q, F, W, Y, P, or C; S95 replaced with D, E, H, K, R, N, Q, F, W, Y, P, or C; L96 replaced with D, E, H, K, R, N, Q, F, W, Y, P, or C; V97 replaced with D, E, H, K, R, N, Q, F, W, Y, P, or C; T98 replaced with D, E, H, K, R, N, Q, F, W, Y, P, or C; L99 replaced with D, E, H, K, R, N, Q, F, W, Y, P, or C; F100 replaced with D, E, H, K, R, N, Q, A, G, I, L, S, T, M, V, P, or C; R101 replaced with D, E, A, G, I, L, S, T, M, V, N, Q, F, W, Y, P, or C; C102 replaced with D, E, H, K, R, A, G, I, L, S, T, M, V, N, Q, F, W, Y, or P; I103 replaced with D, E, H, K, R, N, Q, F, W, Y, P, or C; Q104 replaced with D, E, H, K, R, A, G, I, L, S, T, M, V, F, W, Y, P, or C; N105 replaced with D, E, H, K, R, A, G, I, L, S, T, M, V, F, W, Y, P, or C; M106 replaced with D, E, H, K, R, N, Q, F, W, Y, P, or C; P107 replaced with D, E, H, K, R, A, G, I, L, S, T, M, V, N, Q, F, W, Y, or C; K108 replaced with D, E, A, G, I, L, S, T, M, V, N, Q, F, W, Y, P, or C; T109 replaced with D, E, H, K, R, N, Q, F, W, Y, P, or C; L110 replaced with D, E, H, K, R, N, Q, F, W, Y, P, or C; P111 replaced with D, E, H, K, R, A, G, I, L, S, T, M, V, N, Q, F, W, Y, or C; N112 replaced with D, E, H, K, R, A, G, I, L, S, T, M, V, F, W, Y, P, or C; N113 replaced with D, E, H, K, R, A, G, I, L, S, T, M, V, F, W, Y, P, or C; S114 replaced with D, E, H, K, R, N, Q, F, W, Y, P, or C; C115 replaced with D, E, H, K, R, A, G, I, L, S, T, M, V, N, Q, F, W, Y, or P; Y116 replaced with D, E, H, K, R, N, Q, A, G, I, L, S, T, M, V, P, or C; S117 replaced with D, E, H, K, R, N, Q, F, W, Y, P, or C; A118 replaced with D, E, H, K, R, N, Q, F, W, Y, P, or C; G119 replaced with D, E, H, K, R, N, Q, F, W, Y, P, or C; I120 replaced with D, E, H, K, R, N, Q, F, W, Y, P, or C; A121 replaced with D, E, H, K, R, N, Q, F, W, Y, P, or C; R122 replaced with D, E, A, G, I, L, S, T, M, V, N, Q, F, W, Y, P, or C; L123 replaced with D, E, H, K, R, N, Q, F, W, Y, P, or C; E124 replaced with H, K, R, A, G, I, L, S, T, M, V, N, Q, F, W, Y, P, or C; E125 replaced with H, K, R, A, G, I, L, S, T, M, V, N, Q, F, W, Y, P, or C; G126 replaced with D, E, H, K, R, N, Q, F, W, Y, P, or C; D127 replaced with H, K, R, A, G, I, L, S, T, M, V, N, Q, F, W, Y, P, or C; E128 replaced with H, K, R, A, G, I, L, S, T, M, V, N, Q, F, W, Y, P, or C; I129 replaced with D, E, H, K, R, N, Q, F, W, Y, P, or C; Q130 replaced with D, E, H, K, R, A, G, I, L, S, T, M, V, F, W, Y, P, or C; L131 replaced with D, E, H, K, R, N, Q, F, W, Y, P, or C; A132 replaced with D, E, H, K, R, N, Q, F, W, Y, P, or C; I133 replaced with D, E, H, K, R, N, Q, F, W, Y, P, or C; P134 replaced with D, E, H, K, R, A, G, I, L, S, T, M, V, N, Q, F, W, Y, or C; R135 replaced with D, E, A, G, I, L, S, T, M, V, N, Q, F, W, Y, P, or C; E136 replaced with H, K, R, A, G, I, L, S, T, M, V, N, Q, F, W, Y, P, or C; N137 replaced with D, E, H, K, R, A, G, I, L, S, T, M, V, F, W, Y, P, or C; A138 replaced with D, E, H, K, R, N, Q, F, W. Y, P, or C; Q139 replaced with D, E, H, K, R, A, G, I, L, S, T, M, V, F, W, Y, P, or C; I140 replaced with D, E, H, K, R, N, Q, F, W, Y, P, or C; S141 replaced with D, E, H, K, R, N, Q, F, W, Y, P, or C; R142 replaced with D, E, A, G, I, L, S, T, M, V, N, Q, F, W, Y, P, or C; N143 replaced with D, E, H, K, R, A, G, I, L, S, T, M, V, F, W, Y, P, or C; G144 replaced with D, E, H, K, R, N, Q, F, W, Y, P, or C; D145 replaced with H, K, R, A, G, I, L, S, T, M, V, N, Q, F, W, Y, P, or C; D146 replaced with H, K, R, A, G, I, L, S, T, M, V, N, Q, F, W, Y, P, or C; T147 replaced with D, E, H, K, R, N, Q, F, W, Y, P, or C; F148 replaced with D, E, H, K, R, N, Q, A, G, I, L, S, T, M, V, P, or C; F149 replaced with D, E, H, K, R, N, Q, A, G, I, L, S, T, M, V, P, or C; G150 replaced with D, E, H, K, R, N, Q, F, W, Y, P, or C; A151 replaced with D, E, H, K, R, N, Q, F, W, Y, P, or C; L152 replaced with D, E, H, K, R, N, Q, F, W, Y, P, or C; K153 replaced with D, E, A, G, I, L, S, T, M, V, N, Q, F, W, Y, P, or C; L154 replaced with D, E, H, K, R, N, Q, F, W, Y, P, or C; and/or L155 replaced with D, E, H, K, R, N, Q, F, W, Y, P, or C. Polynucleotides encoding these polypeptides are also encompassed by the invention. The resulting Neutrokine-alpha proteins of the invention may be routinely screened for Neutrokine-alpha and/or Neutrokine-alphaSV functional activities and/or physical properties (such as, for example, enhanced or reduced stability and/or solubility) described throughout the specification and known in the art. Preferably, the resulting proteins of the invention have an increased and/or a decreased Neutrokine-alpha and/or Neutrokine-alphaSV functional activity. More preferably, the resulting Neutrokine-alpha and/or Neutrokine-alphaSV proteins of the invention have more than one increased and/or decreased Neutrokine-alpha and/or Neutrokine-alphaSV functional activity and/or physical property.

In an additional embodiment, Neutrokine-alpha polypeptides of the invention comprise, or alternatively consist of, more than one amino acid (e.g., 2, 3, 4, 5, 6, 7, 8, 9, 10, 15, 20, 30 and 50) replaced with the substituted amino acids as described above (either conservative or nonconservative).

For example, preferred non-conservative substitutions of the Neutrokine-alpha protein sequence provided in SEQ ID NO:38 include: M1 replaced with D, E, H, K, R, N, Q, F, W, Y, P, or C; D2 replaced with H, K, R, A, G, I, L, S, T, M, V, N, Q, F, W, Y, P, or C; E3 replaced with H, K, R, A, G, I, L, S, T, M, V, N, Q, F, W, Y, P, or C; S4 replaced with D, E, H, K, R, N, Q, F, W, Y, P, or C; A5 replaced with D, E, H, K, R, N, Q, F, W, Y, P, or C; K6 replaced with D, E, A, G, I, L, S, T, M, V, N, Q, F, W, Y, P, or C; T7 replaced with D, E, H, K, R, N, Q, F, W, Y, P, or C; L8 replaced with D, E, H, K, R, N, Q, F, W, Y, P, or C; P9 replaced with D, E, H, K, R, A, G, I, L, S, T, M, V, N, Q, F, W, Y, or C; P10 replaced with D, E, H, K, R, A, G, I, L, S, T, M, V, N, Q, F, W, Y, or C; P11 replaced with D, E, H, K, R, A, G, I, L, S, T, M, V, N, Q, F, W, Y, or C; C12 replaced with D, E, H, K, R, A, G, I, L, S, T, M, V, N, Q, F, W, Y, or P; L13 replaced with D, E, H, K, R, N, Q, F, W, Y, P, or C; C14 replaced with D, E, H, K, R, A, G, I, L, S, T, M, V, N, Q, F, W, Y, or P; F15 replaced with D, E, H, K, R, N, Q, A, G, I, L, S, T, M, V, P, or C; C16 replaced with D, E, H, K, R, A, G, I, L, S, T, M, V, N, Q, F, W, Y, or P; S17 replaced with D, E, H, K, R, N, Q, F, W, Y, P, or C; E18 replaced with H, K, R, A, G, I, L, S, T, M, V, N, Q, F, W, Y, P, or C; K19 replaced with D, E, A, G, I, L S, T, M, V, N, Q, F, W, Y, P, or C; G20 replaced with D, E, H, K, R, N, Q, F, W, Y, P, or C; E21 replaced with H, K, R, A, G, I, L, S, T, M, V, N, Q, F, W, Y, P, or C; D22 replaced with H, K, R, A, G, I, L, S, T, M, V, N, Q, F, W, Y, P, or C; M23 replaced with D, E, H, K, R, N, Q, F, W, Y, P, or C; K24 replaced with D, E, A, G, I, L, S, T, M, V, N, Q, F, W, Y, P, or C; V25 replaced with D, E, H, K, R, N, Q, F, W, Y, P, or C; G26 replaced with D, E, H, K, R, N, Q, F, W, Y, P, or C; Y27 replaced with D, E, H, K, R, N, Q, A, G, I, L, S, T, M, V, P, or C; D28 replaced with H, K, R, A, G, I, L, S, T, M, V, N, Q, F, W, Y, P, or C; P29 replaced with D, E, H, K, R, A, G, I, L, S, T, M, V, N, Q, F, W, Y, or C; I30 replaced with D, E, H, K, R, N, Q, F, W, Y, P, or C; T31 replaced with D, E, H, K, R, N, Q, F, W, Y, P, or C; P32 replaced with D, E, H, K, R, A, G, I, L, S, T, M, V, N, Q, F, W, Y, or C; Q33 replaced with D, E, H, K, R, A, G, I, L, S, T, M, V, F, W, Y, P, or C; K34 replaced with D, E, A, G, I, L, S, T, M, V, N, Q, F, W, Y, P, or C; E35 replaced with H, K, R, A, G, I, L, S, T, M, V, N, Q, F, W, Y, P, or C; E36 replaced with H, K, R, A, G, I, L, S, T, M, V, N, Q, F, W, Y, P, or C; G37 replaced with D, E, H, K, R, N, Q, F, W, Y, P, or C; A38 replaced with D, E, H, K, R, N, Q, F, W, Y, P, or C; W39 replaced with D, E, H, K, R, N, Q, A, G, I, L, S, T, M, V, P, or C; F40 replaced with D, E, H, K, R, N, Q, A, G, I, L, S, T, M, V, P, or C; G41 replaced with D, E, H, K, R, N, Q, F, W, Y, P, or C; I42 replaced with D, E, H, K, R, N, Q, F, W, Y, P, or C; C43 replaced with D, E, H, K, R, A, G, I, L, S, T, M, V, N, Q, F, W, Y, or P; R44 replaced with D, E, A, G, I, L, S, T, M, V, N, Q, F, W, Y, P, or C; D45 replaced with H, K, R, A, G, I, L, S, T, M, V, N, Q, F, W, Y, P, or C; G46 replaced with D, E, H, K, R, N, Q, F, W, Y, P, or C; R47 replaced with D, E, A, G, I, L, S, T, M, V, N, Q, F, W, Y, P, or C; L48 replaced with D, E, H, K, R, N, Q, F, W, Y, P, or C; L49 replaced with D, E, H, K, R, N, Q, F, W, Y, P, or C; A50 replaced with D, E, H, K, R, N, Q, F, W, Y, P, or C; A51 replaced with D, E, H, K, R, N, Q, F, W, Y, P, or C; T52 replaced with D, E, H, K, R, N, Q, F, W, Y, P, or C; L53 replaced with D, E, H, K, R, N, Q, F, W, Y, P, or C; L54 replaced with D, E, H, K, R, N, Q, F, W, Y, P, or C; L55 replaced with D, E, H, K, R, N, Q, F, W, Y, P, or C; A56 replaced with D, E, H, K, R, N, Q, F, W, Y, P, or C; L57 replaced with D, E, H, K, R, N, Q, F, W, Y, P, or C; L58 replaced with D, E, H, K, R, N, Q, F, W, Y, P, or C; S59 replaced with D, E, H, K, R, N, Q, F, W, Y, P, or C; S60 replaced with D, E, H, K, R, N, Q, F, W, Y, P, or C; S61 replaced with D, E, H, K, R, N, Q, F, W, Y, P, or C; F62 replaced with D, E, H, K, R, N, Q, A, G, I, L, S, T, M, V, P, or C; T63 replaced with D, E, H, K, R, N, Q, F, W, Y, P, or C; A64 replaced with D, E, H, K, R, N, Q, F, W, Y, P, or C; M65 replaced with D, E, H, K, R, N, Q, F, W, Y, P, or C; S66 replaced with D, E, H, K, R, N, Q, F, W, Y, P, or C; L67 replaced with D, E, H, K, R, N, Q, F, W, Y, P, or C; Y68 replaced with D, E, H, K, R, N, Q, A, G, I, L, S, T, M, V, P, or C; Q69 replaced with D, E, H, K, R, A, G, I, L, S, T, M, V, F, W, Y, P, or C; L70 replaced with D, E, H, K, R, N, Q, F, W, Y, P, or C; A71 replaced with D, E, H, K, R, N, Q, F, W, Y, P, or C; A72 replaced with D, E, H, K, R, N, Q, F, W, Y, P, or C; L73 replaced with D, E, H, K, R, N, Q, F, W, Y, P, or C; Q74 replaced with D, E, H, K, R, A, G, I, L, S, T, M, V, F, W, Y, P, or C; A75 replaced with D, E, H, K, R, N, Q, F, W, Y, P, or C; D76 replaced with H, K, R, A, G, I, L, S, T, M, V, N, Q, F, W, Y, P, or C; L77 replaced with D, E, H, K, R, N, Q, F, W, Y, P, or C; M78 replaced with D, E, H, K, R, N, Q, F, W, Y, P, or C; N79 replaced with D, E, H, K, R, A, G, I, L, S, T, M, V, F, W, Y, P, or C; L80 replaced with D, E, H, K, R, N, Q, F, W, Y, P, or C; R81 replaced with D, E, A, G, I, L, S, T, M, V, N, Q, F, W, Y, P, or C; M82 replaced with D, E, H, K, R, N, Q, F, W, Y, P, or C; E83 replaced with H, K, R, A, G, I, L, S, T, M, V, N, Q, F, W, Y, P, or C; L84 replaced with D, E, H, K, R, N, Q, F, W, Y, P, or C; Q85 replaced with D, E, H, K, R, A, G, I, L, S, T, M, V, F, W, Y, P, or C; S86 replaced with D, E, H, K, R, N, Q, F, W, Y, P, or C; Y87 replaced with D, E, H, K, R, N, Q, A, G, I, L, S, T, M, V, P, or C; R88 replaced with D, E, A, G, I, L, S, T, M, V, N, Q, F, W, Y, P, or C; G89 replaced with D, E, H, K, R, N, Q, F, W, Y, P, or C; S90 replaced with D, E, H, K, R, N, Q, F, W, Y, P, or C; A91 replaced with D, E, H, K, R, N, Q, F, W, Y, P, or C; T92 replaced with D, E, H, K, R, N, Q, F, W, Y, P, or C; P93 replaced with D, E, H, K, R, A, G, I, L, S, T, M, V, N, Q, F, W, Y, or C; A94 replaced with D, E, H, K, R, N, Q, F, W, Y, P, or C; A95 replaced with D, E, H, K, R, N, Q, F, W, Y, P, or C; A96 replaced with D, E, H, K, R, N, Q, F, W, Y, P, or C; G97 replaced with D, E, H, K, R, N, Q, F, W, Y, P, or C; A98 replaced with D, E, H, K, R, N, Q, F, W, Y, P, or C; P99 replaced with D, E, H, K, R, A, G, I, L, S, T, M, V, N, Q, F, W, Y, or C; E100 replaced with H, K, R, A, G, I, L, S, T, M, V, N, Q, F, W, Y, P, or C; L101 replaced with D, E, H, K, R, N, Q, F, W, Y, P, or C; T102 replaced with D, E, H, K, R, N, Q, F, W, Y, P, or C; A103 replaced with D, E, H, K, R, N, Q, F, W, Y, P, or C; G104 replaced with D, E, H, K, R, N, Q, F, W, Y, P, or C; V105 replaced with D, E, H, K, R, N, Q, F, W, Y, P, or C; K106 replaced with D, E, A, G, I, L, S, T, M, V, N, Q, F, W, Y, P, or C; L107 replaced with D, E, H, K, R, N, Q, F, W, Y, P, or C; L108 replaced with D, E, H, K, R, N, Q, F, W, Y, P, or C; T109 replaced with D, E, H, K, R, N, Q, F, W, Y, P, or C; P101 replaced with D, E, H, K, R, A, G, I, L, S, T, M, V, N, Q, F, W, Y, or C; A111 replaced with D, E, H, K, R, N, Q, F, W, Y, P, or C; A112 replaced with D, E, H, K, R, N, Q, F, W, Y, P, or C; P113 replaced with D, E, H, K, R, A, G, I, L, S, T, M, V, N, Q, F, W, Y, or C; R114 replaced with D, E, A, G, I, L, S, T, M, V, N, Q, F, W, Y, P, or C; P115 replaced with D, E, H, K, R, A, G, I, L, S, T, M, V, N, Q, F, W, Y, or C; H116 replaced with D, E, A, G, I, L, S, T, M, V, N, Q, F, W, Y, P, or C; N117 replaced with D, E, H, K, R, A, G, I, L, S, T, M, V, F, W, Y, P, or C; S118 replaced with D, E, H, K, R, N, Q, F, W, Y, P, or C; S119 replaced with D, E, H, K, R, N, Q, F, W, Y, P, or C; R120 replaced with D, E, A, G, I, L, S, T, M, V, N, Q, F, W, Y, P, or C; G121 replaced with D, E, H, K, R, N, Q, F, W, Y, P, or C; H122 replaced with D, E, A, G, I, L, S, T, M, V, N, Q, F, W, Y, P, or C; R123 replaced with D, E, A, G, I, L, S, T, M, V, N, Q, F, W, Y, P, or C; N124 replaced with D, E, H, K, R, A, G, I, L, S, T, M, V, F, W, Y, P, or C; R125 replaced with D, E, A, G, I, L, S, T, M, V, N, Q, F, W, Y, P, or C; R126 replaced with D, E, A, G, I, L, S, T, M, V, N, Q, F, W, Y, P, or C; A127 replaced with D, E, H, K, R, N, Q, F, W, Y, P, or C; F128 replaced with D, E, H, K, R, N, Q, A, G, I, L, S, T, M, V, P, or C; Q129 replaced with D, E, H, K, R, A, G, I, L, S, T, M, V, F, W, Y, P, or C; G130 replaced with D, E, H, K, R, N, Q, F, W, Y, P, or C; P131 replaced with D, E, H, K, R, A, G, I, L, S, T, M, V, N, Q, F, W, Y, or C; E132 replaced with H, K, R, A, G, I, L, S, T, M, V, N, Q, F, W, Y, P, or C; E133 replaced with H, K, R, A, G, I, L, S, T, M, V, N, Q, F, W, Y, P, or C; T134 replaced with D, E, H, K, R, N, Q, F, W, Y, P, or C; E135 replaced with H, K, R, A, G, I, L, S, T, M, V, N, Q, F, W, Y, P, or C; Q136 replaced with D, E, H, K, R, A, G, I, L, S, T, M, V, F, W, Y, P, or C; D137 replaced with H, K, R, A, G, I, L, S, T, M, V, N, Q, F, W, Y, P, or C; V138 replaced with D, E, H, K, R, N, Q, F, W, Y, P, or C; D139 replaced with H, K, R, A, G, I, L, S, T, M, V, N, Q, F, W, Y, P, or C; L140 replaced with D, E, H, K, R, N, Q, F, W, Y, P, or C; S141 replaced with D, E, H, K, R, N, Q, F, W, Y, P, or C; A142 replaced with D, E, H, K, R, N, Q, F, W, Y, P, or C; P143 replaced with D, E, H, K, R, A, G, I, L, S, T, M, V, N, Q, F, W, Y, or C; P144 replaced with D, E, H, K, R, A, G, I, L, S, T, M, V, N, Q, F, W, Y, or C; A145 replaced with D, E, H, K, R, N, Q, F, W, Y, P, or C; P146 replaced with D, E, H, K, R, A, G, I, L, S, T, M, V, N, Q, F, W, Y, or C; C147 replaced with D, E, H, K, R, A, G, I, L, S, T, M, V, N, Q, F, W, Y, or P; L148 replaced with D, E, H, K, R, N, Q, F, W, Y, P, or C; P149 replaced with D, E, H, K, R, A, G, I, L, S, T, M, V, N, Q, F, W, Y, or C; G150 replaced with D, E, H, K, R, N, Q, F, W, Y, P, or C; C151 replaced with D, E, H, K, R, A, G, I, L, S, T, M, V, N, Q, F, W, Y, or P; R152 replaced with D, E, A, G, I, L, S, T, M, V, N, Q, F, W, Y, P, or C; H153 replaced with D, E, A, G, I, L, S, T, M, V, N, Q, F, W, Y, P, or C; S154 replaced with D, E, H, K, R, N, Q, F, W, Y, P, or C; Q155 replaced with D, E, H, K, R, A, G, I, L, S, T, M, V, F, W, Y, P, or C; H156 replaced with D, E, A, G, I, L, S, T, M, V, N, Q, F, W, Y, P, or C; D157 replaced with H, K, R, A, G, I, L, S, T, M, V, N, Q, F, W, Y, P, or C; D158 replaced with H, K, R, A, G, I, L, S, T, M, V, N, Q, F, W, Y, P, or C; N159 replaced with D, E, H, K, R, A, G, I, L, S, T, M, V, F, W, Y, P, or C; G160 replaced with D, E, H, K, R, N, Q, F, W, Y, P, or C; M161 replaced with D, E, H, K, R, N, Q, F, W, Y, P, or C; N162 replaced with D, E, H, K, R, A, G, I, L, S, T, M, V, F, W, Y, P, or C; L163 replaced with D, E, H, K, R, N, Q, F, W, Y, P, or C; R164 replaced with D, E, A, G, I, L, S, T, M, V, N, Q, F, W, Y, P, or C; N165 replaced with D, E, H, K, R, A, G, I, L, S, T, M, V, F, W, Y, P, or C; I166 replaced with D, E, H, K, R, N, Q, F, W, Y, P, or C; I167 replaced with D, E, H, K, R, N, Q, F, W, Y, P, or C; Q168 replaced with D, E, H, K, R, A, G, I, L, S, T, M, V, F, W, Y, P, or C; D169 replaced with H, K, R, A, G, I, L, S, T, M, V, N, Q, F, W, Y, P, or C; C170 replaced with D, E, H, K, R, A, G, I, L, S, T, M, V, N, Q, F, W, Y, or P; L171 replaced with D, E, H, K, R, N, Q, F, W, Y, P, or C; Q172 replaced with D, E, H, K, R, A, G, I, L, S, T, M, V, F, W, Y, P, or C; L173 replaced with D, E, H, K, R, N, Q, F, W, Y, P, or C; I174 replaced with D, E, H, K, R, N, Q, F, W, Y, P, or C; A175 replaced with D, E, H, K, R, N, Q, F, W, Y, P, or C; D176 replaced with H, K, R, A, G, I, L, S, T, M, V, N, Q, F, W, Y, P, or C; S177 replaced with D, E, H, K, R, N, Q, F, W, Y, P, or C; D178 replaced with H, K, R, A, G, I, L, S, T, M, V, N, Q, F, W, Y, P, or C; T179 replaced with D, E, H, K, R, N, Q, F, W, Y, P, or C; P180 replaced with D, E, H, K, R, A, G, I, L, S, T, M, V, N, Q, F, W, Y, or C; A181 replaced with D, E, H, K, R, N, Q, F, W, Y, P, or C; L182 replaced with D, E, H, K, R, N, Q, F, W, Y, P, or C; E183 replaced with H, K, R, A, G, I, L, S, T, M, V, N, Q, F, W, Y, P, or C; E184 replaced with H, K, R, A, G, I, L, S, T, M, V, N, Q, F, W, Y, P, or C; K185 replaced with D, E, A, G, I, L, S, T, M, V, N, Q, F, W, Y, P, or C; E186 replaced with H, K, R, A, G, I, L, S, T, M, V, N, Q, F, W, Y, P, or C; N187 replaced with D, E, H, K, R, A, G, I, L, S, T, M, V, F, W, Y, P, or C; K188 replaced with D, E, A, G, I, L, S, T, M, V, N, Q, F, W, Y, P, or C; I189 replaced with D, E, H, K, R, N, Q, F, W, Y, P, or C; V190 replaced with D, E, H, K, R, N, Q, F, W, Y, P, or C; V191 replaced with D, E, H, K, R, N, Q, F, W, Y, P, or C; R192 replaced with D, E, A, G, I, L, S, T, M, V, N, Q, F, W, Y, P, or C; Q193 replaced with D, E, H, K, R, A, G, I, L, S, T, M, V, F, W, Y, P, or C; T194 replaced with D, E, H, K, R, N, Q, F, W, Y, P, or C; G195 replaced with D, E, H, K, R, N, Q, F, W, Y, P, or C; Y196 replaced with D, E, H, K, R, N, Q, A, G I, L, S, T, M, V, P, or C; F197 replaced with D, E, H, K, R, N, Q, A, G, I, L, S, T, M, V, P, or C; F198 replaced with D, E, H, K, R, N, Q, A, G, I, L, S, T, M, V, P, or C; I199 replaced with D, E, H, K, R, N, Q, F, W, Y, P, or C; Y200 replaced with D, E, H, K, R, N, Q, A, G, I, L, S, T, M, V, P, or C; S201 replaced with D, E, H, K, R, N, Q, F, W, Y, P, or C; Q202 replaced with D, E, H, K, R, A, G, I, L, S, T, M, V, F, W, Y, P, or C; V203 replaced with D, E, H, K, R, N, Q, F, W, Y, P, or C; L204 replaced with D, E, H, K, R, N, Q, F, W, Y, P, or C; Y205 replaced with D, E, H, K, R, N, Q, A, G, I, L, S, T, M, V, P, or C; T206 replaced with D, E, H, K, R, N, Q, F, W, Y, P, or C; D207 replaced with H, K, R, A, G, I, L, S, T, M, V, N, Q, F, W, Y, P, or C; P208 replaced with D, E, H, K, R, A, G, I, L, S, T, M, V, N, Q, F, W, Y, or C; I209 replaced with D, E, H, K, R, N, Q, F, W, Y, P, or C; F210 replaced with D, E, H, K, R, N, Q, A, G, I, L, S, T, M, V, P, or C; A211 replaced with D, E, H, K, R, N, Q, F, W, Y, P, or C; M212 replaced with D, E, H, K, R, N, Q, F, W, Y, P, or C; G213 replaced with D, E, H, K, R, N, Q, F, W, Y, P, or C; H214 replaced with D, E, A, G, I, L, S, T, M, V, N, Q, F, W, Y, P, or C; V215 replaced with D, E, H, K, R, N, Q, F, W, Y, P, or C; I216 replaced with D, E, H, K, R, N, Q, F, W, Y, P, or C; Q217 replaced with D, E, H, K, R, A, G, I, L, S, T, M, V, F, W, Y, P, or C; R218 replaced with D, E, A, G, I, L, S, T, M, V, N, Q, F, W, Y, P, or C; K219 replaced with D, E, A, G, I, L, S, T, M, V, N, Q, F, W, Y, P, or C; K220 replaced with D, E, A, G, I, L, S, T, M, V, N, Q, F, W, Y, P, or C; V221 replaced with D, E, H, K, R, N, Q, F, W, Y, P, or C; H222 replaced with D, E, A, G, I, L, S, T, M, V, N, Q, F, W, Y, P, or C; V223 replaced with D, E, H, K, R, N, Q, F, W, Y, P, or C; F224 replaced with D, E, H, K, R, N, Q, A, G, I, L, S, T, M, V, P, or C; G225 replaced with D, E, H, K, R, N, Q, F, W, Y, P, or C; D226 replaced with H, K, R, A, G, I, L, S, T, M, V, N, Q, F, W, Y, P, or C; E227 replaced with H, K, R, A, G, I, L, S, T, M, V, N, Q, F, W, Y, P, or C; L228 replaced with D, E, H, K, R, N, Q, F, W, Y, P, or C; S229 replaced with D, E, H, K, R, N, Q, F, W, Y, P, or C; L230 replaced with D, E, H, K, R, N, Q, F, W, Y, P, or C; V231 replaced with D, E, H, K, R, N, Q, F, W, Y, P, or C; T232 replaced with D, E, H, K, R, N, Q, F, W, Y, P, or C; L233 replaced with D, E, H, K, R, N, Q, F, W, Y, P, or C; F234 replaced with D, E, H, K, R, N, Q, A, G, I, L, S, T, M, V, P, or C; R235 replaced with D, E, A, G, I, L, S, T, M, V, N, Q, F, W, Y, P, or C; C236 replaced with D, E, H, K, R, A, G, I, L, S, T, M, V, N, Q, F, W, Y, or P; I237 replaced with D, E, H, K, R, N, Q, F, W, Y, P, or C; Q238 replaced with D, E, H, K, R, A, G, I, L, S, T, M, V, F, W, Y, P, or C; N239 replaced with D, E, H, K, R, A, G, I, L, S, T, M, V, F, W, Y, P, or C; M240 replaced with D, E, H, K, R, N, Q, F, W, Y, P, or C; P241 replaced with D, E, H, K, R, A, G, I, L, S, T, M, V, N, Q, F, W, Y, or C; K242 replaced with D, E, A, G, I, L, S, T, M, V, N, Q, F, W, Y, P, or C; T243 replaced with D, E, H, K, R, N, Q, F, W, Y, P, or C; L244 replaced with D, E, H, K, R, N, Q, F, W, Y, P, or C; P245 replaced with D, E, H, K, R, A, G, I, L, S, T, M, V, N, Q, F, W, Y, or C; N246 replaced with D, E, H, K, R, A, G, I, L, S, T, M, V, F, W, Y, P, or C; N247 replaced with D, E, H, K, R, A, G, I, L, S, T, M, V, F, W, Y, P, or C; S248 replaced with D, E, H, K, R, N, Q, F, W, Y, P, or C; C249 replaced with D, E, H, K, R, A, G, I, L, S, T, M, V, N, Q, F, W, Y, or P; Y250 replaced with D, E, H, K, R, N, Q, A, G, I, L, S, T, M, V, P, or C; S251 replaced with D, E, H, K, R, N, Q, F, W, Y, P, or C; A252 replaced with D, E, H, K, R, N, Q, F, W, Y, P, or C; G253 replaced with D, E, H, K, R, N, Q, F, W, Y, P, or C; I254 replaced with D, E, H, K, R, N, Q, F, W, Y, P, or C; A255 replaced with D, E, H, K, R, N, Q, F, W, Y, P, or C; R256 replaced with D, E, A, G, I, L, S, T, M, V, N, Q, F, W, Y, P, or C; L257 replaced with D, E, H. K, R, N, Q, F, W, Y, P, or C; E258 replaced with H, K, R, A, G, I, L, S, T, M, V, N, Q, F, W, Y, P, or C; E259 replaced with H, K, R, A, G, I, L, S, T, M, V, N, Q, F, W, Y, P, or C; G260 replaced with D, E, H, K, R, N, Q, F, W, Y, P, or C; D261 replaced with H, K, R, A, G, I, L, S, T, M, V, N, Q, F, W, Y, P, or C; E262 replaced with H, K, R, A, G, I, L, S, T, M, V, N, Q, F, W, Y, P, or C; I263 replaced with D, E, H, K, R, N, Q, F, W, Y, P, or C; Q264 replaced with D, E, H, K, R, A, G, I, L, S, T, M, V, F, W, Y, P, or C; L265 replaced with D, E, H, K, R, N, Q, F, W, Y, P, or C; A266 replaced with D, E, H, K, R, N, Q, F, W, Y, P, or C; I267 replaced with D, E, H, K, R, N, Q, F, W, Y, P, or C; P268 replaced with D, E, H, K, R, A, G, I, L, S, T, M, V, N, Q, F, W, Y, or C; R269 replaced with D, E, A, G, I, L, S, T, M, V, N, Q, F, W, Y, P, or C; E270 replaced with H, K, R, A, G, I, L, S, T, M, V, N, Q, F, W, Y, P, or C; N271 replaced with D, E, H, K, R, A, G, I, L, S, T, M, V, F, W, Y, P, or C; A272 replaced with D, E, H, K, R, N, Q, F, W, Y, P, or C; Q273 replaced with D, E, H, K, R, A, G, I, L, S, T, M, V, F, W, Y, P, or C; I274 replaced with D, E, H, K, R, N, Q, F, W, Y, P, or C; S275 replaced with D, E, H, K, R, N, Q, F, W, Y, P, or C; R276 replaced with D, E, A, G, I, L, S, T, M, V, N, Q, F, W, Y, P, or C; N277 replaced with D, E, H, K, R, A, G, I, L, S, T, M, V, F, W, Y, P, or C; G278 replaced with D, E, H, K, R, N, Q, F, W, Y, P, or C; D279 replaced with H, K, R, A, G, I, L, S, T, M, V, N, Q, F, W, Y, P, or C; D280 replaced with H, K, R, A, G, I, L, S, T, M, V, N, Q, F, W, Y, P, or C; T281 replaced with D, E, H, K, R, N, Q, F, W, Y, P, or C; F282 replaced with D, E, H, K, R, N, Q, A, G, I, L, S, T, M, V, P, or C; F283 replaced with D, E, H, K, R, N, Q, A, G, I, L, S, T, M, V, P, or C; G284 replaced with D, E, H, K, R, N, Q, F, W, Y, P, or C; A285 replaced with D, E, H, K, R, N, Q, F, W, Y, P, or C; L286 replaced with D, E, H, K, R, N, Q, F, W, Y, P, or C; K287 replaced with D, E, A, G, I, L, S, T, M, V, N, Q, F, W, Y, P, or C; L288 replaced with D, E, H, K, R, N, Q, F, W, Y, P, or C; and/or L289 replaced with D, E, H, K, R, N, Q, F, W, Y, P, or C. Polynucleotides encoding these polypeptides are also encompassed by the invention. The resulting Neutrokine-alpha proteins of the invention may be routinely screened for Neutrokine-alpha and/or Neutrokine-alphaSV functional activities and/or physical properties (such as, for example, enhanced or reduced stability and/or solubility) described throughout the specification and known in the art. Preferably, the resulting proteins of the invention have an increased and/or a decreased Neutrokine-alpha and/or Neutrokine-alphaSV functional activity. More preferably, the resulting Neutrokine-alpha and/or Neutrokine-alphaSV proteins of the invention have more than one increased and/or decreased Neutrokine-alpha and/or Neutrokine-alphaSV functional activity and/or physical property.

In an additional embodiment, Neutrokine-alpha polypeptides of the invention comprise, or alternatively consist of, more than one amino acid (e.g., 2, 3, 4, 5, 6, 7, 8, 9, 10, 15, 20, 30 and 50) replaced with the substituted amino acids as described above (either conservative or nonconservative).

Replacement of amino acids can also change the selectivity of the binding of a ligand to cell surface receptors. For example, Ostade et al., Nature 361:266-268 (1993) describes certain mutations resulting in selective binding of TNF-alpha to only one of two known types of TNF receptors. Since Neutrokine-alpha and Neutrokine-alphaSV are members of the TNF polypeptide family, mutations similar to those in TNF-alpha are likely to have similar effects in Neutrokine-alpha and/or Neutrokine-alphaSV.

Sites that are critical for ligand-receptor binding can also be determined by structural analysis such as crystallization, nuclear magnetic resonance or photoaffinity labeling (Smith et al., J. Mol. Biol. 224:899-904 (1992) and de Vos et al. Science 255:306-312 (1992)).

Since Neutrokine-alpha is a member of the TNF-related protein family, to modulate rather than completely eliminate functional activities (e.g., biological activities) of Neutrokine-alpha, mutations may be made in sequences encoding amino acids in the TNF conserved domain, i.e., in positions Gly-191 through Leu-284 of FIGS. 1A and 1B (SEQ ID NO:2), more preferably in residues within this region which are not conserved in all, most or several members of the TNF family (e.g., TNF-alpha, TNF-beta, LT-beta, and Fas Ligand) (see e.g., FIGS. 2A, 2B, 2C, and 2D). By making a specific mutation in Neutrokine-alpha in the position where such a conserved amino acid is typically found in related TNFs, the Neutrokine-alpha mutein will act as an antagonist, thus possessing activity for example, which inhibits lymphocyte (e.g., B cell) proliferation, differentiation, and/or activation. Accordingly, polypeptides of the present invention include Neutrokine-alpha mutants. Such Neutrokine-alpha mutants comprise, or alternatively consist of, fragments, variants or derivatives of the full-length or preferably the extracellular domain of the Neutrokine-alpha amino acid sequence shown in FIGS. 1A and 1B (SEQ ID NO:2). Polynucleotides encoding the above Neutrokine-alpha mutants are also encompassed by the invention.

Since Neutrokine-alphaSV is a member of the TNF-related protein family, to modulate rather than completely eliminate functional activities (e.g., biological activities) of Neutrokine-alphaSV, mutations may be made in sequences encoding amino acids in the TNF conserved domain, i.e., in positions Gly-172 through Leu-265 of FIGS. 5A and 5B (SEQ ID NO:19), more preferably in residues within this region which are not conserved in all, most or several members of the TNF family (e.g., TNF-alpha, TNF-beta, LT-beta, and Fas Ligand) (see e.g., FIGS. 2A 2B, 2C and 2D). By making a specific mutation in Neutrokine-alphaSV in the position where such a conserved amino acid is typically found in related TNFs, the Neutrokine-alphaSV mutein will act as an antagonist, thus possessing activity for example, which inhibits lymphocyte (e.g., B cell) proliferation, differentiation, and/or activation. Accordingly, polypeptides of the present invention include Neutrokine-alphaSV mutants. Such Neutrokine-alphaSV mutants comprise, or alternatively consist of, fragments, variants or derivatives of the full-length or preferably the extracellular domain of the Neutrokine-alphaSV amino acid sequence shown in FIGS. 5A and 5B (SEQ ID NO:19 Polynucleotides encoding the above Neutrokine-alpha SV mutants are also encompassed by the invention.

In addition, it will be recognized by one of ordinary skill in the art that mutations targeted to regions of a Neutrokine-alpha polypeptide of the invention which encompass the nineteen amino acid residue insertion which is not found in the Neutrokine-alphaSV polypeptide sequence (i.e., amino acid residues Val-142 through Lys-160 of the sequence presented in FIGS. 1A and 1B and in SEQ ID NO:2) may affect the observed functional activities (e.g., biological activity) of the Neutrokine-alpha polypeptide. More specifically, a partial, non-limiting and non-exclusive list of such residues of the Neutrokine-alpha polypeptide sequence which may be targeted for mutation includes the following amino acid residues of the Neutrokine-alpha polypeptide sequence as shown in SEQ ID NO:2: V-142; T-143; Q-144; D-145; C-146; L-147; Q-148; L-149; I-150; A-151; D-152; S-153; E-154; T-155; P-156; T-157; I-158: Q-159; and K-160.

Recombinant DNA technology known to those skilled in the art (see, for instance, DNA shuffling supra) can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Thus, the invention also encompasses Neutrokine-alpha and/or Neutrokine-alphaSV derivatives and analogs that have one or more amino acid residues deleted, added, or substituted to generate Neutrokine-alpha and/or Neutrokine-alphaSV polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the Neutrokine-alpha and/or Neutrokine-alphaSV polypeptides of the invention, and/or an amino acid deletion at the second position of any one or more such recognition sequences will prevent glycosylation of the Neutrokine-alpha and/or Neutrokine-alphaSV at the modified tripeptide sequence (see, e.g., Miyajimo et al., EMBO J 5(6):1193-1197). By way of non-limiting example, mutation of the serine at position 244 to alanine either singly or in combination with mutation of the asparagine at position 242 to glutamine abolishes glycosylation of the mature soluble form of Neutrokine-alpha (amino acids 134-285) of SEQ ID NO:2) when expressed in the yeast *Pichea pastoris*. A mutant Neutrokine-alpha polypeptide in which only the asparagine at position 242 is mutated to glutamine, is still gycosylated when expressed in *Pichea pastoris*. In this mutant, the glycosylation event may be due to the activation or unmasking of an 0-linked glyscosylation site at serine 244. Similar mutations affecting glycosylation could also be made in Neutrokine alpha-SV polypeptide, i.e., aspargine-223 to glutamine and/or serine-224 to alanine of SEQ ID NO:19.

Additionally, one or more of the amino acid residues of the polypeptides of the invention (e.g., arginine and lysine residues) may be deleted or substituted with another residue to elminate undesired processing by proteases such as, for example, furins or kexins. One possible result of such a mutation is that Neutrokine-alpha polypeptide of the invention is not cleaved and released from the cell surface.

In a specific embodiment, Lys-132 and/or Arg-133 of the Neutrokine-alpha sequence shown in SEQ ID NO:2 is mutated to another amino acid residue, or deleted altogether, to prevent or diminish release of the soluble form of Neutrokine-alpha from cells expressing Neutrokine-alpha. In a more specific embodiment, Lys-132 of the Neutrokine-alpha sequence shown in SEQ ID NO:2 is mutated to Ala-132. In another, nonexclusive specific embodiment, Arg-133 of the Neutrokine-alpha sequence shown in SEQ ID NO:2 is mutated to Ala-133. These mutatied proteins, and/or polynucleotides encoding these proteins have uses such as, for example, in ex vivo therapy or gene therapy, to engineer cells expressing a Neutrokine-alpha polypepitde that is retained on the surface of the engineered cells.

In a specific embodiment, Cys-146 of the Neutrokine-alpha sequence shown in SEQ ID NO:2 is mutated to another amino acid residue, or deleted altogether, for example, to aid preventing or diminishing oligomerization of the mutant Neutrokine-alpha polypeptide when expressed in an expression system (essentially as described in Example 1). In a specific embodiment, Cys-146 is replaced with a serine amino acid residue. Polynucleotides encoding these polypeptides are also encompassed by the invention.

In another specific embodiment, Cys-232 of the Neutrokine-alpha sequence shown in SEQ ID NO:2 is mutated to another amino acid residue, or deleted altogether, for example, to aid preventing or diminishing oligomerization of the mutant Neutrokine-alpha polypeptide when expressed in an expression system (essentially as described in Example 1). In a specific embodiment, Cys-232 is replaced with a serine amino acid residue. Polynucleotides encoding these polypeptides are also encompassed by the invention.

In yet another specific embodiment, Cys-245 of the Neutrokine-alpha sequence shown in SEQ ID NO:2 is mutated to another amino acid residue, or deleted altogether, for example, to aid preventing or diminishing oligomerization of the mutant Neutrokine-alpha polypeptide when expressed in an expression system (essentially as described in Example 1). In a specific embodiment, Cys-245 is replaced with a serine amino acid residue. Polynucleotides encoding these polypeptides are also encompassed by the invention.

The polypeptides of the present invention are preferably provided in an isolated form, and preferably are substantially purified. A recombinantly produced version of the Neutrokine-alpha and/or Neutrokine-alphaSV polypeptides can be substantially purified by the one-step method described in Smith and Johnson, Gene 67:31-40 (1988).

The polypeptides of the present invention include the complete polypeptide encoded by the deposited cDNA (ATCC Deposit No. 97768) including the intracellular, transmembrane and extracellular domains of the polypeptide encoded by the deposited cDNA, the mature soluble polypeptide encoded by the deposited cDNA, the extracellular domain minus the intracellular and transmembrane domains of the protein, the complete polypeptide of FIGS. 1A and 1B (amino acid residues 1-285 of SEQ ID NO:2), the mature soluble polypeptide of FIGS. 1A and 1B (amino acids 134-285 of SEQ ID NO:2), the extracellular domain of FIGS. 1A and 1B (amino acid residues 73-285 of SEQ ID NO:2) minus the intracellular and transmembrane domains, as well as polypeptides which have at least 80%, 85%, 90% similarity, more preferably at least 95% similarity, and still more preferably at least 96%, 97%, 98% or 99% similarity to those described above. Polynucleotides encoding these polypeptides are also encompassed by the invention.

The polypeptides of the present invention also include the complete polypeptide encoded by the deposited cDNA including the intracellular, transmembrane and extracellular domains of the polypeptide encoded by the deposited cDNA (ATCC Deposit No. 203518), the mature soluble polypeptide encoded by the deposited cDNA, the extracellular domain minus the intracellular and transmembrane domains of the protein, the complete polypeptide of FIGS. 5A and 5B (amino acid residues 1-266 of SEQ ID NO:19), the mature soluble polypeptide of FIGS. 5A and 5B (amino acid residues 134-266 of SEQ ID NO:19), the extracellular domain of FIGS. 5A and 5B (amino acid residues 73-266 of SEQ ID NO:19) minus the intracellular and transmembrane domains, as well as polypeptides which have at least 80%, 85%, 90% similarity, more preferably at least 95% similarity, and still more preferably at least 96%, 97%, 98% or 99% similarity to those described above. Polynucleotides encoding these polypeptides are also encompassed by the invention.

Further polypeptides of the present invention include polypeptides at least 80%, or at least 85% identical, more preferably at least 90% or 95% identical, still more preferably at least 96%, 97%, 98% or 99% identical to the polypeptide encoded by the deposited cDNA (ATCC Deposit No. 97768) or to the polypeptide of FIGS. 1A and 1B (SEQ ID NO:2), and also include portions of such polypeptides with at least 30 amino acids and more preferably at least 50 amino acids. Polynucleotides encoding these polypeptides are also encompassed by the invention.

Further polypeptides of the present invention include polypeptides at least 80%, or at least 85% identical, more preferably at least 90% or 95% identical, still more preferably at least 96%, 97%, 98% or 99% identical to the polypeptide encoded by the deposited cDNA (ATCC Deposit No. 203518) or to the polypeptide of FIGS. 5A and 5B (SEQ ID NO:19), and also include portions of such polypeptides with at least 30 amino acids and more preferably at least 50 amino acids. Polynucleotides encoding these polypeptides are also encompassed by the invention.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482-489, 1981) to find the best segment of similarity between two sequences.

By a polypeptide having an amino acid sequence at least, for example, 95% "identical" to a reference amino acid sequence of a Neutrokine-alpha and/or Neutrokine-alphaSV polypeptide is intended that the amino acid sequence of the polypeptide is identical to the reference sequence except that the polypeptide sequence may include up to five amino acid alterations per each 100 amino acids of the reference amino acid of the Neutrokine-alpha and/or Neutrokine-alphaSV polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98%, 99% identical to, for instance, the amino acid sequence shown in FIGS. 1A and 1B (SEQ ID NO:2), the amino acid sequence encoded by the deposited cDNA clone HNEDU15 (ATCC Accession No. 97768), or fragments thereof, or, for instance, to the amino acid sequence shown in FIGS. 5A and 5B (SEQ ID NO:19), the amino acid sequence encoded by the deposited cDNA clone HDPMC52 (ATCC Accession No. 203518), or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptides of the present invention have uses that include, but are not limited to, as a molecular weight marker on SDS-PAGE gels or on molecular sieve gel filtration columns using methods well known to those skilled in the art. Additionally, as described in detail below, the polypeptides of the present invention have uses that include, but are not limited to, raising polyclonal and monoclonal antibodies, which are useful in assays for detecting Neutrokine-alpha and/or Neutrokine-alphaSV polypeptide expression as described below or as agonists and antagonists capable of enhancing or inhibiting Neutrokine-alpha and/or Neutrokine-alphaSV function. The polypeptides of the invention also have therapeutic uses as described herein. Further, such polypeptides can be used in the yeast two-hybrid system to "capture" Neutrokine-alpha and/or Neutrokine-alphaSV binding proteins which are also candidate agonists and antagonists according to the present invention. The yeast two hybrid system is described in Fields and Song, Nature 340:245-246 (1989).

Transgenics and "Knock-outs"

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson, et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, 1983, Mol Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety. See also, U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)).

The present invention provides for transgenic animals that carry the transgene in all their cells, as well as animals which carry the transgene in some, but not all their cells, i.e., mosaic or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265: 103-106 (1994)). The regulatory sequences required for such a cell-type specific inactivation will depend upon the particular cell type of interest, and will be apparent to those of skill in the art. In addition to expressing the polypeptide of the present invention in a ubiquitous or tissue specific manner in transgenic animals, it would also be routine for one skilled in the art to generate constructs which regulate expression of the polypeptide by a variety of other means (for example, developmentally or chemically regulated expression).

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, reverse transcriptase-PCR (rt-PCR); and TaqMan PCR. Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; breeding to place the transgene on a distinct background that is appropriate for an experimental model of interest; and breeding of transgenic animals to other animals bearing a distinct transgene or knockout mutation.

Transgenic and "knock-out" animals of the invention have uses which include, but are not limited to, animal model systems useful in elaborating the biological function of Neutrokine-alpha and/or Neutrokine-alphaSV polypeptides, studying conditions and/or disorders associated with aberrant Neutrokine-alpha and/or Neutrokine-alphaSV expression, and in screening for compounds effective in ameliorating such conditions and/or disorders.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Antibodies

Further polypeptides of the invention relate to antibodies and T-cell antigen receptors (TCR) which immunospecifically bind a polypeptide, polypeptide fragment, or variant of SEQ ID NO:2 and/or SEQ ID NO:19, and/or an epitope, of the present invention (as determined by immunoassays well known in the art for assaying specific antibody-antigen binding). In specific embodiments, antibodies of the invention bind homomeric, especially homotrimeric, Neutrokine-alpha polypeptides. In other specific embodiments, antibodies of the invention bind heteromeric, especially heterotrimeric, Neutrokine-alpha polypeptides such as a heterotrimer containing two Neutrokine-alpha polypeptides and one APRIL polypeptide (e.g., SEQ ID NO:20 or SEQ ID NO:47) or a heterotrimer containing one Neutrokine-alpha polypeptide and two APRIL polypeptides.

In particularly preferred embodiments, the antibodies of the invention bind homomeric, especially homotrimeric, Neutrokine-alpha polypeptides, wherein the individual protein components of the multimers consist of the mature form of Neutrokine alpha (e.g., amino acids residues 134-285 of SEQ ID NO:2, or amino acids residuess 134-266 of SEQ ID NO:19.) In other specific embodiments, antibodies of the invention bind heteromeric, especially heterotrimeric, Neutrokine-alpha polypeptides such as a heterotrimer containing two Neutrokine-alpha polypeptides and one APRIL polypeptide or a heterotrimer containing one Neutrokine-alpha polypeptide and two APRIL polypeptides, and wherein the individual protein components of the Neutrokine-alpha heteromer consist of the mature extracellular soluble portion of either Neutrokine-alpha or (e.g., amino acids residues 134-285 of SEQ ID NO:2, or amino acids residues 134-266 of SEQ ID NO:19) or the mature extracellular soluble portion APRIL (e.g., amino acid residues 105-250 of SEQ ID NO:47).

In specific embodiments, the antibodies of the invention bind conformational epitopes of a Neutrokine-alpha and/or Neutrokine-alphaSV monomeric protein. In specific embodiments, the antibodies of the invention bind conformational epitopes of a Neutrokine-alpha and/or Neutrokine-alphaSV multimeric, especially trimeric, protein. In other embodiments, antibodies of the invention bind conformational epitopes that arise from the juxtaposition of Neutrokine-alpha and/or Neutrokine alpha SV with a heterologous polypeptide, such as might be present when Neutrokine-alpha or Neutrokine-alpha SV forms heterotrimers (e.g., with APRIL polypeptides (e.g., SEQ ID NO:20 or SEQ ID NO:47)), or in fusion proteins between Neutrokine alpha and a heterologous polypeptide.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-id antibodies to antibodies of the invention), and epitope-binding fragments of any of the above. The term “antibody,” as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgAl and IgA2) or subclass of immunoglobulin molecule. . In preferred embodiments, the immunoglobulin is an IgG1 or an IgG4 isotype. Immunoglobulins may have both a heavy and light chain. An array of IgG, IgE, IgM, IgD, IgA, and IgY heavy chains may be paired with a light chain of the kappa or lambda forms.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, “human” antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

In specific embodiments, antibodies of the invention bind to polypeptides comprising Phe-115 to Leu-147, Ile-150 to Tyr-163, Ser-171 to Phe-194, Glu-223 to Tyr-246, and Ser-271 to Phe-278 of the amino acid sequence of SEQ ID NO:2. In another specific embodiment, antibodies of the invention bind to polypeptides consisting of Phe-115 to Leu-147, Ile-150 to Tyr-163, Ser-171 to Phe-194, Glu-223 to Tyr-246, and Ser-271 to Phe-278 of the amino acid sequence of SEQ ID NO:2. In a preferred embodiment, antibodies of the invention bind to a polypeptide comprising Glu-223 to Tyr-246 of SEQ ID NO:2. In another preferred embodiment, antibodies of the invention bind to a polypeptide consisting of Glu-223 to Tyr-246 of SEQ ID NO:2. In a more preferred embodiment, antibodies of the invention bind to a polypeptide consisting of Phe-230 to Asn-242 of SEQ ID NO:2. In further preferred, nonexclusive embodiments, the antibodies of the invention inhibit one or more biological activities of Neutrokine-alpha and/or Neutrokine-alphaSV polypeptides of the invention through specific binding. In more preferred embodiments, the antibody of the invention inhibits Neutrokine-alpha- and/or Neutrokine-alphaSV-mediated B cell proliferation.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In a specific embodiment, antibodies of the present invention cross react with APRIL (e.g., SEQ ID NO:20 or SEQ ID NO:47; PCT International Publication Number WO97/33902; GenBank Accession No. AF046888 (nucleotide) and AAC6132 (protein); J. Exp. Med. 188(6): 1185-1190). In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under hybridization conditions (as described herein). Antibodies of the present invention may also be described or specified in terms of their binding affinity to a polypeptide of the invention. In specific embodiments, antibodies of the invention bind Neutrokine-alpha and/or Neutokine-alphaSV polypeptides, or fragments or variants thereof, with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention bind Neutrokine-alpha and/or Neutokine-alphaSV polypeptides or fragments or variants thereof with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind Neutrokine-alpha and/or Neutokine-alphaSV polypeptides or fragments or variants thereof with a dissociation constant or KD less than or equal to $5\times10^{-9}$ M, $10^{-9}$M, $5\times10^{-10}$ M, $10^{-10}$ M, $5\times10^{-11}$ M , $10^{-11}$ M, $5\times10^{-12}$ M, $10^{-12}$ M, $5\times^{-13}$ M, $10^{-13}$ M, $5\times 10^{-14}$ M, $10^{-14}$ M, $5\times10^{-15}$ M, or $10^{-15}$ M. The invention encompasses antibodies that bind Neutrokine-alpha and/or Neutokine-alphaSV polypeptides with a dissociation constant or $K_D$ that is within any one of the ranges that are between each of the individual recited values.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptoraigand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., 3. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N— or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protectingiblocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

A "monoclonal antibody" may comprise, or alternatively consist of, two proteins, i.e., a heavy and a light chain.

Methods for producing and screening for specific antibodies using hybridoma technology are routine and well known in the art and are discussed in detail in the Examples (e.g., Example 9). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Imumunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework region from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2. In another preferred embodiment, the antibody binds specifically to a polypeptide having the amino acid sequence of SEQ ID NO:19. In another preferred embodiment, the antibody binds specifically to a polypeptide having the amino acid sequence of SEQ ID NO:23. In another preferred embodiment, the antibody binds specifically to a polypeptide having the amino acid sequence of SEQ ID NO:28. In another preferred embodiment, the antibody binds specifically to a polypeptide having the amino acid sequence of SEQ ID NO:30. In another preferred embodiment, the antibody binds specifically to a polypeptide having the amino acid sequence of SEQ ID NO:39. In another preferred embodiment, the antibody binds specifically to a polypeptide having the amino acid sequence of SEQ ID NO:40. In another embodiment, the antibody binds specifically to a polypeptide having the amino acid sequence of SEQ ID NO:41. In another embodiment, the antibody binds specifically to a polypeptide having the amino acid sequence of SEQ ID NO:42. In another embodiment, the antibody binds specifically to a polypeptide having the amino acid sequence of SEQ ID NO:43. In another embodiment, the antibody binds specifically to a polypeptide having the amino acid sequence of SEQ ID NO:44.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRS) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host- expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into nonessential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non- essential region of the viral genome (e.g., region E1 or E3) will result in a recombinant virus that is viable and capable of expressing the antibody molecule in infected hosts. (E.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc.

Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalent and non-covalent conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30,40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lent. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fe region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fe portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. Also as discussed, supra, the polypeptides corresponding to a polypeptide, polypeptide fragment, or a variant of SEQ ID NO:19 may be fused or conjugated to the above antibody portions to increase the in vivo half life of the polypeptides or for use in immunoassays using methods known in the art. Moreover, the polypeptides corresponding to SEQ ID NO:19 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide- linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fe part in a fusion protein is beneficial in therapy and diagnosis, and thus can result in, for example, improved pharmacokinetic properties. (EP A 232, 262). Alternatively, deleting the Fe part after the fusion protein has been expressed, detected, and purified, would be desired. For example, the Fe portion may hinder therapy and diagnosis if the fusion protein is used as an antigen for immunizations. In drug discovery, for example, human proteins, such as hIL-5, have been fused with Fe portions for the purpose of high-throughput screening assays to identify antagonists of hIL-5. (See, Bennett et al., J. Molecular Recognition 8:52-58 (1995); Johanson et al., J. Biol. Chem. 270: 9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{131}I$, $^{125}I$, $^{123}I$, $^{121}I$), carbon ($^{14}C$), sulfur ($^{35}S$), tritium ($^{3}H$), indium ($^{115m}In$, $^{113m}In$, $^{112}In$, $^{111}In$), and technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}SC$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, and $^{117}Tin$.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}Bi$. In specific embodiments, antibodies of the invention are attached to macrocyclic chelators useful for conjugating radiometal ions, including but not limited to, $^{111}In$, $^{177}Lu$, $^{90}Y$, $^{166}Ho$, and $^{153}Sm$, to polypeptides. In preferred embodiments, the radiometal ion associated with the macrocyclic chelators attached to antibodies of the invention is $^{111}In$. In preferred embodiments, the radiometal ion associated with the macrocyclic chelators attached to antibodies of the invention is $^{90}Y$. In specific embodiments, the macrocyclic chelator is 1,4,7,10-tetraazacyclododecane-N,N',N",N"'-tetraacetic acid (DOTA). In other specific embodiments, the DOTA is attached to the Neutrokine-alpha and/or Neutrokine-alphaSV polypeptide of the invention via a linker molecule. Examples of linker molecules useful for conjugating DOTA to a polypeptide are commonly known in the art—see, for example, DeNardo et al., Clin Cancer Res. 4(10):2483-90 (1998); Peterson et al., Bioconjug. Chem. 10(4):553-7 (1999); and Zimmerman et al, Nucl. Med. Biol. 26(8):943-50 (1999) which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

A cytotoxin or cytotoxic agent includes any agent that is detrimental to cells and includes such molecules as small molecule toxins and enzymatically active toxins of bacterial, fungal, plant, or animal origin, or fragments thereof. Examples include paclitaxol, cytochalasin B, gramicidin D, ethidium bromide, emetine, mitomycin, etoposide (VP-16), tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine), improsulfan, piposulfan, benzodopa, carboquone, meturedopa, uredopa, altretamine, triethylenemelamine, trietylenephosphoramide, triethylenethiophosphaoramide trimethylolomelamine, chlomaphazine, cholophosphamide, estramustine, ifosfamide, novembichin, phenesterine, prednimustine, trofosfamide, uracil mustard, chlorozotocin, fotemustine, nimustine, ranimustine, aclacinomysins, azaserine, cactinomycin, calichearnicin, carabicin, carminomycin, carzinophilin, chromomycins, detorubicin, 6-diazo-5-oxo-L-norleucine, epirubicin, esorubicin, idarubicin, marcellomycin, mycophenolic acid, nogalamycin, olivomycins, peplomycin, potfiromycin, quelamycin, rodorubicin, streptonigrin, tubercidin, ubenimex, zinostatin, zorubicin, denopterin, pteropterin, trimetrexate, fludarabine, thiamiprine, ancitabine, azacitidine, 6-azauridine, carmofur, dideoxyuridine, doxifluridine, enocitabine, floxuridine, 5-FU, calusterone, dromostanolone propionate, epitiostanol, mepitiostane, testolactone, aminoglutethimide, mitotane, trilostane, frolinic acid, aceglatone, aldophosphamide glycoside, aminolevulinic acid, amsacrine, bestrabucil, bisantrene, edatraxate, defofamine, demecolcine, diaziquone, elfornithine, elliptinium acetate, etoglucid, gallium nitrate, hydroxyurea, lentinan, lonidamine, mitoguazone, mopidamol, nitracrine, pentostatin, phenamet, pirarubicin, podophyllinic acid, 2-ethylhydrazide, procarbazine, PSKO, razoxane, sizofiran, spirogermanium, tenuazonic acid, triaziquone, 2,2',2"-trichlorotriethylamine, urethan, vindesine, dacarbazine mannomustine, mitobronitol, mitolactol, pipobroman, gacytosine, arabinoside ("Ara-C"), taxoids, e.g. paclitaxel ("TAXOL", Bristol-Myers Squibb Oncology, Princeton, N.J.) doxetaxel ("TAXOTERE", Rh6ne-Poulenc Rorer, Antony, France), gemcitabine, ifosfamide, vinorelbine, navelbine, novantrone, teniposide, aminopterin, xeloda, ibandronate, CPT-I 1, topoisomerase inhibitor RFS 2000, difluoromethylornithine (DMFO), retinoic acid, esperamicins, capecitabine, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4 hydroxytamoxifen, trioxifene, keoxifene, LY 117018, onapristone, torernifene (Fareston), and anti-androgens such as flutamide, nilutamide, bicalutamide, leuprolide, and goserelin, and pharmaceutically acceptable salts, acids or derivatives of any of the above.

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), CD40 Ligand, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis Results, And Future Prospective Of The Therapeutic Use Of Radiolabeled Antibody in Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used, include but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^{3}H$ or $^{125}I$) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and ant-idiotypic antibodies as described herein). The antibodies of the invention can be used to treat, inhibit or prevent diseases, disorders or conditions associated with aberrant expression and/or activity of a polypeptide of the invention and/or a receptor for the polypeptide of the invention (e.g., transmembrane activator and CAML interactor (TACI, GenBank accesion number AAC51790), BAFF-R (GenBank Acession Number NP_443177) and B-cell maturation antigen (BCMA, GenBank accession number NP_001183)), including, but not limited to, any one or more of the diseases, disorders, or conditions described herein (e.g., autoimmune diseases, disorders, or conditions associated with such diseases or disorders, including, but not limited to, autoimmune hemolytic anemia (including but not limited to cryoglobinemia or Coombs positive anemia), autoimmune neonatal thrombocytopenia, idiopathic thrombocytopenia purpura, autoimmunocytopenia, autoimmune neutropenia, hemolytic anemia, antiphospholipid syndrome, dermatitis (e.g., atopic dermatitis), allergic encephalomyelitis, myocarditis, relapsing polychondritis, rheumatic heart disease, Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, diabetes mellitus (e.g., Type I diabetes mellitus or insulin dependent diabetes mellitis), juvenile onset diabetes,and autoimmune inflammatory eye, autoimmune thyroiditis, hypothyroidism (i.e., Hashimoto's thyroiditis, systemic lupus erhythematosus, discoid lupus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with ant-collagen antibodies, mixed connective tissue disease, polymyositis/dermatomyositis, pernicious anemia (Addison's disease), idiopathic Addison's disease, infertility, glomerulonephritis such as primary glomerulonephritis, IgA glomerulonephritis, and IgA nephropathy, bullous pemphigoid, Sjogren's syndrome, diabetes millitus, and adrenergic drug resistance (including adrenergic drug resistance with asthma or cystic fibrosis), gluten sensitive enteropathy, dense deposit disease, chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders) and other disorders such as inflammatory skin diseases including psoriasis and sclerosis, responses associated with inflammatory bowel disease (such as Crohn's disease and ulcerative colitis), respiratory distress syndrome (including adult respiratory distress syndrome, ARDS), meningitis, encephalitis, colitis, allergic conditions such as eczema and other conditions involving infiltration of T cells and chronic inflammatory responses, atherosclerosis, leukocyte adhesion deficiency, Reynaud's syndrome, and immune responses associated with acute and delayed hypersensitivity mediated by cytokines and T-lymphocytes typically found in tuberculosis, sarcoidosis, granulomatosis and diseases involving leukocyte diapedesis, central nervous system (CNS) inflammatory disorder, multiple organ injury syndrome, antigen-antibody complex mediated diseases, anti-glomerular basement membrane disease, Lambert-Eaton myasthenic syndrome, Beheet disease, giant cell arteritis, immune complex nephritis, IgA nephropathy, IgM polyneuropathies or autoimmune thrombocytopenia etc.

In a specific embodiment, antibodies of the invention are used to treat, inhibit, prognose, diagnose or prevent rheumatoid arthritis. In a specific embodiment, antibodies of the invention are used to treat, inhibit, prognose, diagnose or prevent advanced rheumatoid arthritis.

In another specific embodiment, antibodies of the invention are used to treat, inhibit, prognose, diagnose or prevent systemic lupus erythematosis.

For example, an antibody, or antibodies, of the present invention are used to treat patients with clinical diagnosis of rheumatoid arthritis (RA). The patient treated will not have a B cell malignancy. Moreover, the patient is optionally further treated with any one or more agents employed for treating RA such as salicylate; nonsteroidal anti-inflammatory drugs such as indomethacin, phenylbutazone, phenylacetic acid derivatives (e.g. ibuprofen and fenoprofen), naphthalene acetic acids (naproxen), pyrrolealkanoic acid (tometin), indoleacetic acids (sulindac), halogenated anthranilic acid (meclofenamate sodium), piroxicam, zomepirac and diflunisal; antimalarials such as chloroquine; gold salts; penicillamine; or immunosuppressive agents such as methotrexate or corticosteroids in dosages known for such drugs or reduced dosages. Preferably however, the patient is only treated with an antibody, or antibodies, of the present invention. Antibodies of the present invention are administered to the RA patient according to a dosing schedule as described infra, which may be readily determined by one of ordinary skill in the art. The primary response is determined by the Paulus index (Paulus et al. Athritis Rheum. 33:477484 (1990)), i.e. improvement in morning stiffness, number of painful and inflamed joints, erythrocyte sedimentation (ESR), and at least a 2-point improvement on a 5-point scale of disease severity assessed by patient and by physician. Administration of an antibody, or antibodies, of the present invention will alleviate one or more of the symptoms of RA in the patient treated as described above.

In a further specific embodiment, antibodies of the invention are used to treat, inhibit, prognose, diagnose or prevent hemolytic anemia. For example, patients diagnosed with autoimmune hemolytic anemia (AIHA), e.g., cryoglobinemia or Coombs positive anemia, are treated with an antibody, or antibodies, of the present invention. AIHA is an acquired hemolytic anemia due to auto-antibodies that react with the patient's red blood cells. The patient treated will not have a B cell malignancy. Further adjunct therapies (such as glucocorticoids, prednisone, azathioprine, cyclophosphamide, vinca-laden platelets or Danazol) may be combined with the antibody therapy, but preferably the patient is treated with an antibody, or antibodies, of the present invention as a single-agent throughout the course of therapy. Antibodies of the present invention are administered to the hemolytic anemia patient according to a dosing schedule as described infra, which may be readily determined by one of ordinary skill in the art. Overall response rate is determined based upon an improvement in blood counts, decreased requirement for transfusions, improved hemoglobin levels and/or a decrease in the evidence of hemolysis as determined by standard chemical parameters. Administration of an antibody, or antibodies of the present invention will improve any one or more of the symptoms of hemolytic anemia in the patient treated as described above. For example, the patient treated as described above will show an increase in hemoglobin and an improvement in chemical parameters of hemolysis or return to normal as measured by serum lactic dehydrogenase and/or bilirubin.

In another specific embodiment, antibodies of the invention are used to treat, inhibit, prognose, diagnose or prevent adult immune thrombocytopenic purpura. Adult immune thrombocytopenic purpura (ITP) is a relatively rare hematologic disorder that constitutes the most common of the immune-mediated cytopenias. The disease typically presents with severe thrombocytopenia that may be associated with acute hemorrhage in the presence of normal to increased megakaryocytes in the bone marrow. Most patients with ITP have an IgG antibody directed against target antigens on the outer surface of the platelet membrane, resulting in platelet sequestration in the spleen and accelerated reticuloendothelial destruction of platelets (Bussell, J. B. Hematol. Oncol. Clin. North Am. (4):179 (1990)). A number of therapeutic interventions have been shown to be effective in the treatment of ITP. Steroids are generally considered first-line therapy, after which most patients are candidates for intravenous immunoglobulin (IVIG), splenectomy, or other medical therapies including vincristine or immunosuppressive/cytotoxic agents. Up to 80% of patients with ITP initially respond to a course of steroids, but far fewer have complete and lasting remissions. Splenectomy has been recommended as standard second-line therapy for steroid failures, and leads to prolonged remission in nearly 60% of cases yet may result in reduced immunity to infection. Splenectomy is a major surgical procedure that may be associated with substantial morbidity (15%) and mortality (2%). IVIG has also been used as second line medical therapy, although only a small proportion of adult patients with ITP achieve remission. Therapeutic options that would interfere with the production of autoantibodies by activated B cells without the associated morbidities that occur with corticosteroids and/or splenectomy would provide an important treatment approach for a proportion of patients with ITP. Patients with clinical diagnosis of ITP are treated with an antibody, or antibodies of the present invention, optionally in combination with steroid therapy. The patient treated will not have a B cell malignancy. Antibodies of the present invention are administered to the RA patient according to a dosing schedule as described infra, which may be readily determined by one of ordinary skill in the art. Overall patient response rate is determined based upon a platelet count determined on two consecutive occasions two weeks apart following treatments as described above. See, George et al. "Idiopathic Thrombocytopenic Purpura: A Practice Guideline Developed by Explicit Methods for The American Society of Hematology", Blood 88:3-40 (1996), expressly incorporated herein by reference.

In other embodiments, antibody agonists of the invention are be used to treat, inhibit or prevent immunodeficiencies, and/or disorders, or conditions associated with immunodeficiencies. Such immunodeficiencies include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

In another specific embodiment, antibodies of the invention are used to treat, inhibit, prognose, diagnose or prevent CVID, or a subgroup of individuals having CVID.

In another specific embodiment, antibody agonists of the invention are used as an adjuvant to stimulate B cell proliferation, immunoglobulin production, and/or to enhance B cell survival.

The treatment and/or prevention of diseases, disorders, or conditions associated with aberrant expression and/or activity of a polypeptide of the invention and/or a receptor for the polypeptide of the invention (e.g., TACI, BCMA or BAFF-R) includes, but is not limited to, alleviating symptoms associated with those diseases, disorders or conditions. The antibodies of the invention may also be used to target and kill cells expressing Neutrokine-alpha on their surface and/or cells having Neutrokine-alpha bound to their surface. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy, anti-tumor agents, antibiotics, and immunoglobulin). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred embodiment, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Clin., Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include, but are not limited to, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic and/or Prophylactic Administration and Composition

The invention provides methods of treatment, inhibition and prophylaxis by administration to a subject of an effective amount of a compound or pharmaceutical composition of the invention, preferably an antibody of the invention. In a preferred embodiment, the compound is substantially purified (e.g., substantially free from substances that limit its effect or produce undesired side effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Press, Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}I$, $^{125}I$, $^{123}I$, $^{121}I$), carbon ($^{14}C$), sulfur ($^{35}S$), tritium ($^{3}H$), indium ($^{115m}In$, $^{113m}In$, $^{112}In$, $^{111}In$), and technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$; luminescent labels, such as luminol; and fluorescent labels, such as fluorescein and rhodamine, and biotin.

In specific embodiments, antibodies of the invention are attached to macrocyclic chelators useful for conjugating radiometal ions, including but not limited to, $^{177}Lu$, $^{90}Y$, $^{166}Ho$, and $^{153}Sm$, to polypeptides. In a preferred embodiment, the radiometal ion associated with the macrocyclic chelator attached to antibodies of the invention is $^{111}In$. In another preferred embodiments, the radiometal ion associated with the macrocyclic chelator attached to antibodies of the invention is $^{90}Y$. In specific embodiments, the macrocyclic chelator is 1,4,7,10-tetraazacyclododecane-N,N',N",N'"-tetraacetic acid (DOTA). In other specific embodiments, the DOTA is attached to the Neutrokine-alpha and/or Neutrokine-alphaSV polypeptide of the invention via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem.

10(4):553-7, 1999; and Zimmerman et al, Nucl. Med. Biol. 26(8):943-50, 1999 which are hereby incorporated by reference in their entirety.

Techniques known in the art may be applied to label proteins of the invention (including antibodies of the invention). Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter, Chloramine-T reaction, and Iodogen®-based labelling).

One embodiment of the invention is the detection and diagnosis of a disease or disorder associated with aberrant expression of a polypeptide of interest in an animal, preferably a mammal and most preferably a human. In one embodiment, diagnosis comprises: (a) administering (for example, parenterally, subcutaneously, or intraperitoneally) to a subject an effective amount of a labeled molecule which specifically binds to the polypeptide of interest; (b) waiting for a time interval following the administering for permitting the labeled molecule to preferentially concentrate at sites in the subject where the polypeptide is expressed (and for unbound labeled molecule to be cleared to background level); (c) determining background level; and (d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system. As described herein, specific embodiments of the invention are directed to the use of the antibodies of the invention to quantitate or qualitate concentrations of cells of B cell lineage or cells of monocytic lineage.

Also as described herein, antibodies of the invention may be used to treat, diagnose, or prognose an individual having an immunodeficiency. In a specific embodiment, antibodies of the invention are used to treat, diagnose, and/or prognose an individual having common variable immunodeficiency disease (CVID) or a subset of this disease. In another embodiment, antibodies of the invention are used to diagnose, prognose, treat or prevent a disorder characterized by deficient serium immunoglobulin production, recurrent infections, and/or immune system dysfunction.

Also as described herein, antibodies of the invention may be used to treat, diagnose, or prognose an individual having an autoimmune disease or disorder. In a specific embodiment, antibodies of the invention are used to treat, diagnose, and/or prognose an individual having systemic lupus erythematosus, or a subset of the disease. In another specific embodiment, antibodies of the invention are used to treat, diagnose and/or prognose an individual having rheumatoid arthritis, or a subset of this disease.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention comprise two or more antibodies (monoclonal and/or polyclonal) that recognize the same and/or different sequences or regions of the polypeptide of the invention. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. Further included are antibodies that bind to Neutrokine-alpha and/or Neutrokine-alphaSV irrespective of whether Neutrokine-alpha or Neutrokine-alphaSV is bound to a Neutrokine-alpha Receptor. These antibodies act as Neutrokine-alpha and/or Neutrokine-alphaSV agonists as reflected in an increase in cellular proliferation in response to binding of Neutrokine-alpha and/or Neutrokine-alphaSV to a Neutrokine-alpha receptor in the presence of these antibodies. The above antibody agonists can be made using methods known in the art. See e.g., WO 96/40281; U.S. Pat. No. 5,811,097; Deng, B. et al., Blood 92(6):1981-1988 (1998); Chen, Z. et al., Cancer Res. 58(16):3668-3678 (1998); Harrop, J. A. et al., J. Immunol. 161(4):1786-1794 (1998); Zhu, Z. et al., Cancer Res. 58(15):3209-3214 (1998); Yoon, D. Y. et al., J. Immunol. 160(7):3170-3179 (1998); Prat, M. et al., J. Cell. Sci. 111 (Pt2):237-247 (1998); Pitard, V. et al., J. Immunol. Methods 205(2):177-190 (1997); Liautard, J. et al., Cytokinde 9(4): 233-241 (1997); Carlson, N. G. et al., J. Biol. Chem. 272(17): 11295-11301 (1997); Taryman, R. E. et al., Neuron 14(4): 755-762 (1995); Muller, Y. A. et al., Structure 6(9):1153-1167 (1998); Bartumek, P. et al., Cytokine 8(1):14-20 (1996) (said references incorporated by reference in their entireties).

At least fourteen murine monoclonal antibodies have been generated against Neutrokine-alpha. These monoclonal antibodies are designated: 12D6, 2E5, 9B6, 1B8, 5F4, 9A5, 10G12, 11G12, 16B4, 3D4, 16C9, 13D5, 15C10, and 12C5. Preliminary analysis of these antibodies indicates that each binds Neutrokine-alpha protein in a Western blot analysis and when Neutrokine-alpha protein is bound to an ELISA plate. However, further analysis of antibodies 12D6, 2E5, 9B6, 1B8, 5F4, 9A5, 10G12, 11G12, and 16B4 indicates that only the antibodies designated 12D6, 9B6, 2E5, 10G12, 9A5, and 11G12 bind a membrane-bound form of Neutrokine-alpha. Thus, a subset of the monoclonal antibodies generated against Neutrokine-alpha have been determined to bind only the membrane-bound form of Neutrokine-alpha (i.e., this subset does not bind the soluble form of Neutrokine-alpha corresponding to amino acids 134 to 285 of SEQ ID NO:2), which as discussed herein, is primarily limited to expression on monocytes and dendritic cells.

Antibody 9B6 has been found to bind specifically to the membrane—bound form of Neutrokine-alpha, but not to the soluble form of Neutrokine-alpha.

Epitope mapping of antibody 9B6 has indicated that this antibody binds specifically to an amino acid sequence contained in amino acid residues from about Ser-171 to about Phe-194 of SEQ ID NO:2. More particularly, epitope mapping has indicated that antibody 9B6 binds specifically to a peptide comprising amino acid residues Lys-173 to Lys-188 of SEQ ID NO:2.

In contrast, antibodies 16C9 and 15C10 have been found to bind the soluble form of Neutrokine-alpha (amino acids 134 to 285 of SEQ ID NO:2) and to inhibit Neutrokine-alpha-mediated proliferation of B cells. See for example, Example 10. The 15C10 antibody has also been found to inhibit binding of Neutrokine-alpha to its receptor. Epitope mapping of antibody 15C10 has indicated that this antibody binds specifically to an amino acid sequence contained in amino acid residues from about Glu-223 to about Tyr-246 of SEQ ID NO:2. More particularly, epitope mapping has indicated that antibody 15C10 binds specifically to a peptide comprising amino acid residues Val-227 to Asn-242 of SEQ ID NO:2. Antibody 15C10 also binds specifically to a peptide comprising amino acid residues Phe-230 to Cys-245 of SEQ ID NO:2. It is likely that the epitope of 15C10 is conformational rather than linear and that antibody 15C10 may make specific binding contacts with amino acid residues in the full length Neutrokine-alpha protein outside of amino acid residues 223-246 of SEQ ID NO:2 as well as within amino acid residues 223-246.

Furthermore, competitive binding studies have shown that antibodies 3D4 and 15C10 bind similar or identical epitopes (see Example 15).

As described above, anti-Neutrokine-alpha monoclonal antibodies have been prepared. Hybridomas producing the antibodies referred to as 9B6 and 15C10 were deposited with the ATCC located at 10801 University Boulevard, Manassas, Va. 20110-2209, on Jan. 27, 2000 and were assigned deposit accession numbers PTA-1159 and PTA-1158, respectively. The ATCC deposits were made pursuant to the terms of the Budapest Treaty on the international recognition of the deposit of microorganisms for the purposes of patent procedure. The amino acid sequence of the VH andVL domains of the 15C10 atnibody are shown in SEQ ID NOS: 58 and 59, respectively.

NS0 cell lines engineered to secrete chimeric forms of antbodies 3D4 and 15C10 were deposited with the ATCC located at 10801 University Boulevard, Manassas, Va. 20110-2209, at on Oct. 24, 2001 and were assigned deposit accession numbers PTA-3795 and PTA-3794, respectively. Chimeric antibodies 3D4 and 15C10 contain murine variable regions and human constant (IgG1 and kappa) regions. The ATCC deposits were made pursuant to the terms of the Budapest Treaty on the international recognition of the deposit of microorganisms for the purposes of patent procedure.

In one embodiment, the antibodies of the invention have one or more of the same biological characteristics as one or more of the antibodies secreted by the deposited cell lines (ATCC accession numbers PTA-1158, PTA-1159, PTA-3795 and PTA-3794). By "biological characteristics" is meant, the in vitro or in vivo activities or properties of the antibodies, such as, for example, the ability to bind to Neutrokine-alpha (e.g., the polypeptide of SEQ ID NO:2, the mature form of Neutrokine-alpha, the membrane-bound form of Neutrokine-alpha, the soluble form of Neutrokine-alpha (amino acids 134 to 285 of SEQ ID NO:2), and an antigenic and/or epitope region of Neutrokine-alpha), the ability to substantially block Neutrokine-alpha/Neutrokine-alpha receptor binding, or the ability to block Neutrokine-alpha mediated biological activity (e.g., stimulation of B cell proliferation and immunoglobulin production). Optionally, the antibodies of the invention will bind to the same epitope as at least one of the antibodies specifically referred to herein. Such epitope binding can be routinely determined using assays known in the art.

Thus, in one embodiment, the invention provides antibodies that specifically bind the membrane-bound form of Neutrokine-alpha and do not bind the soluble form of Neutrokine-alpha. These antibodies have uses which include, but are not limited to, as diagnostic probes for identifying and/or isolating monocyte lineages expressing the membrane bound form of Neutrokine-alpha. For example, the expression of the membrane bound form of Neutrokine-alpha is elevated on activated monocytes, and accordingly, antibodies encompassed by the invention may be used to detect and/or quantitate levels of activated monocytes. Additionally, antibodies that only bind the membrane bound form of Neutrokine-alpha may be used to target toxins to neoplastic, preneoplastic, and/or other cells that express the membrane bound form of Neutrokine-alpha (e.g., monocytes and dendritic cells).

In another embodiment, antibodies of the invention specifically bind only the soluble form of Neutrokine-alpha (amino acids 134 to 285 of SEQ ID NO:2). These antibodies have uses which include, but are not limited to, uses such as diagnostic probes for assaying soluble Neutrokine-alpha in biological samples, and as therapeutic agents that target toxins to cells expressing Neutrokine-alpha receptors (e.g., B cells), and/or to reduce or block in vitro or in vivo Neutrokine-alpha mediated biological acitivty (e.g., stimulation of B cell proliferation and/or immunoglobulin production).

The invention also provides for antibodies that specifically bind both the membrane-bound and soluble form of Neutrokine-alpha.

As described above, the invention encompasses antibodies that inhibit or reduce the ability of Neutrokine-alpha and/or Neutrokine-alphaSV to bind Neutrokine-alpha receptor and/or Neutrokine-alphaSV receptor in vitro and/or in vivo. In a specific embodiment, antibodies of the invention inhibit or reduce the ability of Neutrokine-alpha and/or Neutrokine-alphaSV to bind Neutrokine-alpha receptor and/or Neutrokine-alphaSV receptor in vitro. In another nonexclusive specific embodiment, antibodies of the invention inhibit or reduce the ability of Neutrokine-alpha and/or Neutrokine-alphaSV to bind Neutrokine-alpha receptor and/or Neutrokine-alphaSV receptor in vivo. Such inhibition can be assayed using techniques described herein or otherwise known in the art.

The invention also encompasses, antibodies that bind specifically to Neutrokine-alpha and/or Neutrokine-alphaSV, but do not inhibit the ability of Neutrokine-alpha and/or Neutrokine-alphaSV to bind Neutrokine-alpha receptor and/or Neutrokine-alphaSV receptor in vitro and/or in vivo. In a specific embodiment, antibodies of the invention do not inhibit or reduce the ability of Neutrokine-alpha and/or Neutrokine-alphaSV to bind Neutrokine-alpha receptor and/or Neutrokine-alphaSV receptor in vitro. In another nonexclusive specific embodiment, antibodies of the invention do not inhibit or reduce the ability of Neutrokine-alpha and/or Neutrokine-alphaSV to bind Neutrokine-alpha receptor and/or Neutrokine-alphaSV receptor in vivo.

As described above, the invention encompasses antibodies that inhibit or reduce a Neutrokine-alpha and/or Neutrokine-alphaSV-mediated biological activity in vitro and/or in vivo. In a specific embodiment, antibodies of the invention inhibit or reduce Neutrokine-alpha- and/or Neutrokine-alphaSV-mediated B cell proliferation in vitro. Such inhibition can be assayed by routinely modifying B cell proliferation assays described herein or otherwise known in the art. In another nonexclusive specific embodiment, antibodies of the invention inhibit or reduce Neutrokine-alpha- and/or Neutrokine-alphaSV-mediated B cell proliferation in vivo. In a specific embodiment, the antibody of the invention is 15C10, or a humanized form thereof. In another preferred specific embodiment, the antibody is 16C9, or a humanized form thereof. Thus, in specific embodiments of the invention, a 16C9 and/or 15C10 antibody, or humanized forms thereof, are used to bind soluble Neutrokine-alpha and/or Neutrokine-alphaSV and/or agonists and/or antagonists thereof and thereby inhibit (either partially or completely) B cell proliferation.

Alternatively, the invention also encompasses, antibodies that bind specifically to a Neutrokine-alpha and/or Neutrokine-alphaSV, but do not inhibit or reduce a Neutrokine-alpha and/or Neutrokine-alphaSV-mediated biological activity in vitro and/or in vivo (e.g., stimulation of B cell proliferation). In a specific embodiment, antibodies of the invention do not inhibit or reduce a Neutrokine-alpha and/or Neutrokine-alphaSV-mediated biological activity in vitro. In another non-exclusive embodiment, antibodies of the invention do not inhibit or reduce a Neutrokine-alpha and/or Neutrokine-alphaSV mediated biological activity in vivo. In a specific embodiment, the antibody of the invention is 9B6, or a humanized form thereof.

As described above, the invention encompasses antibodies that specifically bind to the same epitope as at least one of the antibodies specifically referred to herein, in vitro and/or in vivo.

In a specific embodiment, the antibodies of the invention specifically bind to an amino acid sequence contained in amino acid residues from about Ser-171 to about Phe-194 of SEQ ID NO:2, in vitro. In another specific, non-exclusive embodiment, the antibodies of the invention specifically bind to an amino acid sequence contained in amino acid residues from about Ser-171 to about Phe-194 of SEQ ID NO:2, in vivo. In another specific, non-exclusive embodiment, the antibodies of the invention specifically bind to an amino acid sequence contained in amino acid residues from Lys-173 to Lys-188 of SEQ ID NO:2, in vitro. In another specific non-exclusive embodiment, the antibodies of the invention specifically bind to an amino acid sequence contained in amino acid residues from -173 to Lys-188 of SEQ ID NO:2, in vivo.

In an additional specific embodiment, the antibodies of the invention specifically bind to an amino acid sequence contained in amino acid residues from about Glu-223 to about Tyr-246 of SEQ ID NO:2, in vitro. In another specific, non-exclusive embodiment, the antibodies of the invention specifically bind to an amino acid sequence contained in amino acid residues from about Glu-223 to about Tyr-246 of SEQ ID NO:2, in vivo. In another specific, non-exclusive embodiment, the antibodies of the invention specifically bind to an amino acid sequence contained in amino acid residues from Val-227 to Asn-242 of SEQ ID NO:2, in vitro. In another specific non-exclusive embodiment, the antibodies of the invention specifically bind to an amino acid sequence contained in amino acid residues from Val-227 to Asn-242 of SEQ ID NO:2, in vivo. In another specific, non-exclusive embodiment, the antibodies of the invention specifically bind to an amino acid sequence contained in amino acid residues from Phe-230 to Cys-245 of SEQ ID NO:2, in vitro. In another specific, non-exclusive embodiment, the antibodies of the invention specifically bind to an amino acid sequence contained in amino acid residues from Phe-230 to Cys-245 of SEQ ID NO:2, in vivo.

The invention also provides antibodies that competitively inhibit the binding of the 9B6 monoclonal antibody produced by the hybridoma deposited as PTA-1159 to a polypeptide of the invention, preferably the polypeptide of SEQ ID NO:2, more preferable to a polypeptide having the amino acid sequence of residues Ser-171 to Phe-194 of SEQ ID NO:2. Competitive inhibition can be determined by any method known in the art, for example, using the competitive binding assays described herein. In preferred embodiments, the antibody competitively inhibits the binding of 9B6 monoclonal antibody by at least 95%, at least 90%, at least 85%, at least 80%, at least 75%, at least 70%, at least 60%, at least 50%, to the polypeptide of SEQ ID NO:2, or more preferable to a polypeptide having the amino acid sequence of residues Ser-171 to Phe-194 of SEQ ID NO:2.

The invention also provides antibodies that competitively inhibit the binding of the 15C10 monoclonal antibody produced by the hybridoma deposited as PTA-1158 to a polypeptide of the invention, preferably the polypeptide of SEQ ID NO:2, more preferable to a polypeptide having the amino acid sequence of residues Glu-223 to Tyr-246 of SEQ ID NO:2. In preferred embodiments, the antibody competitively inhibits the binding of 15C10 monoclonal antibody by at least 95%, at least 90%, at least 85%, at least 80%, at least 75%, at least 70%, at least 60%, at least 50%, to the polypeptide of SEQ ID NO:2, or more preferable to a polypeptide having the amino acid sequence of residues Glu-223 to Tyr-246 of SEQ ID NO:2.

Additional embodiments of the invention are directed to the 9B6 antibody and to the hybridoma cell line expressing this antibody. A hybridoma cell line expressing Antibody 9B6 was deposited with the ATCC on Jan. 7, 2000 and has been assigned ATCC Deposit No. PTA-1159. In a preferred embodiment, antibody 9B6 is humanized.

Additional embodiments of the invention are directed to the 15C10 antibody and to the hybridoma cell line expressing this antibody. A hybridoma cell line expressing Antibody 15C10 was deposited with the ATCC on Jan. 7, 2000 and has been assigned ATCC Deposit No. PTA-1158. In a preferred embodiment, antibody 15C10 is humanized.

In a specific embodiment, the specific antibodies described above are humanized using techniques described herein or otherwise known in the art and then used as therapeutics as described herein.

In another specific embodiment, any of the antibodies listed above are used in a soluble form.

In another specific embodiment, any of the antibodies listed above are conjugated to a toxin or a label (as described infra). Such conjugated antibodies are used to kill a particular population of cells or to quantitate a particular population of cells. In a preferred embodiment, such conjugated antibodies are used to kill B cells expressing Neutrokine-alpha receptor on their surface. In another preferred embodiment, such conjugated antibodies are used to quantitate B cells expressing Neutrokine-alpha receptor on their surface. In another preferred embodiment, such conjugated antibodies are used to kill monocyte cells expressing the membrane-bound form of Neutrokine-alpha. In another preferred embodiment, such conjugated antibodies are used to quantitate monocyte cells expressing the membrane-bound form of Neutrokine-alpha and/or Neutrokine-alphaSV. In highly preferred embodiments, such conjugated antibodies that bind the membrane bound form of Neutokine-alpha and/or Neutrokine-alphaSV are used to kill Acute Mylegenous Leukemia cells, Chronic Lymphocytic leukemia cells, Multiple Myeloma cells, Non-Hodgkin's Lymphoma cells, and Hodgkins's lymphoma cells.

The antibodies of the invention also have uses as therapeutics and/or prophylactics which include, but are not limited to, in activating monocytes or blocking monocyte activation and/or killing monocyte lineages that express the membrane bound form of Neutrokine-alpha on their cell surfaces (e.g., to treat, prevent, and/or diagnose myeloid leukemias, monocyte based leukemias and lymphomas, monocytosis, monocytopenia, rheumatoid arthritis, and other diseases or conditions associated with activated monocytes). In a specific embodiment, the antibodies of the invention fix complement. In other specific embodiments, as further described herein, the antibodies of the invention (or fragments thereof) are associated with heterologous polypeptides or nucleic acids (e.g. toxins, such as, compounds that bind and activate endogenous cytotoxic effecter systems, and radioisotopes; and cytotoxic prodrugs).

In another embodiment, one or more monoclonal antibodies are produced wherein they recognize or bind Neutrokine-alpha and/or a mutein thereof, but do not recognize or bind Neutrokine-alphaSV and/or a mutein thereof. In a related embodiment, one or more monoclonal antibodies are produced wherein they recognize or bind Neutrokine-alphaSV and/or a mutein thereof, but do not recognize or bind Neutrokine-alpha and/or a mutein thereof.

As discussed above, antibodies to the Neutrokine-alpha and/or Neutrokine-alpha SV polypeptides of the invention can, in turn, be utilized to generate anti-idiotype antibodies that "mimic" the Neutrokine-alpha, using techniques well known to those skilled in the art. (See, e.g., Greenspan & Bona, FASEB J. 7(5):437-444 (1989), and Nissinoff, J. Immunol. 147(8):2429-2438 (1991)). For example, antibodies which bind to Neutrokine-alpha and/or Neutrokine-alpha SV and competitively inhibit the Neutrokine-alpha and/or Neutrokine-alpha SV multimerization and/or binding to ligand can be used to generate anti-idiotypes that "mimic" the Neutrokine-alpha TNF mutimerization and/or binding domain and, as a consequence, bind to and neutralize Neutrokine-alpha or Neutrokine-alpha SV and/or its ligand. Such neutralizing anti-idiotypes or Fab fragments of such anti-idiotypes can be used in therapeutic regimens to neutralize Neutrokine-alpha ligand. For example, such anti-idiotypic antibodies can be used to bind Neutrokine-alpha and/or Neutrokine-alpha SV, or to bind Neutrokine-alpha and/or Neutrokine-alpha SV receptors on the surface of cells of B cell lineage, and thereby block Neutrokine-alpha and/or Neutrokine-alpha SV mediated B cell activation, proliferation, and/or differentiation.

Immune System-Related Disorder Diagnosis

Neutrokine-alpha is expressed in kidney, lung, peripheral leukocyte, bone marrow, T cell lymphoma, B cell lymphoma, activated T cells, stomach cancer, smooth muscle, macrophages, and cord blood tissue, and particularly cells of monocytic lineage. Moreover, Neutrokine-alphaSV is expressed in primary dendritic cells. Additionally, Neutrokine-alpha is expressed on the cell surface of the following non-hematopoietic tumor cell lines. Colon carcinomas HCT 116 (ATCC Accession No. CCL-247) and HT-29 (ATCC Accession No. HTB-38); Colon adenocarcinomas Caco-2 (ATCC Accession No. HTB-37), COLO 201 (ATCC Accession No. CCL-224), and WiDr (ATCC Accession No. CCL-218); Breast adenocarcinoma MDA-MB-231 (ATCC Accession No. HTB-26); Bladder squamous carcinoma SCaBER (ATCC Accession No. HTB-3); Bladder carcinoma HT-1197 (ATCC Accession No. CRL-1473); Kidney carcinomas A498 (ATCC Accession No. HTB44), Caki-1 (ATCC Accession No. HTB46), and Caki-2 (ATCC Accession No. HTG47); Kidney, Wilms tumor SK-NEP-1 (ATCC Accession No. HTB48); and Pancreas carcinomas Hs 766T (ATCC Accession No. HTB-134), MIA PaCa-2 (ATCC Accession No. CRL-1420), and SU.86.86 (ATCC Accession No. CRL-1837). For a number of immune system-related disorders, substantially altered (increased or decreased) levels of Neutrokine-alpha and/or Neutrokine-alphaSV gene expression can be detected in immune system tissue or other cells or bodily fluids (e.g., sera, plasma, urine, synovial fluid or spinal fluid) taken from an individual having such a disorder, relative to a "standard" Neutrokine-alpha and/or Neutrokine-alphaSV gene expression level, that is, the Neutrokine-alpha and/or Neutrokine-alphaSV expression level in immune system tissues or bodily fluids from an individual not having the immune system disorder. Thus, the invention provides a diagnostic method useful during diagnosis of an immune system disorder, which involves measuring the expression level of the gene encoding the Neutrokine-alpha and/or Neutrokine-alphaSV polypeptide in immune system tissue or other cells or body fluid from an individual and comparing the measured gene expression level with a standard Neutrokine-alpha and/or Neutrokine-alphaSV gene expression level, whereby an increase or decrease in the gene expression level compared to the standard is indicative of an immune system disorder or normal activation, proliferation, differentiation, and/or death.

In particular, it is believed that certain tissues in mammals with cancer of cells or tissue of the immune system express significantly enhanced or reduced levels of the Neutrokine-alpha and/or Neutrokine-alphaSV polypeptide and mRNA encoding the Neutrokine-alpha and/or Neutrokine-alphaSV polypeptide when compared to a corresponding "standard" level. Further, it is believed that enhanced or depressed levels of the Neutrokine-alpha and/or Neutrokine-alphaSV polypeptide can be detected in certain body fluids (e.g., sera, plasma, urine, and spinal fluid) or cells or tissue from mammals with such a cancer when compared to sera from mammals of the same species not having the cancer.

For example, as disclosed herein, Neutrokine-alpha is highly expressed in cells of monocytic lineage. Accordingly, polynucleotides of the invention (e.g., polynucleotide sequences complementary to all or a portion of Neutrokine-alpha mRNA and/or Neutrokine-alphaSV mRNA) and antibodies (and antibody fragments) directed against the polypeptides of the invention may be used to quantitate or qualitate concentrations of cells of monocytic lineage (e.g., monocytic leukemia cells) expressing Neutrokine-alpha on their cell surfaces. These antibodies additionally have diagnostic applications in detecting abnormalities in the level of Neutrokine-alpha gene expression, or abnormalities in the structure and/or temporal, tissue, cellular, or subcellular location of Neutrokine-alpha and/or Neutrokine-alphaSV. These diagnostic assays may be performed in vivo or in vitro, such as, for example, on blood samples, biopsy tissue or autopsy tissue.

Additionally, as disclosed herein, Neutrokine-alpha receptor is expressed primarily on cells of B cell lineage. Accordingly, Neutrokine-alpha polypeptides of the invention (including labeled Neutrokine-alpha polypeptides and Neutrokine-alpha fusion proteins), and anti-Neutrokine-alpha antibodies (including anti-Neutrokine-alpha antibody fragments) against the polypeptides of the invention may be used to quantitate or qualitate concentrations of cells of B cell lineage (e.g., B cell related leukemias or lymphomas) expressing Neutrokine-alpha receptor on their cell surfaces.

Neutrokine-alpha polypeptides and antibodies additionally have diagnostic applications in detecting abnormalities in the level of Neutrokine-alpha receptor gene expression (e.g., transmembrane activator and CAML interactor (TACI, GenBank accesion number AAC51790), BAFF-R (GenBank Acession Number NP_443177) and B-cell maturation antigen (BCMA, GenBank accession number NP_001183)), or abnormalities in the structure and/or temporal, tissue, cellular, or subcellular location of Neutrokine-alpha receptor and/or diagnosing activity/defects in signalling pathways associated with Neutrokine-alpha. These diagnostic assays may be performed in vivo or in vitro, such as, for example, on blood samples or biopsy tissue using techniques described herein or otherwise known in the art.

In one embodiment, Neutrokine-alpha and/or Neutrokine-alphaSV polynucleotides or polypeptides or Neutrokine-alpha and/or Neutrokine-alphaSV agonists or antagonists (e.g., anti-Neutrokine-alpha and/or anti-Neutrokine-alphaSV antibodies) of the invention are used to treat, prevent, diagnose, or prognose an individual having an immunodeficiency.

Immunodeficiencies that may be treated, prevented, diagnosed, and/or prognosed with the Neutrokine-alpha and/or Neutrokine-alphaSV polynucleotides or polypeptides or Neutrokine-alpha and/or Neutrokine-alphaSV agonists or antagonists (e.g., anti-Neutrokine-alpha and/or anti-Neutrokine-alphaSV antibodies) of the invention, include, but are not limited to one or more immunodeficiencies selected from: severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), chronic granulomatous disease, Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

According to this embodiment, an individual having an immunodeficiency expresses aberrantly low levels of Neutrokine-alpha and/or Neutrokine-alpha SV when compared to an individual not having an immunodeficiency. Any means described herein or otherwise known in the art may be applied to detect Neutrokine-alpha and/or Neutrokine-alphaSV polynucleotides or polypeptides of the invention (e.g., FACS analysis or ELISA detection of Neutrokine-alpha and/or Neutrokine-alphaSV polypeptides of the invention and hybridization or PCR detection of Neutrokine-alpha and/or Neutrokine-alphaSV polynucleotides of the invention) and to determine the expression profile of Neutrokine-alpha and/or Neutrokine-alphaSV, polynucleotides and/or polypeptides of the invention in a biological sample.

A biological sample of a person afflicted with an immunodeficiency is characterized by low levels of expression of Neutrokine-alpha and/or Neutrokine-alphaSV when compared to that observed in individuals not having an immunodeficiency. Thus, Neutrokine-alpha and/or Neutrokine-alphaSV polynucleotides and/or polypeptides of the invention, and/or agonists or antagonists thereof, may be used according to the methods of the invention in the diagnosis and/or prognosis of an immunodeficiency. For example, a biological sample obtained from a person suspected of being afflicted with an immunodeficiency ("the subject") may be analyzed for the relative expression level(s) of Neutrokine-alpha, and/or Neutrokine-alphaSV polynucleotides and/or polypeptides of the invention. The expression level(s) of one or more of these molecules of the invention is (are) then compared to the expression level(s) of the same molecules of the invention as expressed in a person known not to be afflicted with an immunodeficiency. A significant difference in expression level(s) of Neutrokine-alpha, and/or Neutrokine-alphaSV, polynucleotides and/or polypeptides of the invention, and/or agonists and/or antagonists thereof, between samples obtained from the subject and the control suggests that the subject is afflicted with an immunodeficiency.

In another embodiment, Neutrokine-alpha and/or Neutrokine-alphaSV polynucleotides or polypeptides or Neutrokine-alpha and/or Neutrokine-alphaSV agonists or antagonists (e.g., anti-Neutrokine-alpha and/or anti-Neutrokine-alphaSV antibodies) of the invention are used to treat, diagnose and/or prognose an individual having common variable immunodeficiency disease ("CVID"; also known as "acquired agammaglobulinemia" and "acquired hypogammaglobulinemia") or a subset of this disease. According to this embodiment, an individual having CVID or a subset of individuals having CVID expresses aberrant levels of Neutrokine-alpha and/or Neutrokine-alpha Receptor on their B cells and/or monocytes, when compared to individuals not having CVID. Any means described herein or otherwise known in the art may be applied to detect Neutrokine-alpha polynucleotides or polypeptides of the invention and/or Neutrokine-alpha Receptor polypeptides (e.g., FACS analysis or ELISA detection of Neutrokine-alpha and/or Neutrokine-alphaSV polypeptides of the invention and hybridization or PCR detection of Neutrokine-alpha and/or Neutrokine-alphaSV polynucleotides of the invention) and to determine differentially the expression profile of Neutrokine-alpha, and/or Neutrokine-alphaSV polynucleotides or polypeptides of the invention and/or Neutrokine-alpha receptor polypeptides in a sample containing at least monocyte cells or some component thereof (e.g., RNA) as compared to a sample containing at least B cells or a component thereof (e.g., RNA). In the instance where a sample containing at least monocyte cells or some component thereof (e.g., RNA) is determined to reflect Neutrokine-alpha and/or Neutrokine-alphaSV polynucleotide or polypeptide expression and a sample containing at least B cells or a component thereof (e.g., RNA) is determined to reflect less than normal levels of Neutrokine-alpha receptor polynucleotide or polypeptide expression, the samples may be correlated with the occurrence of CVID (i.e., "acquired agammaglobulinemia" or "acquired hypogammaglobulinemia").

A subset of persons afflicted with CVID are characterized by high levels of expression of both Neutrokine-alpha and the Neutrokine-alpha receptor ("NAR") in peripheral or circulating B cells when compared to that observed in individuals not having CVID. In contrast, persons who are not afflicted with CVID are typically characterized by low levels of Neutrokine-alpha expression and high levels of NAR expression in peripheral or circulating B cells. Thus, Neutrokine-alpha, Neutrokine-alphaSV polypeptides, and/or NAR polypeptides, polynucleotides and/or polypeptides of the invention, and/or agonists or antagonists thereof, may be used according to the methods of the invention in the differential diagnosis of this subset of CVID. For example, a sample of peripherial B cells obtained from a person suspected of being afflicted with CVID ("the subject") may be analyzed for the relative expression level(s) of Neutrokine-alpha, Neutrokine-alphaSV, and/or NAR polynucleotides and/or polypeptides of the invention. The expression level(s) of one or more of these molecules of the invention is (are) then compared to the expression level(s) of the same molecules of the invention as expressed in a person known not to be afflicted with CVID ("the control"). A significant difference in expression level(s) of Neutrokine-alpha and/or Neutrokine-alphaSV polynucleotides or polypeptides of the invention, and/or NAR polypeptides, and/or agonists and/or antagonists thereof, between samples obtained from the subject and the control suggests that the subject is afflicted with this subset of CVID.

Cunningham-Rundles and Bodian followed 248 CVID patients over a period of 1-25 years and discovered that a number of associated diseases or conditions appear with increased frequency in CVID patients (Cunningham-Rundles and Bodian, J. Clin. Immunol., 92:34-48 (1999) which is herein incorporated by reference in its entirety.) The most important clinical events include infections, autoimmunity, inflammatory disorders, marked by gastrointestinal and granulomatous disease, cancer and hepatitis. Most CVID patients are at increased risk of recurrent infections particularly of the respiratory tract. The types of acute and recurring bacterial infections exhibited in most patients include pneumonia, bronchitis and sinusitis. Children with CVID have a marked increased risk of otitis media. Additionally, blood borne infections including sepsis, meningitis, septic arthritis, and osteomyelitis are seen with increased frequency in these patients.

In another specific embodiment, Neutrokine-alpha and/or Neutrokine-alphaSV polynucleotides or polypeptides, or agonists or antagonists thereof (e.g., anti-Neutrokine-alpha, and/or anti-Neutrokine-alphaSV antibodies) are used to diagnose, prognose, treat, or prevent conditions associated with CVID, including, but not limited to, conditions associated with acute and recurring infections (e.g., pneumonia, bronchitis, sinusitis, otitis media, sepsis, meningitis, septic arthritis, and osteomyelitis), chronic lung disease, autoimmunity, granulomatous disease, lymphoma, cancers (e.g., cancers of the breast, stomach, colon, mouth, prostate, lung, vagina, ovary, skin, and melanin forming cells (i.e. melanoma), inflammatory bowel disease (e.g., Crohn's disease, ulcerative colitis, and ulcerative proctitis), malabsoption, Hodgkin's disease, and Waldenstrom's macroglobulinemia.

In a specific embodiment, Neutrokine-alpha and/or Neutrokine-alphaSV polynucleotides or polypeptides, or agonists or antagonists thereof (e.g., anti-Neutrokine-alpha, and/or anti-Neutrokine-alphaSV antibodies) are used to diagnose, prognose, treat, or prevent a disorder characterized by deficient serum immunoglobulin production, recurrent infections, and/or immune system dysfunction. Moreover, Neutrokine-alpha, and/or Neutrokine-alphaSV polynucleotides or polypeptides, or agonists or antagonists thereof (e.g., anti-Neutrokine-alpha and/or anti-Neutrokine-alphaSV antibodies) may be used to diagnose, prognose, treat, or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pneumocystis carnii.

In another embodiment, Neutrokine-alpha and/or Neutrokine-alphaSV polynucleotides or polypeptides or Neutrokine-alpha and/or Neutrokine-alphaSV agonists or antagonists (e.g., anti-Neutrokine-alpha and/or anti-Neutrokine-alphaSV antibodies) of the invention are used to treat, diagnose, or prognose an individual having an autoimmune disease or disorder.

Autoimmune diseases or disorders that may be treated, diagnosed, or prognosed using Neutrokine-alpha and/or Neutrokine-alphaSV polynucleotides or polypeptides or Neutrokine-alpha and/or Neutrokine-alphaSV agonists or antagonists (e.g., anti-Neutrokine-alpha and/or anti-Neutrokine-alphaSV antibodies) of the invention include, but are not limited to, one or more of the following: autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with ant-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders.

According to this embodiment, an individual having an autoimmune disease or disorder expresses aberrantly high levels of Neutrokine-alpha, Neutrokine-alpha SV, and/or NAR when compared to an individual not having an autoimmune disease or disorder. Any means described herein or otherwise known in the art may be applied to detect Neutrokine-alpha, and/or Neutrokine-alphaSV polynucleotides or polypeptides of the invention and/or NAR polypeptides (e.g., FACS analysis or ELISA detection of Neutrokine-alpha and/or Neutrokine-alphaSV polypeptides of the invention and hybridization or PCR detection of Neutrokine-alpha and/or Neutrokine-alphaSV polynucleotides of the invention) and to determine the expression profile of Neutrokine-alpha and/or Neutrokine-alphaSV, polynucleotides and/or polypeptides of the invention and/or NAR polypeptides in a biological sample.

A biological sample of persons afflicted with an autoimmune disease or disorder is characterized by high levels of expression of Neutrokine-alpha, Neutrokine-alphaSV, and/or NAR when compared to that observed in individuals not having an autoimmune disease or disorder. Thus, Neutrokine-alpha and/or Neutrokine-alphaSV polynucleotides and/or polypeptides of the invention, and/or agonists or antagonists thereof, may be used according to the methods of the invention in the diagnosis and/or prognosis of an autoimmune disease or disorder. For example, a biological sample obtained from a person suspected of being afflicted with an autoimmune disease or disorder ("the subject") may be analyzed for the relative expression level(s) of Neutrokine-alpha, and/or Neutrokine-alphaSV polynucleotides and/or polypeptides of the invention and/or NAR polypeptides. The expression level(s) of one or more of these molecules of the invention is (are) then compared to the expression level(s) of the same molecules of the invention as expressed in a person known not to be afflicted with an autoimmune disease or disorder. A significant difference in expression level(s) of Neutrokine-alpha, and/or Neutrokine-alphaSV, polynucleotides and/or polypeptides of the invention, and/or agonists and/or antagonists thereof, and/or NAR polypeptides between samples obtained from the subject and the control suggests that the subject is afflicted with an autoimmune disease or disorder.

In another embodiment, Neutrokine-alpha and/or Neutrokine-alphaSV polynucleotides or polypeptides or Neutrokine-alpha and/or Neutrokine-alphaSV agonists or antagonists (e.g., anti-Neutrokine-alpha and/or anti-Neutrokine-alphaSV antibodies) of the invention are used to treat, diagnose, or prognose an individual having systemic lupus erythematosus or a subset of this disease. According to this embodiment, an individual having systemic lupus erythematosus or a subset of individuals having systemic lupus erythematosus expresses aberrantly high levels of Neutrokine-alpha and/or Neutrokine-alpha SV when compared to an individual not having systemic lupus erythematosus or this subset of systemic lupus erythematosus. Any means described herein or otherwise known in the art may be applied to detect Neutrokine-alpha and/or Neutrokine-alphaSV polynucleotides or polypeptides of the invention (e.g., FACS analysis or ELISA detection of Neutrokine-alpha and/or Neutrokine-alphaSV polypeptides of the invention and hybridization or PCR detection of Neutrokine-alpha and/or Neutrokine-alphaSV polynucleotides of the invention) and to determine the expression profile of Neutrokine-alpha and/or Neutrokine-alphaSV, polynucleotides and/or polypeptides of the invention in a biological sample.

A biological sample of persons afflicted with systemic lupus erythematosus is characterized by high levels of expression of Neutrokine-alpha and/or Neutrokine-alphaSV when compared to that observed in individuals not having systemic lupus erythematosus. Thus, Neutrokine-alpha and/or Neutrokine-alphaSV polynucleotides and/or polypeptides of the invention, and/or agonists or antagonists thereof, may be used according to the methods of the invention in the diagnosis and/or prognosis of systemic lupus erythematosus or a subset of systemic lupus erythematosus. For example, a biological sample obtained from a person suspected of being afflicted with systemic lupus erytheamatosus ("the subject") may be analyzed for the relative expression level(s) of Neutrokine-alpha, and/or Neutrokine-alphaSV polynucleotides and/or polypeptides of the invention. The expression level(s) of one or more of these molecules of the invention is (are) then compared to the expression level(s) of the same molecules of the invention as expressed in a person known not to be afflicted with systemic lupus erythematosus. A significant difference in expression level(s) of Neutrokine-alpha, and/or Neutrokine-alphaSV, polynucleotides and/or polypeptides of the invention, and/or agonists and/or antagonists thereof, between samples obtained from the subject and the control suggests that the subject is afflicted with systemic lupus erythematosus or a subset thereof.

Furthermore, there is a direct correlation between the severity of systemic lupus erythematosus, or a subset of this disease, and the concentration of Neutrokine-alpha and/or Neutrokine-alphaSV polynucleotides (RNA) and/or polypeptides of the invention. Thus, Neutrokine-alpha and/or Neutrokine-alphaSV polynucleotides, (RNA), polypeptides and/or agonists or antagonists of the invention, may be used according to the methods of the invention in prognosis of the severity of systemic lupus erythematosus or a subset of systemic lupus erythematosus. For example, a biological sample obtained from a person suspected of being afflicted with systemic lupus erythematosus ("the subject") may be analyzed for the relative expression level(s) of Neutrokine-alpha, and/or Neutrokine-alphaSV polynucleotides and/or polypeptides of the invention. The expression level(s) of one or more of these molecules of the invention is (are) then compared to the expression level(s) of the same molecules of the invention as expressed in a panel of persons known to represent a range in severities of this disease. According to this method, the match of expression level with a characterized member of the panel indicates the severity of the disease.

Elevated levels of soluble Neutrokine-alpha have been observed in the serum of patients with Systemic Lupus Erythematosus (SLE). In comparing the sera of 150 SLE patients with that of 38 control individuals, it was found that most of the SLE patients had more than 5 ng/ml of serum Neutrokine-alpha, more than 30% of SLE patients had levels greater than 10 ng/ml, and approximately 10% of SLE patients had serum Neutrokine-alpha levels greater than 20 ng/ml. In contrast, the majority of normal controls had Neutrokine-alpha levels less than 5 ng/ml, and less than 10% had levels higher than 10 ng/ml. The elevated levels of Neutrokine-alpha protein in sera is present in the soluble form and has biologic activity as assayed by the ability to stimulate anti-IgM treated B cells in vitro. SLE patients with more than 15 ng/ml serum Neutrokine-alpha were also found to have elevated levels of anti-dsDNA antibodies compared to both normal controls and SLE patients with less than 5 ng/ml of serum Neutrokine-alpha (unpublished data).

In addition the serum of two subgroups of patients which were positive for anti-nuclear antibodies (ANA+) but did not meet the formal requirements of the American College of Rheumatology (ACR) for classification of SLE were anaylzed for Neutrokine-alpha levels. The first subgroup of sera was ANA+ sera that came from patients who did not present with the clinical impression of SLE. This group had only slightly elevated levels of Neutrokine-alpha (~9 ng/ml Neutrokine-alpha). The second subgroup however, which was ANA+ sera from patients who presented with the clinical impression of SLE, had significantly increased Neutrokine-alpha levels (~15 ng/ml). These results suggest that an elevated level of Neutrokine-alpha precedes the formal fulfillment of the ACR criteria. The ACR criteria are desrcibed in Tan, E. M., et al, Arthritis and Rheumatism 25:1271-1277 (1982).

In another embodiment, Neutrokine-alpha and/or Neutrokine-alphaSV polynucleotides or polypeptides or Neutrokine-alpha and/or Neutrokine-alphaSV agonists or antagonists (e.g., anti-Neutrokine-alpha and/or anti-Neutrokine-alphaSV antibodies) of the invention are used to treat, diagnose, or prognose an individual having rheumatoid arthritis or a subset of this disease. According to this embodiment, an individual having rheumatoid arthritis or a subset of individuals having rheumatoid arthritis expresses aberrantly high levels of Neutrokine-alpha and/or Neutrokine-alpha SV when compared to an individual not having rheumatoid arthritis or this subset of rheumatoid arthritis. Any means described herein or otherwise known in the art may be applied to detect Neutrokine-alpha and/or Neutrokine-alphaSV polynucleotides or polypeptides of the invention (e.g., FACS analysis or ELISA detection of Neutrokine-alpha and/or Neutrokine-alphaSV polypeptides of the invention and hybridization or PCR detection of Neutrokine-alpha and/or Neutrokine-alphaSV polynucleotides of the invention) and to determine the expression profile of Neutrokine-alpha and/or Neutrokine-alphaSV, polynucleotides and/or polypeptides of the invention in a biological sample.

A biological sample of persons afflicted with rheumatoid arthritis is characterized by high levels of expression of Neutrokine-alpha and/or Neutrokine-alphaSV when compared to that observed in individuals not having rheumatoid arthritis. Thus, Neutrokine-alpha and/or Neutrokine-alphaSV polynucleotides and/or polypeptides of the invention, and/or agonists or antagonists thereof, may be used according to the methods of the invention in the diagnosis and/or prognosis of rheumatoid arthritis or a subset of rheumatoid arthritis. For example, a biological sample obtained from a person suspected of being afflicted with rheumatoid arthritis ("the subject") may be analyzed for the relative expression level(s) of Neutrokine-alpha, and/or Neutrokine-alphaSV polynucleotides and/or polypeptides of the invention. The expression level(s) of one or more of these molecules of the invention is (are) then compared to the expression level(s) of the same molecules of the invention as expressed in a person known not to be afflicted with rheumatoid arthritis. A significant difference in expression level(s) of Neutrokine-alpha, and/or Neutrokine-alphaSV, polynucleotides and/or polypeptides of the invention, and/or agonists and/or antagonists thereof, between samples obtained from the subject and the control suggests that the subject is afflicted with rheumatoid arthritis or a subset thereof.

In other specific embodiments, antibodies of the invention which specifically bind to Neutrokine-alpha and/or Neutrokine-alphaSV can be used for diagnostic purposes to detect, diagnose, prognose, or monitor Sjogren's Syndrome or conditions associated therewith. The invention provides for the detection of aberrant expression of Neutrokine-alpha and/or Neutrokine-alphaSV comprising: (a) assaying the expression of Neutrokine-alpha and/or Neutrokine-alphaSV in a biological sample of an individual using one or more antibodies of the invention that immunospecifically binds to Neutrokine-alpha and/or Neutrokine-alphaSV; and (b) comparing the level of Neutrokine-alpha and/or Neutrokine-alphaSV with a standard level of Neutrokine-alpha and/or Neutrokine-alphaSV, e.g., in normal biological samples, whereby an increase in the assayed level of Neutrokine-alpha and/or Neutrokine-alphaSV compared to the standard level of Neutrokine-alpha and/or Neutrokine-alphaSV is indicative of Sjogren's Syndrome.

In other specific embodiments, antibodies of the invention which specifically bind to Neutrokine-alpha and/or Neutrokine-alphaSV can be used for diagnostic purposes to detect, diagnose, prognose, or monitor HIV infection or conditions associated therewith (e.g., AIDS) The invention provides for the detection of aberrant expression of Neutrokine-alpha and/or Neutrokine-alphaSV comprising: (a) assaying the expression of Neutrokine-alpha and/or Neutrokine-alphaSV in a biological sample of an individual using one or more antibodies of the invention that immunospecifically binds to Neutrokine-alpha and/or Neutrokine-alphaSV; and (b) comparing the level of Neutrokine-alpha and/or Neutrokine-alphaSV with a standard level of Neutrokine-alpha and/or Neutrokine-alphaSV, e.g., in normal biological samples, whereby an increase in the assayed level of Neutrokine-alpha and/or Neutrokine-alphaSV compared to the standard level of Neutrokine-alpha and/or Neutrokine-alphaSV is indicative of HIV infection.

In another embodiment, Neutrokine-alpha and/or Neutrokine-alphaSV polynucleotides or polypeptides or Neutrokine-alpha and/or Neutrokine-alphaSV agonists or antagonists (e.g., anti-Neutrokine-alpha and/or anti-Neutrokine-alphaSV antibodies) of the invention are used to treat, diagnose, or prognose an individual with an immune-based rheumatologic diseases, including but not limited to, SLE, rheumatoid arthritis, CREST syndrome (a variant of scleroderma characterized by calcinosis, Raynaud's phenomenon, esophageal motility disorders, sclerodactyly, and telangiectasia.), seronegative spondyloarthropathy (SpA), polymyositis/dermatomyositis, microscopic polyangiitis, hepatitis C-asociated arthritis, Takayasu's arteritis, and undifferentiated connective tissue disorder. According to this embodiment, an individual having an immune-based rheumatologic disease or a subset of individuals having a particular immune-based rheumatologic disease expresses aberrantly high levels of Neutrokine-alpha and/or Neutrokine-alpha SV when compared to an individual not having the particular immune-based rheumatologic disease or this subset of individuals having the particular immune-based rheumatologic disease. Any means described herein or otherwise known in the art may be applied to detect Neutrokine-alpha and/or Neutrokine-alphaSV polynucleotides or polypeptides of the invention (e.g., FACS analysis or ELISA detection of Neutrokine-alpha and/or Neutrokine-alphaSV polypeptides of the invention and hybridization or PCR detection of Neutrokine-alpha and/or Neutrokine-alphaSV polynucleotides of the invention) and to determine the expression profile of Neutrokine-alpha and/or Neutrokine-alphaSV, polynucleotides and/or polypeptides of the invention in a biological sample.

A biological sample of persons afflicted with an immune-based rheumatologic disease is characterized by high levels of expression of Neutrokine-alpha and/or Neutrokine-alphaSV when compared to that observed in individuals not having an immune-based rheumatologic disease. Thus, Neutrokine-alpha and/or Neutrokine-alphaSV polynucleotides and/or polypeptides of the invention, and/or agonists or antagonists thereof, may be used according to the methods of the invention in the diagnosis and/or prognosis of an immune-based rheumatologic disease. For example, a biological sample obtained from a person suspected of being afflicted with an immune-based rheumatologic disease ("the subject") may be analyzed for the relative expression level(s) of Neutrokine-alpha, and/or Neutrokine-alphaSV polynucleotides and/or polypeptides of the invention. The expression level(s) of one or more of these molecules of the invention is (are) then compared to the expression level(s) of the same molecules of the invention as expressed in a person known not to be afflicted with an immune-based rheumatologic disease. A significant difference in expression level(s) of Neutrokine-alpha, and/or Neutrokine-alphaSV, polynucleotides and/or polypeptides of the invention, and/or agonists and/or antagonists thereof, between samples obtained from the subject and the control suggests that the subject is afflicted with an immune-based rheumatologic disease.

It has been observed, that serum Neutrokina-alpha levels inversely correlate with nephrotic-range proteinuria (>3 gm proteinuria in a 24 hour urine collection) using a sample of 71 SLE patients (p=0.019). Proteinuria was determined in 71 SLE patients within one month of phlebotomy for serum Neutrokine-alpha determination. Serum Neutrokine-alpha was classified as low, normal, or high based on the $5^{th}$ through $95^{th}$ percentiles for normal controls. Nephrotic-range proteinuria was inversely correlated with serum Neutrokine-alpha levels. Thus, in specific embodiments, serum levels of Neutrokine-alpha in individuals diagnosed with an immune based rheumatologic disease (e.g., SLE, rheumatoid arthritis, CREST syndrome (a variant of scleroderma characterized by calcinosis, Raynaud's phenomenon, esophageal motility disorders, sclerodactyly, and telangiectasia.), seronegative spondyloarthropathy (SpA), polymyositis/dermatomyositis, microscopic polyangiitis, hepatitis C-asociated arthritis, Takayasu's arteritis, and undifferentiated connective tissue disorder) may be used to determine, diagnose, progonose, or monitor the severity of certain aspects or symptoms of the disease, such as nephrotic-range proteinuria.

Thus, the invention provides a diagnostic method useful during diagnosis of a immune system disorder, including cancers of this system, and immunodeficiencies and/or autoimmune diseases which involves measuring the expression level of the gene encoding the Neutrokine-alpha and/or Neutrokine-alphaSV polypeptide in immune system tissue or other cells or body fluid from an individual and comparing the measured gene expression level with a standard Neutrokine-alpha and/or Neutrokine-alphaSV gene expression level, whereby an increase or decrease in the gene expression level compared to the standard is indicative of an immune system disorder.

Levels of soluble Neutrokine-alpha in the serum of patients with follicular non-Hodgkin's lymphoma are elevated compared to levels of soluble neutrokine-alpha in the sera of healthy individuals. Thus, in a specific embodiment, the invention provides method of diagnosing non-Hodgkin's lymphoma which involves measuring the expression level of Neutrokine-alpha and/or Neutrokine-alphaSV polypeptides and/or polynucleotides in immune system tissue or other cells or body fluid from an individual and comparing the measured gene expression level with a standard Neutrokine-alpha and/or Neutrokine-alphaSV gene expression level, whereby an increase in the gene expression level compared to the standard is indicative of non-Hodgkin's Lymphoma. Other forms of Non-Hodgkin's lymphoma which may be diagnosed according to the above method include, but are not limited to, mantle cell lymphoma, diffuse large cell lymphoma, chronic lymphocytic leukemia, small lymphocytic leukemia, and marginal zone lymphoma.

Where a diagnosis of a disorder in the immune system, including, but not limited to, diagnosis of a tumor, diagnosis of an immunodeficiency, and/or diagnosis of an autoimmune disease, has already been made according to conventional methods, the present invention is useful as a prognostic indicator, whereby patients exhibiting enhanced or depressed Neutrokine-alpha and/or Neutrokine-alphaSV gene expression will experience a worse clinical outcome relative to patients expressing the gene at a level nearer the standard level.

By analyzing or determining the expression level of the gene encoding the Neutrokine-alpha and/or Neutrokine-alphaSV polypeptide is intended qualitatively or quantitatively measuring or estimating the level of the Neutrokine-alpha and/or Neutrokine-alphaSV polypeptide or the level of the mRNA encoding the Neutrokine-alpha and/or Neutrokine-alphaSV polypeptide in a first biological sample either directly (e.g., by determining or estimating absolute protein level or mRNA level) or relatively (e.g., by comparing to the Neutrokine-alpha and/or Neutrokine-alphaSV polypeptide level or mRNA level in a second biological sample). Preferably, the Neutrokine-alpha and/or Neutrokine-alphaSV polypeptide level or mRNA level in the first biological sample is measured or estimated and compared to a standard Neutrokine-alpha and/or Neutrokine-alphaSV polypeptide level or mRNA level, the standard being taken from a second biological sample obtained from an individual not having the disorder or being determined by averaging levels from a population of individuals not having a disorder of the immune system. As will be appreciated in the art, once a standard Neutrokine-alpha and/or Neutrokine-alphaSV polypeptide level or mRNA level is known, it can be used repeatedly as a standard for comparison.

By "biological sample" is intended any biological sample obtained from an individual, body fluid, cell line, tissue culture, or other source which contains Neutrokine-alpha and/or Neutrokine-alphaSV polypeptide or mRNA. As indicated, biological samples include body fluids (such as sera, plasma, urine, synovial fluid and spinal fluid) which contain free extracellular domains of the Neutrokine-alpha and/or Neutrokine-alphaSV polypeptide, immune system tissue, and other tissue sources found to express complete or free extracellular domain of the Neutrokine-alpha and/or Neutrokine-alphaSV or a Neutrokine-alpha and/or Neutrokine-alphaSV receptor. Methods for obtaining tissue biopsies and body fluids from mammals are well known in the art. Where the biological sample is to include mRNA, a tissue biopsy is the preferred source.

The compounds of the present invention are useful for diagnosis, prognosis, or treatment of various immune system-related disorders in mammals, preferably humans. Such disorders include, but are not limited to tumors (e.g., B cell and monocytic cell leukemias and lymphomas, See Example ) and tumor metastasis, infections by bacteria, viruses and other parasites, immunodeficiencies, inflammatory diseases, lymphadenopathy, autoimmune diseases (e.g., rheumatoid arhtritis, systemic lupus erythamatosus, Sjogren syndrome, mixed connective tissue disease, and inflammatory myopathies), and graft versus host disease.

Total cellular RNA can be isolated from a biological sample using any suitable technique such as the single-step guanidinium-thiocyanate-phenol-chloroform method described in Chomczynski and Sacchi, Anal. Biochem. 162: 156-159 (1987). Levels of mRNA encoding the Neutrokine-alpha and/or Neutrokine-alphaSV polypeptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying Neutrokine-alpha and/or Neutrokine-alphaSV polypeptide levels in a biological sample can occur using antibody-based techniques. For example, Neutrokine-alpha and/or Neutrokine-alphaSV polypeptide expression in tissues can be studied with classical immunohistological methods (Jalkanen, M., et al., J. Cell. Biol. 101:976-985 (1985); Jalkanen, M., et al., J. Cell Biol. 105:3087-3096 (1987)). Other antibody-based methods useful for detecting Neutrokine-alpha and/or Neutrokine-alphaSV polypeptide gene expression include immunoassays, such as the enzyme linked immunosorbent assay (ELISA), radioimmunoassay (RIA), and fluoresence activated cell sorting (FACS). Suitable antibody assay labels are known in the art and include enzyme labels, (e.g., glucose oxidase, alkaline phosphatase and horse radish peroxidase) and radioisotopes, such as iodine ($^{131}I$, $^{125}I$, $^{123}I$, $^{121}I$), carbon ($^{14}C$), sulfur ($^{35}S$), tritium ($^{3}H$), indium ($^{115m}In$, $^{113m}In$, $^{112}In$, $^{111}In$), and technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter, Chloramine-T reaction, and Iodogen®-based labelling).

The tissue or cell type to be analyzed will generally include those which are known, or suspected, to express the Neutrokine-alpha gene (such as, for example, cells of monocytic lineage) or cells or tissue which are known, or suspected, to express the Neutrokine-alpha receptor gene (such as, for example, cells of B cell lineage and the spleen). The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the Neutrokine-alpha gene or Neutrokine-alpha receptor gene.

For example, antibodies, or fragments of antibodies, such as those described herein, may be used to quantitatively or qualitatively detect the presence of Neutrokine-alpha gene products or conserved variants or peptide fragments thereof. This can be accomplished, for example, by immunofluorescence techniques employing a fluorescently labeled antibody coupled with light microscopic, flow cytometric, or fluorimetric detection.

The antibodies (or fragments thereof) or Neutrokine-alpha polypeptides or polypeptides of the present invention may, additionally, be employed histologically, as in immunofluorescence, immunoelectron microscopy or non-immunological assays, for in situ detection of Neutrokine-alpha gene products or conserved variants or peptide fragments thereof, or for Neutrokine-alpha binding to Neutrokine-alpha receptor. In situ detection may be accomplished by removing a histological specimen from a patient, and applying thereto a labeled antibody or Neutrokine-alpha polypeptide of the present invention. The antibody (or fragment) or Neutrokine-alpha polypeptide is preferably applied by overlaying the labeled antibody (or fragment) onto a biological sample. Through the use of such a procedure, it is possible to determine not only the presence of the Neutrokine-alpha gene product, or conserved variants or peptide fragments, or Neutrokine-alpha polypeptide binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for Neutrokine-alpha gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying Neutrokine-alpha gene products or conserved variants or peptide fragments thereof, and detecting the bound antibody by any of a number of techniques well-known in the art.

Immunoassays and non-immunoassays for Neutrokine-alpha receptor gene products or conserved variants or peptide fragments thereof will typically comprise incubating a sample, such as a biological fluid, a tissue extract, freshly harvested cells, or lysates of cells which have been incubated in cell culture, in the presence of a detectable or labeled Neutrokine-alpha polypeptide capable of identifying Neutrokine-alpha receptor gene products or conserved variants or peptide fragments thereof, and detecting the bound Neutrokine-alpha polypeptide by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-Neutrokine-alpha antibody or detectable Neutrokine-alpha polypeptide. The solid phase support may then be washed with the buffer a second time to remove unbound antibody or polypeptide. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-Neutrokine-alpha antibody or Neutrokine-alpha polypeptide may be determined according to well-known methods. Those skilled in the art will be able to determine operative and optimal assay conditions for each determination by employing routine experimentation.

In addition to assaying Neutrokine-alpha and/or Neutrokine-alphaSV polypeptide levels or polynucleotide levels in a biological sample obtained from an individual, Neutrokine-alpha and/or Neutrokine-alphaSV polypeptides or polynucleotides can also be detected in vivo by imaging. For example, in one embodiment of the invention, Neutrokine-alpha and/or Neutrokine-alphaSV polypeptide and/or anti-Neutrokine-alpha antibody is used to image B cell lymphomas. In another embodiment, Neutrokine-alpha and/or Neutrokine-alphaSV polypepitdes and/or anti-Neutrokine-alpha antibodies and/or Neutrokine-alpha polynucleotides of the invention (e.g., polynucleotides complementary to all or a portion of Neutrokine-alpha and/or Neutrokine-alphaSV mRNA) is used to image lymphomas (e.g., monocyte and B cell lymphomas).

Antibody labels or markers for in vivo imaging of Neutrokine-alpha and/or Neutrokine-alphaSV polypeptide include those detectable by X-radiography, NMR, MRI, CAT-scans or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. Where in vivo imaging is used to detect enhanced levels of Neutrokine-alpha and/or Neutrokine-alphaSV polypeptide for diagnosis in humans, it may be preferable to use human antibodies or "humanized" chimeric monoclonal antibodies. Such antibodies can be produced using techniques described herein or otherwise known in the art. For example methods for producing chimeric antibodies are known in the art. See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

Additionally, any Neutrokine-alpha polypeptide whose presence can be detected, can be administered. For example, Neutrokine-alpha polypeptides labeled with a radio-opaque or other appropriate compound can be administered and visualized in vivo, as discussed, above for labeled antibodies. Further such Neutrokine-alpha polypeptides can be utilized for in vitro diagnostic procedures.

A Neutrokine-alpha and/or Neutrokine-alphaSV polypeptide-specific antibody or antibody fragment which has been labeled with an appropriate detectable imaging moiety, such as a radioisotope (for example, iodine ($^{131}I$, $^{125}I$, $^{123}I$, $^{121}I$), carbon ($^{14}C$), sulfur ($^{35}S$), tritium ($^{3}H$), indium ($^{115m}In$, $^{113m}In$, $^{112}In$, $^{111}In$), and technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain Neutrokine-alpha protein. In vivo tumor imaging is described in S. W. Burchiel et al., "Immunopharmacokinetics of Radiolabeled Antibodies and Their Fragments" (Chapter 13 in Tumor Imaging: The Radiochemical Detection of Cancer, S. W. Burchiel and B. A. Rhodes, eds., Masson Publishing Inc. (1982)).

With respect to antibodies, one of the ways in which the anti-Neutrokine-alpha antibody can be detectably labeled is by linking the same to an enzyme and using the linked product in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville Md.); Voller et al., J. Clin. Pathol. 31:507-520 (1978); Butler, J. E., Meth. Enzymol. 73:482-523 (1981); Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect Neutrokine-alpha through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by means including, but not limited to, a gamma counter, a scintillation counter, or autoradiography.

It is also possible to label the antibody with a fluorescent compound. When the fluorescently labeled antibody is exposed to light of the proper wave-length, its presence can then be detected due to fluorescence. Among the most commonly used fluorescent labeling compounds are fluorescein isothiocyanate, rhodamine, phycoerythrin, phycocyanin, allophycocyanin, ophthaldehyde and fluorescamine.

The antibody can also be detectably labeled using fluorescence emitting metals such as $^{152}Eu$, or others of the lanthanid series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling include, but are not limited to, luciferin, luciferase and aequorin.

Treatment of Immune System-Related Disorders

As noted above, Neutrokine-alpha and/or Neutrokine-alphaSV polynucleotides and polypeptides, and anti-Neutrokine-alpha antibodies, are useful for diagnosis of conditions involving abnormally high or low expression of Neutrokine-alpha and/or Neutrokine-alphaSV activities. Given the cells and tissues where Neutrokine-alpha and/or Neutrokine-alphaSV is expressed as well as the activities modulated by Neutrokine-alpha and/or Neutrokine-alphaSV, it is readily apparent that a substantially altered (increased or decreased) level of expression of Neutrokine-alpha and/or Neutrokine-alphaSV in an individual compared to the standard or "normal" level produces pathological conditions related to the bodily system(s) in which Neutrokine-alpha and/or Neutrokine-alphaSV is expressed and/or is active.

It will also be appreciated by one of ordinary skill that, since the Neutrokine-alpha and/or Neutrokine-alphaSV polypeptides of the invention are members of the TNF family, the extracellular domains of the respective proteins may be released in soluble form from the cells which express Neutrokine-alpha and/or Neutrokine-alphaSV by proteolytic cleavage and therefore, when Neutrokine-alpha and/or Neutrokine-alphaSV polypeptide (particularly a soluble form of the respective extracellular domains) is added from an exogenous source to cells, tissues or the body of an individual, the polypeptide will exert its modulating activities on any of its target cells of that individual. Also, cells expressing this type II transmembrane protein may be added to cells, tissues or the body of an individual whereby the added cells will bind to cells expressing receptor for Neutrokine-alpha and/or Neutrokine-alphaSV whereby the cells expressing Neutrokine-alpha and/or Neutrokine-alphaSV can cause responses (e.g., proliferation or cytotoxicity) in the receptor-bearing target cells.

In one embodiment, the invention provides a method of delivering compositions containing the polypeptides of the invention (e.g., compositions containing Neutrokine-alpha and/or Neutrokine-alphaSV polypeptides or anti-Neutrokine-alpha and/or anti-Neutrokine-alphaSV antibodies associated with heterologous polypeptides, heterologous nucleic acids, toxins, or prodrugs) to targeted cells, such as, for example, B cells expressing Neutrokine-alpha and/or Neutrokine-alphaSV receptor, or monocytes expressing the cell surface bound form of Neutrokine-alpha and/or Neutrokine-alphaSV. Neutrokine-alpha and/or Neutrokine-alphaSV polypeptides or anti-Neutrokine-alpha and/or anti-Neutrokine-alphaSV antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., Neutrokine-alpha and/or Neutrokine-alphaSV polypeptides or anti-Neutrokine-alpha and/or anti-Neutrokine-alphaSV antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides for a method of killing cells of hematopoietic origin, comprising, or alternatively consisting of, contacting Neutrokine-alpha and/or Neutrokine-alphaSV polypeptides with cells of hematopoietic origin. In specific embodiments, the method of killing cells of hematopoietic origin, comprises, or alternatively consists of, administering to an animal in which such killing is desired, a Neutrokine-alpha and/or Neutrokine-alphaSV polypeptide in an amount effective to kill cells of hematopoietic origin. Cells of hematopoietic origin include, but are not limited to, lymphocytes (e.g., B cells and T cells), monocytes, macrophages, dendritic cells, polymorphonuclear leukocytes (e.g., basophils, eosinophils, neutrophils), mast cells, platelets, erythrocytes and progenitor cells of these lineages. Cells of hematopoietic origin include, but are not limited to, healthy and diseased cell as found present in an animal, preferably a mammal and most preferably a human, or as isolated from an animal, transformed cells, cell lines derived from the above listed cell types, and cell cultures derived from the above listed cell types. Cells of hematopoietic origin may be found or isolated in, for example, resting, activated or anergic states.

In another embodiment, the invention provides a method for the specific destruction (i.e., killing) of cells (e.g., the destruction of tumor cells) by administering Neutrokine-alpha and/or Neutrokine-alphaSV polypeptides or Neutrokine-alpha and/or Neutrokine-alphaSV polypeptide conjugates of the invention (e.g., Neutrokine-alpha and/or Neutrokine-alphaSV polypeptides conjugated with radioisotopes, toxins, or cytotoxic prodrugs) in which such destruction of cells is desired. In a specific embodiment, the invention provides a method for the specific destruction of cells of B cell lineage (e.g., B cell related leukemias or lymphomas) by administering Neutrokine-alpha and/or Neutrokine-alphaSV polypeptides in association with toxins or cytotoxic prodrugs prior to or following bone marrow transplant.

In another embodiment, the invention provides a method for the specific destruction of cells (e.g., the destruction of tumor cells) by administering polypeptides of the invention (e.g., Neutrokine-alpha and/or Neutrokine-alphaSV polypeptides or anti-Neutrokine-alpha and/or anti-Neutrokine-alphaSV antibodies) in association with toxins or cytotoxic prodrugs.

In a specific embodiment, the invention provides a method for the specific destruction of cells of B cell lineage (e.g., B cell related leukemias or lymphomas such as myeloma, multiple myeloma and non-Hodgkin's lymphoma) by administering Neutrokine-alpha and/or Neutrokine-alphaSV polypeptides in association with toxins or cytotoxic prodrugs. In a specific embodiment, the invention provides a method for the specific destruction of cells of B cell lineage (e.g., B cell related leukemias or lymphomas such as myeloma, multiple myeloma and non-Hodgkin's lymphoma) by administering Neutrokine-alpha and/or Neutrokine-alphaSV polypeptides in association with toxins or cytotoxic prodrugs prior to, during, or following bone marrow transplant or stem cell transplant (e.g., autologous or non-autologous, single or tandem transplant of CD34+ stem cells).

In another specific embodiment, the invention provides a method for the specific destruction of cells of monocytic lineage (e.g., monocytic leukemias or lymphomas) by administering anti-Neutrokine-alpha and/or anti-Neutrokine-alphaSV antibodies in association with toxins or cytotoxic prodrugs.

Biodistribution studies (See Example 12) of radiolabeled Neutrokine-alpha polypeptide (amino acids 134-285 of SEQ ID NO:2) that had been injected into BALB/c mice demonstrated that Neutrokine-alpha has high in vivo targeting specificity for lymphoid tissues such as spleen and lymph nodes. Thus in specific embodiments, the invention provides a method for the specific destruction or disablement of lymphoid tissue (e.g., lymph nodes and spleen) by administering Neutrokine-alpha, Neutrokine-alphaSV, anti-Neutrokine-alpha, and/or anti-Neutrokine-alphaSV polypeptides in association with radioisotopes, toxins or cytotoxic prodrugs. In preferred embodiments, the lymphoid tissue is not permantly destroyed, but rather is temporarily disabled, (e.g, cells of hematopoietic lineage in lymphoid tissues are destroyed/killed while Neutrokine-alpha, Neutrokine-alphaSV, anti-Neutrokine-alpha, and/or anti-Neutrokine-alpha polypeptides in association with radioisotopes, toxins or cytotoxic prodrugs are administered, but these populations recover once administration of Neutrokine-alpha, Neutrokine-alphaSV, anti-Neutrokine-alpha, and/or anti-Neutrokine-alphaSV polypeptides in association with radioisotopes, toxins or cytotoxic prodrugs is stopped.)

By "toxin" is meant compounds that bind and activate endogenous cytotoxic effector systems, radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin. In specific embodiments Neutrokine-alpha polypeptides, Neutrokine-alphaSV, anti-Neutrokine-alpha antibodies or anti-Neutrokine-alphaSV antibodies of the invention are conjugated or fused to a polypeptide cytotoxin. An example of a suitable polypeptide cytotoxin is a ribosome-inactivating protein. Type I ribosome-inactivating proteins are single-chain proteins, while type II ribosome-inactivating proteins consist of two non-identical subunits (A and B chains) joined by a disulfide bond (for a review, see Soria et al., Targeted Diagn. Ther. 7:193 (1992)). In one embodiment, type I ribosome-inactivating proteins that may be used include, but are not limited to, polypeptides from *Saponaria officinalis* (e.g., saporin-1, saporin-2, saporin-3, saporin-6), *Momordica charantia* (e.g, momordin), *Byronia dioica* (e.g., bryodin, bryodin-2), *Trichosanthes kirilowii* (e.g., trichosanthin, trichokirin), *Gelonium multiflorum* (e.g., gelonin), *Phytolacca americana* (e.g., pokeweed antiviral protein, pokeweed antiviral protein-II, pokeweed antiviral protein-S), *Phytolacca dodecandra* (e.g., dodecandrin, *Mirabilis antiviral* protein). Ribosome-inactivating proteins are described, for example, by Walsh et al., U.S. Pat. No. 5,635,384. In specific embodiments, one or more Neutrokine-alpha polypeptides, Neutrokine-alphaSV, anti-Neutrokine-alpha antibodies or anti-Neutrokine-alphaSV antibodies of the invention are conjugated or fused to a fragment or variant of the ribosome inactivating proteins described above, particularly when said fragment or variant retains activity.

In another embodiment, type II ribosome-inactivating proteins that may be used according to the invention include, but are not limited to, polypeptides from *Ricinus communis* (e.g., ricin), *Abrus precatorius* (e.g., abrin), *Adenia digitata* (e.g., modeccin). Since type II ribosome-inactiving proteins include a B chain that binds galactosides and a toxic A chain that depurinates adensoine, type II ribosome-inactivating protein conjugates should include the A chain. Additional ribosome-inactivating proteins that may be used according to the invention, include but are not limited to, bouganin, clavin, maize ribosome-inactivating proteins, *Vaccaria pyramidata* ribosome-inactivating proteins, nigrine b, basic nigrine 1, ebuline, racemosine b, luffin-a, luffin-b, luffin-S, and other ribosome-inactivating proteins known to those of skill in the art. See, for example, Bolognesi and Stirpe, International Publication No. WO98/55623, Colnaghi et al., International Publication No. WO97/49726, Hey et al., U.S. Pat. No. 5,635,384, Bolognesi and Stirpe, International Publication No. WO95/07297, Arias et al., International Publication No. WO94/20540, Watanabe et al., J. Biochem. 106:6 977 (1989); Islam et al., Agric. Biol. Chem. 55:229 (1991), and Gao et al., FEBS Lett. 347:257 (1994). In specific embodiments, one or more Neutrokine-alpha polypeptides, Neutrokine-alphaSV, anti-Neutrokine-alpha antibodies or anti-Neutrokine-alphaSV antibodies of the invention are conjugated or fused to a fragment or variant of the ribosome inactivating proteins described above, particularly when said fragment or variant retains activity.

Additional ribosome inactivating proteins (RIPs) that may be conjugated or fused to Neutrokine-alpha polypeptides, Neutrokine-alphaSV, anti-Neutrokine-alpha antibodies or anti-Neutrokine-alphaSV antibodies of the invention include, but are not limited to, Type I Plant RIPs such as Pokeweed antiviral proteins, Tritin, Gelonin, Momordin, Saporin, Dianthin, and Maize RIP; Type II Plant RIPs such as Ricin, Abrin, Modecin, Viscumin, Volkensin, Cinnamomin, Mistletoe lectin I and Luffangulin (6 kda); Bacterial RIPS such as Shiga toxin, and Shiga-like toxin; and Fungal RIPS such as alpha-sarcin, mitogillin, and restrictocin. In specific embodiments, one or more Neutrokine-alpha polypeptides, Neutrokine-alphaSV, anti-Neutrokine-alpha antibodies or anti-Neutrokine-alphaSV antibodies of the invention are conjugated or fused to a fragment or variant of the ribosome inactivating proteins described above, particularly when said fragment or variant retains activity.

Ricin A homologues that may be conjugated or fused to Neutrokine-alpha polypeptides, Neutrokine-alphaSV, anti-Neutrokine-alpha antibodies or anti-Neutrokine-alphaSV antibodies of the invention include, but are not limited to, polypeptides that have the same amino acid sequence as a protein selected from the group consisting of: type 2 ribosome-inactivating protein cinnamomin III precursor, abrin-d precursor from Indian licorice or fragment thereof, RIP precursor of *Sambucus nigra*, RIP bryodin II precursor, alpha-trichosanthin, ribosome-inactivating protein precursor from *Sambucus ebulus*, karasurin-B, Trichobakin, Beta-Luffin, Beta-galactoside specific lectin I A chain (MLA; ML-I A), lectin chain A isoform 2 from *Viscum album* subsp. *coloratum*, curcin precursor from *Jatropha curcas*, trichoanguina from snake gourd, ribosome-inactivating protein IRAb from *Iris hollandica*, Momordin, trichoanguin from *Trichosanthes cucumerina*, momordin II from *Momordica balsamina*, gelonin from *Gelonium multiflorum*, ribosome inactivating protein RIPm from *Polygonatum multiflorum*, ribosome inactivating protein Euserratin 2 precursor from *Euphorbia serrata*, alpha-PAP (pokeweed antiviral protein) from *Phytolacca americana*, ribosome-inactivating protein gynostemmin II from *Gynostemma pentaphyllum*, trichosanthin, ribosome-inactivating protein 2 from *Phytolacca insularis*, bouganin from *Bougainvillea spectabilis*, antiviral protein from *Clerodendrum aculeatum*, anti-viral protein PAP from *Phytolacca acinosa*, type I RIP moschatin I, antiviral ribosome inactivating protein from *Chenopodium album*, Beta-vulgin from *Beta vulgaris* subsp. *vulgaris*, ribosome-inactivating protein benincasin from *Benincasa hispida*, ribosome-inactivating protein ME1 from *Mirabilis expansa*, MAP—MIRABILIS—Four-o'clock (Marvel-of-peru), RIP amaranthin, amarandin-S from Amaranthus tricolor, ribosome-inactivating protein from *Spinacia oleracea*, type I RIP musarmin 3 from Muscari, saporin from *Saponaria officinalis*, dianthin 30 from *Dianthus caryophyllus*, and tritin from *Triticum aestivum*. In specific embodiments, one or more Neutrokine-alpha polypeptides, Neutrokine-alphaSV, anti-Neutrokine-alpha antibodies or anti-Neutrokine-alphaSV antibodies of the invention are conjugated or fused to a fragment or variant of the polypeptides described above, particularly when said fragment or variant retains activity.

In specific embodiments, one or more Neutrokine-alpha polypeptides, Neutrokine-alphaSV, anti-Neutrokine-alpha antibodies or anti-Neutrokine-alphaSV antibodies of the invention are conjugated or fused to gelonin (for example as described in GenBank Accession Number P33186, which is herein incorporated by reference. In specific embodiments, one or more Neutrokine-alpha polypeptides, Neutrokine-alphaSV, anti-Neutrokine-alpha antibodies or anti-Neutrokine-alphaSV antibodies of the invention are conjugated or fused to amino acids 47 to 297 of gelonin as disclosed in GenBank Accession Number P33186. In other specific embodiments, one or more Neutrokine-alpha polypeptides, Neutrokine-alphaSV, anti-Neutrokine-alpha antibodies or anti-NeutrokinealphaSV antibodies of the invention are conjugated or fused to amino acids 47 to 297 of gelonin as disclosed in GenBank Accession Number P33186 with the exception that the Asp-297 is changed to Cys 297.

Other toxins that may be conjugated or fused to Neutrokine-alpha polypeptides, Neutrokine-alphaSV, anti-Neutrokine-alpha antibodies or anti-Neutrokine-alphaSV antibodies of the invention include, but are not limited to diptheria toxin, *Pseudomonas exotoxin* A, *Botulinum neurotoxin, Clostridium perfringens epsilon* toxin, Conotoxins, and *Staphylococcal enterotoxins*. In specific embodiments, one or more Neutrokine-alpha polypeptides, Neutrokine-alphaSV, anti-Neutrokine-alpha antibodies or anti-Neutrokine-alphaSV antibodies of the invention are conjugated or fused to a fragment or variant of the polypeptides described above, particularly when said fragment or variant retains activity.

Techniques known in the art may be applied to label polypeptides and antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter, Chloramine-T reaction, and Iodogen® based labeling methods).

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

In specific embodiments, Neutrokine-alpha, Neutrokine-alphaSV, anti-Neutrokine-alpha, and/or anti-Neutrokine-alphaSV polypeptides in association with radioisotopes, toxins or cytotoxic prodrugs are used to treat or ameliorate the symptoms of autoinmmune diseases. In preferred emodiments, Neutrokine-alpha, Neutrokine-alphaSV, anti-Neutrokine-alpha, and/or anti-Neutrokine-alphaSV polypeptides in association with radioisotopes, toxins or cytotoxic prodrugs are used to treat or ameliorate the symptoms of systemic lupus erythematosus. Neutrokine-alpha, Neutrokine-alphaSV, anti-Neutrokine-alpha, and/or anti-Neutrokine-alphaSV polypeptides in association with radioisotopes, toxins or cytotoxic prodrugs are used to treat or ameliorate the symptoms of rheumatoid arthritis including advanced rheumatoid arthritis. In preferred emodiments, Neutrokine-alpha, Neutrokine-alphaSV, anti-Neutrokine-alpha, and/or anti-Neutrokine-alphaSV polypeptides in association with radioisotopes, toxins or cytotoxic prodrugs are used to treat or ameliorate the symptoms of idiopathic thrombocytopenic purpura (ITP).

In other preferred embodiments Neutrokine-alpha, Neutrokine-alphaSV, anti-Neutrokine-alpha, and/or anti-Neutrokine-alphaSV polypeptides in association with radioisotopes, toxins or cytotoxic prodrugs are used to treat or ameliorate the symptoms of Sjōgren's syndrome. In other preferred embodiments, Neutrokine-alpha, Neutrokine-alphaSV, anti-Neutrokine-alpha, and/or anti-Neutrokine-alphaSV polypeptides in association with radioisotopes, toxins or cytotoxic prodrugs are used to treat or ameliorate the symptoms of IgA nephropathy. In other preferred embodiments, Neutrokine-alpha, Neutrokine-alphaSV, anti-Neutrokine-alpha, and/or anti-Neutrokine-alphaSV polypeptides in association with radioisotopes, toxins or cytotoxic prodrugs are used to treat or ameliorate the symptoms of Myasthenia gravis. In preferred emodiments, Neutrokine-alpha, Neutrokine-alphaSV, anti-Neutrokine-alpha, and/or anti-Neutrokine-alphaSV polypeptides in association with radioisotopes, toxins or cytotoxic prodrugs are used to treat or ameliorate the symptoms of multiple sclerosis. In still other preferred embodiments, Neutrokine-alpha, Neutrokine-alphaSV, anti-Neutrokine-alpha, and/or anti-Neutrokine-alphaSV polypeptides in association with radioisotopes, toxins or cytotoxic prodrugs are used to treat or ameliorate the symptoms of vasculitis.

In one embodiment, the invention provides methods and compositions for inhibiting or reducing immunoglobulin production (e.g. IgM, IgG, and/or IgA production), comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide inhibits or reduces Neutrokine-alpha and/or Neutrokine-alphaSV mediated immunoglobulin production. In specific embodiments, the invention provides methods and compositions for inhibiting or reducing immunoglobulin production (e.g. IgM, IgG, and/or IgA production) in response to T cell dependent antigens, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide inhibits or reduces Neutrokine-alpha and/or Neutrokine-alphaSV mediated immunoglobulin production in response to T cell dependent antigens. In specific embodiments, the invention provides methods and compositions for inhibiting or reducing immunoglobulin production (e.g. IgM, IgG, and/or IgA production) in response to T cell independent antigens, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide inhibits or reduces Neutrokine-alpha and/or Neutrokine-alphaSV mediated immunoglobulin production in response to T cell independent antigens.

In another embodiment, the invention provides methods and compositions for inhibiting or reducing immunoglobulin production (e.g. IgM, IgG, and/or IgA production), comprising, or alternatively consisting of, administering to an animal in which such inhibition or reduction is desired, a Neutrokine-alpha and/or Neutrokine-alphaSV polypeptide in an amount effective to inhibit or reduce immunoglobulin production. In another embodiment, the invention provides methods and compositions for inhibiting or reducing immunoglobulin production (e.g. IgM, IgG, and/or IgA production) in response to T cell dependent antigens, comprising, or alternatively consisting of, administering to an animal in which such inhibition or reduction is desired, a Neutrokine-alpha and/or Neutrokine-alphaSV polypeptide in an amount effective to inhibit or reduce immunoglobulin production in response to T cell dependent antigens. In another embodiment, the invention provides methods and compositions for inhibiting or reducing immunoglobulin production (e.g. IgM, IgG, and/or IgA production) in response to T cell independent antigens, comprising, or alternatively consisting of, administering to an animal in which such inhibition or reduction is desired, a Neutrokine-alpha and/or Neutrokine-alphaSV polypeptide in an amount effective to inhibit or reduce immunoglobulin production in response to T cell independent antigens.

In another embodiment, the invention provides methods and compositions for stimulating immunoglobulin production (e.g. IgM, IgG, and/or IgA production), comprising, or alternatively consisting of, contacting an effective amount of Neutrokine-alpha and/or Neutrokine-alphaSV polypeptide with cells of hematopoietic origin, wherein the effective amount of the Neutrokine-alpha and/or Neutrokine-alphaSV polypeptide stimulates Neutrokine-alpha and/or Neutrokine-alphaSV mediated immunoglobulin production. In another embodiment, the invention provides methods and compositions for stimulating immunoglobulin production (e.g. IgM, IgG, and/or IgA production) in response to T cell dependent antigens comprising, or alternatively consisting of, contacting an effective amount of Neutrokine-alpha and/or Neutrokine-alphaSV polypeptide with cells of hematopoietic origin, wherein the effective amount of the Neutrokine-alpha and/or Neutrokine-alphaSV polypeptide stimulates Neutrokine-alpha and/or Neutrokine-alphaSV mediated immunoglobulin production in response to T cell dependent antigens. In another embodiment, the invention provides methods and compositions for stimulating immunoglobulin production (e.g. IgM, IgG, and/or IgA production) in response to T cell independent antigens comprising, or alternatively consisting of, contacting an effective amount of Neutrokine-alpha and/or Neutrokine-alphaSV polypeptide with cells of hematopoietic origin, wherein the effective amount of the Neutrokine-alpha and/or Neutrokine-alphaSV polypeptide stimulates Neutrokine-alpha and/or Neutrokine-alphaSV mediated immunoglobulin production in response to T cell independent antigens.

In another embodiment, the invention provides methods and compositions for stimulating immunoglobulin production (e.g. IgM, IgG, and/or IgA production) comprising, or alternatively consisting of, administering to an animal in which such stimulation is desired, a Neutrokine-alpha and/or Neutrokine-alphaSV polypeptide in an amount effective to stimulate immunoglobulin production. In another embodiment, the invention provides methods and compositions for stimulating immunoglobulin production (e.g. IgM, IgG, and/or IgA production) in response to T cell dependent antigens comprising, or alternatively consisting of, administering to an animal in which such stimulation is desired, a Neutrokine-alpha and/or Neutrokine-alphaSV polypeptide in an amount effective to stimulate immunoglobulin production in response to T cell dependent antigens.

In another embodiment, the invention provides methods and compositions for stimulating immunoglobulin production (e.g. IgM, IgG, and/or IgA production) in response to T cell independent antigens comprising, or alternatively consisting of, administering to an animal in which such stimulation is desired, a Neutrokine-alpha and/or Neutrokine-alphaSV polypeptide in an amount effective to stimulate immunoglobulin production in response to T cell independent antigens.

Determination of immunoglobulin levels are most often performed by comparing the level of immunoglobulin in a sample to a standard containing a known amount of immunoglobulin using ELISA assays. Determination of immunoglobulin levels in a given sample, can readily be determined using ELISA or other method known in the art.

Receptors belonging to the TNF receptor (TNFR) super family (e.g., TACI, BAFF-R and BCMA, receptors to which Neutrokine-alpha polypeptides can bind) can be classified into two types based on the presence or absence of a conserved cytoplasmic domain responsible for apoptosis called a "death domain." TNF receptors without death domains, such as TNF-R2 HVEM/ATAR, RANK, CD27, CD30, CD40, and OX40 interact with TNF receptor associated factors (TRAF 1-6) and mediate anti-apoptotic survival and or proliferative responses via activation of the transcription factor NF-kappaB (reviewed in Wajant et al., Cytokine and Growth Factor Reviews 10(1):15-26, 1999). TACI, BCMA and BAFF-R do not contain death domains.

Investigation of Neutrokine-alpha (which bind TACI, BCMA, and BAFF-R) induced signaling in human tonsillar B cells co-stimulated with Staph. Aureus Cowan consistently revealed that mRNA for ERK-1 and PLK were upregulated by Neutrokine-alpha+ SAC treatment (see Example 11). Polo like kinases (PLK) belong to a sub family of serine/threonine kinases related to *Saccharomyces cerevisiae* cell cycle protein CDC5 (29). The expression of PLK is induced during G2 and S phase of the cell cycle. PLK is reported to play a role in cell proliferation (Lee et al., Proc. Natl. Acad. Sci. 95:9301-9306). The role or extracellular-signal related kinases (ERK1/2) in cell survival and proliferative effects of growth factors and other agonists has been extensively studied. The induced expression of PLK and ERK-1 is consistent with the survival and proliferative effects of Neutrokine-alpha on B cells.

Additionally, in some samples of human tonsillar B cells stimulated with Neutrokine-alpha and SAC, mRNA for CD25 (IL-2Ralpha) was upregulated. Nuclear extracts from Human tonsillar B cells treated with Neutrokine-alpha and from IM-9 cells treated with Neutrokine-alpha were able to shift probes from the CD25 promoter region containing sites for NF-kappaB, SRF, ELF-1 and HMGI/Y in an electromobility shift assay. ELF-1 for example, is a transcription factor that is part of the ETS family of proteins and whose expression appears to be restricted to T and B cells. Binding sites for ELF-1 have been described in the promoters of a number of proteins that are important in the regulation of the immune response.

Thus, Neutrokine-alpha induced signaling has been shown to be consistent with the activation of cellular activation and cellular proliferation pathways as well as with cellular signaling pathways that regulate B cell lifespan. Further, Neutrokine-alpha and/or Neutrokine-alphaSV treatment of B cells induces cellular proliferation immunoglobulin secretion, a characteristic of activated B cells (Moore et al., Science 285:260-263, 1999). Neutrokine-alpha and/or Neutrokine-alphaSV polypeptides may inhibit, stimulate, or not significantly alter these Neutrokine-alpha and/or Neutrokine-alphaSV mediated activities.

In one embodiment, the invention provides methods and compositions for inhibiting or reducing proliferation of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide inhibits or reduces Neutrokine-alpha and/or Neutrokine-alphaSV mediated proliferation of cells of hemtopoietic origin. In another embodiment, the invention provides methods and compositions for inhibiting or reducing proliferation of cells of hematopoietic origin comprising, or alternatively consisting of, administering to an animal in which such inhibition or reduction is desired, a Neutrokine-alpha and/or Neutrokine-alphaSV polypeptide in an amount effective to inhibit or reduce B cell proliferation. In preferred embodiments, the cells of hematopoietic origin are B cells.

In one embodiment, the invention provides methods and compositions for stimulating proliferation of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide stimulates Neutrokine-alpha and/or Neutrokine-alphaSV mediated proliferation of cells of hemtopoietic origin. In another embodiment, the invention provides methods and compositions for stimulating proliferation of cells of hematopoietic origin comprising, or alternatively consisting of, administering to an animal in which such stimulation is desired, a Neutrokine-alpha and/or Neutrokine-alphaSV polypeptide in an amount effective to stimulate B cell proliferation. In preferred embodiments, the cells of hematopoietic origin are B cells. B cell proliferation is most commonly assayed in the art by measuring tritiated thymidine incorporation (see Examples 6 & 7). This and other assays are commonly known in the art and could be routinely adapted for the use of determining the effect of Neutrokine-alpha and/or Neutrokine-alphaSV polypeptides on B cell proliferation.

In one embodiment, the invention provides methods and compositions for inhibiting or reducing activation of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide inhibits or reduces Neutrokine-alpha and/or Neutrokine-alphaSV mediated activation of cells of hematopoietic origin. In one embodiment, the invention provides methods and compositions for inhibiting or reducing activation of cells of hematopoietic origin, comprising, or alternatively consisting of, administering to an animal in which such inhibition or reduction is desired, a Neutrokine-alpha and/or Neutrokine-alphaSV polypeptide in an amount effective to inhibit or reduce activation of cells of hematopoietic origin. In preferred embodiments, the cells of hematopoietic origin are B cells.

In one embodiment, the invention provides methods and compositions for increasing activation of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide increases Neutrokine-alpha and/or Neutrokine-alphaSV mediated activation of cells of hematopoietic origin. In one embodiment, the invention provides methods and compositions for increasing activation of cells of hematopoietic origin, comprising, or alternatively consisting of, administering to an animal in which such increase is desired, a Neutrokine-alpha and/or Neutrokine-alphaSV polypeptide in an amount effective to increase activation of cells of hematopoietic origin. In preferred embodiments, the cells of hematopoietic origin are B cells.

B cell activation can measured in a variety of ways, such as FACS analysis of activation markers expressed on B cells. B cells activation markers include, but are not limited to, CD26, CD 28, CD 30, CD 38, CD 39, CD 69, CD70 CD71, CD 77, CD 83, CD126, CDw130, and B220. Additionally, B cell activation may be measured by analysis of the activation of signaling molecules involved in B cell activation. By way of non-limiting example, such analysis may take the form of analyzing mRNA levels of signaling molecules by Northern analysis or real time PCR (See Example 11). One can also measure, for example, the phosphorylation of signaling molecules using anti-phosphotyrosine antibodies in a Western blot. B cell activation may also be measured by measuring the calcium levels in B cells. These and other methods of determining B cell activation are commonly known in the art and could be routinely adapted for the use of determining the effect of Neutrokine-alpha and/or Neutrokine-alphaSV polypeptides on B cell activation.

In one embodiment, the invention provides methods and compositions for decreasing lifespan of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide inhibits or reduces Neutrokine-alpha and/or Neutrokine-alphaSV regulated lifespan of cells of hematopoietic origin. In one embodiment, the invention provides methods and compositions for decreasing lifespan of cells of hematopoietic origin, comprising, or alternatively consisting of, administering to an animal in which such decrease is desired, a Neutrokine-alpha and/or Neutrokine-alphaSV polypeptide in an amount effective to decrease lifespan of cells of hematopoietic origin. In preferred embodiments, the cells of hematopoietic origin are B cells.

In one embodiment, the invention provides methods and compositions for increasing lifespan of cells of hematopoietic origin, comprising, or alternatively consisting of, contacting an effective amount of Neutrokine-alpha and/or Neutrokine-alphaSV polypeptide with cells of hematopoietic origin, wherein the effective amount of Neutrokine-alpha and/or Neutrokine-alphaSV polypeptide increases Neutrokine-alpha and/or Neutrokine-alphaSV regulated lifespan of cells of hematopoietic origin. In one embodiment, the invention provides methods and compositions for increasing lifespan of cells of hematopoietic origin, comprising, or alternatively consisting of, administering to an animal in which such increase is desired, a Neutrokine-alpha and/or Neutrokine-alphaSV polypeptide in an amount effective to increase lifespan of cells of hematopoietic origin. In preferred embodiments, the cells of hematopoietic origin are B cells.

B cell life span in vivo may be measured by 5-bromo-2'-deoxyuridine (BrdU) labeling experiments which are well known to one skilled in the art. BrdU is a thymidine analogue that gets incorporated into the DNA of dividing cells. Cells containing BrdU in their DNA can be detected using, for example fluorescently labeled anti-BrdU antibody and flow cytometry. Briefly, an animal is injected with BrdU in an amount sufficient to label developing B cells. Then, a sample of B cells is withdrawn from the animal, for example, from peripheral blood, and analyzed for the percentage of cells that contain BrdU. Such an analysis performed at several time points can be used to calculate the half life of B cells. Alternatively, B cell survival may be measured in vitro. For example B cells may be cultured under conditions where proliferation does not occur, (for example the media should contain no reagents that crosslink the immunoglobulin receptor, such as anti-IgM antibodies) for a period of time (usually 2-4 days). At the end of this time, the percent of surviving cells is determined, using for instance, the vital dye Trypan Blue, or by staining cells with propidium iodide or any other agent designed to specifically stain apoptotic cells and analyzing the percentage of cells stained using flow cytometry. One could perform this experiment under several conditions, such as B cells treated with Neutrokine-alpha, B cells treated with Neutrokine-alpha and/or Neutrokine-alphaSV-polypeptide complexes, and untreated B cells in order to determine the effects of Neutrokine-alpha and/or Neutrokine-alphaSV and Neutrokine-alpha polypeptides on B cells survival. These and other methods for determining B cell lifespan are commonly known in the art and could routinely be adapted to determining the effect of Neutrokine-alpha and/or Neutrokine-alphaSV polypeptides on Neutrokine-alpha and/or Neutrokine-alphaSV regulated B cell lifespan.

It will be appreciated that conditions caused by a decrease in the standard or normal level of Neutrokine-alpha and/or Neutrokine-alphaSV activity in an individual, particularly disorders of the immune system, can be treated by administration of Neutrokine-alpha and/or Neutrokine-alphaSV polypeptide (in the form of soluble extracellular domain or cells expressing the complete protein) or agonist. Thus, the invention also provides a method of treatment of an individual in need of an increased level of Neutrokine-alpha and/or Neutrokine-alphaSV activity comprising administering to such an individual a pharmaceutical composition comprising an amount of an isolated Neutrokine-alpha and/or Neutrokine-alphaSV polypeptide of the invention, or agonist thereof, effective to increase the Neutrokine-alpha and/or Neutrokine-alphaSV activity level in such an individual.

It will also be appreciated that conditions caused by a increase in the standard or normal level of Neutrokine-alpha and/or Neutrokine-alphaSV activity in an individual, particularly disorders of the immune system, can be treated by administration of Neutrokine-alpha and/or Neutrokine-alphaSV polypeptides (in the form of soluble extracellular domain or cells expressing the complete protein) or antagonist (e.g, an anti-Neutrokine-alpha antibody). Thus, the invention also provides a method of treatment of an individual in need of an decreased level of Neutrokine-alpha and/or Neutrokine-alphaSV activity comprising administering to such an individual a pharmaceutical composition comprising an amount of an isolated Neutrokine-alpha and/or Neutrokine-alphaSV polypeptide of the invention, or antagonist thereof, effective to decrease the Neutrokine-alpha and/or Neutrokine-alphaSV activity level in such an individual. A non-limiting example of a Neutrokine-alpha and/or Neutrokine-alphaSV polypeptide of the invention that can be administered to an individual in need of an decreased level of Neutrokine-alpha and/or Neutrokine-alphaSV activity, is a dominant negative mutant of a Neutrokine-alpha and/or Neutrokine-alphaSV, which binds to a Neutrokine-alpha and/or Neutrokine-alphaSV receptor but that does not induce signal transduction.

Autoantibody production is common to several autoimmune diseases and contributes to tissue destruction and exacerbation of disease. Autoantibodies can also lead to the occurrence of immune complex deposition complications and lead to many symptoms of systemic lupus erythomatosis, including kidney failure, neuralgic symptoms and death. Modulating antibody production independent of cellular response would also be beneficial in many disease states. B cells have also been shown to play a role in the secretion of arthritogenic immunoglobulins in rheumatoid arthritis, (Korganow et al., Immunity 10:451-61, 1999). As such, inhibition of Neutrokine alpha-mediated antibody production would be beneficial in treatment of autoimmune diseases such as myasthenia gravis and rheumatoid arthritis. Compounds of the invetion that selectively block or neutralize the action of B-lymphocytes would be useful for such purposes. To verify these capabilities in compositions of the present invention, such compositions are evaluated using assays known in the art and described herein.

The invention provides methods employing compositions of the invention (e.g., Neutrokine-alpha and/or Neutrokine-alphaSV polynucleotides or polypeptides of the invention and/or agonists and/or antagonists thereof) for selectively blocking or neutralizing the actions of B-cells in association with end stage renal diseases, which may or may not be associated with autoimmune diseases. Such methods would also be useful for treating immunologic renal diseases. Such methods would be would be useful for treating glomerulonephritis associated with diseases such as membranous nephropathy, IgA nephropathy or Berger's Disease, IgM nephropathy, Goodpasture's Disease, post-infectious glomerulonephritis, mesangioproliferative disease, minimal-change nephrotic syndrome. Such methods would also serve as therapeutic applications for treating secondary glomerulonephritis or vasculitis associated with such diseases as lupus, polyarteritis, Henoch-Schonlein, Scleroderma, HIV-related diseases, amyloidosis or hemolytic uremic syndrome. The methods of the present invention would also be useful as part of a therapeutic application for treating interstitial nephritis or pyelonephritis associated with chronic pyelonephritis, analgesic abuse, nephrocalcinosis, nephropathy caused by other agents, nephrolithiasis, or chronic or acute interstitial nephritis.

The methods of the present invention also include use of compositions of the invention in the treatment of hypertensive or large vessel diseases, including renal artery stenosis or occlusion and cholesterol emboli or renal emboli.

The present invention also provides methods for diagnosis and treatment of renal or urological neoplasms, multiple mylelomas, lymphomas, light chain neuropathy or amyloidosis.

The invention also provides methods for blocking or inhibiting activated B cells using compositions of the invention for the treatment of asthma and other chronic airway diseases such as bronchitis and emphysema.

Neutrokine-alpha, and/or Neutrokine-alphaSV polynucleotides or polypeptides of the invention, or agonists of Neutrokine-alpha, and/or Neutrokine-alphaSV, can be used in the treatment of infectious agents. For example, by increasing the immune response, particularly increasing the proliferation and differentiation of B cells, infectious diseases may be treated. The immune response may be increased by either enhancing an existing immune response, or by initiating a new immune response. Alternatively, Neutrokine-alpha, and/or Neutrokine-alphaSV polynucleotides or polypeptides, or agonists of Neutrokine-alpha, and/or Neutrokine-alphaSV, may also directly inhibit the infectious agent, without necessarily eliciting an immune response.

Viruses are one example of an infectious agent that can cause disease or symptoms that can be treated by Neutrokine-alpha, and/or Neutrokine-alphaSV polynucleotides or polypeptides, or agonists or antagonists of Neutrokine-alpha, and/or Neutrokine-alphaSV. Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. Neutrokine-alpha, and/or Neutrokine-alphaSV polynucleotides or polypeptides, or agonists or antagonists of Neutrokine-alpha, and/or Neutrokine-alphaSV, can be used to treat, prevent, diagnose, and/or detect any of these symptoms or diseases. In specific embodiments, Neutrokine alpha polynucleotides, polypeptides, or agonists are used to treat, prevent, and/or diagnose: meningitis, Dengue, EBV, and/or hepatitis (e.g., hepatitis B). In an additional specific embodiment Neutrokine alpha polynucleotides, polypeptides, or agonists are used to treat patients nonresponsive to one or more other commercially available hepatitis vaccines. In a further specific embodiment, Neutrokine alpha polynucleotides, polypeptides, or agonists are used to treat, prevent, and/or diagnose AIDS. In an additional specific embodiment Neutrokine-alpha and/or Neutrokine-alphaSV and/or Neutrokine-alpha Receptor polynucleotides, polypeptides, agonists, and/or antagonists are used to treat, prevent, and/or diagnose patients with cryptosporidiosis.

Similarly, bacterial or fungal agents that can cause disease or symptoms and that can be treated by Neutrokine-alpha, and/or Neutrokine-alphaSV polynucleotides or polypeptides, or agonists or antagonists of Neutrokine-alpha, and/or Neutrokine-alphaSV, include, but not limited to, the following Gram-Negative and Gram-positive bacteria and bacterial families and fungi: *Actinomycetales* (e.g., *Corynebacterium, Mycobacterium, Norcardia*), *Cryptococcus neoformans, Aspergillosis*, Bacillaceae (e.g., Anthrax, Clostridium), Bacteroidaceae, *Blastomycosis, Bordetella, Borrelia* (e.g., *Borrelia burgdorferi, Brucellosis, Candidiasis, Campylobacter, Coccidioidomycosis, Cryptococcosis, Dermatocycoses, E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter, Legionellosis, Leptospirosis, Listeria* (e.g, *Listeria monocytogenes*), Mycoplasmatales, *Mycobacterium leprae, Vibrio cholerae*, Neisseriaceae (e.g., *Acinetobacter, Gonorrhea, Menigococcal*), *Meisseria meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, *Syphilis, Shigella* spp., *Staphylococcal, Meningiococcal, Pneumococcal* and *Streptococcal* (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chiamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Neutrokine-alpha, and/or Neutrokine-alphaSV polynucleotides or polypeptides, or agonists or antagonists of Neutrokine-alpha, and/or Neutrokine-alphaSV, can be used to treat, prevent, diagnose, and/or detect any of these symptoms or diseases. In specific embodiments, Neutrokine alpha polynucleotides, polypeptides, or agonists thereof are used to treat, prevent, and/or diagnose: tetanus, Diptheria, botulism, and/or meningitis type B.

Moreover, parasitic agents causing disease or symptoms that can be treated by Neutrokine-alpha, and/or Neutrokine-alphaSV polynucleotides or polypeptides, or agonists of Neutrokine-alpha, and/or Neutrokine-alphaSV, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. Neutrokine-alpha, and/or Neutrokine-alphaSV polynucleotides or polypeptides, or agonists or antagonists of Neutrokine-alpha, and/or Neutrokine-alphaSV, can be used to treat, prevent, diagnose, and/or detect any of these symptoms or diseases. In specific embodiments, Neutrokine alpha polynucleotides, polypeptides, or agonists thereof are used to treat, prevent, and/or diagnose malaria.

In another embodiment, Neutrokine-alpha and/or Neutrokine-alphaSV polynucleotides or polypeptides of the invention and/or agonists and/or antagonists thereof, are used to treat, prevent, and/or diagnose inner ear infection (such as, for example, otitis media), as well as other infections characterized by infection with *Streptococcus pneumoniae* and other pathogenic organisms.

In a specific embodiment, Neutrokine-alpha and/or Neutrokine-alphaSV polynucleotides or polypeptides, or agonists or antagonists thereof (e.g., anti-Neutrokine-alpha, and/or anti-Neutrokine-alphaSV antibodies) are used to treat or prevent a disorder characterized by deficient serum immunoglobulin production, recurrent infections, and/or immune system dysfunction. Moreover, Neutrokine-alpha, and/or Neutrokine-alphaSV polynucleotides or polypeptides, or agonists or antagonists thereof (e.g., anti-Neutrokine-alpha, and/or anti-Neutrokine-alphaSV antibodies) may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, multiple myeloma, recurrent bronchitis, sinusitis, otitis media, conjunctivitis, pneumonia, hepatitis, meningitis, herpes zoster (e.g., severe herpes zoster), and/or pheumocystis carnii.

Neutrokine-alpha and/or Neutrokine-alphaSV polynucleotides or polypeptides of the invention, or agonists or antagonists thereof, may be used to diagnose, prognose, treat or prevent one or more of the following diseases or disorders, or conditions associated therewith: primary immunodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

Additionally, Neutrokine-alpha and/or Neutrokine-alphaSV polynucleotides or polypeptides of the invention, or agonists or antagonists thereof, may be used to diagnose, prognose, treat or prevent one or more of the following diseases, disorders, or conditions associated therewith, Guillain-Barre syndrome, anemia (e.g., anemia associated with parvovirus B19, patients with stable mutliple myeloma who are at high risk for infection (e.g., recurrent infection), autoimmune hemolytic anemia (e.g., warm-type autoimmune hemolytic anemia), thrombocytopenia (e.g, neonatal thrombocytopenia), and immune-mediated neutropenia), transplantation (e.g, cytamegalovirus (CMV)-negative recipients of CMV-positive organs), hypogammaglobulinemia (e.g., hypogammaglobulinemic neonates with risk factor for infection or morbidity), epilepsy (e.g, intractable epilepsy), systemic vasculitic syndromes, myasthenia gravis (e.g, decompensation in myasthenia gravis), dermatomyositis, and polymyositis.

Additional preferred embodiments of the invention include, but are not limited to, the use of Neutrokine-alpha and/or Neutrokine-alpha SV polypeptides, Neutrokine-alpha and/or Neutrokine-alpha SV polynucleotides, and functional agonists thereof, in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to promote or enhance immunoglobulin class switching (e.g., to induce a B cell express an IgM antibody to class switch to a different immunoglobulin isotype such as IgG, IgA, or IgE), to induce higher affinity antibody production (e.g., IgG, IgA, IgM, and IgE, for instance, by the modulation of the rate or quantity of somatic hypermutation or by modulation of the process/mechanism of selection of B cells expressing mutated antibodies), and/or to increase an immune response. In a specific nonexclusive embodiment, Neutrokine-alpha polypeptides of the invention, and/or agonists thereof, are administered to boost the immune system to produce increased quantities of IgG. In another specific nonexclusive embodiment, Neutrokine-alpha polypeptides of the invention and/or agonists thereof, are administered to boost the immune system to produce increased quantities of IgA. In another specific nonexclusive embodiment, Neutrokine-alpha polypeptides of the invention and/or agonists thereof, are administered to boost the immune system to produce increased quantities of IgM.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741).

A vaccine adjuvant that enhances immune responsiveness to specific antigen. In a specific embodiment, the vaccine adjuvant is a Neutrokine-alpha and/or Neutrokine-alphaSV polypeptide described herein. In another specific embodiment, the vaccine adjuvant is a Neutrokine-alpha and/or Neutrokine-alphaSV polynucleotide described herein (i.e., the Neutrokine-alpha and/or Neutrokine-alphaSV polynucleotide is a genetic vaccine adjuvant). As discussed herein, Neutrokine-alpha and/or Neutrokine-alphaSV polynucleotides may be administered using techniques known in the art, including but not limited to, liposomal delivery, recombinant vector delivery, injection of naked DNA, and gene gun delivery.

An adjuvant to enhance tumor-specific immune responses.

An adjuvant to enhance anti-viral immune responses. Antiviral immune responses that may be enhanced using the compositions of the invention as an adjuvant, include, but are not limited to, virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions of the invention are used as an adjuvant to enhance an immune response to the HIV gp120 antigen.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B streptococcus, *Shigella* spp., Enterotoxigenic *Escherichia coli*, Enterohemorrhagic *E. coli, Borrelia burgdorferi*, and *Plasmodium* (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria).

As a stimulator of B cell responsiveness to pathogens.

As an agent that elevates the immune status of an individual prior to their receipt of immunosuppressive therapies.

As an agent to induce production of higher affinity antibodies.

As an agent to induce class switching of B cells expressing IgM antibodies.

As an agent to induce class switching of activated B cells expressing IgM antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among B cell immunodeficient individuals, such as, for example, an individual who has undergone a partial or complete splenectomy. B cell immunodeficiencies that may be ameliorated or treated by administering the Neutrokine-alpha and/or Neutrokine-alphaSV polypeptides or polynucleotides of the invention, or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammuaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

As an agent to boost immunoresponsiveness among individuals having an acquired loss of B cell function. Conditions resulting in an acquired loss of B cell function that may be ameliorated or treated by administering the Neutrokine-alpha and/or Neutrokine-alphaSV polypeptides or polynucleotides of the invention, or agonists thereof, include, but are not limited to, HIV Infection, AIDS, bone marrow transplant, multiple myeloma and B cell chronic lymphocytic leukemia (CLL).

Patients with CLL and myeloma are at risk for increased infections. Thus, one aspect of the present invention provides for the use of Neutrokine alpha, Neutrokine alphaSV, anti-Neutrokine-alpha and or anti-Neutrokine alphaSV polynucleotides and/or polypeptides as an agent to boost immunoresponsiveness in CLL and myeloma patients.

As an agent to boost immunoresponsiveness among individuals having a temporary immune deficiency. Conditions resulting in a temporary immune deficiency that may be ameliorated or treated by administering the Neutrokine-alpha and/or Neutrokine-alphaSV polypeptides or polynucleotides of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery, and recovery from bums.

As a regulator of antigen presentation by monocytes, dendritic cells, and/or B-cells. In one embodiment, Neutrokine-alpha and/or Neutrokine-alphaSV polypeptides (in soluble, membrane-bound or transmembrane forms) or polynucleotides enhance antigen presentation or antagonize antigen presentation in vitro or in vivo. Moreover, in related embodiments, this enhancement or antagonization of antigen presentation may be useful in anti-tumor treatment or to modulate the immune system.

As a mediator of mucosal immune responses. The expression of Neutrokine-alpha by monocytes and the responsiveness of B cells to this factor suggests that it may be involved in exchange of signals between B cells and monocytes or their differentiated progeny. This activity is in many ways analogous to the CD40-CD154 signaling between B cells and T cells. Neutrokine-alpha may therefore be an important regulator of T cell independent immune responses to environmental pathogens. In particular, the unconventional B cell populations (CD5+) that are associated with mucosal sites and responsible for much of the innate immunity in humans may respond to Neutrokine-alpha thereby enhancing an individual's protective immune status.

As an agent to direct an individual's immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a B cell specific binding protein to which specific activators or inhibitors of cell growth may be attached. The result would be to focus the activity of such activators or inhibitors onto normal, diseased, or neoplastic B cell populations.

As a means of detecting B-lineage cells by virtue of its specificity. This application may require labeling the protein with biotin or other agents (e.g., as described herein) to afford a means of detection.

As a stimulator of B cell production in pathologies such as AIDS, chronic lymphocyte disorder and/or Common Variable Immunodificiency.

As part of a B cell selection device the function of which is to isolate B cells from a heterogenous mixture of cell types. Neutrokine-alpha could be coupled to a solid support to which B cells would then specifically bind. Unbound cells would be washed out and the bound cells subsequently eluted. A nonlimiting use of this selection would be to allow purging of tumor cells from, for example, bone marrow or peripheral blood prior to transplant.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance Neutrokine-alpha mediated responses.

As a means of activating monocytes/macrophages to defend against parasitic diseases that effect monocytes such as Leshmania.

As pretreatment of bone marrow samples prior to transplant. Such treatment would increase B cell representation and thus accelerate recover.

As a means of regulating secreted cytokines that are elicited by Neutrokine-alpha.

Neutrokine-alpha or Neutrokine-alphaSV polypeptides or polynucleotides of the invention, or agonists may be used to modulate IgE concentrations in vitro or in vivo.

Additionally, Neutrokine-alpha and/or Neutrokine-alphaSV polypeptides or polynucleotides of the invention, or agonists thereof, may be used to treat, prevent, and/or diagnose IgE-mediated allergic reactions. Such allergic reactions include, but are not limited to, asthma, rhinitis, and eczema.

In a specific embodiment, Neutrokine-alpha and/or Neutrokine-alphaSV polypeptides or polynucleotides of the invention, or agonists thereof, is administered to treat, prevent, diagnose, and/or ameliorate selective IgA deficiency.

In another specific embodiment, Neutrokine-alpha and/or Neutrokine-alphaSV polypeptides or polynucleotides of the invention, or agonists thereof, is administered to treat, prevent, diagnose, and/or ameliorate ataxia-telangiectasia.

In another specific embodiment, Neutrokine-alpha and/or Neutrokine-alphaSV polypeptides or polynucleotides of the invention, or agonists thereof, is administered to treat, prevent, diagnose, and/or ameliorate common variable immunodeficiency.

In another specific embodiment, Neutrokine-alpha and/or Neutrokine-alphaSV polypeptides or polynucleotides of the invention, or agonists thereof, is administered to treat, prevent, diagnose, and/or ameliorate X-linked agammaglobulinemia.

In another specific embodiment, Neutrokine-alpha and/or Neutrokine-alphaSV polypeptides or polynucleotides of the invention, or agonists thereof, is administered to treat, prevent, diagnose, and/or ameliorate severe combined immunodeficiency (SCID).

In another specific embodiment, Neutrokine-alpha and/or Neutrokine-alphaSV polypeptides or polynucleotides of the invention, or agonists thereof, is administered to treat, prevent, diagnose, and/or ameliorate Wiskott-Aldrich syndrome.

In another specific embodiment, Neutrokine-alpha and/or Neutrokine-alphaSV polypeptides or polynucleotides of the invention, or agonists thereof, is administered to treat, prevent, diagnose, and/or ameliorate X-linked Ig deficiency with hyper IgM.

In another specific embodiment, Neutrokine-alpha and/or Neutrokine-alphaSV polypeptides or polynucleotides of the invention, or agonists or antagonists (e.g., anti-Neutrokine-alpha antibodies) thereof, is administered to treat, prevent, and/or diagnose chronic myelogenous leukemia, acute myelogenous leukemia, leukemia, hystiocytic leukemia, monocytic leukemia (e.g., acute monocytic leukemia), leukemic reticulosis, Shilling Type monocytic leukemia, and/or other leukemias derived from monocytes and/or monocytic cells and/or tissues.

In another specific embodiment, Neutrokine-alpha and/or Neutrokine-alphaSV polypeptides or polynucleotides of the invention, or agonists thereof, is administered to treat, prevent, diagnose, and/or ameliorate monocytic leukemoid reaction, as seen, for example, with tuberculosis.

In another specific embodiment, Neutrokine-alpha and/or Neutrokine-alphaSV polypeptides or polynucleotides of the invention, or agonists thereof, is administered to treat, prevent, diagnose, and/or ameliorate monocytic leukocytosis, monocytic leukopenia, monocytopenia, and/or monocytosis.

In a specific embodiment, Neutrokine-alpha, and Neutrokine-alphaSV polynucleotides or polypeptides of the invention, and/or anti-Neutrokine-alpha antibodies and/or agonists or antagonists thereof, are used to treat, prevent, detect, and/or diagnose primary B lymphocyte disorders and/or diseases, and/or conditions associated therewith. In one embodiment, such primary B lymphocyte disorders, diseases, and/or conditions are characterized by a complete or partial loss of humoral immunity. Primary B lymphocyte disorders, diseases, and/or conditions associated therewith that are characterized by a complete or partial loss of humoral immunity and that may be prevented, treated, detected and/or diagnosed with compositions of the invention include, but are not limited to, X-Linked Agammaglobulinemia (XLA), severe combined immunodeficiency disease (SCID), and selective IgA deficiency.

In a preferred embodiment, Neutrokine-alpha and Neutrokine-alphaSV polynucleotides, polypeptides, and/or agonists and/or antagonists thereof are used to treat, prevent, and/or diagnose diseases or disorders affecting or conditions associated with any one or more of the various mucous membranes of the body. Such diseases or disorders include, but are not limited to, for example, mucositis, mucoclasis, mucocolitis, mucocutaneous leishmaniasis (such as, for example, American leishmaniasis, leishmaniasis americana, nasopharyngeal leishmaniasis, and New World leishmaniasis), mucocutaneous lymph node syndrome (for example, Kawasaki disease), mucoenteritis, mucoepidermoid carcinoma, mucoepidernoid tumor, mucoepithelial dysplasia, mucoid adenocarcinoma, mucoid degeneration, myxoid degeneration; myxomatous degeneration; myxomatosis, mucoid medial degeneration (for example, cystic medial necrosis), mucolipidosis (including, for example, mucolipidosis 1, mucolipidosis II, mucolipidosis III, and mucolipidosis IV), mucolysis disorders, mucomembranous enteritis, mucoenteritis, mucopolysaccharidosis (such as, for example, type I mucopolysaccharidosis (i.e., Hurler's syndrome), type IS mucopolysaccharidosis (i.e., Scheie's syndrome or type V mucopolysaccharidosis), type II mucopolysaccharidosis (i.e., Hunter's syndrome), type III mucopolysaccharidosis (i.e., Sanfilippo's syndrome), type IV mucopolysaccharidosis (i.e., Morquio's syndrome), type VI mucopolysaccharidosis (i.e., Maroteaux-Lamy syndrome), type VII mucopolysaccharidosis (i.e, mucopolysaccharidosis due to beta-glucuronidase deficiency), and mucosulfatidosis), mucopolysacchariduria, mucopurulent conjunctivitis, mucopus, mucormycosis (i.e., zygomycosis), mucosal disease (i.e., bovine virus diarrhea), mucous colitis (such as, for example, mucocolitis and myxomembranous colitis), and mucoviscidosis (such as, for example, cystic fibrosis, cystic fibrosis of the pancreas, Clarke-Hadfield syndrome, fibrocystic disease of the pancreas, mucoviscidosis, and viscidosis). In a highly preferred embodiment, Neutrokine-alpha, and/or Neutrokine-alphaSV polynucleotides, polypeptides, and/or agonists and/or antagonists thereof are used to treat, prevent, and/or diagnose mucositis, especially as associated with chemotherapy.

In a preferred embodiment, Neutrokine-alpha, and/or Neutrokine-alphaSV polynucleotides, polypeptides, and/or agonists and/or antagonists thereof are used to treat, prevent, and/or diagnose diseases or disorders affecting or conditions associated with sinusitis.

An additional condition, disease or symptom that can be treated, prevented, and/or diagnosed by Neutrokine-alpha, and/or Neutrokine-alphaSV polynucleotides or polypeptides, or agonists of Neutrokine-alpha, and/or Neutrokine-alphaSV, is osteomyelitis.

An additional condition, disease or symptom that can be treated, prevented, and/or diagnosed by Neutrokine-alpha, and/or Neutrokine-alphaSV polynucleotides or polypeptides, or agonists of Neutrokine-alpha, and/or Neutrokine-alphaSV, is endocarditis.

All of the above described applications as they may apply to veterinary medicine.

Antagonists of Neutrokine-alpha include binding and/or inhibitory antibodies, antisense nucleic acids, ribozymes, and Neutrokine-alpha polypeptides of the invention. These would be expected to reverse many of the activities of the ligand described above as well as find clinical or practical application as:

A means of blocking various aspects of immune responses to foreign agents or self. Examples include autoimmune disorders such as lupus, and arthritis, as well as immunoresponsiveness to skin allergies, inflammation, bowel disease, injury and pathogens. Although our current data speaks directly to the potential role of Neutrokine-alpha in B cell and monocyte related pathologies, it remains possible that other cell types may gain expression or responsiveness to Neutrokine-alpha. Thus, Neutrokine-alpha may, like CD40 and its ligand, be regulated by the status of the immune system and the microenvironment in which the cell is located.

A therapy for preventing the B cell proliferation and Ig secretion associated with autoimmune diseases such as idiopathic thrombocytopenic purpura, systemic lupus erythematosus and MS.

An inhibitor of graft versus host disease or transplant rejection.

A therapy for B cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

Neutrokine-alpha or Neutrokine-alphaSV polypeptides or polynucleotides of the invention, or antagonists may be used to modulate IgE concentrations in vitro or in vivo.

In another embodiment, administration of Neutrokine-alpha or Neutrokine-alphaSV polypeptides or polynucleotides of the invention, or antagonists thereof, may be used to treat, prevent, and/or diagnose IgE-mediated allergic reactions including, but not limited to, asthma, rhinitis, and eczema.

An inhibitor of signaling pathways involving ERK1, COX2 and Cyclin D2 which have been associated with Neutrokine-alpha induced B cell activation.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

The agonists and antagonists may be employed in a composition with a pharmaceutically acceptable carrier, e.g., as described herein.

The antagonists may be employed for instance to inhibit Neutrokine-alpha-mediated and/or Neutrokine-alphaSV-mediated chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat, prevent, and/or diagnose infectious diseases including silicosis, sarcoidosis, idiopathic pulmonary fibrosis by preventing the recruitment and activation of mononuclear phagocytes. They may also be employed to treat, prevent, and/or diagnose idiopathic hyper-eosinophilic syndrome by preventing eosinophil production and migration. Endotoxic shock may also be treated by the antagonists by preventing the migration of macrophages and their production of the Neutrokine-alpha and/or Neutrokine-alphaSV polypeptides of the present invention. The antagonists may also be employed for treating atherosclerosis, by preventing monocyte infiltration in the artery wall. The antagonists may also be employed to treat, prevent, and/or diagnose histamine-mediated allergic reactions and immunological disorders including late phase allergic reactions, chronic urficaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat, prevent, and/or diagnose chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat, prevent, and/or diagnose rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by Neutrokine-alpha and/or Neutrokine-alphaSV. The antagonists may also be employed to treat, prevent, and/or diagnose cases of bone marrow failure, for example, aplastic anemia and myelodysplastic syndrome. The antagonists may also be employed to treat, prevent, and/or diagnose asthma and allergy by preventing eosinophil accumulation in the lung. The antagonists may also be employed to treat, prevent, and/or diagnose subepithelial basement membrane fibrosis which is a prominent feature of the asthmatic lung. The antagonists may also be employed to treat, prevent, and/or diagnose lymphomas (e.g., one or more of the extensive, but not limiting, list of lymphomas provided herein).

All of the above described applications as they may apply to veterinary medicine. Moreover, all applications described herein may also apply to veterinary medicine.

Neutrokine-alpha and/or Neutrokine-alphaSV polynucleotides or polypeptides of the invention and/or agonists and/or antagonists thereof, may be used to treat, prevent, and/or diagnose various immune system-related disorders and/or conditions associated with these disorders, in mammals, preferably humans. Many autoimmune disorders result from inappropriate recognition of self as foreign material by immune cells. This inappropriate recognition results in an immune response leading to the destruction of the host tissue. Therefore, the administration of Neutrokine-alpha and/or Neutrokine-alphaSV polynucleotides or polypeptides of the invention and/or agonists and/or antagonists thereof that can inhibit an immune response, particularly the proliferation of B cells and/or the production of immunoglobulins, may be an effective therapy in treating and/or preventing autoimmune disorders. Thus, in preferred embodiments, Neutrokine-alpha and/or Neutrokine-alphaSV antagonists of the invention (e.g., polypeptide fragments of Neutrokine-alpha and/or Neutrokine-alphaSV and anti-Neutrokine-alpha antibodies) are used to treat, prevent, and/or diagnose an autoimmune disorder.

Autoimmune disorders and conditions associated with these disorders that may be treated, prevented, and/or diagnosed with the Neutrokine-alpha polynucleotides, polypeptides, and/or antagonists of the invention (e.g,. anti-Neutrokine-alpha antibodies), include, but are not limited to, autoimmune hemolytic anemia, autoimmune neutropenia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), dense deposit disease, Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, gluten sensitive enetropathy, insulin dependent diabetes mellitis, discoid lupus, and autoimmune inflammatory eye disease.

Additional autoimmune disorders (that are highly probable) that may be treated, prevented, and/or diagnosed with the compositions of the invention include, but are not limited to, autoimmune thyroiditis, hypothyroidism (i.e., Hashimoto's thyroiditis) (often characterized, e.g., by cell-mediated and humoral thyroid cytotoxicity), systemic lupus erhythematosus (often characterized, e.g., by circulating and locally generated immune complexes), Goodpasture's syndrome (often characterized, e.g., by anti-basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.

Additional autoimmune disorders (that are probable) that may be treated, prevented, and/or diagnosed with the compositions of the invention include, but are not limited to, rheumatoid arthritis (often characterized, e.g., by immune complexes in joints), schleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis/dermatomyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes) such as primary glomerulonephritis and IgA nephropathy, bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), inflammatory myopathies, and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using anti-Neutrokine-alpha antibodies and/or anti-Neutrokine-alphaSV.

In a specific preferred embodiment, rheumatoid arthritis is treated, prevented, and/or diagnosed using anti-Neutrokine-alpha antibodies and/or anti-Neutrokine-alphaSV antibodies and/or other antagonist of the invention.

In a specific preferred embodiment, lupus is treated, prevented, and/or diagnosed using anti-Neutrokine-alpha antibodies and/or anti-Neutrokine-alphaSV antibodies and/or other antagonist of the invention.

In a specific preferred embodiment, Sjogren's Syndrome is treated, prevented, and/or diagnosed using anti-Neutrokine-alpha antibodies and/or anti-Neutrokine-alphaSV antibodies and/or other antagonist of the invention.

In a specific preferred embodiment, AIDS is treated, prevented, and/or diagnosed using anti-Neutrokine-alpha antibodies and/or anti-Neutrokine-alphaSV antibodies and/or other antagonist of the invention.

In a specific preferred embodiment, HIV infection is treated, prevented, and/or diagnosed using anti-Neutrokine-alpha antibodies and/or anti-Neutrokine-alphaSV antibodies and/or other antagonist of the invention.

In a specific preferred embodiment, nephritis associated with lupus is treated, prevented, and/or diagnosed using anti-Neutrokine-alpha antibodies and/or anti-Neutrokine-alphaSV antibodies and/or other antagonist of the invention.

In a specific embodiment, Neutrokine-alpha and/or Neutrokine-alphaSV polynucleotides or polypeptides, or antagonists thereof (e.g., anti-Neutrokine-alpha and/or anti-Neutrokine-alphaSv antibodies) are used to treat or prevent systemic lupus erythematosus and/or diseases, disorders or conditions associated therewith. Lupus-associated diseases, disorders, or conditions that may be treated or prevented with Neutrokine-alpha and/or Neutrokine-alphaSV polynucleotides or polypeptides, or antagonists of the invention, include, but are not limited to, hematologic disorders (e.g., hemolytic anemia, leukopenia, lymphopenia, and thrombocytopenia), immunologic disorders (e.g., anti-DNA antibodies, and anti-Sm antibodies), rashes, photosensitivity, oral ulcers, arthritis, fever, fatigue, weight loss, serositis (e.g., pleuritus (pleuricy)), renal disorders (e.g., nephritis), neurological disorders (e.g., seizures, peripheral neuropathy, CNS related disorders), gastroinstestinal disorders, Raynaud phenomenon, and pericarditis. In a preferred embodiment, the Neutrokine-alpha and/or Neutrokine-alphaSV polynucleotides or polypeptides, or antagonists thereof (e.g., anti-Neutrokine-alpha and/or anti-Neutrokine-alphaSV antibodies) are used to treat or prevent renal disorders associated with systemic lupus erythematosus. In a most preferred embodiment, Neutrokine-alpha and/or Neutrokine-alphaSV polynucleotides or polypeptides, or antagonists thereof (e.g., anti-Neutrokine-alpha and/or anti-Neutrokine-alphaSV antibodies) are used to treat or prevent nephritis associated with systemic lupus erythematosus.

Similarly, allergic reactions and conditions, such as asthma (particularly allergic asthma) or other respiratory problems, may also be treated by Neutrokine-alpha and/or Neutrokine-alphaSV polynucleotides or polypeptides of the invention and/or agonists and/or antagonists thereof. Moreover, these molecules can be used to treat, prevent, and/or diagnose anaphylaxis, hypersensitivity to an antigenic molecule, or blood group incompatibility.

Neutrokine-alpha and/or Neutrokine-alphaSV polynucleotides or polypeptides of the invention and/or agonists and/or antagonists thereof, may also be used to treat, prevent, and/or diagnose organ rejection or graft-versus-host disease (GVHD) and/or conditions associated therewith. Organ rejection occurs by host immune cell destruction of the transplanted tissue through an immune response. Similarly, an immune response is also involved in GVHD, but, in this case, the foreign transplanted immune cells destroy the host tissues. The administration of Neutrokine-alpha and/or Neutrokine-alphaSV polynucleotides or polypeptides of the invention and/or agonists and/or antagonists thereof, that inhibits an immune response, particularly the proliferation, differentiation, or chemotaxis of T-cells, may be an effective therapy in preventing organ rejection or GVHD.

Similarly, Neutrokine-alpha and/or Neutrokine-alphaSV polynucleotides or polypeptides of the invention and/or agonists and/or antagonists thereof, may also be used to modulate inflammation. For example, Neutrokine-alpha and/or Neutrokine-alphaSV polynucleotides or polypeptides of the invention and/or agonists and/or antagonists thereof, may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

In a specific embodiment, anti-Neutrokine-alpha antibodies and/or anti-Neutrokine-alphaSV antibodies of the invention are used to treat, prevent, modulate, detect, and/or diagnose inflammation.

In a specific embodiment, anti-Neutrokine-alpha antibodies and/or anti-Neutrokine-alphaSV antibodies of the invention are used to treat, prevent, modulate, detect, and/or diagnose inflamatory disorders.

In another specific embodiment, anti-Neutrokine-alpha antibodies and/or anti-Neutrokine-alphaSV antibodies of the invention are used to treat, prevent, modulate, detect, and/or diagnose allergy and/or hypersensitivity.

In another embodiment, therapeutic or pharmaceutical compositions of the invention (e.g., Neutrokine-alpha and/or Neutrokine-alphaSV polynucleotides or polypeptides of the invention and/or antagonists thereof) are administered to an animal to treat, prevent or ameliorate ischemia and arteriosclerosis. Examples of such disorders include, but are not limited to, reperfusion damage (e.g., in the heart and/or brain) and cardiac hypertrophy.

Neutrokine-alpha and/or Neutrokine-alphaSV polynucleotides or polypeptides of the invention and/or antagonists thereof, may also be used to modulate blood clotting and to treat or prevent blood clotting disorders, such as, for example, antibody-mediated thrombosis (i.e., antiphospholipid antibody syndrome (APS)). For example, Neutrokine-alpha and/or Neutrokine-alphaSV polynucleotides or polypeptides of the invention and/or antagonists thereof, may inhibit the proliferation and differentiation of cells involved in producing anticardiolipin antibodies. These compositions of the invention can be used to treat, prevent, and/or diagnose, thrombotic related events including, but not limited to, stroke (and recurrent stroke), heart attack, deep vein thrombosis, pulmonary embolism, myocardial infarction, coronary artery disease (e.g,. antibody -mediated coronary artery disease), thrombosis, graft reocclusion following cardiovascular surgery (e.g,. coronary arterial bypass grafts, recurrent fetal loss, and recurrent cardiovascular thromboembolic events.

Antibodies against Neutrokine-alpha and/or Neutrokine-alphaSV may be employed to bind to and inhibit Neutrokine-alpha and/or Neutrokine-alphaSV activity to treat, prevent, and/or diagnose ARDS, by preventing infiltration of neutrophils into the lung after injury. The agonists and antagonists of the instant may be employed in a composition with a pharmaceutically acceptable carrier, e.g., as described hereinafter.

Neutrokine-alpha and/or Neutrokine-alphaSV and/or Neutrokine-alpha receptor polynucleotides or polypeptides of the invention and/or agonists and/or antagonists thereof, are used to treat, prevent, and/or diagnose diseases and disorders of the pulmonary system (e.g., bronchi such as, for example, sinopulmonary and bronchial infections and conditions associated with such diseases and disorders and other respiratory diseases and disorders. In specific embodiments, such diseases and disorders include, but are not limited to, bronchial adenoma, bronchial asthma, pneumonia (such as, e.g., bronchial pneumonia, bronchopneumonia, and tuberculous bronchopneumonia), chronic obstructive pulmonary disease (COPD), bronchial polyps, bronchiectasia (such as, e.g., bronchiectasia sicca, cylindrical bronchiectasis, and saccular bronchiectasis), bronchiolar adenocarcinoma, bronchiolar carcinoma, bronchiolitis (such as, e.g., exudative bronchiolitis, bronchiolitis fibrosa obliterans, and proliferative bronchiolitis), bronchiolo-alveolar carcinoma, bronchitic asthma, bronchitis (such as, e.g., asthmatic bronchitis, Castellani's bronchitis, chronic bronchitis, croupous bronchitis, fibrinous bronchitis, hemorrhagic bronchitis, infectious avian bronchitis, obliterative bronchitis, plastic bronchitis, pseudomembranous bronchitis, putrid bronchitis, and verminous bronchitis), bronchocentric granulomatosis, bronchoedema, bronchoesophageal fistula, bronchogenic carcinoma, bronchogenic cyst, broncholithiasis, bronchomalacia, bronchomycosis (such as, e.g., bronchopulmonary aspergillosis), bronchopulmonary spirochetosis, hemorrhagic bronchitis, bronchorrhea, bronchospasm, bronchostaxis, bronchostenosis, Biot's respiration, bronchial respiration, Kussmaul respiration, Kussmaul-Kien respiration, respiratory acidosis, respiratory alkalosis, respiratory distress syndrome of the newborn, respiratory insufficiency, respiratory scleroma, respiratory syncytial virus, and the like.

In a specific embodiment, Neutrokine-alpha and/or Neutrokine-alphaSV polynucleotides or polypeptides of the invention and/or agonists and/or antagonists thereof, are used to treat, prevent, and/or diagnose chronic obstructive pulmonary disease (COPD).

In another embodiment, Neutrokine-alpha and/or Neutrokine-alphaSV polynucleotides or polypeptides of the invention and/or agonists and/or antagonists thereof, are used to treat, prevent, and/or diagnose fibroses and conditions associated with fibroses, such as, for example, but not limited to, cystic fibrosis (including such fibroses as cystic fibrosis of the pancreas, Clarke-Hadfield syndrome, fibrocystic disease of the pancreas, mucoviscidosis, and viscidosis), endomyocardial fibrosis, idiopathic retroperitoneal fibrosis, leptomeningeal fibrosis, mediastinal fibrosis, nodular subepidermal fibrosis, pericentral fibrosis, perimuscular fibrosis, pipestem fibrosis, replacement fibrosis, subadventitial fibrosis, and Symmers' clay pipestem fibrosis.

The TNF family ligands are known to be among the most pleiotropic cytokines, inducing a large number of cellular responses, including cytotoxicity, anti-viral activity, immunoregulatory activities, and the transcriptional regulation of several genes (D. V. Goeddel et al., "Tumor Necrosis Factors: Gene Structure and Biological Activities," Symp. Quant. Biol. 51:597-609 (1986), Cold Spring Harbor; B. Beutler and A. Cerami, Annu. Rev. Biochem. 57:505-518 (1988); L. J. Old, Sci. Am. 258:59-75 (1988); W. Fiers, FEBS Lett. 285: 199-224 (1991)). The TNF-family ligands, including Neutrokine-alpha and/or Neutrokine-alphaSV of the present invention, induce such various cellular responses by binding to TNF-family receptors. Neutrokine-alpha and/or Neutrokine-alphaSV polypeptides are believed to elicit a potent cellular response including any genotypic, phenotypic, and/or morphologic change to the cell, cell line, tissue, tissue culture or patient. As indicated, such cellular responses include not only normal physiological responses to TNF-family ligands, but also diseases associated with increased apoptosis or the inhibition of apoptosis. Apoptosis-programmed cell death-is a physiological mechanism involved in the deletion of peripheral B and/or T lymphocytes of the immune system, and its disregulation can lead to a number of different pathogenic processes (J. C. Ameisen, AIDS 8:1197-1213 (1994); P. H. Krammer et al., Curr. Opin. Immunol. 6:279-289 (1994)).

Diseases associated with increased cell survival, or the inhibition of apoptosis that may be diagnosed, treated, or prevented with the Neutrokine-alpha and/or Neutrokine-alphaSV polynucleotides or polypeptides of the invention, and agonists and antagonists thereof, include cancers (such as follicular lymphomas, carcinomas with p53 mutations, and hormone-dependent tumors, including, but not limited to, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. Thus, in preferred embodiments Neutrokine-alpha and/or Neutrokine-alphaSV polynucleotides or polypeptides of the invention and/or agonists or antagonists thereof, are used to treat, prevent, and/or diagnose autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment Neutrokine-alpha and/or Neutrokine-alphaSV polynucleotides or polypeptides of the invention are used to activate, differentiate or proliferate cancerous cells or tissue (e.g., B cell lineage related cancers (e.g., CLL and MLL), lymphocytic leukemia, or lymphoma) and thereby render the cells more vulnerable to cancer therapy (e.g., chemotherapy or radiation therapy).

Moreover, in other embodiments, Neutrokine-alpha and/or Neutrokine-alphaSV polynucleotides or polypeptides of the invention or agonists or antagonists thereof, are used to inhibit the growth, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, Iymphangioendotheliosarcoma, synovioma, mesothelioma, Ewing's tumor, leiomyosarcoma, rhabdomyosarcoma, colon carcinoma, pancreatic cancer, breast cancer, ovanan cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In specific embodiments Neutrokine-alpha and/or Neutrokine-alphaSV polynucleotides or polypeptides of the invention are used to inhibit the growth, progression, and/or metastases of multiple myeloma. In even more specific embodiments, radiolabeled Neutrokine-alpha polypeptides comprising, or alternatively consisting of amino acids 134-285 of SEQ ID NO:2 (e.g., radiolabeled Neutrokine alpha trimers comprising three polypeptide chains consisting of amino acids 134-285 of SEQ ID NO:2) are used to inhibit the growth, progression, and/or metastases of multiple myeloma. In particular embodiments, the radiolabeled Neutrokine-alpha polypeptides are radiolabeled with an $^{131}I$ radioisotope.

In specific embodiments Neutrokine-alpha and/or Neutrokine-alphaSV polynucleotides or polypeptides of the invention are used to inhibit the growth, progression, and/or metastases of non-Hodgkin's lymphoma. In even more specific embodiments, radiolabeled Neutrokine-alpha polypeptides comprising, or alternatively consisting of amino acids 134-285 of SEQ ID NO:2 (e.g., radiolabeled Neutrokine alpha trimers comprising three polypeptide chains consisting of amino acids 134-285 of SEQ ID NO:2) are used to inhibit the growth, progression, and/or metastases of non-Hodgkin's lymphoma. In particular embodiments, the radiolabeled Neutrokine-alpha polypeptides are radiolabeled with an $^{131}I$ radioisotope.

In specific embodiments Neutrokine-alpha and/or Neutrokine-alphaSV polynucleotides or polypeptides of the invention are used to inhibit the growth, progression, and/or metastases of chronic lymphocytic leukemia (CLL). In even more specific embodiments, radiolabeled Neutrokine-alpha polypeptides comprising, or alternatively consisting of amino acids 134-285 of SEQ ID NO:2 (e.g., radiolabeled Neutrokine alpha trimers comprising three polypeptide chains consisting of amino acids 134-285 of SEQ ID NO:2) are used to inhibit the growth, progression, and/or metastases of CLL. In particular embodiments, the radiolabeled Neutrokine-alpha polypeptides are radiolabeled with an $^{131}I$ radioisotope.

Diseases associated with increased apoptosis that may be diagnosed, treated, or prevented with the Neutrokine-alpha and/or Neutrokine-alphaSV polynucleotides or polypeptides of the invention, and agonists and antagonists thereof,include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia. Thus, in preferred embodiments Neutrokine-alpha and/or Neutrokine-alphaSV polynucleotides or polypeptides of the invention and/or agonists or antagonists thereof, are used to treat, prevent, and/or diagnose the diseases and disorders listed above.

In preferred embodiments, Neutrokine-alpha and/or Neutrokine-alphaSV polypeptides of the invention and/or agonists or antagonists thereof (e.g., anti-Neutrokine-alpha antibodies) inhibit the growth of human histiocytic lymphoma U-937 cells in a dose-dependent manner. In additional preferred embodiments, Neutrokine-alpha and/or Neutrokine-alphaSV polypeptides of the invention and/or agonists or antagonists thereof (e.g., anti-Neutrokine-alpha antibodies) inhibit the growth of PC-3 cells, HT-29 cells, HeLa cells, MCF-7 cells, and A293 cells. In highly preferred embodiments, Neutrokine-alpha and/or Neutrokine-alphaSV polynucleotides or polypeptides of the invention and/or agonists or antagonists thereof (e.g., anti-Neutrokine-alpha antibodies) are used to inhibit growth, progression, and/or metastasis of prostate cancer, colon cancer, cervical carcinoma, and breast carcinoma.

Thus, in additional preferred embodiments, the present invention is directed to a method for enhancing apoptosis induced by a TNF-family ligand, which involves administering to a cell which expresses a Neutrokine-alpha and/or Neutrokine-alphaSV receptor an effective amount of Neutrokine-alpha and/or Neutrokine-alphaSV, or an agonist or antagonist thereof, capable of increasing or decreasing Neutrokine-alpha and/or Neutrokine-alphaSV mediated signaling. Preferably, Neutrokine-alpha and/or Neutrokine-alphaSV mediated signaling is increased or decreased to treat, prevent, and/or diagnose a disease wherein decreased apoptosis or decreased cytokine and adhesion molecule expression is exhibited. An agonist or antagonist can include soluble forms of Neutrokine-alpha and/or Neutrokine-alphaSV and monoclonal antibodies directed against the Neutrokine-alpha and/or Neutrokine-alphaSV polypeptide.

In a further aspect, the present invention is directed to a method for inhibiting apoptosis induced by a TNF-family ligand, which involves administering to a cell which expresses the Neutrokine-alpha and/or Neutrokine-alphaSV receptor an effective amount of an agonist or antagonist capable of increasing or decreasing Neutrokine-alpha and/or Neutrokine-alphaSV mediated signaling. Preferably, Neutrokine-alpha and/or Neutrokine-alphaSV mediated signaling is increased or decreased to treat, prevent, and/or diagnose a disease wherein increased apoptosis or NF-kappaB expression is exhibited. An agonist or antagonist can include soluble forms of Neutrokine-alpha and/or Neutrokine-alphaSV and monoclonal antibodies directed against the Neutrokine-alpha and/or Neutrokine-alphaSV polypeptide.

Because Neutrokine-alpha and/or Neutrokine-alphaSV belong to the TNF superfamily, the polypeptides should also modulate angiogenesis. In addition, since Neutrokine-alpha and/or Neutrokine-alphaSV inhibit immune cell functions, the polypeptides will have a wide range of anti-inflammatory activities. Neutrokine-alpha and/or Neutrokine-alphaSV may be employed as an anti-neovascularizing agent to treat, prevent, and/or diagnose solid tumors by stimulating the invasion and activation of host defense cells, e.g., cytotoxic T cells and macrophages and by inhibiting the angiogenesis of tumors. Those of skill in the art will recognize other non-cancer indications where blood vessel proliferation is not wanted. They may also be employed to enhance host defenses against resistant chronic and acute infections, for example, myobacterial infections via the attraction and activation of microbicidal leukocytes. Neutrokine-alpha and/or Neutrokine-alphaSV may also be employed to inhibit T-cell proliferation by the inhibition of IL-2 biosynthesis for the treatment of T-cell mediated auto-immune diseases and lymphocytic leukemias (including, for example, chronic lymphocytic leukemia (CLL)). Neutrokine-alpha and/or Neutrokine-alphaSV may also be employed to stimulate wound healing, both via the recruitment of debris clearing and connective tissue promoting inflammatory cells. In this same manner, Neutrokine-alpha and/or Neutrokine-alphaSV may also be employed to treat, prevent, and/or diagnose other fibrotic disorders, including liver cirrhosis, osteoarthritis and pulmonary fibrosis. Neutrokine-alpha and/or Neutrokine-alphaSV also increases the presence of eosinophils that have the distinctive function of killing the larvae of parasites that invade tissues, as in schistosomiasis, trichinosis and ascariasis. It may also be employed to regulate hematopoiesis, by regulating the activation and differentiation of various hematopoietic progenitor cells, for example, to release mature leukocytes from the bone marrow following chemotherapy, i.e., in stem cell mobilization. Neutrokine-alpha and/or Neutrokine-alphaSV may also be employed to treat, prevent, and/or diagnose sepsis.

Polynucleotides and/or polypeptides of the invention and/or agonists and/or antagonists thereof are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), Helicobacter pylori infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyclodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

In specific embodiments, polynucleotides and/or polypeptides of the invention and/or agonists and/or antagonists thereof are useful in the diagnosis and treatment or prevention of dilated cadiomyopathy. In specific embodiments, antagonistic anti-neutrokine-alpha antibodies are useful in the diagnosis and treatment or prevention of dilated cadiomyopathy. In other specific embodiments, Neutrokine-alpha polypeptides and/or Neutrokine-alpha SV polypeptides conjugated to or otherwise associated with a cytotoxic prodrug or toxin may be used to treatment or prevention of dilated cadiomyopathy.

In specific embodiments, polynucleotides and/or polypeptides of the invention and/or agonists and/or antagonists thereof are useful in the diagnosis and treatment or prevention of diseases involving increased hypergammaglobulinemia or elevated autoantibody titers. In specific embodiments, antagonists of Neutrokine-alpha, such as an anti-Neutrokine-alpha specific antibody, are useful in the diagnosis and treatment or prevention of diseases involving increased hypergammaglobulinemia or elevated autoantibody titers.

In specific embodiments, polynucleotides and/or polypeptides of the invention and/or agonists and/or antagonists thereof are useful in the diagnosis and treatment or prevention of liver diseases, including but not limited to, primary biliary cirrhosis, primary sclerosing cholangitis, chronic hepatitis C infection, autoimmune hepatitis and alcoholic liver disease. In specific embodiments, antagonists of Neutrokine-alpha, such as an anti-Neutrokine-alpha specific antibody, are useful in the diagnosis and treatment or prevention of liver diseases, including but not limited to, primary biliary cirrhosis, primary sclerosing cholangitis, chronic hepatitis C infection, and alcoholic liver disease.

Polynucleotides and/or polypeptides of the invention and/or agonists and/or antagonists thereof are useful in promoting angiogenesis, wound healing (e.g., wounds, bums, and bone fractures). Polynucleotides and/or polypeptides of the invention and/or agonists and/or antagonists thereof are also useful as an adjuvant to enhance immune responsiveness to specific antigen, anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

Preferably, treatment using Neutrokine-alpha, and/or Neutrokine-alphaSV polynucleotides or polypeptides, and/or agonists or antagonists of Neutrokine-alpha, and/or Neutrokine-alphaSV (e.g., anti-Neutrokine-alpha antibody), could either be by administering an effective amount of Neutrokine-alpha, and/or Neutrokine-alphaSV polypeptide of the invention, or agonist or antagonist thereof, to the patient, or by removing cells from the patient, supplying the cells with Neutrokine-alpha, and/or Neutrokine-alphaSV polynucleotide, and returning the engineered cells to the patient (ex vivo therapy). Moreover, as further discussed herein, the Neutrokine-alpha, and/or Neutrokine-alphaSV polypeptide or polynucleotide can be used as an adjuvant in a vaccine to raise an immune response against infectious disease.

Formulations and Administration

The Neutrokine-alpha and/or Neutrokine-alphaSV polypeptide composition (preferably containing a polypeptide which is a soluble form of the Neutrokine-alpha and/or Neutrokine-alphaSV extracellular domains) will be formulated and dosed in a fashion consistent with good medical practice, taking into account the clinical condition of the individual patient (especially the side effects of treatment with Neutrokine-alpha and/or Neutrokine-alphaSV polypeptide alone), the site of delivery of the Neutrokine-alpha and/or Neutrokine-alphaSV polypeptide composition, the method of administration, the scheduling of administration, and other factors known to practitioners. The "effective amount" of Neutrokine-alpha and/or Neutrokine-alphaSV polypeptide for purposes herein is thus determined by such considerations.

As a general proposition, the total pharmaceutically effective amount of Neutrokine-alpha and/or Neutrokine-alphaSV polypeptide administered parenterally per dose will be in the range of about 1 microgram/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day.

In another embodiment, the Neutrokine-alpha and/or Neutrokine-alphaSV polypeptide of the invention is administered to a human at a dose betweeen 0.0001 and 0.045 mg/kg/day, preferably, at a dose between 0.0045 and 0.045 mg/kg/day, and more preferably, at a dose of about 45 microgram/kg/day in humans; and at a dose of about 3 mg/kg/day in mice.

If given continuously, the Neutrokine-alpha and/or Neutrokine-alphaSV polypeptide is typically administered at a dose rate of about 1 microgram/kg/hour to about 50 micrograms/kg/hour, either by 1-4 injections per day or by continuous subcutaneous infusions, for example, using a mini-pump. An intravenous bag solution may also be employed.

The length of treatment needed to observe changes and the interval following treatment for responses to occur appears to vary depending on the desired effect.

In a specific embodiment, the total pharmaceutically effective amount of Neutrokine-alpha and/or Neutrokine-alphaSV polypeptide administered parenterally per dose will be in the range of about 0.1 microgram/kg/day to 45 micrograms/kg/day of patient body weight, although, as noted above, this will be subject to therapeutic discretion. More preferably, this dose is at least 0.1 microgram/kg/day, and most preferably for humans between about 0.01 and 50 micrograms/kg/day for the protein. Neutrokine-alpha and/or Neutrokine-alphaSV may be administered as a continuous infusion, multiple dicreet injections per day (e.g., three or more times daily, or twice daily), single injection per day, or as discreet injections given intermitently (e.g., twice daily, once daily, every other day, twice weekly, weekly, biweekly, monthly, bimonthly, and quarterly). If given continuously, the Neutrokine-alpha and/or Neutrokine-alphaSV polypeptide is typically administered at a dose rate of about 0.001 to 10 microgram/kg/hour to about 50 micrograms/kg/hour, either by 1-4 injections per day or by continuous subcutaneous infusions, for example, using a mini-pump.

Effective dosages of the compositions of the present invention to be administered may be determined through procedures well known to those in the art which address such parameters as biological half-life, bioavailability, and toxicity. Such determination is well within the capability of those skilled in the art, especially in light of the detailed disclosure provided herein.

Bioexposure of an organism to Neutrokine-alpha and/or Neutrokine-alphaSV polypeptide during therapy may also play an important role in determining a therapeutically and/or pharmacologically effective dosing regime. Variations of dosing such as repeated administrations of a relatively low dose of Neutrokine-alpha and/or Neutrokine-alphaSV polypeptide for a relatively long period of time may have an effect which is therapeutically and/or pharmacologically distinguishable from that achieved with repeated administrations of a relatively high dose of Neutrokine-alpha and/or Neutrokine-alphaSV for a relatively short period of time. See, for instance, the serum immunoglobulin level experiments presented in Example 6.

Using the equivalent surface area dosage conversion factors supplied by Freireich, E. J., et al. (Cancer Chemotherapy Reports 50(4):219-44 (1966)), one of ordinary skill in the art is able to conveniently convert data obtained from the use of Neutrokine-alpha and/or Neutrokine-alphaSV in a given experimental system into an accurate estimation of a pharmaceutically effective amount of Neutrokine-alpha and/or Neutrokine-alphaSV polypeptide to be administered per dose in another experimental system. Experimental data obtained through the administration of Neutrokine-alpha in mice (see, for instance, Example 6) may converted through the conversion factors supplied by Freireich, et al., to accurate estimates of pharmaceutically effective doses of Neutrokine-alpha in rat, monkey, dog, and human. The following conversion table (Table III) is a summary of the data provided by Freireich, et al. Table III gives approximate factors for converting doses expressed in terms of mg/kg from one species to an equivalent surface area dose expressed as mg/kg in another species tabulated.

TABLE III

Equivalent Surface Area Dosage Conversion Factors.

| | TO | | | | |
|---|---|---|---|---|---|
| FROM | Mouse (20 g) | Rat (150 g) | Monkey (3.5 kg) | Dog (8 kg) | Human (60 kg) |
| Mouse | 1 | ½ | ¼ | 1/6 | 1/12 |
| Rat | 2 | 1 | ½ | ¼ | 1/7 |
| Monkey | 4 | 2 | 1 | 3/5 | 1/3 |
| Dog | 6 | 4 | 5/3 | 1 | ½ |
| Human | 12 | 7 | 3 | 2 | 1 |

Thus, for example, using the conversion factors provided in Table III, a dose of 50 mg/kg in the mouse converts to an appropriate dose of 12.5 mg/kg in the monkey because (50 mg/kg)×(¼)=12.5 mg/kg. As an additional example, doses of 0.02, 0.08, 0.8, 2, and 8 mg/kg in the mouse equate to effect doses of 1.667 micrograms/kg, 6.67 micrograms/kg, 66.7 micrograms/kg 166.7 micrograms/kg, and 0.667 mg/kg, respectively, in the human.

In certain embodiments, administration of radiolabeled forms of Neutrokine-alpha, Neutrokine-alphaSV, anti-Neutrokine-alpha antibodies and/or anti-Neutrokine-alphaSV antibodies is contemplated. The radiometric dosage to be applied can vary substantially. The radiolabeled Neutrokine-alpha, Neutrokine-alphaSV, anti-Neutrokine-alpha antibody and/or anti-Neutrokine-alphaSV antibody composition can be administered at a dose of about 0.1 to about 100 mCi per 70 kg body weight. In another embodiment, the radiolabeled Neutrokine-alpha, Neutrokine-alphaSV, anti-Neutrokine-alpha antibody and/or anti-Neutrokine-alphaSV antibody composition can be administered at a dose of about 0.1 to about 50 mCi per 70 kg body weight. In another embodiment, the radiolabeled Neutrokine-alpha, Neutrokine-alphaSV, anti-Neutrokine-alpha antibody and/or anti-Neutrokine-alphaSV antibody composition can be administered at a dose of about 0.1, 0.5, 1, 5, 10, 15, 20, 25, 30, 35, 40, 50, 60, 70, 80, 90 or 100 mCi per 70 kg body weight.

The radiolabeled Neutrokine-alpha, Neutrokine-alphaSV, anti-Neutrokine-alpha antibody and/or anti-Neutrokine-alphaSV antibody composition can be administered at a dose of about 0.1 to about 10 mCi/kg body weight. In another embodiment, the radiolabeled Neutrokine-alpha, Neutrokine-alphaSV, anti-Neutrokine-alpha antibody and/or anti-Neutrokine-alphaSV antibody composition can be administered at a dose of about 0.25 to about 5 mCi/kg body weight. In specific embodiments, the radiolabeled Neutrokine-alpha, Neutrokine-alphaSV, anti-Neutrokine-alpha antibody and/or anti-Neutrokine-alphaSV antibody composition can be administered at a dose of about 0.35, 0.70, 1.35, 1.70, 2.0, 2.5 or 3.0 mCi/kg.

The radiolabeled Neutrokine-alpha, Neutrokine-alphaSV, anti-Neutrokine-alpha antibody and/or anti-Neutrokine-alphaSV antibody composition can be administered at a dose of about 1 to about 50 $mCi/m^2$. In another embodiment, the radiolabeled Neutrokine-alpha, Neutrokine-alphaSV, anti-Neutrokine-alpha antibody and/or anti-Neutrokine-alphaSV antibody composition can be administered at a dose of about 10 to about 30 $mCi/m^2$. In specific embodiments, the radiolabeled Neutrokine-alpha, Neutrokine-alphaSV, anti-Neutrokine-alpha antibody and/or anti-Neutrokine-alphaSV antibody composition can be administered at a dose of about 10, 15, 20, 25, or 30 mCi/m2.

The concentration of total Neutrokine-alpha protein, Neutrokine-alphaSV protein, anti-Neutrokine-alpha antibody and/or anti-Neutrokine-alphaSV antibody in a radiolabelled Neutrokine-alpha, Neutrokine-alphaSV, anti-Neutrokine-alpha antibody and/or anti-Neutrokine-alphaSV antibody composition may also vary, for example from about 1 microgram/kg to about 1 mg/kg. In specific embodiments, the total concentration of Neutrokine-alpha protein, Neutrokine-alphaSV protein, anti-Neutrokine-alpha antibody and/or anti-Neutrokine-alphaSV antibody in a radiolabelled Neutrokine-alpha, Neutrokine-alphaSV, anti-Neutrokine-alpha antibody and/or anti-Neutrokine-alphaSV antibody composition may be about 5, 10, 15, 20, 25, 30, 35, 40, 45, 50, 55, 60, 65, 70, 75, 80, 85, 90, 95 100 micrograms/kg.

For example, lymphomas are known to be radiosensitive tumors. For immunodiagnostic imaging, trace-labeling by the complex may be used, typically 1-20 mg of Neutrokine-alpha protein is labeled with about 1 to 60 mCi of radioisotope. The dose may be somewhat dependent upon the isotope used for imaging; amounts in the higher end of the range, preferably 40 to 60 mCi, may be used with $^{99m}$Tc; amounts in the lower end of the range, preferably 1-20 mCi, may be used with $^{111}$In. For imaging purposes, about 1 to about 30 mg of Neutrokine-alpha complex can be given to the subject. For radioimmunotherapeutic purposes, the Neutrokine-alpha complex is administered to a subject in sufficient amount so that the whole body dose received is up to about 1100 cGy, but preferably less than or equal to 500 cGy. The total amount of Neutrokine-alpha protein administered to a subject, including Neutrokine-alpha protein, Neutrokine-alpha conjugate and Neutrokine-alpha complex, can range from 1.0 □g/kg to 1.0 mg/kg of patient body weight. In another embodiment, total amount of Neutrokine-alpha protein administered to a subject, can range from 20 □g/kg to 100 □g/kg of patient body weight.

An amount of radioactivity which would provide approximately 500 cGy to the whole body of a human is estimated to be about 825 mCi of $^{131}$I. The amounts of radioactivity to be administered depend, in part, upon the isotope chosen. For $^{90}$Y therapy, from about 1 to about 200 mCi amounts of radioactivity are considered appropriate, with preferable amounts being 1 to 150 mCi, and 1 to 100 mCi (e.g., 60 mCi) being most preferred. The preferred means of estimating tissue doses from the amount of administered radioactivity is to perform an imaging or other pharmacokinetic regimen with a tracer dose, so as to obtain estimates of predicted dosimetry. In determining the appropriate dosage of radiopharmaceutical to administer to an individual, it is necessary to consider the amount of radiation that individual organs will receive compared to the maximum tolerance for such organs. Such information is known to those skilled in the art, for example, see Emami et al., International Journal of Radiation Oncology, Biology, Physics 21:109-22 (1991); and Meredith, Cancer Biotherapy & Radiopharmaceuticals 17:83-99 (2002), both of which are hereby incorporated by reference in their entireties.

A "high-dose" protocol, for example in the range of 200 to 600 cGy (or higher) to the whole body, may require the support of a bone-marrow replacement protocol, as the bone-marrow is the tissue which limits the radiation dosage due to toxicity.

In specific embodiments, radiolabelled Neutrokine-alpha, Neutrokine-alphaSV, anti-Neutrokine-alpha antibody and/or anti-Neutrokine-alphaSV antibody compositions can be used to target radiotherapy to cancers, such as B cells cancers (including non-Hodgkins lymphoma and multiple myeloma) while delivering low radiation doses to normal critical organs, such as the lung, liver, kidney, and red marrow.

Pharmaceutical compositions containing Neutrokine-alpha and/or Neutrokine-alphaSV polypeptides of the invention may be administered orally, rectally, parenterally, subcutaneously, intracisternally, intravaginally, intraperitoneally, topically (as by powders, ointments, drops or transdermal patch), bucally, or as an oral or nasal spray (e.g., via inhalation of a vapor or powder). In one embodiment, "pharmaceutically acceptable carrier" means a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can be employed as liquid carriers, particularly for injectable solutions. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The term "parenteral" as used herein refers to modes of administration which include intravenous, intramuscular, intraperitoneal, intrasternal, subcutaneous and intraarticular injection and infusion.

In a preferred embodiment, Neutrokine-alpha and/or Neutrokine-alphaSV compositions of the invention (including polypeptides, polynucleotides, and antibodies, and agonists and/or antagonists thereof) are administered subcutaneously.

In another preferred embodiment, Neutrokine-alpha and/or Neutrokine-alphaSV compositions of the invention (including polypeptides, polynucleotides, and antibodies, and agonists and/or antagonists thereof) are administered intravenously.

Neutrokine-alpha and/or Neutrokine-alphaSV compositions of the invention are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and ganma-ethyl-L-glutamate (Sidman, U. et al., Biopolymers 22:547-556 (1983)), poly(2- hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id) or poly-D-(−)-3-hydroxybutyric acid (EP 133,988).

In a preferred embodiment, Neutrokine-alpha and/or Neutrokine-alphaSV compositions of the invention are formulated in a biodegradable, polymeric drug delivery system, for example as described in U.S. Pat. Nos. 4,938,763; 5,278,201; 5,278,202; 5,324,519; 5,340,849; and 5,487,897 and in International Publication Numbers WO01/35929, WO00/24374, and WO00/06117 which are hereby incorporated by reference in their entirety. In specific preferred embodiments the Neutrokine-alpha and/or Neutrokine-alphaSV compositions of the invention are formulated using the ATRIGEL® Biodegradable System of Atrix Laboratories, Inc. (Fort Collins, Colo.). In other specific embodiments, Neutrokine-alpha and/or Neutrokine-alphaSV compositions of the invention are formulated using the ProLease® sustained relase sytem available from Alkermes, Inc. (Cambridge, Mass.).

Examples of biodegradable polymers which can be used in the formulation of Neutrokine-alpha and/or Neutrokine-alphaSV compositions, include but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), polyvinylpyrrolidone, polyethylene glycol, polyhydroxycellulose, chitin, chitosan, and copolymers, terpolymers, or combinations or mixtures of the above materials. The preferred polymers are those that have a lower degree of crystallization and are more hydrophobic. These polymers and copolymers are more soluble in the biocompatible solvents than the highly crystalline polymers such as polyglycolide and chitin which also have a high degree of hydrogen-bonding. Preferred materials with the desired solubility parameters are the polylactides, polycaprolactones, and copolymers of these with glycolide in which there are more amorphous regions to enhance solubility. In specific preferred embodiments, the biodegradable polymers which can be used in the formulation of Neutrokine-alpha and/or Neutrokine-alphaSV compositions are poly(lactide-co-glycolides). Polymer properties such as molecular weight, hydrophobicity, and lactide/glycolide ratio may be modified to obtain the desired drug Neutrokine-alpha and/or Neutrokine-alphaSV release profile (See, e.g., Ravivarapu et al., Journal of Pharmaceutical Sciences 89:732-741 (2000), which is hereby incorporated by refemce in its entirety).

It is also preferred that the solvent for the biodegradable polymer be non-toxic, water miscible, and otherwise biocompatible. Examples of such solvents include, but are not limited to, N-methyl-2-pyrrolidone, 2-pyrrolidone, C2 to C6 alkanols, C1 to C15 alchohols, dils, triols, and tetraols such as ethanol, glycerine propylene glycol, butanol; C3 to C15 alkyl ketones such as acetone, diethyl ketone and methyl ethyl ketone; C3 to C15 esters such as methyl acetate, ethyl acetate, ethyl lactate; alkyl ketones such as methyl ethyl ketone, C1 to C15 amides such as dimethylformamide, dimethylacetamide and caprolactam; C3 to C20 ethers such as tetrahydrofuran, or solketal; tweens, triacetin, propylene carbonate, decylmethylsulfoxide, dimethyl sulfoxide, oleic acid, 1-dodecylazacycloheptan-2-one, one, Other preferred solvents are benzyl alchohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of the solvating ability and their compatibility.

Additionally, formulations comprising Neutrokine-alpha and/or Neutrokine-alphaSV compositions and a biodegradable polymer may also include release-rate modification agents and/or pore-forming agents. Examples of release-rate modification agents include, but are not limited to, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as C.sub.6-C.sub.12 alkanols, 2-ethoxyethanol, and the like. The release rate modification agent may be used singly or in combination with other such agents. Suitable combinations of release rate modification agents include, but are not limited to, glycerin/propylene glycol, sorbitol/glycerine, ethylene oxide/propylene oxide, butylene glycol/adipic acid, and the like. Preferred release rate modification agents include, but are not limited to, dimethyl citrate, triethyl citrate, ethyl heptanoate, glycerin, and hexanediol. Suitable pore-forming agents that may be used in the polymer composition include, but are not limited to, sugars such as sucrose and dextrose, salts such as sodium chloride and sodium carbonate, polymers such as hydroxylpropylcellulose, carboxymethylcellulose, polyethylene glycol, and polyvinylpyrrolidone. Solid crystals that will provide a defined pore size, such as salt or sugar, are preferred.

In specific preferred embodiments the Neutrokine-alpha and/or Neutrokine-alphaSV compositions of the invention are formulated using the BEMA™ BioErodible Mucoadhesive System, MCA™ MucoCutaneous Absorption System, SMP™ Solvent MicroParticle System, or BCP™ BioCompatible Polymer System of Atrix Laboratories, Inc. (Fort Collins, Colo.).

Sustained-release compositions also include liposomally entrapped compositions of the invention (see generally, Langer, Science 249:1527-1533 (1990); Treat et al., in Liposomes in the Therapy of Infectious Disease and Cancer, Lopez-Berestein and Fidler (eds.), Liss, N.Y., pp. 317-327 and 353-365 (1989)). Liposomes containing Neutrokine-alpha and/or Neutrokine-alphaSV polypeptide my be prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal Neutrokine-alpha and/or Neutrokine-alphaSV polypeptide therapy.

In another embodiment systained release compositions of the invention include crystal formulations known in the art.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527-1533 (1990)).

For parenteral administration, in one embodiment, the Neutrokine-alpha and/or Neutrohdne-alphaSV polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the Neutrokine-alpha and/or Neutrokine-alphaSV polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, sucrose, or dextrins; chelating agents such as EDTA; sugar alcohols such as mannitol or sorbitol; counterions such as sodium; preservatives, such as cresol, phenol, chlorobutanol, benzyl alcohol and parabens, and/or nonionic surfactants such as polysorbates, poloxamers, or PEG.

The Neutrokine-alpha and/or Neutrokine-alphaSV polypeptide is typically formulated in such vehicles at a concentration of about 0.001 mg/ml to 100 mg/ml, or 0.1 mg/ml to 100 mg/ml, preferably 1-10 mg/ml or 1-10 mg/ml, at a pH of about 3 to 10, or 3 to 8, more preferably 5-8, most preferably 6-7. It will be understood that the use of certain of the foregoing excipients, carriers, or stabilizers will result in the formation of Neutrokine-alpha and/or Neutrokine-alphaSV polypeptide salts.

Neutrokine-alpha and/or Neutrokine-alphaSV polypeptide to be used for therapeutic administration must be sterile. Sterility is readily accomplished by filtration through sterile filtration membranes (e.g., 0.2 micron membranes). Therapeutic Neutrokine-alpha and/or Neutrokine-alphaSV polypeptide compositions generally are placed into a container having a sterile access port, for example, an intravenous solution bag or vial having a stopper pierceable by a hypodermic injection needle.

Neutrokine-alpha and/or Neutrokine-alphaSV polypeptide ordinarily will be stored in unit or multi-dose containers, for example, sealed ampoules or vials, as an aqueous solution or as a lyophilized formulation for reconstitution. As an example of a lyophilized formulation, 10-mi vials are filled with 5 ml of sterile-filtered 1% (w/v) aqueous Neutrokine-alpha and/or Neutrokine-alphaSV polypeptide solution, and the resulting mixture is lyophilized. The infusion solution is prepared by reconstituting the lyophilized Neutrokine-alpha and/or Neutrokine-alphaSV polypeptide using bacteriostatic Water-for-Injection.

Alternatively, Neutrokine-alpha and/or Neutrokine-alphaSV polypeptide is stored in single dose containers in lyophilized form. The infusion selection is reconstituted using a sterile carrier for injection.

In specific embodiments, a composition of the invention is a radiolabelled form of Neutrokine-alpha. A composition of the invention may comprise Neutrokine-alpha and/or Neutrokine-alphaSV polypeptide that is radiolabeled, for example, with radioactive isotopes of iodine. Compositions comprising iodinated forms of Neutrokine-alpha and/or Neutrokine-alphaSV polypeptides or fragments or variants thereof, may also comprise radioprotectants and plasma expanders such as sodium ascorbate, gentran40, and glycerol. In specific embodiments, compositions of the invention comprising iodinated forms of Neutrokine-alpha and/or Neutrokine-alphaSV polypeptides or fragments or variants are formulated in 10.0 mM sodium citrate, 140.0 mM sodium chloride, 8.7 mM HEPES, 4% (w/v) sodium ascorbate, 3.3% (w/v) Genetran40. The above described compositions may be used as pharmaceutical compositions.

In specific embodiments, a composition of the invention comprises, at least 1 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition of the invention comprises, at least 2 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition of the invention comprises, at least 3 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition of the invention comprises, at least 4 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In particular embodiments, a composition of the invention comprises, about 4.6 mg/mL of an iodinated form of amino acid residues 134-285 of SEQ ID NO:2, 10.0 mM sodium citrate, 140.0 mM sodium sodium chloride, 8.7 mM HEPES, 4% (w/v) sodium ascorbate, 3.3% (w/v) Gentran-40. The above described compositions may be used as pharmaceutical compositions.

In specific embodiments, a composition of the invention comprises, about between 0.1 mg/mL and 20 mg/mL of an iodinated form of amino acid residues 134-285 of SEQ ID NO:2, 10.0 mM sodium citrate, 140.0 mM sodium chloride, 8.7 mM HEPES, 4% (w/v) sodium sodium ascorbate, 3.3% (w/v) Gentran-40. In specific embodiments, a composition of the invention comprises, between 1 mg/mL and 10 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition of the invention comprises, between 2 mg/mL and 8 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition of the invention comprises, between 3 mg/mL and 6 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. The above described compositions may be used as pharmaceutical compositions.

In other embodiments, a composition of the invention is an anti-neutrokine alpha antibody. In other embodiments, a composition of the invention is an antibody that specifically binds Neutrokine-alpha. In other embodiments, a composition of the invention is an antagonistic anti-neutrokine-alpha antibody. In other embodiments, a composition of the invention is an antibody that specifically binds Neutrokine-alpha and neutralizes neutrokine-alpha biological activity. In other embodiments, a composition of the invention is an anti-neutrokine-alpha antibody that binds a recombinant Neutrokine-alpha protein purified from a cell culture wherein said recombinant Neutrokine-alpha protein is encoded by a polynucleotide encoding at least amino acids 134 to 285 of SEQ ID NO:2. In other embodiments, a composition of the invention is an antibody that specifically binds Neutrokine-alpha wherein said antibody binds a recombinant Neutrokine-alpha protein purified from a cell culture wherein said recombinant Neutrokine-alpha protein is encoded by a polynucleotide encoding at least amino acids 134 to 285 of SEQ ID NO:2.

The invention also provides a pharmaceutical pack or kit comprising one or more containers filled with one or more of the ingredients of the pharmaceutical compositions of the invention. Optionally, associated with such container(s) is a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In a specific embodiment, compositions of the invention (e.g., Neutrokine-alpha and/or Neutrokine-alphaSV polypeptides of the invention, Neutrokine-alpha and/or Neutrokine-alphaSV fragments and variants, and anti-Neutokine-alpha and/or anti-Netrokine-alphaSV antibodies) may be administered to patients as vaccine adjuvants. In a further specific embodiment, compositions of the invention may be administered as vaccine adjuvants to patients suffering from an immune-deficiency. In a further specific embodiment, compositions of the invention may be administered as vaccine adjuvants to patients suffering from HIV.

In a specific embodiment, compositions of the invention may be used to increase or enhance antigen-specific antibody responses to standard and experimental vaccines. In a specific embodiment, compositions of the invention may be used to enhance seroconversion in patients treated with standard and experimental vaccines. In another specific embodiment, compositions of the invention may be used to increase the number of unique epitopes recognized by antibodies elicited by standard and experimental vaccination.

In another specific embodiment, compositions of the invention are used in combination with PNEUMOVAX-23™ to treat, prevent, and/or diagnose infection and/or any disease, disorder, and/or condition associated therewith. In one embodiment, compositions of the invention are used in combination with PNEUMOVAX-23™ to treat, prevent, and/or diagnose any Gram positive bacterial infection and/or any disease, disorder, and/or condition associated therewith. In another embodiment, compositions of the invention are used in combination with PNEUMOVAX-23™ to treat, prevent, and/or diagnose infection and/or any disease, disorder, and/or condition associated with one or more members of the genus *Enterococcus* and/or the genus *Streptococcus*. In another embodiment, compositions of the invention are used in any combination with PNEUMOVAX-23™ to treat, prevent, and/or diagnose infection and/or any disease, disorder, and/or condition associated with one or more members of the Group B streptococci. In another embodiment, compositions of the invention are used in combination with PNEUMOVAX-23™ to treat, prevent, and/or diagnose infection and/or any disease, disorder, and/or condition associated with *Streptococcus pneumoniae.*

The compositions of the invention may be administered alone or in combination with other therapeutic agents, including but not limited to, chemotherapeutic agents, antibiotics, antivirals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II (International Publication No. WO 97/34911), APRIL (J. Exp. Med. 188(6):1185-1190), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12.

In another embodiment, the compositions of the invention are invention are administered in combination with Neutrokine-alpha receptors and/or Neurtokine-alpha SV receptors (e.g., TACI, BCMA and BAFF-R) In preferred in embodiments the Neutrokine-alpha receptors and/or Neurtokine-alpha SV receptors are soluble. In other preferred embodiments the Neutrokine-alpha receptors and/or Neurtokine-alpha SV receptors are fused to the FC region of an immunoglobulin molecule (e.g, amino acid residues 1-154 of TACI (GenBank accesion number AAC51790), amino acids 1-48 of BCMA (GenBank accession number NP_001183 or amino acids 1 to 81 of BAFF-R (GenBank Acession Number NP_443177) fused to the Fc region of an IgG molecule) fused to the Fc region of an IgG molecule.

In a preferred embodiment, the compositions of the invention are administered in combination with CD40 ligand (CD40L), a soluble form of CD40L (e.g., AVREND™), biologically active fragments, variants, or derivatives of CD40L, anti-CD40L antibodies (e.g,. agonistic or antagonistic antibodies), and/or anti-CD40 antibodies (e.g, agonistic or antagonistic antibodies).

In an additional embodiment, the compositions of the invention are administered alone or in combination with an anti-angiogenic agent(s). Anti-angiogenic agents that may be administered with the compositions of the invention include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter “d group” transition metals.

Lighter “d group” transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloffet al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate (“GST”; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or “CCA”; (Takeuchi et al., Agents Actions 36:312-316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. Brem and J. Folkman J Pediatr. Surg. 28:445-51 (1993)); an integrin alpha v beta 3 antagonist (C. Storgard et al., J Clin. Invest. 103:47-54 (1999)); carboxynaminolmidazole; Carboxyamidotriazol (CAI) (National Cancer Institute, Bethesda, Md.); Conbretastatin A-4 (CA4P) (OXiGENE, Boston, Mass.); Squalamine (Magainin Pharmaceuticals, Plymouth Meeting, Pa.); TNP-470, (Tap Pharmaceuticals, Deerfield, Ill.); ZD-0101 AstraZeneca (London, UK); APRA (CT2584); Benefin, Byrostatin-1 (SC339555); CGP-41251 (PKC 412); CM101; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3340) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the compositions of the invention may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the compositions of the invention include, but are not limited to, AG-3340 (Agouron, La Jolla, Calif., BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aeterna, St-Foy, Quebec). Examples of anti-angiogenic inhibitors that act by blocking the function of endothelial cell-extracellular matrix adhesion molecules and which may be administered in combination with the compositions of the invention include, but are not limited to, EMD-121974 (Merck KcgaA Darmstadt, Germany) and Vitaxin (Ixsys, La Jolla, Calif./Medimmune, Gaithersburg, Md.). Examples of anti-angiogenic agents that act by directly antagonizing or inhibiting angiogenesis inducers and which may be administered in combination with the compositions of the invention include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with the compositions of the invention include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In particular embodiments, the use of compositions of the invention in combination with anti-angiogenic agents is contemplated for the treatment, prevention, and/or amelioration of an autoimmune disease, such as for example, an autoimmune disease described herein.

In a particular embodiment, the use of compositions of the invention in combination with anti-angiogenic agents is contemplated for the treatment, prevention, and/or amelioration of arthritis. In a more particular embodiment, the use compositions of the invention in combination with anti-angiogenic agents is contemplated for the treatment, prevention, and/or amelioration of rheumatoid arthritis.

In particular embodiments, the use of compositions of the invention in combination with anti-angiogenic agents is contemplated for the treatment, prevention, and/or amelioration of strokes.

In another embodiment, compositions of the invention are administered in combination with an anticoagulant. Anticoagulants that may be administered with the compositions of the invention include, but are not limited to, heparin, warfarin, and aspirin. In a specific embodiment, compositions of the invention are administered in combination with heparin and/or warfarin. In another specific embodiment, compositions of the invention are administered in combination with warfarin. In another specific embodiment, compositions of the invention are administered in combination with warfarin and aspirin. In another specific embodiment, compositions of the invention are administered in combination with heparin. In another specific embodiment, compositions of the invention are administered in combination with heparin and aspirin.

In another embodiment, compositions of the invention are administered in combination with an agent that suppresses the production of anticardiolipin antibodies. In specific embodiments, the polynucleotides of the invention are administered in combination with an agent that blocks and/or reduces the ability of anticardiolipin antibodies to bind phospholipid-binding plasma protein beta 2-glycoprotein I (b2GPI).

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat, prevent, and/or diagnose AIDS and/or to treat, prevent, and/or diagnose HIV infection.

In certain embodiments, compositions of the invention are administered in combination with antiretroviral agents, nucleoside/nucleotide reverse transcriptase inhibitors (NRTIs), non-nucleoside reverse transcriptase inhibitors (NNRTIs), and/or protease inhibitors (PIs). NRTIs that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). NNRTIs that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

Additional NRTIs include LODENOSINE™ (F-ddA; an acid-stable adenosine NRTI; Triangle/Abbott; COVIRACIL™ (emtricitabine/FTC; structurally related to lamivudine (3TC) but with 3- to 10-fold greater activity in vitro; Triangle/Abbott); dOTC (BCH-10652, also structurally related to lamivudine but retains activity against a substantial proportion of lamivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/Abbott); D-D4FC (related to 3TC, with activity against AZT/3TC-resistant virus); GW420867X (Glaxo Wellcome); ZIAGEN™ (abacavir/159U89; Glaxo Wellcome Inc.); CS-87 (3'azido-2',3'-dideoxyuridine; WO 99/66936); and S-acyl-2-thioethyl (SATE)-bearing prodrug forms of β-L-FD4C and β-L-FddC (WO 98/17281).

Additional NNRTIs include COACTINON™ (Emivirine/MKC-442, potent NNRTI of the HEPT class; Triangle/Abbott); CAPRAVIRINE™ (AG-1549/S-1153, a next generation NNRTI with activity against viruses containing the K103N mutation; Agouron); PNU-142721 (has 20- to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW-420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; Abbott Laboratories); BMS-232632 (an azapeptide; Bristol-Myres Squibb); TIPRANAVIR™ (PNU-140690, a non-peptic dihydropyrone; Pharmacia & Upjohn); PD-178390 (a nonpeptidic dihydropyrone; Parke-Davis); BMS 232632 (an azapeptide; Bristol-Myers Squibb); L-756,423 (an indinavir analog; Merck); DMP-450 (a cyclic urea compound; Avid & DuPont); AG-1776 (a peptidomimetic with in vitro activity against protease inhibitor-resistant viruses; Agouron); VX-175/GW-433908 (phosphate prodrug of amprenavir; Vertex & Glaxo Welcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643-678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX40-4C (a cationic peptide), T22 (an 18 amino acid peptide; Trimeris) and the T22 analogs T134 and T140; CCR5 antagonists such as RANTES (9-68), AOP-RANTES, NNY-RANTES, and TAK-779; and CCR5/CXCR4 antagonists such as NSC 651016 (a distamycin analog). Also included are CCR2B, CCR3, and CCR6 antagonists. Chemokine receptor agonists such as RANTES, SDF-1, MIP-1α, MIP-1β, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compounds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors sucha as VX-497 (Vertex); and myvopholic acids such as CellCept (mycophenolate mofetil; Roche).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1α, MIP-1β, SDF-1α, IL-2, PROLEUKIN™ (aldesleukin/L2-7001; Chiron), IL-4, IL-8, IL-10, IL-12, and IL-13; interferons such as IFN-α2a; antagonists of TNFs, NFκB, GM-CSF, M-CSF, and IL-10; agents that modulate immnune activation such as cyclosporin and prednisone; vaccines such as Remune™ (HIV Immunogen), APL 400-003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targetted to the ER to block surface expression of newly synthesized CCR5 (Yang et al., PNAS 94:11567-72 (1997); Chen et al., Nat. Med. 3:1110-16 (1997)); antibodies such as the anti-CXCR4 antibody 12G5, the anti-CCR5 antibodies 2D7, 5C7, PA8, PA9, PA10, PA11, PA12, and PA14, the anti-CD4 antibodies Q4120 and RPA-T4, the anti-CCR3 antibody 7B11, the anti-gp120 antibodies 17b, 48d, 447-52D, 257-D, 268-D and 50.1, anti-Tat antibodies, anti-TNF-α antibodies, and monoclonal antibody 33A; aryl hydrocarbon (AH) receptor agonists and antagonists such as TCDD, 3,3',4,4',5-pentachlorobiphenyl, 3,3',4,4'-tetrachlorobiphenyl, and α-naphthoflavone (WO 98/30213); and antioxidants such as γ-L-glutamyl-L-cysteine ethyl ester (γ-GCE; WO 99/56764).

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNE™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic Pneumocystis carinii pneumonia infection. In another specific embodiment, compositions of the invention are used in any combination with ISONIAZID™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, compositions of the invention are used in any combination with LEUCOVORIN™ and/or NEUPO- GEN™ to prophylactically treat, prevent, and/or diagnose an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam(glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells. Other immunosuppressive agents, that may be administered in combination with the compositions of the invention include, but are not limited to, prednisolone, methotrexate, thalidomide, methoxsalen, rapamycin, leflunomide, mizoribine (BREDININ™), brequinar, deoxyspergualin, and azaspirane (SKF 105685).

In specific embodiments, compositions of the invention are administered in combination with immunosuppressants. Immunosuppressant preparations that may be administered with the compositions of the invention include, but are not limited to, ORTHOCLONE OKT® 3 (muromonab-CD3), SANDIMMUNE™, NEORAL™, SANGDYA™ (cyclosporine), PROGRAF® (FK506, tacrolimus), CELLCEPT® (mycophenolate motefil, of which the active metabolite is mycophenolic acid), IMURAN™ (azathioprine), glucorticosteroids, adrenocortical steroids such as DELTASONE™ (prednisone) and HYDELTRASOL™ (prednisolone), FOLEX™ and MEXATE™ (methotrexate), OXSORALEN-ULTRA™ (methoxsalen) and RAPAMUNE™ (sirolimus). In a specific embodiment, immunosuppressants may be used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine.

In a preferred embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasennin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In one embodiment, the compositions of the invention are administered in combination with one or more of the following drugs: Infliximab (also known as Remicade™ Centocor, Inc.), Trocade (Roche, RO-32-3555), Leflunomide (also known as Arava™ from Hoechst Marion Roussel), Kineret™ (an IL-1 Receptor antagonist also known as Anakinra from Amgen, Inc.), SCIO-469 (p38 kinase inhibitor from Scios, Inc), Humira® (adalimumab from Abbott Laboratories) and/or ASLERA™ (prasterone, dehydroepiandrosterone, GL701) from Genelabs Technologies Inc.

In a preferred embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, LJP 394 (La Jolla Pharmaceutical Company, San Diego, Calif.), and prednisolone.

In a more preferred embodiment, the compositions of the invention are administered in combination with an antimalarial, methotrexate, anti-TNF antibody, ENBREL™ and/or suflasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another specific embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, and sulfasalazine. In other embodiments, one or more antimalarials is combined with one of the above-recited combinations. In a speefic embodiment, the compositions of the invention are administered in combination with an antimalarial (e.g., hydroxychloroquine), ENBREL™, methotrexate and sulfasalazine. In another specfic embodiment, the compositions of the invention are administered in combination with an antimalarial (e.g., hydroxychloroquine), sulfasalazine, anti-TNF antibody, and methotrexate.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In specific embodiments, the compositions of the invention are administered alone or in combination with anti-CD4 antibody. In one embodiment, coadministration of the compositions of the invention with anti-CD4 antibody is envisoned for treatment of rheumatoid arthritis.

In specific embodiments, the compositions of the invention are administered alone or in combination with anti-IL-15 antibody. In one embodiment, coadministration of the compositions of the invention with anti-IL-15 antibody is envisoned for treatment of rheumatoid arthritis.

In specific embodiments, the compositions of the invention are administered alone or in combination with CTLA4-Ig and LEA29Y. In one embodiment, coadministration of the compositions of the invention with CTLA4-Ig and LEA29Y is envisoned for treatment of rheumatoid arthritis.

In specific embodiments, the compositions of the invention are administered alone or in combination with anti-IL-6 Receptor antibody. In one embodiment, coadministration of the compositions of the invention with anti-IL-6 Receptor antibody is envisoned for treatment of rheumatoid arthritis.

In specific embodiments, the compositions of the invention are administered alone or in combination with anti-C5 (complement component) antibody. In one embodiment, coadministration of the compositions of the invention with anti-C5 antibody is envisoned for treatment of rheumatoid arthritis.

In specific embodiments, the compositions of the invention are administered alone or in combination with complement cascade inhibitors. Complement cascade inhibitors include, but are notl imited to, anti-properdin antibodies (Gliatech); TP-10, a recombinant soluble type I complement receptor (AVANT Immunotheragenetics Inc.); Pexelizmab, a Complement C5 inhibitor (Alexion Phamiaceuticals Inc.); and 5G1.1, a monoclonal antibody that prevents cleavage of complement component C5 into its pro-inflammatory components. In one embodiment, coadministration of the compositions of the invention with complement cascade inhibitors are is envisoned for treatment of Inflammation, Rheumatoid arthritis, and/or cardiovascular disorders.

In another embodiment, compostions of the invention are administered in combination with a chemotherapeutic agent Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or combination of one or more of the components of CHOP. In one embodiment, the compositions of the invention are administered in combination with anti-CD20 antibodies, human monoclonal anti-CD20 antibodies. In another embodiment, the compositions of the invention are administered in combination with anti-CD20 antibodies and CHOP, or anti-CD20 antibodies and any combination of one or more of the components of CHOP, particularly cyclophosphamide and/or prednisone. In a specific embodiment, compositions of the invention are administered in combination with Rituximab. In a further embodiment, compositions of the invention are administered with Rituximab and CHOP, or Rituximab and any combination of one or more of the components of CHOP, particularly cyclophosphamide and/or prednisone. In a specific embodiment, compositions of the invention are administered in combination with tositumomab (anti-CD20 antibody from Coulter Pharmaceuticals, San Francisco, Calif.). In a further embodiment, compositions of the invention are administered with tositumomab and CHOP, or tositumomab and any combination of one or more of the components of CHOP, particularly cyclophosphamide and/or prednisone. Tositumomab may optionally be associated with 131I. The anti-CD20 antibodies may optionally be associated with radioisotopes, toxins or cytotoxic prodrugs.

In another specific embodiment, the compositions of the invention are administered in combination Zevalin™. In a further embodiment, compositions of the invention are administered with Zevalin™ and CHOP, or Zevalin™ and any combination of one or more of the components of CHOP, particularly cyclophosphamide and/or prednisone. Zevalin™ may be associated with one or more radisotopes. Particularly preferred isotopes are $^{90}$Y and $^{111}$In.

In additional preferred embodiments, compositions of the invention are administered in combination with Rituximab (Rituxan™) and/or Ibritumomab Tiuxetan (Zevalin™, e.g., either (In-111) Ibritumomab Tiuxetan or (Y-90) Ibritumomab Tiuxetan). In a specific embodiment, compositions of the invention are administered in combination with Rituximab and/or Ibritumomab Tiuxetan for the treatment of non-Hodgkin's lymphoma.

In additional preferred embodiments, compositions of the invention are administered in combination with imatinib mesylate (Gleevec®: 4-[(4-Methyl-1-piperazinyl)methyl]-N-[4-methyl-3-[[4-(3-pyridinyl)-2-pyrimidinyl]amino]-phenyl]benzamide methanesulfonate). In a specific embodiment, compositions of the invention are administered in combination with imatinib mesylate for the treatment of chronic myelogenous leukemia.

In additional preferred embodiments, compositions of the invention are administered in combination with bortezomib (Velcade™ [(1R)-3-methyl-1-[[(2S)-1-oxo-3-phenyl-2-[(pyrazinylcarbonyl)amino]propyl]amino]butyl]boronic acid). In a specific embodiment, compositions of the invention are administered in combination with bortezomib for the treatment of multiple myeloma.

In additional preferred embodiments, compositions of the invention are administered in combination with Alemtuzumab (Campath®). In a specific embodiment, compositions of the invention are administered in combination with Alemtuzumab for the treatment of chronic lymphocytic leukemia.

In additional preferred embodiments, compositions of the invention are administered in combination with fludarabine phosphate (Fludara®: 9H-Purin-6-amine, 2-fluoro-9-(5-O-phosphono-□-D-arabinofuranosyl)(2-fluoro-ara-AMP)). In a specific embodiment, compositions of the invention are administered in combination with fludarabine phosphate for the treatment of chronic lymphocytic leukemia.

In further particular embodiments, compositions of the present invention are used to treat, ameliorate and/or prevent hematological cancers. Compositions of the present invention may be used in combination with one or more surgical and/or radiological procedures and/or therapeutic agents to treat, ameliorate and/or prevent hematological cancers. Hematological cancers which may be treated using compositions of the present invention include, but are not limited to, non-Hodgkin's lymphoma (e.g., small lymphocytic lymphoma, follicular center cell lymphoma, lymphoplasmacytoid lymphoma, marginal zone lymphoma, mantle cell lymphoma, immunoblastic lymphoma, burkitt's lymphoma, lymphoblastic lymphoma, peripheral T-cell lymphoma, anaplastic large cell lymphoma and intestinal T-cell lymphoma), leukemia, acute lymphocytic leukemia, chronic lymphocytic leukemia and plasma cell neoplasms including multiple myeloma.

In preferred embodiments, compositions of the present invention (e.g. Neutrokine-alpha polypeptides in association with toxins or cytotoxic prodrugs) are used to treat, ameliorate and/or prevent hematological cancers. compositions of the present invention (e.g. Neutrokine-alpha polypeptides in association with toxins or cytotoxic prodrugs) may be used in combination with one or more surgical and/or radiological procedures and/or therapeutic agents to treat, ameliorate and/or prevent hematological cancers. Hematological cancers which may be treated using compositions of the present invention include, but are not limited to, non-Hodgkin's lymphoma (e.g., small lymphocytic lymphoma, follicular center cell lymphoma, lymphoplasmacytoid lymphoma, marginal zone lymphoma, mantle cell lymphoma, immunoblastic lymphoma, burkin's lymphoma, lymphoblastic lymphoma, peripheral T-cell lymphoma, anaplastic large cell lymphoma and intestinal T-cell lymphoma), leukemia, acute lymphocytic leukemia, chronic lymphocytic leukemia and plasma cell neoplasms including multiple myeloma.

In one preferred embodiment, compositions of the present invention (e.g. Neutrokine-alpha polypeptides in association with toxins or cytotoxic prodrugs) are used to treat plasma cell neoplasms. In a specific embodiment, that plasma cell neoplasm is multiple myeloma.

In another preferred embodiment, compositions of the present invention (e.g. Neutrokine-alpha polypeptides in association with toxins or cytotoxic prodrugs) are used to treat non-Hodgkin's lymphoma.

In another preferred embodiment, compositions of the present invention (e.g. Neutrokine-alpha polypeptides in association with toxins or cytotoxic prodrugs) are used to treat leukemia. In a specific embodiment, that leukemia is acute lymphocytic leukemia. In another specific embodiment, that leukemia is chronic lymphocytic leukemia.

compositions of the present invention (e.g. Neutrokine-alpha polypeptides in association with toxins or cytotoxic prodrugs) may be administered in combination with one or more surgical and/or radiological procedures useful in the treatment of hematological cancer including, but not limited to, bone marrow transplantation, external beam radiation and total body irradiation.

In preferred embodiments, compositions of the present invention (e.g. Neutrokine-alpha polypeptides in association with toxins or cytotoxic prodrugs) are administered in combination with one or more surgical and/or radiological procedures useful in the treatment of hematological cancer including, but not limited to, bone marrow transplantation, external beam radiation and total body irradiation.

In one preferred embodiment, compositions of the present invention (e.g. Neutrokine-alpha polypeptides in association with toxins or cytotoxic prodrugs) may be administered in combination with one or more surgical and/or radiological procedures useful in the treatment of multiple myeloma including, but not limited to, allogeneic bone marrow transplantation and peripheral stem cell support.

In another preferred embodiment, compositions of the present invention (e.g. Neutrokine-alpha polypeptides in association with toxins or cytotoxic prodrugs) may be administered in combination with one or more surgical and/or radiological procedures useful in the treatment of non-Hodgkin's lymphoma including, but not limited to, allogeneic bone marrow transplantation and peripheral stem cell support.

In further specific embodiments, compositions of the present invention (e.g. Neutrokine-alpha polypeptides in association with toxins or cytotoxic prodrugs) may be administered in combination with one or more surgical and/or radiological procedures useful in the treatment of leukemia including, but not limited to, allogeneic bone marrow transplantation and peripheral stem cell support. In one specific preferred embodiment, compositions of the present invention (e.g. Neutrokine-alpha polypeptides in association with toxins or cytotoxic prodrugs) of the invention are used to treat acute lymphocytic leukemia (ALL). In another specific preferred embodiment, compositions of the present invention (e.g. Neutrokine-alpha polypeptides in association with toxins or cytotoxic prodrugs) are used to treat chronic lymphocytic leukemia (CLL).

Compositions of the present invention may be administered in combination with one or more therapeutic agents useful in the treatment of multiple mycloma including, but not limited to, Alkylating agents, Anthracyclines, Carmustine (DTI-015, BCNU, BiCNU, Gliadel Wafer®), Cyclophosphamide (Cytoxan®, Neosar®, CTX), Dexamethasone (Decadron®), Doxorubicin (Adriamycin®, Doxil®, Rubex®), Melphalan (L-PAM, Alkeran®, Phenylalanine mustard), Prednisone, Thalidomide and Vincristine (Oncovorin®, Onco TCS®, VCR, Leurocristine®).

In preferred embodiments, compositions of the present invention (e.g. Neutrokine-alpha polypeptides in association with toxins or cytotoxic prodrugs) are administered in combination with one or more of the above-described therapeutic agents in the treatment, amelioration and/or prevention of multiple myeloma.

Preferred combinations of therapeutic agents useful in the treatment of multiple myeloma which may be administered in combination with compositions of the present invention include, but are not limited to, Cyclophosphamide+Prednisone, Melphalan+Prednisone (MP), Vincristine+Adriamycin®+Dexamethasone (VAD), Vincristine+Carmustine+Melphalan+Cyclophosphamide+Prednisone (VBMCP; the M2 protocol), and Vincristine+Melphalan+Cyclophosphamide+Prednisone alternating with Vincristine+Carmustine+Doxorubicin+Prednisone (VMCPNVBAP).

In preferred embodiments, compositions of the present invention (e.g. Neutrokine-alpha polypeptides in association with toxins or cytotoxic prodrugs) are administered in combination with one or more of the above-described therapeutic agent combinations in the treatment, amelioration and/or prevention of multiple myeloma.

Compositions of the present invention may be administered in combination with one or more therapeutic agents useful in the treatment of non-Hodgkin's lymphoma including, but not limited to, 2- chlorodeoxyadenosine, Amifostine (Ethyol®, Ethiofos®, WR-272), Bexarotene (Targretin®, Targretin gel®, Targretin oral®, LGD1069), Bleomycin (Blenoxane®), Busulfan (Busulfex®, Myleran®), Carboplatin (Paraplatin®, CBDCA), Carnustine (DTI-015, BCNU, BiCNU, Gliadel Wafer®), Chlorambucil (Leukeran®), Cisplatin (Platinol®, CDDP), Cladribine (2-CdA, Leustatin®), Cyclophosphamide (Cytoxan®, Neosar®CTX), Cytarabine (Cytosar-U®, ara-C, cytosine arabinoside, DepoCyt®), Dacarbazine (DTIC), Daunorubicin (Daunomycin, DaunoXome®, Daunorubicin®, Cerubidine®), Denileukin diflitox (Ontak®), Dexamethasone (Decadron®), Dolasetron mesylate (Anzemet®), Doxorubicin (Adriamycin®, Doxil®, Rubex®), Erythropoietin (EPO®, Epogen®, Procrit®), Etoposide phosphate (Etopophos®), Etoposide (VP-16, Vepesid®), Fludarabine (Fludara®, FAMP), Granisetron (Kytril®), Hydrocortisone, Idarubicin (Idamycin®, DMDR, IDA), Ifosfamide (IFEX®), Interferon alpha (Alfaferone®, Alpha-IF®), Interferon alpha 2a (Intron A®), Mechlorethamine (Nitrogen Mustard, $HN_2$, Mustargen®), Melphalan (L-PAM, Alkeran®, Phenylalanine mustard), Methotrexate® (MTX, Mexate®, Folex®), Methylprednisolone (Solumedrol®), Mitoxantrone (Novantrone®, DHAD), Ondansetron (Zofran®), Pentostatin (Nipent®, 2-deoxycoformycin), Perfosfamide (4-hydroperoxycyclophosphamide, 4-HC), Prednisone, Procarbazine (Matulane®), Rituximab® (Rituxan®, anti-CD20 MAb), Thiotepa (triethylenethiophosphaoramide, Thioplex®), Topotecan (Hycamtin®, SK&F-104864, NSC-609699, Evotopin®), Vinblastine (Velban®, VLB), Vincristine (Oncovin®, Onco TCS®, VCR, Leurocristine®) and Vindesine (Eldisine®, Fildesin®).

In preferred embodiments, compositions of the present invention (e.g. Neutrokine-alpha polypeptides in association with toxins or cytotoxic prodrugs) are administered in combination with one or more of the above-described therapeutic agents in the treatment, amelioration and/or prevention of non-Hodgkin's lymphoma.

Preferred combinations of therapeutic agents useful in the treatment of non-Hodgkin's lymphoma which may be administered in combination with compositions of the present invention include, but are not limited to, Adriamycin®+Blenoxane+Vinblastine+Dacarbazine (ABVD), Anti-idiotype therapy (BsAb)+Interferon alpha, Anti-idiotype therapy (BsAb)+Chlorambucil, Anti-idiotype therapy (BsAb)+Interleukin-2, BCNU (Carmustine)+Etoposide+Ara-C (Cytarabine)+Melphalen (BEAM), Bleomycin+Etoposide+Adriamycin+Cyclophosphamide+Vincristine+Procarbazine+Prednisone (BEACOPP), Bryostatin+Vincristine, Cyclophosphamide+BCNU (Carmustine)+VP-16 (Etoposide) (CBV), Cyclophosphamide+Vincristine+Prednisone (CVP), Cyclophosphamide+Adriamycin® (Hydroxyldaunomycin)+Vincristine (Oncovorin)+Prednisone (CHOP), Cyclophosphamide+Novantrone® (Mitoxantrone)+Vincristine (Oncovorin)+Prednisone (CNOP), Cyclophosphamide+Doxorubicin+Teniposide+Prednisone, Cyclophosphamide+Adriamycin® (Hydroxyldaunomycin)+Vincristine (Oncovorin)+Prednisone+Rituximab (CHOP+Rituximab), Cyclophosphamide+Doxorubicin+Teniposide+Prednisone+Interferon alpha, Cytarabine+Bleomycin+Vincristine+Methotrexate (CytaBOM), Dexamethasone+Cytarabine+Cisplatin (DHAP), Dexamethasone+Ifosfamide+Cisplatin+Etoposide (DICE), Doxorubicin+Vinblastine+Mechlorethamine+Vincristine+Bleomycin+Etoposide+Prednisone (Stanford V), Etoposide+Vinblastine+Adriamycin (EVA), Etoposide+Methylprednisone+Cytarabine+Cisplatin (ESHAP), Etoposide+Prednisone+Ifosfamide+Cisplatin (EPIC), Fludarabine, Mitoxantrone+Dexamethasone (FMD), Fludarabine, Dexamethasone, Cytarabine (ara-C), +Cisplatin (Platinol®) (FluDAP), Ifosfamide+Cisplatin+Etoposide (ICE), Mechlorethamine+Oncovin® (Vincristine)+Procarbazine+Prednisone (MOPP), Mesna+Ifosfamide+Idarubicin+Etoposide (MIZE), Methotrexate with leucovorin rescue+Bleomycin+Adriamycin+Cyclophosphamide+Oncovorin+Dexamethasone (m-BACOD), Prednisone+Methotrexate+Adriamycin+Cyclophosphamide+Etoposide (ProMACE), Thiotepa+Busulfan+Cyclophosphamide, Thiotepa+Busulfan+Melphalan, Topotecan+Paclitaxel, and Vincristine (Oncovin®)+Adriamycin®+Dexamethasone (VAD).

In preferred embodiments, compositions of the present invention (e.g. Neutrokine-alpha polypeptides in association with toxins or cytotoxic prodrugs) are administered in combination with one or more of the above-described therapeutic agent combinations in the treatment, amelioration and/or prevention of non-Hodgkin's lymphoma.

Further examples of therapeutic agents useful in the treatment of non-Hodgkin's lymphoma which may be administered in combination with compositions of the present invention include, but are not limited to, A007 (4-4'-dihydroxybenzophenone-2,4-dinitrophenylhydrazone), AG-2034 (AG-2024, AG-2032, GARFT [glycinamide ribonucleoside transformylase] inhibitor), Aldesleukin (IL-2, Proleukin®), Alemtuzumab (Campath®), Alitretinoin (Panretin®, LGN-1057), Altretamine (Hexalen®, hexamethylmelamine, Hexastat®), Aminocamptothecin (9-AC, 9-Aminocamptothecin, NSC 603071), Anti-CD19/CD3 MAb (anti-CD19/CD3 scFv, anti-NHL MAb), Anti-idiotype therapy (BsAb), Arabinosylguanine (Ara-G, GW506U78), Arsenic trioxide (Trisenox®, ATO), B43-Genistein (anti-CD19 Ab/genistein conjugate), B7 antibody conjugates, Betathine (Beta-LT), BLyS antagonists, Bryostatin-1 (Bryostatin®, BMY-45618, NSC-339555), CHML (Cytotropic Heterogeneous Molecular Lipids), Clofarabine (chlorofluoro-araA), Daclizumab (Zenapax®), Depsipeptide (FR901228, FK228), Dolastatin-10 (DOLA-10, NSC-376128), Epirubicin (Ellence®, EPI, 4' epi-doxorubicin), Epratuzumab (Lymphocide®, humanized anti-CD22, HAT), Fly3/flk2 ligand (Mobista®), G3139 (Genasense®, GentaAnticode®, Bcl-2 antisense), Hu1D10 (anti-HLA-DR MAb, SMART 1D10), HumaLYM (anti-CD20 MAb), Ibritumomab tiuxetan (Zevalin®), Interferon gamma (Gamma-interferon, Gamma 100®, Gamma-IF), Irinotecan (Camptosar®, CPT-11, Topotecin®, CaptoCPT-1), ISIS-2053, ISIS-3521 (PKC-alpha antisense), Lmb-2 inmmunotoxin (anti-CD25 recombinant immuno toxin, anti-Tac(Fv)-PE38), Leuvectin® (cytofectin+IL-2 gene, IL-2 gene therapy), Lym-1 (131-I LYM-1), Lymphoma vaccine (Genitope), Nelarabine (Compound 506, U78), Neugene compounds (Oncomyc-NG®, Resten-NG®, myc antisense), NovoMAb-G2 scFv (NovoMAb-G2 IgM), O6-benzylguanine (BG, Procept®), Oxaliplatin (Eloxatine®, Eloxatin®), Paclitaxel (Paxene®, Taxol®), Paclitaxel-DHA (Taxoprexin®), Peldesine (BCX-34, PNP inhibitor), Rebeccamycin and Rebeccamycin analogues, SCH-66336, Sobuzoxane (MST-16, Perazolin®), SU5416 (Semaxanib®, VEGF inhibitor), TER-286, Thalidomide, TNP-470 (AGM-1470), Tositumomab (Bexxar®), Valspodar (PSC 833), Vaxid (B-cell lymphoma DNA vaccine), Vinorelbine (Navelbine®), WF10 (macrophage regulator) and XR-9576 (XR-9351, P-glycoprotein/MDR inhibitor).

In preferred embodiments, compositions of the present invention (e.g. Neutrokine-alpha polypeptides in association with toxins or cytotoxic prodrugs) are administered in combination with one or more of the above-described therapeutic agents in the treatment, amelioration and/or prevention of non-Hodgkin's lymphoma.

Compositions of the present invention may be administered in combination with one or more therapeutic agents useful in the treatment of acute lymphocytic leukemia including, but not limited to, Amsacrine, Carboplatin (Paraplatin®, CBDCA), Carmustine (DTI-015, BCNU, BiCNU, Gliadel Wafer®), Cholecaliferol, Cyclophosphamide (Cytoxan®, Neosar®, CTX), Cytarabine (Cytosar-U®, ara-C, cytosine arabinoside, DepoCyt®), Daunorubicin (Daunomycin, DaunoXome®, Daunorubicin®, Cerubidine®), Dexamethasone (Decadron®), Doxorubicin (Adriamycin®, Doxil®, Rubex®), Etoposide (VP-16, Vepesid®), Filgrastam® (Neupogen®, G-CSF, Leukine®), Fludarabine (Fludara®, FAMP), Idarubicin (Idamycin®, DMDR, IDA), Ifosfamide (IFEX®), Imatinib mesylate (STI-571, Imatinib®, Glivec®, Gleevec®, Ab1 tyrosine kinase inhibitor), Interferon gamma (Gamma-interferon, Gamma 100®, Gamma-1F), L-asparaginase (Elspar®, Crastinin®, Asparaginase medac®, Kidrolase®), Mercaptopurine (6-mercaptopurine, 6-MP), Methotrexate® (MTX, Mexate®, Folex®), Mitoxantrone (Novantrone®, DHAD), Pegaspargase® (Oncospar®), Prednisone, Retinoic acid, Teniposide (VM-26, Vumon®), Thioguanine (6-thioguanine, 6-TG), Topotecan (Hycamtin®, SK&F-104864, NSC-609699, Evotopin®), Tretinoin (Retin-A®), Atragen®, ATRA, Vesanoid®) and Vincristine (Oncovorin®, Onco TCS®, VCR, Leurocristine®).

In preferred embodiments, compositions of the present invention (e.g. Neutrokine-alpha polypeptides in association with toxins or cytotoxic prodrugs) are administered in combination with one or more of the above-described therapeutic agents in the treatment, amelioration and/or prevention of acute lymphocytic leukemia.

Further examples of therapeutic agents useful in the treatment of acute lymphocytic leukemia which may be administered in combination with compositions of the present invention include, but are not limited to, Aminocamptothecin (9-AC, 9-Aminocamptothecin, NSC 603071), Aminopterin, Annamycin (AR-522, annamycin LF, Aronex®), Arabinosylguanine (Ara-G, GW506U78, Nelzarabine®), Arsenic trioxide (Trisenox®, ATO, Atrivex®), B43-Genistein (anti-CD19 Ab/genistein conjugate B43-PAP (anti-CD19 Ab/pokeweed antiviral protein conjugate), Cordycepin, CS-682, Decitabine (5-aza-2'-deoxyytidine), Dolastin-10 (DOLA-10, NSC-376128), G3139 (Genasense®, GentaAnticode®, Bcl-2 antisense), Irofulven (MGI-114, Ivofulvan, Acylfulvene analogue), MS-209, Phenylbutyrate, Quinine, TNP-470 (AGM-1470, Fumagillin), Trimetrexate (Neutrexin®), Troxacitabine (BCH-204, BCH-4556, Troxatyl®), UCN-01 (7-hydroxystaurosporine), WHI-P131 and WT1 Vaccine.

In preferred embodiments, compositions of the present invention (e.g. Neutrokine-alpha polypeptides in association with toxins or cytotoxic prodrugs) are administered in combination with one or more of the above-described therapeutic agents in the treatment, amelioration and/or prevention of acute lymphocytic leukemia.

Preferred combinations of therapeutic agents useful in the treatment of acute lymphocytic leukemia which may be administered in combination with compositions of the present invention include, but are not limited to, Carboplatin+Mitoxantrone, Carmustine+Cyclophosphamide+Etoposide, Cytarabine+Daunorubicin, Cytarabine+Doxorubicin, Cytarabine+Idarubicin, Cytarabine+Interferon gamma, Cytarabine+L-asparaginase, Cytarabine+Mitoxantrone, Cytarabine+Fludarabine and Mitoxantrone, Etoposide+Cytarabine, Etoposide+Ifosfamide, Etoposide+Mitoxantrone, Ifosfamide+Etoposide+Mitoxantrone, Ifosfamide+Teniposide, Methotrexate+Mercaptopurine, Methotrexate+Mercaptopurine+Vincristine+Prednisone, Phenylbutyrate+Cytarabine Phenylbutyrate+Etoposide, Phenylbutyrate+Topotecan, Phenylbutyrate+Tretinoin, Quinine+Doxorubicin, Quinine+Mitoxantron+Cytarabine, Thioguanine+Cytarabine+Amsacrine, Thioguanine+Etoposide+Idarubicin, Thioguanine+Retinoic acid+Cholecaliferol, Vincnistine+Prednisone, Vincristine+Prednisone and L-asparaginase, Vincristine+Dexamethasone/Prednisone+Asparaginase+Daunorubicin/Doxorubicin, Vincristine+Dexamethasone/Prednisone+Asparaginase+Daunorubicin/Doxorubicin+Filgrastim, Vincristine+Dexamethasone/Prednisone+Asparaginase+Daunorubicin/Doxorubicin+Cyclophosphamide+Methotrexate, and Vincristine+Dexamethasone/Prednisone+Asparaginase+Daunorubicin/Doxorubicin+Cyclophosphamide+Methotrexate+Filgrastim.

In preferred embodiments, compositions of the present invention (e.g. Neutrokine-alpha polypeptides in association with toxins or cytotoxic prodrugs) are administered in combination with one or more of the above-described therapeutic agent combinations in the treatment, amelioration and/or prevention of acute lymphocytic leukemia.

Compositions of the present invention may be administered in combination with one or more therapeutic agents useful in the treatment of chronic lymphocytic leukemia including, but not limited to, Chlorambucil (Leukeran®), Cladribine (2-CdA, Leustatin®), Cyclophosphamide (Cytoxan®, Neosar®, CTX), Cytarabine (Cytosar-U®, ara-C, cytosine arabinoside, DepoCyt®, cytarabine ocfosfate, ara-CMP), Doxorubicin (Adriamycin®, Doxil®, Rubex®), Fludarabine (Fludara®, FAMP), Pentostatin (Nipent®, 2-deoxycoformycin), Prednisone and Vincristine (Oncovorin®, Onco TCS®, VCR, Leurocristine®).

In preferred embodiments, compositions of the present invention (e.g. Neutrokine-alpha polypeptides in association with toxins or cytotoxic prodrugs) are administered in combination with one or more of the above-described therapeutic agents in the treatment, amelioration and/or prevention of chronic lymphocytic leukemia.

Further examples of therapeutic agents useful in the treatment of chronic lymphocytic leukemia which may be administered in combination with compositions of the present invention include, but are not limited to, Alemtuzumab (Campath®), Aminocamptothecin (9-AC, 9-Aminocamptothecin, NSC 603071), Aminopterin, Annamycin (AR-522, annamycin LF, Aronex®), Arabinosylguanine (Ara-G, GW506U78, Nelzarabine®, Compound 506U78), Arsenic trioxide (Trisenox®), ATO, Atrivex®), Bryostatin-1 (Bryostatin®, BMY-45618, NSC-339555), CS-682, Dolastatin-10 (DOLA-10, NSC-376128), Filgrastim (Neupogen®, G-CSF, Leukine), Flavopiridol (NSC-649890, HMR-1275), G3139 (Genasense®, GentaAnticode®, Bcl-2 antisense), Irofulven (MGI-114, Ivofulvan, Acylfulvene analogue), MS-209, Phenylbutyrate, Rituximab® (Rituxan®, anti-CD20 MAb), Thalidomide, Theophylline, TNP-470 (AGM-1470, Fumagillin), UCN-01 (7-hydroxystaurosporine) and WHI-P131.

In preferred embodiments, compositions of the present invention (e.g. Neutrokine-alpha polypeptides in association with toxins or cytotoxic prodrugs) are administered in combination with one or more of the above-described therapeutic agents in the treatment, amelioration and/or prevention of chronic lymphocytic leukemia.

Preferred combinations of therapeutic agents useful in the treatment of chronic lymphocytic leukemia which may be administered in combination with compositions of the present invention include, but are not limited to, Fludarabine+Prednisone, and Cyclophosphamide+Doxorubicin+Vincristine+Prednisone (CHOP).

In preferred embodiments, compositions of the present invention (e.g. Neutrokine-alpha polypeptides in association with toxins or cytotoxic prodrugs) are administered in combination with one or more of the above-described therapeutic agent combinations in the treatment, amelioration and/or prevention of chronic lymphocytic leukemia.

In an additional embodiment, the compositions of the invention are administered in combination with cytokines. Cytokines that may be administered with the compositions of the invention include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In another embodiment, compositions of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, the compositions of the invention are administered in combination with IL4 and IL10. Both IL4 and IL10 have been observed by the inventors to enhance Neutrokine-alpha mediated B cell proliferation.

In vitro, IFN gamma and IL-10 have each been observed by the inventors to enhance cell surface expression of Neutrokine-alpha in monocytes and macrophages (macrophages were obtained by culturing primary monocytes with 20 ng/mL of M-CSF for 12-15 days), whereas IL-4 treatment decreased cell surface expression of Neutrokine-alpha in monocytes and macrophages. IL-4 administered with IL-10 resulted in a complete inhibition of the IL-10 induced cell surface expression of Neutrokine-alpha. IL-4 administered with IFN-gamma resulted in increased cell-surface expression of Neutrokine-alpha. Treatment of macrophages with IFN-gamma and IL-10 resulted in a 3 fold increase of soluble (active) Neutrokine-alpha released into the culture medium compared to untreated macrophages.

In an additional embodiment, the compositions of the invention are administered with a chemokine. In another embodiment, the compositions of the invention are administered with chemokine beta-8, chemokine beta-1, and/or macrophage inflammatory protein-4. In a preferred embodiment, the compositions of the invention are administered with chemokine beta-8.

In an additional embodiment, the compositions of the invention are administered in combination with an IL-4 antagonist. IL-4 antagonists that may be administered with the compositions of the invention include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-ILA antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, the compositions of the invention are administered in combination with hematopoietic growth factors. Hematopoietic growth factors that may be administered with the compositions of the invention include, but are not limited to, LEUKINE™ (SARGRAMOSTIM™) and NEUPOGEN™ (FILGRASTIM™).

In an additional embodiment, the compositions of the invention are administered in combination with fibroblast growth factors. Fibroblast growth factors that may be administered with the compositions of the invention include, but are not limited to, FGF-1, FGF-2, FGF-3, FGF4, FGF-5, FGF-6, FGF-7, FGF-8, FGF-9, FGF-10, FGF-11, FGF-12, FGF-13, FGF-14, FGF-15.

Additionally, the compositions of the invention may be administered alone or in combination with other therapeutic regimens, including but not limited to, radiation therapy. Such combinatorial therapy may be administered sequentially and/or concomitantly.

Agonists and Antagonists—Assays and Molecules

The invention also provides a method of screening compounds to identify those which enhance or block the action of Neutrokine-alpha and/or Neutrokine-alphaSV polypeptide on cells, such as its interaction with Neutrokine-alpha and/or Neutrokine-alphaSV binding molecules such as receptor molecules. An agonist is a compound which increases the natural biological functions of Neutrokine-alpha and/or Neutrokine-alphaSV or which functions in a manner similar to Neutrokine-alpha and/or Neutrokine-alphaSV while antagonists decrease or eliminate such functions.

In another embodiment, the invention provides a method for identifying a receptor protein or other ligand-binding protein which binds specifically to a Neutrokine-alpha and/or Neutrokine-alphaSV polypeptide. For example, a cellular compartment, such as a membrane or a preparation thereof, may be prepared from a cell that expresses a molecule that binds Neutrokine-alpha and/or Neutrokine-alphaSV. The preparation is incubated with labeled Neutrokine-alpha and/or Neutrokine-alphaSV and complexes of Neutrokine-alpha and/or Neutrokine-alphaSV bound to the receptor or other binding protein are isolated and characterized according to routine methods known in the art. Alternatively, the Neutrokine-alpha and/or Neutrokine-alphaSV polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds Neutrokine-alpha and/or Neutrokine-alphaSV such as a molecule of a signaling or regulatory pathway modulated by Neutrokine-alpha and/or Neutrokine-alphaSV. The preparation is incubated with labeled Neutrokine-alpha and/or Neutrokine-alphaSV in the absence or the presence of a candidate molecule which may be a Neutrokine-alpha and/or Neutrokine-alphaSV agonist or antagonist. The ability of the candidate molecule to bind the binding molecule is reflected in decreased binding of the labeled ligand. Molecules which bind gratuitously, i.e., without inducing the effects of Neutrokine-alpha on binding the Neutrokine-alpha and/or Neutrokine-alphaSV binding molecule, are most likely to be good antagonists. Molecules that bind well and elicit effects that are the same as or closely related to Neutrokine-alpha and/or Neutrokine-alphaSV are agonists.

Neutrokine-alpha- and/or Neutrokine-alphaSV-like effects of potential agonists and antagonists may by measured, for instance, by determining activity of a second messenger system following interaction of the candidate molecule with a cell or appropriate cell preparation, and comparing the effect with that of Neutrokine-alpha and/or Neutrokine-alphaSV or molecules that elicit the same effects as Neutrokine-alpha and/or Neutrokine-alphaSV. Second messenger systems that may be useful in this regard include but are not limited to AMP guanylate cyclase, ion channel or phosphoinositide hydrolysis second messenger systems.

Another example of an assay for Neutrokine-alpha and/or Neutrokine-alphaSV antagonists is a competitive assay that combines Neutrokine-alpha and/or Neutrokine-alphaSV and a potential antagonist with membrane-bound receptor molecules or recombinant Neutrokine-alpha and/or Neutrokine-alphaSV receptor molecules under appropriate conditions for a competitive inhibition assay. Neutrokine-alpha and/or Neutrokine-alphaSV can be labeled, such as by radioactivity, such that the number of Neutrokine-alpha and/or Neutrokine-alphaSV molecules bound to a receptor molecule can be determined accurately to assess the effectiveness of the potential antagonist.

Potential antagonists include small organic molecules, peptides, polypeptides (e.g., IL-13), and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing Neutrokine-alpha and/or Neutrokine-alphaSV induced activities, thereby preventing the action of Neutrokine-alpha and/or Neutrokine-alphaSV by excluding Neutrokine-alpha and/or Neutrokine-alphaSV from binding.

Other potential antagonists include antisense molecules. Antisense technology can be used to control gene expression through antisense DNA or RNA or through triple-helix formation. Antisense techniques are discussed, for example, in Okano, J. Neurochem. 56: 560 (1991); Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the extracellular domain of the polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of Neutrokine-alpha and/or Neutrokine-alphaSV. The antisense RNA oligonucleotide hybridizes to the mRNA in vivo and blocks translation of the mRNA molecule into Neutrokine-alpha and/or Neutrokine-alphaSV polypeptide. The oligonucleotides described above can also be delivered to cells such that the antisense RNA or DNA may be expressed in vivo to inhibit production of Neutrokine-alpha and/or Neutrokine-alphaSV.

In one embodiment, the Neutrokine-alpha and/or Neutrokine-alphaSV antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the Neutrokine-alpha and/or Neutrokine-alphaSV antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding Neutrokine-alpha and/or Neutrokine-alphaSV, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304-310 (1981), the promoter contained in the 3' long terminal repeat of Rous sarcoma virus (Yamamoto et al., Cell 22:787-797 (1980), the herpes thymidine promoter (Wagner et al., Proc. Natl. Acad. Sci. U.S.A. 78:1441-1445 (1981), the regulatory sequences of the metallothionein gene (Brinster, et al., Nature 296:3942 (1982)), etc.

The antisense nucleic acids of the invention comprise a sequence complementary to at least a portion of an RNA transcript of a Neutrokine-alpha and/or Neutrokine-alphaSV gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded Neutrokine-alpha and/or Neutrokine-alphaSV antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a Neutrokine-alpha and/or Neutrokine-alphaSV RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-

335. Thus, oligonucleotides complementary to either the 5'- or 3'-non- translated, non-coding regions of non-Neutrokine-alpha and Neutrokine-alphaSV shown in FIGS. 1A-B and 5A-B, respectively, could be used in an antisense approach to inhibit translation of endogenous Neutrokine-alpha and/or Neutrokine-alphaSV mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of Neutrokine-alpha and/or Neutrokine-alphaSV mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., Proc. Natl. Acad. Sci. 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., BioTechniques 6:958-976 (1988)) or intercalating agents. (See, e.g., Zon, Pharm. Res. 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al., Nucl. Acids Res. 15:6625-6641 (1987)). The oligonucleotide is a 2-0-methylribonucleotide (Inoue et al., Nucl. Acids Res. 15:6131-6148 (1987)), or a chimeric RNA-DNA analogue (Inoue et al., FEBS Lett. 215:327-330 (1997)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448-7451 (1988)), etc.

While antisense nucleotides complementary to the Neutrokine-alpha and/or Neutrokine-alphaSV coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222-1225 (1990). While ribozymes that cleave mRNA at site specific recognition sequences can be used to destroy Neutrokine-alpha and/or Neutrokine-alphaSV mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of Neutrokine-alpha and Neutrokine-alphaSV (FIGS. 1A-B and 5A-B, respectively). Preferably, the ribozyme is engineered so that the cleavage recognition site is located near the 5' end of the Neutrokine-alpha and/or Neutrokine-alphaSV mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express Neutrokine-alpha and/or Neutrokine-alphaSV in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous Neutrokine-alpha and/or Neutrokine-alphaSV messages and inhibit translation. Since ribozymes unlike antisense molecules, are catalytic, a lower intracellular concentration is required for efficiency.

Endogenous gene expression can also be reduced by inactivating or "knocking out" the Neutrokine-alpha and/or Neutrokine-alphaSV gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In other embodiments, antagonists according to the present invention include soluble forms of Neutrokine-alpha and/or Neutrokine-alphaSV (e.g., fragments of Neutrokine-alpha shown in FIGS. 1A-B that include the ligand binding domain, TNF conserved domain, and/or extracellular domain of Neutrokine-alpha and/or Neutrokine-alphaSV and fragments of Neutrokine-alphaSV shown in FIGS. 5A-B that include the ligand binding domain, TNF conserved domain, and/or extracellular domain of Neutrokine-alpha and/or Neutrokine-alphaSV). Such soluble forms of the Neutrokine-alpha and/or Neutrokine-alphaSV, which may be naturally occurring or synthetic, antagonize Neutrokine-alpha and/or Neutrokine-alphaSV mediated signaling by competing with native Neutrokine-alpha and/or Neutrokine-alphaSV for binding to Neutrokine-alpha and/or Neutrokine-alphaSV receptors (e.g., DR5 (See, International Publication No. WO 98/41629), TR10 (See, International Publication No. WO 98/54202), 312C2 (See, International Publication No. WO 98/06842), and TR11, TR11SV1, and TR11SV2 (See, U.S. application Ser. No. 09/176,200)), and/or by forming a multimer that may or may not be capable of binding the receptor, but which is incapable of inducing signal transduction. Preferably, these antagonists inhibit Neutrokine-alpha and/or Neutrokine-alphaSV mediated stimulation of lymphocyte (e.g., B-cell) proliferation, differentiation, and/or activation. Antagonists of the present invention also include antibodies specific for TNF-family ligands (e.g., CD30) and Neutrokine-alpha-Fc and/or Neutrokine-alphaSV-Fc fusion proteins.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-alpha, lymphotoxin-alpha (LT-alpha, also known as TNF-beta), LT-beta (found in complex heterotrimer LT-alpha2-beta), FasL, CD40L, (TNF-gamma (International Publication No. WO 96/14328), AIM-I (International Publication No. WO 97/33899), AIM-II (International Publication No. WO 97/34911), APRIL (J. Exp. Med. 188(6):1185-1190), endokine-alpha (International Publication No. WO 98/07880), neutrokine-alpha (International Publication No. WO 98/18921), CD27L, CD30L, 4-IBBL, OX40L, CD27, CD30, 4-1BB, OX40, and nerve growth factor (NGF). In preferred embodiments, the Neutrokine-alpha and/or Neutrokine-alphaSV TNF-family ligands of the invention are DR5 (See, International Publication No. WO 98/41629), TR10 (See, International Publication No. WO 98/54202), 312C2 (See, International Publication No. WO 98/06842), and TR11, TR11SV1, and TR11SV2 (See, U.S. application Ser. No. 09/176,200).

Antagonists of the present invention also include antibodies specific for TNF-family receptors or the Neutrokine-alpha and/or Neutrokine-alphaSV polypeptides of the invention. Antibodies according to the present invention may be prepared by any of a variety of standard methods using Neutrokine-alpha and/or Neutrokine-alphaSV immunogens of the present invention. As indicated, such Neutrokine-alpha and/or Neutrokine-alphaSV immunogens include the complete Neutrokine-alpha and Neutrokine-alphaSV polypeptides depicted in FIGS. 1A-B (SEQ ID NO:2) and FIGS. 5A-B (SEQ ID NO:19), respectively, (which may or may not include the leader sequence) and Neutrokine-alpha and/or Neutrokine-alphaSV polypeptide fragments comprising, for example, the ligand binding domain, TNF-conserved domain, extracellular domain, transmembrane domain, and/or intracellular domain, or any combination thereof.

Polyclonal and monoclonal antibody agonists or antagonists according to the present invention can be raised according to the methods disclosed in Tartaglia and Goeddel, J. Biol. Chem. 267(7):43044307(1992)); Tartaglia et al., Cell 73:213-216 (1993)), and PCT Application WO 94/09137 and are preferably specific to (i.e., bind uniquely to polypeptides of the invention having the amino acid sequence of SEQ ID NO:2. The term "antibod" (Ab) or "monoclonal antibody" (mAb) as used herein is meant to include intact molecules as well as fragments thereof (such as, for example, Fab and F(ab') fragments) which are capable of binding an antigen. Fab, Fab' and F(ab') fragments lack the Fc fragment intact antibody, clear more rapidly from the circulation, and may have less non-specific tissue binding of an intact antibody (Wahl et al., J. Nucl. Med., 24:316-325 (1983)).

In a preferred method, antibodies according to the present invention are mabs. Such mAbs can be prepared using hybridoma technology (Kohler and Millstein, Nature 256:495-497 (1975) and U.S. Pat. No. 4,376,110; Harlow et al., Antibodies: A Laboratory Manual, Cold Spring Harbor Laboratory Press, Cold Spring Harbor, N.Y., 1988; Monoclonal Antibodies and Hybridomas: A New Dimension in Biological Analyses, Plenum Press, New York, N.Y., 1980; Campbell, "Monoclonal Antibody Technology," In: Laboratory Techniques in Biochemistry and Molecular Biology, Volume 13 (Burdon et al., eds.), Elsevier, Amsterdam (1984)).

Proteins and other compounds which bind the Neutrokine-alpha and/or Neutrokine-alphaSV domains are also candidate agonists and antagonists according to the present invention. Such binding compounds can be "captured" using the yeast two-hybrid system (Fields and Song, Nature 340:245-246 (1989)). A modified version of the yeast two-hybrid system has been described by Brent and his colleagues (Gyuris, Cell 75:791-803 (1993); Zervos et al., Cell 72:223-232 (1993)). Preferably, the yeast two-hybrid system is used according to the present invention to capture compounds which bind to the ligand binding domain, extracellular, intracellular, transmembrane, and death domain of the Neutrokine-alpha and/or Neutrokine-alphaSV. Such compounds are good candidate agonists and antagonists of the present invention.

For example, using the two-hybrid assay described above, the extracellular or intracellular domain of the Neutrokine-alpha and/or Neutrokine-alphaSV receptor, or a portion thereof, may be used to identify cellular proteins which interact with Neutrokine-alpha and/or Neutrokine-alphaSV the receptor in vivo. Such an assay may also be used to identify ligands with potential agonistic or antagonistic activity of Neutrokine-alpha and/or Neutrokine-alphaSV receptor function. This screening assay has previously been used to identify protein which interact with the cytoplasmic domain of the murine TNF-RII and led to the identification of two receptor associated proteins. Rothe et al., Cell 78:681 (1994). Such proteins and amino acid sequences which bind to the cytoplasmic domain of the Neutrokine-alpha and/or Neutrokine-alphaSV receptors are good candidate agonist and antagonist of the present invention.

Other screening techniques include the use of cells which express the polypeptide of the present invention (for example, transfected CHO cells) in a system which measures extracellular pH changes caused by receptor activation, for example, as described in Science, 246:181-296 (1989). In another example, potential agonists or antagonists may be contacted with a cell which expresses the polypeptide of the present invention and a second messenger response, e.g., signal transduction may be measured to determine whether the potential antagonist or agonist is effective.

Agonists according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and—amyloid peptide. (Science 267:1457-1458 (1995)).

Preferred agonists are fragments of Neutrokine-alpha and/or Neutrokine-alphaSV polypeptides of the invention which stimulate lymphocyte (e.g., B cell) proliferation, differentiation and/or activation. Further preferred agonists include polyclonal and monoclonal antibodies raised against the Neutrokine-alpha and/or Neutrokine-alphaSV polypeptides of the invention, or a fragment thereof. Such agonist antibodies raised against a TNF-family receptor are disclosed in Tartaglia et al., Proc. Natl. Acad. Sci. USA 88:9292-9296(1991); and Tartaglia et al., J. Biol. Chem. 267:4304-4307(1992). See, also, PCT Application WO 94/09137.

In an additional embodiment, immunoregulatory molecules such as, for example, IL2, IL3, ILA, IL5, IL6, IL7, IL10, IL12, IL13, IL15, anti-CD40, CD40L, IFN-gamma and TNF-alpha, may be used as agonists of Neutrokine-alpha and/or Neutrokine-alphaSV polypeptides of the invention which stimulate lymphocyte (e.g., B cell) proliferation, differentiation and/or activation. In a specific embodiment, IL4 and/or IL10 are used to enhance the Neutrokine-alpha- and/or Neutrokine-alphaSV-mediated proliferation of B cells.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

In yet another embodiment of the invention, the activity of Neutrokine-alpha and/or Neutrokine-alphaSV polypeptide can be reduced using a “dominant negative.” To this end, constructs which encode defective Neutrokine-alpha and/or Neutrokine-alphaSV polypeptide, such as, for example, mutants lacking all or a portion of the TNF-conserved domain, can be used in gene therapy approaches to diminish the activity of Neutrokine-alpha and/or Neutrokine-alphaSV on appropriate target cells. For example, nucleotide sequences that direct host cell expression of Neutrokine-alpha and/or Neutrokine-alphaSV polypeptide in which all or a portion of the TNF-conserved domain is altered or missing can be introduced into monocytic cells or other cells or tissues (either by in vivo or ex vivo gene therapy methods described herein or otherwise known in the art). Alternatively, targeted homologous recombination can be utilized to introduce such deletions or mutations into the subject's endogenous Neutrokine-alpha and/or Neutrokine-alphaSV gene in monocytes. The engineered cells will express non-functional Neutrokine-alpha and/or Neutrokine-alphaSV polypeptides (i.e., a ligand (e.g., multimer) that may be capable of binding, but which is incapable of inducing signal transduction).

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA and/or polynucleotides herein disclosed is used to clone genomic DNA of a Neutrokine-alpha and/or Neutrokine-alphaSV gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., Human Chromosomes: A Manual Of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance In Man, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Utilizing the techniques described above, the chromosomal location of Neutrokine-alpha and Neutrokine-alphaSV was determined with high confidence using a combination of somatic cell hybrids and radiation hybrids to chromosome position 13q34.

EXAMPLES

Having generally described the invention, the same will be more readily understood by reference to the following examples, which are provided by way of illustration and are not intended as limiting. Many of the following examples are set forth referring specifically to Neutrokine-alpha polynucleotides and polypeptides of the invention. Each example may also be practiced to generate and/or examine Neutrokine-alphaSV polynucleotides and/or polypeptides of the invention. One of ordinary skill in the art would easily be able to direct the following examples to Neutrokine-alphaSV.

Example 1a

Expression and Purification of "His-tagged" Neutrokine-alpha in *E. coli*

The bacterial expression vector pQE9 (pD10) is used for bacterial expression in this example. (QIAGEN, Inc., supra). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni—NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6× His tag") covalently linked to the amino terminus of that polypeptide.

The DNA sequence encoding the desired portion of the Neutrokine-alpha protein comprising the extracellular domain sequence is amplified from the deposited cDNA clone using PCR oligonucleotide primers which anneal to the amino terminal sequences of the desired portion of the protein and to sequences in the deposited construct 3' to the cDNA coding sequence. Additional nucleotides containing restriction sites to facilitate cloning in the pQE9 vector are added to the 5' and 3' pimer sequences, respectively.

For cloning the extracellular domain of the protein, the 5' primer has the sequence 5'-GTG GGA TCC AGC CTC CGG GCA GAG CTG-3' (SEQ ID NO:10) containing the underlined Bam HI restriction site followed by 18 nucleotides of the amino terminal coding sequence of the extracellular domain of the sequence in FIGS. 1A and 1B. One of ordinary skill in the art would appreciate, of course, that the point in the protein coding sequence where the 5' primer begins may be varied to amplify a DNA segment encoding any desired portion of the complete Neutrokine a protein shorter or longer than the extracellular domain of the form. The 3' primer has the sequence 5'-GTG AAG CTT TTA TTA CAG CAG TTT CAA TGC ACC-3' (SEQ ID NO:11) containing the underlined Hind III restriction site followed by two stop codons and 18 nucleotides complementary to the 3' end of the coding sequence of the DNA sequence in FIGS. 1A and 1B.

The amplified DNA fragment and the vector pQE9 are digested with Bam HI and Hind III and the digested DNAs are then ligated together. Insertion of the DNA into the restricted pQE9 vector places the protein coding region downstream from the IPTG-inducible promoter and in-frame with an initiating AUG and the six histidine codons.

The ligation mixture is transformed into competent *E. coli* cells using standard procedures such as those described in Sambrook et al., Molecular Cloning: a Laboratory Manual, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan$^r$"), is used in carrying out the illustrative example described herein. This strain, which is only one of many that are suitable for expressing protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing. Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-beta-D-thiogalactopyranoside ("IPTG") is then added to a final concentration of 1 mM to induce transcription from the lac repressor sensitive promoter, by inactivating the lac repressor. Cells subsequently are incubated further for 3 to 4 hours. Cells then are harvested by centrifugation.

The cells are then stirred for 3-4 hours at 4° C. in 6M guanidine-HCl, pH 8. The cell debris is removed by centrifugation, and the supernatant containing the is loaded on to a nickel-nitrilo-tri-acetic acid ("Ni-NTA") affinity resin column (available from QIAGEN, Inc., supra). Proteins with a 6× His tag bind to the Ni-NTA resin with high affinity and can be purified in a simple one-step procedure (for details see:

The QIAexpressionist, 1995, QIAGEN, Inc., supra). Briefly the supernatant is loaded on to the column in 6 M guanidine-HCl, pH 8, the column is first washed with 10 volumes of 6 M guanidine-HCl, pH 8, then washed with 10 volumes of 6 M guanidine-HCl pH 6, and finally the Neutrokine-alpha and/or Neutrokine-alphaSV polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

Example 1b

Expression and Purification of Neutrokine-alpha in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6× His tag") covalently linked to the carboxyl terminus of that polypeptide However, in this example, the polypeptide coding sequence is inserted such that translation of the six His codons is prevented and, therefore, the polypeptide is produced with no 6× His tag.

The DNA sequence encoding the desired portion of the protein comprising the extracellular domain sequence is amplified from the deposited cDNA clone using PCR oligonucleotide primers which anneal to the amino terminal sequences of the desired portion of the protein and to sequences in the deposited construct 3' to the cDNA coding sequence. Additional nucleotides containing restriction sites to facilitate cloning in the pQE60 vector are added to the 5' and 3' sequences, respectively.

For cloning the extracellular domain of the protein, the 5' primer has the sequence 5'-GTG TCA TGA GCC TCC GGG CAG AGC TG-3' (SEQ ID NO:12) containing the underlined Bsp HI restriction site followed by 17 nucleotides of the amino terminal coding sequence of the extracellular domain of the sequence in FIGS. 1A and 1B. One of ordinary skill in the art would appreciate, of course, that the point in the protein coding sequence where the 5' primer begins may be varied to amplify a desired portion of the complete protein shorter or longer than the extracellular domain of the form. The 3' primer has the sequence 5'-GTG AAG CTT TTA TTA CAG CAG TTT CAA TGC ACC-3' (SEQ ID NO:13) containing the underlined Hind III restriction site followed by two stop codons and 18 nucleotides complementary to the 3' end of the coding sequence in the DNA sequence in FIGS. 1A and 1B.

The amplified DNA fragments and the vector pQE60 are digested with Bsp HI and Hind III and the digested DNAs are then ligated together. Insertion of the DNA into the restricted pQE60 vector places the protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., Molecular Cloning: a Laboratory Manual, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

One of ordinary skill in the art recognizes that any of a number of bacterial expression vectors may be useful in place of pQE9 and pQE60 in the expression protocols presented in this example. For example, the novel pHE4 series of bacterial expression vectors, in particular, the pHE4-5 vector may be used for bacterial expression in this example (ATCC Accession No. 209311; and variations thereof). The plasmid DNA designated pHE4-5/MPIFD23 in ATCC Deposit No. 209311 is vector plasmid DNA which contains an insert which encodes another ORF. The construct was deposited with the American Type Culture Collection, 10801 University Boulevard, Manassas, Va. 20110-2209, on Sep. 30, 1997. Using the Nde I and Asp 718 restriction sites flanking the irrelevant MPIF ORF insert, one of ordinary skill in the art could easily use current molecular biological techniques to replace the irrelevant ORF in the pHE4-5 vector with the Neutrokine-alpha ORF of the present invention.

The pHE4-5 bacterial expression vector includes a neomycin phosphotransferase gene for selection, an *E. coli* origin of replication, a T5 phage promoter sequence, two lac operator sequences, a Shine-Delgarno sequence, and the lactose operon repressor gene (lacIq). These elements are arranged such that an inserted DNA fragment encoding a polypeptide expresses that polypeptide with the six His residues (i.e., a "6× His tag") covalently linked to the amino terminus of that polypeptide. The promoter and operator sequences of the pHE4-5 vector were made synthetically. Synthetic production of nucleic acid sequences is well known in the art (CLONETECH 95/96 Catalog, pages 215-216, CLONETECH, 1020 East Meadow Circle, Palo Alto, Calif. 94303).

Clones containing the desired Neutrokine-alpha constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6 isopropyl-beta-D-thiogalactopyranoside ("IPTG") is then added to a final concentration of 1 mM to induce transcription from the lac repressor sensitive promoter, by inactivating the lad repressor. Cells subsequently are incubated further for 3 to 4 hours. Cells then are harvested by centrifugation.

The cells are then stirred for 3-4 hours at 4° C. in 6M guanidine-HCl, pH 8. The cell debris is removed by centrifugation, and the supernatant containing the Neutrokine a is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure protein. The purified protein is stored at 4° C. or frozen at −80° C.

In certain embodiments, it is preferred to generate expression constructs as detailed in this Example to mutate one or more of the three cysteine residues in the Neutrokine-alpha polypeptide sequence. The cysteine residues in the Neutrokine-alpha polypeptide sequence are located at positions 147, 232, and 245 as shown in SEQ ID NO:2 and at positions 213 and 226 of the Neutrokine-alpha polypeptide sequence as shown in SEQ ID NO:19 (there is no cysteine in the Neutrokine-alphaSV polypeptide sequence which corresponds to Cys-147 in the Neutrokine-alpha polypeptide sequence because amino acid residues 143-160 of the Neutrokine-alpha polypeptide sequence are not present in the Neutrokine-alphaSV polypeptide sequence).

Example 2

Cloning, Expression, and Purification of Neutrokine-alpha Protein in a Baculovirus Expression System In this illustrative example, the plasmid shuttle vector pA2GP is used to insert the cloned DNA encoding the extracellular domain of the protein, lacking its naturally associated intracellular and transmembrane sequences, into a baculovirus to express the extracellular domain of the Neutrokine-alpha protein, using a baculovirus leader and standard methods as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the *Autographa califonica* nuclear polyhedrosis virus (AcMNPV) followed by the secretory signal peptide (leader) of the baculovirus gp67 protein and convenient restriction sites such as Bam HI, Xba I and Asp 718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

The cDNA sequence encoding an N-terminally deleted form of the extracellular domain of the Neutrokine-alpha protein in the deposited clone, lacking the AUG initiation codon, the naturally associated intracellular and transmembrane domain sequences, and amino acids Gln-73 through Leu-79 shown in FIGS. 1A and 1B (SEQ ID NO:2), is amplified using PCR oligonucleotide primers corresponding to the 5' and 3' sequences of the gene. The 5' primer has the sequence 5'-GTG GGA TCC CCG GGC AGA GCT GCA GGG C-3' (SEQ ID NO:14) containing the underlined Bam HI restriction enzyme site followed by 18 nucleotides of the sequence of the extracellular domain of the Neutrokine-alpha protein shown in FIGS. 1A and 1B, beginning with the indicated N-terminus of the extracellular domain of the protein. The 3' primer has the sequence 5'-GTG GGA TCC TTA TTA CAG CAG TTT CAA TGC ACC-3' (SEQ ID NO:15) containing the underlined Bam HI restriction site followed by two stop codons and 18 nucleotides complementary to the 3' coding sequence in FIGS. 1A and 1B.

In certain other embodiments, constructs designed to express the entire predicted extracellular domain of the Neutrokine-alpha (i.e., amino acid residues Gln-73 through Leu-285) are preferred. One of skill in the art would be able to use the polynucleotide and polypeptide sequences provided as SEQ ID NO:1 and SEQ ID NO:2, respectively, to design polynucleotide primers to generate such a clone.

In a further preferred embodiment, a pA2GP expression construct encodes amino acid residues Leu-112 through Leu-285 of the Neutrokine-alpha polypeptide sequence shown as SEQ ID NO:2.

In another preferred embodiment, a pA2GP expression construct encodes amino acid residues Ser-78 through Leu-285 of Neutrokine-alpha polypeptide sequence shown as SEQ ID NO:2.

The amplified fragment is isolated from a 1% agarose gel using a commercially available kit ("Geneclean," BIO 101 Inc., La Jolla, Calif.). The fragment then is digested with Bam HI and again is purified on a 1% agarose gel. This fragment is designated herein F1.

The plasmid is digested with the restriction enzymes Bam HI and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human gene by digesting DNA from individual colonies using Bam HI and then analyzing the digestion product by gel electrophoresis. The sequence of the cloned fragment is confirmed by DNA sequencing. This plasmid is designated herein pA2GP-Neutrokine-alpha.

Five micrograms of the plasmid pA2GP-Neutrokine-alpha is co-transfected with 1.0 microgram of a commercially available linearized baculovirus DNA ("BaculoGold™ baculovirus DNA", Pharmingen, San Diego, Calif.), using the lipofection method described by Felgner et al., Proc. Natl. Acad. Sci. USA 84: 7413-7417 (1987). One μg of BaculoGold™ virus DNA and 5 micrograms of the plasmid pA2GP Neutrokine-alpha are mixed in a sterile well of a microtiter plate containing 50 microliters of serum-free Grace's medium (Life Technologies Inc., Gaithersburg, Md.). Afterwards, 10 microliters Lipofectin plus 90 microliters Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Rockville, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Rockville, Md., page 9-10). After appropriate incubation, blue stained plaques are picked with the tip of a micropipettor (e.g., Eppendorf). The agar containing the recombinant viruses is then resuspended in a microcentrifuge tube containing 200 microliters of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-Neutrokine-alpha.

To verify the expression of the Neutrokine-alpha gene Sf9 cells are grown in Grace's medium supplemented with 10% heat-inactivated FBS. The cells are infected with the recombinant baculovirus V-Neutrokine-alpha at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 microcuries of $^{35}$S-methionine and 5 microcuries $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the extracellular domain of the protein and thus the cleavage point and length of the secretory signal peptide.

In a specific experimental example, recombinant Neutrokine-alpha was purified from baculovirus infected Sf9 cell supernatants as follows. The insect cells were grown in EXCEL401 medium (JRH Scientific) with 1% (v/v) fetal bovine serum. At 92 hours post-infection, the harvested supernatant was clarified by centrifugation at 18,000×g followed by 0.45 m depth filtration. A de-lipid filtration step might be also used to remove the lipid contaminants and in turn to improve initial capturing of the Neutrokine-alpha protein.

The supernatant was loaded on to a set of Poros HS-50/HQ-50 in tandem mode. As alternatives, Toyopearl QAE, Toyopearl Super Q (Tosohass), Q-Sepharose (Pharmacia) and equivalent resins might be used. This step is used as a negative purification step to remove strong anion binding contaminants. The HS/HQ flow through material was adjusted to pH 7.5 with 1 M Tris-HCl pH 8, diluted with equal volume of 50 mM Tris-HCl pH 8, and loaded onto a poros PI-20 or PI-50 column. The P1 column was washed first with 4 column volumes of 75 mM sodium chloride in 50 mM Tris-HCl at pH 7.5, then eluted using 3 to 5 column volumes of a stepwise gradient of 300 mM, 750 mM, 1500 mM sodium chloride in 50 mM Tris-HCl pH 7.5. Neutrokine-alpha protein appears as a 17 KD band on reduced SDS-PAGE and is present in the 0.75 M to 1.5M Sodium chloride fractions.

The PI fraction was further purified through a Sephacryl S100 HR (Pharmacia) size exclusion column equilibrated with 0.15 M sodium chloride, 50 mM sodium acetate at pH 6. The S200 fractions were mixed with sodium chloride to a final concentration of 3 M and loaded onto a Toyopearl Hexyl 650C (Tosohass) column. The Hexyl column was eluted with a linear gradient from 3 M to 0.05 M sodium chloride in 50 mM Sodium acetate pH 6 in 5 to 15 column volumes. The sodium chloride gradient can also be replaced by ammonium sulfate gradient of 1M to 0 M in 50 mM sodium acetate pH 6 in the Hexyl chromatographic step. Fractions containing purified Neutrokine-alpha as analyzed through SDS-PAGE were combined and dialyzed against a buffer containing 150 mM Sodium chloride, 50 mM Sodium acetate, pH 6.

The final purified Neutrokine-alpha protein expressed in a baculovirus system as explained herein has an N-terminus sequence which begins with amino acid residue Ala-134 of SEQ ID NO:2. RP-HPLC analysis shows a single peak of greater than 95% purity. Endotoxin level was below the detection limit in LAL assay.

In another example, recombinant Neutrokine-alpha was purified from baculovirus infected Sf9 cell supernatants containing 0.25% bovine serum as follows.

The Sf9 supernatant was harvested by centrifugation at 18,000×g. The supernatant was then treated with 10 mM calcium chloride in slightly alkaline conditions for 10-15 minutes followed by centrifugation and then 0.22 micrometer depth filtration. The resulting Sf-9 cell supernatant was then diluted 2-fold and loaded on to a Poros P1-50 column (available from PE Biosystems). The column was equilibrated with 50 mM Tris (pH=7.4). The PI-50 column was washed with 1 CV of 50 mM Tris (pH=7.4) and then eluted with 1.5 M NaCl in 50 mM NaOAc (pH=6) over 3 CV. The PI fraction was loaded on to a Sephacryl S200 column equilibrated with 50 mM NaOAc (pH=6), 125 mM NaCl. The S200 fraction was mixed with salts to final concentrations of 0.7 M ammonium sulfate and 0.6 M NaCl and loaded on to a Toyopearl Hexyl 650C column (available from Toso Haas) that had been equilibrated in a buffer containing 0.6 M NaCl, 0.7 M ammonium sulfate in 50 mM NaOAc (pH=6). The column was then washed with 2 CV of the same buffer. Recombinant Neutrokine-alpha was then eluted stepwise with 3 CV of 50 mM NaOAc (pH=6) followed by 2 CV of 20% ethanol wash. The recombinant Neutrokine-alpha protein was then eluted at the end of the ammonium sulfate (0.3 to 0 M salt) gradient. The appropriate fractions were pooled and dialyzed against a buffer containing 50 mM NaOAc (pH=6), and then passed through a Poros 50 HQ column. The HQ flow-through was diluted to 4 ms and loaded on to a Toyopearl DEAD 650M column and then eluted with 25 mM NaCitrate, 125 mM NaCl.

In another example, recombinant Neutrokine-alpha was expressed and purified using a baculoviral vector system in Sf+ insect cells.

First, a polynucleotide encoding amino acid residues Ser-78 through Leu-285 of the Neutrokine-alpha polypeptide sequence shown in FIGS. 1A and 1B (which is exactly identical to amino acid residues Ser-78 through Leu-285 of the Neutrokine-alpha polypeptide sequence shown as SEQ ID NO:2) was subcloned into the baculovirus transfer construct PSC to generate a baculovirus expression plasmid. The pA2GP transfer vector, derived from pVL941, contains the gp67 signal peptide, a modified multiple cloning site, and the lac Z gene cloned downstream of the *Drosophila* heat-shock promoter for selection of blue plaques. Using the sequence of Neutrokine-alpha (SEQ ID NO:2) and the sequence of the pA2GP vector, a cloning strategy was designed for seamlessly fusing the PSC signal peptide coding sequence to the Neutrokine-alpha coding sequence at Ala-134 (SEQ ID NO:2 and FIGS. 1A and 1B) and inserting it into a PSC baculovirus transfer plasmid. The strategy involved the use of a two-stage polymerase chain reaction (PCR) procedure. First, primers were designed for amplifying the Neutrokine-alpha sequences. The 5' primer consisted of the sequence encoding Ala-134 and following residues (5'-GGT CGC CGT TTC TAA CGC GGC CGT TCA GGG TCC AGA AG-3'; SEQ ID NO:31), preceded by the sequence encoding the PSC signal peptide C-terminus. The 3' primer (5'-CTG GTT CGG CCC AAG GTA CCA AGC TTG TAC CTT AGA TCT TTT CTA GAT C-3'; SEQ ID NO:32) consisted of the reverse complement of the pA2GP vector sequence immediately downstream from the Neutrokine-alpha coding sequence, preceded by a Kpn I restriction endonuclease site and a spacer sequence (for increased cutting efficiency by Kpn I). PCR was performed with the pA2GP containing Neutrokine-alpha plasmid template and primers O-1887 and O-1888, and the resulting PCR product was purified using standard techniques.

An additional PCR reaction was performed using the PSC baculovirus transfer plasmid pMGS12 as a template. The pMGS12 plasmid consists of the AcNPV EcoRI "I" fragment inserted into pUC8, with the polyhedrin coding sequences after the ATG start codon replaced with the PSC signal peptide and a polylinker site. The PCR reaction used pMGS 12 as a template, a 5' primer (5'-CTG GTA GTT CTT CGG AGT GTG-3'; SEQ ID NO:33) which annealed in AcNPV ORF603 upstream of the unique NgoM IV and EcoR V sites, and a 3' primer (5'-CGC GTT AGA AAC GGC GAC C-3'; SEQ ID NO:34) which annealed to the 3' end of the sequence encoding the PSC signal peptide.

To generate a PCR product in which the PSC signal peptide was seamlessly fused to the Ala-134 of the Neutrokine-alpha coding sequence, the PCR product was combined with the PSC signal peptide-polyhedrin upstream region PCR product and subjected to an additional round of PCR. Because the 3' end of the PSC signal peptide PCR product (pMGS12/O-959/O-1044) overlapped the 5' end of the Neutrokine-alpha PCR product prepared with primers O-1887/O-1888, the two PCR products were combined and overlap-extended by PCR using primers O-959 and O-1888.

The resulting overlap-extended PCR product containing the PSC signal peptide fused to the Neutrokine-alpha sequence subsequently was inserted into baculovirus transfer plasmid pMGS12. The PCR product was digested with NgoM IV and Kpn I, and the fragment was purified and ligated into NgoM IV-Kpn I-cut pMGS12. After transformation of competent *E. coli* DH5alpha cells with the ligation mix, colonies were picked and plasmid DNA mini-preps were prepared. Several positive clones from each ligation were identified by restriction digestion analysis of the plasmid DNA, and three clones (pAcC9669, pAcC9671, and pAcC9672) were selected for large scale plasmid purification. The resulting plasmid DNA was subjected to DNA sequence analysis to confirm and sequence the Neutrokine-alpha insert.

The following steps describe the recovery and purification process of recombinant Neutrokine-alpha from Sf+ insect cells. Unless stated otherwise, the process is conducted at 2-8° C.

Recovery

Step 1. $CaCl_2$ Treatment

Sf+ cell supernatant was harvested by centrifugation at 8,000×g. Recovery buffer-1 (1M $CaCl_2$) was added to the supernatant so that the final concentration of $CaCl_2$ was 10 mM. (In a further preferred embodiment, 1M $ZnCl_2$ is used in place of 1M $CaCl_2$.) The pH of the solution was adjusted to 7.7+ with Recovery buffer-2 (1M Tris pH 8 (+0.2)). The solution was incubated for 15 minutes and then centrifuged at 8,000×g.

Purification

Step 1. Chromatography on Poros PI-50 Column

Sf+ cell supernatant was loaded on to a Poros PI-50 column (PE Biosystem). The column was equilibrated in PI-1 buffer (50 mM Tris, 50 mM NaCl, pH 7.4 (±0.2)). The PI-50 column was washed with 1-2 CV of PI-1 buffer and the eluted with PI-2 buffer (50 mM Na Citrate pH 6 (±0.2)) over 3 CV linear gradient. The elution was monitored by ultraviolet (UV) absorbance at 280 nm. Fractions were collected across the eluate peak and analyzed by SDS page. Appropriate fractions were pooled.

Step 2. Chromatography on Toyopearl Hexyl 650C Column

The PI pool was mixed with salts to final concentrations of 0.7M $(NH_4)_2SO_4$ and loaded on to a Toyopearl Hexyl 650C (Toso Haas) column equilibrated in HIC-1 buffer (50 mM NaOAc, 0.6M NaCl, 0.7M $(NH_4)_2SO_4$ pH 6 (±0.2)). The column was then washed with 2 CV of HIC-1 buffer. Subsequently, recombinant Neutrokine-alpha was then eluted stepwise with 3-5 CV of HIC-2 buffer (50 mM NaOAc pH 6.0 (±0.2)) followed by a 2 CV 20% ethanol wash. The elution was monitored by UV absorbance at 280 nm and conductivity. Fractions were collected across the eluate peak and analyzed by SDS-PAGE. The appropriate fractions were then pooled.

Step 3. Chromatography on SP Sepharose FF

The Hexyl fraction was dialyzed and ajusted to pH 4.5 with SP-1 buffer (50 mM sodium acetate pH 4.5 (±0.2)), diluted to 4 ms and loaded through a SP sepharose (cation exchanger, Pharmacia) column equilibrated with SP-1 buffer (50 mM sodium acetate pH 4.5 (±0.2)). Recombinant Neutrokine-alpha protein was then eluted from the SP column with SP-2 buffer (50 mM sodium acetate pH 5.5 (±0.2)) at pH 5.5. The elution was then monitored by ultraviolet (UV) absorbance at 280 nm. Fractions were collected across the eluate peak and analyzed by SDS page. Appropriate fractions were pooled.

Step 4. Dialysis of Recombinant Neutrokine-alpha

The SP fractions were placed into a 6-8 kd cutoff membrane device and then dialyzed or diafiltered into Dialysis Buffer (10 mM sodium citrate, 140 mM sodium chloride pH 6 (±0.2)) overnight.

Step 5. Filtration and Fill

The protein concentration of the recombinant Neutrokine-alpha solution from Step 6 was determined by bicinchoninic acid (BCA) protein assay. Recombinant Neutrokine-alpha formulation was adjusted to the final protein concentration with the appropriate buffer and filtered under controlled conditions. The filtrate (bulk substance) was stored in suitable sterilized containers below −20° C.

In a specific embodiment, Neutrokine-alpha protein of the invention produced as described infra was adjusted to a final protein concentration of 1 to 5 mg/ml and buffered in 10 mM sodium citrate, 140 mM sodium chloride, pH=6.0±(0.4) and stored at or below −20° C. in Type 1 glass vials.

During chromatography runs, the processes are monitered by UV absorbance at 280 nm. When applicable, in-process chromatography intermediates are tested for conductivity, pH, and monitored by SDS and/or RP-HPLC.

Columns and purification equipment are cleaned and sanitized with 0.2 or 0.5 M NaOH followed by deionized water and then 0.1 or 0.5 M acetic acid. The column and purification equipment are rinsed with deionized water and, if necessary, stored in the appropriate storage solution. Prior to use, the equipment is equilibrated with appropriate buffers (as described herein or as is well known in the art).

In a further preferred embodiment, 1M $ZnCl_2$ is used in place of 1M $CaCl_2$ in Step 1 of the Recovery section described above. Also, in this embodiment, a combination of $ZnCl_2$ and $CaCl_2$ may be used. Many combinations of 0.1 M $ZnCl_2$ and 0.9 M $CaCl_2$, may be used in the Recovery process of recombinant Neutrokine-alpha protein such as, for example, but not limited to, a combination of 0.1 M $ZnCl_2$ and 0.9 M $CaCl_2$, 0.2 M $ZnCl_2$ and 0.8 M $CaCl_2$, 0.3 M $ZnCl_2$ and 0.7 M $CaCl_2$, 0.4 M $ZnCl_2$ and 0.6 M $CaCl_2$, 0.5 M $ZnCl_2$ and 0.5 M $CaCl_2$, 0.6 M $ZnCl_2$ and 0.4 M $CaCl_2$, 0.7 M $ZnCl_2$ and 0.3 M $CaCl_2$, 0.8 M $ZnCl_2$ and 0.2 M $CaCl_2$, 0.9 M $ZnCl_2$ and 0.1 M $CaCl_2$, and others. However, the presence of EDTA will inhibit the recovery process. Moreover, the presence of $ZnCl_2$ and/or $CaCl_2$ in Recovery Buffer-1 will induce the formation of larger amounts of higher molecular weight (or molecular mass) Neutrokine-alpha multimers.

Example 3

Cloning and Expression of Neutrokine-alpha in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLV1, HIV1 and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12M1 (ATCC 67109). Mammalian host cells that could be used include, human HeLa, 293, H9 and Jurkat cells, mouse NIH3T3 and C127 cells, Cos 1, Cos 7 and CV1, quail QC1-3 cells, mouse L cells, Chinese hamster ovary (CHO) cells CHO-K1, NSO and HEK 293 cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., Biochem J. 227:277-279 (1991); Bebbington et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., Molecular and Cellular Biology, 438-447 (March, 1985)) plus a fragment of the CMV-enhancer (Boshart et al., Cell 41:521-530 (1985)). Multiple cloning sites, e.g., with the restriction enzyme cleavage sites Bam HI, Xba I and Asp 718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pNeutrokine-alpha-HA, is made by cloning a portion of the deposited cDNA encoding the extracellular domain of the protein into the expression vector pcDNAI/Amp or pcDNAIII (which can be obtained from Invitrogen, Inc.). To produce a soluble, secreted form of the polypeptide, the extracellular domain is fused to the secretory leader sequence of the human IL-6 gene.

The expression vector pcDNAI/amp contains: (I) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., Cell 37: 767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the extracellular domain of the Neutrokine-alpha polypeptide is cloned into the polylinker region of the vector so that recombinant protein expression is directed by the CMV promoter. The plasmid construction strategy is as follows. The Neutrokine-alpha cDNA of the deposited clone is amplified using primers that contain convenient restriction sites, much as described above for construction of vectors for expression of Neutrokine-alpha in *E. coli*. Suitable primers include the following, which are used in this example. The 5' primer, containing the underlined Bam HI site, a Kozak sequence, an AUG start codon, a sequence encoding the secretory leader peptide from the human IL-6 gene, and 18 nucleotides of the 5' coding region of the extracellular domain of Neutrokine-alpha protein, has the following sequence: 5'-GCG GGA TCC GCC ACC ATG AAC TCC TTC TCC ACA AGC GCC TTC GGT CCA GTT GCC TTC TCC CTG GGG CTG CTC CTG GTG TUG CCT GCT GCC TTC CCT GCC CCA GTT GTG AGA CAA GGG GAC CTG GCC AGC-3' (SEQ ID NO:16). The 3' primer, containing the underlined Bam HI restriction site and 18 of nucleotides complementary to the 3' coding sequence immediately before the stop codon, has the following sequence: 5'-GTG GGA TCC TTA CAG CAG TTT CAA TGC ACC-3' (SEQ ID NO:17).

The PCR amplified DNA fragment and the vector, pcDNAI/Amp, are digested with Bam HI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the Neutrokine-alpha extracellular domain.

For expression of recombinant Neutrokine-alpha, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y. (1989). Cells are incubated under conditions for expression of Neutrokine-alpha by the vector.

Expression of the Neutrokine-alpha-HA fusion protein is detected by radiolabeling and immunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP40, 0.1% SDS, 1% NP40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of Neutrokine-alpha protein. Plasmid pC4 is a derivative of the plasmid pSV2-dhfr (ATCC Accession No. 37146). To produce a soluble, secreted form of the Neutrokine-alpha polypeptide, the portion of the deposited cDNA encoding the extracellular domain is fused to the secretory leader sequence of the human IL-6 gene. The vector plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357-1370, Hamlin, J. L. and Ma, C. 1990, Biochem. et Biophys. Acta, 1097:107-143, Page, M. J. and Sydenham, M. A. 1991, Biotechnology 9:64-68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., Molecular and Cellular Biology, March 1985:438-447) plus a fragment isolated from the enhancer of the immediate early gene of human cytomegalovirus (CMV) (Boshart et al., Cell 41:521-530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human beta-actin promoter, the SV40 early or late promoters or the long terminal repeats from other retroviruses, e.g., HIV and HTLV1. Clontech's Tet-Off and Tet-On gene expression systems and similar systems can be used to express the Neutrokine-alpha in a regulated way in mammalian cells (Gossen, M., & Bujard, H. 1992, Proc. Natl. Acad. Sci. USA 89: 5547-5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and then dephosphorylated using calf intestinal phosphates by procedures known in the art. The vector is then isolated from a 1% agarose gel.

The DNA sequence encoding the extracellular domain of the Neutrokine-alpha protein is amplified using PCR oligonucleotide primers corresponding to the 5' and 3' sequences of the gene. The 5' primer, containing the underlined Bam HI site, a Kozak sequence, an AUG start codon, a sequence encoding the secretory leader peptide from the human IL-6 gene, and 18 nucleotides of the 5' coding region of the extracellular domain of Neutrokine-alpha protein, has the following sequence: 5'-GCG GGA TCC GCC ACC ATG AAC TCC TTC TCC ACA AGC GCC TTC GGT CCA GTT GCC TTC TCC CTG GGG CTG CTC CTG GTG TTG CCT GCT GCC TTC CCT GCC CCA GTT GTG AGA CAA GGG GAC CTG GCC AGC-3' (SEQ ID NO:16). The 3' primer, containing the underlined Bam HI and 18 of nucleotides complementary to the 3' coding sequence immediately before the stop codon, has the following sequence: 5'-GTG GGA TCC TTA CAG CAG TTT CAA TGC ACC-3' (SEQ ID NO:17).

The amplified fragment is digested with the endonuclease Bam HI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five jug of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100-200 μM. Expression of the desired gene product is analyzed, for instance, by SDS-PAGE and Western blot or by reversed phase HPLC analysis.

At least six Neutrokine-alpha expression constructs have been generated by the inventors herein to facilitate the production of Neutrokine-alpha and/or Neutrokine-alphaSV polypeptides of several sizes and in several systems. The expression constructs are as follows: (1) pNa.A71-L285 (expresses amino acid residues Ala-71 through Leu-285), (2) pNa.A81-L285 (expresses amino acid residues Ala-81 through Leu-285), (3) pNa.L112-L285 (expresses amino acid residues Leu-112 through Leu-285), (4) pNa.A134-L285 (expresses amino acid residues Ala-134 through Leu-285), (5) pNa.L147-L285 (expresses amino acid residues Leu-147 through Leu-285), and (6) pNa.G161-L285 (expresses amino acid residues Gly-161 through Leu-285).

In preferred embodiments, the expression constructs are used to express various Neutrokine-alpha muteins from bacterial, baculoviral, and mammalian systems.

In certain additional preferred embodiments, the constructs express a Neutrokine-alpha polypeptide fragment fused at the N- and/or C-terminus to a heterologous polypeptide, e.g., the signal peptide from human IL-6, the signal peptide from CK-beta8 (amino acids −21 to −1 of the CK-beta8 sequence disclosed in published PCT application PCT/US95/09058), or the human IgG Fc region. Other sequences could be used which are known to those of skill in the art.

Example 4

Tissue Distribution of Neutrokine-alpha mRNA Expression

Northern blot analysis is carried out to examine Neutrokine-alpha gene expression in human tissues, using methods described by, among others, Sambrook et al., cited above. A cDNA probe containing the entire nucleotide sequence of the Neutrokine-alpha protein (SEQ ID NO:1) is labeled with $^{32}P$ using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for Neutrokine-alpha and/or Neutrokine-alpha mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

To determine the pattern of Neutrokine-alpha and/or Neutrokine-alpha expression a panel of multiple tissue Northern blots were probed. This revealed predominant expression of single 2.6 kb mRNA in peripheral blood leukocytes, spleen, lymph node and bone marrow, and detectable expression in placenta, heart, lung, fetal liver, thymus and pancreas. Analysis of a panel of cell lines demonstrated high expression of Neutrokine-alpha and/or Neutrokine-alpha in HL60 cells, detectable expression in K562, but no expression in Raji, HeLa, or MOLT-4 cells. Overall it appears that Neutrokine-alpha and/or Neutrokine-alpha mRNA expression is enriched in the immune system.

Example 5

Gene Therapy Using Endogenous Neutrokine-alpha Gene

Another method of gene therapy according to the present invention involves operably associating the endogenous Neutrokine-alpha sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous Neutrokine-alpha, flanking the promoter. The targeting sequence will be sufficiently near the 5' end of Neutrokine-alpha so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous Neutrokine-alpha sequence. This results in the expression of Neutrokine-alpha in the cell. Expression may be detected by immunological staining, or any other method known in the art.

Fibroblasts are obtained from a subject by skin biopsy. The resulting tissue is placed in DMEM +10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the Neutrokine-alpha locus, plasmid pUC18 (MBI Fermentas, Amherst, N.Y.) is digested with HindIII. The CMV promoter is amplified by PCR with an XbaI site on the 5' end and a BamHI site on the 3'end. Two Neutrokine-alpha non-coding sequences are amplified via PCR: one Neutrokine-alpha non-coding sequence (Neutrokine-alpha fragment 1) is amplified with a HindIII site at the 5' end and an Xba site at the 3'end; the other Neutrokine-alpha non-coding sequence (Neutrokine-alpha fragment 2) is amplified with a BamHI site at the 5'end and a HindIII site at the 3'end. The CMV promoter and Neutrokine-alpha fragments are digested with the appropriate enzymes (CMV promoter—XbaI and BamHI; Neutrokine-alpha fragment 1—XbaI; Neutrokine-alpha fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio- Rad). The final DNA concentration is generally at least 120 μg/ml. 0.5 ml of the cell suspension (containing approximately 1.5×106 cells) is then added to the cuvette, and the cell suspension and DNA solutions are gently mixed. Electroporation is performed with a Gene-Pulser apparatus (Bio-Rad). Capacitance and voltage are set at 960 μF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 6

Neutrokine-alpha, a Novel Member of the Tumor Necrosis Factor Ligand Family that Functions as a B Lymphocyte Stimulator A 285 amino acid protein was identified in a human neutrophil/monocyte-derived cDNA library that shared significant homology within its predicted extracellular receptor-ligand binding domain to APRIL (28.7%) (Hahne, M., et al., J. Exp. Med. 188,1185-90 (1998)), TNF-alpha (16.2%) (Pennica, D., et al., Nature 312,724-729 (1984)) and LT-alpha (14.1%) (Gray, Nature 312,721-724 (1984)) (FIGS. 7A-1 and 7A-2). We have designated this cytokine Neutrokine-alpha (we have also designated this molecule as B Lymphocyte Stimulator (BLyS) based on its biological activity). Hydrophobicity analyses of the Neutrokine-alpha protein sequence have revealed a potential transmembrane spanning domain between amino acid residues 47 and 73 which is preceded by non-hydrophobic amino acids suggesting that Neutrokine-alpha, like other members of the TNF ligand family, is a type II membrane bound protein (Cosman, D. Stem. Cells. 12:440-55 (1994)). Expression of this cDNA in mammalian cells (HEK 293 and Chinese Hamster Ovary) and Sf9 insect cells identified a 152 amino acid soluble form with an N-terminal sequence beginning with the alanine residue at amino acid 134 (arrow in FIGS. 7A-1 and 7A-2). Reconstruction of the mass to charge ratio defined a mass for Neutrokine-alpha of 17,038 Daltons, a value in consistent with that predicted for this 152 amino acid protein with a single disulfide bond (17037.5 Daltons).

Using human/hamster somatic cell hybrids and a radiation-hybrid mapping panel, the gene encoding Neutrokine-alpha was found linked to marker SHGC-36171 which maps to human chromosome 13q34, a region not previously associated with any other member of the TNF superfamily of genes (Cosman, D. Stem. Cells. 12:440-55 (1994)).

The expression profile of Neutrokine-alpha was assessed by Northern blot (FIG. 7B) and flow cytometric analyses (Table V and FIGS. 8A, 8B and 8C). Neutrokine-alpha is encoded by a single 2.6 kb mRNA found at high levels in peripheral blood leukocytes, spleen, lymph node and bone marrow. Lower expression levels were detected in placenta, heart, lung, fetal liver, thymus and pancreas. Among a panel of cell lines, Neutrokine-alpha mRNA was detected in HL-60 and K562, but not in Raji, HeLa, or MOLT-4 cells. These results were confirmed by flow cytometric analyses using the Neutrokine-alpha-specific mAb 2E5. As shown in Table V, Neutrokine-alpha expression is not detected on T or B lineage cells but rather restricted to cells within the myeloid origin. Further analyses of normal blood cell types demonstrated significant expression on resting monocytes that was upregulated approximately 4-fold following exposure of cells to IFN-gamma (100 U/mL) for three days (FIGS. 8A and 8B). A concomitant increase in Neutrokine-alpha-specific mRNA was also detected (FIG. 8C). By contrast, Neutrokine-alpha was not expressed on freshly isolated peripheral blood granulocytes, T cells, B cells, or NK cells.

Purified recombinant Neutrokine-alpha ("rNeutrokine-alpha") was assessed for its ability to induce activation, proliferation, differentiation or death in numerous cell based assays involving B cells, T cells, monocytes, NK cells, hematopoietic progenitors, and a variety of cell types of endothelial and epithelial origin. Among these assays, Neutrokine-alpha was specifically found to increase B cell proliferation in a standard co-stimulatory assay in which purified tonsillar B cells are cultured in the presence of either formalin-fixed *Staphylococcus aureus* Cowan I (SAC) or immobilized anti-human IgM as priming agents (Sieckmann, D. G., et al., J. Exp. Med. 147:814-29 (1978); Ringden, O., et al., Scand. J. Immunol. 6:1159-69 (1977)). As shown in FIG. 9A, recombinant Neutrokine-alpha induced a dose-dependent proliferation of tonsillar B cells. This response was similar to that of rIL2 over the dose range from 0.1 to 10,000 ng/mL. Neutrokine-alpha also induces B cell proliferation when cultured with cells co-stimulated with immobilized anti-IgM (FIG. 9B). A dose-dependent response is readily observed as the amount of crosslinking agent increases in the presence of a fixed concentration of either IL2 or rNeutrokine-alpha.

In an attempt to correlate the specific biological activity on B cells with receptor expression, purified Neutrokine-alpha was biotinylated. The resultant biotin-Neutrokine-alpha protein retained biological function in the standard B cell proliferation assays. Lineage-specific analyses of whole human peripheral blood cells indicated that binding of biotinylated Neutrokine-alpha was undetectable on T cells, monocytes, NK cells and granulocytes as assessed by CD3, CD14, CD56, and CD66b respectively (FIGS. 10A, 10B, 10C, 10D and 10E). In contrast, biotinylated Neutrokine-alpha bound peripheral $CD20^+$ B cells. Receptor expression was also detected on the B cell tumor lines REH, ARH-77, Raji, Namalwa, RPMI 8226, and IM-9 but not any of the myeloid-derived lines tested including THP-1, HL-60, K-562, and U-937. Representative flow cytometric profiles for the myeloma cell line IM-9 and the histiocytic line U-937 are shown in FIGS. 10F and 10G. Similar results were also obtained using a biologically active FLAG-tagged Neutrokine-alpha protein instead of the chemically modified biotin-Neutrokine-alpha. Taken together, these results confirm that Neutrokine-alpha displays a clear B cell tropism in both its receptor distribution and biological activity. It remains to be shown whether cellular activation may induce expression of Neutrokine-alpha receptors on peripheral blood cells, other normal cell types or established cell lines.

To examine the species specificity of Neutrokine-alpha, mouse splenic B cells were cultured in the presence of human Neutrokine-alpha and SAC. Results demonstrate that rNeutrokine-alpha induced in vitro proliferation of murine splenic B cells and bound to a cell surface receptor on these cells. Interestingly, immature surface Ig negative B cell precursors isolated from mouse bone marrow did not proliferate in response to Neutrokine-alpha nor did they bind the ligand.

To assess the in vivo activity of rNeutrokine-alpha, BALB/c mice (3/group) were injected (i.p.) twice per day with buffer only, or 0.08 mg/kg, 0.8 mg/kg, 2 mg/kg or 8 mg/kg of rNeutrokine-alpha. Mice received this treatment for 4 consecutive days at which time they were sacrificed and various tissues and serum collected for analyses. In an alternative embodiment, BALB/c mice may be injected (i.p.) twice per day with any amount of rNeutrokine-alpha in a range of 0.01 to 10 mg/kg. In a preferred embodiment, BALB/c mice are injected (i.p.) twice per day with any amount of rNeutrokine-alpha in a range of 0.01 to 3 mg/kg (specific preferred exemplary dosages in this embodiment include, but are not limited to, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, and 3.0 mg/kg). In an additional preferred embodiment, BALB/c mice are injected (i.p.) twice per day with any amount of rNeutrokine-alpha in a range of 0.02 to 2 mg/kg (specific preferred exemplary dosages in this embodiment include, but are not limited to, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.6 mg/kg, 1.7 mg/kg, 1.8 mg/kg, 1.9 mg/kg, and 2.0 mg/kg).

Microscopically, the effects of Neutrokine-alpha administration were clearly evident in sections of spleen stained with routine hematoxylin and eosin (H&E) and immunohistochemically with a mAb specific for CD45R(B220) (FIG. 11A). Normal splenic architecture was altered by a dramatic expansion of the white pulp marginal zone and a distinct increase in cellularity of the red pulp (FIG. 11A). Marginal zone expansion appeared to be the result of increased numbers of lymphocytes expressing the B cell marker CD45R (B220). In addition, the T cell dense periarteriolar lymphoid sheath (PALS) areas were also infiltrated by moderate numbers of CD45R(B220) positive cells. This suggests the white pulp changes were due to increased numbers of B cells. The densely packed cell population that frequently filled red pulps spaces did not stain with CD45R(B220). Additional experiments will be required to characterize all the cell types involved and further define the mechanism by which Neutrokine-alpha alters splenic architecture.

Flow cytometric analyses of the spleens from mice treated with 2 mg/kg Neutrokine-alpha-treated indicated that Neutrokine-alpha increased the proportion of mature (CD45R (B220)$^{dull}$, ThB$^{bright}$) B cells approximately 10-fold over that observed in control mice (FIGS. 11B and 11C). Further analyses performed in which mice were treated with buffer, 0.08 mg/kg, 0.8 mg/kg, 2 mg/kg, or 8 mg/kg Neutrokine-alpha indicated that 0.08 mg/kg, 0.8 mg/kg, and 2 mg/kg each increased the proportion of mature (CD45R(B220)$^{dull}$, Th B$^{bright}$) B cells approximately 10-fold over that observed in control mice, whereas buffer and 8 mg/kg produced approximately equal proportions of mature B cells. See, Table IV.

TABLE IV

FACS Analysis of Mouse Spleen B cell Population.

| Neutrokine-alpha (mg/kg) | % Mature B Cells (R2) | % CD45R-positive (R1) |
|---|---|---|
| Control (buffer) | 1.26 | 52.17 |
| 0.08 mg/kg | 16.15 | 56.53 |
| 0.8 mg/kg | 18.54 | 57.56 |
| 2 mg/kg | 16.54 | 57.55 |
| 8 mg/kg | 1.24 | 61.42 |

A potential consequence of increased mature B cell representation in vivo is a relative increase in serum Ig titers. Accordingly, serum IgA, IgG and IgM levels were compared between buffer and Neutrokine-alpha-treated mice (FIGS. 11D, 11E, and 11F). Neutrokine-alpha administration resulted in a 2- and 5-fold increase in IgA and IgM serum levels respectively. Interestingly, circulating levels of IgG did not increase.

Moreover, a dose-dependent response was observed in serum IgA titers in mice treated with various amounts of Neutrokine-alpha over a period of four days, whereas no apparent dose-dependancy was observed by administration of the same amounts of Neutrokine-alpha over a period of two days. In the case of administration over four days, administration of 8, 2, 0.8, 0.08, and 0 mg/kg, Neutrokine-alpha resulted in serum IgA titers of approximately 800 micrograms/ml, 700 micrograms/ml, 400 micrograms/ml, 200 micrograms/ml and 200 micrograms/ml. That is, administration of 8, 2, 0.8, and 0.08 mg/kg Neutrokine-alpha over four days resulted in approximately 4-fold, 3.75-fold, 2-fold, and minimal-fold, respectively, increases in IgA serum levels over background or basal levels observed by administration of buffer only. In an alternative embodiment, these experiments may be performed with any amount of rNeutrokine-alpha in a range of 0.01 to 10 mg/kg. In a preferred embodiment, Neutrokine-alpha is administered in a range of 0.01 to 3 mg/kg (specific preferred exemplary dosages in this embodiment include, but are not limited to, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, and 3.0 mg/kg). In an additional preferred embodiment, Neutrokine-alpha is administered in a range of 0.02 to 2 mg/kg (specific preferred exemplary dosages in this embodiment include, but are not limited to, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.6 mg/kg, 1.7 mg/kg, 1.8 mg/kg, 1.9 mg/kg, and 2.0 mg/kg).

The data presented herein define Neutrokine-alpha, as a novel member of the TNF-ligand superfamily that induces both in vivo and in vitro B cell proliferation and differentiation. Neutrokine-alpha is distinguished from other B cell growth and differentiation factors such as IL2 (Metzger, D. W., et al., Res. Immunol. 146:499-505 (1995)), IL4 (Armitage, R. J., et al., Adv. Exp. Med. Biol. 292:121-30 (1991); Yokota, T., et al., Proc. Natl. Acad. Sci. U.S.A. 83:5894-98 (1986)), IL5 (Takatsu, K., et al., Proc. Natl. Acad. Sci. U.S.A. 84:4234-38 (1987); Bertolini, J. N., et al., Eur. J. Immunol. 23:398-402 (1993)), IL6 (Poupart, P., et al., EMBO J. 6:1219-24 (1987); Hirano, T., et al., Nature 324:73-76 (1986)) IL7 (Goodwin, R. G., et al., Proc. Natl. Acad. Sci. U.S.A. 86:302-06 (1989); Namen, A. E., et al., Nature 333:571-73 (1988)), IL13 (Punnonen, J., et al., Allergy. 49:576-86 (1994)), IL15 (Armitage, R. J., et al., J. Immunol. 154:483-90 (1995)), CD40L (Armitage, R. J., et al., Nature 357:80-82 (1992); Van Kooten, C. and Banchereau, J. Int. Arch. Allergy. Immunol. 113:393-99 (1997)) or CD27L (CD70) (Oshima, H., et al., Int. Immunol. 10:517-26 (1998); Lens, S. M., et al., Semin. Immunol. 10:491-99 (1998)) by its monocyte-specific gene/protein expression pattern and its specific receptor distribution and biological activity on B lymphocytes. Taken together these data suggest that Neutrokine-alpha is likely involved in the exchange of signals between B cells and monocytes or their differentiated progeny. Although all B cells may utilize this mode of signaling, the restricted expression patterns and Ig secretion suggest a role for Neutrokine-alpha in the activation of $CD5^+$ or "unconventional" B cell responses. These B cells provide a critical component to the innate immune system and provide protection from environmental pathogens through their secretion of polyreactive IgM and IgA antibodies (Pennell, C. A., et al., Eur. J. Immunol. 19:1289-95 (1989); Hayakawa, K., et al., Proc. Natl. Acad. Sci. U.S.A. 81:2494-98 (1984)). Alternatively, Neutrokine-alpha may function as a regulator of T cell independent responses in a manner analogous to that of CD40 and CD40L in T cell dependent antigen activation (van den Eertwegh, A. J., et al., J. Exp. Med. 178: 1555-65 (1993); Grabstein, K. H., et al., J. Immunol. 150: 3141-47 (1993)). As such, Neutrokine-alpha, its receptor or related antagonists have utility in the treatment of B cell disorders associated with autoimmunity, neoplasia and/or immunodeficient syndromes.

Methods

Mice. BALB/cAnNCR (6-8 weeks) were purchased from Charles River Laboratories, Inc. and maintained according to recommended standards (National Research Council, Guide for the care and use of laboratory animals (1999)) in microisolator cages with recycled paper bedding (Harlan Sprague Dawley, Inc., Indianapolis, Ind.) and provided with pelleted rodent diet (Harlan Sprague Dawley, Inc) and bottled drinking water on an ad libitum basis. The animal protocols used in this study were reviewed and approved by the HGS Institutional Animal Care and Use Committee.

Isolation of full length Neutrokine-alpha cDNA. The BLAST algorithm was used to search the Human Genome Sciences Inc. expressed sequence tag (EST) database for sequences with homology to the receptor-binding domain of the TNF family. A full length Neutrokine-alpha clone was identified, sequenced and submitted to GenBank (Accession number AF132600). The Neutrokine-alpha open reading frame was PCR amplified utilizing a 5' primer (5'-CAG ACT GGA TCC GCC ACC ATG GAT GAC TCC ACA GAA AG-3') annealing at the predicted start codon and a 3 ' primer (5'-CAG ACT GGT ACC GTC CTG CGT GCA CTA CAT GGC-3') designed to anneal at the predicted downstream stop codon. The resulting amplicon was tailed with Bam HI and Asp 718 restriction sites and subcloned into a mammalian expression vector. Neutrokine-alpha was also expressed in p-CMV-1 (Sigma Chemicals).

Purification of recombinant human Neutrokine-alpha. The full length cDNA encoding Neutrokine-alpha was subcloned into the baculovirus expression vector pA2 and transfected into Sf9 insect cells (Patel, V. P., et al., J. Exp. Med. 185:1163-72 (1997)). Recombinant Neutrokine-alpha was purified from cell supernatants at 92 h post-infection using a combination of anion-exchange, size exclusion, and hydrophobic interaction columns. The purified protein was formulated in a buffer containing 0.15 M NaCl, 50 mM NaOAc at pH 6, sterile filtered and stored at 4° C. until needed. Both SDS-PAGE and RP-HPLC analyses indicate that rNeutrokine-alpha is greater than 95% pure. Endotoxin levels were below the detection limit in the LAL assay (Associates of Cape Cod, Falmouth, Mass.). The final purified Neutrokine-alpha protein has an N-terminus sequence of Ala-Val-Gln-Gly-Pro. This corresponds identically to the sequence of soluble Neutrokine-alpha derived from CHO cell lines stably transfected with the full length Neutrokine-alpha gene.

Monoclonal antibody generation. BALB/cAnNCR mice were immunized with 50 micrograms of HisTag-Neutrokine-alpha suspended in complete Freund's adjuvant followed by 2 challenges in incomplete Freund's adjuvant. Hybridomas and monoclonal antibodies were prepared as described (Gefter, M. L., et al., Somatic. Cell Genet. 3:231-36 (1977); Akerstrom, B., et al., J. Immunol. 135:2589-92 (1985)).

Cell lines. All human cell lines were purchased from ATCC (American Type Culture Collection, Manassas, Va.).

FACS analysis. Neutrokine-alpha expression was assessed on human cell lines, freshly isolated normal peripheral blood nucleated cells, and in vitro cultured monocytes, a mouse anti-human Neutrokine-alpha mAb 2E5 (IgG1) followed by PE-conjugated F(ab')2 goat antibody to mouse IgG (CALTAG Laboratories, Burlingame, Calif.). Cells were analyzed using a FACScan (Becton Dickinson Immunocytometry Systems, San Jose, Calif.) with propidium iodide to exclude dead cells. Neutrokine-alpha binding was assessed using rNeutrokine-alpha biotinylated with a N-hydroxysuccinimidobiotin reagent (Pierce, Rockford, Ill.) followed by PE-conjugated streptavidin (Dako Corp, Glostrup, Denmark).

Chromosomal mapping. To determine the chromosomal location of the Neutrokine-alpha gene, a panel of monochromosomal somatic cell hybrids (Quantum Biotechnology, Canada) retaining individual chromosomes was screened by PCR using Neutrokine-alpha specific primers (5' primer: 5'-TGG TGT CTT TCT ACC AGG TGG-3' and 3' primer: 5'-TTT CTT CTG GAC CCT GAA CGG-3'). The predicted 233 bp PCR product was only detected in human chromosome 13 hybrids. Using a panel of 83 radiation hybrids (Research Genetics, St. Louis, Mo.) and the Stanford Human Genome Center Database, (http://www.shgc.stanford-.edu.RH/rhserver). Neutrokine-alpha was found linked to the SHGC-36171 marker on chromosome 13. Superposition of this map with the cytogenetic map of human chromosome 13 allowed the assignment of human Neutrokine-alpha to chromosomal band 13q34.

B lymphocyte proliferation assay. Human tonsillar B cells were purified by magnetic bead (MACS) depletion of CD3- positive cells. The resulting cell population was routinely greater than 95% B cells as assessed by expression of CD19 and CD20. Various dilutions of human rNeutrokine-alpha or the control protein recombinant human IL2 were placed into individual wells of a 96-well plate to which was added $10^5$ B cells suspended in culture medium (RPMI 1640 containing 10% FBS, $5\times10^{-5}$M 2ME, 100 U/ml penicillin, 100 microgram/ml streptomycin, and $10^{-5}$ dilution of Pansorbin (SAC) or anti-IgM) in a total volume of 150 microliters. Proliferation was quantitated by a 20 h pulse (1 microCi/well) of $^3$H-thymidine (6.7 Ci/mM) beginning 72 h post factor addition.

Histological analyses. Spleens were fixed in 10% neutral buffered formalin, embedded in paraffin, sectioned at 5 micrometers, mounted on glass slides and stained with hematoxylin and eosin or by enzyme-labeled indirect method immunohistochemistry for CD45R(B220) (Hilbert, D. M., et al., Eur. J. Immunol. 23:2412-18 (1993)).

TABLE V

Neutrokine-alpha cell surface expression

| Cell line | Cellular Morphology | Neutrokine-alpha cell surface expression |
|---|---|---|
| Monocytic lineage | | |
| U-937 | Lymphoma, histiocytic/macrophage | + |
| BL-60 | Leukemia, acutepromyelocytic | + |
| K-562 | Leukemia, chronlcmyelogenous | + |
| THP-1 | Leukemia, acutemonocytic | + |
| T-lineage | | |
| Jurkat | Leukemia, T lymphocytic | – |
| SUP-T13 | Leukemia, T lymphoblastic | – |
| MOLT-4 | Leukemia, T lymphoblastic | – |
| B-lineage | | |
| Daudi | Burkitt's, lymphoblastic | – |
| Namalwa | Burkitt's, lymphocyte | – |
| Raji | Burkitt's, lymphocyte | – |
| Reh | Leukemia, lymphocytic | – |
| ARH-77 | Leukemia, plasma cell | – |
| IM9 | Myeloma | – |
| RPMI 8226 | Myeloma | – |

Example 7

Assays to Detect Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL4, IL5, IL6, IL-7, IL10, IL-13, IL14 and IL15. Interestingly, these signals are by themselves weak effectors but can, in combination with various co-stimulatory proteins, induce activation, proliferation, differentiation, homing, tolerance and death among B cell populations. One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro assay-Purified Neutrokine-alpha and/or Neutrokine-alphaSV protein, or truncated forms thereof, is assessed for its ability to induce activation, proliferation, differentiation or inhibition and/or death in B-cell populations and their precursors. The activity of Neutrokine-alpha and/or Neutrokine-alphaSV protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and ISM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220). Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with $^3$H-thymidine (6.7 Ci/mM) beginning 72 h post factor addition. The positive and negative controls are IL2 and medium respectively.

Agonists (including Neutrokine-alpha and/or Neutrokine-alphaSV polypeptide fragments) demonstrate an increased B cell proliferation when compared to that observed when the same number of B cells is contacted with the same concentration of priming agent. Antagonists according to the invention exhibit a decreased B cell proliferation when compared to controls containing the same number of B cells, the same concentration of priming agent, and the same concentration of a soluble form of Neutrokine-alpha that elicits an increase in B cell proliferative activity (e.g., 71-285, 81-285, 112-285 or 134-285 of the Neutrokine-alpha polypeptide shown in SEQ ID NO:2) in the absence the antagonist.

In Vivo assay-BALB/c mice are injected (i.p.) twice per day with buffer only, or 2 mg/Kg of Neutrokine-alpha and/or Neutrokine-alphaSV protein, or truncated forms thereof. Mice receive this treatment for 4 consecutive days, at which time they are sacrificed and various tissues and serum collected for analyses. Comparison of H&E sections from normal and Neutrokine-alpha and/or Neutrokine-alphaSV protein-treated spleens identify the results of the activity of Neutrokine-alpha and/or Neutrokine-alphaSV protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from Neutrokine-alpha and/or Neutrokine-alphaSV protein-treated mice is used to indicate whether Neutrokine-alpha and/or Neutrokine-alphaSV protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and Neutrokine-alpha and/or Neutrokine-alphaSV protein-treated mice.

Example 8

Effect of Neutrokine-alpha and its Agonists in Treating Graft-versus-host Disease Associated Lymphoid Atrophy and Hypoplasia in Mice An analysis of the use of Neutrokine-alpha to treat, prevent, and/or diagnose graft-versus-host disease (GVHD)-associated lymphoid hypoplasia/atrophy is performed through the use of a C57BL/6 parent into (BALB/c×C57BL/6) F1 (CBF1) mouse model. This parent into F1 mouse model is a well-characterized and reproducible animal model of GVHD in bone marrow transplant patients, which is well know to one of ordinary skill in the art (see, Gleichemann, et al., Immunol. Today 5:324, 1984). Soluble Neutrokine-alpha is expected to induced the proliferation and differentiation of B lymphocyte, and correct the lymphoid hypoplasia and atrophy observed in this animal model of GVHD (Piguet, et al., J. Exp. Med. 166:1280 (1987); Hattori, et al., Blood 90:542 (1997)).

Initiation of the GVHD condition is induced by the intravenous injection of approximately 1-5×$10^8$ spleen cells from C57BL/6 mice into (BALB/c×C57BL/6) F1 mice (both are available from Jackson Lab, Bar Harbor, Me.). Groups of 6 to 8 mice receive daily either 0.1 to 5.0 mg/kg of Neutrokine-alpha or buffer control intraperitoneally, intramascullarly or intradermally starting from the days when lymphoid hypoplasia and atrophy are mild (~day 5), moderate (~day 12) or severe (~day 20) following the parental cell injection. The effect of Neutrokine-alpha on lymphoid hypoplasia and atrophy of spleen is analyzed by FACS and histopathology at multiple time points (3-4) between day 10-30. Briefly, splenocytes are prepared from normal CBF1, GVHD or Neutrokine-alpha-treated mice, and stained with fluorescein phycoerythrin-conjugated anti- H-2Kb, biotin-conjugated anti-H-2Kd, and FITC-conjugated anti-CD4, anti-CD8, or anti-B220, followed by a CyChrome-conjugated avidin. All of these conjugated antibodies can be purchased from PharMingen (San Diego, Calif.). Cells are then analysis on a FACScan (Becton Dickinson, San Jose, Calif.). Recipient and donor lymphocytes are identified as H-2Kb+ Kd+ and H-2Kb+ Kd− cells, respectively. Cell numbers of CD4+T, CD8+T and B220+ B cells of recipient or donor origin are calculated from the total numbers of splenocytes recovered and the percentages of each subpopulation are determined by the three color analysis. Histological evaluation of the relative degree of tissue damage in other GVHD-associated organs (liver, skin and intestine) may be conducted after sacrificing the animals.

Finally, Neutrokine-alpha and buffer-treated animals undergo a clinical evaluation every other day to assess cachexia, body weight and lethality.

Neutrokine-alpha agonists and antagonists may also be examed in this acute GVHD murine model.

Example 9

Isolation of Antibody Fragments Directed Against Neutrokine-alpha Polypeptides from a Library of scFvs Naturally occurring V-genes isolated from human PBLs are constructed into a large library of antibody fragments which contain reactivities against Neutrokine-alpha and/or Neutrokine-alphaSV to which the donor may or may not have been exposed (see e.g., U.S. Pat. No. 5,885,793 incorporated herein in its entirety by reference).

Rescue of the Library.

A library of scFvs is constructed from the RNA of human PBLs as described in WO92/01047 (which is hereby incorporated by reference in its entirety). To rescue phage displaying antibody fragments, approximately $10^9$ *E. coli* harboring the phagemid are used to inoculate 50 ml of 2× TY containing 1% glucose and 100 micrograms/ml of ampicillin (2× TY-AMP-GLU) and grown to an O.D. of 0.8 with shaking. Five ml of this culture is used to inoculate 50 ml of 2× TY-AMP-GLU, 2×$10^8$ TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2× TY containing 100 micrograms/ml ampicillin and 50 micrograms/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells were spun down (IEC-Centra 8, 4000 revs/min for 10 min), resuspended in 300 ml 2× TY broth containing 100 micrograms ampicillin/ml and 25 micrograms kanamycin/ml (2× TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 micrometer filter (Minisart NML; Sartorius) to give a final concentration of approximately $10^{13}$ transducing units/ml (ampicillin-resistant clones).

Panning the Library.

Immunotubes (Nunc) are coated overnight in PBS with 4 ml of either 100 micrograms/ml or 10 micrograms/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 micrograms/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders.

Eluted phage from the third and fourth rounds of selection are used to infect *E. coli* HB 2151 and soluble scFv is produced (Marks, et al., 1991) from single colonies for assay. ELISAs are performed with microtiter plates coated with either 10 picograms/ml of the polypeptide of the present invention in 50 mM bicarbonate pH 9.6. Clones positive in ELISA are further characterized by PCR fingerprinting (see e.g., WO92/01047) and then by sequencing.

Example 10

Neutralization of Neutrokine-alpha/Neutrokine-alpha Receptor Interaction with an Anti-Neutrokine-alpha Monoclonal Antibody Monoclonal antibodies were generated against Neutrokine-alpha protein according to the following method. Briefly, mice were given a subcutaneous injection (front part of the dorsum) of 50 micrograms of His-tagged Neutrokine-alpha protein produced by the method of Example 2 in 100 microliters of PBS emulsified in 100 microliters of complete Freunds adjuvant. Three additional subcutaneous injections of 25 micrograms of Neutrokine-alpha in incomplete Freunds adjuvant were given at 2-week intervals. The animals were rested for a mounth before they received the final intraperitoneal boost of 25 micrograms of Neutrokine-alpha in PBS. Four days later mice were sacrificed and splenocytes taken for fusion.

The process of "Fusion" was accomplished by fusing splenocytes from one spleen were with 2×10E7 P3×63Ag8.653 plasmacytoma cells using PEG 1500 (Boehringer Mannheim), according to the manufacturer's modifications of an earlier described method. (See, Gefter, M. L., et al. Somatic Cell Genet 3:231-36 (1977); Boehringer Mannheim, PEG 1500 (Cat.No. 783641), product description.)

After fusion, the cells were resuspended in 400 ml of HAT medium supplemented with 20% FBS and 4% Hybridoma Supplement (Boehringer Mannheim) and distributed to 96 well plates at a density of 200 microliters per well. At day 7 post-fusion, 100 microliters of medium was aspirated and replaced with 100 microliters of fresh medium. At day 14 post-fusion, the hybridomas were screened for antibody production.

Hybridoma supernatants were screened by ELISA for binding to Neutrokine-alpha protein immobilized on plates. Plates were coated with Neutrokine-alpha by overnight incubation of 100 microliters per well of Neutrokine-alpha in PBS at a concentration of 2 micrograms per ml. Hybridoma supernatants were diluted 1:10 with PBS were placed in individual wells of Neutrokine-alpha-coated plates and incubated overnight at 4° C. On the following day, the plates were washed 3 times with PBS containing 0.1% Tween-20 and developed using the anti-mouse IgG ABC system (Vector Laboratories). The color development reaction was stopped with the addition of 25 ml/well of 2M $H_2SO_4$. The plates were then read at 450 nm.

Hybridoma supernatants were checked for Ig isotype using Isostrips. Cloning was done by the method of limiting dilutions on HT medium. About 3×10E6 cells in 0.9 ml of HBSS were injected in pristane-primed mice. After 7-9 days, ascitic fluid was collected using a 19 g needle. All antibodies were purified by protein G affinity chromatography using the Acta FPLC system (Pharmacia).

After primary and two consecutive subcutaneous injections, all three mice developed a strong immune response; the serum titer was 10E-7 as assessed by ELISA on Neutrokine-alpha-coated plates.

In one experiment, using the splenocytes from the positive mouse more than 1000 primary hybridomas were generated. 917 of them were screened for producing anti-Neutrokine-alpha antibody. Screening was performed using 1:1 diluted supernatants in order to detect all positive clones. Of 917 hybridomas screened, 76 were found to be positive and 17 of those were found to be IgG producers. After affinity testing and cloning, 9 of them were chosen for further expansion and purification.

All purified monoclonal antibodies were able to bind different forms of Neutrokine-alpha (including His-tagged and protein produced from a baculoviral system (see Example 2)) in both Western blot analysis and ELISA. Six of nine clones were also able to bind Neutrokine-alpha on the surface of THP-1 cells. However, none of the antibodies tested were able to capture Neutrokine-alpha from solution.

High affinity anti-Neutrokine-alpha monoclonal antibodies were generated that recognize Neutrokine-alpha expressed on the cell surface but not in solution can be used for neutralization studies in vivo and in monocyte and B cell assays in vitro. These antibodies are also useful for sensitive detection of Neutrokine-alpha on Western blots.

In an independent experiment, using the splenocytes from the positive mouse, more than 1000 primary hybridomas were generated. 729 of the primary hybridomas were then screened for the production of an anti-Neutrokine-alpha antibody. Screening was performed under stringent conditions using 1:10 diluted supernatants in order to pick up only clones of higher affinity. Of 729 hybridomas screened, 23 were positive, including 16 IgM and 7 IgG producers (among the latter, 4 gave a strong IgM background). In this experiment, the isotype distribution of IgG antibodies was biased towards the IgG2 subclasses. Three of seven IgG hybridomas produced antibodies of IgG2a subclass and two produced an antibody of IgG2b subclass, while the remaining two were IgG1 producers.

Supernatants from all positive hybridomas generated in the second experiment were tested for the ability to inhibit Neutrokine-alpha-mediated proliferation of B cells. In the first screening experiment, two hybridomas producing IgG-neutralizing antibodies were detected (these are antibodies 16C9 and 12C5). In additional experiments, the IgG-neutralizing activity of the hybridomas (i.e., 16C9 and 12C5) were confirmed and two additional strongly neutralizing supernatants from hybridomas 15C10 and 4A6 were indentified.

Three clones were subsequently expanded in vivo (a single clone, i.e., 15C10, was also expanded in a hollow fiber system), and the antibody purified by affinity chromatography. All three of the clones were able to bind Neutrokine-alpha on the surface of THP-1 cells and were also able to bind (i.e., "capture") Neutrokine-alpha from solution.

Specifically, experiments were performed using the anti-Neutrokine-alpha monoclonal antibodies described in the second experiment above to determine whether the antibodies neutralize Neutrokine-alpha/Neutrokine-alpha Receptor binding. Briefly, Neutrokine-alpha protein was biotinylated using the EZ-link T NHS-biotin reagent (Pierce, Rockford, Ill.). Biotinylated Neutrokine-alpha was then used to identify cell surface proteins that bind Neutrokine-alpha. Preliminary experiments demonstrated that Neutrokine-alpha binds to a receptor on B lymphoid cells.

The inclusion of anti-Neutrokine-alpha antibodies generated in the second experiment described above neutralized binding of Neutrokine-alpha to a Neutrokine-alpha receptor. In a specific embodiment, anti-Neutrokine-alpha antibody 15C10 neutralizes binding of Neutrokine-alpha to a Neutrokine-alpha Receptor.

Thus, the anti-Neutrokine-alpha monoclonal antibodies generated in the second experiment described above (in particular, antibody 15C10) recognize and bind to both membrane-bound and soluble Neutrokine-alpha protein and neutralize Neutrokine-alpha/Neutrokine-alpha Receptor binding in vitro.

Example 11

Neutrokine-alpha Induced Signalling in B Cells

Total RNA was prepared from tonsillar B cells unstimulated or stimulated with SAC or SAC plus soluble Neutrokine-alpha (amino acids 134-285 of SEQ ID NO:2, 100 ng/mL) for 12 hours. Messenger RNA levels of ERK-1 and PLK was determined by real time quantitaive PCR using ABI 7700 Taqman sequence detector. Amplification primers and probes were designed to span the region from nucleotides 252-332 of the human PLK sequence and nucleotides 373 to 446 of the human ERK-1 mRNA (Genbank accession numbers X75932 and X60188, respectively). For quantitation of RNA, the comparative delta CT method was used (Perkin-Elmer user Bulletin #2 and #4, 1997) using an 18S ribosomal RNA probeas endogenous reference. Expression levels were characterized relative to observed levels in unstimulated B-cells.

Example 12

Rapid and Specific Targeting of Radiolabeled Neutrokine-alpha to Lymphoid Tissues Here, biodistribution studies of radiolabeled Neutrokine-alpha are reported that demonstrate high in vivo targeting specificity of Neutrokine-alpha for lymphoid tissues. Neutrokine-alpha was radiolabeled with $^{125}$I and injected intravenously into BALB/c mice. Three doses and 4 timepoints over a 24-hr period were studied. Biodistribution was measured by direct counting of the radioactivity in dissected whole organs or tissues and by whole body quantitative autoradiography (QAR).

Spleen and lymph nodes showed the highest concentration of radioactivity among the dissected organs and tissues. Three hr after injection of 0.01 mg/kg Neutrokine-alpha, 63% and 23% injected dose (ID)/g were measured in spleen and lymph node, respectively, compared to ~5% for both kidney and liver. As the dose was increased, the % ID/g in spleen and lymph node decreased but was unchanged in liver and kidney, suggesting that targeting to spleen and lymph nodes is mediated by saturable binding. With increasing time, the ratio of the concentration in spleen and lymph node to the concentration in either kidney or liver increased. QAR confirmed the high uptake of radiolabeled Neutrokine-alpha in spleen and lymph nodes at 3 hr, and revealed high uptake in bone marrow, gut-associated lymphoid tissue (GALT) and intestinal contents as well. At 24 hr, spleen, lymph nodes and GALT were still strongly positive for radiolabeled Neutrokine-alpha by QAR whereas liver and kidney no longer had observable levels. A cytotoxic radionuclide coupled to Neutrokine-alpha could irradiate neoplastic B-cells trafficking through or residing in lymphoid tissues. Thus, the rapid and highly specific targeting of radiolabeled Neutrokine-alpha to lymphoid tissues provides a rationale for its application in the treatment of B-cell malignancies.

Example 13

Pharmacological Effects of $^{131}$I-labeled Neutrokine-alpha in BCL1 Tumor-Bearing Mice and J558 Tumor Bearing Mice $^{131}$I-Neutrokine-alpha Administration to BCL1 Tumor-Bearing Mice The BCL1 tumor cell line was derived from a spontaneous murine B cell tumor. Intraperitoneal inoculation of the BCL1 cell line in BALB/c mice results in splenomegaly, and subsequent death. The BCL1 tumor cell phenotype is IgM positive, complement receptor negative, Fe receptor positive and has marginal IgD expression (Knapp et al., J. Immunol. 123:992-999 (1979) and Vitetta et al Blood 89:4425-36. (1997)). Based on FACS analysis using biotinylated Neutrokine-alpha, BCL1 cells freshly isolated from the spleens of BALB/c mice express Neutrokine-alpha receptors on their cell surface. The BCL1 tumor model is a relevant mouse model for human B cell lymphoma, providing a means to test the ability of $^{131}$I-labeled Neutrokine-alpha to kill leukemic B cells and consequently prolong survival of tumor-bearing mice. Three lots of $^{131}$I-labeled Neutrokine-alpha (Lots TX1, TX2 and TX3) were prepared by MDS Nordion (Ontario, Canada) and used in 3 different experiments to evaluate the effects of $^{131}$I-labeled Neutrokine-alpha in this murine model.

Female BALB/c mice were injected intraperitoneally (ip) on Day 0 with $1\times10^5$ viable BCL1 cells that had been propagated in vivo. Treatment groups for the 3 experiments are described in Table VI. Ten days after injection of tumor cells, the animals were administered $^{131}$I-labeled Neutrokine-alpha iv in 110 μL. The doses administered were 11.9 or 15.3 mCi/kg (TX1), 17.5 mCi/kg (TX2), or 37.7 mCi/kg (TX3) for the 3 experiments. To identify potentially toxic effects of the administered $^{131}$I-labeled Neutrokine-alpha, age-matched control BALB/c mice without BCL1 tumors were injected with identical doses of the $^{131}$I-labeled protein. An additional group of BALB/c mice, bearing BCL1 tumors and receiving an iv injection of the vehicle, served as the normal tumor control group. Survival was then monitored for 48, 44, or 40 days for the TX1, TX2, and TX3 experiments, respectively.

TABLE VI

Treatment groups for TX1, TX2 and TX3 experiments

| Exp. | Group | $^{131}$I-Neutrokine-alpha Dose (mCi/kg) | n | BCL1 Tumor Inoculated ip (No. of cells) |
|---|---|---|---|---|
| 1 (TX1) | 1 Vehicle | 0 | 15 | $1 \times 10^5$ |
| | 2 $^{131}$I-Neutrokine-alpha | 11.9 | 10 | $1 \times 10^5$ |
| | 3 $^{131}$I-Neutrokine-alpha | 15.3 | 10 | $1 \times 10^5$ |
| | 4 $^{131}$I-Neutrokine-alpha | 11.9 | 10 | 0 |
| | 5 $^{131}$I-Neutrokine-alpha | 15.3 | 10 | 0 |
| 2 (TX2) | 1 Vehicle | 0 | 12 | $1 \times 10^5$ |
| | 2 $^{131}$I-Neutrokine-alpha | 17.5 | 12 | $1 \times 10^5$ |
| | 3 $^{131}$I-Neutrokine-alpha | 17.5 | 8 | 0 |
| 3 (TX3) | 1 Vehicle | 0 | 14 | $1 \times 10^5$ |
| | 2 $^{131}$I-Neutrokine-alpha | 37.7 | 14 | $1 \times 10^5$ |
| | 3 $^{131}$I-Neutrokine-alpha | 37.7 | 8 | 0 |

The endpoint monitored in the 3 experiments was survival (days) following ip inoculation of BCL1 tumor cells. All animals were examined daily. The day post-inoculation that mice were either found dead or in moribund condition (the latter being immediately euthanized for humane reasons) was recorded.

A single iv administration of either 11.9 or 15.3 mCi/kg (TX1), 17.5 mCi/kg (TX2), or 37.7 mCi/kg (TX3) of $^{131}$I-labeled Neutrokine-alpha injected 10 days after intraperitoneal inoculation of BCL1 cells in BALB/c mice significantly improved survival compared with mice inoculated with tumor and treated with the $^{131}$I-labeled Neutrokine-alpha vehicle (FIGS. 12-14; in FIGS. 12-14, $^{131}$I-labeled Neutrokine-alpha is indicated as LR131). The median survival time for the vehicle-treated, tumor-bearing mice was 18, 21, and 19 days post-tumor cell injection for the TX1, TX2, and TX3 experiments, respectively. In the TX1 experiment, $^{131}$I-labeled Neutrokine-alpha administration at dose levels of 11.9 and 15.3 mCi/kg doubled the median survival time of tumor-bearing mice to 35.5 (11.9 mCi/kg) and 34 (15.3 mCi/kg) days post-treatment, respectively. In the TX2 and TX3 experiments, $^{131}$I-labeled Neutrokine-alpha administration at a dose of 17.5 or 37.7 mCi/kg increased the median survival time of tumor-bearing mice to 30 and 22 days post-treatment, respectively. Tumor-bearing mice treated with all doses of $^{131}$I-labeled Neutrokine-alpha in the 3 experiments had a significantly lower risk of dying than tumor-bearing mice treated with vehicle (Table VII).

TABLE VII

Incidence of mortality for TX1-TX3 experiments

| Experiment | Treatment Group | Median Survival Time (Days) |
|---|---|---|
| TX1 | 1, BCL1 + $^{131}$I-labeled Neutrokine-alpha (11.9 mCi/kg) | 35.5 |
| | 2, BCL1 + $^{131}$I-labeled Neutrokine-alpha (15.3 mCi/kg) | 34 |
| | 3, BCL1 Tumor Only | 18 |
| | 4, No Tumor + $^{131}$I-labeled Neutrokine-alpha (11.9 mCi/kg) | >48 |
| | 5, No Tumor + $^{131}$I-labeled Neutrokine-alpha (15.3 mCi/kg) | >48 |
| TX2 | 1, BCL1 + $^{131}$I-labeled Neutrokine-alpha (17.5 mCi/kg) | 30 |
| | 2, BCL1 Tumor Only + vehicle | 21 |
| | 3, No Tumor + $^{131}$I-labeled Neutrokine-alpha (17.5 mCi/kg) | >44 |
| TX3 | 1, BCL1 + vehicle | 19 |
| | 2, BCL1 + $^{131}$I-labeled Neutrokine-alpha (37.7 mCi/kg) | 22 |
| | 3, No tumor + $^{131}$I-labeled Neutrokine-alpha (37.7 mCi/kg) | >40 |

In the TX1-TX3 series of experiments, the effect that increasing the dose of $^{131}$I-labeled Neutrokine-alpha had on the survival of the BCL1 tumor-bearing animals was investigated. A maximal survival benefit was achieved with the low doses of $^{131}$I-labeled Neutrokine-alpha (11.9 and 15.3 mCi/kg). The much reduced effectiveness of $^{131}$I-labeled Neutrokine-alpha in TX3 may be due to toxicity associated with the high dose of the material used.

In conclusion, a single iv administration of $^{131}$I-labeled Neutrokine-alpha administered to mice bearing BCL1 leukemia cell splenic tumors significantly improved survival compared with tumor-bearing mice treated with vehicle.

$^{131}$I-Neutrokine-alpha Administration to J558 Tumor-Bearing Mice

In a similar experiment as that described above, BALB/c mice were injected subcutaneously with J558 plasmacytoma cells (ATCC # TIB-6) and treated with a single intravenous treatment of 25 mCi/kg of $^{131}$I-labeled Neutrokine-alpha. 24 BALB/c mice (NCI, 4 weeks old, average weight 18 g) were divided into 2 groups (12 mice per group) and injected sc with $2.5\times10^5$ J558 cells in 100 mL of PBS. At Day 9 after injection, mice in Group 1 were injected intavenously with 100 mL of formulation buffer, and mice in Group 2 were injected iv with a dose of 25 mCi/kg of $^{131}$I-Neutrokine-alpha in 100 mL of formulation buffer. The average body weight at the time of $^{131}$I-Neutrokine-alpha injection was 19.5 g.

Two parameters were evaluated during this study the tumor size and the time to tumor response. To evaluate tumor size the short and long axes of the tumor were measured using an electronic digital caliper. Tumor size was calculated by multiplication of the lengths of the short and long axes and expressed in $mm^2$. The time to tumor response was characterized by the day after cell inoculation when a visible tumor (>2 mm) was detected on a mouse. In addition, mice were monitored for survival and signs of radiation induced toxicity (general appearance, activity, breathing frequency, stool consistence).

One mouse in the $^{131}$I-Neutrokine-alpha-treated group died on Day 25 (16 days after $^{131}$I-Neutrokine-alpha treatment) with no obvious signs of radiation related toxicity. A second mouse died in the same group on Day 30, when all animals in the control group were terminated because of large tumor size.

The first tumors of measurable size were detected at Day 14 in the buffer control group, where 4 out of 12 animals developed tumors. In the $^{131}$I-Neutrokine-alpha treated animals, tumor formation was delayed by 6 days. Only one mouse out of 12 developed a tumor at Day 20. At Day 22, there was only one tumor-bearing mouse in the $^{131}$I-Neutrokine-alpha treated group out of 12 animals, whereas in the buffer control group, 11 out of 12 mice developed tumors of different sizes. At Day 27, the mean tumor size in the buffer control group was 489 $mm^2$ (all tumor positive mice in this group were terminated at this time point). In the $^{131}$I-Neutrokine-alpha treated group, the mean tumor size was 32.7 mm2, 15 times smaller than in the buffer control group. Taken together, these data suggest a strong inhibition of J558 tumor development in mice treated with $^{131}$I-Neutrokine-alpha at a dose of 25 mCi/kg and tumor load of $2.5\times10^5$ cells/mouse.

In conclusion, a single intravenous administration of $^{131}$I-Neutrokine-alpha into BALB/c mice at a dose of 25 mCi/kg significantly inhibits subcutaneous growth of J558 plasma cell tumors. At the initial tumor load of 2.5×105 cells/mouse, a 6 day delay in tumor formation and a 15-fold reduction in tumor size was observed in $^{131}$I-Neutrokine-alpha treated animals.

The anti-neoplastic effects of $^{131}$I-Neutrokine-alpha were accompanied by the expected B lymphocyte hypoplasia and a transient (<20 days) depletion of $cKit^+$ bone marrow precursors and peripheral platelets. Peripheral neutrophil, red blood cell, and monocyte counts were unaffected by $^{131}$I-Neutrokine-alpha treatment. Taken together, the results demonstrate that $^{131}$I-Neutrokine-alpha inhibits in vivo tumor growth in two models of B cell neoplasia. Moreover, $^{131}$I-Neutrokine-alpha efficacy was not accompanied by significant bone marrow toxicities or peripheral myelosuppression.

Example 14

Improved Method for Producing Neutrokine-alpha Using a Stringent Promoter and Low Expression Level Neutrokine-alpha has been produced in *Escherichia coli* K-12 from the periplasmic fraction of the cell lysate. Using this system, soluble, properly folded, active Neutrokine-alpha is not obtainable from simple shake flask experiments. Yields of soluble Neutrokine-alpha from complex media fermentations in small and large-scale bioreactors are on the order of 1-5 mg/L. Greater yields (25-38 mg/L) of soluble, properly folded, active Neutrokine-alpha can be accomplished in bioreactors at low to medium cell density under defined medium conditions. Moreover, this low quantity of protein is difficult to purify via conventional methods.

This example describes a method for the production of high yields of soluble, properly folded, active Neutrokine-alpha in the periplasm of *Escherichia coli*, which permits the use of conventional methods for Neutrokine-alpha purification, such as those described below or in Example 2 (paragraphs [0994]-[1004], with modifications for *E. coli*, as would be apparent to one of ordinary skill in the art). Additionally, Neutrokine-alpha protein may be purified using affinity columns comprising Neutrokine-alpha binding peptides such as those described in WO 02/02641, which is herein incorporated by reference in its entirety. Purified Neutrokine-alpha may be quantified using RP-HPLC.

This method relies on the expression of Neutrokine-alpha protein from the bacterial phoA promoter. The phoA promoter is a very tightly regulated system that exhibits a very low level of transcription in the presence of excess phosphate. As the phosphate level in the medium decreases below a threshold of ~4 micromolar (Wanner, B. L., J Cell Biochem 51:47 (1993)), transcription is induced about 1000-fold. The phoA promoter yields a gradual build-up of recombinant protein, instead of a sharp increase of induction that occurs with other systems. This gradual or steady increase in recombinant protein minimizes the chance of overwhelming the components of the bacterial expression system and may also minimize the formation of inclusion bodies. Furthermore, this gradual build up permits the expression of proteins that might have been toxic to the cell if they were induced to high levels over a short period of time.

Expression Vector pML124

The expression vector, pML124, was created using pBR322 as the starting backbone. First, the endogenous NdeI site of pBR322 was eliminated by digesting it with NdeI, filling in the overhanging ends with the Klenow enzyme, then re-ligating the two blunt-ends back together (this created pML123). Next, pML123 was digested with EcoRI and BamHI restriction enzymes and the linear plasmid (loss of ~375 bp of DNA) was agarose gel purified (Qiagen).

The phoA promoter region was PCR-amplified from the *E. coli* K-12 chromosome (W3110; ATCC Catalogue No. 27325) with EcoRI (5') and BamHI (3') engineered sites. NdeI and KpnI sites were also engineered downstream of the phoA promoter to facilitate cloning of recombinant genes. Finally, the Shine-Dalgarno (SD) box was optimized for protein expression. The wild-type SD box and its adjacent sequence is as follows (the putative SD boxes are underlined and in bold):

5'-TTTGTACATGGAGAAAATAAA (SEQ ID NO:56):-[ATG, start of coding sequence]-3'

Optimized SD box and adjacent sequence is as follows:

5'-CACGTAAAGGAAGTATCTCAT (SEQ ID NO:57)-[ATG, start of coding sequence]-3'

The digested (EcoRI and BamHI) and purified phoA promoter PCR product was ligated into the agarose gel purified pML123 (described above). The ligation mixture was transformed into highly competent *E. coli* cells using standard techniques. Positive clones were identified via restriction analysis and DNA sequencing.

pML124 contains a gene for ampicillin resistance, a ColE1 replicon (pBR322-based), Rop, phoA promoter, the optimized Shine-Dalgarno (SD) box (above) and a multiple cloning site. FIG. 15 is a plasmid map of pML124 and SEQ ID NO:52 is the nucleotide sequence of pML124. Additionally, plasmid pML124 was deposited at the American Type Culture Collection (ATCC) on October 8, 2001 and given ATCC Deposit No. PTA-3778. ATCC Deposit Nos. PTA-3778 was made pursuant to the terms of the Budapest Treaty on the International Recognition of the Deposit of Microorganisms for the Purposes of Patent Procedure. The ATCC (American Type Culture Collection) is located at 10801 University Boulevard, Manassas, Va. 20110-2209.

Neutrokine-alpha Expression Vector pML124-MBPssBLyS

A fusion construct of the maltose binding protein signal sequence (MBPss) and Neutrokine-alpha was placed behind the phoA promoter in pML124 as follows. A 549 bp NdeI/KpnI MBPss-Neutrokine-alpha containing DNA insert was ligated into NdeI/KpnI digested and gel purified pML124 to form pML124-MBPss-BLyS. (FIG. 16, SEQ ID NO:53 ATCC Deposit No. PTA-3867, deposited Nov. 16, 2001). ATCC Deposit No. PTA-3867 was made pursuant to the terms of the Budapest Treaty on the International Recognition of the Deposit of Microorganisms for the Purposes of Patent Procedure. The ATCC (American Type Culture Collection) is located at 10801 University Boulevard, Manassas, Va. 20110-2209.

The pML124 plasmid (FIG. 15, SEQ ID NO:52) is described in above and in U.S. Provisional Applications 60/329,508 filed Oct. 17, 2001, 60/329,747 filed Oct. 18, 2001 and 60/331,478 filed Nov. 16, 2001 which are herein incorporated by reference in their entireties. The phoA promoter region is located at nucleotides 111-410 SEQ ID NOs: 52 and 53. The MBP signal sequence is encoded by nucleotides 423-500 of SEQ ID NO:53 and nucleotides 501-959 of SEQ ID NO:53 encode amino acids 134-285 of Neutrokine-alpha (SEQ ID NO:2). The amino acid sequence of the MBP signal sequence is shown in SEQ ID NO:54 and the amino acid sequence of the full length MBP signal sequence-neutrokine-alpha protein encoded by the pML124-MBPss-BLyS vector is shown in SEQ ID NO:55

Neutrokine-alpha Expression in *E. coli*

Plasmid pML124-MBPss-BLyS was transformed into *E. coli* cells, e.g. K-12 based strains, by standard methods. Ampicillin resistant transformants were screened for the proper DNA insert by restriction enzyme analysis and DNA sequence. For example, digestion of pML124-MBPss-BLyS™ with NdeI and KpnI results in two nucleotide fragments: 549 and 4,431 base pairs in length. Positive clones were subsequently grown in City Broth-Low Phosphate media (see recipe below). Neutrokine-alpha expression levels were examined via SDS-PAGE and subsequent Coomassie staining. Using simple shake flask experiments, more than 260 mg/L of Neutrokine-alpha was obtained.

Next, positive clones were grown to high cell density in complex media in small scale bioreactors, similar to the method described by Joly et al., PNAS 95:2773-2777 (1998), which is hereby incorporated by reference in its entirety. Specifically, the initial fermentation medium for the 5L bioreactor was composed of 55.7 mM ammonium sulfate, 13.9 mM sodium monobasic phosphate, 21.9 mM potassium dibasic phosphate, 5 mM sodium citrate, 29.6 mM potassium chloride, 14.7 mM magnesium sulfate, 1.11% NZ-amine AS, 1.11% yeast extract, 5 g/L glucose, 0.002% ferric chloride, 25 □g/ml kanamycin. A trace element solution (2.5 ml/3.4 L) was added containing 100 mM ferric chloride plus 30 mM of the following components: zinc sulfate, cobalt chloride, sodium molybdate, copper sulfate, boric acid and manganese sulfate. The fermenter was operated at 30° C., 650 rpm agitation, 10 standard liter/minute aeration. When the initial glucose was depleted, a concentrated glucose solution (50%) was added until the dissolved oxygen (DO) concentration reached 20% of air saturation as measured by an on-line oxygen electrode. When the optical density (600 nm) reached 40 OD600, a solution of 20% NZ amine AS, 20% yeast extract was fed at 0.2 ml/min for the rest of the fermentation. Neutrokine-alpha production was on the order of 260-570 mg/L.

Low Phosphate Containing Media:

City Broth-Low Phosphate:

30 mM $(NH_4)_2SO_4$; 2.25 mM NaCitrate-$2H_2O$; 12 mM $MgSO_4$; 15 mM KCl; 5% Yeast extract; 2% Casamino acids; 110 mM MOPS; 33 mM Glucose; pH 7.3

Vegan City Broth-Low Phosphate:

30 mM $(NH_4)_2SO_4$; 2.25 mM NaCitrate-$2H_2O$; 12 mM $MgSO_4$; 15 mM KCl; 5% Phytone; 2% Casamino acids; 110 mM MOPS; 33 mM Glucose; pH 7.3

The only difference between the two media is that Phytone is substituted for Yeast extract in the Vegan recipe.

Purification of Neutrokine-alpha 10 grams of *E. coli* cell paste are suspended in 50 milliliters of 5mM sodium citrate, pH 6.0 and placed at 4° C. for 1 hour with gentle shaking. Cells are then disrupted by passing them through an M-Y110 Microfluidizer® Processor (Microfluidics, Inc., Newton, Mass.) set at 7500 psi four times. The suspension is then centrifuged at 22,000×g for twenty minutes at 4° C. using a Sorvall SLA-1500 rotor. The supernatant is then collected and filtered through a 0.45 micron bottle top filter (Nalgene).

Filtered supernatant is then loaded at 9 centimeters/hour on a Fast Flow Sepharose DEAE column (Amersham Biosciences, Piscataway, N.J.) previously equilibrated with 5 mM sodium citrate, pH 6.0 (equilibration buffer). After loading, the column is washed with 5 to 10 column volumes of equilibration buffer. The Neutrokine-alpha protein is eluted with a 200 mM NaCl step in equilibration buffer. Buffers used with the Fast Flow Sepharose DEAE chromatography column are pre-filtered using a 0.22 micron CA bottle top filter (Nalgene) and pre-chilled to 4° C. The Fast Flow Sepharose DEAE column is used at 4° C. Prior to use, columns are cleaned with 0.5 M NaOH.

Relevant fractions, as determined by the ratio of contaminating proteins to Neutrokine-alpha protein seen in Coomassie stained SDS-PAGE gels, are pooled and diluted 1:1 with 10 mM sodium citrate, pH 6.0, 2M $(NH_4)SO_4$. Pooled fractions are loaded at 17 centimeters/hour onto a Polypropylene Glycol Hydrophobic Interaction chromatography column (Tosoh Biosep, Montgomeryville, Pa.) previously equilibrated with 10 mM sodium citrate, pH 6.0, 1M $(NH_4)SO_4$ (loading buffer). After loading, the column is washed with 5-10 volumes of loading buffer. The Neutrokine-alpha protein is eluted with a 5 column volume gradient from loading buffer to elution buffer (10 mM sodium citrate, pH 6.0). Neutrokine-alpha elutes in the second peak toward the end of the gradient absorbance at 280 nm. Buffers used with the Polypropylene Glycol Hydrophobic Interaction chromatography column are pre-filtered using a 0.22 micron CA bottle top filter (Nalgene) and used at room temperature. The Polypropylene Glycol Hydrophobic Interaction chromatography column is also used at room temperature. Prior to use, columns are cleaned with 0.5 M NaOH.

Relevant fractions, determined by the ratio of contaminating proteins to Neutrokine-alpha protein as monitored by Coomassie stained SDS-PAGE gels, are pooled and are dialyzed overnight (12 hours) into 50 mM Tris, pH 7.4, 50 mM NaCl at 4° C. The dialyzed pool is then loaded onto a POROS PI-50 anion exchange chromatography column (Applied Biosystems, Foster City, Calif.), previously equilibrated with 50 mM Tris, pH 7.4, 50 mM NaCl, at 17 centimeters/hour. After loading, column is washed with 5-10 volumes of loading buffer. Neutrokine-alpha is eluted using a pH step from 50 mM Tris, pH 7.4, 50 mM NaCl buffer to 50 mM sodium citrate, pH 6.0. Relevant fractions, as determined by the ratio of contaminating proteins to Neutrokine-alpha protein seen in Coomassie stained SDS-PAGE gels, are pooled and stored at 4° C. Buffers used with the POROS P1-50 anion exchange chromatography column are pre-filtered using a 0.22 micron CA bottle top filter (Nalgene) and pre-chilled to 4° C. The POROS PI-50 anion exchange chromatography column is used at 4° C. Prior to use, columns are cleaned with 0.5 M NaOH.

This purification protocol yields 0.5-1 milligram per gram of starting cell paste based on BCA protein assay (Pierce Biotechnology, Rockford, Ill.) and absorbance at 280 nanometers. The protein is 96% pure as determined by reverse phase-high performance liquid chromatography (RP-HPLC). Native-PAGE and size exclusion chromatography-HPLC (SEC-HPLC) analysis indicates the protein is predominantly in trimeric form.

The production of MBPss-Neutrokine-alpha under control of the phoA promoter allowed more stringent, slower expression, and resulted in increased yields. In summary, the production of Neutrokine-alpha from the phoA system is scaleable and achieves 10 to 20-fold more soluble, properly folded, active material than the current system.

Example 15

Competitive Binding Studies Between Antibody 15C10 and 3D4

To determine if antibodies 15C10 and 3D4 bind similar or distinct epitopes, competitive binding studies were performed Soluble Neutrokine-alpha (amino acids 134-284 of SEQ ID NO:2) was preincubated with 15C10 or 3D4 antibodies. Hereinafter in this example, the antibody with which Neutrokine-alpha was preincubated will be referred to as the “competing antibody”. After preincubation, soluble Neutrokine-alpha-competing antibody complexes were captured on an ELISA plate coated with either 3D4 or 15C10. Hereinafter in this example, the antibody coated on the ELISA plate will be referred to as the “capture antibody”. After binding, and wash steps, soluble Neutrokine-alpha-competing antibody complexes captured on the 3D4 or 15C10-coated ELISA plates was detected using a biotinylated polyclonal anti-Neutrokine-alpha antibody followed by a streptavidin-coupled detection agent such as horse radish peroxidase or alkaline phosphatase.

If there is no competition between the competing antibody and the capture antibody on the ELISA plate (i.e., if the two antibodies bind non-overlapping epitopes), soluble Neutrokine-alpha will be not prevented from binding to the capture antibody on the ELISA plate and the ELISA will give a positive signal. On the other hand, if there is competition between the competing antibody and the capture antibody on the ELISA plate (i.e., if the two antibodies bind overlapping or identical epitopes), a decreased (or no) amount of soluble Neutrokine-alpha will be bound to the ELISA plate and the ELISA will give a decreased signal, compared to the signal given in the absence of competition between the two antibodies.

When an assay similar to that described above was performed using monoclonal antibodies 15C10 and 3D4, it was found that the two antibodies competed with each other, irrespective of which antibody was the competing antibody and which antibody was the capture antibody. These results indicate that 15C10 and 3D4 at least have overlapping epitopes. Isotype matched controls of irrelevant specificity (non-Neutrokine-alpha binding) were not able to compete for binding.

Example 16

Optimization of BLyS Production and Purification from *Escherichia coli*

In this example numbers in square brackets ([#]) refer to the list of references found at the end of this example.

In order to generate large quantities of sBLyS, *Escherichia coli* was chosen as the host for the production of recombinant soluble BLyS (rsBLyS). The initial *E. coli* expression system utilized a high copy number plasmid, pHE4 (see, e.g., U.S. Pat. No. 6,194,168 B1), which contains a strong, isopropyl-β-D-thiogalactopyranoside (IPTG) inducible promoter. From defined media fermentations, this system generated 25-38 mg of rsBLyS per liter of culture. Due to this low level of expression, a BLyS-affinity resin was required to completely capture this quantity of protein. Despite these rsBLyS yields, this process successfully produced sufficient quantities of rsBLyS for use in preclinical studies and early clinical trials.

However, in order to develop a more robust manufacturing process, rsBLyS yields needed to be increased significantly. After testing dozens of host strain and vector combinations, and using multiple growth and induction conditions, high yields of properly folded, biologically active, trimeric rsBLyS were achieved using a phoA promoter system. This promoter has been used for the high yield production of numerous other recombinant proteins [13-18]. Briefly, protein expression is induced by a transmembrane signal transduction system in which the PhoR and PhoB proteins are critical for transcriptional activation [19-22]. Signaling begins when extracellular inorganic phosphate ($P_i$) drops below 4 μM causing membrane-bound PhoR to undergo a conformational change and autophosphorylate [20-22]. Next, PhoR transfers the phosphate moiety to the PhoB protein, which in turn acts as a transcriptional activator for the phoA promoter [20,22]. Activated PhoB also acts as a self-regulating transcriptional activator and as an inducer of PhoR production [19,22-24]. This regulation allows the machinery for the induction of the phoA promoter to gradually build up once $P_i$ levels have dropped below the 4 μM threshold. The result is that a gradual accumulation of heterologous protein occurs, in contrast to the acute induction that is characteristic of promoter systems that rely on exogenous inducers.

This Example details the achievement of small-scale production yields of approximately 435 mg/L using the phoA promoter system. This constitutes at least an 11-fold increase over earlier manufacturing production yields. With this increased level of production, a conventional purification scheme that eliminates the need for the BLyS-affinity resin has also been developed.

Materials and Methods

Media and Reagents

Luria-Bertani broth (LB) was prepared as previously described [25] with the ingredients supplied by Difco. When required, liquid and solid media were supplemented with 25 μg/ml kanamycin (Sigma). All enzymes, including modification enzymes and restriction enzymes, were obtained from New England Biolabs. Taq DNA polymerase was purchased from Roche. Platinum Pfx was obtained from Invitrogen. Ligations were performed using a Fast-Link™ DNA Ligation Kit (Epicentre). Oligonucleotides were purchased from Sigma-Genosys or synthesized in-house. MultiMark® Multi-Colored Standard and Mark12™ unstained standard were purchased from Invitrogen. Low Range Rainbow Molecular Weight Marker was purchased from Amersham Biosciences, Corp. All other chemicals were of analytical grade.

BLyS Plasmid Construction and Bacterial Strains

To construct the phoA inducible rsBLyS production vector, pML123 was used as the backbone. pML123 is identical to pBR322 [26] except that its unique NdeI restriction site has been eliminated. This was accomplished by digesting pBR322 with NdeI, filling in the overhangs with T4 DNA polymerase, and ligating the blunt ends together. Next, a DNA segment containing the phoA promoter region, an optimized Shine-Dalgarno (SD) box, flanking EcoRI and BamHI restriction sites, and a multiple cloning site that includes NdeI and KpnI restriction sites was amplified by polymerase chain reaction (PCR) from the *E. coli* genome. The resulting PCR product was purified and digested with EcoRI and BamHI and ligated into a similarly digested pML123 vector. This intermediate phoA promoter plasmid was named pML124. Next, the codon-optimized rsBLyS gene with a maltose binding protein signal sequence was isolated and gel purified from a previous BLyS production vector by digesting it with NdeI and KpnI. The MBPss-rsBLyS insert was ligated into pML124, generating pML126. Finally, the ampicillin resistance gene of pML126 was replaced with a gene conferring kanamycin resistance. This was accomplished by PCR amplification of the kanamycin resistance gene of pACYC177 [27] using oligonucleotides that created flanking EcoRI and PstI sites. The PCR product was digested with PstI and the overhanging end was filled in using the T4 DNA polymerase. This fragment was then digested with EcoRI and ligated into pML126 that had been digested with EcoRI and ScaI. The resulting plasmid was designated p2615 (FIG. 2). All constructs were confirmed by DNA sequencing and restriction endonuclease analyses (data not shown).

For the production of rsBLyS, the phoA production vector, p2615, was transformed into the *E. coli* K-12 host W3110 (F-, λ-, mcrA, mcrB, IN(rrnD-rrnE)1, rph1, ilvG) [28]. This strain, designated 8D1, was propagated in LB supplemented with kanamycin (25 μg/ml).

Shake Flask Production of rsBLyS

Strain 8D1 was tested for rsBLyS expression in shake flasks using a complex, low phosphate medium known as C.R.A.P. [18]. A MOPS solution is used to buffer this medium since it contains minimal quantities of phosphate or other buffering agents. Typically, 800 mL of C.R.A.P. was aseptically added to a 4-L baffled shake flask along with 25 mg/L of kanamycin for plasmid retention. Shake flasks were inoculated to a starting $OD_{600}$ of 0.1 from an overnight culture grown in LB supplemented with kanamycin (25 mg/L). Cultures were grown for 18 hr at 30° C. and 220 rpm in an Innova 4300 shaker/incubator (New Brunswick Scientific, Inc) Cells were harvested by centrifugation at 5,663 rcf for 15 min and yielded about 9 grams of cell paste per liter of culture.

SDS-PAGE and Western Blot Analysis

BLyS protein production and purification was examined via SDS-PAGE [29,30] on 18% Novex® Tris-glycine gels (Invitrogen). For Western blot analyses, proteins were transferred to nitrocellulose membranes (0.22 □m; Invitrogen)

after SDS-PAGE using a BIO-RAD Trans-Blot Semi-Dry electrophoretic cell [31]. Western blot analyses were carried out using a BLyS-specific mouse monoclonal antibody (internal), followed by a phosphatase-labeled goat □-mouse IgG obtained from Kirkegaard & Perry Laboratories (KPL). Western Blue Stabilized Substrate (Promega) for alkaline phosphatase was used for detection.

Fermentation Set-up and Operation

A starter culture of the appropriate strain was grown in 1 L of MLB medium (12 g/L yeast extract (Difco), 7 g/L NaCl, 2.5 g/L phytone (Becton Dickinson), and 0.2 g/L L-methionine) and kanamycin (25 mg/L) in a 4-L baffled shake flask. Shake flask cultures were inoculated with one seed vial (1.5 ml) and grown at 220 rpm and 30° C. until the culture reached an $OD_{600}$ of 2-3. The culture was used to inoculate fermentors to a starting $OD_{600}$ of 0.2.

Medium-cell density production of rsBLyS was performed using 5-L Bioflo 3000 fermentors from New Brunswick Scientific, Inc. Fermentations were performed in semi-defined media in a manner similar to that described previously [18] using the following parameters: 30° C., pH 7, airflow 5 Lpm (1 vvm), agitation 650 rpm, and dissolved oxygen (DO) 30%. The $OD_{600}$ of the culture was tested frequently using a Genesys 8 spectrophotometer (Spectronic Unicam). Additional samples were tested for glucose concentration using the YSI 2700 Select Biochemistry Analyzer equipped with the YSI 2365 Glucose Membrane (YSI Inc.). The culture was allowed to grow for a total of 48 hours and then harvested by centrifugation at 4369 rcf for 25 min.

Affinity Purification of rsBLyS

*E. coli* cell paste (~10 g) expressing rsBLyS was resuspended in 80 milliliters of 100 mM Tris pH 7 at 4° C. for 1 hr with stirring. Cells were disrupted with four passes through an M-Y110 Microfluidizer (Microfluidics, Inc.) set to 7,500 psi, and then centrifuged at 22,000 rcf for 20 min at 4° C. The supernatant was filtered through a 0.2 μm cellulose acetate (CA) membrane (Corning Inc.) and loaded at 100 cm/hr on a 1.6 cm (ID)×4 cm (h) Octyl Sepharose (Amersham Biosciences) column in tandem with a 1.6 cm (ID)×3.5 cm (h) BLyS-affinity column; both were equilibrated with 100 mM Tris pH 7. The Octyl Sepharose column was used as a negative purification step to remove host cell proteins, DNA and lipids. Host proteins were removed with a 1 M NaCl salt wash in the same buffer. rsBLyS was eluted with a pH step from the load buffer to 100 mM NaAcetate pH 4.5, 50% Ethylene Glycol. Relevant fractions containing rsBLyS as judged by the ratio of rsBLyS to host cell proteins were pooled and dialyzed into 10 mM NaCitrate pH 6, 140 mM NaCl and stored at 4° C. Samples were analyzed via SDS-polyacrylamide gel electrophoresis (SDS-PAGE) and Coomassie staining. RP-HPLC analyses were performed on a Waters Alliance 2690 Separations Module with 996 Photodiode Array Detector (Waters, Inc.) using a 5 □m, 50 mm by 2 mm BetaBasic CYANO column (Keystone Scientific, Inc.). To quantify BLyS protein concentrations via HPLC, a 50 ml blank of final buffer was injected at the beginning of each sample set and then subtracted from all standards and samples to eliminate any potential background peaks caused by the elution buffer. A standard curve was run with each sample set consisting of 0.5 mg, 5 mg, and 10 mg by injecting 2.5 ml, 25 ml, and 50 ml respectively of a 0.2 mg/ml BlyS standard. The amount of BLyS in each sample was then quantified based on the sample peak area compared to the standard curve.

Conventional Purification of rsBLyS

*E. coli* cell paste (~7 g) was resuspended in 40 milliliters of 5 mM NaCitrate pH 6 at 4° C. for 1 hr with stirring. The cells were disrupted with four passes through an M-Y110 Microfluidizer set to 7,500 psi. The suspension was centrifuged at 22,000 ref for 20 min at 4° C. The supernatant was collected and filtered through a 0.2 μm CA membrane. The filtrate was loaded at 60 cm/hr onto a 2.6 cm (ID)×12 cm (h) Fast Flow Sepharose DEAE (Amersham Biosciences) column that had been equilibrated with 5 mM NaCitrate pH 6 (Equilibration Buffer 1). After loading, the column was washed with 10 column volumes (CV) of Equilibration Buffer 1. Soluble, trimeric rsBLyS was eluted with a 200 mM NaCl step in the same buffer.

Relevant fractions were determined by the ratio of contaminating proteins to rsBLyS as observed via SDS-PAGE followed by Coomassie staining. Fractions were pooled (30 milliliters) and diluted 1:1 with 10 mM NaCitrate, pH 6, 2 M $(NH_4)_2SO_4$ and loaded at 150 cm/hr onto a 1.6 cm (ID)×11 cm (h) Polypropylene Glycol (PPG) HIC (Tosoh Biosep) column that had been equilibrated with 10 mM NaCitrate pH 6, 1 M $(NH_4)_2SO_4$ (Equilibration Buffer 2). After loading, the column was washed with 10 CV of Equilibration Buffer 2. Elution of rsBLyS was accomplished with a 5 CV gradient from Equilibration Buffer 2 to 10 mM NaCitrate pH 6.

Fractions containing rsBLyS were pooled (50 milliliters), concentrated to 15 milliliters and dialyzed in 1 liter of 50 mM Tris pH 7.4, 50 mM NaCl for 12 hr at 4° C. with stirring. The dialyzed pool (~15 milliliters) was loaded at 150 cm/hr onto a 1.6 cm (ID)×10.4 cm (h) POROS PI-50 (Applied Biosystems) column equilibrated with 50 mM Tris pH 7.4, 50 mM NaCl (Equilibration Buffer 3). This column was then washed with 5 CV of Equilibration Buffer 3 and purified rsBLyS was eluted with a pH step from the Equilibration Buffer 3 to 50 mM NaCitrate pH 6. All purification steps were performed at 4° C. and all buffers were filtered prior to use with a 0.2 μm CA bottle top filter. Aliquots of rsBLyS were stored at −80° C. RP-HPLC analysis was performed as described above.

Preparation of Bacterial Lysates and rsBLyS Analysis

Cells from 8D1 shake flask and fermentor cultures were harvested at regular intervals, normalized to the same OD600 (0.5) per ml and pelleted at 16,100 rcf. Pellets were stored at −20° C. Whole cell lysates were prepared by boiling the normalized cell pellets in 100 μL SDS-PAGE sample buffer (Invitrogen) containing 5% β-mercaptoethanol for 5 min. Then, 20 μL of each sample was analyzed via SDS-PAGE or on 18% Novex® glycine gels (Invitrogen) followed by Coomassie staining and Western blotting.

In order to analyze the soluble and insoluble protein fractions, cell paste was resuspended in PBS so that resuspensions being compared were of equivalent $OD_{600}$. These resuspensions were passed through an M-Y110 Microfluidizer four times at 7,500 psi to ensure that nearly all cells had been ruptured. Aliquots of 1 ml were then taken from the cell lysates and microcentrifuged at 16,100 rcf to pellet the insoluble material. Supernatants were transferred to a separate tube and the insoluble pellet was resupended in 1 ml of PBS. The resulting soluble and insoluble fractions were each mixed in a 1:1 ratio with SDS-PAGE sample buffer containing 5% β-mercaptoethanol and boiled for 5 min. Equal volumes were analyzed via SDS-PAGE on 18% Novex® Tris-glycine gels in followed by Western Blotting.

B Cell Proliferation Assay

The biological activity of purified rsBLyS was tested in a murine B cell proliferation assay as described previously [32]Unpurified murine splenocytes were plated at $10^5$/well, in the presence of rsBLyS and *Staphylococcus aureus* cells (SAC), using a final dilution of 1:100,000. Cells were incubated at 37° C. for 72 hr, after which they were pulsed with 0.5 mCi/well of $^3$H-thymidine for 20 to 24 hr, and then harvested. Incorporation of thymidine was used as a measure of cellular proliferation. The BLyS positive control was from a previously defined reference standard purified from Baculovirus [33].

Results

Expression of rsBLyS in Shake Flask Cultures

The codon-optimized gene encoding rsBLyS was cloned behind the phoA promoter in an attempt to increase yields. This production plasmid, p2615, was transformed into W3110, host 8D1, and rsBLyS expression was monitored in C.R.A.P. medium [18] as described in the Materials and methods. Yields were determined by purifying rsBLyS using the BLyS-affinity resin and quantifying the protein via HPLC. Initial screening of rsBLyS production from 8D1 in shake flask cultures typically yielded 1 mg of rsBLyS per gram of cell paste. Shake flask yields from the previous production vector (data not shown) and host combination, production strain 3C3, averaged only 0.04 mg/g. The use of p2615 increased shake flask yields 25-fold based on milligrams of rsBLyS per g of cell paste, or 75-fold when compared as mg of rsBLyS per L of culture (the g/L of cell paste is increased three-fold for C.R.A.P. compared to LB). Based on Western blot data, the overall increase in rsBLyS production stems mainly from a sizable increase in cellular production. Examination of soluble and insoluble fractions of the induced cell paste showed that 8D1 actually contains a higher percentage of insoluble monomeric BLyS. Whole cell lysates revealed an overall increase in total cellular production of monomeric BLyS.

rsBLyS Production in Bioreactors

Next, strain 8D1 was grown in 5-L fermentors to examine whether the increased rsBLyS yields could be maintained, or even amplified, at a larger scale. The 5-L fermentation strategy allowed the culture to grow to a final $OD_{600}$ of 130-140 and gave a wet cell weight of 125-145 g/L. Typically, the batch glucose would be exhausted at an elapsed fermentation time (EFT) of 8-9 hours at which point the 50% glucose feed would be activated to maintain the DO at 30%. The glucose feed reached a maximum rate around an EFT of 15 hours and then dropped off significantly over the next 8 hours. After this dynamic flux in the glucose feed rate, a small increase in the feed rate was observed followed by a reduction over the remainder of the fermentation. This pattern of glucose uptake was common to all similarly run fermentations using the 8D1 host. The growth of the culture was characterized by an initial logarithmic growth phase followed by a prolonged linear phase. The logarithmic phase lasted for the first 10 hours of the fermentation while the cells consumed the batch glucose. Once the batch glucose was exhausted and the glucose feed was started, the culture shifted into a steady linear growth phase that continued to the end of the run. At an EFT of 15 hours, induction of the phoA promoter and consummate production of rsBLyS was initiated. This induction point also coincides with fluctuations in the glucose feed rate describe above. rsBLyS gradually builds up per $OD_{600}$ until the end of the fermentation. Similar to the shake flask experiments, a large portion of the BLyS produced by 8D1 in fermentors was insoluble but overall cellular production was increased when compared to a previous bioreactor process. The increased yields may also be attributed in part to the increased biomass of the culture. Final volumetric yields of periplasmic, properly folded, biologically active, trimeric rsBLyS from 5-L fermentations reached levels above 435 mg/L (equivalent to about 3 mg of rsBLyS per g of cell paste).

Conventional Purification and Characterization of rsBLyS

Host and vector modifications, as well as fermentation optimization, dramatically increased rsBLyS production from *E. coli*. The rsBLyS production process described in this work permits the protein to be purified using commercially available, conventional resins. For example, trimeric rsBLyS was purified from *E. coli* cell paste using resins and buffers that were cost efficient and amenable to a larger manufacturing scale. The first step consisted of a Fast Flow Sepharose DEAE column (Table VIII) and used a low concentration of sodium citrate to enhance rsBLyS capture. A PPG HIC column was used next, followed by a POROS PI-50 to eliminate residual contaminants (Table VIII). Endotoxin levels were measured by LAL and it was determined that the POROS PI-50 column was also effective in reducing the level of endotoxin contamination (Table VIII). Purification yields were determined by $OD_{280}$ and RP-HPLC analyses and were found to be about 0.76 mg of rsBLyS per gram of cell paste (~110 mg/L).

TABLE VIII

Conventional Purification Scheme for rsBLyS[a]

| Step | Principle | Total Protein (mg) | Percent Total protein[b] | Approximate mg rsBLyS | Cumulative Yield (%)[c] | Endotoxin Level (EU/ml) |
|---|---|---|---|---|---|---|
| 1 | Cell lysis | 900 | 2-3 | 21 | 100 | N/D |
| 2 | Sepaharose FF DEAE | 116 | 12 | 14 | 67 | 25,900 |
| 3 | Polypropylene glycol HIC | 51 | 20 | 10 | 48 | 1,950 |
| 4 | POROS PI-50 | 5.5 | >97 | 5.3 | 25 | 0.245 |

[a]Based on the purification from 7 g of fermentation cell paste.
[b]Percentage of rsBLyS compared to total protein. Numbers based on SDS-PAGE analysis except for Step 4, which is based on RP-HPLC.
[c]Percentage of cumulative rsBLyS recovered based on SDS-PAGE analysis.
N/D = not determined Methods to characterize the final purified product were employed to determine the level of purity and biological activity. The final product was judged to be 97% pure by means of RP-HPLC (data not shown) and appeared to be identical to the material used previously for clinical trials. Moreover, rsBLyS produced by this process and purified via conventional resins was examined in B cell proliferation assays. The results showed that rsBLyS produced by this conventional scheme exhibited similar or slightly increased biological activity.

Discussion

In this work, an expression plasmid and host combination was generated that yielded a high concentration of rsBLyS from *E. coli*. This system utilized the phoA promoter to maximize periplasmic expression of the heterologous protein. Initial shake flask yields were increased to 1 mg of rsBLyS per gram of cell paste over the 0.04 mg/g produced by a previous expression system. Additionally, a 5-L fermentation process was developed for this expression system that yields 435 mg of purified rsBLyS per L of culture (3 mg of rsBLyS per g of cell paste). This is an 11-fold increase over earlier manufacturing production yields. The increased yields appear to stem from a large increase in overall cellular production and have facilitated the development of a conventional purification scheme that eliminates the need for the BLyS-affinity resin.

The inventors have found that when optimizing IPTG-induced, rsBLyS production in *E. coli*, periplasmic expression of the protein was necessary to obtain any appreciable amounts of properly folded, trimeric rsBLyS. Moreover, it was discovered that the MBP signal sequence in combination with the codon-optimized BLyS gene exhibited the best ratio of mature to precursor protein. The expression vector was further refined to include the use of the phoA promoter. The use of this promoter system led to the largest increase of rsBLyS yields. Furthermore, the copy number of the production plasmid was also reduced, however, copy number seems to be of only minor significance since lower copy number IPTG-inducible vectors were tested without success.

Previous work has shown the phoA promoter to be superior to other induction systems for the production of periplasmically targeted recombinant proteins [13-18]. This may be due to the fact that the phoA promoter allows for the gradual build up of recombinant protein versus the acute induction characteristic of other promoter systems. A slower build up of recombinant protein may not only permit or enhance proper folding but it also allows the cells to adjust to potentially toxic proteins when compared to the rapid accumulation indicative of other promoter systems [34, 35]. In addition, slower recombinant protein production is less likely to overload protein synthesis components or the secretion apparatus [35]. These factors can be highly beneficial to the bacterial production workhorse and may allow the cell to maintain its regular cellular functions during the induction phase.

The implementation of a phosphate depleted small-scale fermentation was used successfully for the production of rsBLyS. In contrast to the current production system, the exogenous inducer, IPTG, is not required for protein expression. This is a point of interest because it not only avoids the addition of another reagent to the fermentor, but also eliminates a large cost component of the fermentation process. In addition, the glucose feed has been simplified and there is no need for other additions (i.e. salt feeds). The only drawback to the process is that the total run time is nearly twice that of the current manufacturing production process. If the time necessary for protein recovery and turn over of the fermentors is taken into consideration, as well as the difference in rsBLyS yields between these two production systems, this extended fermentation time is of little significance.

The increased rsBLyS yields described in this example allowed for the development of a purification scheme that utilizes conventional resins. This is of utmost importance since the affinity resin currently being used to purify rsBLyS is specially manufactured strictly for that task. This fact makes it a large cost component of the recovery process. Therefore, the use of conventional resins will result in a large reduction in the costs associated with the purification of rsBLyS. Furthermore, the resins chosen for the conventional purification of rsBLyS are completely scaleable which is crucial to any future manufacturing plans involving rsBLyS.

List of References for Example 16

1. P. A. Moore, O. Belvedere, A. Orr, K. Pieri, D. W. LaFleur, P. Feng, D. Soppet, M. Charters, R. Gentz, D. Parmelee, Y. Li, O. Galperina, J. Giri, V. Rocshke, B. Nardelli, J. Carrell, S. Sosnovtseva, W. Greenfield, S. M. Ruben, H. S. Olsen, J. Fikes, D. M. Hilbert, BLyS: Member of the tumor necrosis factor family and B lymphocyte stimulator, Science 285 (1999) 260-263.
2. P. Schneider, F. MacKay, V. Steiner, K. Hofmann, J. L. Bodmer, N. Holler, C. Ambrose, P. Lawton, S. Bixler, H. Acha-Orbea, D. Valmori, P. Romero, C. Werner-Favre, R. H. Zubler, J. L. Browning, J. Tschopp, BAFF, a novel ligand of the tumor necrosis factor family, stimulates B cell growth, J. Exp. Med. 189 (1999)1747-1756.
3. B. Nardelli, O. Belvedere, V. Roschke, P. A. Moore, H. S. Olsen, T. S. Migone, S. Sosnovtseva, J. A. Carrell, P. Feng, J. G. Giri, D. M. Hilbert, Synthesis and release of B-lymphocyte stimulator from myeloid cells, Blood 97 (2001) 198-204.
4. S. D. Khare, I. Sarosi, X.-Z. Xia, S. McCabe, K. Miner, I. Solovyev, N. Hawkins, M. Kelley, D. Chang, G. Van, L. Ross, J. Delaney, L. Wang, D. Lacey, W. J. Boyle, H. Hsu, Severe B cell hyperplasia and autoimmune disease in TALL-1 transgenic mice, Proc. Natl. Acad. Sci. U.S.A. 97 (2000) 3370-3375.
5. T. J. Parry, T. A. Riccobene, S. J. Strawn, R. Williams, R. Daoud, J. Carrell, S. Sosnovtseva, R. C. Miceli, C. M. Poortman, L. Sekut, Y. Li, J. Fikes, C. Sung, Pharmacokinetics and immunological effects of exogenously administered recombinant human B lymphocyte stimulator (BLyS) in mice, J. Pharmacol. Exp. Ther. 296 (2001) 396-404.
6. Y. Wu, D. Bressette, J. A. Carrell, T. Kaufman, P. Feng, K. Taylor, Y. Gan, Y. H. Cho, A. D. Garcia, E. Gollatz, D. Dimke, D. LaFleur, T. S. Migone, B. Nardelli, P. Wei, S. M. Ruben, S. J. Ullrich, H. S. Olsen, P. Kanakaraj, P. A. Moore, K. P. Baker, Tumor necrosis factor (TNF) receptor superfamily member TACI is a high affinity receptor for TNF family members APRIL and BLyS, J. Biol. Chem. 275 (2000) 35478-35485.
7. G. Yu, T. Boone, J. Delaney, N. Hawkins, M. Kelley, M. Ramakrishnan, S. McCabe, W. R. Qiu, M. Kornuc, X. Z. Xia, J. Guo, M. Stolina, W. J. Boyle, I. Sarosi, H. Hsu, G. Senaldi, L. E. Theill, APRIL and TALL-I and receptors BCMA and TACI: system for regulating humoral immunity, Nat. Immunol. 1 (2000) 252-256.
8. J. A. Gross, J. Johnston, S. Mudri, R. Enselman, S. R. Dillon, K. Madden, W. Xu, J. Parrish-Novak, D. Foster, C. Lofton-Day, M. Moore, A. Littau, A. Grossman, H. Haugen, K. Foley, H. Blumberg, K. Harrison, W. Kindsvogel, C. H. Clegg, TACI and BCMA are receptors for a TNF homologue implicated in B-cell autoimmune disease, Nature 404 (2000) 995-999.
9. J. S. Thompson, S. A. Bixler, F. Qian, K. Vora, M. L. Scott, T. G. Cachero, C. Hession, P. Schneider, I. D. Sizing, C. Mullen, K. Strauch, M. Zafari, C. D. Benjamin, J. Tschopp, J. L. Browning, C. Ambrose, BAFF-R, a newly identified TNF receptor that specifically interacts with BAFF, Science 293 (2001) 2108-2111.
10. R. K. Do, E. Hatada, H. Lee, M. R. Tourigny, D. Hilbert, S. Chen-Kiang, Attenuation of apoptosis underlies B lymphocyte stimulator enhancement of humoral immune response, J. Exp. Med. 192 (2000) 953-964.
11. B. Nardelli, P. A. Moore, Y. Li, D. M. Hilbert, B lymphocyte stimulator (BLyS): a therapeutic trichotomy for the treatment of B lymphocyte diseases, Leuk. Lymphoma 43 (2002) 1367-1373.
12. J. Zhang, V. Roschke, K. P. Baker, Z. Wang, G. S. Alarcon, B. J. Fessler, H. Bastian, R. P. Kimberly, T. Zhou, Cutting edge: a role for B lymphocyte stimulator in systemic lupus erythematosus, J. Immunol. 166 (2001) 6-10.

13. C. J. Paddon, R. W. Hartley, Expression of *Bacillus amyloliquefaciens* extracellular ribonuclease (bamase) in *Escherichia coli* following an inactivating mutation, Gene 53 (1987)11-19.
14. C. N. Chang, M. Rey, B. Bochner, H. Heyneker, G. Gray, High-level secretion of human growth hormone by *Escherichia coli*, Gene 55 (1987)189-196.
15. J. H. Lee, D. N. Garboczi, P. J. Thomas, P. L. Pedersen, Mitochondrial ATP synthase. cDNA cloning, amino acid sequence, overexpression, and properties of the rat liver alpha subunit, J. Biol. Chem. 265 (1990) 4664-4669.
16. J. C. Joly, W. S. Leung, J. R. Swartz, Overexpression of *Escherichia coli* oxidoreductases increases recombinant insulin-like growth factor-1 accumulation, Proc. Natl. Acad. Sci. U.S.A. 95 (1998) 2773-2777.
17. R. Xu, P. Du, J. J. Fan, Q. Zhang, T. P. Li, R. B. Gan, High-level expression and secretion of recombinant mouse endostatin by *Escherichia coli*, Protein Expr. Purif. 24 (2002) 453-459.
18. L. C. Simmons, D. Reilly, L. Klimowski, T. S. Raju, G. Meng, P. Sims, K. Hong, R. L. Shields, L. A. Damico, P. Rancatore, D. G. Yansura, Expression of full-length immunoglobulins in *Escherichia coli*: rapid and efficient production of aglycosylated antibodies, J. Immunol. Methods 263 (2002) 133-147.
19. K. Makino, H. Shinagawa, M. Amemura, A. Nakata, Nucleotide sequence of the phoB gene, the positive regulatory gene for the phosphate regulon of *Escherichia coil* K-12, J. Mol. Biol. 190 (1986) 37-44.
20. K. Makino, H. Shinagawa, M. Amemura, T. Kawamoto, M. Yamada, A. Nakata, Signal transduction in the phosphate regulon of *Escherichia coli* involves phosphotransfer between PhoR and PhoB proteins, J. Mol. Biol. 210 (1989) 551-559.
21. M. Yamada, K. Makino, H. Shinagawa, A. Nakata, Regulation of the phosphate regulon of *Escherichia coli*: properties of phoR deletion mutants and subcellular localization of PhoR protein, Mol. Gen. Genet. 220 (1990) 366-372.
22. B. L. Wanner, Phosphorus assimilation and control of the phosphate regulon, in: F. C. Neidhardt, R. Curtis, J. L. Ingraham, E. C. C. Lin, K. B. Low, B. Magasanik, W. S. Reznikoff, M. Riley, M. Schaechter, H. E. Umbarger (Eds.), *Escherchia coli* and *Salmonella typhimurium*: cellular and molecular biology, American Society for Microbiology, Washington, D.C., 1996, pp. 1357-1381.
23. C. D. Guan, B. Wanner, H. Inouye, Analysis of regulation of phob expression using a phoB-cat fusion, J. Bacteriol. 156 (1983) 710-717.
24. K. Makino, H. Shinagawa, A. Nakata, Regulation of the phosphate regulon of *Escherichia coli* K-12: regulation and role of the regulatory gene phoR, J. Mol. Biol. 184 (1985) 231-240.
25. T. J. Silhavy, M. L. Berman, L. W. Enquist, Experiments with Gene Fusions, Cold Spring Harbor Laboratory Press, Cold Spring Harbor, N.Y., 1984.
26. F. Bolivar, R. L. Rodriguez, M. C. Betlach, H. W. Boyer, Construction and characterization of new cloning vehicles I. Ampicillin-resistant derivatives of the plasmid pMB9. Gene 2 (1977) 75-93.
27. R. E. Rose, The nucleotide sequence of pACYC177, Nucleic Acids Res. 16 (1988) 356.
28. C. W. Hill, B. W. Hamish, Inversions between ribosomal RNA genes of *Escherchia coli*, Pro. Natl. Acad. Sci. U.S.A. 78 (1981) 7069-7072.
29. U. K. Laemmli, Cleavage of structural proteins during the assembly of the head of bacteriophage T4, Nature 227 (1970) 680-685.
30. B. Lugtenberg, J. Meijers, R. Peters, P. van der Hoek, L. van Alphen, Electrophoretic resolution of the major outer-membrane proteins of *Escherichia coli* K-12 into four bands, FEBS Lett. (1975) 254-258.
31. H. Towbin, T. Staehelin, J. Gordon, Electrophoretic transfer of proteins from polyacrylamide gels to nitrocellulose sheets: procedure and some applications, Proc. Natl. Acad. Sci. U.S.A. 76 (1979) 4350-4354.
32. V. Roschke, S. Sosnovtseva, C. D. Ward, J. S. Hong, R. Smith, V. Albert, W. Stohl, K. P. Baker, S. Ullrich, B. Nardelli, D. M. Hilbert, T. S. Migone, BLyS and APRIL form biologically active heterotrimers that are expressed in patients with systemic immune-based rheumatic diseases, J. Immunol. 169 (2002) 4314-4321.
33. Oren, D. A., Y. Li, Y. Volovik, T. S. Morris, C. Dharia, K. Das, O. Galperina, R. Gentz, E. Arnold, Structural basis of BLyS receptor recognition, Nat. Struct. Biol. 9 (2002) 288-292.
34. G. Sawers, M. Jarsch, Alternative regulation principles for the production of recombinant proteins in *Escherichia coli*, Appl. Microbiol. Biotechnol. 46 (1996) 1-9.
35. J. Sambrook, D. W. Russell, Expression of secreted foreign Proteins using the alkaline phosphatase promoter (phoA) and signal sequence, in: Molecular Cloning: A Laboratory Manual, Cold Spring Harbor Laboratory Press, Cold Spring Harbor, N.Y., 2001,pp. 15.30-15.35.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith in both computer and paper forms are hereby incorporated by reference in their entireties. Additionally, the entire disclosure (including the specification, sequence listing, and drawings) of each of the following U.S. Provisional and Non-Provisional Patent Applications and International Patent Applications are herein incorporated by reference in their entireties: U.S. Provisional Application Nos. 60/543,261 filed Feb. 11, 2004, 60/580,387 filed Jun. 18, 2004, 60/617,191 filed Oct. 12, 2004, 60/368,548 filed Apr. 1, 2002, 60/336,726 filed Dec. 7, 2001, 60/331,478 filed Nov. 16, 2001, 60/330,835 filed Oct. 31, 2001, 60/329,747 filed Oct. 18, 2001, and 60/329,508 filed Oct. 17, 2001, 60/225,628 filed Aug. 15, 2000, 60/227,008 filed Aug. 23, 2000, 60/234,338 filed Sep. 22, 2000, 60/240,806 filed Oct. 17, 2000, 60/250,020 filed Nov. 30, 2000, 60/276,248 filed Mar. 6, 2001, 60/293,499 filed May 25, 2001, 60/296,122 filed Jun. 7, 2001, 60/304,809 filed Jul. 13 2001, 60/122,388 filed Mar. 2, 1999, 60/124,097 filed Mar. 12, 1999, 60/126,599 filed Mar. 26, 2000, 60/127,598 filed Apr. 2,1999, 60/130,412 filed Apr. 16, 1999, 60/130,696 filed Apr. 23, 1999, 60/131,278 filed Apr. 27, 1999, 60/131,673 filed Apr. 29, 1999, 60/136,784 filed May 28, 1999, 60/142,659 filed Jul. 6, 1999, 60/145,824 filed Jul. 27, 1999, 60/167,239 filed Nov. 24, 1999, 60/168,624 filed Dec. 3, 1999, 60/171,108 filed Dec. 16, 1999, 60/171,626 filed Dec. 23, 1999, 60/176,015 filed Jan. 14, 2000, and 60/036,100 filed Jan. 14, 1997; U.S. Nonprovisional application Ser. No. 10,739,042 filed Dec. 19, 2003, Ser. No. 10/735,865 filed Dec. 16, 2003, Ser. No. 10/270,487 filed Oct. 16, 2002, Ser. No. 09/929,493, filed Aug. 14, 2001, Ser. No. 09/588,947 filed Jun. 8, 2000, Ser. No. 09/589,285 filed Jun. 8, 2000, Ser. No. 09/589,286 filed Jun. 8, 2000, Ser. No. 09/589,287 filed Jun. 8, 2000, Ser. No. 09/589/288 filed Jun. 8, 2000, Ser. No. 09/507,968 filed Feb. 22, 2000, Ser. No. 09/255,794 filed Feb. 23, 1999, and Ser. No. 09/005,874 filed Jan. 12, 1998; and International Patent Application Serial Nos. PCT/US01/25549 filed Aug. 15, 2001, PCT/US00/04336, filed Feb. 22, 2000, and PCT/US96/17957, filed Oct. 25, 1996.

What is claimed is:

1. An isolated protein comprising a Neutrokine-alpha protein fused to a toxin protein, wherein said Neutrokine-alpha protein comprises an amino acid sequence selected from the group consisting of:

(a) the amino acid sequence of amino acid residues 134-285 of SEQ ID NO:2; and (b) an amino acid sequence that is at least 90% identical to amino acid residues 134-285 of SEQ ID NO:2.

2. The protein of claim 1, wherein said toxin protein is selected from the group consisting of:

(a) a ribosome inactivating protein;

(b) a cytotoxin; and (c) a cytotoxic prodrug.

3. The protein of claim 1, wherein said toxin protein is thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin, or cholera toxin.

4. A composition comprising the isolated protein of claim 1 and a carrier.

5. A kit comprising the composition of claim 4.

6. An isolated protein comprising a Neutrokine-alpha protein fused to a toxin protein, wherein said Neutrokine-alpha protein comprises an amino acid sequence selected from the group consisting of:

(a) the amino acid sequence of amino acid residues 134-285 of SEQ ID NO:2; and (b) an amino acid sequence that is at least 90% identical to amino acid residues 134-285 of SEQ ID NO:2;

and wherein said toxin protein comprises an amino acid sequence selected from the group consisting of:

(i) a polypeptide comprising the full-length gelonin polypeptide;

(ii) a polypeptide comprising amino acids 47 to 297 of the full-length gelonin polypeptide; and (iii) a polypeptide comprising amino acids 47 to 297 of the full-length gelonin polypeptide wherein Asp-297 is changed to Cys-297.

7. A composition comprising the isolated protein of claim 6 and a carrier.

8. A kit comprising the composition of claim 7.

* * * * *